US009085561B2

(12) United States Patent
Tsuno et al.

(10) Patent No.: US 9,085,561 B2
(45) Date of Patent: Jul. 21, 2015

(54) CYCLIC UREA- OR LACTAM-SUBSTITUTED QUINOXALINE-TYPE PIPERIDINES AS ORL-1 MODULATORS

(71) Applicants: Purdue Pharma L.P., Stamford, CT (US); Shionogi & Co., Ltd., Osaka (JP)

(72) Inventors: Naoki Tsuno, Toyonaka (JP); Tatsuhiko Ueno, Toyanaka (JP); Xiaoming Zhou, Plainsboro, NJ (US)

(73) Assignees: Purdue Pharma L.P., Stamford, CT (US); Shionogi & Co., Ltd. (JP)

( * ) Notice: Subject to any disclaimer, the term of this patent is extended or adjusted under 35 U.S.C. 154(b) by 0 days.

(21) Appl. No.: 13/952,284

(22) Filed: Jul. 26, 2013

(65) Prior Publication Data

US 2014/0045830 A1      Feb. 13, 2014

Related U.S. Application Data

(60) Provisional application No. 61/677,326, filed on Jul. 30, 2012, provisional application No. 61/784,128, filed on Mar. 14, 2013.

(51) Int. Cl.
| | |
|---|---|
| *A61K 31/498* | (2006.01) |
| *C07D 487/04* | (2006.01) |
| *C07D 401/14* | (2006.01) |
| *C07D 498/08* | (2006.01) |
| *C07D 471/08* | (2006.01) |

(52) U.S. Cl.
CPC ............ *C07D 401/14* (2013.01); *C07D 471/08* (2013.01); *C07D 498/08* (2013.01)

(58) Field of Classification Search
CPC ............................ A61K 31/498; C07D 487/04
USPC .................. 514/249; 544/180, 333, 354, 408; 546/112, 243, 268.1; 548/317.1
See application file for complete search history.

(56) References Cited

U.S. PATENT DOCUMENTS

| | | | |
|---|---|---|---|
| 3,536,809 A | 10/1970 | AppleZweig | |
| 3,598,123 A | 8/1971 | Zaffaroni et al. | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,354,556 A | 10/1994 | Sparks et al. | |
| 5,591,767 A | 1/1997 | Mohr et al. | |
| 5,639,476 A | 6/1997 | Oshlack et al. | |
| 5,674,533 A | 10/1997 | Santus et al. | |
| 5,698,155 A | 12/1997 | Grosswald et al. | |
| 5,733,566 A | 3/1998 | Lewis | |
| 6,136,839 A | 10/2000 | Isakson et al. | |
| 6,562,319 B2 | 5/2003 | Mishani et al. | |
| 6,635,653 B2 | 10/2003 | Goehring et al. | |
| 7,355,045 B2 | 4/2008 | Dey et al. | |
| 2005/0256000 A1 | 11/2005 | Schaper et al. | |
| 2010/0022519 A1 | 1/2010 | Brown et al. | |
| 2010/0216726 A1 | 8/2010 | Fuchino et al. | |
| 2011/0021426 A1 | 1/2011 | Toll et al. | |
| 2011/0178090 A1 | 7/2011 | Fuchino et al. | |

FOREIGN PATENT DOCUMENTS

| | | |
|---|---|---|
| WO | WO 99/46260 | 9/1999 |
| WO | WO 99/50254 | 10/1999 |
| WO | WO 01/90102 | 11/2001 |
| WO | WO 03/062234 | 7/2003 |
| WO | WO 2005/028451 | 5/2005 |
| WO | WO 2005/075459 | 8/2005 |
| WO | WO 2009/027820 | 3/2009 |
| WO | WO 2012/085648 | 6/2012 |
| WO | WO 2014/020405 | * 2/2014 |

OTHER PUBLICATIONS

Jordan, V. C. Nature Reviews: Drug Discovery, 2, 2003, 205.*
Hackam, et al. JAMA, 296(14), 2006, 1731-1732.*
Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990).
Berdini et al., "A Modified Palladium Catalyzed Reductive Amination Procedure," *Tetrahedron*, 58:5669-5674 (2002).
Bingham et al., "Over one hundred solvates of sulfathiazole," *Chem. Comm.*, pp. 603-604 (2001).
Buchwald et al., "Long-term, Continuous Intravenous Heparin Administration by an Implantable Infusion Pump in Ambulatory Patients with Recurrent Venous Thrombosis," *Surgery* 88:507-516 (1980).

(Continued)

*Primary Examiner* — Douglas M Willis
(74) *Attorney, Agent, or Firm* — Dechert LLP

(57) ABSTRACT

The disclosure relates to Cyclic Urea- or Lactam-Substituted Quinoxaline-Type Piperidine Compounds of Formula (I):

(I)

and pharmaceutically acceptable derivatives thereof wherein $R_1$, $R_2$, $Q_a$, $Y_1$, Z, A, B, $Q_x$, E, G, J, M, U, W, and a are as defined herein, compositions comprising an effective amount of a Cyclic Urea- or Lactam-Substituted Quinoxaline-Type Piperidine Compound, and methods to treat or prevent a condition, such as pain, comprising administering to an animal in need thereof an effective amount of a Cyclic Urea- or Lactam-Substituted Quinoxaline-Type Piperidine Compound.

58 Claims, No Drawings

(56) References Cited

OTHER PUBLICATIONS

Bulusu et al., "Selective photochemical cleavage of an α-ketoamide in a highly functionalised macrolide ascomycin," *Tetrahedron Lett.* 45(12):2527-2530 (2004).
Bundgaard et al., "(C) Means to Enhance Penetration (1) Prodrugs as a means to improve the delivery of peptide drugs," *Adv. Drug Delivery Revs.* 8:1-38 (1992).
Bundgaard et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988).
Bundgaard, "Design and Application of Prodrugs," *A Textbook of Drug Design and Development*, Krogsgaard-Larsen and Bundgaard, eds., Harwood Academic Publishers, Chapter 5, pp. 113-191 (1991).
Bundgaard, ed., *Design of Prodrugs*, Elsevier, Amsterdam (1985).
Caira et at, "Preparation and Crystal Characterization of a Polymorph, a Monohydrate, and an Ethyl Acetate Solvate of the Antifungal Fluconazole," *J. Pharmaceut. Sci.*, 93(3):601-611 (2004).
Colowick et al., "Drug and Enzyme Targeting, Part A," Widder et al., eds., *Methods in Enzymology*, vol. 112, Academic Press (1985).
D'Amour et al., "A Method for Determining Loss of Pain Sensation," *J. Pharmacol. Exp. Ther.* 72:74-79 (1941).
Dudash et al., "Synthesis and evaluation of 3-anilino-quinoxalinones as glycogen phosphorylase inhibitors," *Bioorg. Med. Chem. Lett.*, 15(21):4790-4793 (2005).
During et al., "Controlled Release of Dopamine from a Polymeric Brain Implant: In Vivo Characterization," *Ann. Neurol.* 25:351-356 (1989).
Filer, "The Preparation and Characterization of Tritiated Neurochemicals," *Isotopes in the Physical and Biomedical Sciences*, vol. 1, *Labeled Compounds (Part A)*, E. Buncel et al, eds., Chapter 6, pp. 155-192 (1987).
Goodson, "Dental Applications," in *Medical Applications of Controlled Release*, vol. 2, *Applications and Evaluation*, Langer and Wise, eds., CRC Press, Chapter 6, pp. 115-138 (1984).
Grupp et al., "Protection against Hypoxia-reoxygenation in the Absence of Poly (ADP-ribose) Synthetase in Isolated Working Hearts," *J. Mol. Cell Cardiol.* 31:297-303 (1999).
Hanson, "Analgesic, Antipyretic and Anti-Inflammatory Drugs," pp. 1196-1221 in *Remington: The Science and Practice of Pharmacy* vol. II (Gennaro, ed., 19th Ed., Mack Publishing, Easton, PA, 1995).
Hargreaves et al., "A New and Sensitive Method for Measuring Thermal Nociception in Cutaneous Hyperalgesia," *Pain* 32(1):77-88 (1988).
Henderson et al., "The orphan opioid receptor and its endogenous ligand—nociceptin/orphanin FQ," *Trends Pharmacol. Sci.* 18(8):293-300 (1997).
House et al., *J Org. Chem.* 44(16):2819-2824 (1979).
House et al., *J. Org. Chem.* 45(10):1800-1806 (1980).
Howard et al., "Intracerebral drug delivery in rats with lesion-induced memory deficits," *J. Neurosurg.* 71:105-112 (1989).
Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., eds., 9th Ed., McGraw-Hill, New York 1996).
International Search Report for PCT/IB2013/001654 dated Oct. 22, 2013.
McNaught et al., IUPAC Compendium of Chemical Terminology, 2nd Ed. (the "Gold Book"), eds., Blackwell Scientific Publications, Oxford (1997), entries for "Stereoisomers" and "Cis-trans isomers".
Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698 (1984).
Kim, "An Experimental Model for Peripheral Neuropathy Produced by Segmental Spinal Nerve Ligation in the Rat," *Pain* 50(3):355-363 (1992).
King, "Tablets, Capsules, and Pills," pp. 1553-1593 in *Remington's Pharmaceutical Sciences* (Osol, ed., 16th Ed., Mack Publishing, Easton, PA, 1980).
Langer et al., "Chemical and Physical Structure of Polymers as Carriers for Controlled Release of Bioactive Agents: A Review," *J. Macromol. Sci. Rev. Macromol. Chem.* C23(1):61-126 (1983).
Langer, "New Methods of Drug Delivery," *Science* 249:1527-1533 (1990).
Lazareno, "Measurement of Agonist-stimulated [$^{35}$S]GTPγS Binding to Cell Membranes," *Methods in Molecular Biology* 106:231-245 (1999).
Levy et al., "Inhibition of Calcification of Bioprosthetic Heart Valves by Local Controlled-Release Diphosphonate," *Science* 228:190-192 (1985).
Lewin et al., "Molecular Features Associated with Polyamine Modulation of NMDA Receptors," *J. Med. Chem.* 41:988-995 (1998).
Milligan, "Principles: Extending the Utility of [$^{35}$S]GTPγS Binding Assays," *TIPS* 24(2):87-90 (2003).
Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999).
Perregaard et al., "Studies on Organophosphorus Compounds XVIII*. Oxidation of Tertiary Alicyclic Amines with Elemental Sulfur in Hexamethylphosphoric Triam ide (HMPA). Oxidative Rearrangements of Hexahydroazepines and Octahydroazocines to bis(3-Pyrrolyl)Polysulfides.," *Bull. Soc. Chim. Belg.* 86:679-691 (1977).
*Pharmaceutical Dosage Forms: Disperse Systems* (Lieberman et al., eds., 2nd Ed., Marcel Dekker, Inc., 1996 & 1998).
*Pharmaceutical Dosage Forms: Tablets* (Lieberman et al., eds., 2nd Ed., Marcel Dekker, Inc., 1989 & 1990).
Pizey, "Thionyl Chloride," Ch. 4 in *Synthetic Reagents*, John Wiley & Sons, New York, vol. 1, pp. 321-357 (1974).
Porter, "The Zinin Reduction of Nitroarenes," *Org. Reactions*, 20:455-481 (1973).
Radebough et al., "Preformulation," pp. 1447-1676 in *Remington's Pharmaceutical Sciences* vol. 2 (Gennaro, ed., 19th Ed., Mack Publishing, Easton, PA, 1995).
Ross et al., "Pharmacodynamics: Mechanisms of Drug Action and the Relationship Between Drug Concentration and Effect," in *Goodman & Gilman's The Pharmacological Basis of Therapeutics* pp. 31-43 (Goodman et al., eds., 10th Ed., McGraw-Hill, New York 2001).
Rylander, "Hydrogenation of Nitro Compounds," in *Hydrogenation Methods* pp. 104-116 (Academic Press, London, 1985).
Saudek et al., "A Preliminary Trial of the Programmable Implantable Medication System for Insulin Delivery," *New Engl. J. Med.* 321:574-579 (1989).
Sefton, "Implantable Pumps," in *CRC Crit. Rev. Biomed. Eng.* 14(3):201-240 (1987).
Seltzer et al., "A Novel Behavioral Model of Neuropathic Pain Disorders Produced in Rats by Partial Sciatic Nerve Injury," *Pain* 43:205-218 (1990).
Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996).
Smolen et al., "Drug Product Design and Performance," *Controlled Drug Bioavailability* vol. 1, John Wiley & Sons, New York (1984).
Stein, "Unilateral Inflammation of the Hindpaw in Rats as a Model of Prolonged Noxious Stimulation: Alterations in Behavior and Nociceptive Thresholds," *Pharmacol. Biochem. Behavior* 31:451-455 (1988).
Tortolani et al., "A Convenient Synthesis to N-Aryl-Substituted 4-Piperidones," *Org. Lett.* 1:1261-1262 (1999).
Treat et al., "Liposome Encapsulated Doxorubicin Preliminary Results of Phase I and Phase II Trials," pp. 317-327 and 353-365 in *Liposomes in the Therapy of Infectious Disease and Cancer* (1989).
Van Tonder et al., "Preparation and Physicochemical Characterization of 5 Niclosamide Solvates and 1 Hemisolvate," *AAPS Pharm. Sci. Tech.*, 5(1):Article 12 (2004).

* cited by examiner

CYCLIC UREA- OR LACTAM-SUBSTITUTED QUINOXALINE-TYPE PIPERIDINES AS ORL-1 MODULATORS

CROSS REFERENCE TO RELATED APPLICATIONS

This application claims the benefit under 35 U.S.C. §119 (e) of provisional application Ser. No. 61/677,326, filed Jul. 30, 2012, and provisional application Ser. No. 61/784,128, filed Mar. 14, 2013, the contents of all of which are incorporated herein by reference.

1. FIELD

The disclosure relates to Cyclic Urea- or Lactam-Substituted Quinoxaline-Type Piperidine Compounds, compositions comprising an effective amount of a Cyclic Urea- or Lactam-Substituted Quinoxaline-Type Piperidine Compound and methods to treat or prevent a condition, such as pain, comprising administering to an animal in need thereof an effective amount of a Cyclic Urea- or Lactam-Substituted Quinoxaline-Type Piperidine Compound.

2. BACKGROUND

Chronic pain is a major contributor to disability and is the cause of much suffering. The successful treatment of severe and chronic pain is a primary goal of the physician, with opioid analgesics being preferred drugs for doing so.

Three major classes of opioid receptors in the central nervous system (CNS) have long been known, with each class having subtype receptors. These receptor classes are known as $\mu$, $\kappa$ and $\delta$. As opiates have a high affinity for these receptors while not being endogenous to the body, research followed in order to identify and isolate the endogenous ligands to these receptors. These ligands were identified as endorphins, dynorphins and enkephalins, respectively.

Experimentation eventually led to the identification of a cDNA encoding an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for $\mu$, $\kappa$ and $\delta$ receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand-nociceptin/orphanin FQ," *Trends Pharmacol. Set.* 18(8):293-300 (1997).

Subsequent research led to the isolation and structure of the endogenous ligand of the ORL-1 receptor (i.e., nociceptin; also known as orphanin FQ (OFQ)). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

International PCT Publication Nos. WO 99/46260, WO 99/50254, WO 01/90102, WO 2005/028451, WO 2003/062234, and U.S. Pat. App. No. 2005/0256000, respectively, describe quinoxalines or derivatives thereof as (i) inhibitors of protein kinase C, (ii) serine protease inhibitors, (iii) herbicides, (iv) M2 acetylcholine receptor agonists, (v) medicaments for diseases involving poly(ADP-ribose) polymerase, and (vi) safeners for plants.

Citation of any reference in Section 2 of this application is not to be construed as an admission that such reference is prior art to the present application.

3. SUMMARY

In one aspect of the disclosure, new compounds that exhibit affinity for the ORL-1 receptor are described.

In some embodiments, such new compounds exhibit agonist activity or partial agonist activity at the ORL-1 receptor. In other embodiments, such new compounds exhibit agonist activity at the ORL-1 receptor. In other embodiments, such new compounds exhibit partial agonist activity at the ORL-1 receptor. In yet other embodiments, such new compounds exhibit antagonist activity at the ORL-1 receptor.

In another embodiment of the disclosure, such new compounds exhibit affinity for the ORL-1 receptor, and also for one or more of the $\mu$, $\kappa$ or $\delta$ receptors. In some embodiments, a new compound of the disclosure exhibits affinity for both the ORL-1 receptor and the $\mu$ receptor. In other embodiments, a new compound of the disclosure acts as an ORL-1 receptor agonist or partial agonist and as a $\mu$ receptor agonist or partial agonist. In other embodiments, a new compound of the disclosure acts as an ORL-1 receptor agonist and as a $\mu$ receptor agonist or partial agonist. In other embodiments, a new compound of the disclosure acts as an ORL-1 receptor partial agonist and as a $\mu$ receptor agonist or partial agonist. In other embodiments, a new compound of the disclosure acts as an ORL-1 receptor agonist or partial agonist and as a $\mu$ receptor agonist. In other embodiments, a new compound of the disclosure acts as an ORL-1 receptor agonist or partial agonist and as a $\mu$ receptor partial agonist. In other embodiments, a new compound of the disclosure acts as an ORL-1 receptor agonist and as a $\mu$ receptor agonist. In other embodiments, a new compound of the disclosure acts as an ORL-1 receptor agonist and as a $\mu$ receptor partial agonist. In other embodiments, a new compound of the disclosure acts as an ORL-1 receptor partial agonist and as a $\mu$ receptor agonist. In other embodiments, a new compound of the disclosure acts as an ORL-1 receptor partial agonist and as a $\mu$ receptor partial agonist. In other embodiments, a new compound of the disclosure acts as an ORL-1 receptor agonist or partial agonist and as a $\mu$ receptor antagonist. In other embodiments, a new compound of the disclosure acts as an ORL-1 receptor agonist and as a $\mu$ receptor antagonist. In other embodiments, a new compound of the disclosure acts as an ORL-1 receptor partial agonist and as a $\mu$ receptor antagonist. In other embodiments, a new compound of the disclosure acts as an ORL-1 receptor antagonist and as a $\mu$ receptor agonist or partial agonist. In other embodiments, a new compound of the disclosure acts as an ORL-1 receptor antagonist and as a $\mu$ receptor agonist. In other embodiments, a new compound of the disclosure acts as an ORL-1 receptor antagonist and as a $\mu$ receptor partial agonist.

Certain new compounds of the disclosure can be used to treat an animal suffering from chronic or acute pain.

In another embodiment of the disclosure, methods for treating chronic or acute pain in an animal by administering one or more Cyclic Urea- or Lactam-Substituted Quinoxaline-Type Piperidine Compounds to an animal in need of such treatment are described. In certain embodiments, such new Cyclic Urea- or Lactam-Substituted Quinoxaline-Type Piperidine Compounds effectively treat chronic or acute pain in the animal, while producing fewer or reduced side effects compared to previously available compounds.

Compounds of Formula (I) are herein disclosed:

(I)

or a pharmaceutically acceptable derivative thereof where:
$Y_1$ is O or S;
$Q_a$ is benzo or (5- or 6-membered)heteroaryl;
each $R_2$ is independently selected from:
(a) -halo, —CN, —$NO_2$, —$OT_3$, —C(=O)$T_3$, —C(=O)$OT_3$, —C(=O)N($T_1$)($T_2$), —S(=O)$_2OT_3$, —S(=O)$T_3$, —S(=O)$_2T_3$, —O—S(=O)$_2T_3$, —S(=O)$_2N(T_1)(T_2)$, —N($T_1$)($T_2$), —N($T_3$)C(=O)$T_3$, —N($T_3$)C(=O)N($T_1$)($T_2$), —N($T_3$)S(=O)$T_3$, —N($T_3$)S(=O)$_2T_3$, —N($T_3$)C(=O)$OT_3$, and —N($T_3$)S(=O)$_2N(T_1)(T_2)$; and
(b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, -(5- or 6-membered)heterocycle, and -(7- to 10-membered)bicycloheterocycle, each of which is unsubstituted or substituted with 1, 2, or 3 independently selected $R_8$ groups; and
(c) -phenyl, -naphthalenyl, —($C_{14}$)aryl, or -(5- or 6-membered)heteroaryl, each of which is unsubstituted or substituted with 1, 2, or 3 independently selected $R_7$ groups;
a is an integer selected from 0, 1, and 2;
E is N or C($R_{90}$);
G, M, and U are independently selected from N($R_{90}$), C(=O), C(=S), and C($R_{90}$)($R_{91}$);
J is N($R_{90}$), C(=O), or C(=S);
W is N($R_{90}$), C($R_{90}$)($R_{91}$), or absent;
each dashed line of the $Q_x$ ring independently is either present and denotes the presence of one bond of a double bond or is absent, provided that when one dashed line attached to an atom is present to form a double bond, then the other dashed line attached to said atom is absent and the $R_{90}$ group attached to said atom is absent, where the maximum number of double bonds is 3 for a 6-membered $Q_x$ ring and the maximum number of double bonds is 2 for a 5-membered $Q_x$ ring;
each $R_{90}$, when present, and each $R_{91}$ is independently selected from —H, —CN, -halo, —($C_1$-$C_3$)alkyl, —N($R_{92}$)($R_{93}$), —($CH_2$)$_c$—(C($R_{94}$)($R_{95}$))$_d$—C(=O)$R_{92}$, —($CH_2$)$_x$—(C($R_{94}$)($R_{95}$))$_d$—C(=O)$R_{92}$, —($CH_2$)$_c$—(C($R_{94}$)($R_{95}$))$_d$—N($R_{92}$)—C(=O)$R_{92}$, and —($CH_2$)$_c$—(C($R_{94}$)($R_{95}$))$_d$—C(=O)N($R_{92}$)($R_{93}$);
each $R_{92}$, $R_{93}$, $R_{94}$, and $R_{95}$ is independently selected from —H and —($C_1$-$C_3$)alkyl;

each c is independently an integer selected from 0, 1, 2, and 3;
each d is independently an integer selected from 0, 1, and 2;
provided that the ring atoms of the $Q_x$ ring are constituents of at least one lactam group or cyclic urea group, provided that G is C(=O) or C(=S) when E is N, provided that at least two of the ring atoms of the $Q_x$ ring are carbon, and provided that 1, 2, or 3 of the ring atoms of the $Q_x$ ring are nitrogen;
A and B are independently selected from:
(a) —H, —CN, —C(=O)$OT_3$, and —C(=O)N($T_1$)($T_2$); and
(b) —($C_3$-$C_{12}$)cycloalkyl, —($C_3$-$C_{12}$)cycloalkoxy, —($C_1$-$C_6$)alkyl, —($C_2$-$C_6$)alkenyl, —($C_2$-$C_6$)alkynyl, and —($C_1$-$C_6$)alkoxy, each of which is unsubstituted or substituted with 1 or 2 substituents independently selected from —OH, —S(=O)$_2NH_2$, —N($R_6$)$_2$, =$NR_6$, —C(=O)$OT_3$, —C(=O)N($R_6$)$_2$, —N($R_6$)C(=O)$R_9$, and -(5- or 6-membered)heterocycle, or 1, 2, or 3 independently selected -halo; or
(c) A-B can together form a ($C_2$-$C_6$)bridge, which is unsubstituted or substituted with 1, 2, 3, 4, 5, 6, 7 or 8 substituents independently selected from —OH, —($C_1$-$C_4$)alkyl, -halo, and —C(halo)$_3$, and which bridge optionally contains —HC=CH— or —O— within the ($C_2$-$C_6$)bridge; where the 6-membered, nitrogen-containing ring that is fused to the $Q_a$ ring can be in the endo- or exo-configuration with respect to the A-B bridge; or
(d) A-B can together form a —$CH_2$—N($R_a$)—$CH_2$— bridge, a

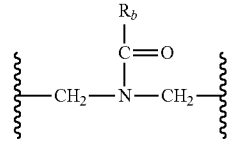

bridge, or a

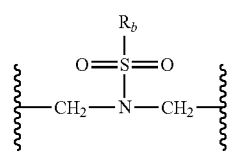

bridge;
where the 6-membered, nitrogen-containing ring that is fused to the $Q_a$ ring can be in the endo- or exo-configuration with respect to the A-B bridge;
$R_a$ is —H, —($C_1$-$C_6$)alkyl, —($C_3$-$C_7$)cycloalkyl, —$CH_2$—C(=O)—$R_c$, —($CH_2$)—C(=O)—$OR_c$, —($CH_2$)—C(=O)—N($R_c$)$_2$, —($CH_2$)$_2$—O—$R_c$, —($CH_2$)$_2$—S(=O)$_2$—N($R_9$)$_2$, $R_c$, or —($CH_2$)$_2$—N($R_c$)S(=O)$_2$—$R_9$;
$R_b$ is selected from:
(a) —H, —($C_1$-$C_6$)alkyl, —($C_3$-$C_7$)cycloalkyl, -(3- to 7-membered)heterocycle, —N($R_c$)$_2$, —N($R_c$)—($C_3$-$C_7$)cycloalkyl, and —N($R_c$)-(3- to 7-membered)heterocycle; and
(b) -phenyl, -naphthalenyl, and -(5- or 6-membered)heteroaryl, each of which is unsubstituted or substituted with 1, 2, or 3 independently selected $R_7$ groups; and
(c) —N($R_c$)-phenyl, —N($R_c$)-naphthalenyl, —N($R_c$)—($C_{14}$)aryl, and —N($R_c$)-(5- to 10-membered)heteroaryl, each of which is unsubstituted or substituted with 1, 2, or 3 independently selected $R_7$ groups;

each $R_c$ is independently —H or —$(C_1$-$C_4)$alkyl;

Z is —[$(C_1$-$C_{10})$alkyl optionally substituted by $R_{13}]_h$—, where h is 0 or 1; or —[$(C_2$-$C_{10})$alkenyl optionally substituted by $R_{13}$]—; or —$(C_1$-$C_{10})$alkyl-N$(R_6)$C(=Y)—, where Y is O or S;

$R_1$ is selected from:
(a) —H, -halo, —CN, —OH, —CH$_2$OH, —CH$_2$CH$_2$OH, —NO$_2$, —N$(R_6)_2$, —S(=O)NH$_2$, —S(=O)$_2$NH$_2$, —C(=O)OV$_1$, and —C(=O)CN; and
(b) —$(C_1$-$C_{10})$alkyl, —$(C_2$-$C_{10})$alkenyl, —$(C_2$-$C_{10})$alkynyl, —O$(C_1$-$C_6)$alkyl, —$(C_3$-$C_7)$cycloalkoxy, —$(C_6$-$C_{14})$bicycloalkyl, —$(C_8$-$C_{20})$tricycloalkyl, —$(C_5$-$C_{14})$cycloalkenyl, —$(C_7$-$C_{14})$bicycloalkenyl, —$(C_8$-$C_{20})$tricycloalkenyl, and -(3- to 7-membered)heterocycle, each of which is unsubstituted or substituted with 1, 2, 3, or 4 independently selected $R_8$ groups; and (c)

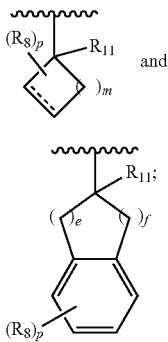

and
(d) -phenyl, -naphthalenyl, —$(C_{14})$aryl, and -(5- to 10-membered)heteroaryl, each of which is unsubstituted or substituted with 1, 2, or 3 independently selected $R_7$ groups; or —Z—$R_1$ is 3,3-diphenylpropyl-optionally substituted at the 3 carbon of the propyl with —CN, —C(=O)N$(R_6)_2$, —C(=O)OV$_1$, or -tetrazolyl; or —Z—$R_1$ is —$(C_1$-$C_4)$alkyl substituted with tetrazolyl;

each $R_5$ is independently —$(C_1$-$C_4)$alkyl, —$(C_2$-$C_6)$alkenyl, —$(C_2$-$C_6)$alkynyl, -(5- or 6-membered)heteroaryl, —$(C_1$-$C_6)$alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N$(R_9)$, —N$(R_9)(C_1$-$C_6)$alkyl-C(=O)OR$_9$, —N$(R_9)_2$, —N$(R_9)$OH, —N$(R_9)$S(=O)R$_{12}$, —N$(R_9)$S(=O)$_2$R$_{12}$, —N$(R_9)$C(=O)R$_{12}$, —N$(R_9)$C(=O)OR$_{12}$, —C(=O)R$_9$, —C(=O)OR$_9$, —OC(=O)R$_9$, —OC(=O)OR$_9$, —S(=O)R$_9$, or —S(=O)$_2$R$_9$;

each $R_6$ is independently —H, —$(C_1$-$C_6)$alkyl, or —$(C_3$-$C_7)$cycloalkyl, or two $R_6$ groups attached to the same nitrogen atom can together form a 5- to 8-membered ring, where the number of atoms in the ring includes the nitrogen atom, and in which one of the 5- to 8-membered ring carbon atoms is optionally replaced by O, S, or N$(T_3)$;

each $R_7$ is independently —$(C_1$-$C_4)$alkyl, —$(C_2$-$C_6)$alkenyl, —$(C_2$-$C_6)$alkynyl, —OR$_9$, —SR$_9$, —C(halo)$_3$, —CH(halo)$_2$, —CH$_2$(halo), —CN, -halo, —N$_3$, —NO$_2$, —CH=N$(R_9)$, —N$(R_9)_2$, —N$(R_9)$OH, —N$(R_9)$S(=O)R$_{12}$, —N$(R_9)$S(=O)$_2$R$_{12}$, NR$_9)$C(=O)R$_{12}$, —N$(R_9)$C(=O)N$(T_1)(T_2)$, —N$(R_9)$C(=O)OR$_{12}$, —C(=O)R$_9$, —C(=O)N$(T_1)(T_2)$, —C(=O)OR$_9$, —OC(=O)R$_9$, —OC(=O)N$(T_1)(T_2)$, —OC(=O)OR$_9$, —S(=O)R$_9$, or —S(=O)$_2$R$_9$;

each $R_8$ is independently —$(C_1$-$C_4)$alkyl, —$(C_2$-$C_6)$alkenyl, —$(C_2$-$C_6)$alkynyl, -(5- or 6-membered)heteroaryl, —$(C_1$-$C_6)$alkyl-C(=O)OR$_9$, —N$(R_9)(C_1$-$C_6)$alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N$(R_9)$, —N$(R_9)_2$, —N$(R_9)$OH, —N$(R_9)$S(=O)R$_{12}$, —N$(R_9)$S(=O)$_2$R$_{12}$, —N$(R_9)$C(=O)R$_{12}$, —N$(R_9)$C(=O)N$(T_1)(T_2)$, —N$(R_9)$C(=O)OR$_{12}$, —C(=O)R$_9$, —C(=O)N$(T_1)(T_2)$, —C(=O)OR$_9$, —OC(=O)R$_9$, —OC(=O)N$(T_1)(T_2)$, —OC(=O)OR$_9$, —S(=O)R$_9$, or —S(=O)$_2$R$_9$;

each $R_9$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, -(3- to 7-membered)heterocycle, —C(halo)$_3$, —CH(halo)$_2$, or —CH$_2$(halo);

if h is 0, then $R_{11}$ can be —H, —CN, —C(=O)OR$_9$, or —C(=O)N$(R_6)_2$ or $R_{11}$ can be —$(C_1$-$C_4)$alkyl which is unsubstituted or substituted with —OH, —$(C_1$-$C_4)$alkoxy, —N$(R_6)_2$, —C(=O)OR$_9$, or —C(=O)N$(R_6)_2$;

if h is 1, then $R_{11}$ can be —H, —CN, —OH, -halo, —C(=O)OR$_9$, or —C(=O)N$(R_6)_2$ or $R_{11}$ can be —$(C_1$-$C_4)$alkyl which is unsubstituted or substituted with —OH, —$(C_1$-$C_4)$alkoxy, —N$(R_6)_2$, —C(=O)OR$_9$, or —C(=O)N$(R_6)_2$;

otherwise, where Z is —[$(C_2$-$C_{10})$alkenyl optionally substituted by $R_{13}$]— or —$(C_1$-$C_{10})$alkyl-N$(R_6)$C(=Y)—, then $R_{11}$ can be —H, —CN, —C(=O)OR$_9$, or —C(=O)N$(R_6)_2$ or $R_{11}$ can be —$(C_1$-$C_4)$alkyl which is unsubstituted or substituted with —OH, —$(C_1$-$C_4)$alkoxy, —N$(R_6)_2$, —C(=O)OR$_9$, or —C(=O)N$(R_6)_2$;

each $R_{12}$ is independently —H or —$(C_1$-$C_4)$alkyl;

$R_{13}$ is selected from:
(a) -halo, —CN, —OH, —CH$_2$OH, —CH$_2$CH$_2$OH, —NO$_2$, —N$(R_6)_2$, —S(=O)NH$_2$, —S(=O)$_2$NH$_2$, —C(=O)OV$_1$, and —C(=O)CN; and
(b) —$(C_1$-$C_{10})$alkyl, —$(C_2$-$C_{10})$alkenyl, —$(C_2$-$C_{10})$alkynyl, —O$(C_1$-$C_6)$alkyl, —$(C_3$-$C_7)$cycloalkoxy, —$(C_5$-$C_{14})$cycloalkenyl, and -(3- to 7-membered)heterocycle, each of which is unsubstituted or substituted with 1, 2, 3, or 4 independently selected $R_8$ groups; and (c)

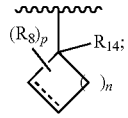

and
(d) -phenyl and -(5- to 10-membered)heteroaryl, each of which is unsubstituted or substituted with 1, 2, or 3 independently selected $R_7$ groups;

$R_{14}$ is —H, —CN, —OH, -halo, —C(=O)OR$_9$, or —C(=O)N$(R_6)_2$ or $R_{14}$ can be —$(C_1$-$C_4)$alkyl which is unsubstituted or substituted with —OH, —$(C_1$-$C_4)$alkoxy, —N$(R_6)_2$, —C(=O)OR$_9$, or —C(=O)N$(R_6)_2$;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4;

each $T_1$ and $T_2$ is independently —H or —$(C_1$-$C_{10})$alkyl which is unsubstituted or substituted with 1, 2, or 3 independently selected $R_5$ groups and, optionally, in which any —$(C_1$-$C_{10})$alkyl carbon atom except the carbon atom bonded directly to the atom to which $T_1$ or $T_2$ is attached is independently replaced by O, S, or N($R_6$), or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2, or 3 independently selected $R_5$ groups and, optionally, any carbon atom in said 5- to 8-membered ring is independently replaced by O, S, or N($R_6$);

each $T_3$ is independently —H or —$(C_1$-$C_{10})$alkyl which is unsubstituted or substituted with 1, 2, or 3 independently selected $R_5$ groups and, optionally, in which any —$(C_1$-$C_{10})$ alkyl carbon atom except the carbon atom bonded directly to the atom to which $T_3$ is attached is independently replaced by O, S, or N($R_{12}$);

each $V_1$ is independently —H, —$(C_1$-$C_6)$alkyl, —$(C_3$-$C_7)$ cycloalkyl, -phenyl, or benzyl; and each halo is independently —F, —Cl, —Br, or —I.

In one embodiment, the $Q_x$ ring is not:

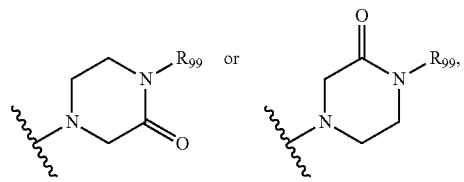

where:

$R_{99}$ is —H, —$(C_1$-$C_3)$alkyl, —$(CH_2)_j$—C(=O)OH, or —$(CH_2)_j$—C(=O)O—$(C_1$-$C_3)$alkyl; and j is an integer selected from 0, 1, 2, and 3.

In another embodiment, the $Q_x$ ring is not:

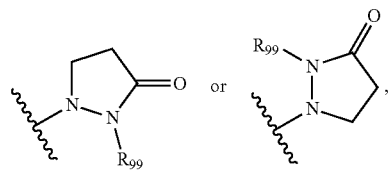

where $R_{99}$ is as defined above. In another embodiment, the $Q_x$ ring does not contain 3 consecutive ring nitrogen atoms. In another embodiment, the $Q_x$ ring is not:

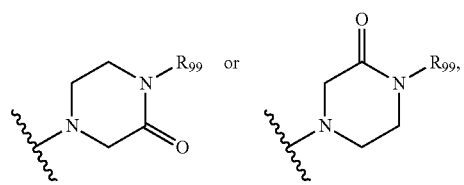

where $R_{99}$ is as defined above and the $Q_x$ ring does not contain 3 consecutive ring nitrogen atoms. In another embodiment, the $Q_x$ ring is not:

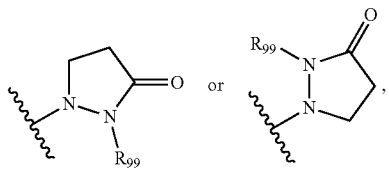

where $R_{99}$ is as defined above and the $Q_x$ ring does not contain 3 consecutive ring nitrogen atoms. In another embodiment, the $Q_x$ ring is not:

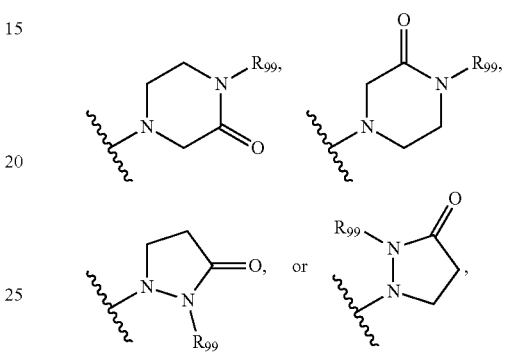

where $R_{99}$ is as defined above. In another embodiment, the $Q_x$ ring is not:

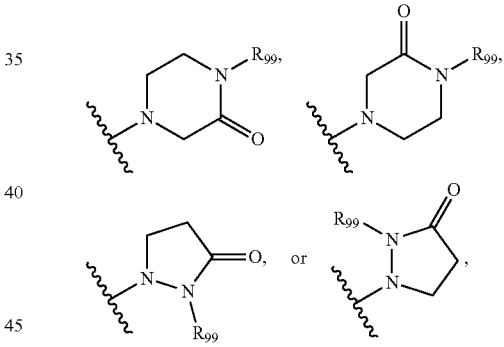

where $R_{99}$ is as defined above and the $Q_x$ ring does not contain 3 consecutive ring nitrogen atoms.

A compound of Formula (I) or a pharmaceutically acceptable derivative thereof (an "Cyclic Urea- or Lactam-Substituted Quinoxaline-Type Piperidine Compound") is useful, e.g., as an analgesic, anti-inflammatory, diuretic, anesthetic agent, neuroprotective agent, anti-hypertensive, an anxiolytic agent, an agent for appetite control, hearing regulator, antitussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias, anti-epileptic, anti-convulsant, agent to treat withdrawal from alcohol, agent to treat withdrawal from drug(s) of addiction, agent to control water balance, agent to control sodium excretion, and/or agent to control arterial blood pressure disorder(s).

A Cyclic Urea- or Lactam-Substituted Quinoxaline-Type Piperidine Compound, a pharmaceutically acceptable derivative thereof, a composition containing a Cyclic Urea- or Lactam-Substituted Quinoxaline-Type Piperidine Compound, and/or a composition containing a pharmaceutically acceptable derivative of a Cyclic Urea- or Lactam-Substituted Quinoxaline-Type Piperidine Compound is useful for treating and/or preventing pain, anxiety, cough, diarrhea, high blood pressure, epilepsy, anorexia/cachexia, urinary incontinence, drug abuse, memory disorders, obesity, constipation, depression, dementia, or Parkinsonism (each being a "Condition") in an animal.

Compositions comprising an effective amount of a Cyclic Urea- or Lactam-Substituted Quinoxaline-Type Piperidine Compound or a pharmaceutically acceptable derivative thereof and a pharmaceutically acceptable carrier or excipient are disclosed. The compositions are useful for treating or preventing a Condition in an animal.

Methods for treating or preventing a Condition, comprising administering to an animal in need thereof an effective amount of a Cyclic Urea- or Lactam-Substituted Quinoxaline-Type Piperidine Compound, a pharmaceutically acceptable derivative thereof, a composition containing a Cyclic Urea- or Lactam-Substituted Quinoxaline-Type Piperidine Compound, and/or a composition containing a pharmaceutically acceptable derivative of a Cyclic Urea- or Lactam-Substituted Quinoxaline-Type Piperidine Compound are disclosed. Cyclic Urea- or Lactam-Substituted Quinoxaline-Type Piperidine Compounds, e.g., of Formula (I), may also be used in the manufacture of a medicament useful for treating a Condition or for preventing a Condition.

Methods for inhibiting ORL-1 receptor function in a cell, comprising contacting a cell capable of expressing the ORL-1 receptor with an ORL-1 receptor function inhibiting amount of a Cyclic Urea- or Lactam-Substituted Quinoxaline-Type Piperidine Compound or a pharmaceutically acceptable derivative thereof are disclosed. In further embodiments of the disclosure, methods for activating ORL-1 receptor function in a cell, comprising contacting a cell capable of expressing the ORL-1 receptor with an ORL-1 receptor function activating amount of a Cyclic Urea- or Lactam-Substituted Quinoxaline-Type Piperidine Compound or a pharmaceutically acceptable derivative thereof are disclosed. In yet another embodiment, methods for preparing a composition, comprising the step of admixing a Cyclic Urea- or Lactam-Substituted Quinoxaline-Type Piperidine Compound or a pharmaceutically acceptable derivative thereof and a pharmaceutically acceptable carrier or excipient, are disclosed.

An embodiment of the disclosure relates to a kit comprising a container containing an effective amount of a Cyclic Urea- or Lactam-Substituted Quinoxaline-Type Piperidine Compound or a pharmaceutically acceptable derivative thereof.

Another embodiment of the disclosure provides novel intermediates for use in making the Cyclic Urea- or Lactam-Substituted Quinoxaline-Type Piperidine Compounds.

The disclosure can be understood more fully by reference to the following detailed description and illustrative examples, which are intended to exemplify non-limiting embodiments of the disclosure.

4. DETAILED DESCRIPTION

The invention includes the following:
(1) A compound of Formula (I):

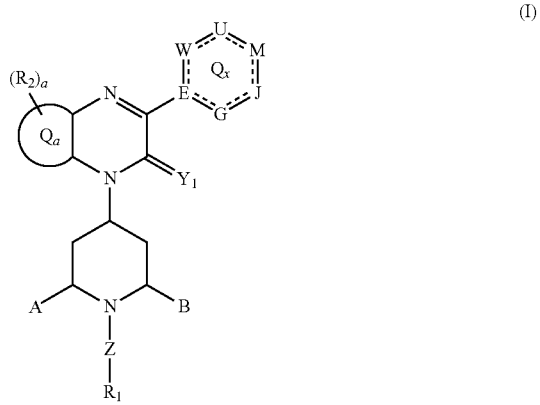

or a pharmaceutically acceptable derivative thereof wherein:
$Y_1$ is O or S;
$Q_a$ is benzo or (5- or 6-membered)heteroaryl;
each $R_2$ is independently selected from:
(a) -halo, —CN, —NO$_2$, —OT$_3$, —C(=O)T$_3$, —C(=O)OT$_3$, —C(=O)N(T$_1$)(T$_2$), —S(=O)$_2$OT$_3$, —S(=O)T$_3$, —S(=O)$_2$T$_3$, —O—S(=O)$_2$T$_3$, —S(=O)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(=O)T$_3$, —N(T$_3$)S(=O)$_2$T$_3$, —N(T$_3$)C(=O)OT$_3$, and —N(T$_3$)S(=O)$_2$N(T$_1$)(T$_2$); and
(b) —(C$_1$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, -(5- or 6-membered)heterocycle, and -(7- to 10-membered)bicycloheterocycle, each of which is unsubstituted or substituted with 1, 2, or 3 independently selected $R_8$ groups; and
(c) -phenyl, -naphthalenyl, —(C$_{14}$)aryl, or -(5- or 6-membered)heteroaryl, each of which is unsubstituted or substituted with 1, 2, or 3 independently selected $R_7$ groups;
a is an integer selected from 0, 1, and 2;
E is N or C(R$_{90}$);
G, M, and U are independently selected from N(R$_{90}$), C(=O), C(=S), and C(R$_{90}$)(R$_{91}$);
J is N(R$_{90}$), C(=O), or C(=S);
W is N(R$_{90}$), C(R$_{90}$)(R$_{91}$), or absent;
each dashed line of the Q$_x$ ring independently is either present and denotes the presence of one bond of a double bond or is absent, provided that when one dashed line attached to an atom is present to form a double bond, then the other dashed line attached to said atom is absent and the R$_{90}$ group attached to said atom is absent, wherein the maximum number of double bonds is 3 for a 6-membered Q$_x$ ring and the maximum number of double bonds is 2 for a 5-membered Q$_x$ ring;
each R$_{90}$, when present, and each R$_{91}$ is independently selected from —H, —CN, -halo, —(C$_1$-C$_3$)alkyl, —N(R$_{92}$)(R$_{93}$), —(CH$_2$)$_x$—(C(R$_{94}$)(R$_{95}$))$_d$—C(=O)R$_{92}$, —(CH$_2$)$_c$—(C(R$_{94}$)(R$_{95}$))$_d$—C(=O)OR$_{92}$, —(CH$_2$)$_c$—(C(R$_{94}$)(R$_{95}$))$_d$—N(R$_{92}$)—C(=O)R$_{92}$, and —(CH$_2$)$_c$—(C(R$_{94}$)(R$_{95}$))$_d$—C(=O)N(R$_{92}$)(R$_{93}$);

each $R_{92}$, $R_{93}$, $R_{94}$, and $R_{95}$ is independently selected from —H and —$(C_1$-$C_3)$alkyl;

each c is independently an integer selected from 0, 1, 2, and 3;

each d is independently an integer selected from 0, 1, and 2;

provided that the ring atoms of the $Q_x$ ring are constituents of at least one lactam group or cyclic urea group, provided that G is C(=O) or C(=S) when E is N, provided that at least two of the ring atoms of the $Q_x$ ring are carbon, and provided that 1, 2, or 3 of the ring atoms of the $Q_x$ ring are nitrogen;

A and B are independently selected from:
(a) —H, —CN, —C(=O)O$T_3$, and —C(=O)N($T_1$)($T_2$); and
(b) —$(C_3$-$C_{12})$cycloalkyl, —$(C_3$-$C_{12})$cycloalkoxy, —$(C_1$-$C_6)$alkyl, —$(C_2$-$C_6)$alkenyl, —$(C_2$-$C_6)$alkynyl, and —$(C_1$-$C_6)$alkoxy, each of which is unsubstituted or substituted with 1 or 2 substituents independently selected from —OH, —S(=O)$_2$NH$_2$, —N(R$_6$)$_2$, =NR$_6$, —C(=O)OT$_3$, —C(=O)N(R$_6$)$_2$, —N(R$_6$)C(=O)R$_9$, and -(5- or 6-membered)heterocycle, or 1, 2, or 3 independently selected -halo; or
(c) A-B can together form a $(C_2$-$C_6)$bridge, which is unsubstituted or substituted with 1, 2, 3, 4, 5, 6, 7 or 8 substituents independently selected from —OH, —$(C_1$-$C_4)$alkyl, -halo, and —C(halo)$_3$, and which bridge optionally contains —HC=CH— or —O— within the $(C_2$-$C_6)$bridge; wherein the A-B bridge can be in the endo- or exo-configuration with respect to the 6-membered, nitrogen-containing ring that is fused to the $Q_a$ ring; or
(d) A-B can together form a —CH$_2$—N(R$_a$)—CH$_2$— bridge, a

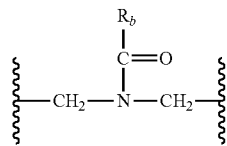

bridge, or a

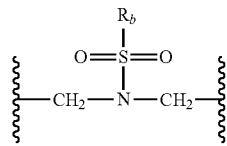

bridge;

wherein the A-B bridge can be in the endo- or exo-configuration with respect to the 6-membered, nitrogen-containing ring that is fused to the $Q_a$ ring;

$R_a$ is —H, —$(C_1$-$C_6)$alkyl, —$(C_3$-$C_7)$cycloalkyl, —CH$_2$—C(=O)—R$_c$, —(CH$_2$)—C(=O)—OR$_c$, —(CH$_2$)—C(=O)—N(R$_c$)$_2$, —(CH$_2$)$_2$—O—R$_c$, —(CH$_2$)$_2$—S(=O)$_2$—N(R$_c$)$_2$, R$_c$, or —(CH$_2$)$_2$—N(R$_c$)S(=O)$_2$—R$_c$;

$R_b$ is selected from:
(a) —H, —$(C_1$-$C_6)$alkyl, —$(C_3$-$C_7)$cycloalkyl, -(3- to 7-membered)heterocycle, —N(R$_c$)$_2$, —N(R$_c$)—(C$_3$-C$_7$)cycloalkyl, and —N(R$_c$)-(3- to 7-membered)heterocycle; and
(b) -phenyl, -naphthalenyl, and -(5- or 6-membered)heteroaryl, each of which is unsubstituted or substituted with 1, 2, or 3 independently selected R$_7$ groups; and (c) —N(R$_c$)-phenyl, —N(R$_c$)-naphthalenyl, —N(R$_c$)—(C$_{14}$)aryl, and —N(R$_c$)-(5- to 10-membered)heteroaryl, each of which is unsubstituted or substituted with 1, 2, or 3 independently selected R$_7$ groups;

each R$_c$ is independently —H or —$(C_1$-$C_4)$alkyl;

Z is —[$(C_1$-$C_{10})$alkyl optionally substituted by R$_{13}$]$_h$—, wherein h is 0 or 1; or —[$(C_2$-$C_{10})$alkenyl optionally substituted by R$_{13}$]—; or —$(C_1$-$C_{10})$alkyl-N(R$_6$)C(=Y)—, wherein Y is O or S;

$R_1$ is selected from:
(a) —H, -halo, —CN, —OH, —CH$_2$OH, —CH$_2$CH$_2$OH, —NO$_2$, —N(R$_6$)$_2$, —S(=O)NH$_2$, —S(=O)$_2$NH$_2$, —C(=O)OV$_1$, and —C(=O)CN; and
(b) —$(C_1$-$C_{10})$alkyl, —$(C_2$-$C_{10})$alkenyl, —$(C_2$-$C_{10})$alkynyl, —O$(C_1$-$C_6)$alkyl, —$(C_3$-$C_7)$cycloalkoxy, —$(C_3$-$C_{14})$cycloalkyl, —$(C_6$-$C_{14})$bicycloalkyl, —$(C_8$-$C_{20})$tricycloalkyl, —$(C_5$-$C_{14})$cycloalkenyl, —$(C_7$-$C_{14})$bicycloalkenyl, —$(C_8$-$C_{20})$tricycloalkenyl, and -(3- to 7-membered)heterocycle, each of which is unsubstituted or substituted with 1, 2, 3, or 4 independently selected R$_8$ groups; and (c)

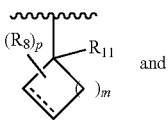

and

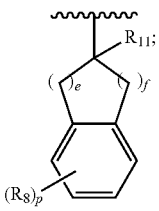

and
(d) -phenyl, -naphthalenyl, —$(C_{14})$aryl, and -(5- to 10-membered)heteroaryl, each of which is unsubstituted or substituted with 1, 2, or 3 independently selected R$_7$ groups; or —Z—R$_1$ is 3,3-diphenylpropyl- optionally substituted at the 3 carbon of the propyl with —CN, —C(=O)N(R$_6$)$_2$, —C(=O)OV$_1$, or -tetrazolyl; or —Z—R$_1$ is —$(C_1$-$C_4)$alkyl substituted with tetrazolyl;

each R$_5$ is independently —$(C_1$-$C_4)$alkyl, —$(C_2$-$C_6)$alkenyl, —$(C_2$-$C_6)$alkynyl, -(5- or 6-membered)heteroaryl, —$(C_1$-$C_6)$alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N(R$_9$), —N(R$_9$)$(C_1$-$C_6)$alkyl-C(=O)OR$_9$, —N(R$_9$)$_2$, —N(R$_9$)OH, —N(R$_9$)S(=O)R$_{12}$, —N(R$_9$)S(=O)$_2$R$_{12}$, —N(R$_9$)C(=O)R$_{12}$, —N(R$_9$)C(=O)OR$_{12}$, —C(=O)R$_9$, —C(=O)OR$_9$, —OC(=O)R$_9$, —OC(=O)OR$_9$, —S(=O)R$_9$, or —S(=O)$_2$R$_9$;

each R$_6$ is independently —H, —$(C_1$-$C_6)$alkyl, or —$(C_3$-$C_7)$cycloalkyl, or two R$_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N(T$_3$);

each R$_7$ is independently —$(C_1$-$C_4)$alkyl, —$(C_2$-$C_6)$alkenyl, —$(C_2$-$C_6)$alkynyl, —OR$_9$, —SR$_9$, —C(halo)$_3$, —CH(halo)$_2$, —CH$_2$(halo), —CN, -halo, —N$_3$, —NO$_2$, —CH=N $(R_9)$, —$N(R_9)_2$, —$N(R_9)OH$, —$N(R_9)S(=O)R_{12}$, —$N(R_9)S(=O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$OC(=O)N(T_1)(T_2)$, —$OC(=O)OR_9$, —$S(=O)R_9$, or —$S(=O)_2R_9$;

each $R_8$ is independently —$(C_1-C_4)$alkyl, —$(C_2-C_6)$alkenyl, —$(C_2-C_6)$alkynyl, -(5- or 6-membered)heteroaryl, —$(C_1-C_6)$alkyl-$C(=O)OR_9$, —$N(R_9)(C_1-C_6)$alkyl-$C(=O)OR_9$, —$OR_9$, —$SR_9$, —$C(halo)_3$, —$CH(halo)_2$, —$CH_2(halo)$, —$CN$, =O, =S, -halo, —$N_3$, —$NO_2$, —$CH=N(R_9)$, —$N(R_9)_2$, —$N(R_9)OH$, —$N(R_9)S(=O)R_{12}$, —$N(R_9)S(=O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$OC(=O)N(T_1)(T_2)$, —$OC(=O)OR_9$, —$S(=O)R_9$, or —$S(=O)_2R_9$;

each $R_9$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, -(3- to 7-membered)heterocycle, —$C(halo)_3$, —$CH(halo)_2$, or —$CH_2(halo)$;

if h is 0, then $R_{11}$ can be —H, —CN, —$C(=O)OR_9$, or —$C(=O)N(R_6)_2$ or $R_{11}$ can be —$(C_1-C_4)$alkyl which is unsubstituted or substituted with —OH, —$(C_1-C_4)$alkoxy, —$N(R_6)_2$, —$C(=O)OR_9$, or —$C(=O)N(R_6)_2$;

if h is 1, then $R_{11}$ can be —H, —CN, —OH, -halo, —$C(=O)OR_9$, or —$C(=O)N(R_6)_2$ or $R_n$ can be —$(C_1-C_4)$alkyl which is unsubstituted or substituted with —OH, —$(C_1-C_4)$alkoxy, —$N(R_6)_2$, —$C(=O)OR_9$, or —$C(=O)N(R_6)_2$;

otherwise, wherein Z is —[$(C_2-C_{10})$alkenyl optionally substituted by $R_{13}$]— or —$(C_1-C_{10})$alkyl-$N(R_6)C(=Y)$—, then $R_{11}$ can be —H, —CN, —$C(=O)OR_9$, or —$C(=O)N(R_6)_2$ or $R_{11}$ can be —$(C_1-C_4)$alkyl which is unsubstituted or substituted with —OH, —$(C_1-C_4)$alkoxy, —$N(R_6)_2$, —$C(=O)OR_9$, or —$C(=O)N(R_6)_2$;

each $R_{12}$ is independently —H or —$(C_1-C_4)$alkyl;

$R_{13}$ is selected from:
(a) -halo, —CN, —OH, —$CH_2OH$, —$CH_2CH_2OH$, —$NO_2$, —$N(R_6)_2$, —$S(=O)NH_2$, —$S(=O)_2NH_2$, —$C(=O)OV_1$, and —$C(=O)CN$; and
(b) —$(C_1-C_{10})$alkyl, —$(C_2-C_{10})$alkenyl, —$(C_2-C_{10})$alkynyl, —$O(C_1-C_6)$alkyl, —$(C_3-C_7)$cycloalkoxy, —$(C_5-C_{14})$cycloalkenyl, and -(3- to 7-membered)heterocycle, each of which is unsubstituted or substituted with 1, 2, 3, or 4 independently selected $R_8$ groups; and (c)

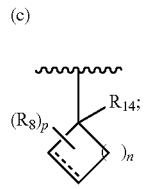

(iv)

and
(d) -phenyl and -(5- to 10-membered)heteroaryl, each of which is unsubstituted or substituted with 1, 2, or 3 independently selected $R_7$ groups;

$R_{14}$ is —H, —CN, —OH, -halo, —$C(=O)OR_9$, or —$C(=O)N(R_6)_2$ or $R_{14}$ can be —$(C_1-C_4)$alkyl which is unsubstituted or substituted with —OH, —$(C_1-C_4)$alkoxy, —$N(R_6)_2$, —$C(=O)OR_9$, or —$C(=O)N(R_6)_2$;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4;

each $T_1$ and $T_2$ is independently —H or —$(C_1-C_{10})$alkyl which is unsubstituted or substituted with 1, 2, or 3 independently selected $R_5$ groups and, optionally, in which any —$(C_1-C_{10})$alkyl carbon atom except the carbon atom bonded directly to the atom to which $T_1$ or $T_2$ is attached is independently replaced by O, S, or $N(R_6)$, or $T_1$ and $T_2$ can together form a 5- to 8-membered ring wherein the number of atoms in the ring includes the nitrogen atom to which $T_1$ and $T_2$ are bonded, said 5- to 8-membered ring is unsubstituted or substituted with 1, 2, or 3 independently selected $R_5$ groups and, optionally, any carbon atom in said 5- to 8-membered ring is independently replaced by O, S, or $N(R_6)$;

each $T_3$ is independently —H or —$(C_1-C_{10})$alkyl which is unsubstituted or substituted with 1, 2, or 3 independently selected $R_5$ groups and, optionally, in which any —$(C_1-C_{10})$alkyl carbon atom except the carbon atom bonded directly to the atom to which $T_3$ is attached is independently replaced by O, S, or $N(R_{12})$;

each $V_1$ is independently —H, —$(C_1-C_6)$alkyl, —$(C_3-C_7)$cycloalkyl, -phenyl, or benzyl; and each halo is independently —F, —Cl, —Br, or —I.

(2) The compound of the above (1) or a pharmaceutically acceptable derivative thereof, provided the $Q_x$ ring is not:

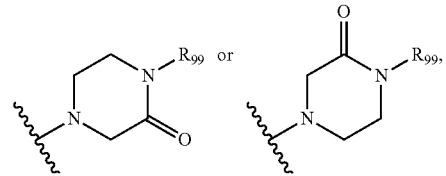

wherein:

$R_{99}$ is —H, —$(C_1-C_3)$alkyl, —$(CH_2)_j$—$C(=O)OH$, or —$(CH_2)_j$—$C(=O)O$—$(C_1-C_3)$alkyl; and j is an integer selected from 0, 1, 2, and 3.

(3) The compound of the above (1) or (2) or a pharmaceutically acceptable derivative thereof, provided the $Q_x$ ring is not:

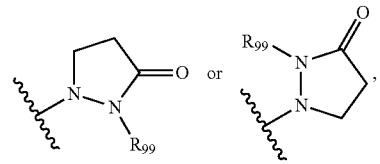

wherein:

$R_{99}$ is —H, —$(C_1-C_3)$alkyl, —$(CH_2)_j$—$C(=O)OH$, or —$(CH_2)_j$—$C(=O)O$—$(C_1-C_3)$alkyl; and j is an integer selected from 0, 1, 2, and 3.

(4) The compound of any one of the above (1) to (3) or a pharmaceutically acceptable derivative thereof, provided the $Q_x$ ring does not contain 3 consecutive ring nitrogen atoms.

(5) The compound of any one of the above (1) to (4) or a pharmaceutically acceptable derivative thereof, wherein $Y_1$ is O.

(6) The compound of any one of the above (1) to (5) or a pharmaceutically acceptable derivative thereof, wherein $R_1$ is selected from:
(a) -halo, —CN, —OH, —$CH_2OH$, —$CH_2CH_2OH$, —$NO_2$, —$N(R_6)_2$, —$S(=O)NH_2$, —$S(=O)_2NH_2$, —$C(=O)OV_1$, and —$C(=O)CN$; and (b) —($C_1$-$C_{10}$)alkyl, —O($C_1$-$C_6$)alkyl, —($C_3$-$C_7$)cycloalkoxy, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R_8$ groups; and (c) -phenyl, -naphthalenyl, —($C_{14}$)aryl, and -(5- to 10-membered)heteroaryl, each of which is unsubstituted or substituted with 1, 2, or 3 independently selected $R_7$ groups.

(7) The compound of any one of the above (1) to (6) or a pharmaceutically acceptable derivative thereof, wherein $Q_a$ is benzo, pyridino, pyrimidino, pyrazino, or pyridazino, and preferably $Q_a$ is benzo or pyridino, wherein preferably the 2- and 3-positions of the pyridino are fused to the 6-membered, nitrogen-containing ring.

(8) The compound of any one of the above (1) to (7) or a pharmaceutically acceptable derivative thereof, wherein $Q_a$ is benzo.

(9) The compound of any one of the above (1) to (8) or a pharmaceutically acceptable derivative thereof, wherein a is 0.

(10) The compound of any one of the above (1) to (9) or a pharmaceutically acceptable derivative thereof, wherein:
$Q_a$ is benzo;
a is 0;
A-B together form a ($C_2$-$C_6$)bridge, which is unsubstituted or substituted with 1, 2, 3, 4, 5, 6, 7 or 8 substituents independently selected from —OH, —($C_1$-$C_4$)alkyl, -halo, and —C(halo)$_3$, and which bridge optionally contains —HC=CH— or —O— within the ($C_2$-$C_6$)bridge; wherein the A-B bridge can be in the endo- or exo-configuration with respect to the 6-membered, nitrogen-containing ring that is fused to the $Q_a$ ring;
Z is —[($C_1$-$C_{10}$)alkyl]$_h$—, wherein h is 0 or 1; and
$R_1$ is selected from:
(a) —CN, —OH, —CH$_2$OH, —CH$_2$CH$_2$OH, —NO$_2$, —N($R_6$)$_2$, —S(=O)NH$_2$, —S(=O)$_2$NH$_2$, —C(=O)OV$_1$, and —C(=O)CN; and (b) —($C_1$-$C_{10}$)alkyl, —O($C_1$-$C_6$)alkyl, —($C_3$-$C_7$)cycloalkoxy, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R_8$ groups; and (c)

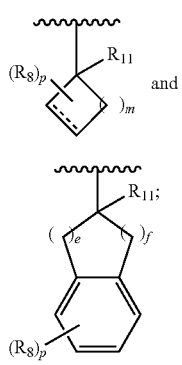

and (d) -phenyl and -(5- to 10-membered)heteroaryl, each of which is unsubstituted or substituted with 1, 2, or 3 independently selected $R_7$ groups.

(11) The compound of any one of the above (1) to (10) or a pharmaceutically acceptable derivative thereof, wherein --E---G---J-- of the $Q_x$ ring is —N—C(=O)—N($R_{90}$)— or —N—C(=O)—N=.

(12) The compound of any one of the above (1) to (11) or a pharmaceutically acceptable derivative thereof, wherein the $Q_x$ ring is:

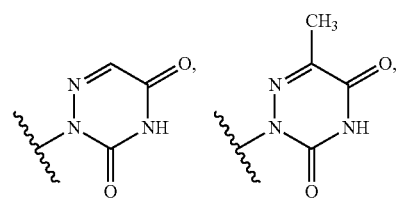

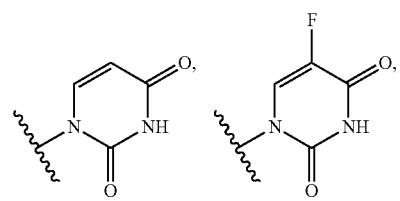

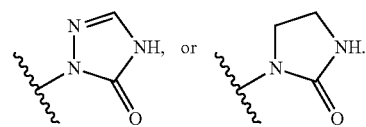

(13) The compound of any one of the above (1) to (12) or a pharmaceutically acceptable derivative thereof, wherein the Q$_x$ ring is:
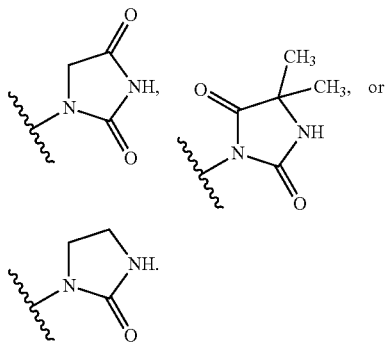
(14) The compound of any one of the above (1) to (12) or a pharmaceutically acceptable derivative thereof, wherein the Q$_x$ ring is:
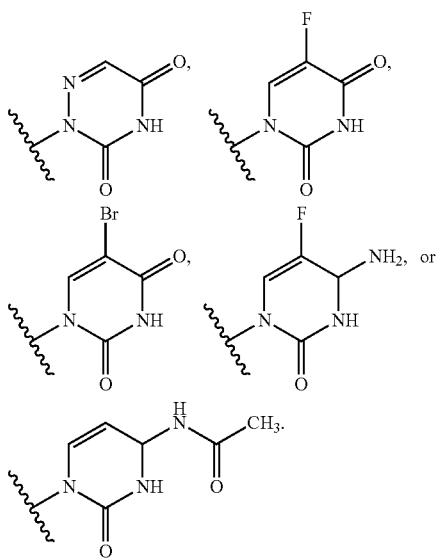
(15) The compound of any one of the above (1) to (12), which is:
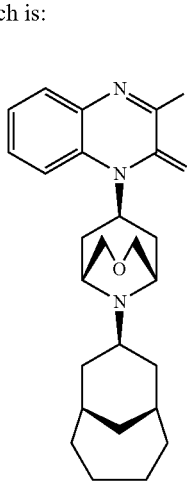
-continued
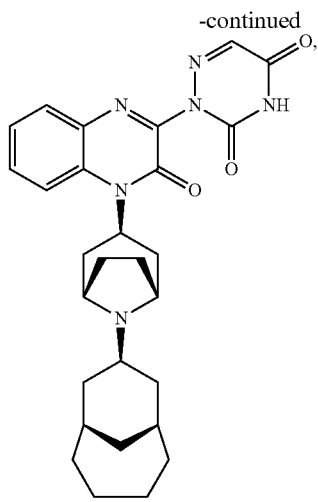
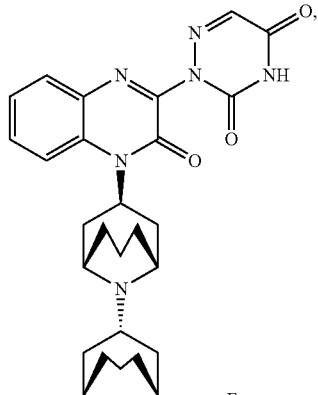
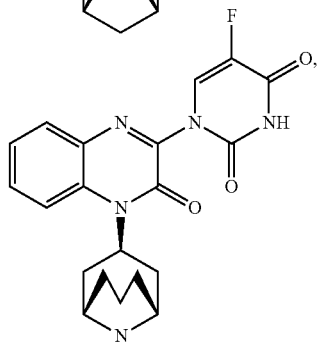
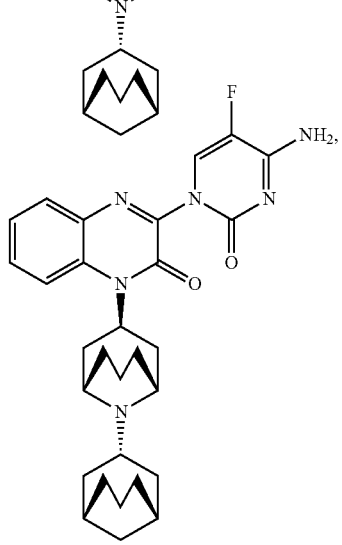

-continued
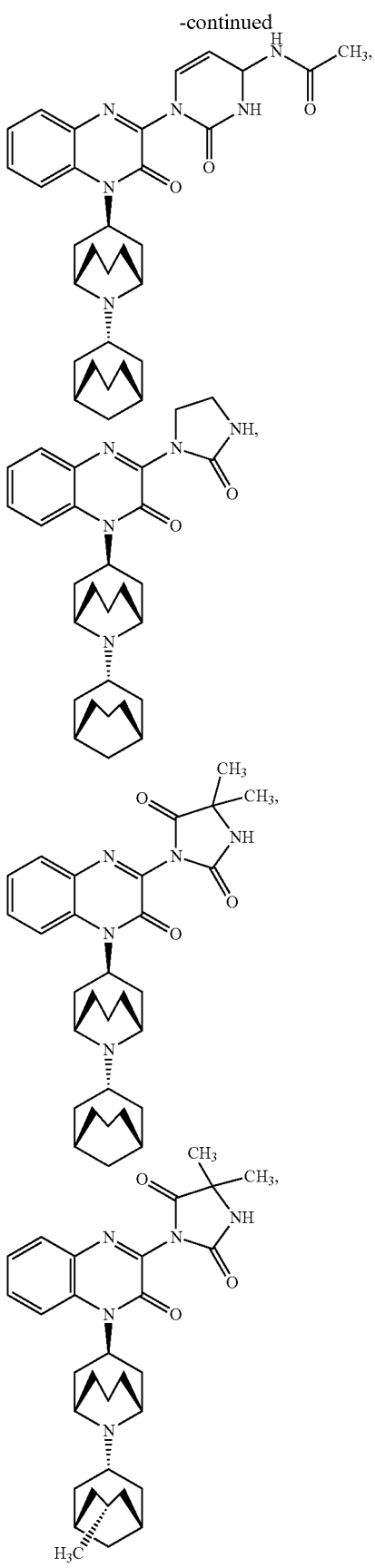
or a pharmaceutically acceptable derivative thereof.
(16) The compound of any one of the above (1) to (12) or (14), which is:
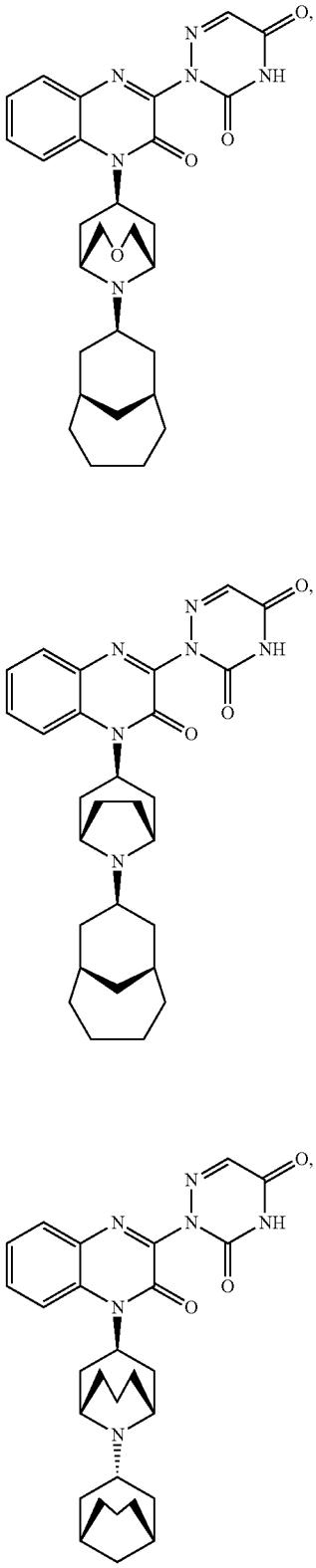

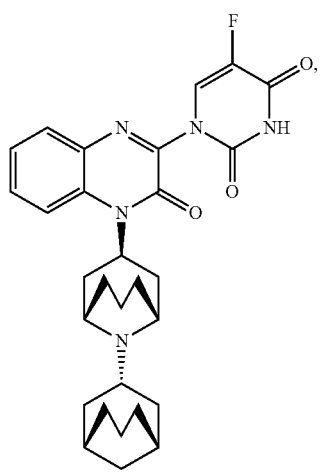

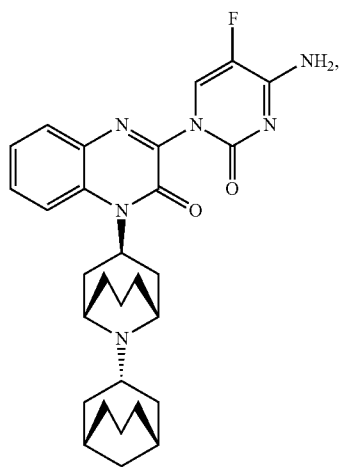

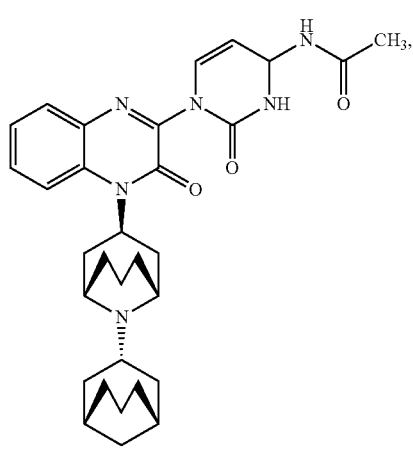

or a pharmaceutically acceptable derivative thereof.

(17) The compound of any one of the above (1) to (10) or a pharmaceutically acceptable derivative thereof, wherein E of the $Q_x$ ring is $C(R_{90})$.

(18) The compound of any one of the above (1) to (10) or (17) or a pharmaceutically acceptable derivative thereof, wherein the $Q_x$ ring is:

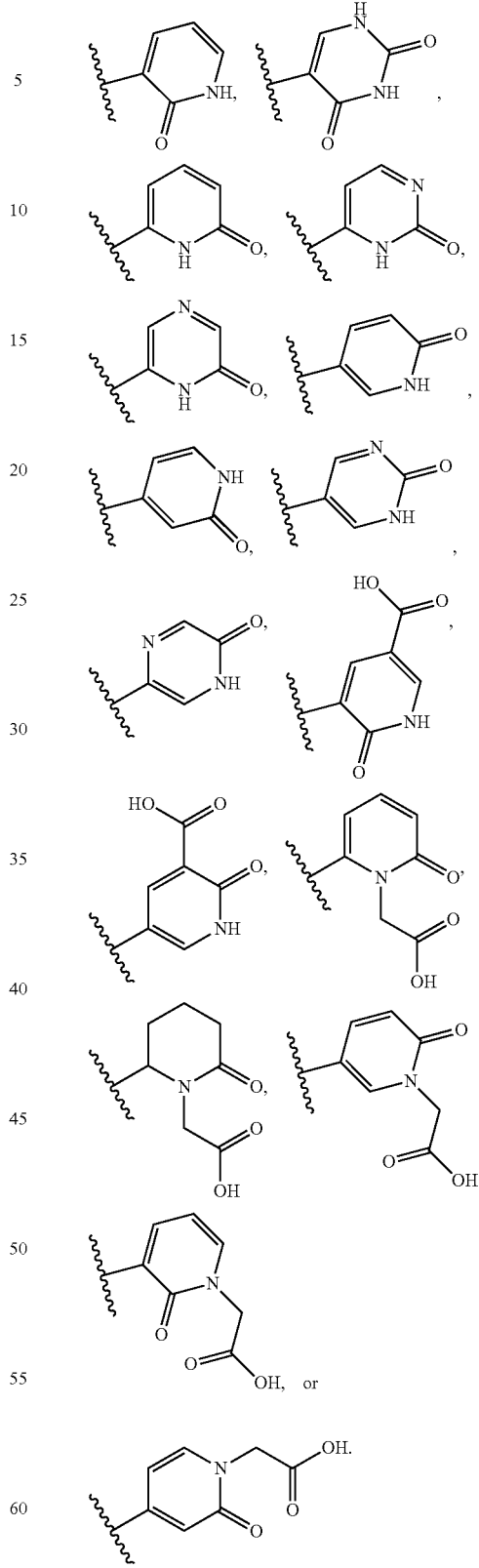

(19) The compound of any one of the above (1) to (10), (17), or (18) or a pharmaceutically acceptable derivative thereof, wherein the $Q_x$ ring is:

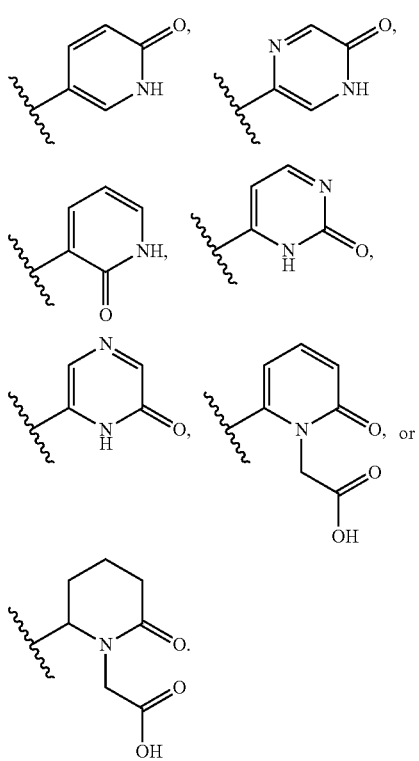
(20) The compound of any one of the above (1) to (10) or (17) to (19), which is:
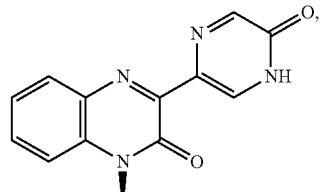
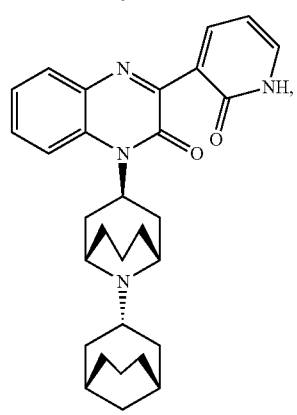
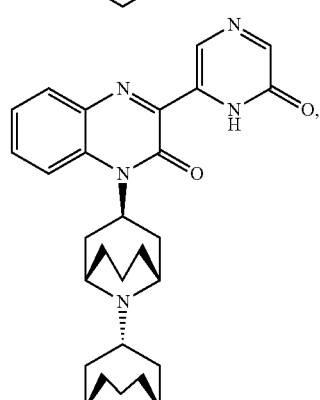
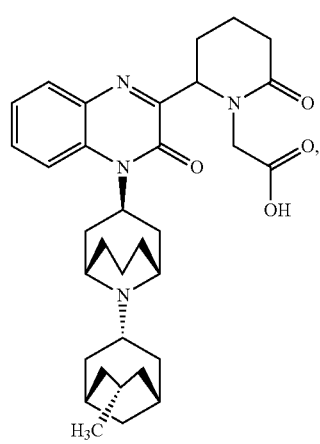

-continued

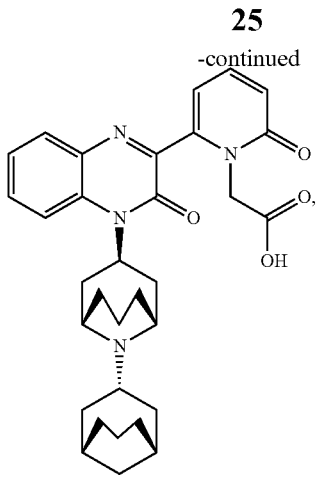

or a pharmaceutically acceptable derivative thereof.

(21) The compound of any one of the above (1) to (10) or (17) or a pharmaceutically acceptable derivative thereof, wherein in the $C(R_{90})$ of the E of the $Q_x$ ring, $R_{90}$ is absent.

(22) The compound of any one of the above (1) to (10), (17) to (19), or (21) or a pharmaceutically acceptable derivative thereof, wherein the $Q_x$ ring is:

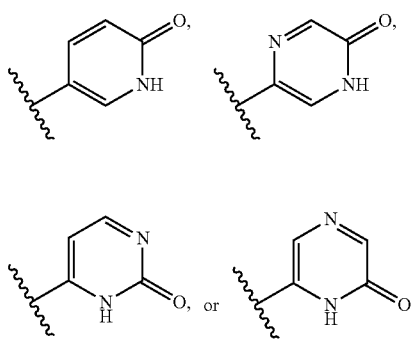 [SMILES: *c1ccc(=O)[nH]c1 ; *c1c[nH]c(=O)cn1 ; *c1ccnc(=O)[nH]1 ; *c1cncc(=O)[nH]1]

(23) The compound of any one of the above (1) to (10) or (17) to (22), which is:

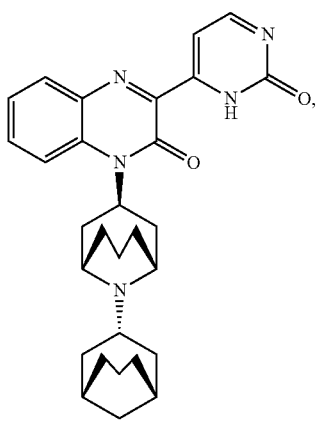

-continued

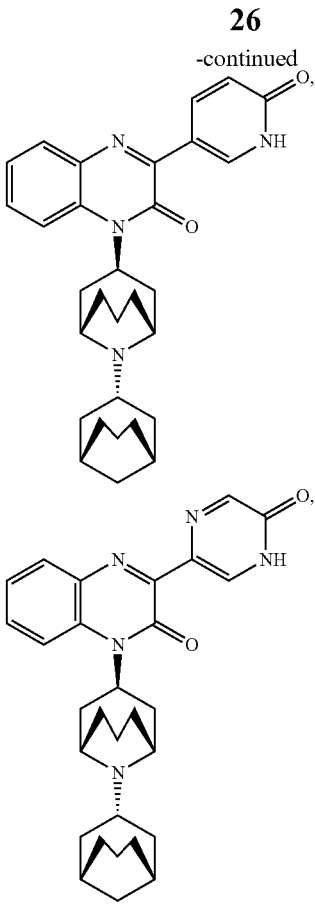

or a pharmaceutically acceptable derivative thereof.

(24) The compound of any one of the above (1) to (14), (17) to (19), (21), or (22) or a pharmaceutically acceptable derivative thereof, wherein h is 1.

(25) The compound of any one of the above (1) to (9), (11) to (14), (17) to (19), (21), (22), or (24) or a pharmaceutically acceptable derivative thereof, wherein Z is —($C_1$-$C_3$)alkyl- optionally substituted by $R_{13}$.

(26) The compound of any one of the above (1) to (25) or a pharmaceutically acceptable derivative thereof; wherein $R_{13}$ is absent.

(27) The compound of any one of the above (1) to (14), (17) to (19), (21), (22), or (24) to (26) or a pharmaceutically acceptable derivative thereof, wherein $R_{13}$ is absent and Z is —$CH_2$—$CH_2$—.

(28) The compound of any one of the above (1) to (14), (17) to (19), (21), (22), or (24) to (27) or a pharmaceutically acceptable derivative thereof, wherein —Z—$R_1$ is:

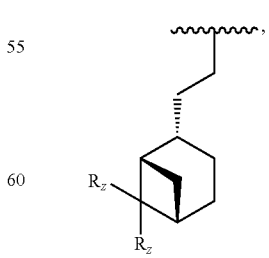

wherein each $R_z$ is independently —H, —($C_1$-$C_4$)alkyl, —OH, or —CN and preferably each $R_z$ is independently —H, —$CH_3$, or —$CH_2CH_3$.

(29) The compound of any one of the above (1) to (23) or a pharmaceutically acceptable derivative thereof; wherein h is 0.

(30) The compound of any one of the above (1) to (14), (17) to (19), (21), (22), or (24) to (29) or a pharmaceutically acceptable derivative thereof; wherein A and B are independently —H or —($C_1$-$C_6$)alkyl and preferably A and B are each —H or A is —H and B is —$CH_3$ or A is —$CH_3$ and B is —H.

(31) The compound of any one of the above (1) to (29) or a pharmaceutically acceptable derivative thereof; wherein A and B together form a bridge such that the bridged-piperidine is:

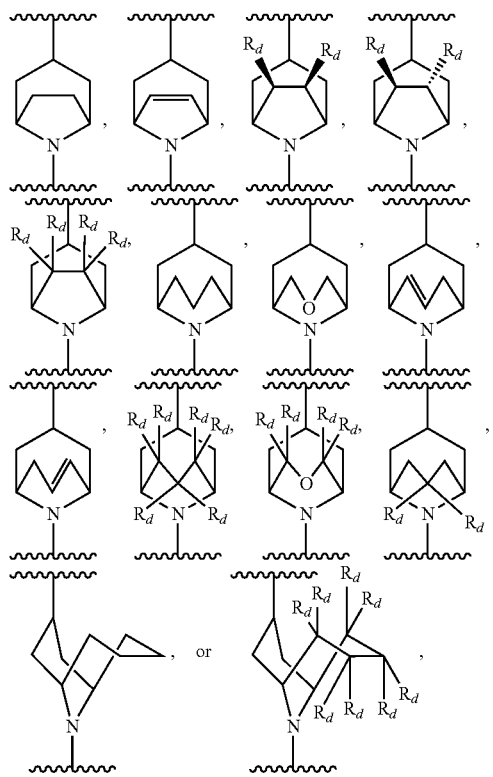

wherein each $R_d$ is independently —H, —($C_1$-$C_4$)alkyl, -halo, or —C(halo)$_3$.

(32) The compound of any one of the above (1) to (29) or (31) or a pharmaceutically acceptable derivative thereof, wherein A and B together form a bridge such that the bridged-piperidine is:

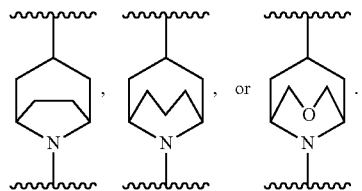

(33) The compound of any one of the above (1) to (29), (31), or (32) or a pharmaceutically acceptable derivative thereof, wherein A and B together form a bridge such that the bridged-piperidine is:

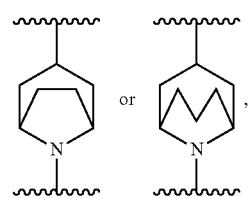 [SMILES: *C1CC2CCC(C1)N2* ; *C1CC2CCCC(C1)N2*]

(34) The compound of any one of the above (1) to (29) or (31) to (330) or a pharmaceutically acceptable derivative thereof, wherein the A-B bridge of the bridged-piperidine is in the endo-configuration with respect to the 6-membered, nitrogen-containing ring that is fused to the $Q_a$ ring.

(35) The compound of any one of the above (1) to (23) or (29) to (34) or a pharmaceutically acceptable derivative thereof, wherein:

(a) h is 0;

(b) $R_1$ is —($C_1$-$C_{10}$)alkyl, —($C_3$-$C_{14}$)cycloalkyl, —($C_5$-$C_{14}$)cycloalkenyl, —($C_6$-$C_{14}$)bicycloalkyl, —($C_7$-$C_{14}$)bicycloalkenyl, or —($C_8$-$C_{20}$)tricycloalkyl, each of which is unsubstituted or substituted with 1, 2, 3, or 4 independently selected $R_8$ groups and preferably $R_1$ is —($C_3$-$C_{14}$)cycloalkyl, —($C_5$-$C_{14}$)cycloalkenyl, —($C_6$-$C_{14}$)bicycloalkyl, —($C_7$-$C_{14}$)bicycloalkenyl, or —($C_8$-$C_{20}$)tricycloalkyl, each of which is unsubstituted or substituted with 1, 2, 3, or 4 independently selected $R_8$ groups; and (c) each $R_8$ is independently —($C_1$-$C_4$)alkyl, —($C_1$-$C_6$)alkyl-C(=O)O$R_9$, —N($R_9$)($C_1$-$C_6$)alkyl-C(=O)O$R_9$, —O$R_9$, —C(halo)$_3$, —CH(halo)$_2$, —CH$_2$(halo), -halo, —N($R_9$)$_2$, —C(=O)N($T_1$)($T_2$), or —C(=O)O$R_9$.

(36) The compound of any one of the above (1) to (23) or (29) to (35) or a pharmaceutically acceptable derivative thereof, wherein —Z—$R_1$ is:

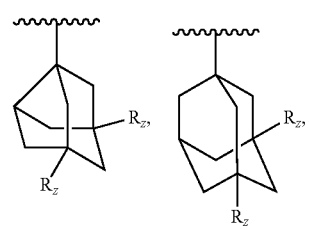

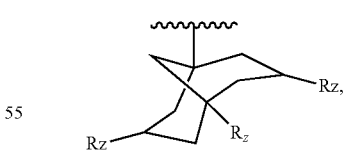

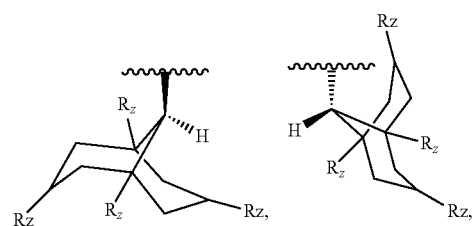

-continued

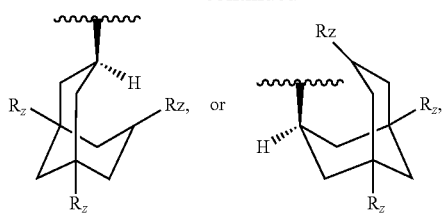

wherein each $R_z$ is independently —($C_1$-$C_4$)alkyl, —OH, or —CN and preferably each R is independently —H, —$CH_3$, or —$CH_2CH_3$.

(37) The compound of any one of the above (1) to (23) or (29) to (35) or a pharmaceutically acceptable derivative thereof, wherein —Z—$R_1$ is:

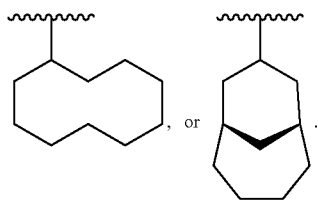 [SMILES: *C1CCCCCCCCC1 ; *C1C[C@H]2CCCC[C@@H](C1)C2]

(38) The compound of any one of the above (1) to (23) or (29) to (36) or a pharmaceutically acceptable derivative thereof, wherein —Z—$R_1$ is:

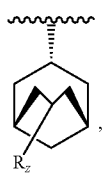

wherein $R_z$ is —H, —$CH_3$, or —$CH_2CH_3$.

(39) The compound of any one of the above (1) to (8), (11) to (14), (17) to (19), (21), (22), or (24) to (38) or a pharmaceutically acceptable derivative thereof, wherein a is 1 and $R_2$ is -halo, preferably $R_2$ is —F.

(40) The compound of any one of the above (1) to (23), (29), or (31) to (39) or a pharmaceutically acceptable derivative thereof, wherein the $R_1$ group is in the exo-configuration with respect to the A-B bridge of the bridged piperidine.

(41) The compound of any one of the above (1) to (11), (31), (32), or (34) or a pharmaceutically acceptable derivative thereof, wherein the compound is:

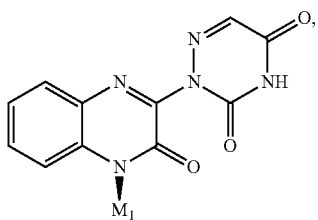

-continued

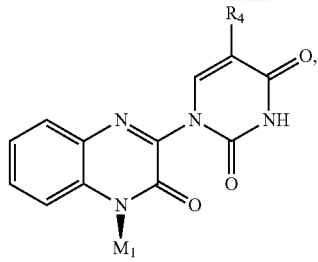

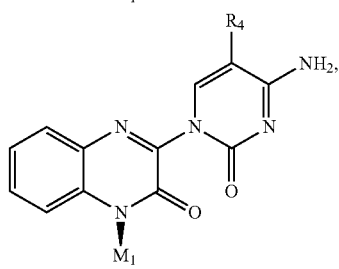

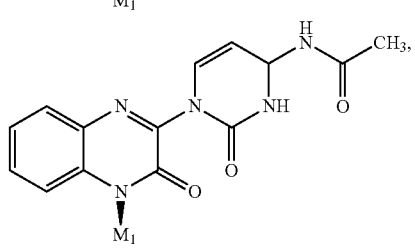

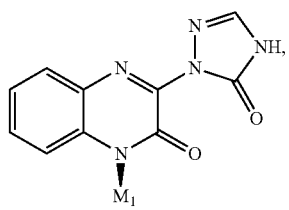

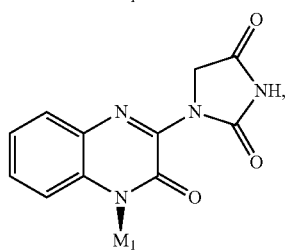

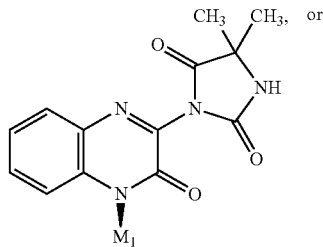

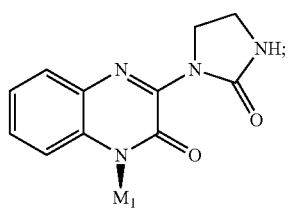

wherein $R_4$ is H or halo;
$M_1$ is:
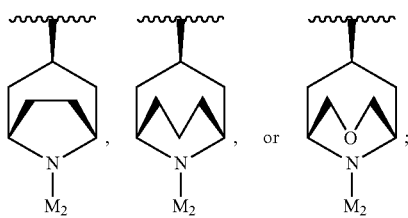
and $M_2$ is:
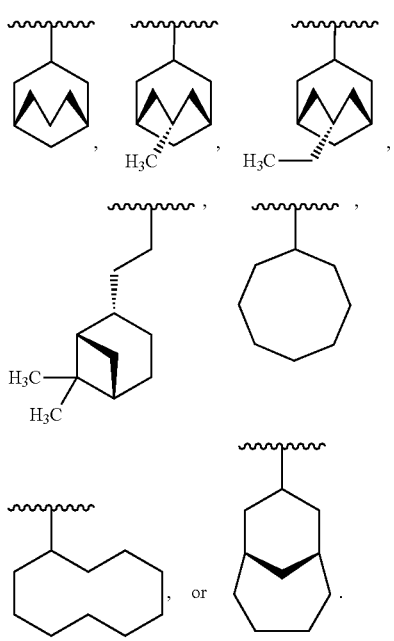
(42) The compound of any one of the above (1) to (11), (31), (32), (34), or (41) or a pharmaceutically acceptable derivative thereof, wherein the compound is:
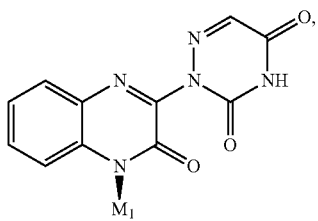
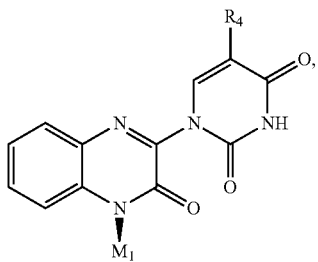
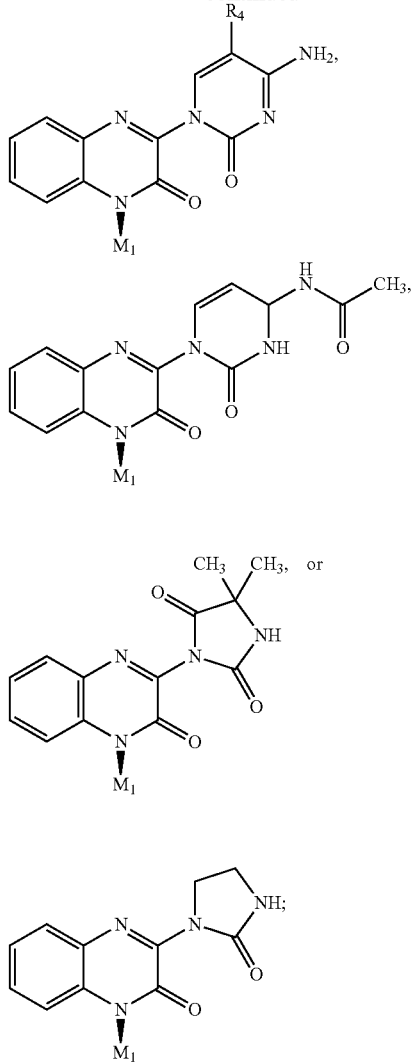
and wherein $M_2$ is:
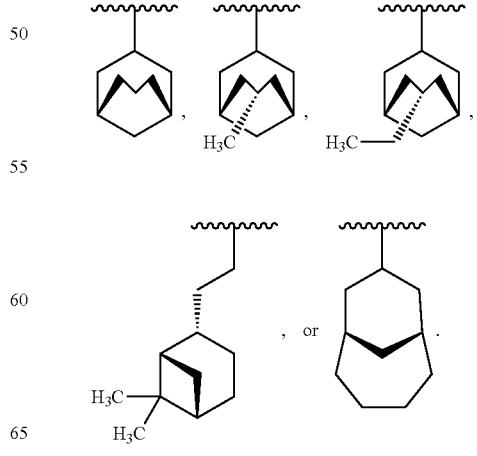

(43) The compound of any one of the above (1) to (12), (26), (29), (31), or (32), which is:
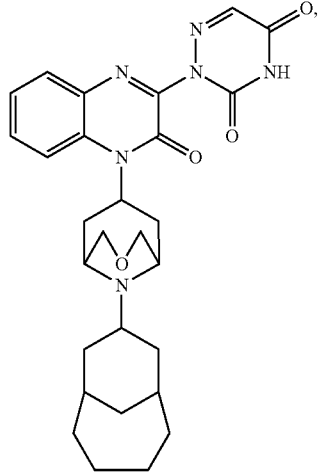
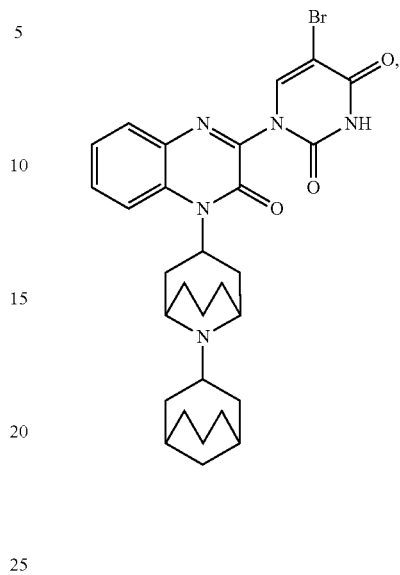
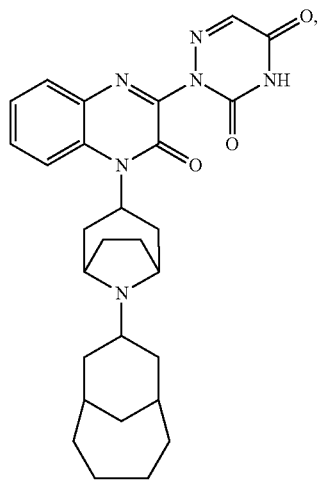
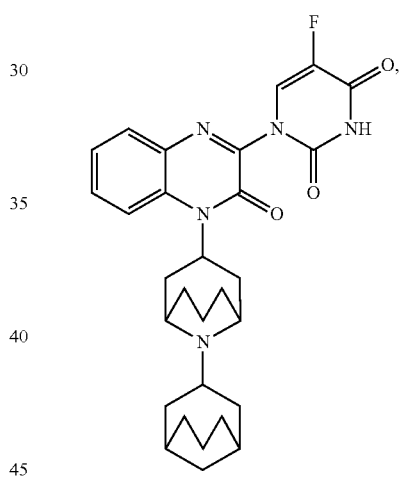
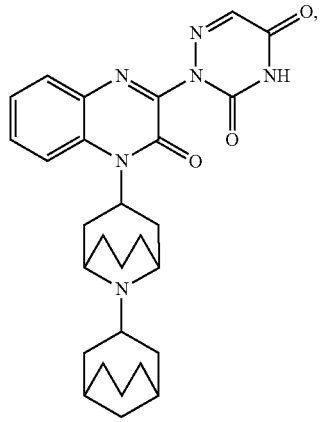
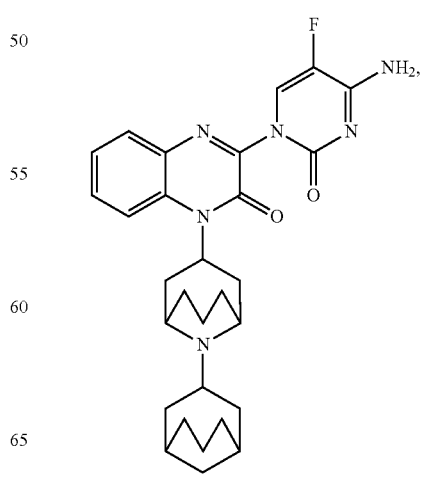

-continued
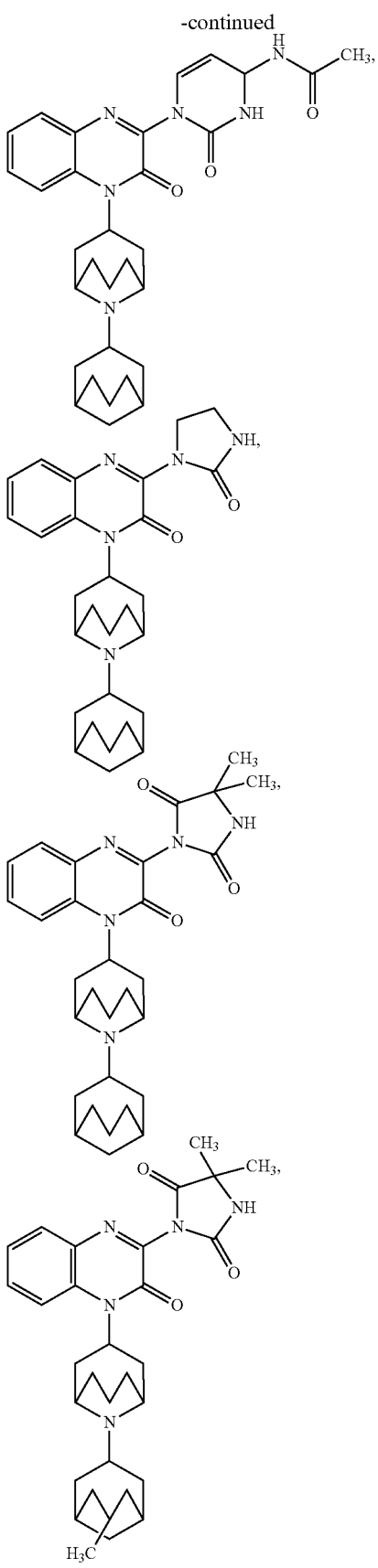
or a pharmaceutically acceptable salt thereof
(44) The compound of any one of the above (1) to (12), (26), (29), (31), (32), (34), or (41) to (40), which is:
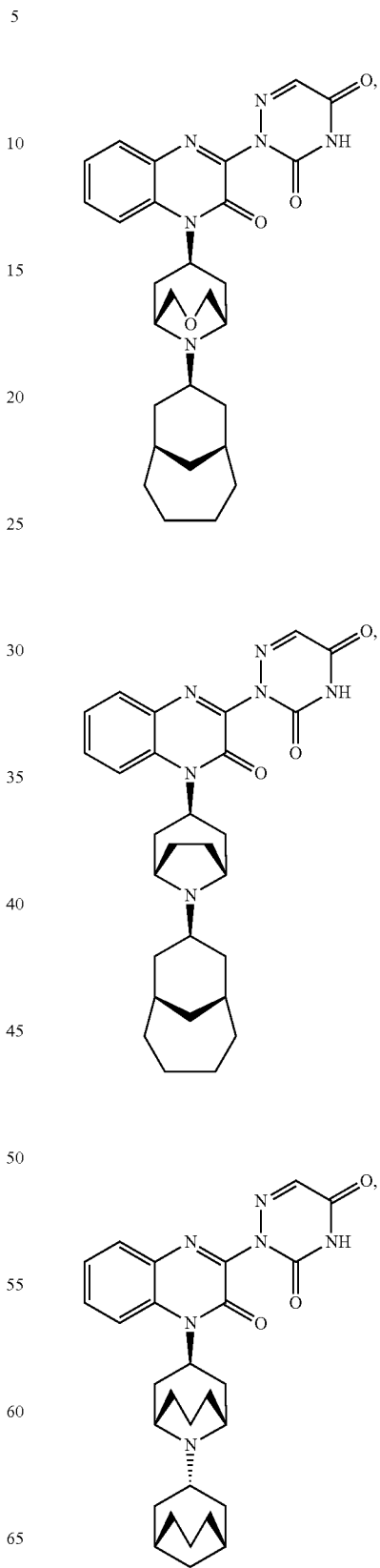

37
-continued
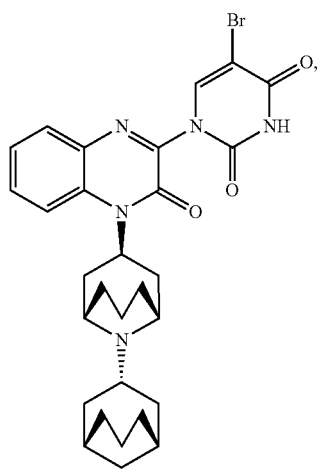
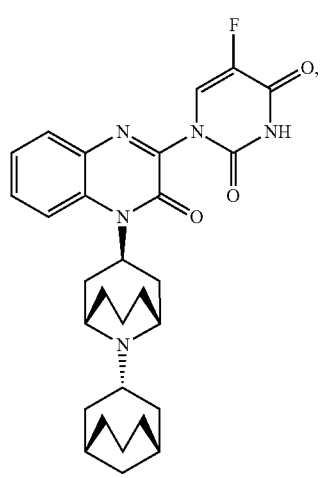
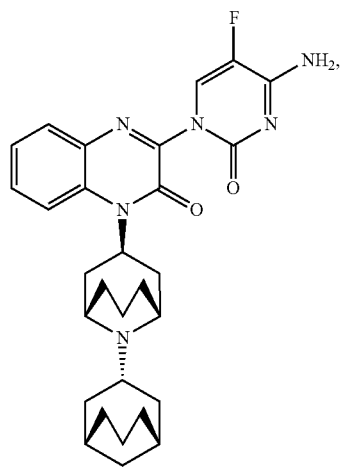
38
-continued
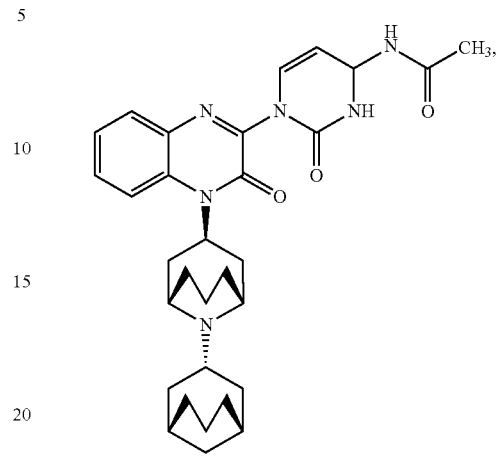
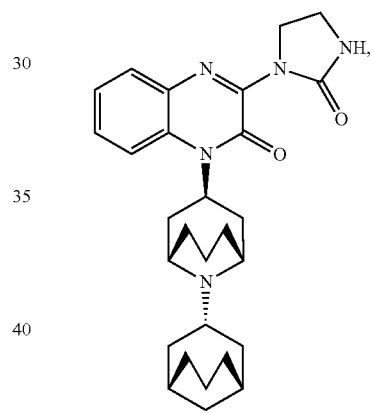
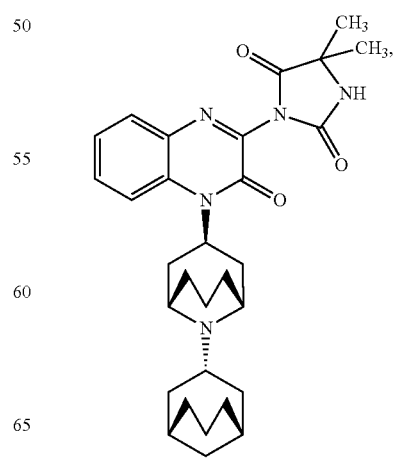

-continued

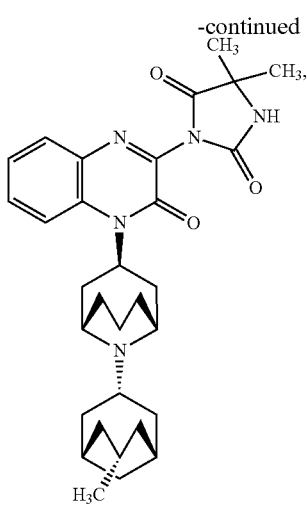

or a pharmaceutically acceptable salt thereof.

(45) The compound of the above (44) having the formula:

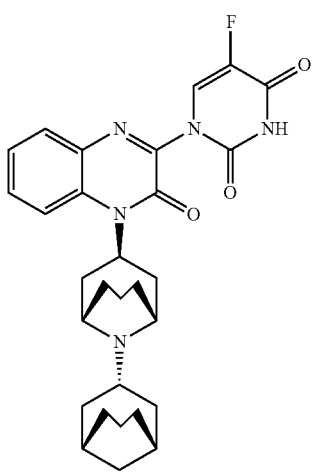 [SMILES: O=c1[nH]c(=O)n(-c2nc3ccccc3n([C@H]3C[C@H]4CCC[C@@H](C3)N4[C@H]3C[C@@H]4CCC[C@@H](C4)C3)c2=O)cc1F]

or a pharmaceutically acceptable salt thereof.

(46) The compound of the above (44) having the formula:

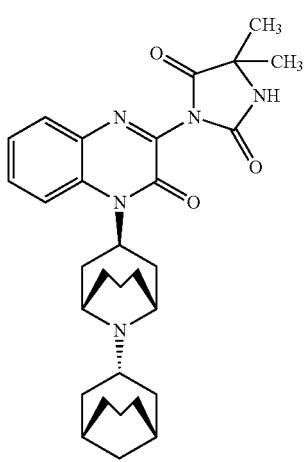 [SMILES: CC1(C)NC(=O)N(c2nc3ccccc3n([C@H]3C[C@H]4CCC[C@@H](C3)N4[C@H]3C[C@@H]4CCC[C@@H](C4)C3)c2=O)C1=O]

or a pharmaceutically acceptable salt thereof.

(47) The compound of the above (44) having the formula:

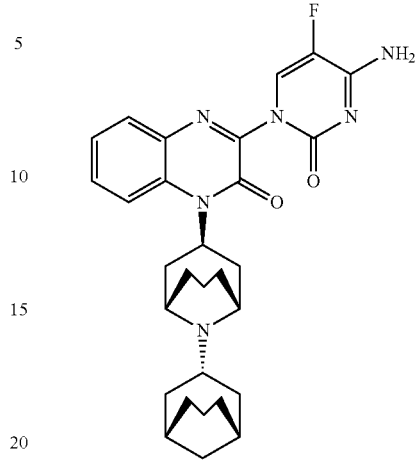

or a pharmaceutically acceptable salt thereof.

(48) The compound of the above (44) having the formula:

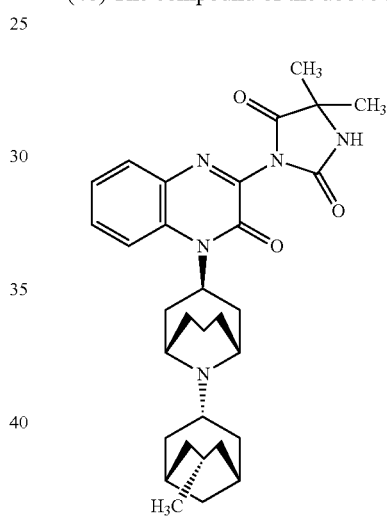

or a pharmaceutically acceptable salt thereof.

(49) The compound of the above (44) having the formula:

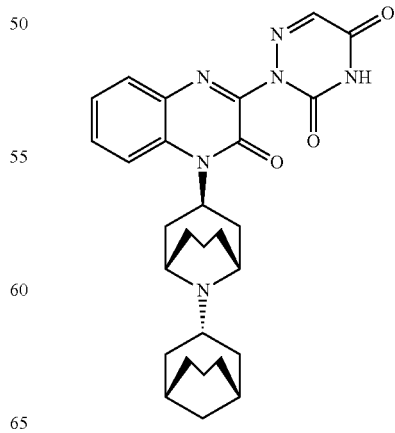

or a pharmaceutically acceptable salt thereof.

(50) The compound of the above (44) having the formula:
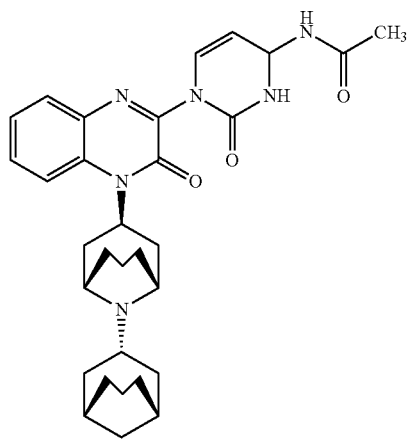 [SMILES: CC(=O)NC1C=CN(c2nc3ccccc3n([C@H]3C[C@H]4CCC[C@@H](C3)N4[C@H]3C[C@@H]4CCC[C@@H](C4)C3)c2=O)C(=O)N1]
or a pharmaceutically acceptable salt thereof.
(51) The compound of the above (44) having the formula:
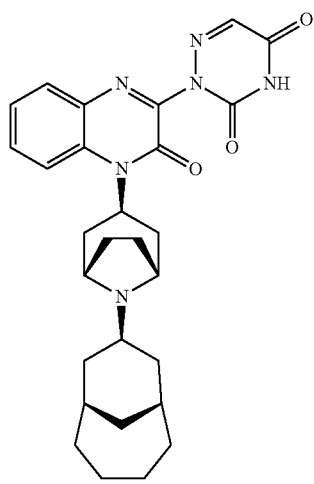 [SMILES: O=c1cnn(-c2nc3ccccc3n([C@H]3C[C@H]4CC[C@@H](C3)N4[C@@H]3C[C@@H]4CCCC[C@@H](C4)C3)c2=O)c(=O)[nH]1]
or a pharmaceutically acceptable salt thereof.
(52) The compound of the above (44) having the formula:
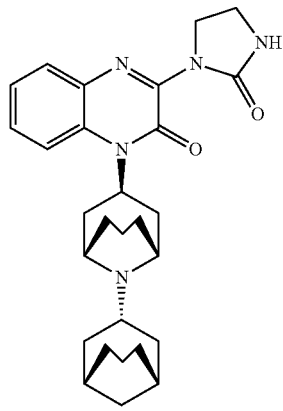 [SMILES: O=C1NCCN1c1nc2ccccc2n([C@H]2C[C@H]3CCC[C@@H](C2)N3[C@H]2C[C@@H]3CCC[C@@H](C3)C2)c1=O]
or a pharmaceutically acceptable salt thereof.
(53) The compound of any one of the above (1) to (10), (17) to (19), (26), (29), (31) to (33), (36), or (38), which is:
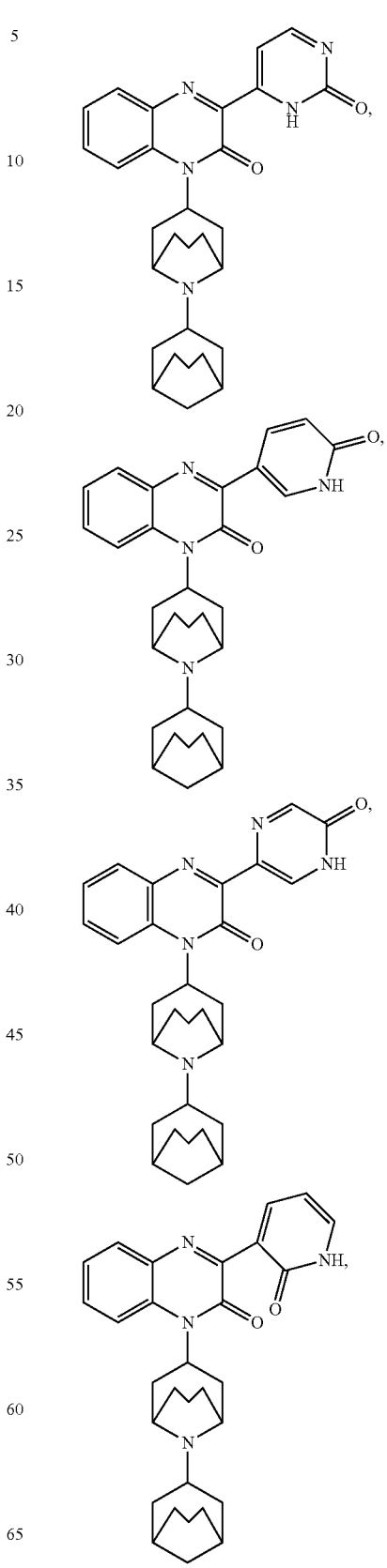

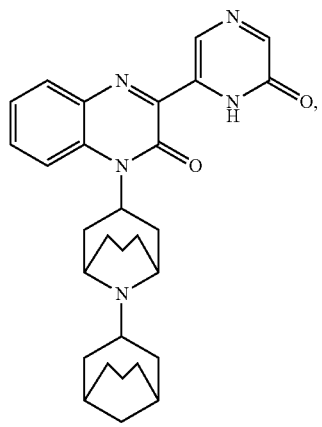
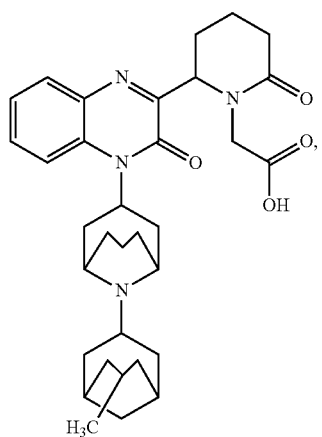
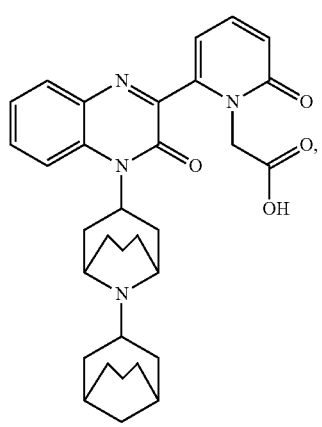
or a pharmaceutically acceptable salt thereof.
(54) The compound of any one of the above (1) to (10), (17) to (19), (26), (29), (31) to (34), (36), (38), (40), or (53), which is:
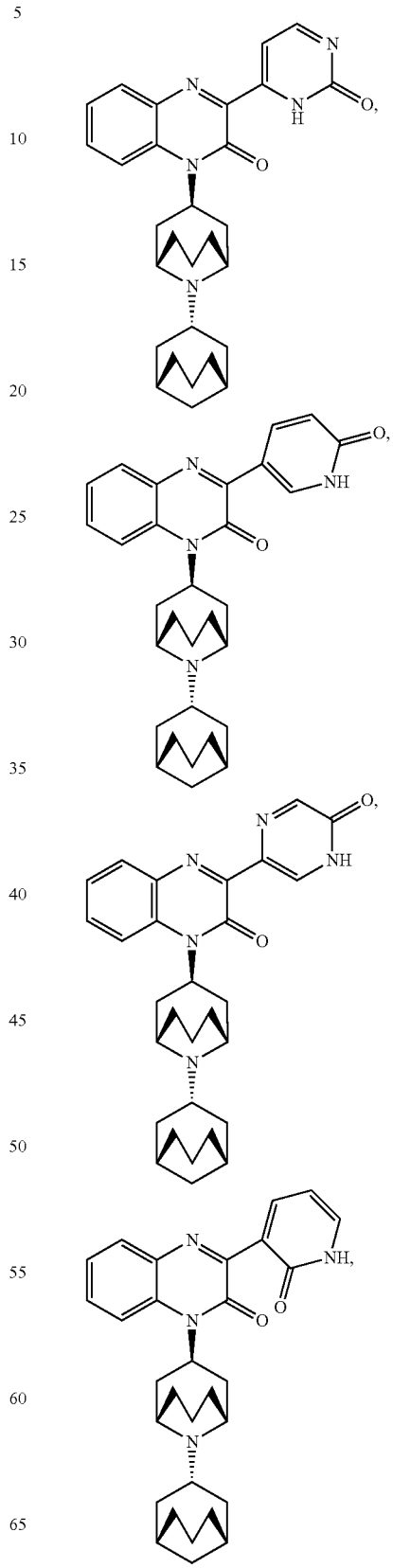

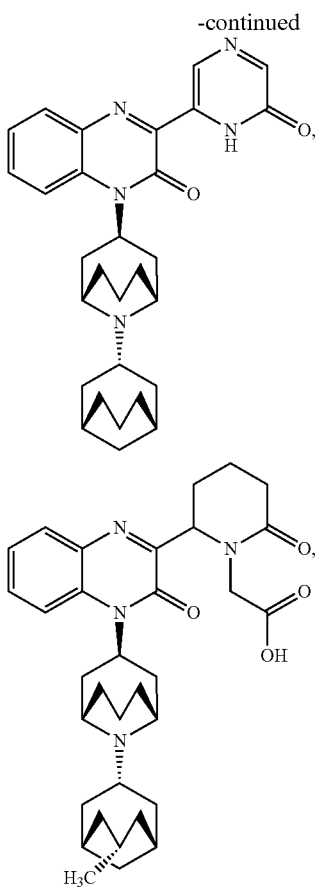

or a pharmaceutically acceptable salt thereof.

(55) The compound of any one of the above (1) to (54) or a pharmaceutically acceptable derivative thereof, which is radiolabeled.

(56) The compound of any one of the above (1) to (55) or a pharmaceutically acceptable derivative thereof, wherein the % de of the compound is at least about 95%.

(57) The compound of the above (56) or a pharmaceutically acceptable derivative thereof, wherein the % de of the compound is at least about 99%.

(58) The compound of any one of the above (1) to (57), wherein the pharmaceutically acceptable derivative is a pharmaceutically acceptable salt, preferably a hydrochloride-salt, a sodium-salt, a potassium-salt, or a para-toluenesulfonic acid-salt.

(59) A composition comprising an effective amount of the compound or a pharmaceutically acceptable derivative of the compound of any one of the above (1) to (58) and a pharmaceutically acceptable carrier or excipient.

(60) A method for preparing a composition, comprising the step of admixing a compound or a pharmaceutically acceptable derivative of the compound of any one of the above (1) to (58) and a pharmaceutically acceptable carrier or excipient.

(61) A method for modulating ORL-1 receptor function in a cell, comprising contacting a cell capable of expressing the ORL-1 receptor with an effective amount of the composition or the compound or a pharmaceutically acceptable derivative of the compound of any one of the above (1) to (59).

(62) The method of the above (61), wherein the composition or the compound or the pharmaceutically acceptable derivative of the compound acts as an agonist at the ORL-1 receptor.

(63) The method of the above (61), wherein the composition or the compound or the pharmaceutically acceptable derivative of the compound acts as a partial agonist at the ORL-1 receptor.

(64) The method of the above (61), wherein the composition or the compound or the pharmaceutically acceptable derivative of the compound acts as an antagonist at the ORL-1 receptor.

(65) A method for treating pain in an animal, comprising administering to an animal in need thereof an effective amount of the composition or the compound or a pharmaceutically acceptable derivative of the compound of any one of the above (1) to (59).

(66) A method for treating a memory disorder, obesity, constipation, depression, dementia, Parkinsonism, anxiety, cough, diarrhea, high blood pressure, epilepsy, anorexia/cachexia, urinary incontinence, or drug abuse in an animal, comprising administering to an animal in need thereof an effective amount of the composition or the compound or a pharmaceutically acceptable derivative of the compound of any one of the above (1) to (59).

(67) Use of a compound or the pharmaceutically acceptable derivative of the compound of any one of the above (1) to (58) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, or drug abuse.

(68) The compound or the pharmaceutically acceptable derivative of the compound of any one of the above (1) to (58) for use in the treatment of pain, a memory disorder, obesity, constipation, depression, dementia, Parkinsonism, anxiety, cough, diarrhea, high blood pressure, epilepsy, anorexia/cachexia, urinary incontinence, or drug abuse.

(69) A kit, comprising a container containing an effective amount of the composition or the compound or a pharmaceutically acceptable derivative of the compound of any one of the above (1) to (59).

4.1 Cyclic Urea- or Lactam-Substituted Quinoxaline-Type Piperidine Compounds of Formula (I)

As stated above, the disclosure encompasses Cyclic Urea- or Lactam-Substituted Quinoxaline-Type Piperidine Compounds of Formula (I):

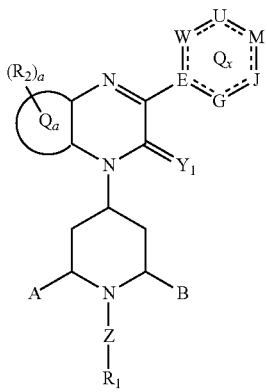

(I)

or a pharmaceutically acceptable derivative thereof where $R_1$, $R_2$, $Q_a$, $Y_1$, Z, A, B, $Q_x$, E, G, J, M, U, W, and a are defined above for the Cyclic Urea- or Lactam-Substituted Quinoxaline-Type Piperidine Compounds.

In one embodiment, $Y_1$ is O. In another embodiment, $Y_1$ is S.

In another embodiment, a is 0 or 1. In another embodiment, a is 0. In another embodiment, a is 1. In another embodiment, a is 2.

In another embodiment, each $R_2$ is independently -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl, or -(5- or 6-membered)heteroaryl.

In another embodiment, a is 1 and $R_2$ is -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl, or -(5- or 6-membered)heteroaryl. In another embodiment, a is 1 and $R_2$ is -halo, —OH, —$NH_2$, —CN, methyl, ethyl, n-propyl, iso-propyl, cyclopentyl, cyclohexyl, cycloheptyl, or phenyl. In another embodiment, a is 1 and $R_2$ is -halo. In another embodiment, a is 1 and $R_2$ is —F or —Cl. In another embodiment, a is 1 and $R_2$ is —F. In another embodiment, a is 1 and $R_2$ is —Cl.

In another embodiment, a is 2 and each $R_2$ is independently -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl, or -(5- or 6-membered)heteroaryl. In another embodiment, a is 2 and each $R_2$ is independently -halo, —OH, —$NH_2$, —CN, methyl, ethyl, n-propyl, iso-propyl, cyclopentyl, cyclohexyl, cycloheptyl, or phenyl. In another embodiment, a is 2 and each $R_2$ is -halo. In another embodiment, a is 2 and each $R_2$ is —F or —Cl. In another embodiment, a is 2 and each $R_2$ is —F. In another embodiment, a is 2 and each $R_2$ is —Cl.

In another embodiment, $Q_a$ is benzo, pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino. In another embodiment, $Q_a$ is benzo, pyrrolino, imidazolino, pyrazolino, triazolino, furano, oxazolino, isoxazolino, oxadiazolino, thiopheno, thiazolino, isothiazolino, or thiadiazolino. In another embodiment, $Q_a$ is benzo, imidazolino, pyrazolino, triazolino, oxazolino, isoxazolino, oxadiazolino, thiazolino, isothiazolino, or thiadiazolino. In another embodiment, $Q_a$ is benzo, pyrrolino, imidazolino, pyrazolino, or triazolino. In another embodiment, $Q_a$ is benzo, furano, oxazolino, isoxazolino, or oxadiazolino. In another embodiment, $Q_a$ is benzo, oxazolino, isoxazolino, or oxadiazolino. In another embodiment, $Q_a$ is benzo, thiopheno, thiazolino, isothiazolino, or thiadiazolino. In another embodiment, $Q_a$ is benzo, thiazolino, isothiazolino, or thiadiazolino. In another embodiment, $Q_a$ is benzo, pyrrolino, furano, or thiopheno. In another embodiment, $Q_a$ is pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino. In another embodiment, $Q_a$ is pyrrolino, imidazolino, pyrazolino, triazolino, furano, oxazolino, isoxazolino, oxadiazolino, thiopheno, thiazolino, isothiazolino, or thiadiazolino. In another embodiment, $Q_a$ is imidazolino, pyrazolino, triazolino, oxazolino, isoxazolino, oxadiazolino, thiazolino, isothiazolino, or thiadiazolino. In another embodiment, $Q_a$ is pyrrolino, imidazolino, pyrazolino, or triazolino. In another embodiment, $Q_a$ is furano, oxazolino, isoxazolino, or oxadiazolino. In another embodiment, $Q_a$ is oxazolino, isoxazolino, or oxadiazolino. In another embodiment, $Q_a$ is thiopheno, thiazolino, isothiazolino, or thiadiazolino. In another embodiment, $Q_a$ is thiazolino, isothiazolino, or thiadiazolino. In another embodiment, $Q_a$ is pyrrolino, furano, or thiopheno. In another embodiment, $Q_a$ is benzo, pyridino, pyrimidine, pyrazino, or pyridazino. In another embodiment, $Q_a$ is benzo, pyrimidino, pyrazino, or pyridazino. In another embodiment, $Q_a$ is pyridino, pyrimidino, pyrazino, or pyridazino. In another embodiment, $Q_a$ is pyrimidino, pyrazino, or pyridazino. In another embodiment, $Q_a$ is benzo or pyridino. In another embodiment, $Q_a$ is benzo. In another embodiment, $Q_a$ is pyridino.

In another embodiment, each $R_{90}$, when present, is, independently, —H, —CN, -halo, —($C_1$-$C_3$)alkyl, or —N($R_{92}$)($R_{93}$). In another embodiment, each $R_{90}$, when present, is, independently, —H, —CN, -halo, —$CH_3$, —$CH_2CH_3$, or —N($R_{92}$)($R_{93}$). In another embodiment, each $R_{91}$ is, independently, —H, —CN, -halo, —($C_1$-$C_3$)alkyl, or —N($R_{92}$)($R_{93}$). In another embodiment, each $R_{91}$ is, independently, —H, —CN, -halo, —$CH_3$, —$CH_2CH_3$, or —N($R_{92}$)($R_{93}$).

In another embodiment, each $R_{92}$ is, independently, —H, —$CH_3$, or —$CH_2CH_3$. In another embodiment, each $R_{92}$ is, independently, —H, or —$CH_3$. In another embodiment, each $R_{92}$ is —H. In another embodiment, each $R_{93}$ is, independently, —H, —$CH_3$, or —$CH_2CH_3$. In another embodiment, each $R_{93}$ is, independently, —H, or —$CH_3$. In another embodiment, each $R_{93}$ is —H. In another embodiment, each $R_{94}$ is, independently, —H, —$CH_3$, or —$CH_2CH_3$. In another embodiment, each $R_{94}$ is, independently, —H, or —$CH_3$. In another embodiment, each $R_{94}$ is —H. In another embodiment, each $R_{95}$ is, independently, —H, —$CH_3$, or —$CH_2CH_3$. In another embodiment, each $R_{95}$ is, independently, —H, or —$CH_3$. In another embodiment, each $R_{95}$ is —H.

In another embodiment, E is N or C. In another embodiment, E is N or C($R_{90}$). In another embodiment, E is N or CH. In another embodiment, E is C or C($R_{90}$). In another embodiment, E is C or CH. In another embodiment, E is N. In another embodiment, E is C. In another embodiment, E is C($R_{90}$). In another embodiment, E is CH.

In another embodiment, G is N($R_{90}$), C(=O), C(=S), or CH. In another embodiment, G is N($R_{90}$), C(=O), or C(=S). In another embodiment, G is N($R_{90}$), C(=O), or CH. In another embodiment, G is $N(R_{90})$, $C(=S)$, or CH. In another embodiment, G is $C(=O)$, $C(=S)$, or CH. In another embodiment, G is $N(R_{90})$ or $C(=O)$. In another embodiment, G is $N(R_{90})$ or $C(=S)$. In another embodiment, G is $N(R_{90})$ or CH. In another embodiment, G is $C(=O)$ or $C(=S)$. In another embodiment, G is $C(=O)$ or CH. In another embodiment, G is $C(=S)$ or CH. In another embodiment, G is $N(R_{90})$. In another embodiment, G is N(H). In another embodiment, G is $C(=O)$. In another embodiment, G is $C(=S)$. In another embodiment, G is CH.

In another embodiment, J is N, N(H), $C(=O)$, or $C(=S)$. In another embodiment, J is N, N(H), or $C(=O)$. In another embodiment, J is N, N(H), or $C(=S)$. In another embodiment, J is N, $C(=O)$, or $C(=S)$. In another embodiment, J is N(H), $C(=O)$, or $C(=S)$. In another embodiment, J is N or N(H). In another embodiment, J is N or $C(=O)$. In another embodiment, J is N or $C(=S)$. In another embodiment, J is N(H) or $C(=O)$. In another embodiment, J is N(H) or $C(=S)$. In another embodiment, J is $C(=O)$ or $C(=S)$. In another embodiment, J is N. In another embodiment, J is N(H). In another embodiment, J is $C(=O)$. In another embodiment, J is $C(=S)$.

In another embodiment, M is N, $N(R_{90})$, $C(=O)$, $C(=S)$, $C(R_{91})$, $CH(R_{91})$, $CH_2$, or $C(CH_3)_2$. In another embodiment, M is N, $N(R_{90})$, $C(=O)$, $C(R_{91})$, $CH(R_{91})$, or $CH_2$. In another embodiment, M is N, $N(R_{90})$, $C(=O)$, $C(R_{91})$, $CH(R_{91})$, or $C(CH_3)_2$. In another embodiment, M is N, $N(R_{90})$, $C(=O)$, $C(R_{91})$, $CH_2$, or $C(CH_3)_2$. In another embodiment, M is N, $N(R_{90})$, $C(=O)$, $CH(R_{91})$, $CH_2$, or $C(CH_3)_2$. In another embodiment, M is N, $N(R_{90})$, $C(R_{91})$, $CH(R_{91})$, $CH_2$, or $C(CH_3)_2$. In another embodiment, M is N, $C(=O)$, $C(R_{91})$, $CH(R_{91})$, $CH_2$, or $C(CH_3)_2$. In another embodiment, M is $N(R_{90})$, $C(=O)$, $C(R_{91})$, $CH(R_{91})$, $CH_2$, or $C(CH_3)_2$. In another embodiment, M is N or $N(R_{90})$. In another embodiment, M is N or $C(=O)$. In another embodiment, M is N or $C(R_{91})$ In another embodiment, M is N or $CH(R_{91})$ In another embodiment, M is N or $CH_2$. In another embodiment, M is N or $C(CH_3)_2$. In another embodiment, M is $N(R_{90})$ or $C(=O)$. In another embodiment, M is $N(R_{90})$ or $C(R_{91})$. In another embodiment, M is $N(R_{90})$ or $CH_2$. In another embodiment, M is $N(R_{90})$ or $C(CH_3)_2$. In another embodiment, M is $C(=O)$ or $C(R_{91})$. In another embodiment, M is $C(=O)$ or $CH(R_{91})$. In another embodiment, M is $C(=O)$ or $CH_2$. In another embodiment, M is $C(R_{91})$ or $CH(R_{91})$. In another embodiment, M is $C(R_{91})$ or $CH_2$. In another embodiment, M is $CH(R_{91})$ or $CH_2$. In another embodiment, M is N. In another embodiment, M is $N(R_{90})$. In another embodiment, M is N(H). In another embodiment, M is $N(CH_2C(=O)OCH_3)$. In another embodiment, M is $N(CH_2C(=O)OH)$. In another embodiment, M is $C(=O)$. In another embodiment, M is $C(=S)$. In another embodiment, M is $CH(R_{91})$. In another embodiment, M is $CH_2$. In another embodiment, M is $C(NH_2)$. In another embodiment, M is $C(N(H)C(=O)CH_3)$. In another embodiment, M is $C(CH_3)_2$.

In another embodiment, U is N, N(H), $C(=O)$, $C(=S)$, $C(R_{91})$, or $CH_2$. In another embodiment, U is N, N(H), $C(=O)$, $C(R_{91})$, or $CH_2$. In another embodiment, U is N, N(H), $C(=O)$, or $C(R_{91})$. In another embodiment, U is N, N(H), $C(=O)$, or $CH_2$. In another embodiment, U is N, N(H), $C(R_{91})$, or $CH_2$. In another embodiment, U is N, $C(=O)$, $C(R_{91})$, or $CH_2$. In another embodiment, U is N(H), $C(=O)$, $C(R_{91})$, or $CH_2$. In another embodiment, U is N or N(H). In another embodiment, U is N or $C(=O)$. In another embodiment, U is N or $C(R_{91})$. In another embodiment, U is N or $CH_2$. In another embodiment, U is N(H) or $C(=O)$. In another embodiment, U is N(H) or $C(R_{91})$. In another embodiment, U is N(H) or $CH_2$. In another embodiment, U is $C(=O)$ or $C(R_{91})$. In another embodiment, U is $C(=O)$ or $CH_2$. In another embodiment, U is $C(R_{91})$, or $CH_2$. In another embodiment, U is N. In another embodiment, U is N(H). In another embodiment, U is g=0). In another embodiment, U is $C(=S)$. In another embodiment, U is $CH_2$. In another embodiment, U is $C(R_{91})$. In another embodiment, U is C(halo). In another embodiment, U is C(F). In another embodiment, U is C(Cl). In another embodiment, U is C(Br). In another embodiment, U is $C(CH_3)$. In another embodiment, U is C(CN). In another embodiment, U is $C(C(=O)OH)$. In another embodiment, U is $C(C(=O)NH_2)$.

In another embodiment, W is N, CH, $CH_2$, or absent. In another embodiment, W is N, CH, or $CH_2$. In another embodiment, W is N, CH, or absent. In another embodiment, W is N, $CH_2$, or absent. In another embodiment, W is CH, $CH_2$, or absent. In another embodiment, W is N or CH. In another embodiment, W is N or $CH_2$. In another embodiment, W is N or absent. In another embodiment, W is CH or $CH_2$. In another embodiment, W is CH or absent. In another embodiment, W is $CH_2$ or absent.

In another embodiment, W is N. In another embodiment, W is CH. In another embodiment, W is $CH_2$. In another embodiment, W is absent.

In another embodiment, --E---G-- is —N—C(=O)— or —N—C(=S)—. In another embodiment, --E---G-- is —N—C(=O)—. In another embodiment, --E---G-- is —N—C(=S)—. In another embodiment, --E---G-- is =C—C(=O)— or =C—C(=S)—. In another embodiment, --E---G-- is =C—C(=O)—. In another embodiment, --E---G-- is =C—C(=S)—. In another embodiment, --E---G-- is —CH—C(=O)— or —CH—C(=S)—. In another embodiment, --E---G-- is —CH—C(=O)—. In another embodiment, --E---G-- is —CH—C(=S)—. In another embodiment, --E---G-- is =C—$N(R_{90})$— or —CH—N$(R_{90})$—. In another embodiment, --E---G-- is =C—N$(R_{90})$—. In another embodiment, --E---G-- is —CH—N$(R_{90})$—. In another embodiment, --E---G-- is =C—N(H)— or —CH—N(H)—. In another embodiment, --E---G-- is =C—N(H)—. In another embodiment, --E---G-- is —CH—N(H)—. In another embodiment, --E---G-- is =C—N(H)—, =C—N($CH_2COOH$)—, =C—N($CH_2COOCH_3$)—, =C—N($CH_2COOCH_2CH_3$)—, —CH—N(H)—, —CH—N($CH_2COOH$)—, —CH—N($CH_2COOCH_3$)—, or —CH—N($CH_2COOCH_2CH_3$)—. In another embodiment, --E---G-- is =C—N(H)—, =C—N($CH_2COOH$)—, =C—N($CH_2COOCH_3$)—, or =C—N($CH_2COOCH_2CH_3$)—. In another embodiment, --E---G-- is —CH—N(H)—, —CH—N($CH_2COOH$)—, —CH—N($CH_2COOCH_3$)—, or —CH—N($CH_2COOCH_2CH_3$)—. In another embodiment, --E---G-- is =C—N($CH_2COOH$)—, =C—N($CH_2COOCH_3$)—, =C—N($CH_2COOCH_2CH_3$)—, —CH—N($CH_2COOH$)—, —CH—N($CH_2COOCH_3$)—, or —CH—N($CH_2COOCH_2CH_3$)—. In another embodiment, --E---G-- is =C—N($CH_2COOCH_3$)—, =C—N($CH_2COOCH_2CH_3$)—, —CH—N($CH_2COOCH_3$)—, or —CH—N($CH_2COOCH_2CH_3$)—. In another embodiment, --E---G-- is =C—N($CH_2COOH$)— or —CH—N($CH_2COOH$)—. In another embodiment, --E---G-- is =C—N($CH_2COOCH_3$)— or —CH—N($CH_2COOCH_3$)—. In another embodiment, --E---G-- is =C—N($CH_2COOCH_2CH_3$)— or —CH—N($CH_2COOCH_2CH_3$)—.

In another embodiment, --G---J-- is —C(=O)—N$(R_{90})$—, —C(=S)—N$(R_{90})$—, —N$(R_{90})$—C(=O)—, or —N$(R_{90})$—C(=S)—. In another embodiment, --G---J-- is —C(=O)—N$(R_{90})$— or —N$(R_{90})$—C(=O)—. In another embodiment, --G---J-- is —C(=S)—N$(R_{90})$— or —N$(R_{90})$—C(=S)—. In another embodiment, --G---J-- is —C(=O)—N($R_{90}$)— or —C(=S)—N($R_{90}$)—. In another embodiment, --G---J-- is —N($R_{90}$)—C(=O)— or —N($R_{90}$)—C(=S)—. In another embodiment, --G---J-- is —C(=O)—N($R_{90}$)—. In another embodiment, --G---J-- is —C(=S)—N($R_{90}$)—. In another embodiment, --G---J-- is —N($R_{90}$)—C(=O)—. In another embodiment, --G---J-- is —N($R_{90}$)—C(=S)—. In another embodiment, --G---J-- is —C(=O)—N(H)—, —C(=S)—N(H)—, —N(H)—C(=O)—, or —N(H)—C(=S)—. In another embodiment, --G---J-- is —C(=O)—N(H)— or —N(H)—C(=O)—. In another embodiment, --G---J-- is —C(=S)—N(H)— or —N(H)—C(=S)—. In another embodiment, --G---J-- is —C(=O)—N(H)— or —C(=S)—N(H)—. In another embodiment, --G---J-- is —N(H)—C(=O)— or —N(H)—C(=S)—. In another embodiment, --G---J-- is —C(=O)—N(H)—. In another embodiment, --G---J-- is —C(=S)—N(H)—. In another embodiment, --G---J-- is —N(H)—C(=O)—. In another embodiment, --G---J-- is —N(H)—C(=S)—. In another embodiment, --G---J-- is —C(=O)—N($R_{90}$)—, —C(=S)—N($R_{90}$)—, —C(=O)—N=, or —C(=S)—N=. In another embodiment, --G---J-- is —C(=O)—N($R_{90}$)— or —C(=O)—N=. In another embodiment, --G---J-- is —C(=S)—N($R_{90}$)— or —C(=S)—N=. In another embodiment, --G---J-- is —C(=O)—N=, or —C(=S)—N=. In another embodiment, --G---J-- is —C(=O)—N=. In another embodiment, --G---J-- is —C(=S)—N=. In another embodiment, --G---J-- is —C(=O)—N(H)—, —C(=S)—N(H)—, —C(=O)—N=, or —C(=S)—N=. In another embodiment, --G---J-- is —C(=O)—N(H)— or —C(=O)—N=. In another embodiment, --G---J-- is —C(=S)—N(H)— or —C(=S)—N=.

In another embodiment, --J---M-- is —N($R_{90}$)—C(=O)—, —N($R_{90}$)—C(=S)—, —N($R_{90}$)—C($R_{90}$)($R_{91}$)—, —N($R_{90}$)—C($R_{91}$)=, —N=C($R_{91}$)—, —C(=O)—C($R_{90}$)($R_{91}$)—, —C(=S)—C($R_{90}$)($R_{91}$)—, —C(=O)—C($R_{91}$)=, —C(=S)—C($R_{91}$)=, —C(=O)—N($R_{90}$)—, —C(=S)—N($R_{90}$)—, —C(=O)—N=, or —C(=S)—N=. In another embodiment, --J---M-- is —N($R_{90}$)—C(=O)—, —N($R_{90}$)—CH($R_{91}$)—, —N($R_{90}$)—C($R_{91}$)=, —N=C($R_{91}$)—, —C(=O)—CH($R_{91}$)—, —C(=O)—C($R_{91}$)=, —C(=O)—N($R_{90}$)—, or —C(=O)—N=. In another embodiment, --J---M-- is —N($R_{90}$)—C(=O)—, —N($R_{90}$)—CH($R_{91}$)—, —N($R_{90}$)—C($R_{91}$)=, or —N=C($R_{91}$)—. In another embodiment, --J---M-- is —N($R_{90}$)—C(=O)—. In another embodiment, --J---M-- is —N($R_{90}$)—CH($R_{91}$)—, —N($R_{90}$)—C($R_{91}$)=, or —N=C($R_{91}$)—. In another embodiment, --J---M-- is —N($R_{90}$)—CH($R_{91}$)—. In another embodiment, --J---M-- is —N($R_{90}$)—C($R_{91}$)=. In another embodiment, --J---M-- is —N=C($R_{91}$)—. In another embodiment, --J---M-- is —C(=O)—CH($R_{91}$)—, —C(=O)—C($R_{91}$)=, —C(=O)—N($R_{90}$)—, or —C(=O)—N=. In another embodiment, --J---M-- is —C(=O)—CH($R_{91}$)— or —C(=O)—C($R_{91}$)=. In another embodiment, --J---M-- is —C(=O)—CH($R_{91}$)—. In another embodiment, --J---M-- is —C(=O)—C($R_{91}$)=. In another embodiment, --J---M-- is —C(=O)—N($R_{90}$)— or —C(=O)—N=. In another embodiment, --J---M-- is —C(=O)—N($R_{90}$)—. In another embodiment, --J---M-- is —C(=O)—N=.

In another embodiment, --J---M-- is —N(H)—C(=O)—, —N(H)—C(=S)—, —N(H)—C($R_{90}$)($R_{91}$)—, —N(H)—C($R_{91}$)=, —N=C($R_{91}$)—, —C(=O)—C($R_{90}$)($R_{91}$)—, —C(=S)—C($R_{90}$)($R_{91}$)—, —C(=O)—C($R_{91}$)=, —C(=S)—C($R_{91}$)=, —C(=O)—N(H)—, —C(=S)—N(H)—, —C(=O)—N=, or —C(=S)—N=. In another embodiment, --J---M-- is —N(H)—C(=O)—, —N(H)—C($R_{90}$)($R_{91}$)—, —N(H)—C($R_{91}$)=, or —N=C($R_{91}$)—. In another embodiment, --J---M-- is —N(H)—C($R_{90}$)($R_{91}$)—. In another embodiment, --J---M-- is —N(H)—C($R_{91}$)=. In another embodiment, --J---M-- is —N=C($R_{91}$)—. In another embodiment, --J---M-- is —C(=O)—C($R_{90}$)($R_{91}$)—, —C(=O)—C($R_{91}$)=, —C(=O)—N(H)—, or —C(=O)—N=. In another embodiment, --J---M-- is —C(=O)—C($R_{90}$)($R_{91}$)— or —C(=O)—C($R_{91}$)=. In another embodiment, --J---M-- is —C(=O)—C($R_{90}$)($R_{91}$)—. In another embodiment, --J---M-- is —C(=O)—N(H)—, or —C(=O)—N=. In another embodiment, --J---M-- is —C(=O)—N(H)—. In another embodiment, --J---M-- is —N($R_{90}$)—C(=O)—, —N($R_{90}$)—C(=S)—, —N($R_{90}$)—CH($R_{91}$)—, —N($R_{90}$)—C($R_{91}$)=, —N=C($R_{91}$)—, —C(=O)—CH($R_{91}$)—, —C(=S)—CH($R_{91}$)—, —C(=O)—C($R_{91}$)=, —C(=S)—C($R_{91}$)=, —C(=O)—N($R_{90}$)—, —C(=S)—N($R_{90}$)—, —C(=O)—N=, or —C(=S)—N=. In another embodiment, --J---M-- is —N($R_{90}$)—C(=O)—, —N($R_{90}$)—CH($R_{91}$)—, —N($R_{90}$)—C($R_{91}$)=, —N=C($R_{91}$)—, —C(=O)—CH($R_{91}$)—, —C(=O)—C($R_{91}$)=, —C(=O)—N($R_{90}$)—, or —C(=O)—N=. In another embodiment, --J---M-- is —N($R_{90}$)—C(=O)—, —N($R_{90}$)—CH($R_{91}$)—, —N($R_{90}$)—C($R_{91}$)=, or —N=C($R_{91}$)—. In another embodiment, --J---M-- is —N($R_{90}$)—CH($R_{91}$)—, —N($R_{90}$)—C($R_{91}$)=, or —N=C($R_{91}$)—. In another embodiment, --J---M-- is —N(H)—C(=O)—, —N(H)—C(=S)—, —N(H)—CH($R_{91}$)—, —N(H)—C($R_{91}$)=, —N=C($R_{91}$)—, —C(=O)—CH($R_{91}$)—, —C(=S)—CH($R_{91}$)—, —C(=O)—C($R_{91}$)=, —C(=S)—C($R_{91}$)=, —C(=O)—N(H)—, —C(=S)—N($R_{90}$)—, —C(=O)—N=, or —C(=S)—N=. In another embodiment, --J---M-- is —N(H)—C(=O)—, —N(H)—CH($R_{91}$)—, —N(H)—C($R_{91}$)=, —N=C($R_{91}$)—, —C(=O)—CH($R_{91}$)—, —C(=O)—C($R_{91}$)=, —C(=O)—N(H)—, or —C(=O)—N=. In another embodiment, --J---M-- is —N(H)—C(=O)—, —N(H)—CH($R_{91}$)—, —N(H)—C($R_{91}$)=, or —N=C($R_{91}$)—. In another embodiment, --J---M-- is —N(H)—CH($R_{91}$)—, —N(H)—C($R_{91}$)=, or —N=C($R_{91}$)—. In another embodiment, --J---M-- is —N(H)—CH($R_{91}$)—. In another embodiment, --J---M-- is —C(=O)—N(H)— or —C(=O)—N=. In another embodiment, --J---M-- is —C(=O)—N(H)—.

In another embodiment, --M---U-- is —C(=O)—C($R_{90}$)($R_{91}$)—, —C(=S)—C($R_{90}$)($R_{91}$)—, —C(=O)—N($R_{90}$)—, —C(=S)—N($R_{90}$)—, —C(=O)—N=, —C(=S)—N=, —C(=O)—C($R_{91}$)=, —C(=S)—C($R_{91}$)=, —C($R_{91}$)=C($R_{91}$)—, —C($R_{90}$)($R_{91}$)—C($R_{90}$)($R_{91}$)—, —C($R_{90}$)($R_{91}$)—C(=O)—, —C($R_{90}$)($R_{91}$)—C(=S)—, —C($R_{91}$)=N—, —N=C($R_{91}$)—, or —N($R_{90}$)—C($R_{91}$)=. In another embodiment, --M---U-- is —C(=O)—C($R_{90}$)($R_{91}$)—, —C(=O)—N($R_{90}$)—, —C(=O)—N=, —C(=O)—C($R_{91}$)=, —C($R_{91}$)=C($R_{91}$)—, —C($R_{90}$)($R_{91}$)—C($R_{90}$)($R_{90}$)—, —C($R_{90}$)($R_{91}$)—C(=O)—, —C($R_{91}$)=N—, —N=C($R_{91}$)—, or —N($R_{90}$)—C($R_{91}$)=. In another embodiment, --M---U-- is —C(=O)—C($R_{90}$)($R_{91}$)—, —C(=O)—N($R_{90}$)—, —C(=O)—N=, —C(=O)—C($R_{91}$)=, or —C($R_{90}$)($R_{91}$)—C(=O)—. In another embodiment, --M---U-- is —C(=O)—C($R_{90}$)($R_{91}$)—, —C(=O)—C($R_{91}$)=, or —C($R_{90}$)($R_{91}$)—C(=O)—. In another embodiment, --M---U-- is —C(=O)—C($R_{90}$)($R_{91}$)— or —C(=O)—C($R_{91}$)=. In another embodiment, --M---U-- is —C(=O)—C($R_{90}$)($R_{91}$)—. In another embodiment, --M---U-- is —C(=O)—C($R_{91}$)= or —C($R_{90}$)

($R_{91}$)—C(=O)—. In another embodiment, --M---U-- is —C(=O)—C($R_{90}$)($R_{91}$)—. In another embodiment, --M---U-- is —C(=O)—C($R_{91}$)=. In another embodiment, --M---U-- is —C($R_{90}$)($R_{91}$)—C(=O)—. In another embodiment, --M---U-- is —C(=O)—CH($R_{91}$)—, —C(=O)—N($R_{90}$)—, —C(=O)—N=, —C(=O)—C($R_{91}$)=, or —CH($R_{91}$)—C(=O)—. In another embodiment, --M---U-- is —C(=O)—CH($R_{91}$)—, —C(=O)—C($R_{91}$)=, or —CH($R_{91}$)—C(=O)—. In another embodiment, --M---U-- is —C(=O)—CH($R_{91}$)— or —C(=O)—C($R_{91}$)=. In another embodiment, --M---U-- is —C(=O)—CH($R_{91}$)— or —CH($R_{91}$)—C(=O)—. In another embodiment, --M---U-- is —C(=O)—C($R_{91}$)= or —CH($R_{91}$)—C(=O)—. In another embodiment, --M---U-- is —C(=O)—CH($R_{91}$)—. In another embodiment, --M---U-- is —C(=O)—C($R_{91}$)=. In another embodiment, --M---U-- is —CH($R_{91}$)—C(=O)—. In another embodiment, --M---U-- is —C(=O)—C($R_{90}$)($R_{91}$)—, —C(=O)—N(H)—, —C(=O)—N, —C(=O)—C($R_{91}$)=, or —C($R_{90}$)($R_{91}$)—C(=O)—. In another embodiment, --M---U-- is —C(=O)—CH($R_{91}$)—, —C(=O)—N(H)—, —C(=O)—N=, —C(=O)—C($R_{91}$)=, or —CH($R_{91}$)—C(=O)—.

In another embodiment, --M---U-- is —C(=O)—N($R_{90}$)— or —C(=O)—N=. In another embodiment, --M---U-- is —C(=O)—N($R_{90}$)—. In another embodiment, --M---U-- is —C(=O)—N=. In another embodiment, --M---U-- is —C(=O)—N(H)— or —C(=O)—N=. In another embodiment, --M---U-- is —C(=O)—N(H)—. In another embodiment, --M---U-- is —C(=O)—N($R_{90}$)—, —C($R_{91}$)=N—, —N=C($R_{91}$)—, or —N($R_{90}$)—C($R_{91}$)=. In another embodiment, --M---U-- is —C($R_{91}$)=N—, —N=C($R_{91}$)—, or —N($R_{90}$)—C($R_{91}$)=. In another embodiment, --M---U-- is —C($R_{91}$)=N— or —N=C($R_{91}$)—. In another embodiment, --M---U-- is —C($R_{91}$)=N— or —N=C($R_{91}$)—. In another embodiment, --M---U-- is —C($R_{91}$)=N— or —N($R_{90}$)—C($R_{91}$)=. In another embodiment, --M---U-- is —C($R_{91}$)=N—. In another embodiment, --M---U-- —N=C($R_{91}$)—. In another embodiment, --M---U-- is —N($R_{90}$)—C($R_{91}$)=. In another embodiment, --M---U-- is —C(=O)—N(H)—, —C(=O)—N=, —C($R_{91}$)=N—, —N=C($R_{91}$)—, or —N(H)—C($R_{91}$)=. In another embodiment, --M---U-- is —C($R_{91}$)=N—, —N=C($R_{91}$)—, or —N(H)—C($R_{91}$)=. In another embodiment, --M---U-- is —C($R_{91}$)=N— or —N(H)—C($R_{91}$)=. In another embodiment, --M---U-- is —C($R_{91}$)=C($R_{91}$)— or —C($R_{90}$)($R_{91}$)—C($R_{90}$)($R_{91}$)—. In another embodiment, --M---U-- is —C($R_{91}$)=C($R_{91}$)—. In another embodiment, --M---U-- is —C($R_{90}$)($R_{91}$)—C($R_{90}$)($R_{91}$)—. In another embodiment, --M---U-- is —C($R_{91}$)=C($R_{91}$)— or —CH($R_{91}$)—CH($R_{91}$)=. In another embodiment, --M---U-- is —CH=C($R_{91}$)—. In another embodiment, --M---U-- is —C($R_{91}$)=CH—. In another embodiment, --M---U-- is —CH($R_{91}$)—CH($R_{91}$)—. In another embodiment, --M---U-- is —CH$_2$—CH($R_{91}$)—. In another embodiment, --M---U-- is —CH($R_{91}$)—CH$_2$—. In another embodiment, --M---U-- is —CH$_2$—CH$_2$—. In another embodiment, --M---U-- is —CH=CH—.

In another embodiment, --U---W-- is —C($R_{91}$)=C($R_{91}$)—, —N=C($R_{91}$)—, —C($R_{91}$)=N—, —N($R_{90}$)—C($R_{90}$)($R_{91}$)—, —N($R_{90}$)—C($R_{91}$)=, or —C($R_{90}$)($R_{91}$)—C($R_{90}$)($R_{91}$)—. In another embodiment, --U---W-- is —C($R_{91}$)=C($R_{91}$)—, —N=C($R_{91}$)—, —C($R_{91}$)=N—, —N($R_{90}$)—C($R_{90}$)($R_{91}$)—, or —N($R_{90}$)—C($R_{91}$)=. In another embodiment, --U---W-- is —C($R_{91}$)=C($R_{91}$)—, —N=C($R_{91}$)—, —N($R_{90}$)—C($R_{90}$)($R_{91}$)—, or —C($R_{90}$)($R_{91}$)—C($R_{90}$)($R_{91}$)—. In another embodiment, --U---W-- is —C($R_{91}$)=C($R_{91}$)—, —N=C($R_{91}$)—, —N($R_{90}$)—C($R_{90}$) ($R_{91}$)—, —N($R_{90}$)—C($R_{91}$)=, or —C($R_{90}$)($R_{91}$)—C($R_{90}$)($R_{91}$)—. In another embodiment, --U---W-- is —C($R_{91}$)=C($R_{91}$)—, —C($R_{91}$)=N—, —N($R_{90}$)—C($R_{90}$)($R_{91}$)—, —N($R_{90}$)—C($R_{91}$)=, or —C($R_{90}$)($R_{91}$)—C($R_{90}$)($R_{91}$)—. In another embodiment, --U---W-- is —N=C($R_{91}$)—, —C($R_{91}$)=N—, —N($R_{90}$)—C($R_{90}$)($R_{91}$)—, —N($R_{90}$)—C($R_{91}$)=, or —C($R_{90}$)($R_{91}$)—C($R_{90}$)($R_{91}$)—. In another embodiment, --U---W-- is —C($R_{91}$)=C($R_{91}$)—, —N=C($R_{91}$)—, —C($R_{91}$)=N—, or —N($R_{90}$)—C($R_{90}$)($R_{91}$)—. In another embodiment, --U---W-- is —C($R_{91}$)=C($R_{91}$)—, —N=C($R_{91}$)—, —C($R_{91}$)=N—, or —C($R_{90}$)($R_{91}$)—C($R_{90}$)($R_{91}$)—. In another embodiment, --U---W-- is —C($R_{91}$)=C($R_{91}$)—, —N=C($R_{91}$)—, —NR$_{90}$—C($R_{91}$)=, or —C($R_{90}$)($R_{91}$)—C($R_{90}$)($R_{91}$)—. In another embodiment, --U---W-- is —C($R_{91}$)=C($R_{91}$)—, —N($R_{90}$)—C($R_{90}$)($R_{91}$)—, —N($R_{90}$)—C($R_{91}$)=, or —C($R_{90}$)($R_{91}$)—C($R_{90}$)($R_{91}$)—. In another embodiment, --U---W-- is —C($R_{91}$)=N—, —N($R_{90}$)—C($R_{90}$)($R_{91}$)—, —N($R_{90}$)—C($R_{91}$)=, or —C($R_{90}$)($R_{91}$)—C($R_{90}$)($R_{91}$)—. In another embodiment, --U---W-- is —N=C($R_{91}$)—, —N($R_{90}$)—C($R_{90}$)($R_{91}$)—, —N($R_{90}$)—C($R_{91}$)=, or —C($R_{90}$)($R_{91}$)—C($R_{90}$)($R_{91}$)—. In another embodiment, --U---W-- is —N=C($R_{91}$)—, —C($R_{91}$)=N—, —N($R_{90}$)—C($R_{91}$)=, or —C($R_{90}$)($R_{91}$)—C($R_{90}$)($R_{91}$)—. In another embodiment, --U---W-- is —N=C($R_{91}$)—, —C($R_{91}$)=N—, —N($R_{90}$)—C($R_{90}$)($R_{91}$)—, or —C($R_{90}$)($R_{91}$)—C($R_{90}$)($R_{91}$)—. In another embodiment, --U---W-- is —N=C($R_{91}$)—, —C($R_{91}$)=N—, —N($R_{90}$)—C($R_{90}$)($R_{91}$)—, or —N($R_{90}$)—C($R_{91}$)=. In another embodiment, --U---W-- is —C($R_{91}$)=C($R_{91}$)—, —C($R_{91}$)=N—, —N($R_{90}$)—C($R_{90}$)($R_{91}$)—, or —C($R_{90}$)($R_{91}$)—C($R_{90}$)($R_{91}$)—. In another embodiment, --U---W-- is —C($R_{91}$)=C($R_{91}$)—, —C($R_{91}$)=N—, —N($R_{90}$)—C($R_{90}$)($R_{91}$)—, or —N($R_{90}$)—C($R_{91}$)=. In another embodiment, --U---W-- is —C($R_{91}$)=C($R_{91}$)—, —N=C($R_{91}$)—, —N($R_{90}$)—C($R_{90}$)($R_{91}$)—, or —C($R_{90}$)($R_{91}$)—C($R_{90}$)($R_{91}$)—. In another embodiment, --U---W-- is —C($R_{91}$)=C($R_{91}$)—, —N=C($R_{91}$)—, —N($R_{90}$)—C($R_{90}$)($R_{91}$)—, or —N($R_{90}$)—C($R_{91}$)=. In another embodiment, --U---W-- is —C($R_{91}$)=C($R_{91}$)—, —N=C($R_{91}$)—, —C($R_{91}$)=N—, or —N($R_{90}$)—C($R_{91}$)=. In another embodiment, --U---W-- is —C($R_{91}$)=C($R_{91}$)—. In another embodiment, --U---W-- is —N=C($R_{91}$)—. In another embodiment, --U---W-- is —C($R_{91}$)=N—. In another embodiment, --U---W-- is —N($R_{90}$)—C($R_{90}$)($R_{91}$)—. In another embodiment, --U---W-- is —N($R_{90}$)—C($R_{91}$)=. In another embodiment, --U---W-- is —C($R_{90}$)($R_{91}$)—C($R_{90}$)($R_{91}$)—.

In another embodiment, --U---W-- is —C(H)=C(H)—, —C(halo)=C(H)—, —N=C(H)—, —C(H)=N—, —N(H)—C(H)($R_{91}$)—, —N(H)—CH$_2$—, —N(H)—C(H)=, —C(H)($R_{91}$)—C(H)($R_{91}$)—, —CH$_2$—C(H)($R_{91}$)—, —C(H)($R_{91}$)—CH$_2$—, or —CH$_2$—CH$_2$—. In another embodiment, --U---W-- is —C(H)=C(H)— or —C(halo)=C(H)—. In another embodiment, --U---W-- is —C(H)=C(H)—. In another embodiment, --U---W-- is —C(halo)=C(H)—. In another embodiment, --U---W-- is —N=C(H)— or —C(H)=N—. In another embodiment, --U---W-- is —N=C(H)—. In another embodiment, --U---W-- is —C(H)=N—. In another embodiment, --U---W-- is —N(H)—C(H)($R_{91}$)— or —N(H)—CH$_2$—. In another embodiment, --U---W-- is —N(H)—C(H)($R_{91}$)—. In another embodiment, --U---W-- is —N(H)—CH$_2$—. In another embodiment, --U ---W-- is —N(H)—C(H)=. In another embodiment, --U---W-- is —C(H)($R_{91}$)—C(H)($R_{91}$)—. In another embodiment, --U---W-- is —$CH_2$—C(H)($R_{91}$)—, —C(H)($R_{91}$)—$CH_2$—, or —$CH_2$—$CH_2$—. In another embodiment, --U---W-- is —$CH_2$—C(H)($R_{91}$)—. In another embodiment, --U---W-- is —C(H)($R_{91}$)—$CH_2$—. In another embodiment, --U---W-- is —$CH_2$—$CH_2$—.

In another embodiment, --W---E-- is —C($R_{91}$)=C—, —N=C—, =C($R_{91}$)—N—, =N—N—, or —C($R_{90}$)($R_{91}$)—CH—. In another embodiment, --W---E-- is —C($R_{91}$)=C—, —N=C—, =C($R_{91}$)—N—, or =N—N—. In another embodiment, --W---E-- is —C($R_{91}$)=C—, —N=C—, =C($R_{91}$)—N—, or —C($R_{90}$)($R_{91}$)—CH—. In another embodiment, --W---E-- is —C($R_{91}$)=C—, —N=C—, =N—N—, or —C($R_{90}$)($R_{91}$)—CH—. In another embodiment, --W---E-- is —C($R_{91}$)=C—, =C($R_{91}$)—N—, =N—N—, or —C($R_{90}$)($R_{91}$)—CH—. In another embodiment, --W---E-- is —N=C—, =C($R_{91}$)—N—, =N—N—, or —C($R_{90}$)($R_{91}$)—CH—. In another embodiment, --W---E-- is —C($R_{91}$)=C—, —N=C—, =C($R_{91}$)—N—, =N—N—, or —CH($R_{91}$)—CH—. In another embodiment, --W---E-- is —C($R_{91}$)=C—, —N=C—, =C($R_{91}$)—N—, or —CH($R_{91}$)—CH—. In another embodiment, --W---E-- is —C($R_{91}$)=C—, —N=C—, =N—N—, or —CH($R_{91}$)—CH—. In another embodiment, --W---E-- is —C($R_{91}$)=C—, =C($R_{91}$)—N—, =N—N—, or —CH($R_{91}$)—CH—. In another embodiment, --W---E-- is —N=C—, =C($R_{91}$)—N—, =N—N—, or —CH($R_{91}$)—CH—. In another embodiment, --W---E-- is —CH=C—, —N=C—, =CH—N—, =N—N—, or —$CH_2$—CH—. In another embodiment, --W---E-- is —CH=C—, —N=C—, =CH—N—, or =N—N—. In another embodiment, --W---E-- is —CH=C—, —N=C—, =CH—N—, or —$CH_2$—CH—. In another embodiment, --W---E-- is —CH=C—, —N=C—, =N—N—, or —$CH_2$—CH—. In another embodiment, --W---E-- is —CH=C—, =CH—N—, =N—N—, or —$CH_2$—CH—. In another embodiment, --W---E-- is —N=C—, =CH—N—, =N—N—, or —$CH_2$—CH—. In another embodiment, --W---E-- is —CH=C—, —N=C—, or =CH—N—. In another embodiment, --W---E-- is —CH=C—, —N=C—, or =N—N—. In another embodiment, --W---E-- is —CH=C—, =CH—N—, or =N—N—. In another embodiment, --W---E-- is —N=C—, =CH—N—, or =N—N—. In another embodiment, --W---E-- is —CH=C— or —N=C—. In another embodiment, --W---E-- is —CH=C— or =CH—N—. In another embodiment, --W---E-- is —CH=C— or =N—N—. In another embodiment, --W---E-- is —N=C— or =CH—N—. In another embodiment, --W---E-- is —N=C— or =N—N—. In another embodiment, --W---E-- is =CH—N— or =N—N—. In another embodiment, --W---E-- is —CH=C—. In another embodiment, --W---E-- is —N=C—. In another embodiment, --W---E-- is =CH—N—. In another embodiment, --W---E-- is =N—N—.

In another embodiment, W is absent and --U---E-- is —C($R_{90}$)($R_{91}$)—N—, —C(=O)—N—, —C(=S)—N—, —N($R_{90}$)—N—, or =N—N—. In another embodiment, W is absent and --U---E-- is —C($R_{90}$)($R_{91}$)—N—, —C(=O)—N—, —N($R_{90}$)—N—, or =N—N—. In another embodiment, W is absent and --U---E-- is —CH($R_{91}$)—N—, —C(=O)—N—, —N($R_{90}$)—N—, or =N—N—. In another embodiment, W is absent and --U---E-- is —C($R_{90}$)($R_{91}$)—N—, —C(=O)—N—, —N(H)—N—, or =N—N—. In another embodiment, W is absent and --U---E-- is —CH($R_{91}$)—N—, —C(=O)—N—, —N(H)—N—, or =N—N—. In another embodiment, W is absent and --U---E-- is —$CH_2$—N—, —C(=O)—N—, —N(H)—N—, or =N—N—. In another embodiment, W is absent and --U---E-- is —C($R_{90}$)($R_{91}$)—N—. In another embodiment, W is absent and --U---E-- is —CH($R_{91}$)—N—. In another embodiment, W is absent and --U---E-- is —$CH_2$—N—. In another embodiment, W is absent and --U---E-- is —C(=O)—N—. In another embodiment, W is absent and --U---E-- is —N($R_{90}$)—N—. In another embodiment, W is absent and --U---E-- is —N(H)—N—. In another embodiment, W is absent and --U---E-- is =N—N—. In another embodiment, W is absent and --U---E-- is —C($R_{90}$)($R_{91}$)—N—, —C(=O)—N—, or =N—N—. In another embodiment, W is absent and --U---E-- is —C($R_{90}$)($R_{91}$)—N— or —C(=O)—N—. In another embodiment, W is absent and --U---E-- is —C(=O)—N— or =N—N—. In another embodiment, W is absent and --U---E-- is —C($R_{90}$)($R_{91}$)—N— or =N—N—. In another embodiment, W is absent and --U---E-- is —CH($R_{91}$)—N—, —C(=O)—N—, or =N—N—. In another embodiment, W is absent and --U---E-- is —CH($R_{91}$)—N— or —C(=O)—N—. In another embodiment, W is absent and --U---E-- is —CH($R_{91}$)—N— or =N—N—. In another embodiment, W is absent and --U---E-- is —$CH_2$—N—, —C(=O)—N—, or =N—N—. In another embodiment, W is absent and --U---E-- is —$CH_2$—N— or —C(=O)—N—. In another embodiment, W is absent and --U---E-- is —$CH_2$—N— or =N—N—.

In another embodiment, --E---G---J-- is —N—C(=O)—N($R_{90}$)— or —N—C(=O)—N=. In another embodiment, --E---G---J-- is —N—C(=O)—N(H)— or —N—C(=O)—N=. In another embodiment, --E---G---J-- is —N—C(=O)—N=. In another embodiment, --E---G---J-- is —N—C(=O)—N($R_{90}$)—. In another embodiment, --E---G---J-- is —N—C(=O)—N(H)—. In another embodiment, --E---G---J-- is =C—C(=O)—N($R_{90}$)— or =C—N($R_{90}$)—C(=O)—. In another embodiment, --E---G---J-- is =C—C(=O)—N(H)($R_{90}$)— or =C—N($R_{90}$)—C(=O)—. In another embodiment, --E---G---J-- is =C—C(=O)—N(H)($R_{90}$)—. In another embodiment, --E---G---J-- is =C—C(=O)—N($R_{90}$)($R_{90}$)—. In another embodiment, --E---G---J-- is =C—N($R_{90}$)—C(=O)—.

In another embodiment, --G---J---M-- is —N($R_{90}$)—C(=O)—N($R_{90}$)—, —N($R_{90}$)—C(=O)—N=, =N—C(=O)—N($R_{90}$)—, or =N—C(=O)—N=. In another embodiment, --G---J---M-- is —N($R_{90}$)—C(=O)—N($R_{90}$)—, —N($R_{90}$)—C(=O)—N=, or =N—C(=O)—N($R_{90}$)—. In another embodiment, --G---J---M-- is —N($R_{90}$)—C(=O)—N=, =N—C(=O)—N($R_{90}$)—, or =N—C(=O)—N=. In another embodiment, --G---J---M-- is —N($R_{90}$)—C(=O)—N($R_{90}$)—, =N—C(=O)—N($R_{90}$)—, or =N—C(=O)—N=. In another embodiment, --G---J---M-- is —N($R_{90}$)—C(=O)—N($R_{90}$)—, —N($R_{90}$)—C(=O)—N=, or =N—C(=O)—N=. In another embodiment, --G---J---M-- is —N($R_{90}$)—C(=O)—N($R_{90}$)— or —N($R_{90}$)—C(=O)—N=. In another embodiment, --G---J---M-- is =N—C(=O)—N($R_{90}$)— or =N—C(=O)—N=. In another embodiment, --G---J---M-- is —N($R_{90}$)—C(=O)—N= or =N—C(=O)—N($R_{90}$)—. In another embodiment, --G---J---M-- is —N($R_{90}$)—C(=O)—N($R_{90}$)— or =N—C(=O)—N=. In another embodiment, --G---J---M-- is —N($R_{90}$)—C(=O)—N($R_{90}$)—. In another embodiment, --G---J---M-- is —N($R_{90}$)—C(=O)—N=. In another embodiment, --G---J---M-- is =N—C(=O)—N($R_{90}$)—. In another embodiment, --G---J---M-- is =N—C(=O)—N=. In another embodiment, --G---J---M-- is —N(H)—C(=O)—N($R_{90}$)—, —N($R_{90}$)—C(=O)—N(H)—, —N(H)—C(=O)—N(H)—, —N(H)—C(=O)—N=, =N—C(=O)—N(H)—, or =N—C(=O)—N=. In another embodiment, --G---J---M-- is —N(H)—C(=O)—N(R$_{90}$)—, —N(R$_{90}$)—C(=O)—N(H)—, —N(H)—C(=O)—N(H)—, —N(H)—C(=O)—N=, or =N—C(=O)—N(H)—. In another embodiment, --G---J---M-- is —N(H)—C(=O)—N=, =N—C(=O)—N(H)—, or =N—C(=O)—N=. In another embodiment, --G---J---M-- is —N(H)—C(=O)—N(R$_{90}$)—, —N(R$_{90}$)—C(=O)—N(H)—, —N(H)—C(=O)—N(H)—, =N—C(=O)—N(H)—, or =N—C(=O)—N=. In another embodiment, --G---J---M-- is —N(H)—C(=O)—N(R$_{90}$)—, —N(R$_{90}$)—C(=O)—N(H)—, —N(H)—C(=O)—N(H)—, —N(H)—C(=O)—N=, or =N—C(=O)—N=. In another embodiment, --G---J---M-- is —N(H)—C(=O)—N(R$_{90}$)—, —N(R$_{90}$)—C(=O)—N(H)—, —N(H)—C(=O)—N(H)—, or —N(H)—C(=O)—N=. In another embodiment, --G---J---M-- is =N—C(=O)—N(H)— or =N—C(=O)—N=. In another embodiment, --G---J---M-- is —N(H)—C(=O)—N= or =N—C(=O)—N(H)—. In another embodiment, --G---J---M-- is —N(H)—C(=O)—N(R$_{90}$)—, —N(R$_{90}$)—C(=O)—N(H)—, —N(H)—C(=O)—N(H)—, or =N—C(=O)—N=. In another embodiment, --G---J---M-- is —N(H)—C(=O)—N(R$_{90}$)—. In another embodiment, --G---J---M-- is —N(R$_{90}$)—C(=O)—N(H)—. In another embodiment, --G---J---M-- is —N(H)—C(=O)—N(H)—. In another embodiment, --G---J---M-- is —N(H)—C(=O)—N=. In another embodiment, --G---J---M-- is =N—C(=O)—N(H)—. In another embodiment, --G---J---M-- is =N—C(=O)—N=.

In another embodiment, --G---J---M-- is —C(=O)—N(R$_{90}$)—C(R$_{91}$)=, —C(=O)—N(R$_{90}$)—C(=O)—, —C(=O)—N(R$_{90}$)—N(R$_{90}$)—, —N(R$_{90}$)—C(=O)—C(R$_{91}$)=, —N(R$_{90}$)—C(=O)—N=, —N(R$_{90}$)—C(=O)—N(R$_{90}$)—, or —N(R$_{90}$)—C(=O)—C(R$_{90}$)(R$_{91}$)—. In another embodiment, --G---J---M-- is —C(=O)—N(R$_{90}$)—C(R$_{91}$)=, —C(=O)—N(R$_{90}$)—N(R$_{90}$)—, —N(R$_{90}$)—C(=O)—C(R$_{91}$)=, —NR$_{90}$)—C(=O)—N=, or —N(R$_{90}$)—C(=O)—CH$_2$—. In another embodiment, --G---J---M-- is —C(=O)—N(R$_{90}$)—C(H)=, —C(=O)—N(R$_{90}$)—C(=O)—, —C(=O)—N(R$_{90}$)—N(H)—, —N(R$_{90}$)—C(=O)—C(H)=, —N(R$_{90}$)—C(=O)—N=, —N(R$_{90}$)—C(=O)—N(H)—, or —N(R$_{90}$)—C(=O)—CH$_2$—. In another embodiment, --G---J---M-- is —C(=O)—N(R$_{90}$)—C(H)=, —C(=O)—N(R$_{90}$)—N(H)—, —N(R$_{90}$)—C(=O)—C(H)=, —N(R$_{90}$)—C(=O)—N=, or —N(R$_{90}$)—C(=O)—CH$_2$—. In another embodiment, --G---J---M-- is —C(=O)—N(R$_{90}$)—C(R$_{91}$)=, —C(=O)—N(R$_{90}$)—C(=O)—, or —C(=O)—N(R$_{90}$)—N(R$_{90}$)—. In another embodiment, --G---J---M-- is —N(R$_{90}$)—C(=O)—C(R$_{91}$)=, —N(R$_{90}$)—C(=O)—N=, —N(R$_{90}$)—C(=O)—N(R$_{90}$)—, or —N(R$_{90}$)—C(=O)—C(R$_{90}$)(R$_{91}$)—. In another embodiment, --G---J---M-- is —C(=O)—N(R$_{90}$)—C(H)=, —C(=O)—N(R$_{90}$)—C(=O)—, or —C(=O)—N(R$_{90}$)—N(H)—. In another embodiment, --G---J---M-- is —N(R$_{90}$)—C(=O)—C(H)=, —N(R$_{90}$)—C(=O)—N=, —N(R$_{90}$)—C(=O)—N(H)—, or —N(R$_{90}$)—C(=O)—CH$_2$—. In another embodiment, --G---J---M-- is —C(=O)—N(R$_{90}$)—C(R$_{91}$)= or —C(=O)—N(R$_{90}$)—N(R$_{90}$)—. In another embodiment, --G---J---M-- is —N(R$_{90}$)—C(=O)—C(R$_{91}$)=, —N(R$_{90}$)—C(=O)—N=, or —N(R$_{90}$)—C(=O)—C(R$_{90}$)(R$_{91}$)—. In another embodiment, --G---J---M-- is —N(R$_{90}$)—C(=O)—C(R$_{91}$)=, —N(R$_{90}$)—C(=O)—N=, or —N(R$_{90}$)—C(=O)—CH$_2$—. In another embodiment, --G---J---M-- is —C(=O)—N(R$_{90}$)—C(H)= or —C(=O)—N(R$_{90}$)—N(H)—. In another embodiment, --G---J---M-- is —N(R$_{90}$)—C(=O)—C(H)=, —N(R$_{90}$)—C(=O)—N=, or —N(R$_{90}$)—C(=O)—CH$_2$—.

In another embodiment, --J---M---U-- is —N(R$_{90}$)—C(=O)—N(R$_{90}$)—, —N(R$_{90}$)—C(=O)—N=, =N—C(=O)—N(R$_{90}$)—, or =N—C(=O)—N=. In another embodiment, --J---M---U-- is —N(R$_{90}$)—C(=O)—N(R$_{90}$)—, —N(R$_{90}$)—C(=O)—N=, or =N—C(=O)—N(R$_{90}$)—. In another embodiment, --J---M---U-- is —N(R$_{90}$)—C(=O)—N=, =N—C(=O)—N(R$_{90}$)—, or =N—C(=O)—N=. In another embodiment, --J---M---U-- is —N(R$_{90}$)—C(=O)—N(R$_{90}$)—, =N—C(=O)—N(R$_{90}$)—, or =N—C(=O)—N. In another embodiment, --J---M---U-- is —N(R$_{90}$)—C(=O)—N(R$_{90}$)—, —N(R$_{90}$)—C(=O)—N=, or =N—C(=O)—N=. In another embodiment, --J---M---U-- is —N(R$_{90}$)—C(=O)—N(R$_{90}$)— or —N(R$_{90}$)—C(=O)—N=. In another embodiment, --J---M---U-- is =N—C(=O)—N(R$_{90}$)— or =N—C(=O)—N=. In another embodiment, --J---M---U-- is —N(R$_{90}$)—C(=O)—N= or =N—C(=O)—N(R$_{90}$)—. In another embodiment, --J---M---U-- is —N(R$_{90}$)—C(=O)—N(R$_{90}$)— or =N—C(=O)—N=. In another embodiment, --J---M---U-- is —N(R$_{90}$)—C(=O)—N(R$_{90}$)—. In another embodiment, --J---M---U-- is —N(R$_{90}$)—C(=O)—N=. In another embodiment, --J---M---U-- is =N—C(=O)—N(R$_{90}$)—. In another embodiment, --J---M---U-- is =N—C(=O)—N=. In another embodiment, --J---M---U-- is —N(H)—C(=O)—N(R$_{90}$)—, —N(R$_{90}$)—C(=O)—N(H)—, —N(H)—C(=O)—N(H)—, —N(H)—C(=O)—N=, =N—C(=O)—N(H)—, or =N—C(=O)—N=. In another embodiment, --J---M---U-- is —N(H)—C(=O)—N(R$_{90}$)—, —N(R$_{90}$)—C(=O)—N(H)—, —N(H)—C(=O)—N(H)—, —N(H)—C(=O)—N=, or =N—C(=O)—N(H)—. In another embodiment, --J---M---U-- is —N(H)—C(=O)—N=, =N—C(=O)—N(H)—, or =N—C(=O)—N=. In another embodiment, --J---M---U-- is —N(H)—C(=O)—N(R$_{90}$)—, —N(R$_{90}$)—C(=O)—N(H)—, —N(H)—C(=O)—N(H)—, =N—C(=O)—N(H)—, or =N—C(=O)—N=. In another embodiment, --J---M---U-- is —N(H)—C(=O)—N(R$_{90}$)—, —N(R$_{90}$)—C(=O)—N(H)—, —N(H)—C(=O)—N(H)—, —N(H)—C(=O)—N=, or =N—C(=O)—N=. In another embodiment, --J---M---U-- is —N(H)—C(=O)—N(R$_{90}$)—, —N(R$_{90}$)—C(=O)—N(H)—, —N(H)—C(=O)—N(H)—, or —N(H)—C(=O)—N=. In another embodiment, --J---M---U-- is =N—C(=O)—N(H)— or =N—C(=O)—N=. In another embodiment, --J---M---U-- is —N(H)—C(=O)—N= or =N—C(=O)—N(H)—. In another embodiment, --J---M---U-- is —N(H)—C(=O)—N(R$_{90}$)—, —N(R$_{90}$)—C(=O)—N(H)—, —N(H)—C(=O)—N(H)—, or =N—C(=O)—N=. In another embodiment, --J---M---U-- is —N(H)—C(=O)—N(R$_{90}$)—. In another embodiment, --J---M---U-- is —N(R$_{90}$)—C(=O)—N(H)—. In another embodiment, --J---M---U-- is —N(H)—C(=O)—N(H)—. In another embodiment, --J---M---U-- is —N(H)—C(=O)—N=. In another embodiment, --J---M---U-- is N—C(=O)—N(H)—. In another embodiment, --J---M---U-- is =N—C(=O)—N=. In another embodiment, --J---M---U-- is —C(=O)—N(R$_{90}$)—C(R$_{91}$)=, —C(=O)—N(R$_{90}$)—C(=O)—, —N(R$_{90}$)—C(=O)—N(R$_{90}$)—, or —N(R$_{90}$)—C(=O)—C(R$_{91}$)=. In another embodiment, --J---M---U-- is —C(=O)—N(R$_{90}$)—C(H)=, —C(=O)—N(R$_{90}$)—C(=O)—, —N(H)—C(=O)—N(R$_{90}$)—, —N(R$_{90}$)—C(=O)—N(H)—, —N(R$_{90}$)—C(=O)—C(H)=, —N(H)—C(=O)—C(R$_{91}$)=. In another embodiment, --J---M---U-- is —C(=O)—N(R$_{90}$)—C(H)=, —N(R$_{90}$)—C(=O)—C(H)=, or —N(H)—C(=O)—C(R$_{91}$)=.

In another embodiment, E---G---J---M is not N—C(R$_{90}$)(R$_{91}$)—C(=O)—N(R$_{90}$) and M---U---W---E is not N(R$_{90}$)—C(=O)—C(R$_{90}$)(R$_{91}$)—N. In another embodiment, E---G---J is not N—N(R$_{90}$)—C(=O), and, when W is absent, M---U---E is not C(=O)—N(R$_{90}$)—N. In another embodiment, the Q$_x$ ring does not contain 3 consecutive ring nitrogen atoms. In another embodiment, E---G---J---M is not N—C(R$_{90}$)(R$_{91}$)—C(=O)—N(R$_{90}$), M---U---W---E is not N(R$_{90}$)—C(=O)—C(R$_{90}$)(R$_{91}$)—N, E---G---J is not N—N(R$_{90}$)—C(=O), and, when W is absent, M---U---E is not C(=O)—N(R$_{90}$)—N. In another embodiment, E---G---J---M is not N—C(R$_{90}$)(R$_{91}$)—C(=O)—N(R$_{90}$), M---U---W---E is not N(R$_{90}$)—C(=O)—C(R$_{90}$)(R$_{91}$)—N, and the Q$_x$ ring does not contain 3 consecutive ring nitrogen atoms. In another embodiment, E---G---J is not N—N(R$_{90}$)—C(=O), when W is absent, M---U---E is not C(=O)—N(R$_{90}$)—N, and the Q$_x$ ring does not contain 3 consecutive ring nitrogen atoms. In another embodiment, E---G---J---M is not N—C(R$_{90}$)(R$_{91}$)—C(=O)—N(R$_{90}$), M---U---W---E is not N(R$_{90}$)—C(=O)—C(R$_{90}$)(R$_{91}$)—N, E---G---J is not N—N(R$_{90}$)—C(=O), when W is absent, M---U---E is not C(=O)—N(R$_{90}$)—N, and the Q$_x$ ring does not contain 3 consecutive ring nitrogen atoms.

In another embodiment, the Q$_x$ ring is not:

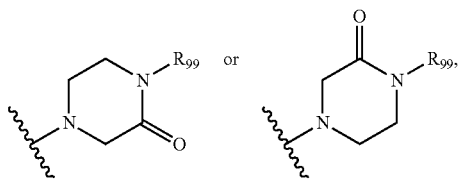

where R$_{99}$ is as defined above. In another embodiment, the Q$_x$ ring is not:

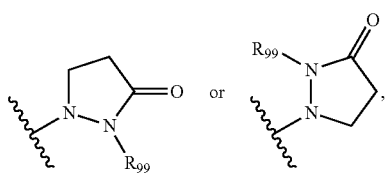

where R$_{99}$ is as defined above. In another embodiment, the Q$_x$ ring does not contain 3 consecutive ring nitrogen atoms. In another embodiment, the Q$_x$ ring is not:

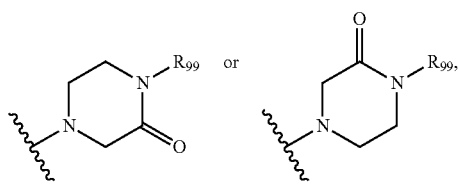

where R$_{99}$ is as defined above and the Q$_x$ ring does not contain 3 consecutive ring nitrogen atoms. In another embodiment, the Q$_x$ ring is not:

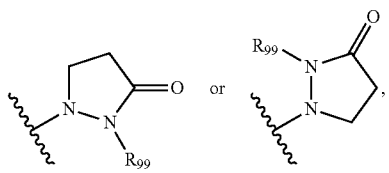

where R$_{99}$ is as defined above and the Q$_x$ ring does not contain 3 consecutive ring nitrogen atoms. In another embodiment, the Q$_x$ ring is not:

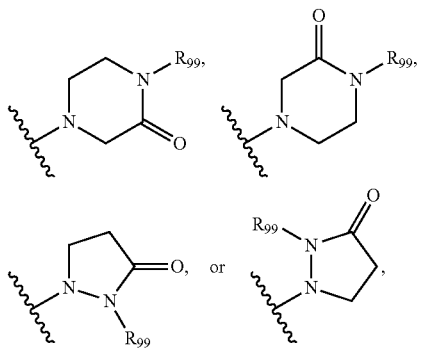

where R$_{99}$ is as defined above and the Q$_x$ ring does not contain 3 consecutive ring nitrogen atoms.

In another embodiment, the Q$_x$ ring is not:

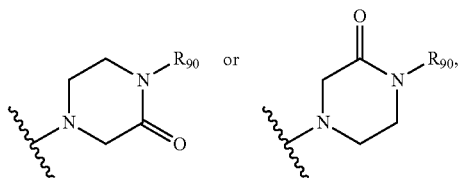

where:
R$_{90}$ is —H, —CN, -halo, —(C$_1$-C$_3$)alkyl, —N(R$_{92}$)(R$_{93}$), —(CH$_2$)$_c$—(C(R$_{94}$)(R$_{95}$))$_d$—C(=O)R$_{92}$, —(CH$_2$)$_c$—(C(R$_{94}$)(R$_{95}$))$_d$—C(=O)OR$_{92}$, —(CH$_2$)$_c$—(C(R$_{94}$)(R$_{95}$))$_d$—N(R$_{92}$)—C(=O)R$_{92}$, or —(CH$_2$)$_c$—(C(R$_{94}$)(R$_{95}$))$_d$—C(=O)N(R$_{92}$)(R$_{93}$);

each R$_{92}$, R$_{93}$, R$_{94}$, and R$_{95}$ is independently selected from —H and —(C$_1$-C$_3$)alkyl;

each c is independently an integer selected from 0, 1, 2, and 3; and each d is independently an integer selected from 0, 1, and 2.

In another embodiment, the Q$_x$ ring is not:

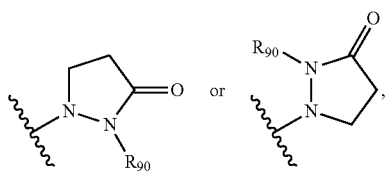

where:
R$_{90}$ is —H, —CN, -halo, —(C$_1$-C$_3$)alkyl, —N(R$_{92}$)(R$_{93}$), —(CH$_2$)$_c$—(C(R$_{94}$)(R$_{95}$))$_d$—C(=O)R$_{92}$, —(CH$_2$)$_c$—(C $(R_{94})(R_{95}))_d$—C(=O)OR$_{92}$, —(CH$_2$)$_c$—(C(R$_{94}$)(R$_{95}$))$_d$—N(R$_{92}$)—C(=O)R$_{92}$, or —(CH$_2$)$_c$—(C(R$_{94}$)(R$_{95}$))$_d$—C(=O)N(R$_{92}$)(R$_{93}$);

each $R_{92}$, $R_{93}$, $R_{94}$, and $R_{95}$ is independently selected from —H and —(C$_1$-C$_3$)alkyl;

each c is independently an integer selected from 0, 1, 2, and 3; and each d is independently an integer selected from 0, 1, and 2.

In another embodiment, the $Q_x$ ring does not contain 3 consecutive ring nitrogen atoms.

In another embodiment, the $Q_x$ ring does not contain 3 consecutive ring nitrogen atoms and the $Q_x$ ring is not:

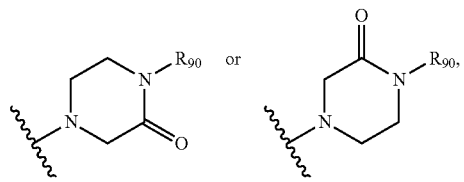

where:

$R_{90}$ is —H, —CN, -halo, —(C$_1$-C$_3$)alkyl, —N(R$_{92}$)(R$_{93}$), —(CH$_2$)$_c$—(C(R$_{94}$)(R$_{95}$))$_d$—C(=O)R$_{92}$, —(CH$_2$)$_c$—(C(R$_{94}$)(R$_{95}$))$_d$—C(=O)OR$_{92}$, —(CH$_2$)$_c$—(C(R$_{94}$)(R$_{95}$))$_d$—N(R$_{92}$)—C(=O)R$_{92}$, or —(CH$_2$)$_c$—(C(R$_{94}$)(R$_{95}$))$_d$—C(=O)N(R$_{92}$)(R$_{93}$);

each $R_{92}$, $R_{93}$, $R_{94}$, and $R_{95}$ is independently selected from —H and —(C$_1$-C$_3$)alkyl;

each c is independently an integer selected from 0, 1, 2, and 3; and each d is independently an integer selected from 0, 1, and 2.

In another embodiment, the $Q_x$ ring does not contain 3 consecutive ring nitrogen atoms and the $Q_x$ ring is not:

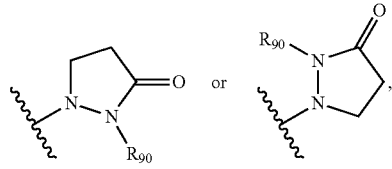

where:

$R_{90}$ is —H, —CN, -halo, —(C$_1$-C$_3$)alkyl, —N(R$_{92}$)(R$_{93}$), —(CH$_2$)—(C(R$_{94}$)(R$_{95}$))$_d$—C(=O)R$_{92}$, —(CH$_2$)$_c$—(C(R$_{94}$)(R$_{95}$))$_d$—C(=O)OR$_{92}$, —(CH$_2$)$_c$—(C(R$_{94}$)(R$_{95}$))$_d$—N(R$_{92}$)—C(=O)R$_{92}$, or —(CH$_2$)$_c$—(C(R$_{94}$)(R$_{95}$))$_d$—C(=O)N(R$_{92}$)(R$_{93}$);

each $R_{92}$, $R_{93}$, $R_{94}$, and $R_{95}$ is independently selected from —H and —(C$_1$-C$_3$)alkyl;

each c is independently an integer selected from 0, 1, 2, and 3; and each d is independently an integer selected from 0, 1, and 2.

In another embodiment, the $Q_x$ ring is not:

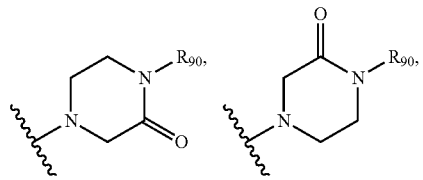

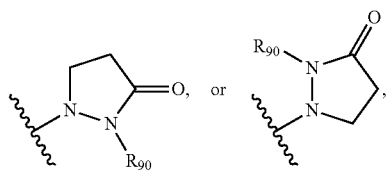

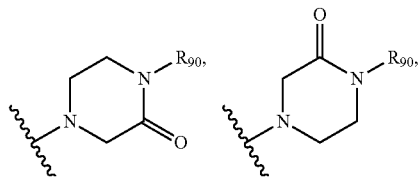

where:

$R_{90}$ is —H, —CN, -halo, —(C$_1$-C$_3$)alkyl, —N(R$_{92}$)(R$_{93}$), —(CH$_2$)$_c$—(C(R$_{94}$)(R$_{95}$))$_d$—C(=O)R$_{92}$, —(CH$_2$)$_c$—(C(R$_{94}$)(R$_{95}$))$_d$—C(=O)OR$_{92}$, —(CH$_2$)$_c$—(C(R$_{94}$)(R$_{95}$))$_d$—N(R$_{92}$)—C(=O)R$_{92}$, or —(CH$_2$)$_c$—(C(R$_{94}$)(R$_{95}$))$_d$—C(=O)N(R$_{92}$)(R$_{93}$);

each $R_{92}$, $R_{93}$, $R_{94}$, and $R_{95}$ is independently selected from —H and —(C$_1$-C$_3$)alkyl;

each c is independently an integer selected from 0, 1, 2, and 3; and each d is independently an integer selected from 0, 1, and 2.

In another embodiment, the Cyclic Urea- or Lactam-Substituted Quinoxaline-Type Piperidine Compound is not:

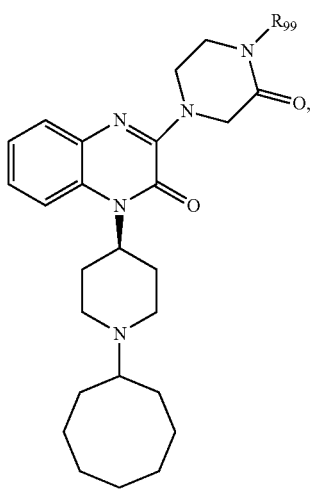

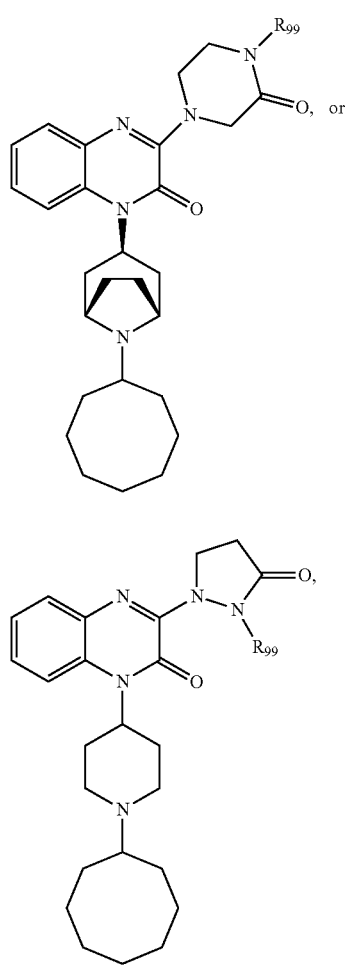

or a pharmaceutically acceptable derivative thereof where:

$R_{99}$ is —H, —($C_1$-$C_3$)alkyl, —($CH_2$)$_j$—C(=O)OH, or —($CH_2$), —C(=O)O—($C_1$-$C_3$)alkyl; and j is an integer selected from 0, 1, 2, and 3.

In another embodiment, the Cyclic Urea- or Lactam-Substituted Quinoxaline-Type Piperidine Compound is not:

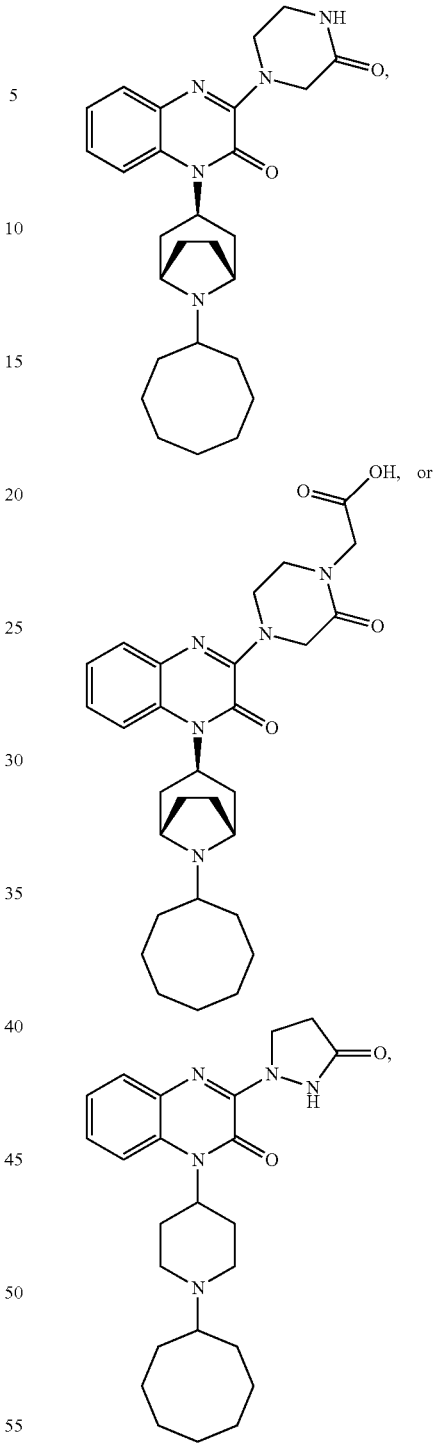

or a pharmaceutically acceptable derivative thereof.

In another embodiment, the $Q_x$ ring is a 6-membered ring. In another embodiment, the $Q_x$ ring contains one cyclic urea group. In another embodiment, the $Q_x$ ring is a 6-member ring that contains one cyclic urea group. In another embodiment, the 6-member $Q_x$ ring containing one cyclic urea group contains three nitrogen atoms, including the nitrogen atoms of the cyclic urea group. In another embodiment, the 6-member $Q_x$ ring containing one cyclic urea group contains another carbonyl carbon atom or thiocarbonyl carbon atom in addition to the carbonyl carbon atom or thiocarbonyl carbon atom of the cyclic urea group. In another embodiment, the 6-member $Q_x$ ring containing one cyclic urea group contains three nitrogen atoms, including the nitrogen atoms of the cyclic urea group, and another carbonyl carbon atom or thiocarbonyl carbon atom in addition to the carbonyl carbon atom or thiocarbonyl carbon atom of the cyclic urea group.

In another embodiment, the $Q_x$ ring is a 5-membered ring. In another embodiment, the $Q_x$ ring is a 5-member ring that contains one cyclic urea group. In another embodiment, the 5-member $Q_x$ ring containing one cyclic urea group contains three nitrogen atoms, including the nitrogen atoms of the cyclic urea group. In another embodiment, the 5-member $Q_x$ ring containing one cyclic urea group contains another carbonyl carbon atom or thiocarbonyl carbon atom in addition to the carbonyl carbon atom or thiocarbonyl carbon atom of the cyclic urea group. In another embodiment, the 5-member $Q_x$ ring containing one cyclic urea group contains three nitrogen atoms, including the nitrogen atoms of the cyclic urea group, and another carbonyl carbon atom or thiocarbonyl carbon atom in addition to the carbonyl carbon atom or thiocarbonyl carbon atom of the cyclic urea group.

In another embodiment, the $Q_x$ ring contains one lactam group. In another embodiment, the $Q_x$ ring is a 6-member ring that contains one lactam group. In another embodiment, the 6-member $Q_x$ ring containing one lactam group contains two nitrogen atoms, including the nitrogen atom of the lactam group. In another embodiment, the 6-member $Q_x$ ring containing one lactam group contains three nitrogen atoms, including the nitrogen atom of the lactam group. In another embodiment, the 6-member $Q_x$ ring containing one lactam group contains another carbonyl carbon atom or thiocarbonyl carbon atom in addition to the carbonyl carbon atom or thiocarbonyl carbon atom of the lactam group. In another embodiment, the 6-member $Q_x$ ring containing one lactam group contains two nitrogen atoms, including the nitrogen atom of the lactam group, and another carbonyl carbon atom or thiocarbonyl carbon atom in addition to the carbonyl carbon atom or thiocarbonyl carbon atom of the lactam group. In another embodiment, the 6-member $Q_x$ ring containing one lactam group contains three nitrogen atoms, including the nitrogen atom of the lactam group, and another carbonyl carbon atom or thiocarbonyl carbon atom in addition to the carbonyl carbon atom or thiocarbonyl carbon atom of the lactam group.

In another embodiment, the $Q_x$ ring is a 5-member ring that contains one lactam group. In another embodiment, the 5-member $Q_x$ ring containing one lactam group contains two nitrogen atoms, including the nitrogen atom of the lactam group. In another embodiment, the 5-member $Q_x$ ring containing one lactam group contains three nitrogen atoms, including the nitrogen atom of the lactam group. In another embodiment, the 5-member $Q_x$ ring containing one lactam group contains another carbonyl carbon atom or thiocarbonyl carbon atom in addition to the carbonyl carbon atom or thiocarbonyl carbon atom of the lactam group. In another embodiment, the 5-member $Q_x$ ring containing one lactam group contains two nitrogen atoms, including the nitrogen atom of the lactam group, and another carbonyl carbon atom or thiocarbonyl carbon atom in addition to the carbonyl carbon atom or thiocarbonyl carbon atom of the lactam group. In another embodiment, the 5-member $Q_x$ ring containing one lactam group contains three nitrogen atoms, including the nitrogen atom of the lactam group, and another carbonyl carbon atom or thiocarbonyl carbon atom in addition to the carbonyl carbon atom or thiocarbonyl carbon atom of the lactam group.

In another embodiment, the $Q_x$ ring is:

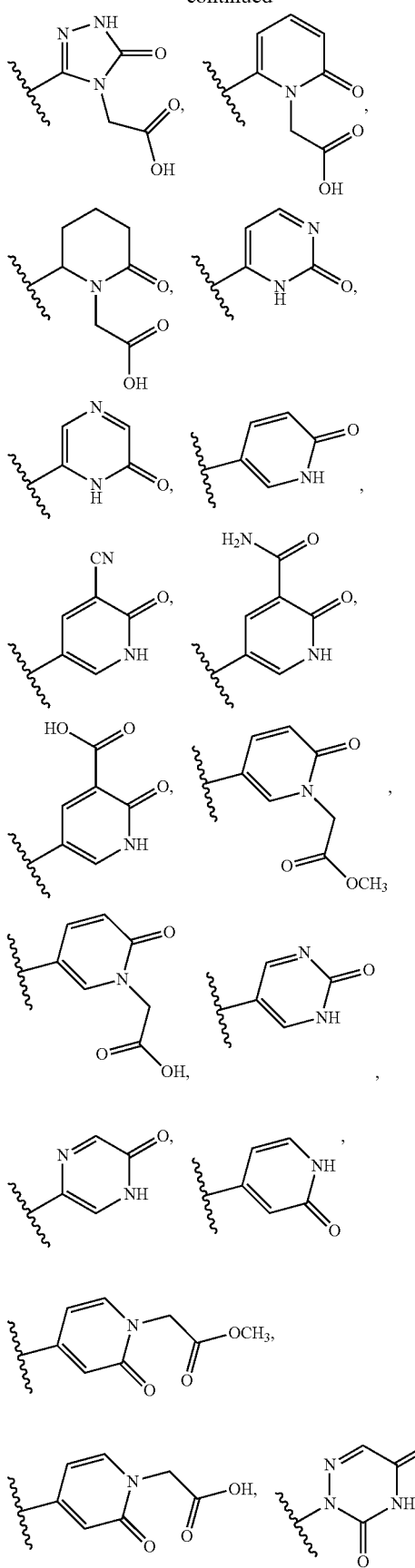
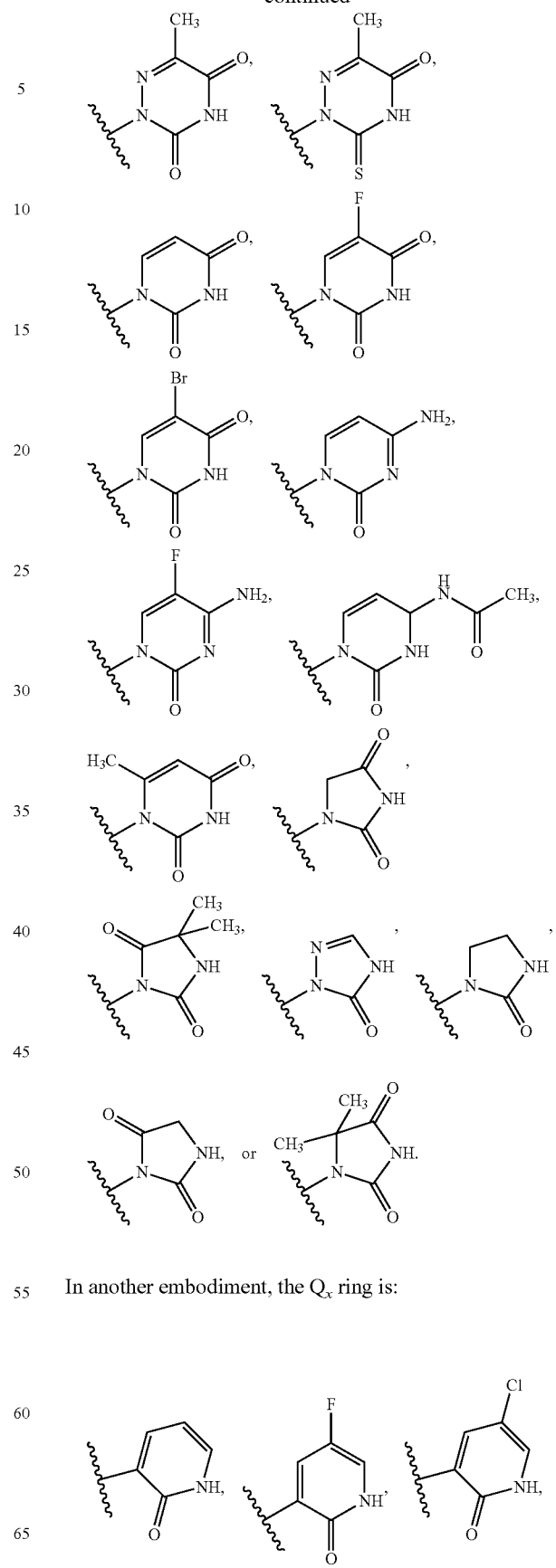
In another embodiment, the $Q_x$ ring is:
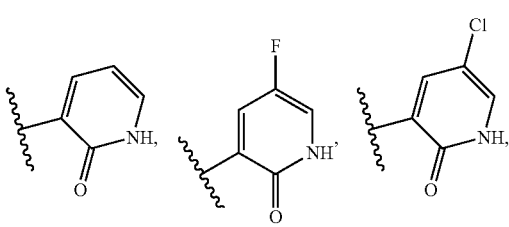

-continued
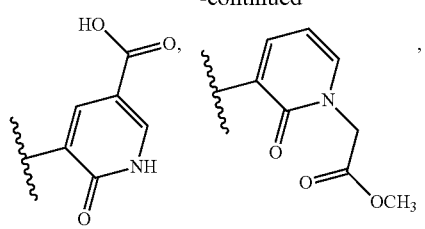
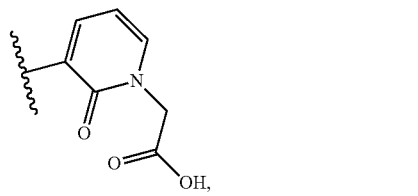
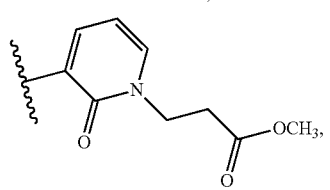
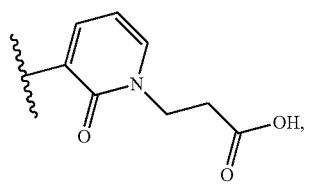
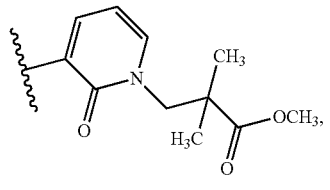
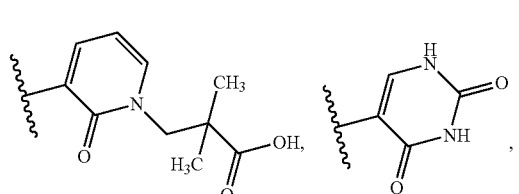
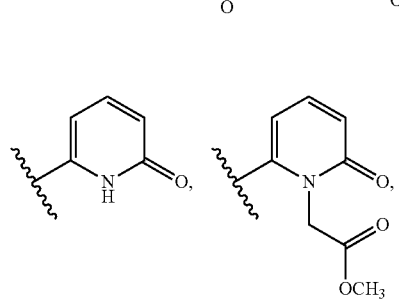
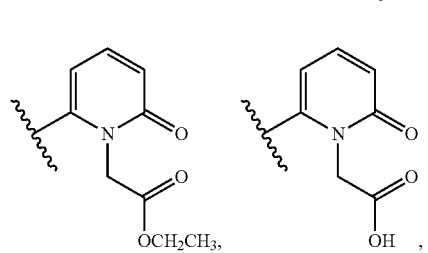
-continued
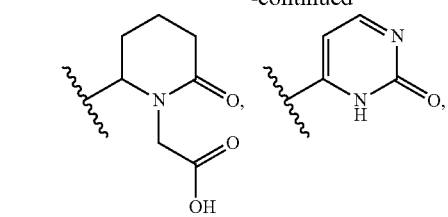
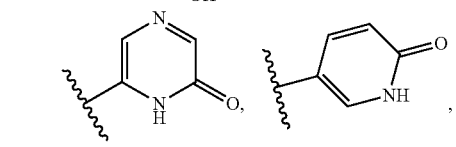
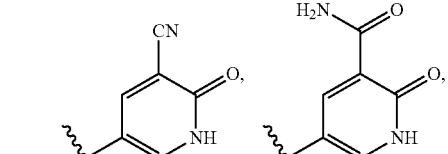
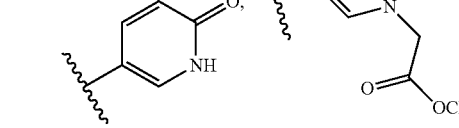
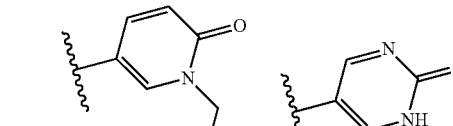
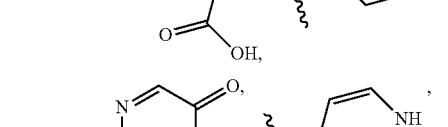
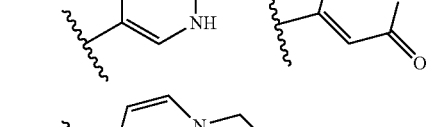
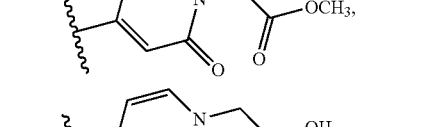
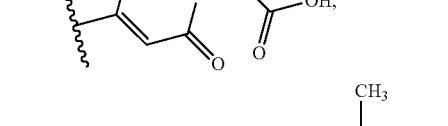
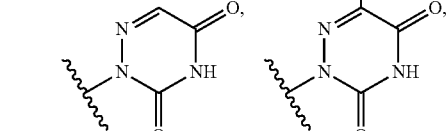
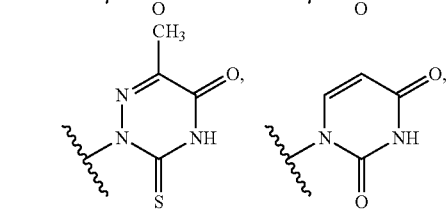

-continued
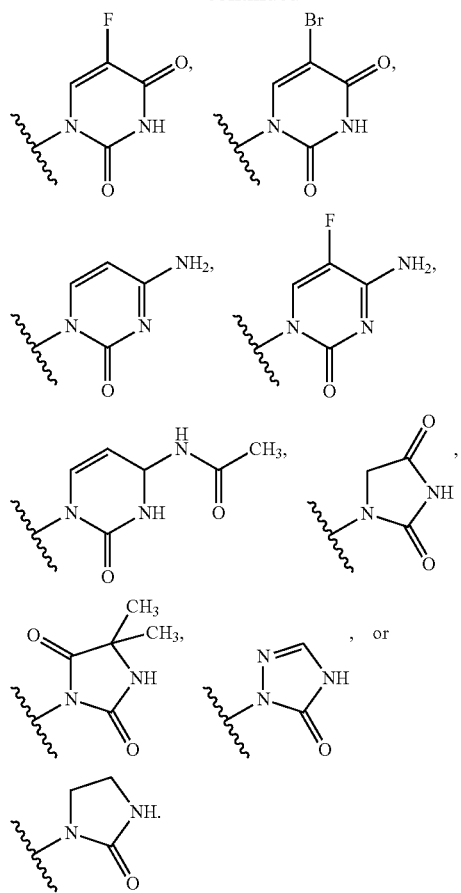
In another embodiment, the $Q_x$ ring is:
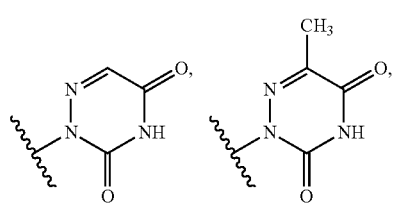
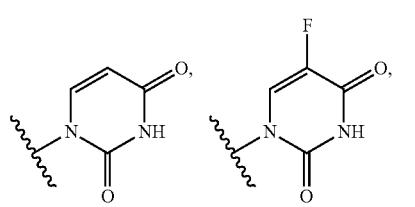
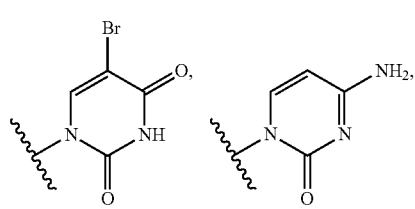
-continued
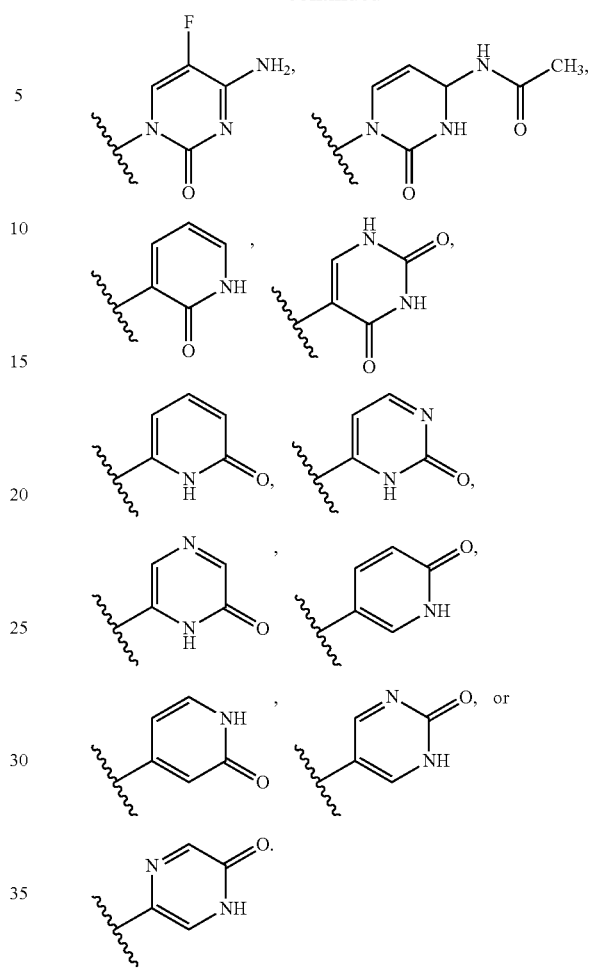
In another embodiment, the $Q_x$ ring is:
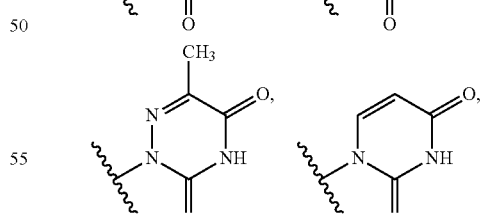
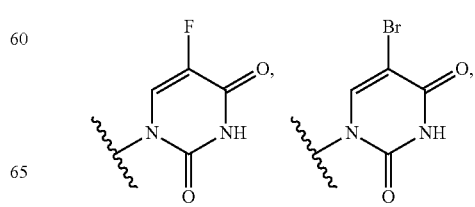

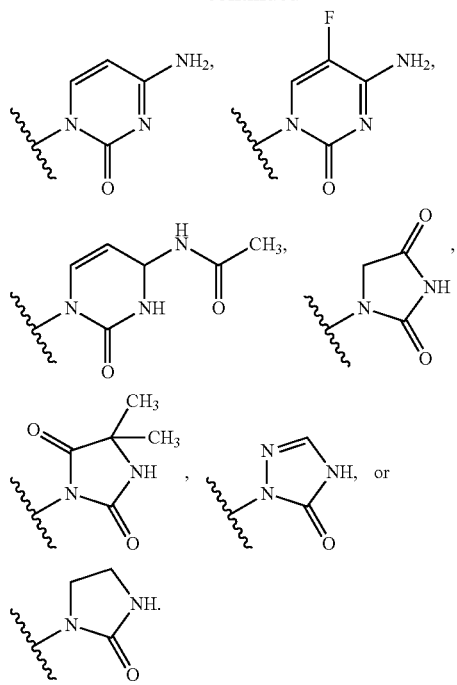
In another embodiment, the Q_x ring is:
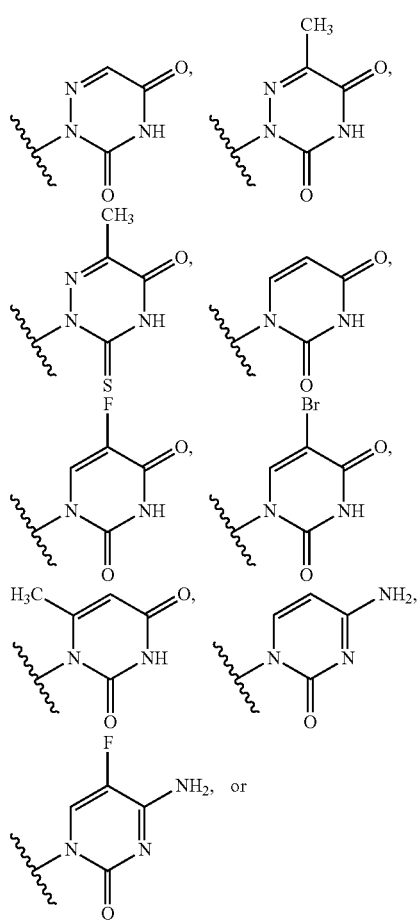
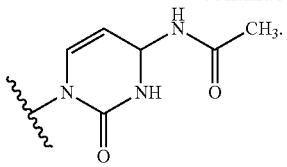
In another embodiment, the Q_x ring is:
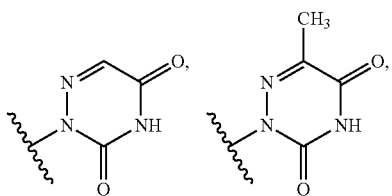
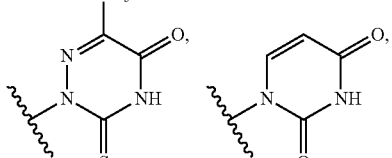
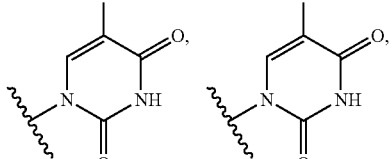
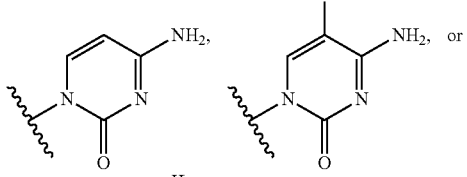
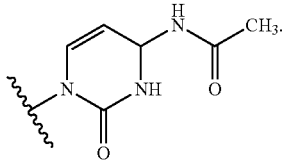
In another embodiment, the Q_x ring is:
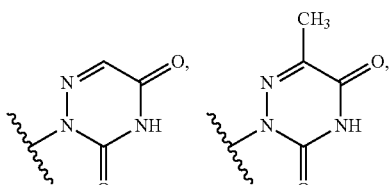
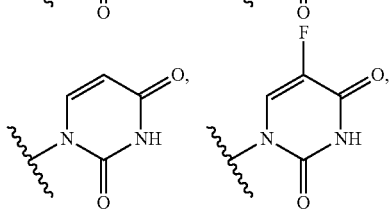

-continued
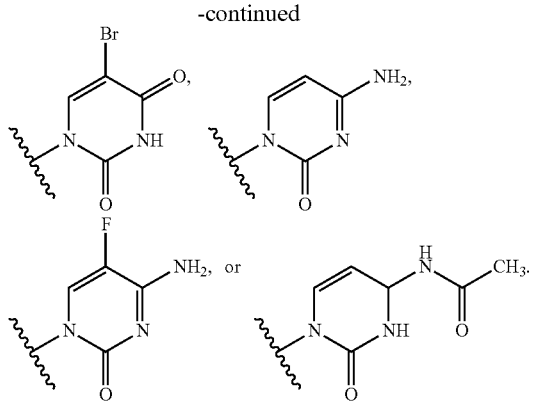
In another embodiment, the $Q_x$ ring is:
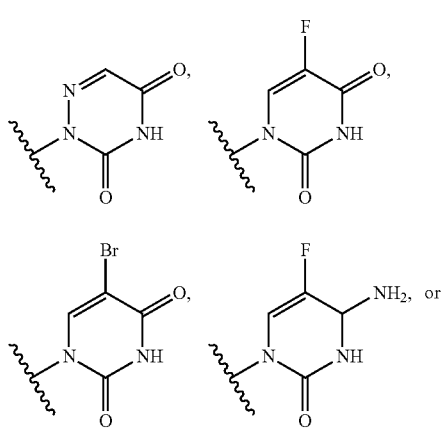
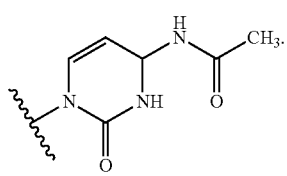
In another embodiment, the $Q_x$ ring is:
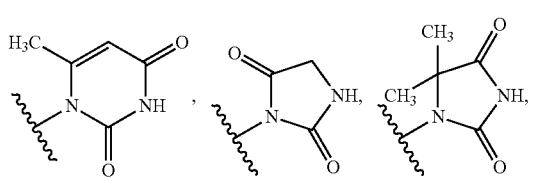
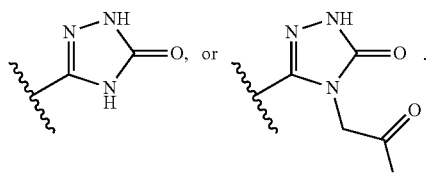
In another embodiment, the $Q_x$ ring is:
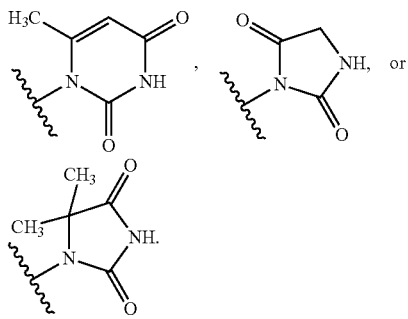
In another embodiment, the $Q_x$ ring is:
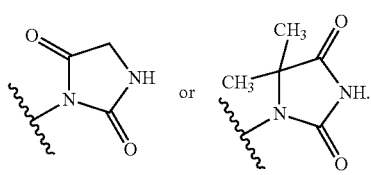
In another embodiment, the $Q_x$ ring is:
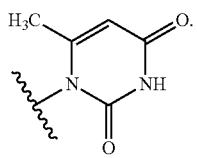
In another embodiment, the $Q_x$ ring is:
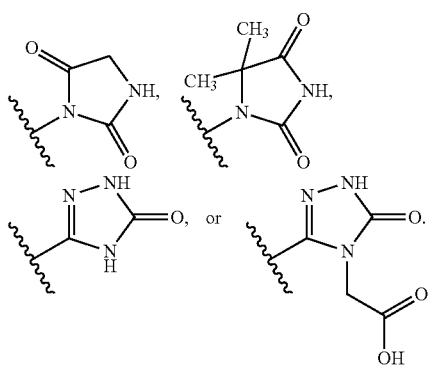
In another embodiment, the $Q_x$ ring is:
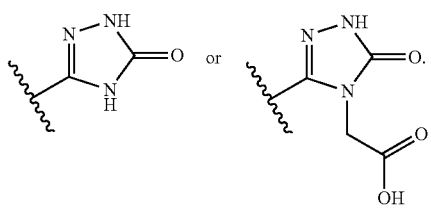 [SMILES: *c1n[nH]c(=O)[nH]1 ; *c1n[nH]c(=O)n1CC(=O)O]

In another embodiment, the Q_x ring is:
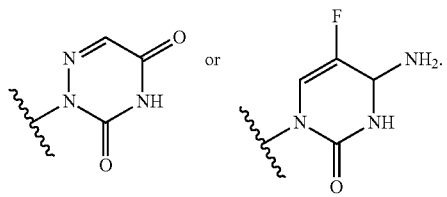 [SMILES: *n1ncc(=O)[nH]c1=O ; *N1C=C(F)C(N)NC1=O] or 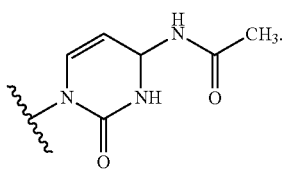
In another embodiment, the Q_x ring is:
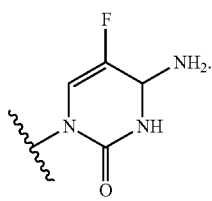 [SMILES: *N1C=C(F)C(N)NC1=O]
In another embodiment, the Q_x ring is:
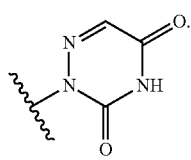 [SMILES: *n1ncc(=O)[nH]c1=O]
In another embodiment, the Q_x ring is:
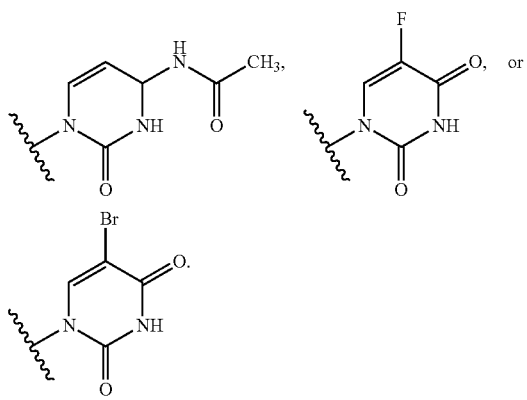
In another embodiment, the Q_x ring is:
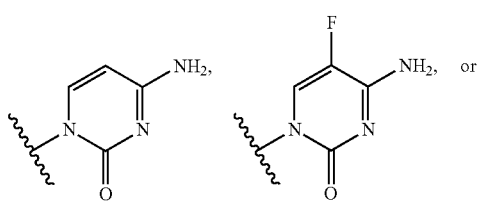
In another embodiment, the Q_x ring is:
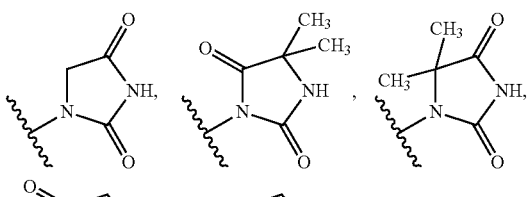
In another embodiment, the Q_x ring is:
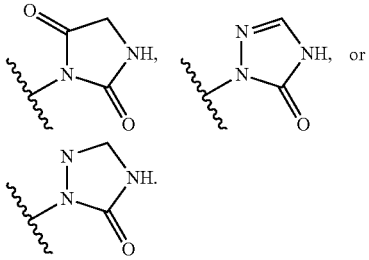
In another embodiment, the Q_x ring is:
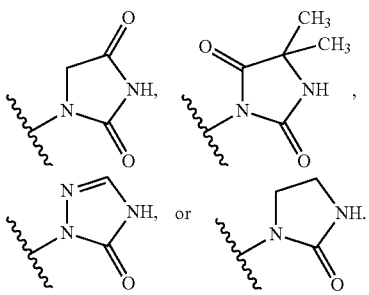
In another embodiment, the Q_x ring is:
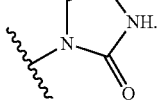

In another embodiment, the Q$_x$ ring is:
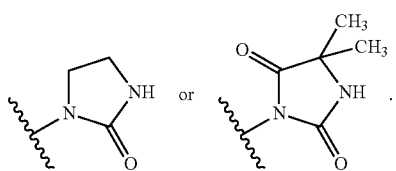 or
In another embodiment, the Q$_x$ ring is:
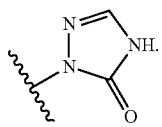 [SMILES: *n1nc[nH]c1=O]
In another embodiment, the Q$_x$ ring is:
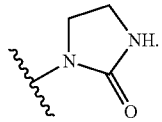
In another embodiment, the Q$_x$ ring is:
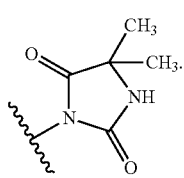 [SMILES: *N1C(=O)NC(C)(C)C1=O]
In another embodiment, the Q$_x$ ring is:
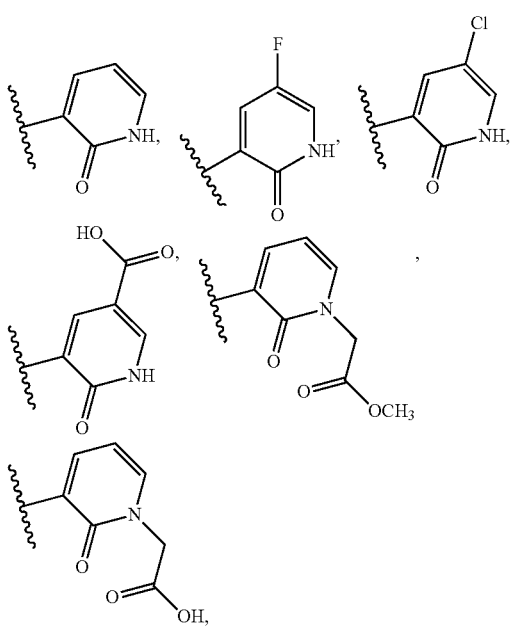
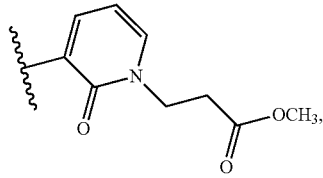
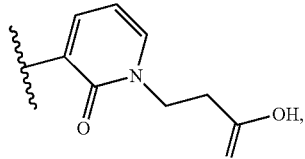
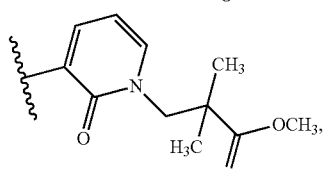
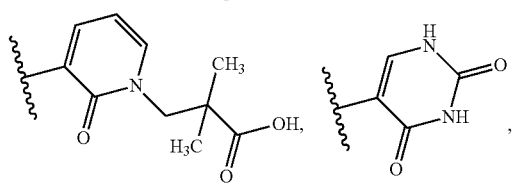
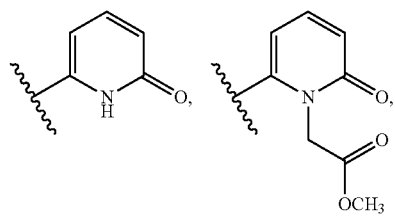
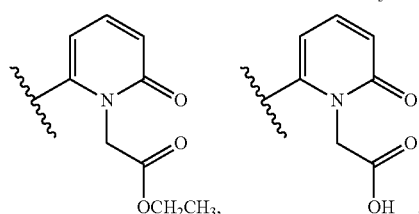
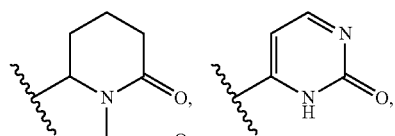
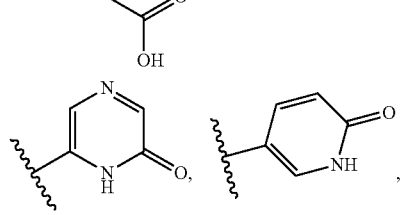
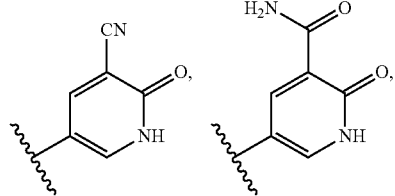

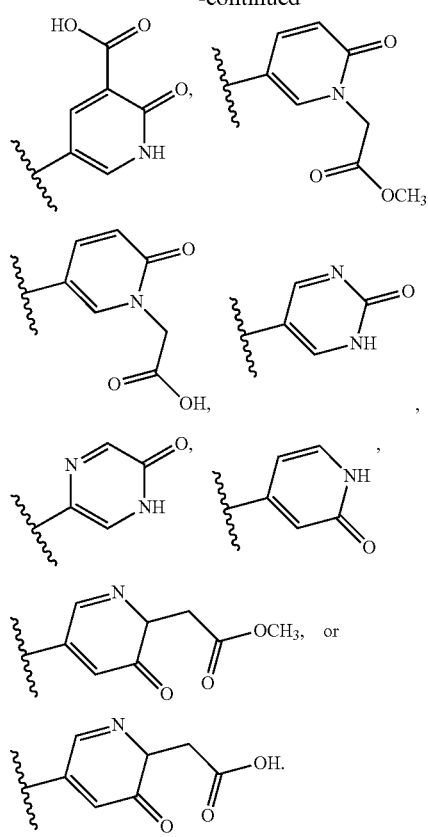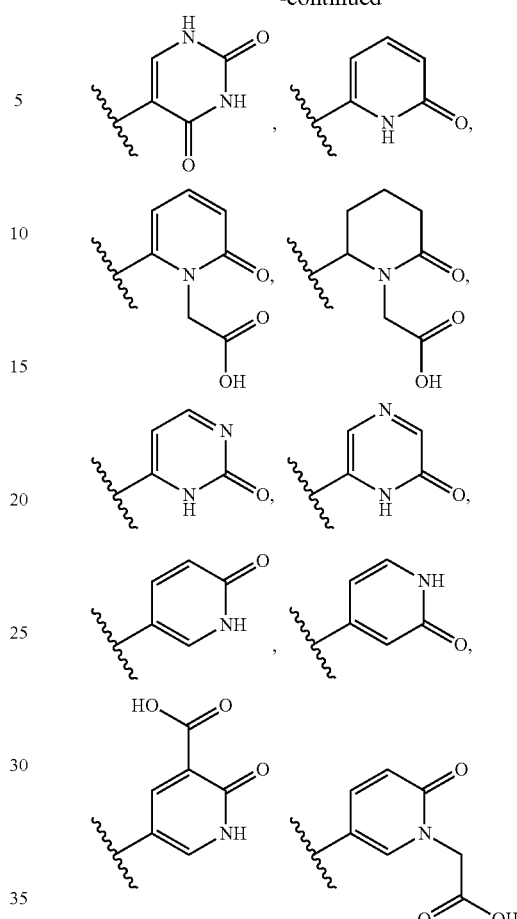
In another embodiment, the $Q_x$ ring is:
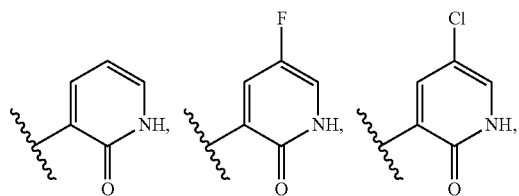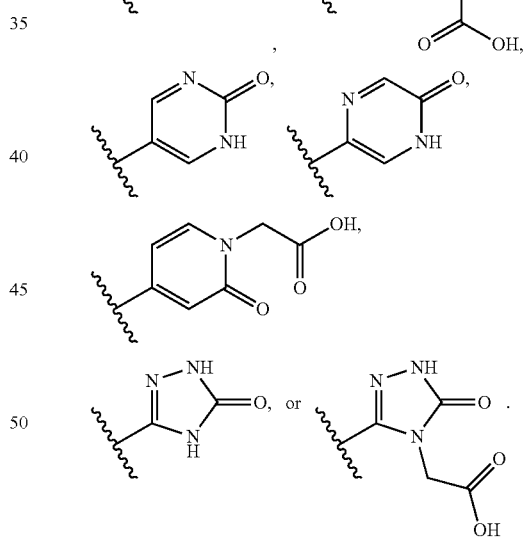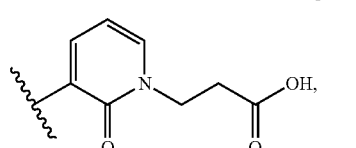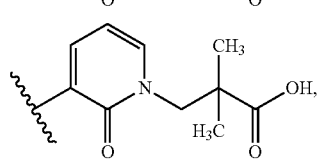
In another embodiment, the $Q_x$ ring is:
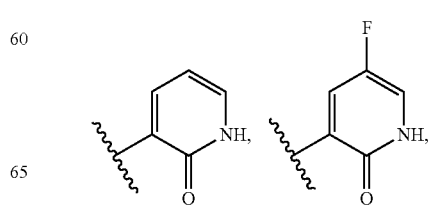

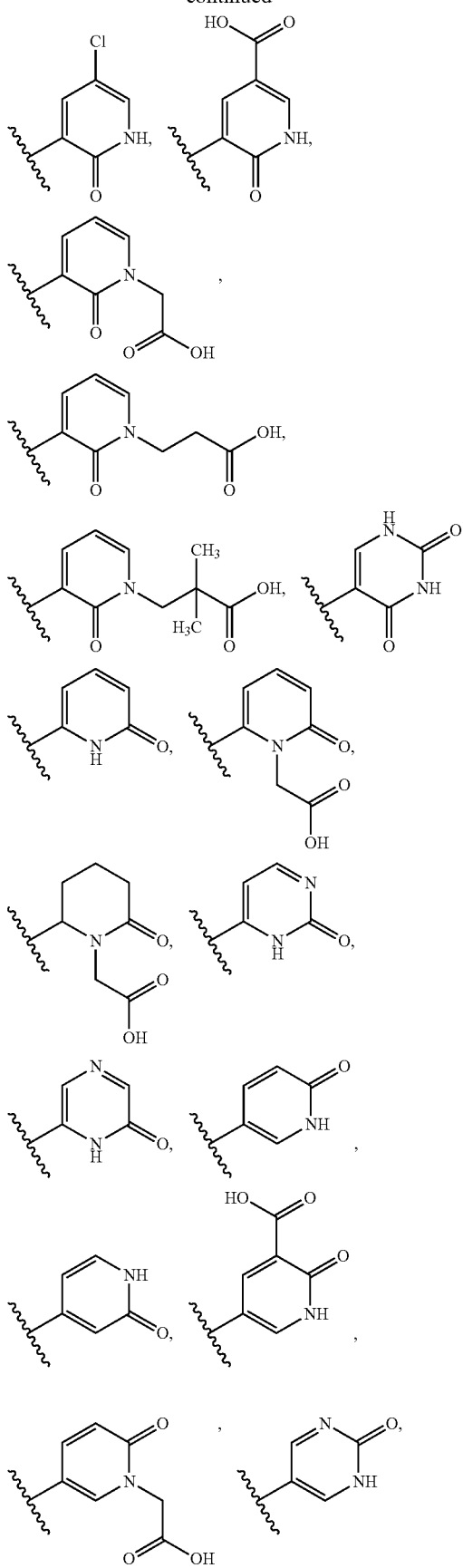
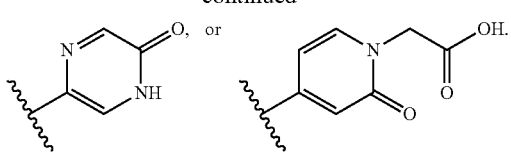
In another embodiment, the $Q_x$ ring is:

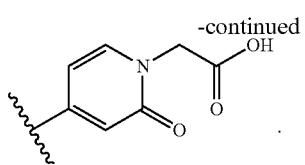
In another embodiment, the $Q_x$ ring is:
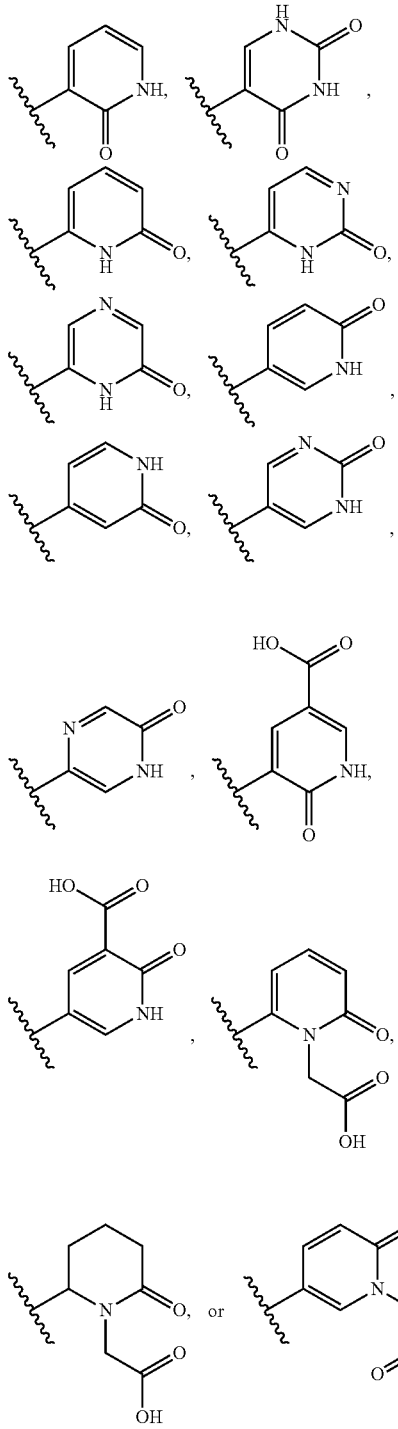
In another embodiment, the $Q_x$ ring is:
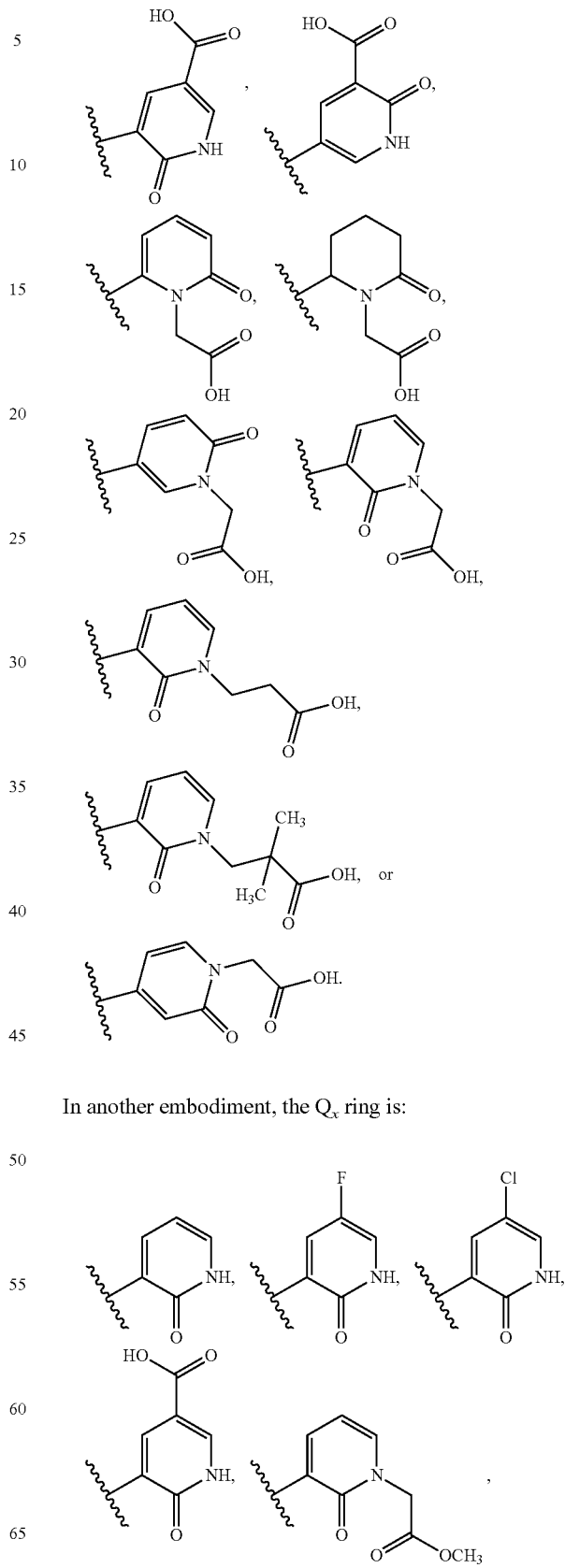

-continued
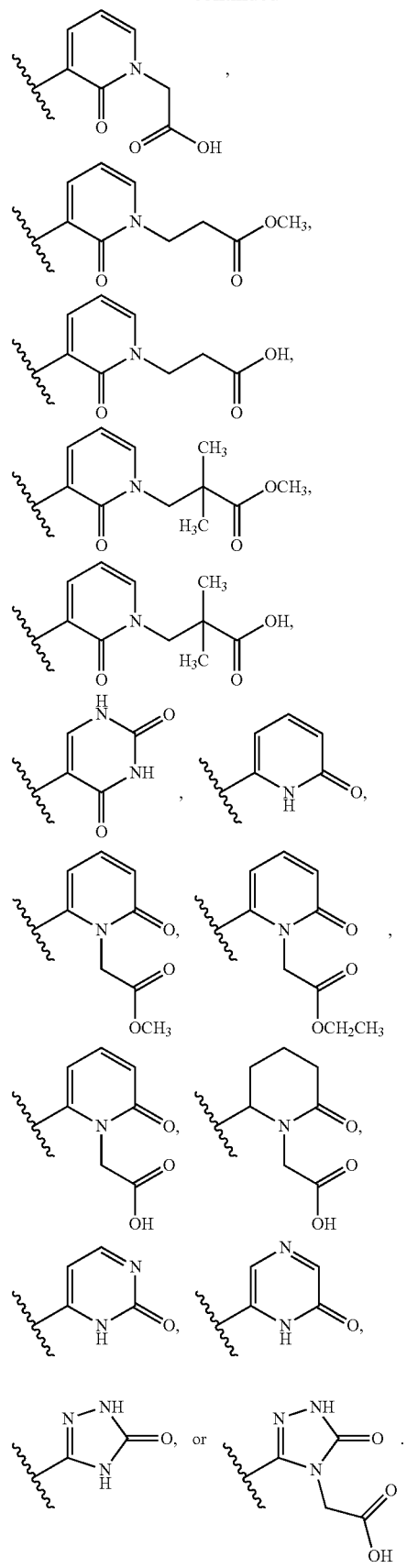
In another embodiment, the $Q_x$ ring is:
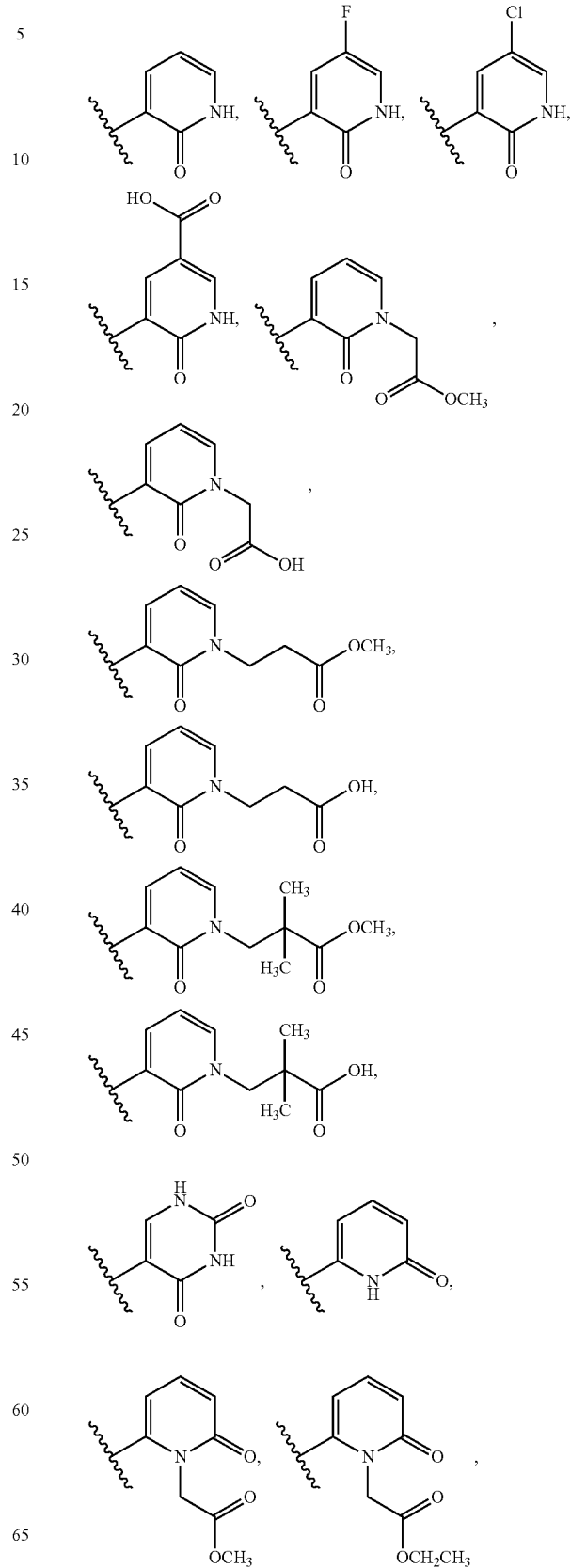

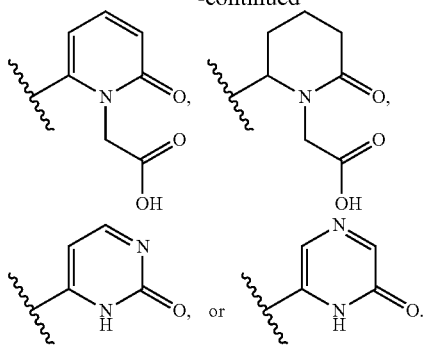
In another embodiment, the $Q_x$ ring is:
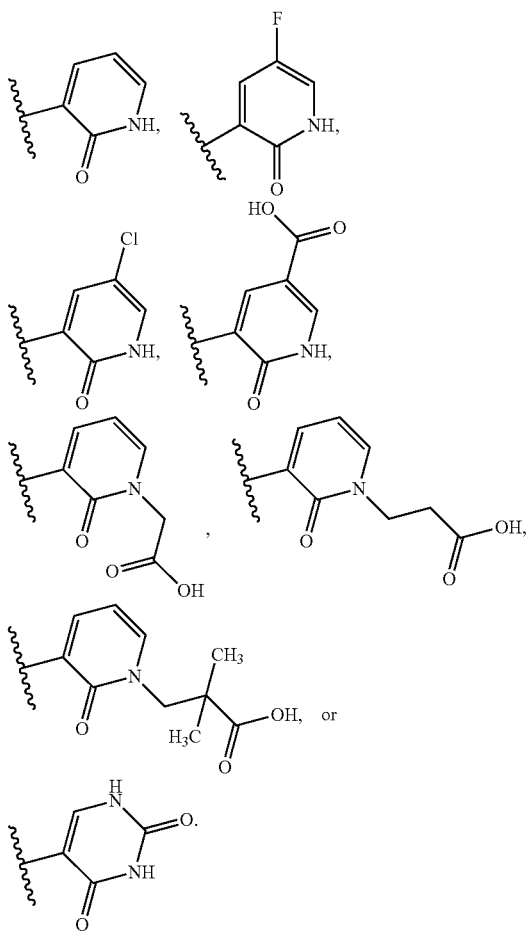
In another embodiment, the $Q_x$ ring is:
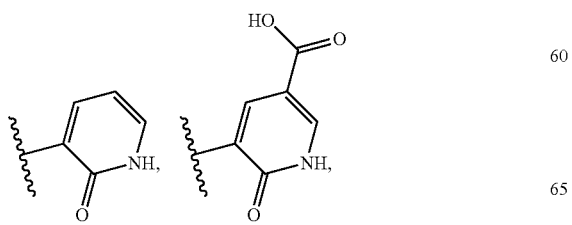
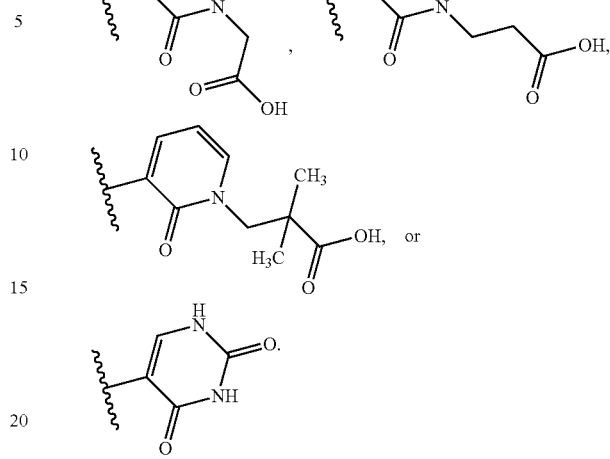
In another embodiment, the $Q_x$ ring is:
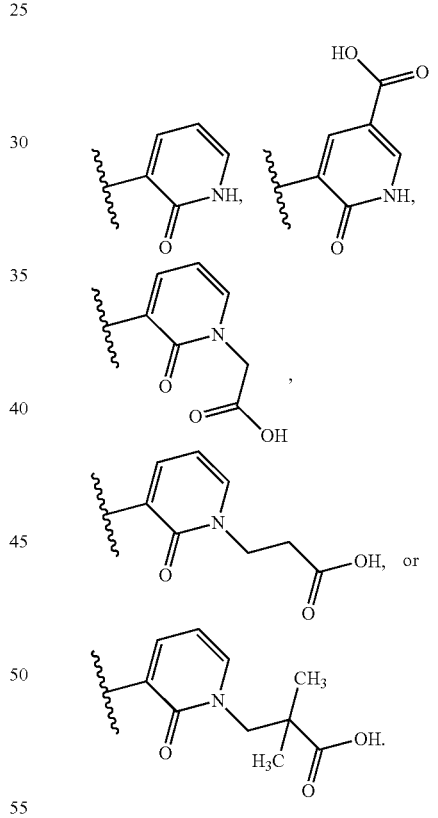
In another embodiment, the $Q_x$ ring is:
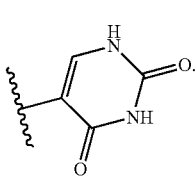 [SMILES: *c1c[nH]c(=O)[nH]c1=O]

In another embodiment, the Q$_x$ ring is:
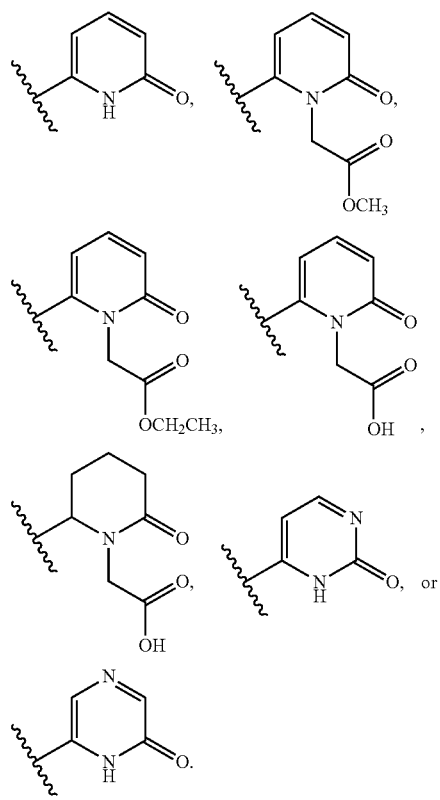
In another embodiment, the Q$_x$ ring is:
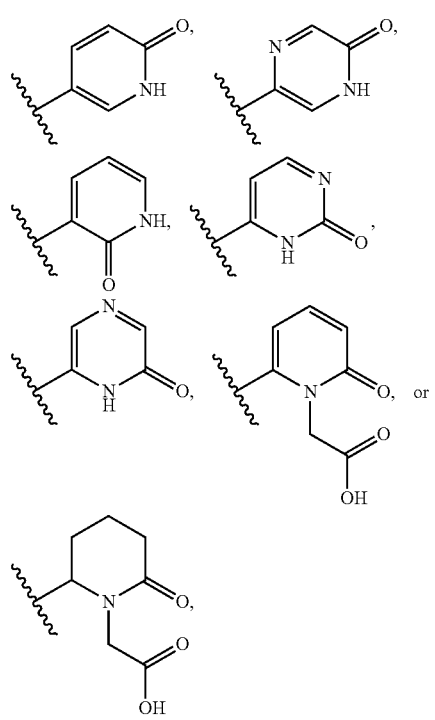
In another embodiment, the Q$_x$ ring is:
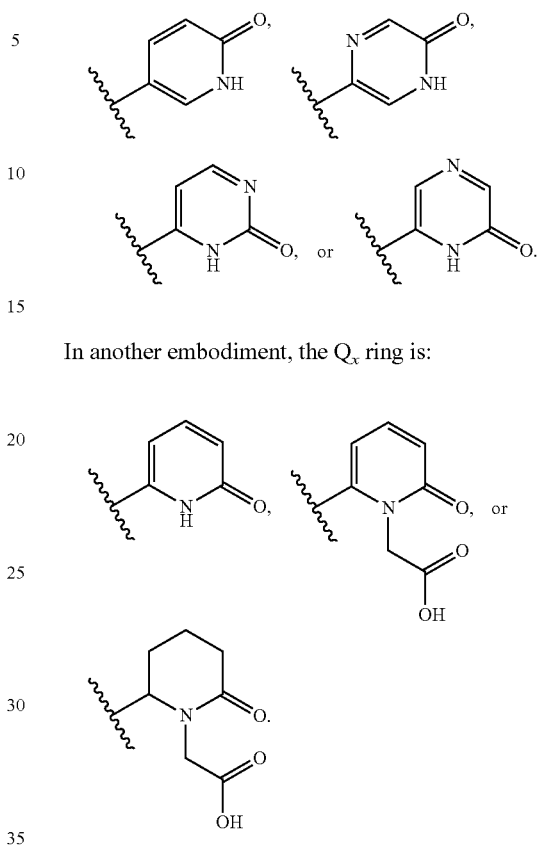
In another embodiment, the Q$_x$ ring is:
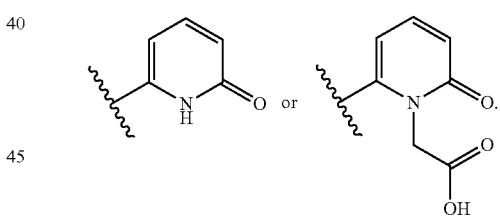
In another embodiment, the Q$_x$ ring is:
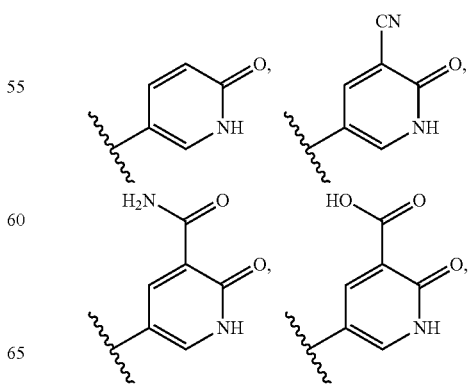

-continued
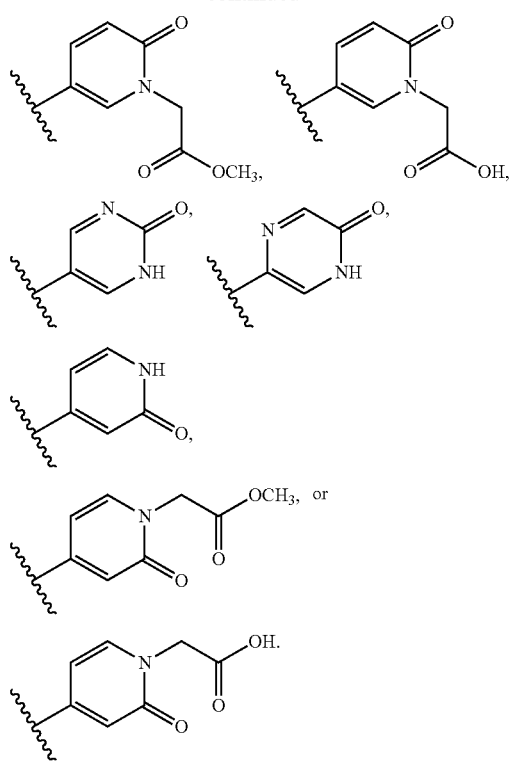
In another embodiment, the $Q_x$ ring is:
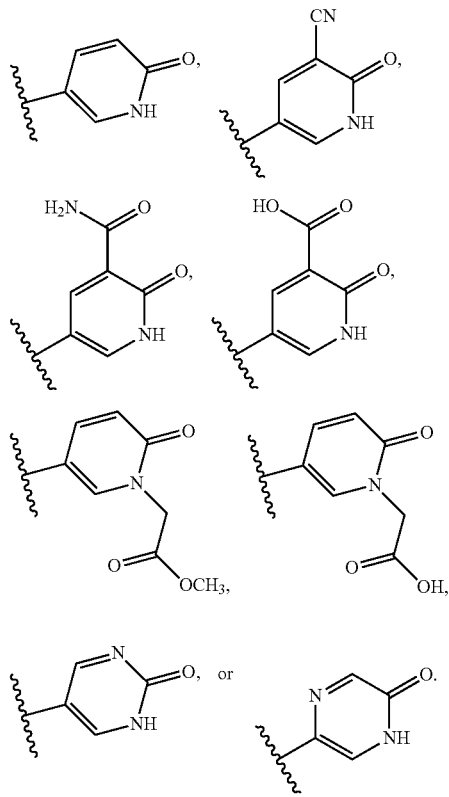
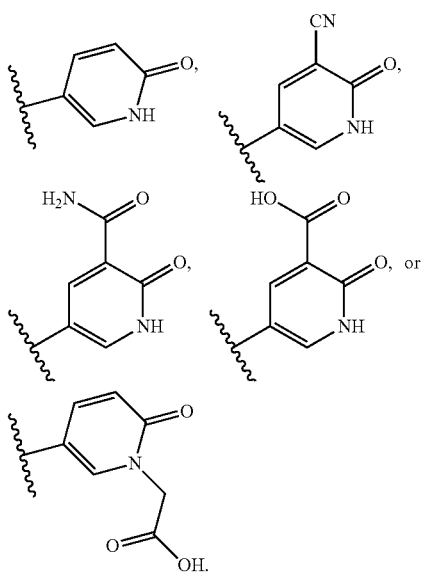
In another embodiment, the $Q_x$ ring is:
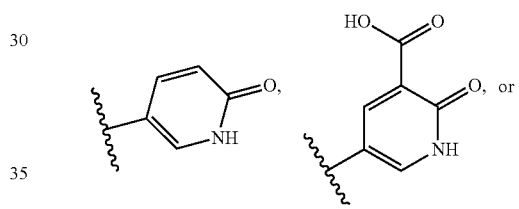
In another embodiment, the $Q_x$ ring is:
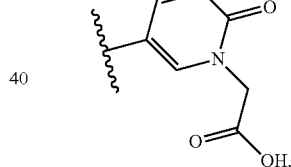
In another embodiment, the $Q_x$ ring is:
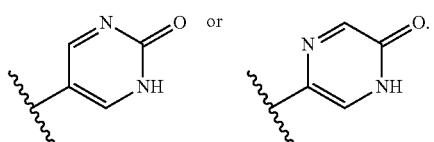 [SMILES: *c1cnc(=O)[nH]c1 ; *c1c[nH]c(=O)cn1]
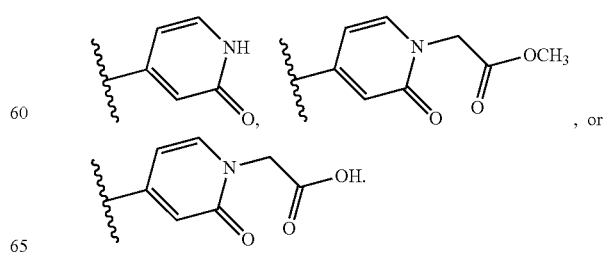

95

In another embodiment, the $Q_x$ ring is:

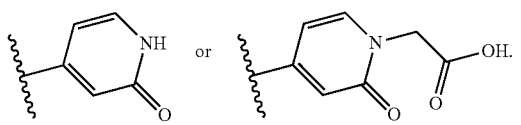 [SMILES: *c1cc[nH]c(=O)c1 ; *c1ccn(CC(=O)O)c(=O)c1]

In another embodiment, a is 1, $Q_a$ is benzo or pyridino, and $R_2$ is attached at the position shown below, denoted for purposes of the $R_2$-attachment-position herein as the "6-position", of the benzo or pyridino, e.g., as illustrated below:

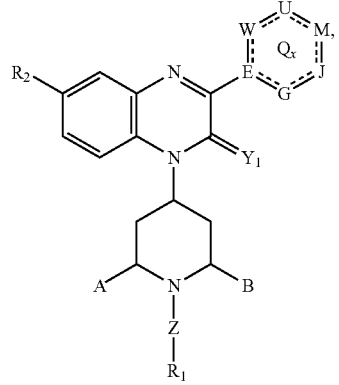

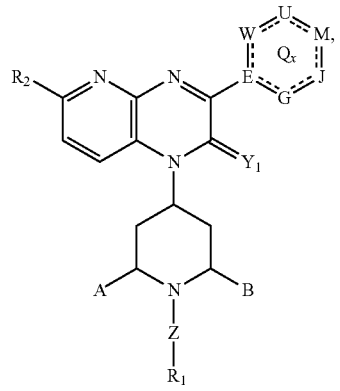

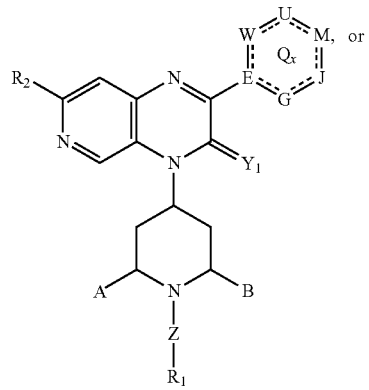

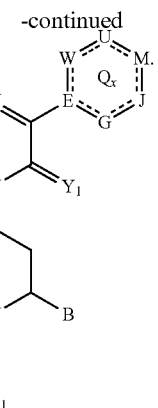

In another embodiment, a is 1, $Q_a$ is benzo or pyridino, $R_2$ is -halo, and $R_2$ is attached at the 6-position of the benzo or pyridino as illustrated immediately above. In another embodiment, a is 1, $Q_a$ is benzo or pyridino, $R_2$ is —F or —Cl, and $R_2$ is attached at the 6-position of the benzo or pyridino as illustrated immediately above. In another embodiment, a is 1, $Q_a$ is benzo or pyridino, $R_2$ is —F, and $R_2$ is attached at the 6-position of the benzo or pyridino as illustrated immediately above.

In another embodiment, $Q_a$ is benzo. In another embodiment, $Q_a$ is pyridino. In another embodiment, $Q_a$ is pyridino and the 2- and 3-positions of the pyridino are fused to the 6-membered, nitrogen-containing ring as illustrated, inter alia, for compounds according to Formula (IB) in Table 1, and the like. In another embodiment, $Q_a$ is pyridino and the 2- and 3-positions of the pyridino are fused to the 6-membered, nitrogen-containing ring as illustrated, inter alia, for compounds according to Formula (IC) in Table 1, and the like.

In another embodiment, each $R_7$ is independently selected from —$(C_1$-$C_4)$alkyl, —$OR_9$, —$SR_9$, —$C(halo)_3$, —$CH(halo)_2$, —$CH_2(halo)$, -halo, —$N(R_9)_2$, —$N(R_9)C(=O)OR_{12}$, —$C(=O)OR_9$, and —$OC(=O)R_9$. In another embodiment, each $R_7$ is independently selected from —$(C_1$-$C_4)$alkyl, —$OR_9$, —$C(halo)_3$, —$CH(halo)_2$, —$CH_2(halo)$, -halo, —$N(R_9)_2$, —$C(=O)OR_9$, and —$OC(=O)R_9$. In another embodiment, each $R_7$ is independently selected from —$(C_1$-$C_4)$alkyl, —$OR_9$, —$C(halo)_3$, -halo, —$N(R_9)_2$, and —$C(=O)OR_9$.

In another embodiment, each $R_8$ is independently selected from —$(C_1$-$C_4)$alkyl, —$(C_2$-$C_6)$alkenyl, —$(C_2$-$C_6)$alkynyl, -(5- or 6-membered)heteroaryl, —$(C_1$-$C_6)$alkyl-$C(=O)OR_9$, —$N(R_9)(C_1$-$C_6)$alkyl-$C(=O)OR_9$, —$OR_9$, —$SR_9$, —$C(halo)_3$, —$CH(halo)_2$, —$CH_2(halo)$, —$CN$, $=O$, $=S$, -halo, —$NO_2$, —$CH=N(R_9)$, —$N(R_9)_2$, —$N(R_9)OH$, —$N(R_9)S(=O)R_{12}$, —$N(R_9)S(=O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$S(=O)R_9$, and —$S(=O)_2R_9$. In another embodiment, each $R_8$ is independently selected from —$(C_1$-$C_4)$alkyl, —$(C_2$-$C_6)$alkenyl, -(5- or 6-membered)heteroaryl, —$(C_1$-$C_6)$alkyl-$C(=O)OR_9$, —$N(R_9)(C_1$-$C_6)$alkyl-$C(=O)OR_9$, —$OR_9$, —$SR_9$, —$C(halo)_3$, —$CH(halo)_2$, —$CH_2(halo)$, $=O$, $=S$, -halo, —$CH=N(R_9)$, —$N(R_9)_2$, —$N(R_9)OH$, —$N(R_9)S(=O)R_{12}$, —$N(R_9)S(=O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$S(=O)R_9$, and —$S(=O)_2R_9$. In another embodiment, each $R_8$ is independently selected from —$(C_1$-$C_4)$alkyl, —$(C_2$-$C_6)$alkenyl, -(5- or 6-membered)heteroaryl, —$(C_1$-$C_6)$alkyl-$C(=O)OR_9$, —$N(R_9)(C_1$-$C_6)$alkyl-$C(=O)$ $OR_9$, $-OR_9$, $-SR_9$, $-C(halo)_3$, $-CH(halo)_2$, $-CH_2(halo)$, -halo, $-CH=N(R_9)$, $-N(R_9)_2$, $-N(R_9)OH$, $-N(R_9)S(=O)_2R_{12}$, $-N(R_9)C(=O)R_{12}$, $-N(R_9)C(=O)N(T_1)(T_2)$, $-N(R_9)C(=O)OR_{12}$, $-C(=O)R_9$, $-C(=O)N(T_1)(T_2)$, $-C(=O)OR_9$, $-OC(=O)R_9$, and $-S(=O)_2R_9$. In another embodiment, each $R_8$ is independently selected from $-(C_1-C_4)$alkyl, -(5- or 6-membered)heteroaryl, $-(C_1-C_6)$alkyl-C(=O)OR_9, $-N(R_9)(C_1-C_6)$alkyl-C(=O)OR_9, $-OR_9$, $-SR_9$, $-C(halo)_3$, $-CH(halo)_2$, $-CH_2(halo)$, -halo, $-N(R_9)_2$, $-N(R_9)S(=O)_2R_{12}$, $-N(R_9)C(=O)R_{12}$, $-N(R_9)C(=O)N(T_1)(T_2)$, $-N(R_9)C(=O)OR_{12}$, $-C(=O)R_9$, $-C(=O)N(T_1)(T_2)$, $-C(=O)OR_9$, $-OC(=O)R_9$, and $-S(=O)_2R_9$. In another embodiment, each $R_8$ is independently selected from $-(C_1-C_4)$alkyl, -(5- or 6-membered)heteroaryl, $-(C_1-C_6)$alkyl-C(=O)OR_9, $-N(R_9)(C_1-C_6)$alkyl-C(=O)OR_9, $-OR_9$, $-SR_9$, $-C(halo)_3$, $-CH(halo)_2$, $-CH_2(halo)$, -halo, $-N(R_9)_2$, $-N(R_9)S(=O)_2R_{12}$, $-N(R_9)C(=O)R_{12}$, $-C(=O)R_9$, $-C(=O)N(T_1)(T_2)$, $-C(=O)OR_9$, $-OC(=O)R_9$, and $-S(=O)_2R_9$. In another embodiment, each $R_8$ is independently selected from $-(C_1-C_4)$alkyl, $-(C_1-C_6)$alkyl-C(=O)OR_9, $-N(R_9)(C_1-C_6)$alkyl-C(=O)OR_9, $-OR_9$, $-C(halo)_3$, $-CH(halo)_2$, $-CH_2(halo)$, -halo, $-N(R_9)_2$, $-C(=O)N(T_1)(T_2)$, and $-C(=O)OR_9$.

In another embodiment, each $R_9$ is independently $-H$, $-(C_1-C_6)$alkyl, $-(C_2-C_6)$alkenyl, $-(C_3-C_8)$cycloalkyl, -phenyl, -benzyl, -(3- to 7-membered)heterocycle, $-C(halo)_3$, $-CH(halo)_2$, or $-CH_2(halo)$. In another embodiment, each $R_9$ is independently $-H$, $-(C_1-C_6)$alkyl, $-(C_3-C_8)$cycloalkyl, -phenyl, -benzyl, -(3- to 7-membered)heterocycle, $-C(halo)_3$, $-CH(halo)_2$, or $-CH_2(halo)$. In another embodiment, each $R_9$ is independently $-H$, $-(C_1-C_6)$alkyl, $-C(halo)_3$, $-CH(halo)_2$, or $-CH_2(halo)$. In another embodiment, each $R_9$ is independently $-H$ or $-(C_1-C_3)$alkyl.

In another embodiment, each $T_1$ and $T_2$ is independently $-H$ or $-(C_1-C_3)$alkyl which is unsubstituted or substituted with an independently selected $R_5$ group. In another embodiment, each $T_1$ and $T_2$ is independently $-H$ or $-(C_1-C_3)$alkyl which is unsubstituted. In another embodiment, each $T_1$ and $T_2$ is independently $-H$ or $-CH_3$. In another embodiment, each $T_3$ is independently $-H$ or $-(C_1-C_3)$alkyl which is unsubstituted or substituted with an independently selected $R_5$ group. In another embodiment, each $T_3$ is independently $-H$ or $-(C_1-C_3)$alkyl which is unsubstituted. In another embodiment, each $T_3$ is independently $-H$ or $-CH_3$.

In another embodiment, each $R_5$ is independently selected from $-(C_1-C_4)$alkyl, $-(C_2-C_6)$alkenyl, $-(C_2-C_6)$alkynyl, -(5- or 6-membered)heteroaryl, $-(C_1-C_6)$alkyl-C(=O)OR_9, $-N(R_9)(C_1-C_6)$alkyl-C(=O)OR_9, $-OR_9$, $-SR_9$, $-C(halo)_3$, $-CH(halo)_2$, $-CH_2(halo)$, $-CN$, $=O$, $=S$, -halo, $-NO_2$, $-CH=N(R_9)$, $-N(R_9)_2$, $-N(R_9)OH$, $-N(R_9)S(=O)R_{12}$, $-N(R_9)S(=O)_2R_{12}$, $-N(R_9)C(=O)R_{12}$, $-N(R_9)C(=O)OR_{12}$, $-C(=O)R_9$, $-C(=O)OR_9$, $-OC(=O)R_9$, $-S(=O)R_9$, and $-S(=O)_2R_9$. In another embodiment, each $R_5$ is independently selected from $-(C_1-C_4)$alkyl, $-(C_2-C_6)$alkenyl, -(5- or 6-membered)heteroaryl, $-(C_1-C_6)$alkyl-C(=O)OR_9, $-N(R_9)(C_1-C_6)$alkyl-C(=O)OR_9, $-OR_9$, $-SR_9$, $-C(halo)_3$, $-CH(halo)_2$, $-CH_2(halo)$, $=O$, $=S$, -halo, $-CH=N(R_9)$, $-N(R_9)_2$, $-N(R_9)OH$, $-N(R_9)S(=O)R_{12}$, $-N(R_9)S(=O)_2R_{12}$, $-N(R_9)C(=O)R_{12}$, $-N(R_9)C(=O)OR_{12}$, $-C(=O)R_9$, $-C(=O)OR_9$, $-OC(=O)R_9$, $-S(=O)R_9$, and $-S(=O)_2R_9$. In another embodiment, each $R_5$ is independently selected from $-(C_1-C_4)$alkyl, $-(C_2-C_6)$alkenyl, -(5- or 6-membered)heteroaryl, $-(C_1-C_6)$alkyl-C(=O)OR_9, $-N(R_9)(C_1-C_6)$alkyl-C(=O)OR_9, $-OR_9$, $-SR_9$, $-C(halo)_3$, $-CH(halo)_2$, $-CH_2(halo)$, -halo, $-CH=N(R_9)$, $-N(R_9)_2$, $-N(R_9)OH$, $-N(R_9)S(=O)_2R_{12}$, $-N(R_9)C(=O)R_{12}$, $-N(R_9)C(=O)OR_{12}$, $-C(=O)R_9$, $-C(=O)OR_9$, $-OC(=O)R_9$, and $-S(=O)_2R_9$. In another embodiment, each $R_5$ is independently selected from $-(C_1-C_4)$alkyl, -(5- or 6-membered)heteroaryl, $-(C_1-C_6)$alkyl-C(=O)OR_9, $-N(R_9)(C_1-C_6)$alkyl-C(=O)OR_9, $-OR_9$, $-SR_9$, $-C(halo)_3$, $-CH(halo)_2$, $-CH_2(halo)$, -halo, $-N(R_9)_2$, $-N(R_9)S(=O)_2R_{12}$, $-N(R_9)C(=O)R_{12}$, $-N(R_9)C(=O)OR_{12}$, $-C(=O)R_9$, $-C(=O)OR_9$, $-OC(=O)R_9$, and $-S(=O)_2R_9$. In another embodiment, each $R_5$ is independently selected from $-(C_1-C_4)$alkyl, -(5- or 6-membered)heteroaryl, $-(C_1-C_6)$alkyl-C(=O)OR_9, $-N(R_9)(C_1-C_6)$alkyl-C(=O)OR_9, $-OR_9$, $-SR_9$, $-C(halo)_3$, $-CH(halo)_2$, $-CH_2(halo)$, -halo, $-N(R_9)_2$, $-N(R_9)S(=O)_2R_{12}$, $-N(R_9)C(=O)R_{12}$, $-C(=O)R_9$, $-C(=O)OR_9$, $-OC(=O)R_9$, and $-S(=O)_2R_9$. In another embodiment, each $R_5$ is independently selected from $-(C_1-C_4)$alkyl, $-(C_1-C_6)$alkyl-C(=O)OR_9, $-N(R_9)(C_1-C_6)$alkyl-C(=O)OR_9, $-OR_9$, $-C(halo)_3$, $-CH(halo)_2$, $-CH_2(halo)$, -halo, $-N(R_9)_2$, and $-C(=O)OR_9$.

In another embodiment, $R_{11}$ is $-H$, $-CN$, or $-C(=O)N(R_6)_2$ or $R_{11}$ is $-(C_1-C_4)$alkyl which is unsubstituted or substituted with $-OH$, $-(C_1-C_4)$alkoxy, or $-N(R_6)_2$. In another embodiment, $R_{11}$ is $-H$ or $-(C_1-C_4)$alkyl which is unsubstituted or substituted with $-OH$, $-(C_1-C_4)$alkoxy, or $-N(R_6)_2$. In another embodiment, $R_{11}$ is $-H$. In another embodiment, $R_{11}$ is not $-C(=O)OH$. In another embodiment, $R_{14}$ is $-H$. In another embodiment, $R_{14}$ is not $-C(=O)OH$. In another embodiment, $R_{11}$ is $-H$ and $R_{14}$ is $-H$. In another embodiment, $R_{11}$ is not $-C(=O)OH$ and $R_{14}$ is not $-C(=O)OH$.

In another embodiment, h is 0. In another embodiment, h is 1. In another embodiment, h is 1 and $R_{13}$ is absent. In another embodiment, h is 0 and $R_{11}$ is $-H$. In another embodiment, h is 1 and $R_{11}$ is $-H$. In another embodiment, h is 0 or 1 and Z is $-(C_1-C_{10})$alkyl unsubstituted by $R_{13}$, i.e., Z is $-[(C_1-C_{10})$alkyl$]_h$.

In another embodiment, h is 1 and Z is $-(C_1-C_3)$alkyl optionally substituted by $R_{13}$. In another embodiment, h is 1, $R_{13}$ is absent, and Z is $-CH_2-$. In another embodiment, h is 1, $R_{13}$ is absent, and Z is $-CH_2-CH_2-$. In another embodiment, h is 1, $R_{13}$ is absent and Z is $-CH_2-CH_2-CH_2-$. In another embodiment, h is 1, Z is $-(C_1-C_3)$alkyl-, $R_1$ is phenyl, and the Z group (i.e., $-(C_1-C_3)$alkyl-) is substituted by $R_{13}$. In another embodiment, h is 1, Z is a $-(C_1-C_3)$alkyl-, $R_1$ is optionally-substituted phenyl, and the Z group is substituted by $R_{13}$ which is optionally-substituted phenyl. In another embodiment, h is 1, Z is a $-(C_1-C_3)$alkyl-, $R_1$ is unsubstituted phenyl, and the Z group is substituted by $R_{13}$ which is unsubstituted phenyl. In another embodiment, h is 1, Z is a $-(C_1-C_3)$alkyl-, and the Z group is substituted by $R_{13}$ which is $-CF_3$. In another embodiment, h is 1 and Z—$R_{13}$ is $-CH_2-CH(CF_3)-CH_2-$.

In another embodiment, $R_1$ is $-(C_1-C_6)$alkyl, $-(C_2-C_6)$alkenyl, $-(C_2-C_6)$alkynyl, $-O(C_1-C_6)$alkyl, $-(C_3-C_7)$cycloalkoxy, $-(C_6-C_{14})$bicycloalkyl, $-(C_8-C_{20})$tricycloalkyl, $-(C_5-C_{14})$cycloalkenyl, $-(C_7-C_{14})$bicycloalkenyl, $-(C_8-C_{20})$tricycloalkenyl, -(3- to 7-membered)heterocycle, or -(7- to 10-membered)bicycloheterocycle, each of which is unsubstituted or substituted with 1, 2, 3, or 4 independently selected $R_8$ groups.

In another embodiment, Z is $-(C_2-C_{10})$alkenyl-. In another embodiment, Z is $-(C_2-C_6)$alkenyl-. In another embodiment, Z is $-CH_2-CH=CH-$. In another embodiment, Z is $-CH_2-CH=CH-CH_2-$. In another embodiment, Z is a $-(C_3)$alkenyl-. In another embodiment, Z is n-prop-1,3-diyl and $R_1$ is an optionally substituted —($C_6$-$C_{14}$)bicycloalkyl or optionally substituted —($C_8$-$C_{20}$)tricycloalkyl. In another embodiment, Z—$R_1$ is —$CH_2$—CH=$R_1$. In another embodiment, Z—$R_1$ is —$CH_2$—$CH_2$—CH=$R_1$ or —CH($CH_3$)—CH=$R_1$ where $R_1$ is —($C_6$-$C_{14}$) bicycloalkyl or —($C_8$-$C_{20}$)tricycloalkyl, each of which is optionally substituted. In another embodiment, h is 1, and Z—$R_1$ is

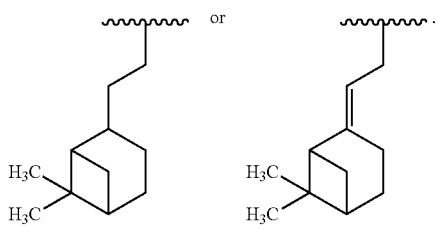 [SMILES: *CCC1CCC2CC1C2(C)C ; *C/C=C1\CCC2CC1C2(C)C]

In another embodiment, Y is O. In another embodiment, Y is S.

In another embodiment, Z is —$CH_2$—NH—C(=O)—. In another embodiment, Z is —$CH_2$—$CH_2$—NH—C(=O)—. In another embodiment, Z is —$CH_2$—NH—C(=S)—. In another embodiment, Z is —$CH_2$—$CH_2$—NH—C(=S)—. In another embodiment, Z is —$CH_2$—N($CH_3$)—C(=O)—. In another embodiment, Z is —$CH_2$—$CH_2$—N($CH_3$)—C(=O)—. In another embodiment, Z is —$CH_2$—N($CH_3$)—C(=S)—. In another embodiment, Z is —$CH_2$—$CH_2$—N($CH_3$)—C(=S)—.

In another embodiment, $R_1$ is selected from:
(a) -halo, —CN, —OH, —$CH_2OH$, —$CH_2CH_2OH$, —$NO_2$, —$N(R_6)_2$, —S(=O)$NH_2$, —S(=O)$_2NH_2$, —C(=O)$OV_1$, and —C(=O)CN; and
(b) —($C_1$-$C_{10}$)alkyl, —O($C_1$-$C_6$)alkyl, —($C_3$-$C_7$)cycloalkoxy, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R_8$ groups; and
(c) -phenyl, -naphthalenyl, —($C_{14}$)aryl, and -(5- to 10-membered)heteroaryl, each of which is unsubstituted or substituted with 1, 2, or 3 independently selected $R_7$ groups.

In another embodiment, $R_1$ is selected from:
(a) -halo, —CN, —OH, —$CH_2OH$, —$CH_2CH_2OH$, —$NO_2$, —$N(R_6)_2$, —S(=O)$NH_2$, —S(=O)$_2NH_2$, —C(=O)$OV_1$, and —C(=O)CN; and
(b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{14}$) cycloalkenyl, —($C_7$-$C_{14}$)bicycloalkenyl, —($C_8$-$C_{20}$) tricycloalkenyl, and -(3- to 7-membered)heterocycle, each of which is unsubstituted or substituted with 1, 2, 3, or 4 independently selected $R_8$ groups; and (c)

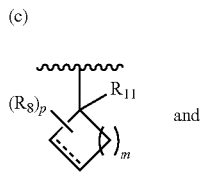

and

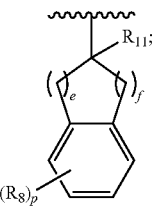

(d) -phenyl, -naphthalenyl, —($C_{14}$)aryl, and -(5- to 10-membered)heteroaryl, each of which is unsubstituted or substituted with 1, 2, or 3 independently selected $R_7$ groups.

In another embodiment, $R_1$ is selected from:
(a) -halo, —CN, —OH, —$CH_2OH$, —$CH_2CH_2OH$, —$NO_2$, —$N(R_6)_2$, —S(=O)$NH_2$, —S(=O)$_2NH_2$, —C(=O)$OV_1$, and —C(=O)CN; and
(b) —($C_1$-$C_{10}$)alkyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocycle, each of which is unsubstituted or substituted with 1, 2, 3, or 4 independently selected $R_8$ groups; and (c)

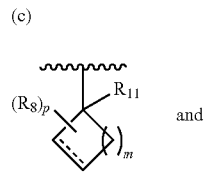

and

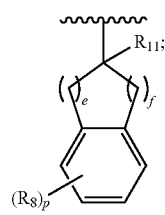

and
(d) -phenyl and -(5- to 10-membered)heteroaryl, each of which is unsubstituted or substituted with 1, 2, or 3 independently selected $R_7$ groups.

In another embodiment, m is 1, 2, 3, 4, 5, 6, 7, 8, or 9. In another embodiment, m is 2, 3, 4, 5, 6, 7, or 8. In another embodiment, m is 2, 3, 4, 5, 6, or 7. In another embodiment, m is 2, 3, 4, 5, or 6. In another embodiment, m is 2, 3, 4, or 5. In another embodiment, m is 2. In another embodiment, m is 3. In another embodiment, m is 4. In another embodiment, m is 5. In another embodiment, m is 6. In another embodiment, m is 7.

In another embodiment, n is 2, 3, 4, 5, 6, 7, or 8. In another embodiment, n is 2, 3, 4, 5, 6, or 7. In another embodiment, n is 2, 3, 4, 5, or 6. In another embodiment, n is 2, 3, 4, or 5. In another embodiment, n is 2. In another embodiment, n is 3. In another embodiment, n is 4. In another embodiment, n is 5. In another embodiment, n is 6. In another embodiment, n is 7.

In another embodiment, m is 1, 2, 3, 4, 5, 6, 7, 8, or 9 and n is 2, 3, 4, 5, 6, 7, or 8. In another embodiment, m is 2, 3, 4, 5, 6, 7, or 8 and n is 2, 3, 4, 5, 6, 7, or 8. In another embodiment, m is 2, 3, 4, 5, 6, or 7 and n is 2, 3, 4, 5, 6, or 7. In another embodiment, m is 2, 3, 4, 5, or 6 and n is 2, 3, 4, 5, or 6. In another embodiment, m is 2, 3, 4, or 5 and n is 2, 3, 4, or 5. In another embodiment, m=n. In another embodiment, m and n are each 2. In another embodiment, m and n are each 3. In another embodiment, m and n are each 4. In another embodiment, m and n are each 5. In another embodiment, m and n are each 6. In another embodiment, m and n are each 7.

In another embodiment, e is 0 and f is 0. In another embodiment, e is 0 and f is 1. In another embodiment, e is 1 and f is 0. In another embodiment, e is 1 and f is 1. In another embodiment, e is 1 and f is 2. In another embodiment, e is 2 and f is 1. In another embodiment, e is 2 and f is 2.

In another embodiment, p is 0, 1, 2, or 3. In another embodiment, p is 0, 1, or 2. In another embodiment, p is 1 or 2. In another embodiment, p is 2. In another embodiment, p is 1. In another embodiment, p is 0.

In another embodiment, $R_1$ is optionally substituted cyclooctyl. In another embodiment, $R_1$ is optionally substituted cyclooctenyl. In another embodiment, $R_1$ is optionally substituted anthryl.

In another embodiment, h is 0 and $R_1$ is optionally substituted cyclooctyl. In another embodiment, h is 0 and $R_1$ is optionally substituted cycloundecyl. In another embodiment, h is 0 and $R_1$ is optionally substituted cyclooctenyl. In another embodiment, h is 0 and $R_1$ is optionally substituted anthryl. In another embodiment, h is 0 and $R_1$ is optionally substituted —($C_6$-$C_{14}$)bicycloalkyl. In another embodiment, h is 0 and $R_1$ is optionally substituted bicyclo[3.3.1]nonyl. In another embodiment, h is 0 and $R_1$ is optionally substituted bicyclo[2.2.1]hepyl. In another embodiment, h is 0 and $R_1$ is optionally substituted —($C_8$-$C_{20}$)tricycloalkyl. In another embodiment, h is 0 and $R_1$ is optionally substituted adamantyl. In another embodiment, h is 0 and $R_1$ is optionally substituted noradamantyl.

In another embodiment, —Z—$R_1$ is:

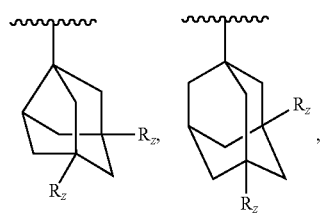

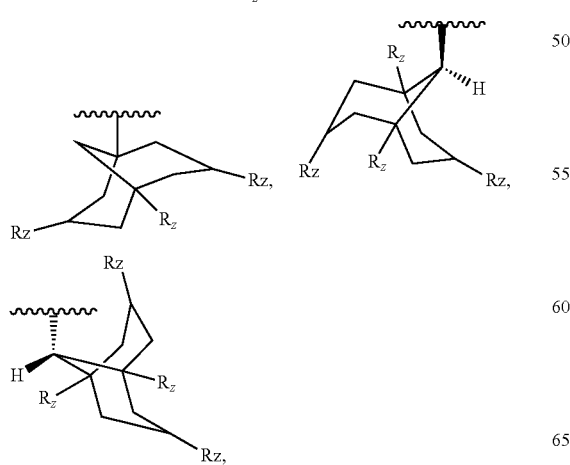

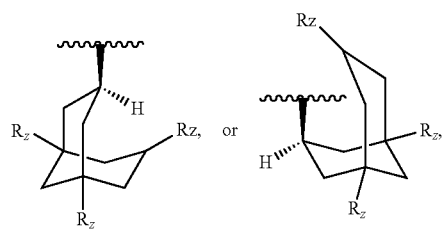

where each $R_z$ is independently —H, —($C_1$-$C_4$)alkyl, —OH, or —CN and preferably each $R_z$ is independently —H, —$CH_3$, or —$CH_2CH_3$. In another embodiment, —Z—$R_1$ is:

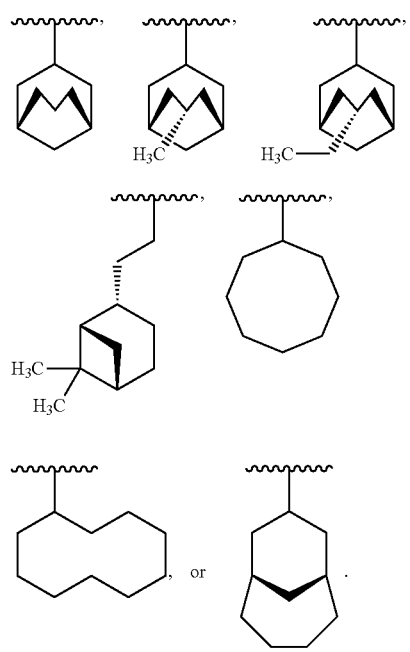

In another embodiment, —Z—$R_1$ is:

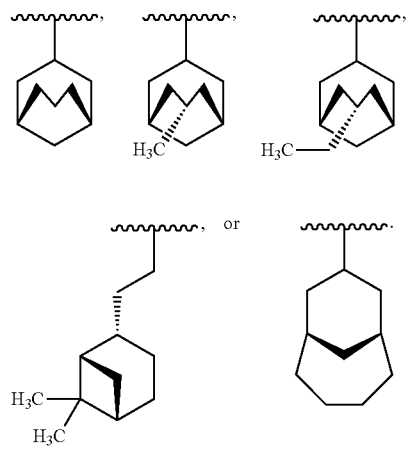

In another embodiment, —Z—R$_1$ is:

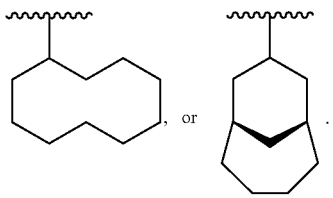 [SMILES: *C1CCCCCCCCC1 ; *C1C[C@H]2CCCC[C@@H](C1)C2], or

In another embodiment, —Z—R$_1$ is:

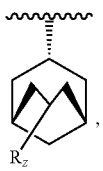, where R$_z$ is —H, —CH$_3$, or —CH$_2$CH$_3$.

In another embodiment, Y$_1$ is O, A and B are each H, and a is 0 or 1. In another embodiment, Y$_1$ is S, A and B are each H, and a is 0 or 1. In another embodiment, Y$_1$ is O, A and B are each H, and a is 0. In another embodiment, Y$_1$ is S, A and B are each H, and a is 0. In another embodiment, Y$_1$ is O, A and B are each H, and a is 1. In another embodiment, Y$_1$ is S, A and B are each H, and a is 1.

In another embodiment, Y$_1$ is O, A and B are each H, h is 0, and a is 0 or 1. In another embodiment, Y$_1$ is S, A and B are each H, h is 0, and a is 0 or 1. In another embodiment, Y$_1$ is O, A and B are each H, h is 0, and a is 0. In another embodiment, Y$_1$ is S, A and B are each H, h is 0, and a is 0. In another embodiment, Y$_1$ is O, A and B are each H, h is 0, and a is 1. In another embodiment, Y$_1$ is S, A and B are each H, h is 0, and a is 1. In another embodiment, Y$_1$ is O, A and B are each H, h is 1, Z is (C$_1$-C$_4$)alkyl unsubstituted by R$_{13}$, and a is 0 or 1. In another embodiment, Y$_1$ is S, A and B are each H, h is 1, Z is (C$_1$-C$_4$)alkyl unsubstituted by R$_{13}$, and a is 0 or 1. In another embodiment, Y$_1$ is O, A and B are each H, h is 1, Z is (C$_1$-C$_4$)alkyl unsubstituted by R$_{13}$, and a is 0. In another embodiment, Y$_1$ is S, A and B are each H, h is 1, Z is (C$_1$-C$_4$)alkyl unsubstituted by R$_{13}$, and a is 0. In another embodiment, Y$_1$ is O, A and B are each H, h is 1, Z is (C$_1$-C$_4$)alkyl unsubstituted by R$_{13}$, and a is 1. In another embodiment, Y$_1$ is S, A and B are each H, h is 1, Z is (C$_1$-C$_4$)alkyl unsubstituted by R$_{13}$, and a is 1.

In another embodiment, A and B are independently selected from:
(a) —H, —CN, —C(=O)OT$_3$, and —C(=O)N(T$_1$)(T$_2$); and
(b) —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl, and —(C$_1$-C$_6$)alkoxy, each of which is unsubstituted or substituted with 1 or 2 substituents independently selected from —OH, —S(=O)$_2$NH$_2$, —N(R$_6$)$_2$, =NR$_6$, —C(=O)OT$_3$, —C(=O)N(R$_6$)$_2$, —N(R$_6$)C(=O)R$_9$, and -(5- or 6-membered)heterocycle, or 1, 2, or 3 independently selected -halo; or
(c) A-B can together form a (C$_2$-C$_6$)bridge, which is unsubstituted or substituted with 1, 2, 3, 4, 5, 6, 7 or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 6-membered, nitrogen-containing ring that is fused to the Q$_a$ ring can be in the endo- or exo-configuration with respect to the A-B bridge.

In another embodiment, A and B are each independently —H or —(C$_1$-C$_6$)alkyl. In another embodiment, A is —(C$_1$-C$_6$)alkyl. In another embodiment, B is —(C$_1$-C$_6$)alkyl. In another embodiment, A and B are each independently —(C$_1$-C$_6$)alkyl. In another embodiment, A is —(C$_1$-C$_6$)alkyl and B is H. In another embodiment, A is —H and B is —(C$_1$-C$_6$)alkyl. In another embodiment, A and B are each independently —H or —CH$_3$. In another embodiment, A is —CH$_3$. In another embodiment, B is —CH$_3$. In another embodiment, A and B are each —CH$_3$. In another embodiment, A is —CH$_3$ and B is H. In another embodiment, A is —H and B is —CH$_3$. In another embodiment, A is H. In another embodiment, B is H. In another embodiment, A and B are each H.

In another embodiment, A-B together form a (C$_2$)bridge which bridge is substituted or unsubstituted. In another embodiment, A-B together form a (C$_2$)bridge which bridge is unsubstituted. In another embodiment, A-B together form a (C$_2$)bridge which bridge is substituted by one or two methyl groups. In another embodiment, A-B together form a (C$_3$) bridge which bridge is substituted or unsubstituted. In another embodiment, A-B together form a (C$_3$)bridge which bridge is unsubstituted. In another embodiment, A-B together form a (C$_3$)bridge which bridge is substituted by one or two methyl groups. In another embodiment, A-B together form a (C$_4$) bridge which bridge is substituted or unsubstituted. In another embodiment, A-B together form a (C$_4$)bridge which bridge is unsubstituted. In another embodiment, A-B together form a (C$_4$)bridge which bridge is substituted by one or two methyl groups. In another embodiment, A-B together form a (C$_5$) bridge which bridge is substituted or unsubstituted. In another embodiment, A-B together form a (C$_5$)bridge which bridge is unsubstituted. In another embodiment, A-B together form a (C$_5$)bridge which bridge is substituted by one or two methyl groups. In another embodiment, A-B together form a (C$_6$) bridge which bridge is substituted or unsubstituted. In another embodiment, A-B together form a (C$_6$)bridge which bridge is unsubstituted. In another embodiment, A-B together form a (C$_6$)bridge which bridge is substituted by one or two methyl groups.

In another embodiment, A-B together form a (C$_2$)bridge which bridge is —HC=CH— and is substituted or unsubstituted. In another embodiment, A-B together form a (C$_2$) bridge which bridge is —HC=CH— and is unsubstituted. In another embodiment, A-B together form a (C$_2$)bridge which is —HC=CH— and is substituted by one or two methyl groups. In another embodiment, A-B together form a (C$_3$) bridge which is —CH$_2$—HC=CH— or —HC=CH—CH$_2$— and is substituted or unsubstituted. In another embodiment, A-B together form a (C$_3$)bridge which is —CH$_2$—HC=CH— or —HC=CH—CH$_2$— and is unsubstituted. In another embodiment, A-B together form a (C$_3$)bridge which is —CH$_2$—HC=CH— or —HC=CH—CH$_2$— and is substituted by one or two methyl groups. In another embodiment, A-B together form a (C$_4$)bridge which is —CH$_2$—CH$_2$—HC=CH—, —CH$_2$—HC=CH—CH$_2$—, or —HC=CH—CH$_2$—CH$_2$— and is substituted or unsubstituted. In another embodiment, A-B together form a (C$_4$)bridge which is —CH$_2$—CH$_2$—HC=CH—, —CH$_2$—HC=CH—CH$_2$—, or —HC=CH—CH$_2$—CH$_2$— and is unsubstituted. In another embodiment, A-B together form a (C$_4$)bridge which is —CH$_2$—CH$_2$—HC=CH—, —CH$_2$—HC=CH—CH$_2$—, or —HC=CH—CH$_2$—CH$_2$— and is substituted by one or two methyl groups.

In another embodiment, A-B together form a (C$_2$)bridge which is —CH$_2$—O—CH$_2$— and is substituted or unsubstituted. In another embodiment, A-B together form a (C$_2$) bridge which is —CH$_2$—O—CH$_2$— and is unsubstituted. In another embodiment, A-B together form a (C$_2$)bridge which is —CH$_2$—O—CH$_2$— and is substituted by one or two methyl groups. In another embodiment, A-B together form a (C$_3$)bridge which is —CH$_2$—O—CH$_2$—CH$_2$— or —CH$_2$—CH$_2$—O—CH$_2$— and is substituted or unsubstituted. In another embodiment, A-B together form a (C$_3$)bridge which is —CH$_2$—O—CH$_2$—CH$_2$— or —CH$_2$—CH$_2$—O—CH$_2$— and is unsubstituted. In another embodiment, A-B together form a (C$_3$)bridge which is —CH$_2$—O—CH$_2$—CH$_2$— or —CH$_2$—CH$_2$—O—CH$_2$— and is substituted by one or two methyl groups. In another embodiment, A-B together form a (C$_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted or unsubstituted. In another embodiment, A-B together form a (C$_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is unsubstituted. In another embodiment, A-B together form a (C$_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted by one or two methyl groups.

In another embodiment, A-B together form a —CH$_2$—NH—CH$_2$— bridge. In another embodiment, A-B together form a —CH$_2$—N(CH$_3$)—CH$_2$— bridge. In another embodiment, A-B together form a —CH$_2$—N(cyclohexyl)-CH$_2$— bridge. In another embodiment, A-B together form a —CH$_2$—N(CH$_2$—CH$_2$—OH)—CH$_2$— bridge.

In another embodiment, A-B together form a

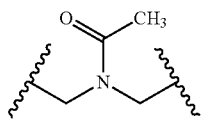 [SMILES: *CN(C*)C(C)=O]

bridge. In another embodiment, A-B together form a

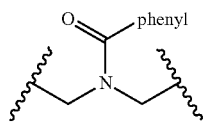

bridge. In another embodiment, A-B together form a

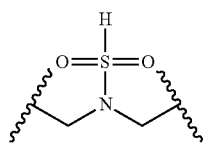

bridge. In another embodiment, A-B together form a

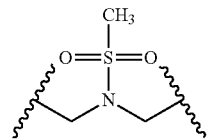

bridge.

In another embodiment, A and B together form a bridge such that the bridged-piperidine is:

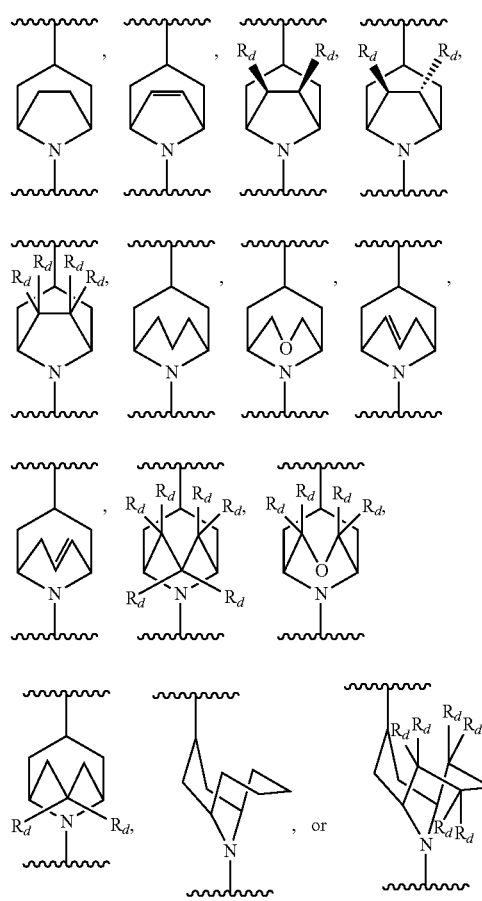

wherein each $R_d$ is independently —H, —(C$_1$-C$_4$) alkyl, -halo, or —C(halo)$_3$. In another embodiment, A and B together form a bridge such that the bridged-piperidine is:

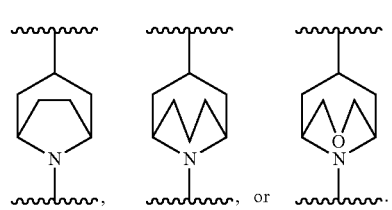 [SMILES: *C1CC2CCC(C1)N2* ; *C1CC2CCCC(C1)N2* ; *C1CC2COCC(C1)N2*]

In another embodiment, A and B together form a bridge such that the bridged-piperidine is:

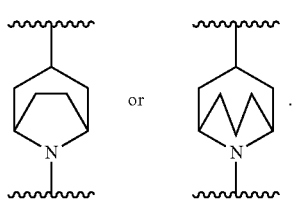 [SMILES: *C1CC2CCC(C1)N2* ; *C1CC2CCCC(C1)N2*]

In another embodiment, the A-B bridge of the bridged-piperidine is in the endo-configuration with respect to the 6-membered, nitrogen-containing ring that is fused to the $Q_a$ ring.

In another embodiment, the Cyclic Urea- or Lactam-Substituted Quinoxaline-Type Piperidine Compound is:

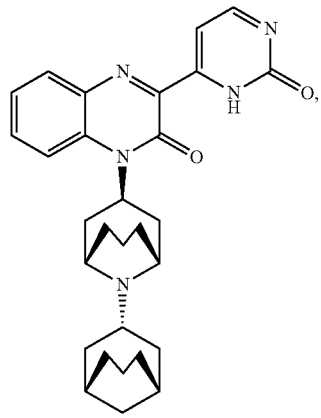

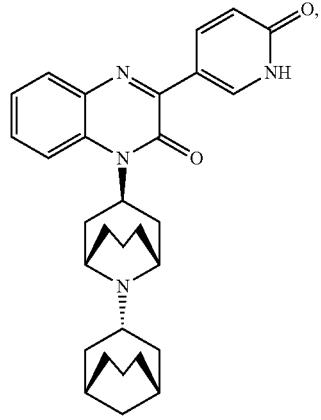

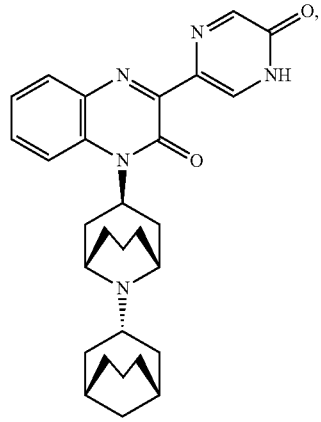

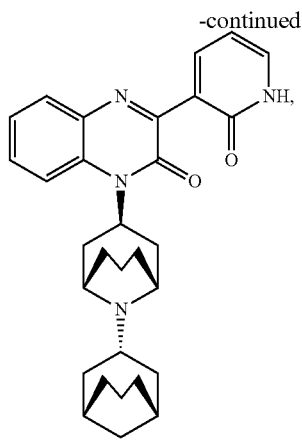

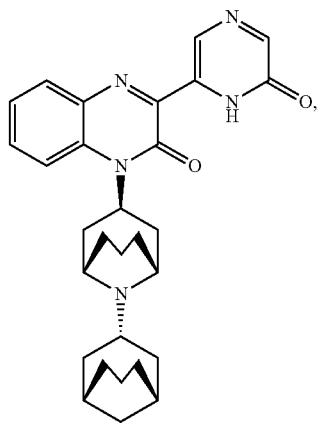

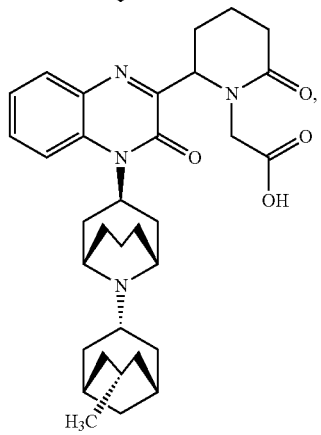

or a pharmaceutically acceptable derivative thereof.

In another embodiment, the Cyclic Urea- or Lactam-Substituted Quinoxaline-Type Piperidine Compound is not 5-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-2-oxo-1,2-dihydropyridine-3-carboxamide. In another embodiment, the Cyclic Urea- or Lactam-Substituted Quinoxaline-Type Piperidine Compound is not 1-((1R,3R,5S)-8-((1R,3 r,5S,7S)-7-methylbicyclo[3.3.1]nonan-3-yl)-8-azabicyclo[3.2.1]octan-3-yl)-3-(2-oxo-1,2-dihydropyridin-3-yl)quinoxalin-2(1H)-one. In another embodiment, the Cyclic Urea- or Lactam-Substituted Quinoxaline-Type Piperidine Compound is not 5-(4-((1R,1'R,3r,3'R,5S,5'S,7 S)-7-methyl-[3,9'-bi(9'-azabicyclo[3.3.1]nonan)]-3'-yl)-3-oxo-3,4-dihydroquinoxalin-2-yl)-2-oxo-1,2-dihydropyridine-3-carboxamide or 1-((1R,3R,5S)-8-((1R,3r,5S,7S)-7-methylbicyclo

[3.3.1]nonan-3-yl)-8-azabicyclo[3.2.1]octan-3-yl)-3-(2-oxo-1,2-dihydropyridin-3-yl)quinoxalin-2(1H)-one.

In another embodiment, the pharmaceutically acceptable derivative of a compounds of Formula (I) is a pharmaceutically acceptable salt. In another embodiment, the pharmaceutically acceptable salt is a hydrochloride salt. In another embodiment, the pharmaceutically acceptable salt is a sodium salt. In another embodiment, the pharmaceutically acceptable salt is a potassium salt. In another embodiment, the pharmaceutically acceptable salt is a para-toluenesulfonic acid salt.

In other embodiments, the Cyclic Urea- or Lactam-Substituted Quinoxaline-Type Piperidine Compound of Formula (I) has one of the formulae of Table 1.

TABLE 1

| Formula | Compound |
|---|---|
| IA | 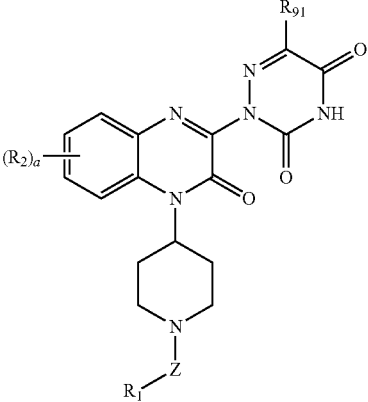 |
| IB | 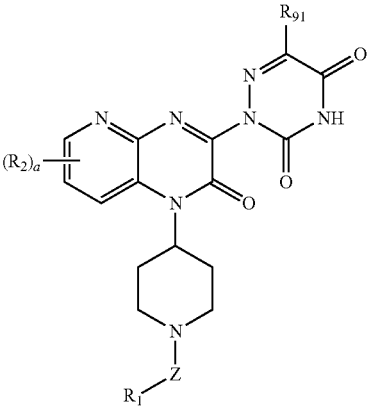 |
| IC | 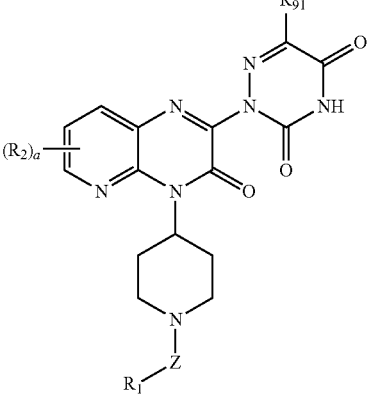 |

TABLE 1-continued

| Formula | Compound |
|---|---|
| ID | 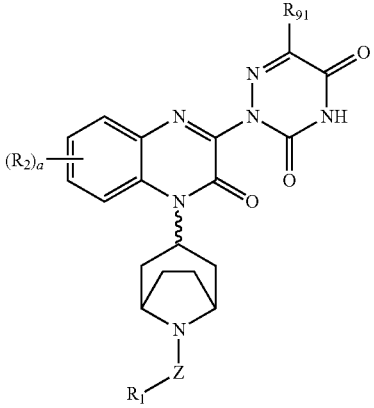 |
| ID$_1$† | 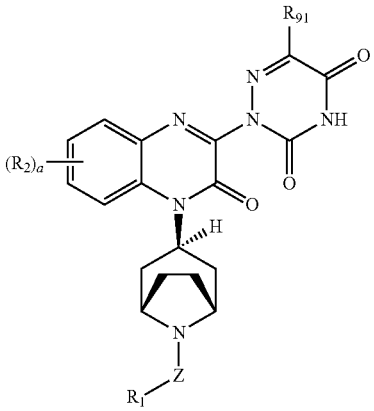 |
| ID$_2$‡ | 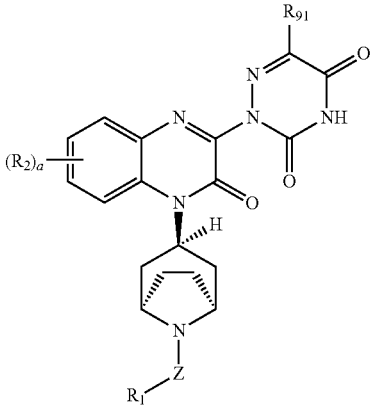 |

TABLE 1-continued
| Formula | Compound |
|---|---|
| IE | 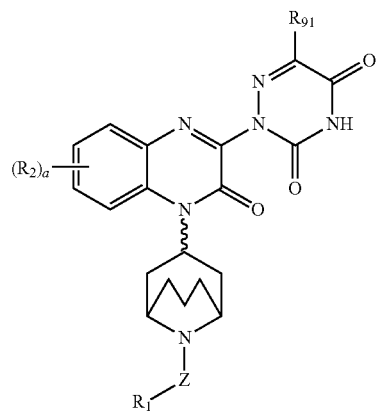 |
| IE₁† | 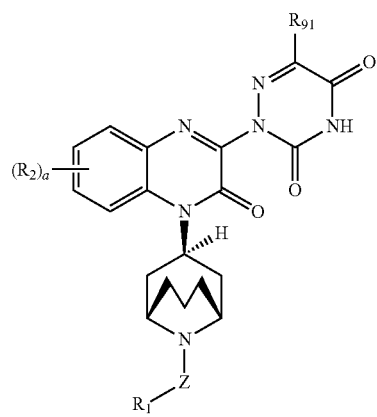 |
| IE₂‡ | 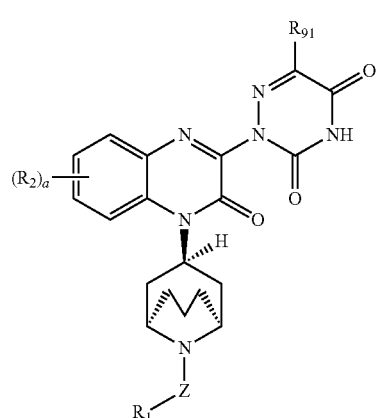 |
TABLE 1-continued
| Formula | Compound |
|---|---|
| IF | 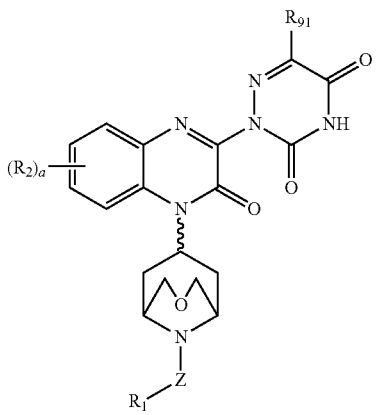 |
| IF₁† | |
| IF₂‡ | |

TABLE 1-continued
| Formula | Compound |
|---|---|
| IG | 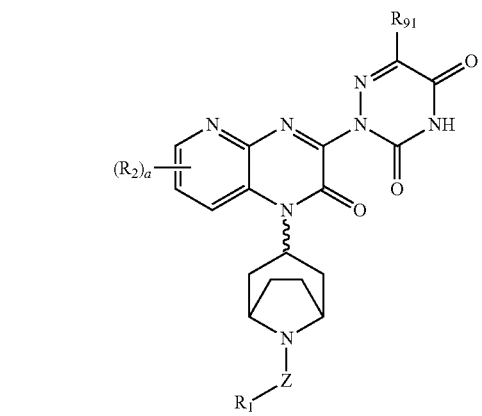 |
| IG$_1$† | 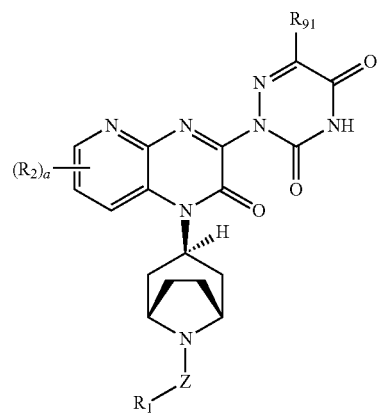 |
| IG$_2$‡ | 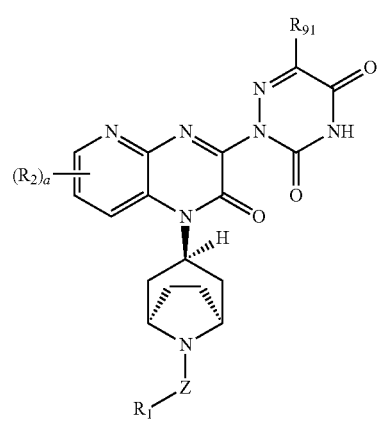 |
TABLE 1-continued
| Formula | Compound |
|---|---|
| IH | 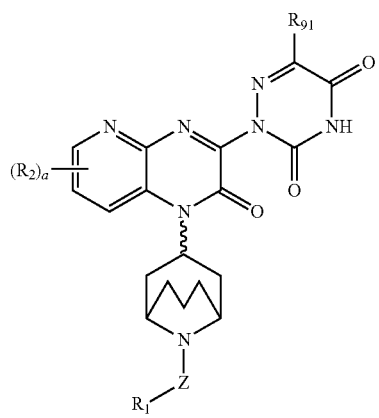 |
| IH$_1$† | 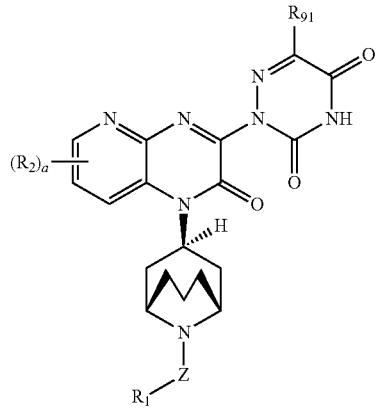 |
| IH$_2$‡ | |

TABLE 1-continued
| Formula | Compound |
|---|---|
| IJ | 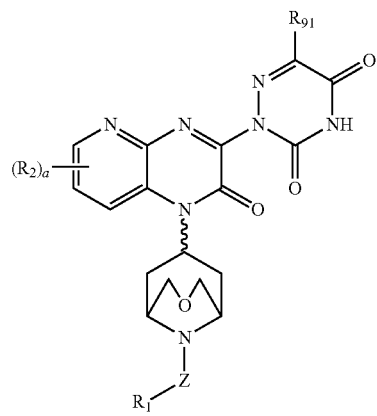 |
| IJ₁† | 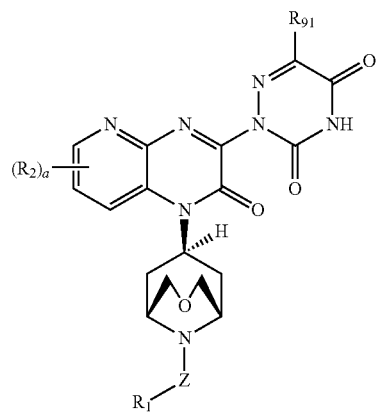 |
| IJ₂‡ | 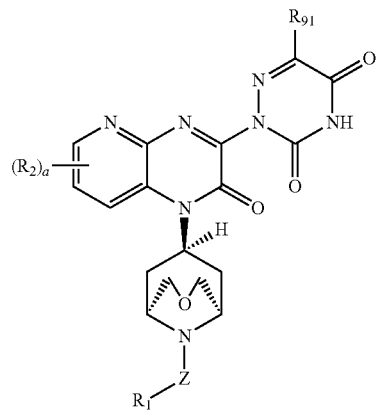 |
TABLE 1-continued
| Formula | Compound |
|---|---|
| IK | 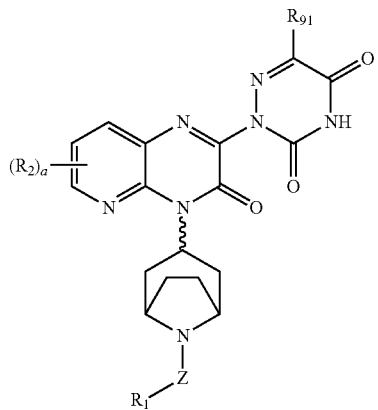 |
| IK₁† | 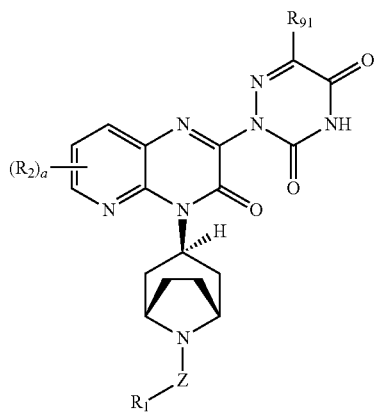 |
| IK₂‡ | 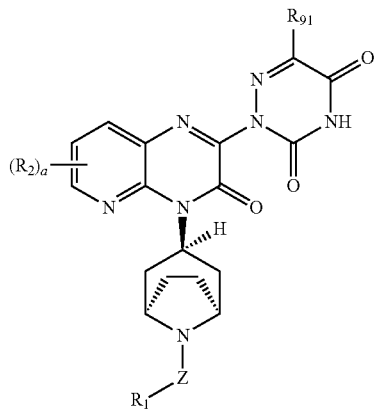 |

TABLE 1-continued

| Formula | Compound |
|---|---|
| IL | |
| IL₁† | |
| IL₂‡ | |
| IM | |
| IM₁† | |
| IM₂‡ | |

†indicates the 6-membered, nitrogen-containing ring that is fused to the benzo or pyridino is in the endo-configuration with respect to the alkyl or —CH₂—O—CH₂— bridge.

‡indicates the 6-membered, nitrogen-containing ring that is fused to the benzo or pyridino is in the exo-configuration with respect to the alkyl or —CH₂—O—CH₂— bridge.

where $R_1$, $R_2$, $R_{91}$, Z, and a are as defined above for the Cyclic Urea- or Lactam-Substituted Quinoxaline-Type Piperidine Compounds of Formula (I).

Illustrative Compounds of Formula (I) are listed below in Tables 2-16.

TABLE 2

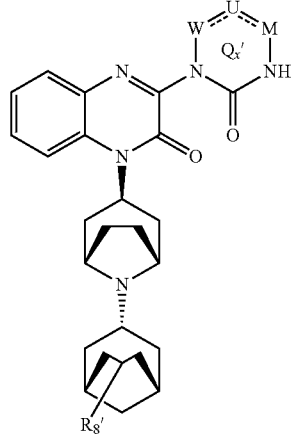

(a)

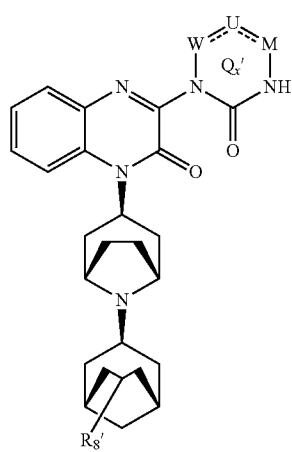

(b)

and pharmaceutically acceptable derivatives thereof, where:

| Compound | M * | U | W | R$_8$' |
|---|---|---|---|---|
| A A1 a or b | C(NHR$_{92}$) | C(H) | N | H |
| A2 a or b | C(NHR$_{92}$) | C(CH$_3$) | N | H |
| A3 a or b | C(NHR$_{92}$) | C(F) | N | H |
| A4 a or b | C(NHR$_{92}$) | C(Br) | N | H |
| A5 a or b | C(NHR$_{92}$) | C(H) | C(H) | H |
| A6 a or b | C(NHR$_{92}$) | C(CH$_3$) | C(H) | H |
| A7 a or b | C(NHR$_{92}$) | C(F) | C(H) | H |
| A8 a or b | C(NHR$_{92}$) | C(Br) | C(H) | H |
| A9 a or b | C(=O) | C(H) | N | H |
| A10 a or b | C(=O) | C(CH$_3$) | N | H |
| A11 a or b | C(=O) | C(F) | N | H |
| A12 a or b | C(=O) | C(Br) | N | H |
| A13 a or b | C(=O) | C(H) | C(H) | H |
| A14 a or b | C(=O) | C(CH$_3$) | C(H) | H |
| A15 a or b | C(=O) | C(F) | C(H) | H |
| A16 a or b | C(=O) | C(Br) | C(H) | H |
| A17 a or b | C(=O) | CH$_2$ | Absent | H |
| A18 a or b | C(=O) | CH(CH$_3$) | Absent | H |
| A19 a or b | C(=O) | C(CH$_3$)$_2$ | Absent | H |
| A20 a or b | CH$_2$ | C(=O) | Absent | H |
| A21 a or b | CH(CH$_3$) | C(=O) | Absent | H |
| A22 a or b | C(CH$_3$)$_2$ | C(=O) | Absent | H |
| A23 a or b | C(H) | N | Absent | H |
| A24 a or b | N | C(H) | Absent | H |
| A25 a or b | CH$_2$ | CH$_2$ | Absent | H |
| A26 a or b | C(NHR$_{92}$) | C(H) | N | CH$_3$ |
| A27 a or b | C(NHR$_{92}$) | C(CH$_3$) | N | CH$_3$ |
| A28 a or b | C(NHR$_{92}$) | C(F) | N | CH$_3$ |
| A29 a or b | C(NHR$_{92}$) | C(Br) | N | CH$_3$ |
| A30 a or b | C(NHR$_{92}$) | C(H) | C(H) | CH$_3$ |

TABLE 2-continued

| A31 a or b | C(NHR$_{92}$) | C(CH$_3$) | C(H) | CH$_3$ |
|---|---|---|---|---|
| A32 a or b | C(NHR$_{92}$) | C(F) | C(H) | CH$_3$ |
| A33 a or b | C(NHR$_{92}$) | C(Br) | C(H) | CH$_3$ |
| A34 a or b | C(=O) | C(H) | N | CH$_3$ |
| A35 a or b | C(=O) | C(CH$_3$) | N | CH$_3$ |
| A36 a or b | C(=O) | C(F) | N | CH$_3$ |
| A37 a or b | C(=O) | C(Br) | N | CH$_3$ |
| A38 a or b | C(=O) | C(H) | C(H) | CH$_3$ |
| A39 a or b | C(=O) | C(CH$_3$) | C(H) | CH$_3$ |
| A40 a or b | C(=O) | C(F) | C(H) | CH$_3$ |
| A41 a or b | C(=O) | C(Br) | C(H) | CH$_3$ |
| A42 a or b | C(=O) | CH$_2$ | Absent | CH$_3$ |
| A43 a or b | C(=O) | CH(CH$_3$) | Absent | CH$_3$ |
| A44 a or b | C(=O) | C(CH$_3$)$_2$ | Absent | CH$_3$ |
| A45 a or b | CH$_2$ | C(=O) | Absent | CH$_3$ |
| A46 a or b | CH(CH$_3$) | C(=O) | Absent | CH$_3$ |
| A47 a or b | C(CH$_3$)$_2$ | C(=O) | Absent | CH$_3$ |
| A48 a or b | C(H) | N | Absent | CH$_3$ |
| A49 a or b | N | C(H) | Absent | CH$_3$ |
| A50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 3

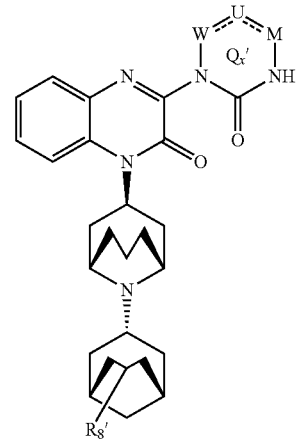

(a)

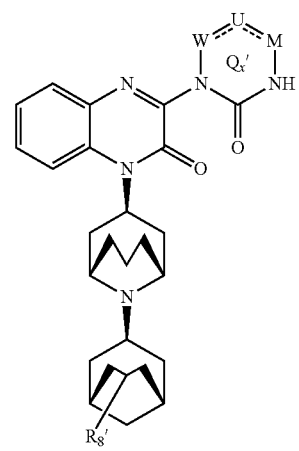

(b)

and pharmaceutically acceptable derivatives thereof, where:

| Compound | M * | U | W | R$_8$' |
|---|---|---|---|---|
| B B1 a or b | C(NHR$_{92}$) | C(H) | N | H |
| B2 a or b | C(NHR$_{92}$) | C(CH$_3$) | N | H |
| B3 a or b | C(NHR$_{92}$) | C(F) | N | H |
| B4 a or b | C(NHR$_{92}$) | C(Br) | N | H |
| B5 a or b | C(NHR$_{92}$) | C(H) | C(H) | H |
| B6 a or b | C(NHR$_{92}$) | C(CH$_3$) | C(H) | H |
| B7 a or b | C(NHR$_{92}$) | C(F) | C(H) | H |

TABLE 3-continued

| | | | | |
|---|---|---|---|---|
| B8 a or b | C(NHR$_{92}$) | C(Br) | C(H) | H |
| B9 a or b | C(=O) | C(H) | N | H |
| B10 a or b | C(=O) | C(CH$_3$) | N | H |
| B11 a or b | C(=O) | C(F) | N | H |
| B12 a or b | C(=O) | C(Br) | N | H |
| B13 a or b | C(=O) | C(H) | C(H) | H |
| B14 a or b | C(=O) | C(CH$_3$) | C(H) | H |
| B15 a or b | C(=O) | C(F) | C(H) | H |
| B16 a or b | C(=O) | C(Br) | C(H) | H |
| B17 a or b | C(=O) | CH$_2$ | Absent | H |
| B18 a or b | C(=O) | CH(CH$_3$) | Absent | H |
| B19 a or b | C(=O) | C(CH$_3$)$_2$ | Absent | H |
| B20 a or b | CH$_2$ | C(=O) | Absent | H |
| B21 a or b | CH(CH$_3$) | C(=O) | Absent | H |
| B22 a or b | C(CH$_3$)$_2$ | C(=O) | Absent | H |
| B23 a or b | C(H) | N | Absent | H |
| B24 a or b | N | C(H) | Absent | H |
| B25 a or b | CH$_2$ | CH$_2$ | Absent | H |
| B26 a or b | C(NHR$_{92}$) | C(H) | N | CH$_3$ |
| B27 a or b | C(NHR$_{92}$) | C(CH$_3$) | N | CH$_3$ |
| B28 a or b | C(NHR$_{92}$) | C(F) | N | CH$_3$ |
| B29 a or b | C(NHR$_{92}$) | C(Br) | N | CH$_3$ |
| B30 a or b | C(NHR$_{92}$) | C(H) | C(H) | CH$_3$ |
| B31 a or b | C(NHR$_{92}$) | C(CH$_3$) | C(H) | CH$_3$ |
| B32 a or b | C(NHR$_{92}$) | C(F) | C(H) | CH$_3$ |
| B33 a or b | C(NHR$_{92}$) | C(Br) | C(H) | CH$_3$ |
| B34 a or b | C(=O) | C(H) | N | CH$_3$ |
| B35 a or b | C(=O) | C(CH$_3$) | N | CH$_3$ |
| B36 a or b | C(=O) | C(F) | N | CH$_3$ |
| B37 a or b | C(=O) | C(Br) | N | CH$_3$ |
| B38 a or b | C(=O) | C(H) | C(H) | CH$_3$ |
| B39 a or b | C(=O) | C(CH$_3$) | C(H) | CH$_3$ |
| B40 a or b | C(=O) | C(F) | C(H) | CH$_3$ |
| B41 a or b | C(=O) | C(Br) | C(H) | CH$_3$ |
| B42 a or b | C(=O) | CH$_2$ | Absent | CH$_3$ |
| B43 a or b | C(=O) | CH(CH$_3$) | Absent | CH$_3$ |
| B44 a or b | C(=O) | C(CH$_3$)$_2$ | Absent | CH$_3$ |
| B45 a or b | CH$_2$ | C(=O) | Absent | CH$_3$ |
| B46 a or b | CH(CH$_3$) | C(=O) | Absent | CH$_3$ |
| B47 a or b | C(CH$_3$)$_2$ | C(=O) | Absent | CH$_3$ |
| B48 a or b | C(H) | N | Absent | CH$_3$ |
| B49 a or b | N | C(H) | Absent | CH$_3$ |
| B50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 4

(a)

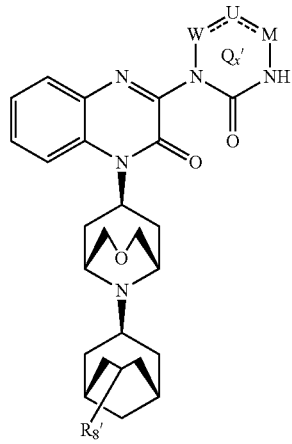

(b)

and pharmaceutically acceptable derivatives thereof, where:

| Compound | M * | U | W | R$_8$' |
|---|---|---|---|---|
| C C1 a or b | C(NHR$_{92}$) | C(H) | N | H |
| C2 a or b | C(NHR$_{92}$) | C(CH$_3$) | N | H |
| C3 a or b | C(NHR$_{92}$) | C(F) | N | H |
| C4 a or b | C(NHR$_{92}$) | C(Br) | N | H |
| C5 a or b | C(NHR$_{92}$) | C(H) | C(H) | H |
| C6 a or b | C(NHR$_{92}$) | C(CH$_3$) | C(H) | H |
| C7 a or b | C(NHR$_{92}$) | C(F) | C(H) | H |
| C8 a or b | C(NHR$_{92}$) | C(Br) | C(H) | H |
| C9 a or b | C(=O) | C(H) | N | H |
| C10 a or b | C(=O) | C(CH$_3$) | N | H |
| C11 a or b | C(=O) | C(F) | N | H |
| C12 a or b | C(=O) | C(Br) | N | H |
| C13 a or b | C(=O) | C(H) | C(H) | H |
| C14 a or b | C(=O) | C(CH$_3$) | C(H) | H |
| C15 a or b | C(=O) | C(F) | C(H) | H |
| C16 a or b | C(=O) | C(Br) | C(H) | H |
| C17 a or b | C(=O) | CH$_2$ | Absent | H |
| C18 a or b | C(=O) | CH(CH$_3$) | Absent | H |
| C19 a or b | C(=O) | C(CH$_3$)$_2$ | Absent | H |
| C20 a or b | CH$_2$ | C(=O) | Absent | H |
| C21 a or b | CH(CH$_3$) | C(=O) | Absent | H |
| C22 a or b | C(CH$_3$)$_2$ | C(=O) | Absent | H |
| C23 a or b | C(H) | N | Absent | H |
| C24 a or b | N | C(H) | Absent | H |
| C25 a or b | CH$_2$ | CH$_2$ | Absent | H |
| C26 a or b | C(NHR$_{92}$) | C(H) | N | CH$_3$ |
| C27 a or b | C(NHR$_{92}$) | C(CH$_3$) | N | CH$_3$ |
| C28 a or b | C(NHR$_{92}$) | C(F) | N | CH$_3$ |
| C29 a or b | C(NHR$_{92}$) | C(Br) | N | CH$_3$ |
| C30 a or b | C(NHR$_{92}$) | C(H) | C(H) | CH$_3$ |
| C31 a or b | C(NHR$_{92}$) | C(CH$_3$) | C(H) | CH$_3$ |
| C32 a or b | C(NHR$_{92}$) | C(F) | C(H) | CH$_3$ |
| C33 a or b | C(NHR$_{92}$) | C(Br) | C(H) | CH$_3$ |
| C34 a or b | C(=O) | C(H) | N | CH$_3$ |
| C35 a or b | C(=O) | C(CH$_3$) | N | CH$_3$ |
| C36 a or b | C(=O) | C(F) | N | CH$_3$ |
| C37 a or b | C(=O) | C(Br) | N | CH$_3$ |
| C38 a or b | C(=O) | C(H) | C(H) | CH$_3$ |
| C39 a or b | C(=O) | C(CH$_3$) | C(H) | CH$_3$ |
| C40 a or b | C(=O) | C(F) | C(H) | CH$_3$ |
| C41 a or b | C(=O) | C(Br) | C(H) | CH$_3$ |
| C42 a or b | C(=O) | CH$_2$ | Absent | CH$_3$ |
| C43 a or b | C(=O) | CH(CH$_3$) | Absent | CH$_3$ |
| C44 a or b | C(=O) | C(CH$_3$)$_2$ | Absent | CH$_3$ |
| C45 a or b | CH$_2$ | C(=O) | Absent | CH$_3$ |
| C46 a or b | CH(CH$_3$) | C(=O) | Absent | CH$_3$ |
| C47 a or b | C(CH$_3$)$_2$ | C(=O) | Absent | CH$_3$ |
| C48 a or b | C(H) | N | Absent | CH$_3$ |
| C49 a or b | N | C(H) | Absent | CH$_3$ |
| C50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 5

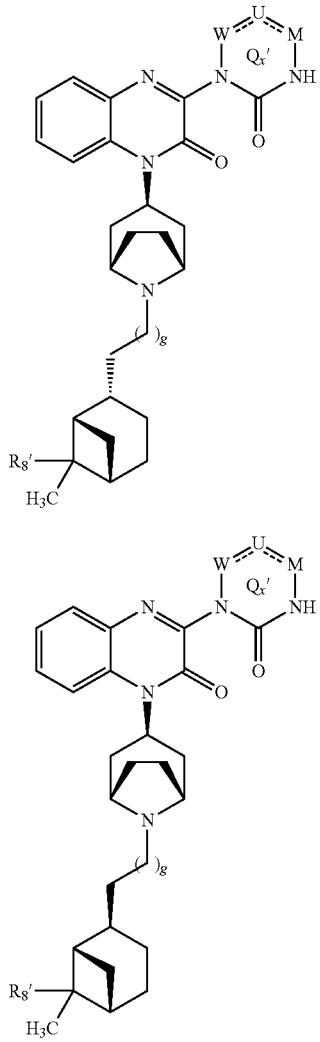

and pharmaceutically acceptable derivatives thereof, where:

| Compound | M * | U | W | $R_8'$ | g |
|---|---|---|---|---|---|
| D D1 a or b | $C(NHR_{92})$ | C(H) | N | H | 0 |
| D2 a or b | $C(NHR_{92})$ | $C(CH_3)$ | N | H | 0 |
| D3 a or b | $C(NHR_{92})$ | C(F) | N | H | 0 |
| D4 a or b | $C(NHR_{92})$ | C(Br) | N | H | 0 |
| D5 a or b | $C(NHR_{92})$ | C(H) | C(H) | H | 0 |
| D6 a or b | $C(NHR_{92})$ | $C(CH_3)$ | C(H) | H | 0 |
| D7 a or b | $C(NHR_{92})$ | C(F) | C(H) | H | 0 |
| D8 a or b | $C(NHR_{92})$ | C(Br) | C(H) | H | 0 |
| D9 a or b | C(=O) | C(H) | N | H | 0 |
| D10 a or b | C(=O) | $C(CH_3)$ | N | H | 0 |
| D11 a or b | C(=O) | C(F) | N | H | 0 |
| D12 a or b | C(=O) | C(Br) | N | H | 0 |
| D13 a or b | C(=O) | C(H) | C(H) | H | 0 |
| D14 a or b | C(=O) | $C(CH_3)$ | C(H) | H | 0 |
| D15 a or b | C(=O) | C(F) | C(H) | H | 0 |
| D16 a or b | C(=O) | C(Br) | C(H) | H | 0 |
| D17 a or b | C(=O) | $CH_2$ | Absent | H | 0 |
| D18 a or b | C(=O) | $CH(CH_3)$ | Absent | H | 0 |
| D19 a or b | C(=O) | $C(CH_3)_2$ | Absent | H | 0 |
| D20 a or b | $CH_2$ | C(=O) | Absent | H | 0 |
| D21 a or b | $CH(CH_3)$ | C(=O) | Absent | H | 0 |
| D22 a or b | $C(CH_3)_2$ | C(=O) | Absent | H | 0 |
| D23 a or b | C(H) | N | Absent | H | 0 |
| D24 a or b | N | C(H) | Absent | H | 0 |
| D25 a or b | $CH_2$ | $CH_2$ | Absent | H | 0 |
| D26 a or b | $C(NHR_{92})$ | C(H) | N | $CH_3$ | 0 |
| D27 a or b | $C(NHR_{92})$ | $C(CH_3)$ | N | $CH_3$ | 0 |
| D28 a or b | $C(NHR_{92})$ | C(F) | N | $CH_3$ | 0 |
| D29 a or b | $C(NHR_{92})$ | C(Br) | N | $CH_3$ | 0 |
| D30 a or b | $C(NHR_{92})$ | C(H) | C(H) | $CH_3$ | 0 |
| D31 a or b | $C(NHR_{92})$ | $C(CH_3)$ | C(H) | $CH_3$ | 0 |
| D32 a or b | $C(NHR_{92})$ | C(F) | C(H) | $CH_3$ | 0 |
| D33 a or b | $C(NHR_{92})$ | C(Br) | C(H) | $CH_3$ | 0 |
| D34 a or b | C(=O) | C(H) | N | $CH_3$ | 0 |
| D35 a or b | C(=O) | $C(CH_3)$ | N | $CH_3$ | 0 |
| D36 a or b | C(=O) | C(F) | N | $CH_3$ | 0 |
| D37 a or b | C(=O) | C(Br) | N | $CH_3$ | 0 |
| D38 a or b | C(=O) | C(H) | C(H) | $CH_3$ | 0 |
| D39 a or b | C(=O) | $C(CH_3)$ | C(H) | $CH_3$ | 0 |
| D40 a or b | C(=O) | C(F) | C(H) | $CH_3$ | 0 |
| D41 a or b | C(=O) | C(Br) | C(H) | $CH_3$ | 0 |
| D42 a or b | C(=O) | $CH_2$ | Absent | $CH_3$ | 0 |
| D43 a or b | C(=O) | $CH(CH_3)$ | Absent | $CH_3$ | 0 |
| D44 a or b | C(=O) | $C(CH_3)_2$ | Absent | $CH_3$ | 0 |
| D45 a or b | $CH_2$ | C(=O) | Absent | $CH_3$ | 0 |
| D46 a or b | $CH(CH_3)$ | C(=O) | Absent | $CH_3$ | 0 |
| D47 a or b | $C(CH_3)_2$ | C(=O) | Absent | $CH_3$ | 0 |
| D48 a or b | C(H) | N | Absent | $CH_3$ | 0 |
| D49 a or b | N | C(H) | Absent | $CH_3$ | 0 |
| D50 a or b | $CH_2$ | $CH_2$ | Absent | $CH_3$ | 0 |
| D51 a or b | $C(NHR_{92})$ | C(H) | N | H | 1 |
| D52 a or b | $C(NHR_{92})$ | $C(CH_3)$ | N | H | 1 |
| D53 a or b | $C(NHR_{92})$ | C(F) | N | H | 1 |
| D54 a or b | $C(NHR_{92})$ | C(Br) | N | H | 1 |
| D55 a or b | $C(NHR_{92})$ | C(H) | C(H) | H | 1 |
| D56 a or b | $C(NHR_{92})$ | $C(CH_3)$ | C(H) | H | 1 |
| D57 a or b | $C(NHR_{92})$ | C(F) | C(H) | H | 1 |
| D58 a or b | $C(NHR_{92})$ | C(Br) | C(H) | H | 1 |
| D59 a or b | C(=O) | C(H) | N | H | 1 |
| D60 a or b | C(=O) | $C(CH_3)$ | N | H | 1 |
| D61 a or b | C(=O) | C(F) | N | H | 1 |
| D62 a or b | C(=O) | C(Br) | N | H | 1 |
| D63 a or b | C(=O) | C(H) | C(H) | H | 1 |
| D64 a or b | C(=O) | $C(CH_3)$ | C(H) | H | 1 |
| D65 a or b | C(=O) | C(F) | C(H) | H | 1 |
| D66 a or b | C(=O) | C(Br) | C(H) | H | 1 |
| D67 a or b | C(=O) | $CH_2$ | Absent | H | 1 |
| D68 a or b | C(=O) | $CH(CH_3)$ | Absent | H | 1 |
| D69 a or b | C(=O) | $C(CH_3)_2$ | Absent | H | 1 |
| D70 a or b | $CH_2$ | C(=O) | Absent | H | 1 |
| D71 a or b | $CH(CH_3)$ | C(=O) | Absent | H | 1 |
| D72 a or b | $C(CH_3)_2$ | C(=O) | Absent | H | 1 |
| D73 a or b | C(H) | N | Absent | H | 1 |
| D74 a or b | N | C(H) | Absent | H | 1 |
| D75 a or b | $CH_2$ | $CH_2$ | Absent | H | 1 |
| D76 a or b | $C(NHR_{92})$ | C(H) | N | $CH_3$ | 1 |
| D77 a or b | $C(NHR_{92})$ | $C(CH_3)$ | N | $CH_3$ | 1 |
| D78 a or b | $C(NHR_{92})$ | C(F) | N | $CH_3$ | 1 |
| D79 a or b | $C(NHR_{92})$ | C(Br) | N | $CH_3$ | 1 |
| D80 a or b | $C(NHR_{92})$ | C(H) | C(H) | $CH_3$ | 1 |
| D81 a or b | $C(NHR_{92})$ | $C(CH_3)$ | C(H) | $CH_3$ | 1 |
| D82 a or b | $C(NHR_{92})$ | C(F) | C(H) | $CH_3$ | 1 |
| D83 a or b | $C(NHR_{92})$ | C(Br) | C(H) | $CH_3$ | 1 |
| D84 a or b | C(=O) | C(H) | N | $CH_3$ | 1 |
| D85 a or b | C(=O) | $C(CH_3)$ | N | $CH_3$ | 1 |
| D86 a or b | C(=O) | C(F) | N | $CH_3$ | 1 |
| D87 a or b | C(=O) | C(Br) | N | $CH_3$ | 1 |
| D88 a or b | C(=O) | C(H) | C(H) | $CH_3$ | 1 |
| D89 a or b | C(=O) | $C(CH_3)$ | C(H) | $CH_3$ | 1 |
| D90 a or b | C(=O) | C(F) | C(H) | $CH_3$ | 1 |
| D91 a or b | C(=O) | C(Br) | C(H) | $CH_3$ | 1 |
| D92 a or b | C(=O) | $CH_2$ | Absent | $CH_3$ | 1 |
| D93 a or b | C(=O) | $CH(CH_3)$ | Absent | $CH_3$ | 1 |
| D94 a or b | C(=O) | $C(CH_3)_2$ | Absent | $CH_3$ | 1 |
| D95 a or b | $CH_2$ | C(=O) | Absent | $CH_3$ | 1 |
| D96 a or b | $CH(CH_3)$ | C(=O) | Absent | $CH_3$ | 1 |
| D97 a or b | $C(CH_3)_2$ | C(=O) | Absent | $CH_3$ | 1 |
| D98 a or b | C(H) | N | Absent | $CH_3$ | 1 |
| D99 a or b | N | C(H) | Absent | $CH_3$ | 1 |
| D100 a or b | $CH_2$ | $CH_2$ | Absent | $CH_3$ | 1 |
| D101 a or b | $C(NHR_{92})$ | C(H) | N | H | 2 |
| D102 a or b | $C(NHR_{92})$ | $C(CH_3)$ | N | H | 2 |
| D103 a or b | $C(NHR_{92})$ | C(F) | N | H | 2 |
| D104 a or b | $C(NHR_{92})$ | C(Br) | N | H | 2 |
| D105 a or b | $C(NHR_{92})$ | C(H) | C(H) | H | 2 |
| D106 a or b | $C(NHR_{92})$ | $C(CH_3)$ | C(H) | H | 2 |
| D107 a or b | $C(NHR_{92})$ | C(F) | C(H) | H | 2 |

TABLE 5-continued

| | | | | | |
|---|---|---|---|---|---|
| D108 a or b | C(NHR$_{92}$) | C(Br) | C(H) | H | 2 |
| D109 a or b | C(=O) | C(H) | N | H | 2 |
| D110 a or b | C(=O) | C(CH$_3$) | N | H | 2 |
| D111 a or b | C(=O) | C(F) | N | H | 2 |
| D112 a or b | C(=O) | C(Br) | N | H | 2 |
| D113 a or b | C(=O) | C(H) | C(H) | H | 2 |
| D114 a or b | C(=O) | C(CH$_3$) | C(H) | H | 2 |
| D115 a or b | C(=O) | C(F) | C(H) | H | 2 |
| D116 a or b | C(=O) | C(Br) | C(H) | H | 2 |
| D117 a or b | C(=O) | CH$_2$ | Absent | H | 2 |
| D118 a or b | C(=O) | CH(CH$_3$) | Absent | H | 2 |
| D119 a or b | C(=O) | C(CH$_3$)$_2$ | Absent | H | 2 |
| D120 a or b | CH$_2$ | C(=O) | Absent | H | 2 |
| D121 a or b | CH(CH$_3$) | C(=O) | Absent | H | 2 |
| D122 a or b | C(CH$_3$)$_2$ | C(=O) | Absent | H | 2 |
| D123 a or b | C(H) | N | Absent | H | 2 |
| D124 a or b | N | C(H) | Absent | H | 2 |
| D125 a or b | CH$_2$ | CH$_2$ | Absent | H | 2 |
| D126 a or b | C(NHR$_{92}$) | C(H) | N | CH$_3$ | 2 |
| D127 a or b | C(NHR$_{92}$) | C(CH$_3$) | N | CH$_3$ | 2 |
| D128 a or b | C(NHR$_{92}$) | C(F) | N | CH$_3$ | 2 |
| D129 a or b | C(NHR$_{92}$) | C(Br) | N | CH$_3$ | 2 |
| D130 a or b | C(NHR$_{92}$) | C(H) | C(H) | CH$_3$ | 2 |
| D131 a or b | C(NHR$_{92}$) | C(CH$_3$) | C(H) | CH$_3$ | 2 |
| D132 a or b | C(NHR$_{92}$) | C(F) | C(H) | CH$_3$ | 2 |
| D133 a or b | C(NHR$_{92}$) | C(Br) | C(H) | CH$_3$ | 2 |
| D134 a or b | C(=O) | C(H) | N | CH$_3$ | 2 |
| D135 a or b | C(=O) | C(CH$_3$) | N | CH$_3$ | 2 |
| D136 a or b | C(=O) | C(F) | N | CH$_3$ | 2 |
| D137 a or b | C(=O) | C(Br) | N | CH$_3$ | 2 |
| D138 a or b | C(=O) | C(H) | C(H) | CH$_3$ | 2 |
| D139 a or b | C(=O) | C(CH$_3$) | C(H) | CH$_3$ | 2 |
| D140 a or b | C(=O) | C(F) | C(H) | CH$_3$ | 2 |
| D141 a or b | C(=O) | C(Br) | C(H) | CH$_3$ | 2 |
| D142 a or b | C(=O) | CH$_2$ | Absent | CH$_3$ | 2 |
| D143 a or b | C(=O) | CH(CH$_3$) | Absent | CH$_3$ | 2 |
| D144 a or b | C(=O) | C(CH$_3$)$_2$ | Absent | CH$_3$ | 2 |
| D145 a or b | CH$_2$ | C(=O) | Absent | CH$_3$ | 2 |
| D146 a or b | CH(CH$_3$) | C(=O) | Absent | CH$_3$ | 2 |
| D147 a or b | C(CH$_3$)$_2$ | C(=O) | Absent | CH$_3$ | 2 |
| D148 a or b | C(H) | N | Absent | CH$_3$ | 2 |
| D149 a or b | N | C(H) | Absent | CH$_3$ | 2 |
| D150 a or b | CH$_2$ | CH$_2$ | Absent | CH$_3$ | 2 |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 6

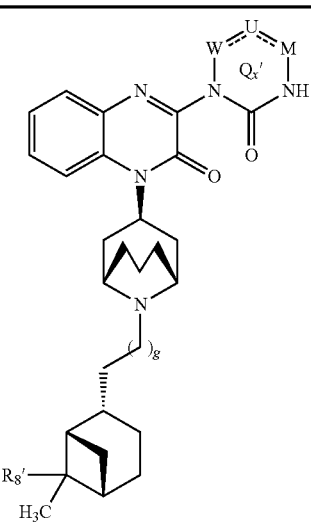

(a)

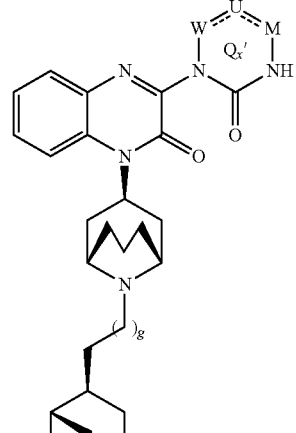

(b)

and pharmaceutically acceptable derivatives thereof, where:

| Compound | M * | U | W | R$_8$' | g |
|---|---|---|---|---|---|
| E E1 a or b | C(NHR$_{92}$) | C(H) | N | H | 0 |
| E2 a or b | C(NHR$_{92}$) | C(CH$_3$) | N | H | 0 |
| E3 a or b | C(NHR$_{92}$) | C(F) | N | H | 0 |
| E4 a or b | C(NHR$_{92}$) | C(Br) | N | H | 0 |
| E5 a or b | C(NHR$_{92}$) | C(H) | C(H) | H | 0 |
| E6 a or b | C(NHR$_{92}$) | C(CH$_3$) | C(H) | H | 0 |
| E7 a or b | C(NHR$_{92}$) | C(F) | C(H) | H | 0 |
| E8 a or b | C(NHR$_{92}$) | C(Br) | C(H) | H | 0 |
| E9 a or b | C(=O) | C(H) | N | H | 0 |
| E10 a or b | C(=O) | C(CH$_3$) | N | H | 0 |
| E11 a or b | C(=O) | C(F) | N | H | 0 |
| E12 a or b | C(=O) | C(Br) | N | H | 0 |
| E13 a or b | C(=O) | C(H) | C(H) | H | 0 |
| E14 a or b | C(=O) | C(CH$_3$) | C(H) | H | 0 |
| E15 a or b | C(=O) | C(F) | C(H) | H | 0 |
| E16 a or b | C(=O) | C(Br) | C(H) | H | 0 |
| E17 a or b | C(=O) | CH$_2$ | Absent | H | 0 |
| E18 a or b | C(=O) | CH(CH$_3$) | Absent | H | 0 |
| E19 a or b | C(=O) | C(CH$_3$)$_2$ | Absent | H | 0 |
| E20 a or b | CH$_2$ | C(=O) | Absent | H | 0 |
| E21 a or b | CH(CH$_3$) | C(=O) | Absent | H | 0 |
| E22 a or b | C(CH$_3$)$_2$ | C(=O) | Absent | H | 0 |
| E23 a or b | C(H) | N | Absent | H | 0 |
| E24 a or b | N | C(H) | Absent | H | 0 |
| E25 a or b | CH$_2$ | CH$_2$ | Absent | H | 0 |
| E26 a or b | C(NHR$_{92}$) | C(H) | N | CH$_3$ | 0 |
| E27 a or b | C(NHR$_{92}$) | C(CH$_3$) | N | CH$_3$ | 0 |
| E28 a or b | C(NHR$_{92}$) | C(F) | N | CH$_3$ | 0 |
| E29 a or b | C(NHR$_{92}$) | C(Br) | N | CH$_3$ | 0 |
| E30 a or b | C(NHR$_{92}$) | C(H) | C(H) | CH$_3$ | 0 |
| E31 a or b | C(NHR$_{92}$) | C(CH$_3$) | C(H) | CH$_3$ | 0 |
| E32 a or b | C(NHR$_{92}$) | C(F) | C(H) | CH$_3$ | 0 |
| E33 a or b | C(NHR$_{92}$) | C(Br) | C(H) | CH$_3$ | 0 |
| E34 a or b | C(=O) | C(H) | N | CH$_3$ | 0 |
| E35 a or b | C(=O) | C(CH$_3$) | N | CH$_3$ | 0 |
| E36 a or b | C(=O) | C(F) | N | CH$_3$ | 0 |
| E37 a or b | C(=O) | C(Br) | N | CH$_3$ | 0 |
| E38 a or b | C(=O) | C(H) | C(H) | CH$_3$ | 0 |
| E39 a or b | C(=O) | C(CH$_3$) | C(H) | CH$_3$ | 0 |
| E40 a or b | C(=O) | C(F) | C(H) | CH$_3$ | 0 |
| E41 a or b | C(=O) | C(Br) | C(H) | CH$_3$ | 0 |
| E42 a or b | C(=O) | CH$_2$ | Absent | CH$_3$ | 0 |
| E43 a or b | C(=O) | CH(CH$_3$) | Absent | CH$_3$ | 0 |
| E44 a or b | C(=O) | C(CH$_3$)$_2$ | Absent | CH$_3$ | 0 |
| E45 a or b | CH$_2$ | C(=O) | Absent | CH$_3$ | 0 |
| E46 a or b | CH(CH$_3$) | C(=O) | Absent | CH$_3$ | 0 |
| E47 a or b | C(CH$_3$)$_2$ | C(=O) | Absent | CH$_3$ | 0 |
| E48 a or b | C(H) | N | Absent | CH$_3$ | 0 |
| E49 a or b | N | C(H) | Absent | CH$_3$ | 0 |
| E50 a or b | CH$_2$ | CH$_2$ | Absent | CH$_3$ | 0 |
| E51 a or b | C(NHR$_{92}$) | C(H) | N | H | 1 |
| E52 a or b | C(NHR$_{92}$) | C(CH$_3$) | N | H | 1 |

TABLE 6-continued

| | | | | | |
|---|---|---|---|---|---|
| E53 a or b | C(NHR$_{92}$) | C(F) | N | H | 1 |
| E54 a or b | C(NHR$_{92}$) | C(Br) | N | H | 1 |
| E55 a or b | C(NHR$_{92}$) | C(H) | C(H) | H | 1 |
| E56 a or b | C(NHR$_{92}$) | C(CH$_3$) | C(H) | H | 1 |
| E57 a or b | C(NHR$_{92}$) | C(F) | C(H) | H | 1 |
| E58 a or b | C(NHR$_{92}$) | C(Br) | C(H) | H | 1 |
| E59 a or b | C(=O) | C(H) | N | H | 1 |
| E60 a or b | C(=O) | C(CH$_3$) | N | H | 1 |
| E61 a or b | C(=O) | C(F) | N | H | 1 |
| E62 a or b | C(=O) | C(Br) | N | H | 1 |
| E63 a or b | C(=O) | C(H) | C(H) | H | 1 |
| E64 a or b | C(=O) | C(CH$_3$) | C(H) | H | 1 |
| E65 a or b | C(=O) | C(F) | C(H) | H | 1 |
| E66 a or b | C(=O) | C(Br) | C(H) | H | 1 |
| E67 a or b | C(=O) | CH$_2$ | Absent | H | 1 |
| E68 a or b | C(=O) | CH(CH$_3$) | Absent | H | 1 |
| E69 a or b | C(=O) | C(CH$_3$)$_2$ | Absent | H | 1 |
| E70 a or b | CH$_2$ | C(=O) | Absent | H | 1 |
| E71 a or b | CH(CH$_3$) | C(=O) | Absent | H | 1 |
| E72 a or b | C(CH$_3$)$_2$ | C(=O) | Absent | H | 1 |
| E73 a or b | C(H) | N | Absent | H | 1 |
| E74 a or b | N | C(H) | Absent | H | 1 |
| E75 a or b | CH$_2$ | CH$_2$ | Absent | H | 1 |
| E76 a or b | C(NHR$_{92}$) | C(H) | N | CH$_3$ | 1 |
| E77 a or b | C(NHR$_{92}$) | C(CH$_3$) | N | CH$_3$ | 1 |
| E78 a or b | C(NHR$_{92}$) | C(F) | N | CH$_3$ | 1 |
| E79 a or b | C(NHR$_{92}$) | C(Br) | N | CH$_3$ | 1 |
| E80 a or b | C(NHR$_{92}$) | C(H) | C(H) | CH$_3$ | 1 |
| E81 a or b | C(NHR$_{92}$) | C(CH$_3$) | C(H) | CH$_3$ | 1 |
| E82 a or b | C(NHR$_{92}$) | C(F) | C(H) | CH$_3$ | 1 |
| E83 a or b | C(NHR$_{92}$) | C(Br) | C(H) | CH$_3$ | 1 |
| E84 a or b | C(=O) | C(H) | N | CH$_3$ | 1 |
| E85 a or b | C(=O) | C(CH$_3$) | N | CH$_3$ | 1 |
| E86 a or b | C(=O) | C(F) | N | CH$_3$ | 1 |
| E87 a or b | C(=O) | C(Br) | N | CH$_3$ | 1 |
| E88 a or b | C(=O) | C(H) | C(H) | CH$_3$ | 1 |
| E89 a or b | C(=O) | C(CH$_3$) | C(H) | CH$_3$ | 1 |
| E90 a or b | C(=O) | C(F) | C(H) | CH$_3$ | 1 |
| E91 a or b | C(=O) | C(Br) | C(H) | CH$_3$ | 1 |
| E92 a or b | C(=O) | CH$_2$ | Absent | CH$_3$ | 1 |
| E93 a or b | C(=O) | CH(CH$_3$) | Absent | CH$_3$ | 1 |
| E94 a or b | C(=O) | C(CH$_3$)$_2$ | Absent | CH$_3$ | 1 |
| E95 a or b | CH$_2$ | C(=O) | Absent | CH$_3$ | 1 |
| E96 a or b | CH(CH$_3$) | C(=O) | Absent | CH$_3$ | 1 |
| E97 a or b | C(CH$_3$)$_2$ | C(=O) | Absent | CH$_3$ | 1 |
| E98 a or b | C(H) | N | Absent | CH$_3$ | 1 |
| E99 a or b | N | C(H) | Absent | CH$_3$ | 1 |
| E100 a or b | CH$_2$ | CH$_2$ | Absent | CH$_3$ | 1 |
| E101 a or b | C(NHR$_{92}$) | C(H) | N | H | 2 |
| E102 a or b | C(NHR$_{92}$) | C(CH$_3$) | N | H | 2 |
| E103 a or b | C(NHR$_{92}$) | C(F) | N | H | 2 |
| E104 a or b | C(NHR$_{92}$) | C(Br) | N | H | 2 |
| E105 a or b | C(NHR$_{92}$) | C(H) | C(H) | H | 2 |
| E106 a or b | C(NHR$_{92}$) | C(CH$_3$) | C(H) | H | 2 |
| E107 a or b | C(NHR$_{92}$) | C(F) | C(H) | H | 2 |
| E108 a or b | C(NHR$_{92}$) | C(Br) | C(H) | H | 2 |
| E109 a or b | C(=O) | C(H) | N | H | 2 |
| E110 a or b | C(=O) | C(CH$_3$) | N | H | 2 |
| E111 a or b | C(=O) | C(F) | N | H | 2 |
| E112 a or b | C(=O) | C(Br) | N | H | 2 |
| E113 a or b | C(=O) | C(H) | C(H) | H | 2 |
| E114 a or b | C(=O) | C(CH$_3$) | C(H) | H | 2 |
| E115 a or b | C(=O) | C(F) | C(H) | H | 2 |
| E116 a or b | C(=O) | C(Br) | C(H) | H | 2 |
| E117 a or b | C(=O) | CH$_2$ | Absent | H | 2 |
| E118 a or b | C(=O) | CH(CH$_3$) | Absent | H | 2 |
| E119 a or b | C(=O) | C(CH$_3$)$_2$ | Absent | H | 2 |
| E120 a or b | CH$_2$ | C(=O) | Absent | H | 2 |
| E121 a or b | CH(CH$_3$) | C(=O) | Absent | H | 2 |
| E122 a or b | C(CH$_3$)$_2$ | C(=O) | Absent | H | 2 |
| E123 a or b | C(H) | N | Absent | H | 2 |
| E124 a or b | N | C(H) | Absent | H | 2 |
| E125 a or b | CH$_2$ | CH$_2$ | Absent | H | 2 |
| E126 a or b | C(NHR$_{92}$) | C(H) | N | CH$_3$ | 2 |
| E127 a or b | C(NHR$_{92}$) | C(CH$_3$) | N | CH$_3$ | 2 |
| E128 a or b | C(NHR$_{92}$) | C(F) | N | CH$_3$ | 2 |
| E129 a or b | C(NHR$_{92}$) | C(Br) | N | CH$_3$ | 2 |
| E130 a or b | C(NHR$_{92}$) | C(H) | C(H) | CH$_3$ | 2 |
| E131 a or b | C(NHR$_{92}$) | C(CH$_3$) | C(H) | CH$_3$ | 2 |
| E132 a or b | C(NHR$_{92}$) | C(F) | C(H) | CH$_3$ | 2 |
| E133 a or b | C(NHR$_{92}$) | C(Br) | C(H) | CH$_3$ | 2 |
| E134 a or b | C(=O) | C(H) | N | CH$_3$ | 2 |
| E135 a or b | C(=O) | C(CH$_3$) | N | CH$_3$ | 2 |
| E136 a or b | C(=O) | C(F) | N | CH$_3$ | 2 |
| E137 a or b | C(=O) | C(Br) | N | CH$_3$ | 2 |
| E138 a or b | C(=O) | C(H) | C(H) | CH$_3$ | 2 |
| E139 a or b | C(=O) | C(CH$_3$) | C(H) | CH$_3$ | 2 |
| E140 a or b | C(=O) | C(F) | C(H) | CH$_3$ | 2 |
| E141 a or b | C(=O) | C(Br) | C(H) | CH$_3$ | 2 |
| E142 a or b | C(=O) | CH$_2$ | Absent | CH$_3$ | 2 |
| E143 a or b | C(=O) | CH(CH$_3$) | Absent | CH$_3$ | 2 |
| E144 a or b | C(=O) | C(CH$_3$)$_2$ | Absent | CH$_3$ | 2 |
| E145 a or b | CH$_2$ | C(=O) | Absent | CH$_3$ | 2 |
| E146 a or b | CH(CH$_3$) | C(=O) | Absent | CH$_3$ | 2 |
| E147 a or b | C(CH$_3$)$_2$ | C(=O) | Absent | CH$_3$ | 2 |
| E148 a or b | C(H) | N | Absent | CH$_3$ | 2 |
| E149 a or b | N | C(H) | Absent | CH$_3$ | 2 |
| E150 a or b | CH$_2$ | CH$_2$ | Absent | CH$_3$ | 2 |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 7

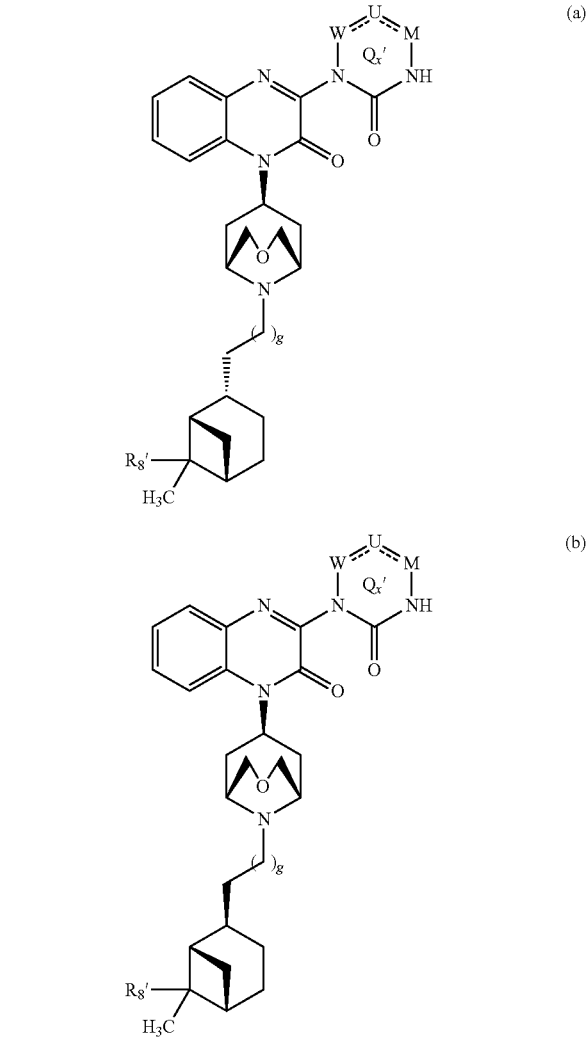

and pharmaceutically acceptable derivatives thereof, where:

| Compound | M * | U | W | R$_8$' | g |
|---|---|---|---|---|---|
| F F1 a or b | C(NHR$_{92}$) | C(H) | N | H | 0 |
| F2 a or b | C(NHR$_{92}$) | C(CH$_3$) | N | H | 0 |

TABLE 7-continued

| | | | | | |
|---|---|---|---|---|---|
| F3 a or b | C(NHR$_{92}$) | C(F) | N | H | 0 |
| F4 a or b | C(NHR$_{92}$) | C(Br) | N | H | 0 |
| F5 a or b | C(NHR$_{92}$) | C(H) | C(H) | H | 0 |
| F6 a or b | C(NHR$_{92}$) | C(CH$_3$) | C(H) | H | 0 |
| F7 a or b | C(NHR$_{92}$) | C(F) | C(H) | H | 0 |
| F8 a or b | C(NHR$_{92}$) | C(Br) | C(H) | H | 0 |
| F9 a or b | C(=O) | C(H) | N | H | 0 |
| F10 a or b | C(=O) | C(CH$_3$) | N | H | 0 |
| F11 a or b | C(=O) | C(F) | N | H | 0 |
| F12 a or b | C(=O) | C(Br) | N | H | 0 |
| F13 a or b | C(=O) | C(H) | C(H) | H | 0 |
| F14 a or b | C(=O) | C(CH$_3$) | C(H) | H | 0 |
| F15 a or b | C(=O) | C(F) | C(H) | H | 0 |
| F16 a or b | C(=O) | C(Br) | C(H) | H | 0 |
| F17 a or b | C(=O) | CH$_2$ | Absent | H | 0 |
| F18 a or b | C(=O) | CH(CH$_3$) | Absent | H | 0 |
| F19 a or b | C(=O) | C(CH$_3$)$_2$ | Absent | H | 0 |
| F20 a or b | CH$_2$ | C(=O) | Absent | H | 0 |
| F21 a or b | CH(CH$_3$) | C(=O) | Absent | H | 0 |
| F22 a or b | C(CH$_3$)$_2$ | C(=O) | Absent | H | 0 |
| F23 a or b | C(H) | N | Absent | H | 0 |
| F24 a or b | N | C(H) | Absent | H | 0 |
| F25 a or b | CH$_2$ | CH$_2$ | Absent | H | 0 |
| F26 a or b | C(NHR$_{92}$) | C(H) | N | CH$_3$ | 0 |
| F27 a or b | C(NHR$_{92}$) | C(CH$_3$) | N | CH$_3$ | 0 |
| F28 a or b | C(NHR$_{92}$) | C(F) | N | CH$_3$ | 0 |
| F29 a or b | C(NHR$_{92}$) | C(Br) | N | CH$_3$ | 0 |
| F30 a or b | C(NHR$_{92}$) | C(H) | C(H) | CH$_3$ | 0 |
| F31 a or b | C(NHR$_{92}$) | C(CH$_3$) | C(H) | CH$_3$ | 0 |
| F32 a or b | C(NHR$_{92}$) | C(F) | C(H) | CH$_3$ | 0 |
| F33 a or b | C(NHR$_{92}$) | C(Br) | C(H) | CH$_3$ | 0 |
| F34 a or b | C(=O) | C(H) | N | CH$_3$ | 0 |
| F35 a or b | C(=O) | C(CH$_3$) | N | CH$_3$ | 0 |
| F36 a or b | C(=O) | C(F) | N | CH$_3$ | 0 |
| F37 a or b | C(=O) | C(Br) | N | CH$_3$ | 0 |
| F38 a or b | C(=O) | C(H) | C(H) | CH$_3$ | 0 |
| F39 a or b | C(=O) | C(CH$_3$) | C(H) | CH$_3$ | 0 |
| F40 a or b | C(=O) | C(F) | C(H) | CH$_3$ | 0 |
| F41 a or b | C(=O) | C(Br) | C(H) | CH$_3$ | 0 |
| F42 a or b | C(=O) | CH$_2$ | Absent | CH$_3$ | 0 |
| F43 a or b | C(=O) | CH(CH$_3$) | Absent | CH$_3$ | 0 |
| F44 a or b | C(=O) | C(CH$_3$)$_2$ | Absent | CH$_3$ | 0 |
| F45 a or b | CH$_2$ | C(=O) | Absent | CH$_3$ | 0 |
| F46 a or b | CH(CH$_3$) | C(=O) | Absent | CH$_3$ | 0 |
| F47 a or b | C(CH$_3$)$_2$ | C(=O) | Absent | CH$_3$ | 0 |
| F48 a or b | C(H) | N | Absent | CH$_3$ | 0 |
| F49 a or b | N | C(H) | Absent | CH$_3$ | 0 |
| F50 a or b | CH$_2$ | CH$_2$ | Absent | CH$_3$ | 0 |
| F51 a or b | C(NHR$_{92}$) | C(H) | N | H | 1 |
| F52 a or b | C(NHR$_{92}$) | C(CH$_3$) | N | H | 1 |
| F53 a or b | C(NHR$_{92}$) | C(F) | N | H | 1 |
| F54 a or b | C(NHR$_{92}$) | C(Br) | N | H | 1 |
| F55 a or b | C(NHR$_{92}$) | C(H) | C(H) | H | 1 |
| F56 a or b | C(NHR$_{92}$) | C(CH$_3$) | C(H) | H | 1 |
| F57 a or b | C(NHR$_{92}$) | C(F) | C(H) | H | 1 |
| F58 a or b | C(NHR$_{92}$) | C(Br) | C(H) | H | 1 |
| F59 a or b | C(=O) | C(H) | N | H | 1 |
| F60 a or b | C(=O) | C(CH$_3$) | N | H | 1 |
| F61 a or b | C(=O) | C(F) | N | H | 1 |
| F62 a or b | C(=O) | C(Br) | N | H | 1 |
| F63 a or b | C(=O) | C(H) | C(H) | H | 1 |
| F64 a or b | C(=O) | C(CH$_3$) | C(H) | H | 1 |
| F65 a or b | C(=O) | C(F) | C(H) | H | 1 |
| F66 a or b | C(=O) | C(Br) | C(H) | H | 1 |
| F67 a or b | C(=O) | CH$_2$ | Absent | H | 1 |
| F68 a or b | C(=O) | CH(CH$_3$) | Absent | H | 1 |
| F69 a or b | C(=O) | C(CH$_3$)$_2$ | Absent | H | 1 |
| F70 a or b | CH$_2$ | C(=O) | Absent | H | 1 |
| F71 a or b | CH(CH$_3$) | C(=O) | Absent | H | 1 |
| F72 a or b | C(CH$_3$)$_2$ | C(=O) | Absent | H | 1 |
| F73 a or b | C(H) | N | Absent | H | 1 |
| F74 a or b | N | C(H) | Absent | H | 1 |
| F75 a or b | CH$_2$ | CH$_2$ | Absent | H | 1 |
| F76 a or b | C(NHR$_{92}$) | C(H) | N | CH$_3$ | 1 |
| F77 a or b | C(NHR$_{92}$) | C(CH$_3$) | N | CH$_3$ | 1 |
| F78 a or b | C(NHR$_{92}$) | C(F) | N | CH$_3$ | 1 |
| F79 a or b | C(NHR$_{92}$) | C(Br) | N | CH$_3$ | 1 |
| F80 a or b | C(NHR$_{92}$) | C(H) | C(H) | CH$_3$ | 1 |
| F81 a or b | C(NHR$_{92}$) | C(CH$_3$) | C(H) | CH$_3$ | 1 |
| F82 a or b | C(NHR$_{92}$) | C(F) | C(H) | CH$_3$ | 1 |
| F83 a or b | C(NHR$_{92}$) | C(Br) | C(H) | CH$_3$ | 1 |
| F84 a or b | C(=O) | C(H) | N | CH$_3$ | 1 |
| F85 a or b | C(=O) | C(CH$_3$) | N | CH$_3$ | 1 |
| F86 a or b | C(=O) | C(F) | N | CH$_3$ | 1 |
| F87 a or b | C(=O) | C(Br) | N | CH$_3$ | 1 |
| F88 a or b | C(=O) | C(H) | C(H) | CH$_3$ | 1 |
| F89 a or b | C(=O) | C(CH$_3$) | C(H) | CH$_3$ | 1 |
| F90 a or b | C(=O) | C(F) | C(H) | CH$_3$ | 1 |
| F91 a or b | C(=O) | C(Br) | C(H) | CH$_3$ | 1 |
| F92 a or b | C(=O) | CH$_2$ | Absent | CH$_3$ | 1 |
| F93 a or b | C(=O) | CH(CH$_3$) | Absent | CH$_3$ | 1 |
| F94 a or b | C(=O) | C(CH$_3$)$_2$ | Absent | CH$_3$ | 1 |
| F95 a or b | CH$_2$ | C(=O) | Absent | CH$_3$ | 1 |
| F96 a or b | CH(CH$_3$) | C(=O) | Absent | CH$_3$ | 1 |
| F97 a or b | C(CH$_3$)$_2$ | C(=O) | Absent | CH$_3$ | 1 |
| F98 a or b | C(H) | N | Absent | CH$_3$ | 1 |
| F99 a or b | N | C(H) | Absent | CH$_3$ | 1 |
| F100 a or b | CH$_2$ | CH$_2$ | Absent | CH$_3$ | 1 |
| F101 a or b | C(NHR$_{92}$) | C(H) | N | H | 2 |
| F102 a or b | C(NHR$_{92}$) | C(CH$_3$) | N | H | 2 |
| F103 a or b | C(NHR$_{92}$) | C(F) | N | H | 2 |
| F104 a or b | C(NHR$_{92}$) | C(Br) | N | H | 2 |
| F105 a or b | C(NHR$_{92}$) | C(H) | C(H) | H | 2 |
| F106 a or b | C(NHR$_{92}$) | C(CH$_3$) | C(H) | H | 2 |
| F107 a or b | C(NHR$_{92}$) | C(F) | C(H) | H | 2 |
| F108 a or b | C(NHR$_{92}$) | C(Br) | C(H) | H | 2 |
| F109 a or b | C(=O) | C(H) | N | H | 2 |
| F110 a or b | C(=O) | C(CH$_3$) | N | H | 2 |
| F111 a or b | C(=O) | C(F) | N | H | 2 |
| F112 a or b | C(=O) | C(Br) | N | H | 2 |
| F113 a or b | C(=O) | C(H) | C(H) | H | 2 |
| F114 a or b | C(=O) | C(CH$_3$) | C(H) | H | 2 |
| F115 a or b | C(=O) | C(F) | C(H) | H | 2 |
| F116 a or b | C(=O) | C(Br) | C(H) | H | 2 |
| F117 a or b | C(=O) | CH$_2$ | Absent | H | 2 |
| F118 a or b | C(=O) | CH(CH$_3$) | Absent | H | 2 |
| F119 a or b | C(=O) | C(CH$_3$)$_2$ | Absent | H | 2 |
| F120 a or b | CH$_2$ | C(=O) | Absent | H | 2 |
| F121 a or b | CH(CH$_3$) | C(=O) | Absent | H | 2 |
| F122 a or b | C(CH$_3$)$_2$ | C(=O) | Absent | H | 2 |
| F123 a or b | C(H) | N | Absent | H | 2 |
| F124 a or b | N | C(H) | Absent | H | 2 |
| F125 a or b | CH$_2$ | CH$_2$ | Absent | H | 2 |
| F126 a or b | C(NHR$_{92}$) | C(H) | N | CH$_3$ | 2 |
| F127 a or b | C(NHR$_{92}$) | C(CH$_3$) | N | CH$_3$ | 2 |
| F128 a or b | C(NHR$_{92}$) | C(F) | N | CH$_3$ | 2 |
| F129 a or b | C(NHR$_{92}$) | C(Br) | N | CH$_3$ | 2 |
| F130 a or b | C(NHR$_{92}$) | C(H) | C(H) | CH$_3$ | 2 |
| F131 a or b | C(NHR$_{92}$) | C(CH$_3$) | C(H) | CH$_3$ | 2 |
| F132 a or b | C(NHR$_{92}$) | C(F) | C(H) | CH$_3$ | 2 |
| F133 a or b | C(NHR$_{92}$) | C(Br) | C(H) | CH$_3$ | 2 |
| F134 a or b | C(=O) | C(H) | N | CH$_3$ | 2 |
| F135 a or b | C(=O) | C(CH$_3$) | N | CH$_3$ | 2 |
| F136 a or b | C(=O) | C(F) | N | CH$_3$ | 2 |
| F137 a or b | C(=O) | C(Br) | N | CH$_3$ | 2 |
| F138 a or b | C(=O) | C(H) | C(H) | CH$_3$ | 2 |
| F139 a or b | C(=O) | C(CH$_3$) | C(H) | CH$_3$ | 2 |
| F140 a or b | C(=O) | C(F) | C(H) | CH$_3$ | 2 |
| F141 a or b | C(=O) | C(Br) | C(H) | CH$_3$ | 2 |
| F142 a or b | C(=O) | CH$_2$ | Absent | CH$_3$ | 2 |
| F143 a or b | C(=O) | CH(CH$_3$) | Absent | CH$_3$ | 2 |
| F144 a or b | C(=O) | C(CH$_3$)$_2$ | Absent | CH$_3$ | 2 |
| F145 a or b | CH$_2$ | C(=O) | Absent | CH$_3$ | 2 |
| F146 a or b | CH(CH$_3$) | C(=O) | Absent | CH$_3$ | 2 |
| F147 a or b | C(CH$_3$)$_2$ | C(=O) | Absent | CH$_3$ | 2 |
| F148 a or b | C(H) | N | Absent | CH$_3$ | 2 |
| F149 a or b | N | C(H) | Absent | CH$_3$ | 2 |
| F150 a or b | CH$_2$ | CH$_2$ | Absent | CH$_3$ | 2 |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 8

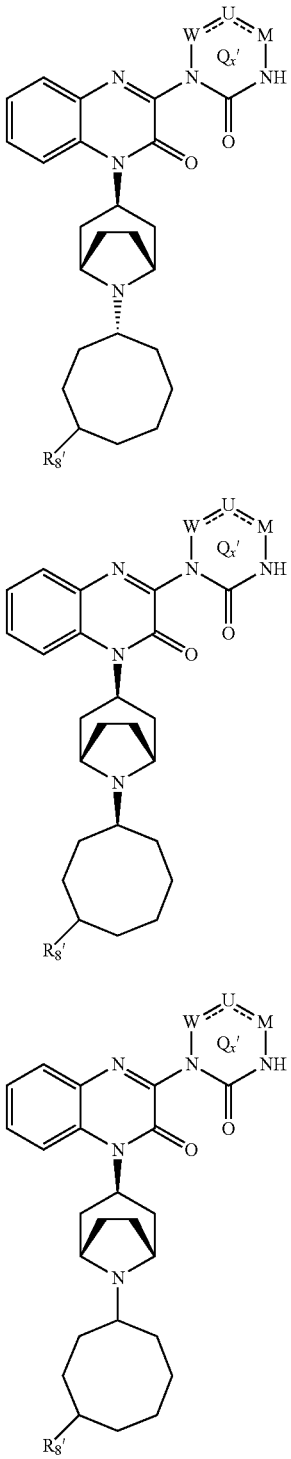

(a), (b), (c)

and pharmaceutically acceptable derivatives thereof, where:

| Compound | M * | U | W | $R_8'$ |
|---|---|---|---|---|
| G G1 c | $C(NHR_{92})$ | C(H) | N | H |
| G2 c | $C(NHR_{92})$ | $C(CH_3)$ | N | H |
| G3 c | $C(NHR_{92})$ | C(F) | N | H |
| G4 c | $C(NHR_{92})$ | C(Br) | N | H |
| G5 c | $C(NHR_{92})$ | C(H) | C(H) | H |
| G6 c | $C(NHR_{92})$ | $C(CH_3)$ | C(H) | H |
| G7 c | $C(NHR_{92})$ | C(F) | C(H) | H |

TABLE 8-continued

| | M * | U | W | $R_8'$ |
|---|---|---|---|---|
| G8 c | $C(NHR_{92})$ | C(Br) | C(H) | H |
| G9 c | C(=O) | C(H) | N | H |
| G10 c | C(=O) | $C(CH_3)$ | N | H |
| G11 c | C(=O) | C(F) | N | H |
| G12 c | C(=O) | C(Br) | N | H |
| G13 c | C(=O) | C(H) | C(H) | H |
| G14 c | C(=O) | $C(CH_3)$ | C(H) | H |
| G15 c | C(=O) | C(F) | C(H) | H |
| G16 c | C(=O) | C(Br) | C(H) | H |
| G17 c | C(=O) | $CH_2$ | Absent | H |
| G18 c | C(=O) | $CH(CH_3)$ | Absent | H |
| G19 c | C(=O) | $C(CH_3)_2$ | Absent | H |
| G20 c | $CH_2$ | C(=O) | Absent | H |
| G21 c | $CH(CH_3)$ | C(=O) | Absent | H |
| G22 c | $C(CH_3)_2$ | C(=O) | Absent | H |
| G23 c | C(H) | N | Absent | H |
| G24 c | N | C(H) | Absent | H |
| G25 c | $CH_2$ | $CH_2$ | Absent | H |
| G26 a or b | $C(NHR_{92})$ | C(H) | N | $CH_3$ |
| G27 a or b | $C(NHR_{92})$ | $C(CH_3)$ | N | $CH_3$ |
| G28 a or b | $C(NHR_{92})$ | C(F) | N | $CH_3$ |
| G29 a or b | $C(NHR_{92})$ | C(Br) | N | $CH_3$ |
| G30 a or b | $C(NHR_{92})$ | C(H) | C(H) | $CH_3$ |
| G31 a or b | $C(NHR_{92})$ | $C(CH_3)$ | C(H) | $CH_3$ |
| G32 a or b | $C(NHR_{92})$ | C(F) | C(H) | $CH_3$ |
| G33 a or b | $C(NHR_{92})$ | C(Br) | C(H) | $CH_3$ |
| G34 a or b | C(=O) | C(H) | N | $CH_3$ |
| G35 a or b | C(=O) | $C(CH_3)$ | N | $CH_3$ |
| G36 a or b | C(=O) | C(F) | N | $CH_3$ |
| G37 a or b | C(=O) | C(Br) | N | $CH_3$ |
| G38 a or b | C(=O) | C(H) | C(H) | $CH_3$ |
| G39 a or b | C(=O) | $C(CH_3)$ | C(H) | $CH_3$ |
| G40 a or b | C(=O) | C(F) | C(H) | $CH_3$ |
| G41 a or b | C(=O) | C(Br) | C(H) | $CH_3$ |
| G42 a or b | C(=O) | $CH_2$ | Absent | $CH_3$ |
| G43 a or b | C(=O) | $CH(CH_3)$ | Absent | $CH_3$ |
| G44 a or b | C(=O) | $C(CH_3)_2$ | Absent | $CH_3$ |
| G45 a or b | $CH_2$ | C(=O) | Absent | $CH_3$ |
| G46 a or b | $CH(CH_3)$ | C(=O) | Absent | $CH_3$ |
| G47 a or b | $C(CH_3)_2$ | C(=O) | Absent | $CH_3$ |
| G48 a or b | C(H) | N | Absent | $CH_3$ |
| G49 a or b | N | C(H) | Absent | $CH_3$ |
| G50 a or b | $CH_2$ | $CH_2$ | Absent | $CH_3$ |

* (i) Indicates that $R_{92}$ is —H, (ii) indicates that $R_{92}$ is —C(=O)$CH_3$, and (iii) indicates that $R_{92}$ is —$CH_2$—C(=O)OH.

TABLE 9

(a)

TABLE 9-continued

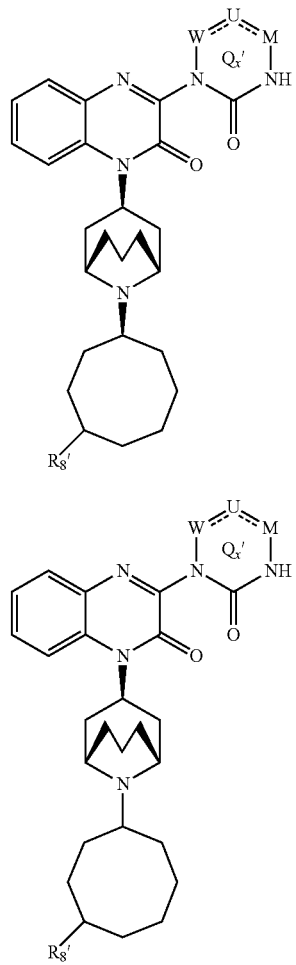

and pharmaceutically acceptable derivatives thereof, where:

| Compound | M * | U | W | $R_8'$ |
|---|---|---|---|---|
| H H1 c | C(NHR$_{92}$) | C(H) | N | H |
| H2 c | C(NHR$_{92}$) | C(CH$_3$) | N | H |
| H3 c | C(NHR$_{92}$) | C(F) | N | H |
| H4 c | C(NHR$_{92}$) | C(Br) | N | H |
| H5 c | C(NHR$_{92}$) | C(H) | C(H) | H |
| H6 c | C(NHR$_{92}$) | C(CH$_3$) | C(H) | H |
| H7 c | C(NHR$_{92}$) | C(F) | C(H) | H |
| H8 c | C(NHR$_{92}$) | C(Br) | C(H) | H |
| H9 c | C(=O) | C(H) | N | H |
| H10 c | C(=O) | C(CH$_3$) | N | H |
| H11 c | C(=O) | C(F) | N | H |
| H12 c | C(=O) | C(Br) | N | H |
| H13 c | C(=O) | C(H) | C(H) | H |
| H14 c | C(=O) | C(CH$_3$) | C(H) | H |
| H15 c | C(=O) | C(F) | C(H) | H |
| H16 c | C(=O) | C(Br) | C(H) | H |
| H17 c | C(=O) | CH$_2$ | Absent | H |
| H18 c | C(=O) | CH(CH$_3$) | Absent | H |
| H19 c | C(=O) | C(CH$_3$)$_2$ | Absent | H |
| H20 c | CH$_2$ | C(=O) | Absent | H |
| H21 c | CH(CH$_3$) | C(=O) | Absent | H |
| H22 c | C(CH$_3$)$_2$ | C(=O) | Absent | H |
| H23 c | C(H) | N | Absent | H |
| H24 c | N | C(H) | Absent | H |
| H25 c | CH$_2$ | CH$_2$ | Absent | H |
| H26 a or b | C(NHR$_{92}$) | C(H) | N | CH$_3$ |
| H27 a or b | C(NHR$_{92}$) | C(CH$_3$) | N | CH$_3$ |
| H28 a or b | C(NHR$_{92}$) | C(F) | N | CH$_3$ |
| H29 a or b | C(NHR$_{92}$) | C(Br) | N | CH$_3$ |
| H30 a or b | C(NHR$_{92}$) | C(H) | C(H) | CH$_3$ |
| H31 a or b | C(NHR$_{92}$) | C(CH$_3$) | C(H) | CH$_3$ |
| H32 a or b | C(NHR$_{92}$) | C(F) | C(H) | CH$_3$ |
| H33 a or b | C(NHR$_{92}$) | C(Br) | C(H) | CH$_3$ |
| H34 a or b | C(=O) | C(H) | N | CH$_3$ |
| H35 a or b | C(=O) | C(CH$_3$) | N | CH$_3$ |
| H36 a or b | C(=O) | C(F) | N | CH$_3$ |
| H37 a or b | C(=O) | C(Br) | N | CH$_3$ |
| H38 a or b | C(=O) | C(H) | C(H) | CH$_3$ |
| H39 a or b | C(=O) | C(CH$_3$) | C(H) | CH$_3$ |
| H40 a or b | C(=O) | C(F) | C(H) | CH$_3$ |
| H41 a or b | C(=O) | C(Br) | C(H) | CH$_3$ |
| H42 a or b | C(=O) | CH$_2$ | Absent | CH$_3$ |
| H43 a or b | C(=O) | CH(CH$_3$) | Absent | CH$_3$ |
| H44 a or b | C(=O) | C(CH$_3$)$_2$ | Absent | CH$_3$ |
| H45 a or b | CH$_2$ | C(=O) | Absent | CH$_3$ |
| H46 a or b | CH(CH$_3$) | C(=O) | Absent | CH$_3$ |
| H47 a or b | C(CH$_3$)$_2$ | C(=O) | Absent | CH$_3$ |
| H48 a or b | C(H) | N | Absent | CH$_3$ |
| H49 a or b | N | C(H) | Absent | CH$_3$ |
| H50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 10

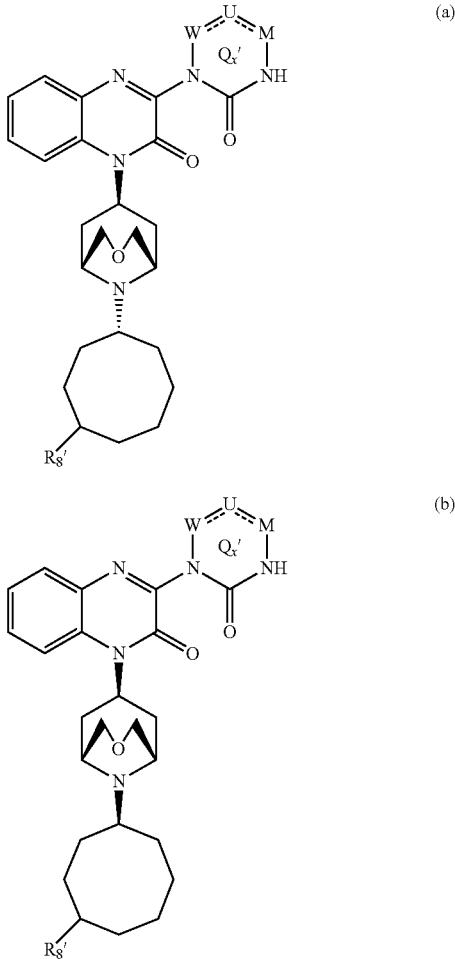

TABLE 10-continued

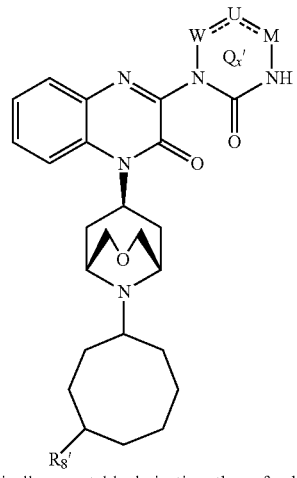

(c)

and pharmaceutically acceptable derivatives thereof, where:

| Compound | M * | U | W | R<sub>8</sub>' |
|---|---|---|---|---|
| J J1 c | C(NHR$_{92}$) | C(H) | N | H |
| J2 c | C(NHR$_{92}$) | C(CH$_3$) | N | H |
| J3 c | C(NHR$_{92}$) | C(F) | N | H |
| J4 c | C(NHR$_{92}$) | C(Br) | N | H |
| J5 c | C(NHR$_{92}$) | C(H) | C(H) | H |
| J6 c | C(NHR$_{92}$) | C(CH$_3$) | C(H) | H |
| J7 c | C(NHR$_{92}$) | C(F) | C(H) | H |
| J8 c | C(NHR$_{92}$) | C(Br) | C(H) | H |
| J9 c | C(=O) | C(H) | N | H |
| J10 c | C(=O) | C(CH$_3$) | N | H |
| J11 c | C(=O) | C(F) | N | H |
| J12 c | C(=O) | C(Br) | N | H |
| J13 c | C(=O) | C(H) | C(H) | H |
| J14 c | C(=O) | C(CH$_3$) | C(H) | H |
| J15 c | C(=O) | C(F) | C(H) | H |
| J16 c | C(=O) | C(Br) | C(H) | H |
| J17 c | C(=O) | CH$_2$ | Absent | H |
| J18 c | C(=O) | CH(CH$_3$) | Absent | H |
| J19 c | C(=O) | C(CH$_3$)$_2$ | Absent | H |
| J20 c | CH$_2$ | C(=O) | Absent | H |
| J21 c | CH(CH$_3$) | C(=O) | Absent | H |
| J22 c | C(CH$_3$)$_2$ | C(=O) | Absent | H |
| J23 c | C(H) | N | Absent | H |
| J24 c | N | C(H) | Absent | H |
| J25 c | CH$_2$ | CH$_2$ | Absent | H |
| J26 a or b | C(NHR$_{92}$) | C(H) | N | CH$_3$ |
| J27 a or b | C(NHR$_{92}$) | C(CH$_3$) | N | CH$_3$ |
| J28 a or b | C(NHR$_{92}$) | C(F) | N | CH$_3$ |
| J29 a or b | C(NHR$_{92}$) | C(Br) | N | CH$_3$ |
| J30 a or b | C(NHR$_{92}$) | C(H) | C(H) | CH$_3$ |
| J31 a or b | C(NHR$_{92}$) | C(CH$_3$) | C(H) | CH$_3$ |
| J32 a or b | C(NHR$_{92}$) | C(F) | C(H) | CH$_3$ |
| J33 a or b | C(NHR$_{92}$) | C(Br) | C(H) | CH$_3$ |
| J34 a or b | C(=O) | C(H) | N | CH$_3$ |
| J35 a or b | C(=O) | C(CH$_3$) | N | CH$_3$ |
| J36 a or b | C(=O) | C(F) | N | CH$_3$ |
| J37 a or b | C(=O) | C(Br) | N | CH$_3$ |
| J38 a or b | C(=O) | C(H) | C(H) | CH$_3$ |
| J39 a or b | C(=O) | C(CH$_3$) | C(H) | CH$_3$ |
| J40 a or b | C(=O) | C(F) | C(H) | CH$_3$ |
| J41 a or b | C(=O) | C(Br) | C(H) | CH$_3$ |
| J42 a or b | C(=O) | CH$_2$ | Absent | CH$_3$ |
| J43 a or b | C(=O) | CH(CH$_3$) | Absent | CH$_3$ |
| J44 a or b | C(=O) | C(CH$_3$)$_2$ | Absent | CH$_3$ |
| J45 a or b | CH$_2$ | C(=O) | Absent | CH$_3$ |
| J46 a or b | CH(CH$_3$) | C(=O) | Absent | CH$_3$ |
| J47 a or b | C(CH$_3$)$_2$ | C(=O) | Absent | CH$_3$ |
| J48 a or b | C(H) | N | Absent | CH$_3$ |
| J49 a or b | N | C(H) | Absent | CH$_3$ |
| J50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 11

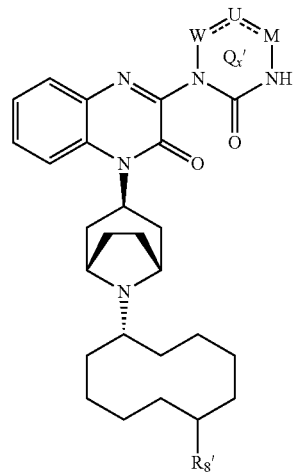

(a)

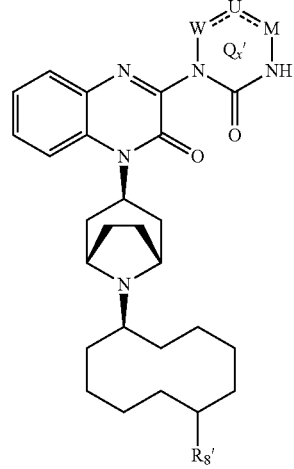

(b)

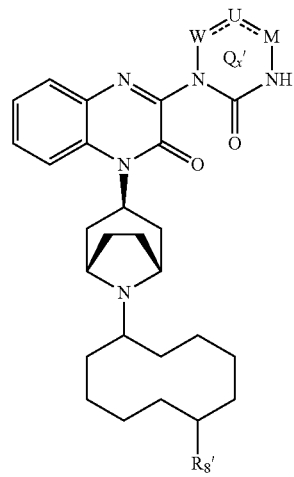

(c)

and pharmaceutically acceptable derivatives thereof, where:

| Compound | M * | U | W | R<sub>8</sub>' |
|---|---|---|---|---|
| K K1 c | C(NHR$_{92}$) | C(H) | N | H |
| K2 c | C(NHR$_{92}$) | C(CH$_3$) | N | H |
| K3 c | C(NHR$_{92}$) | C(F) | N | H |
| K4 c | C(NHR$_{92}$) | C(Br) | N | H |
| K5 c | C(NHR$_{92}$) | C(H) | C(H) | H |
| K6 c | C(NHR$_{92}$) | C(CH$_3$) | C(H) | H |
| K7 c | C(NHR$_{92}$) | C(F) | C(H) | H |

TABLE 11-continued

| | | | | |
|---|---|---|---|---|
| K8 c | C(NHR$_{92}$) | C(Br) | C(H) | H |
| K9 c | C(=O) | C(H) | N | H |
| K10 c | C(=O) | C(CH$_3$) | N | H |
| K11 c | C(=O) | C(F) | N | H |
| K12 c | C(=O) | C(Br) | N | H |
| K13 c | C(=O) | C(H) | C(H) | H |
| K14 c | C(=O) | C(CH$_3$) | C(H) | H |
| K15 c | C(=O) | C(F) | C(H) | H |
| K16 c | C(=O) | C(Br) | C(H) | H |
| K17 c | C(=O) | CH$_2$ | Absent | H |
| K18 c | C(=O) | CH(CH$_3$) | Absent | H |
| K19 c | C(=O) | C(CH$_3$)$_2$ | Absent | H |
| K20 c | CH$_2$ | C(=O) | Absent | H |
| K21 c | CH(CH$_3$) | C(=O) | Absent | H |
| K22 c | C(CH$_3$)$_2$ | C(=O) | Absent | H |
| K23 c | C(H) | N | Absent | H |
| K24 c | N | C(H) | Absent | H |
| K25 c | CH$_2$ | CH$_2$ | Absent | H |
| K26 a or b | C(NHR$_{92}$) | C(H) | N | CH$_3$ |
| K27 a or b | C(NHR$_{92}$) | C(CH$_3$) | N | CH$_3$ |
| K28 a or b | C(NHR$_{92}$) | C(F) | N | CH$_3$ |
| K29 a or b | C(NHR$_{92}$) | C(Br) | N | CH$_3$ |
| K30 a or b | C(NHR$_{92}$) | C(H) | C(H) | CH$_3$ |
| K31 a or b | C(NHR$_{92}$) | C(CH$_3$) | C(H) | CH$_3$ |
| K32 a or b | C(NHR$_{92}$) | C(F) | C(H) | CH$_3$ |
| K33 a or b | C(NHR$_{92}$) | C(Br) | C(H) | CH$_3$ |
| K34 a or b | C(=O) | C(H) | N | CH$_3$ |
| K35 a or b | C(=O) | C(CH$_3$) | N | CH$_3$ |
| K36 a or b | C(=O) | C(F) | N | CH$_3$ |
| K37 a or b | C(=O) | C(Br) | N | CH$_3$ |
| K38 a or b | C(=O) | C(H) | C(H) | CH$_3$ |
| K39 a or b | C(=O) | C(CH$_3$) | C(H) | CH$_3$ |
| K40 a or b | C(=O) | C(F) | C(H) | CH$_3$ |
| K41 a or b | C(=O) | C(Br) | C(H) | CH$_3$ |
| K42 a or b | C(=O) | CH$_2$ | Absent | CH$_3$ |
| K43 a or b | C(=O) | CH(CH$_3$) | Absent | CH$_3$ |
| K44 a or b | C(=O) | C(CH$_3$)$_2$ | Absent | CH$_3$ |
| K45 a or b | CH$_2$ | C(=O) | Absent | CH$_3$ |
| K46 a or b | CH(CH$_3$) | C(=O) | Absent | CH$_3$ |
| K47 a or b | C(CH$_3$)$_2$ | C(=O) | Absent | CH$_3$ |
| K48 a or b | C(H) | N | Absent | CH$_3$ |
| K49 a or b | N | C(H) | Absent | CH$_3$ |
| K50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 12

(a) [Structure: quinoxalinone core with W=U–M/Q$_x'$–NH ring substituent, N-linked bicyclic amine connected to cyclohexane bearing R$_8'$]

(b) [Structure variant b]

(c) [Structure variant c]

and pharmaceutically acceptable derivatives thereof, where:

| Compound | M * | U | W | R$_8'$ |
|---|---|---|---|---|
| L L1 c | C(NHR$_{92}$) | C(H) | N | H |
| L2 c | C(NHR$_{92}$) | C(CH$_3$) | N | H |
| L3 c | C(NHR$_{92}$) | C(F) | N | H |
| L4 c | C(NHR$_{92}$) | C(Br) | N | H |
| L5 c | C(NHR$_{92}$) | C(H) | C(H) | H |
| L6 c | C(NHR$_{92}$) | C(CH$_3$) | C(H) | H |
| L7 c | C(NHR$_{92}$) | C(F) | C(H) | H |
| L8 c | C(NHR$_{92}$) | C(Br) | C(H) | H |
| L9 c | C(=O) | C(H) | N | H |
| L10 c | C(=O) | C(CH$_3$) | N | H |
| L11 c | C(=O) | C(F) | N | H |
| L12 c | C(=O) | C(Br) | N | H |
| L13 c | C(=O) | C(H) | C(H) | H |
| L14 c | C(=O) | C(CH$_3$) | C(H) | H |
| L15 c | C(=O) | C(F) | C(H) | H |
| L16 c | C(=O) | C(Br) | C(H) | H |
| L17 c | C(=O) | CH$_2$ | Absent | H |
| L18 c | C(=O) | CH(CH$_3$) | Absent | H |
| L19 c | C(=O) | C(CH$_3$)$_2$ | Absent | H |
| L20 c | CH$_2$ | C(=O) | Absent | H |
| L21 c | CH(CH$_3$) | C(=O) | Absent | H |
| L22 c | C(CH$_3$)$_2$ | C(=O) | Absent | H |
| L23 c | C(H) | N | Absent | H |
| L24 c | N | C(H) | Absent | H |
| L25 c | CH$_2$ | CH$_2$ | Absent | H |
| L26 a or b | C(NHR$_{92}$) | C(H) | N | CH$_3$ |
| L27 a or b | C(NHR$_{92}$) | C(CH$_3$) | N | CH$_3$ |
| L28 a or b | C(NHR$_{92}$) | C(F) | N | CH$_3$ |
| L29 a or b | C(NHR$_{92}$) | C(Br) | N | CH$_3$ |
| L30 a or b | C(NHR$_{92}$) | C(H) | C(H) | CH$_3$ |

TABLE 12-continued

| | | | | |
|---|---|---|---|---|
| L31 a or b | C(NHR$_{92}$) | C(CH$_3$) | C(H) | CH$_3$ |
| L32 a or b | C(NHR$_{92}$) | C(F) | C(H) | CH$_3$ |
| L33 a or b | C(NHR$_{92}$) | C(Br) | C(H) | CH$_3$ |
| L34 a or b | C(=O) | C(H) | N | CH$_3$ |
| L35 a or b | C(=O) | C(CH$_3$) | N | CH$_3$ |
| L36 a or b | C(=O) | C(F) | N | CH$_3$ |
| L37 a or b | C(=O) | C(Br) | N | CH$_3$ |
| L38 a or b | C(=O) | C(H) | C(H) | CH$_3$ |
| L39 a or b | C(=O) | C(CH$_3$) | C(H) | CH$_3$ |
| L40 a or b | C(=O) | C(F) | C(H) | CH$_3$ |
| L41 a or b | C(=O) | C(Br) | C(H) | CH$_3$ |
| L42 a or b | C(=O) | CH$_2$ | Absent | CH$_3$ |
| L43 a or b | C(=O) | CH(CH$_3$) | Absent | CH$_3$ |
| L44 a or b | C(=O) | C(CH$_3$)$_2$ | Absent | CH$_3$ |
| L45 a or b | CH$_2$ | C(=O) | Absent | CH$_3$ |
| L46 a or b | CH(CH$_3$) | C(=O) | Absent | CH$_3$ |
| L47 a or b | C(CH$_3$)$_2$ | C(=O) | Absent | CH$_3$ |
| L48 a or b | C(H) | N | Absent | CH$_3$ |
| L49 a or b | N | C(H) | Absent | CH$_3$ |
| L50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 13

(a)
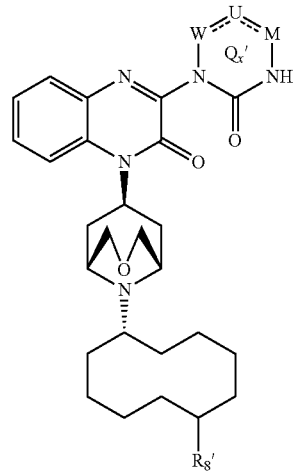

(b)
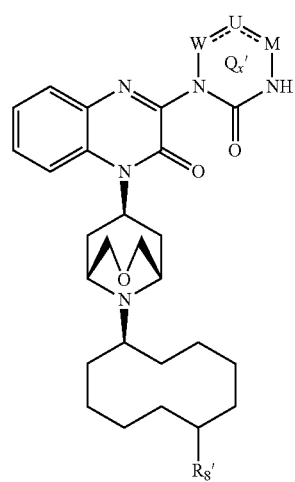

(c)

and pharmaceutically acceptable derivatives thereof, where:

| Compound | M * | U | W | R$_8'$ |
|---|---|---|---|---|
| M M1 c | C(NHR$_{92}$) | C(H) | N | H |
| M2 c | C(NHR$_{92}$) | C(CH$_3$) | N | H |
| M3 c | C(NHR$_{92}$) | C(F) | N | H |
| M4 c | C(NHR$_{92}$) | C(Br) | N | H |
| M5 c | C(NHR$_{92}$) | C(H) | C(H) | H |
| M6 c | C(NHR$_{92}$) | C(CH$_3$) | C(H) | H |
| M7 c | C(NHR$_{92}$) | C(F) | C(H) | H |
| M8 c | C(NHR$_{92}$) | C(Br) | C(H) | H |
| M9 c | C(=O) | C(H) | N | H |
| M10 c | C(=O) | C(CH$_3$) | N | H |
| M11 c | C(=O) | C(F) | N | H |
| M12 c | C(=O) | C(Br) | N | H |
| M13 c | C(=O) | C(H) | C(H) | H |
| M14 c | C(=O) | C(CH$_3$) | C(H) | H |
| M15 c | C(=O) | C(F) | C(H) | H |
| M16 c | C(=O) | C(Br) | C(H) | H |
| M17 c | C(=O) | CH$_2$ | Absent | H |
| M18 c | C(=O) | CH(CH$_3$) | Absent | H |
| M19 c | C(=O) | C(CH$_3$)$_2$ | Absent | H |
| M20 c | CH$_2$ | C(=O) | Absent | H |
| M21 c | CH(CH$_3$) | C(=O) | Absent | H |
| M22 c | C(CH$_3$)$_2$ | C(=O) | Absent | H |
| M23 c | C(H) | N | Absent | H |
| M24 c | N | C(H) | Absent | H |
| M25 c | CH$_2$ | CH$_2$ | Absent | H |
| M26 a or b | C(NHR$_{92}$) | C(H) | N | CH$_3$ |
| M27 a or b | C(NHR$_{92}$) | C(CH$_3$) | N | CH$_3$ |
| M28 a or b | C(NHR$_{92}$) | C(F) | N | CH$_3$ |
| M29 a or b | C(NHR$_{92}$) | C(Br) | N | CH$_3$ |
| M30 a or b | C(NHR$_{92}$) | C(H) | C(H) | CH$_3$ |
| M31 a or b | C(NHR$_{92}$) | C(CH$_3$) | C(H) | CH$_3$ |
| M32 a or b | C(NHR$_{92}$) | C(F) | C(H) | CH$_3$ |
| M33 a or b | C(NHR$_{92}$) | C(Br) | C(H) | CH$_3$ |
| M34 a or b | C(=O) | C(H) | N | CH$_3$ |
| M35 a or b | C(=O) | C(CH$_3$) | N | CH$_3$ |
| M36 a or b | C(=O) | C(F) | N | CH$_3$ |
| M37 a or b | C(=O) | C(Br) | N | CH$_3$ |
| M38 a or b | C(=O) | C(H) | C(H) | CH$_3$ |
| M39 a or b | C(=O) | C(CH$_3$) | C(H) | CH$_3$ |
| M40 a or b | C(=O) | C(F) | C(H) | CH$_3$ |
| M41 a or b | C(=O) | C(Br) | C(H) | CH$_3$ |
| M42 a or b | C(=O) | CH$_2$ | Absent | CH$_3$ |
| M43 a or b | C(=O) | CH(CH$_3$) | Absent | CH$_3$ |
| M44 a or b | C(=O) | C(CH$_3$)$_2$ | Absent | CH$_3$ |
| M45 a or b | CH$_2$ | C(=O) | Absent | CH$_3$ |
| M46 a or b | CH(CH$_3$) | C(=O) | Absent | CH$_3$ |
| M47 a or b | C(CH$_3$)$_2$ | C(=O) | Absent | CH$_3$ |
| M48 a or b | C(H) | N | Absent | CH$_3$ |
| M49 a or b | N | C(H) | Absent | CH$_3$ |
| M50 a or b | CH$_2$ | CH$_2$ | Absent | CH$_3$ |

* (i) Indicates that R$_{92}$ is —H,
(ii) indicates that R$_{92}$ is —C(=O)CH$_3$, and
(iii) indicates that R$_{92}$ is —CH$_2$—C(=O)OH.

TABLE 14

(a)

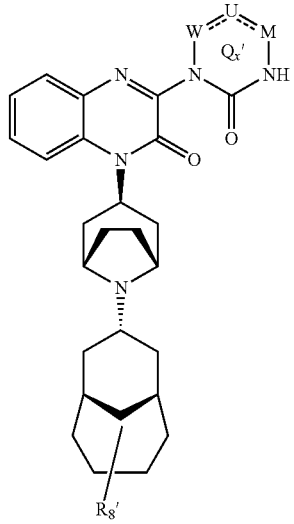

(b)

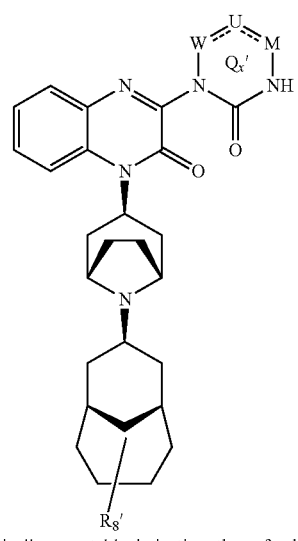

and pharmaceutically acceptable derivatives thereof, where:

| Compound | M * | U | W | $R_8'$ |
|---|---|---|---|---|
| N N1 a or b | C(NHR$_{92}$) | C(H) | N | H |
| N2 a or b | C(NHR$_{92}$) | C(CH$_3$) | N | H |
| N3 a or b | C(NHR$_{92}$) | C(F) | N | H |
| N4 a or b | C(NHR$_{92}$) | C(Br) | N | H |
| N5 a or b | C(NHR$_{92}$) | C(H) | C(H) | H |
| N6 a or b | C(NHR$_{92}$) | C(CH$_3$) | C(H) | H |
| N7 a or b | C(NHR$_{92}$) | C(F) | C(H) | H |
| N8 a or b | C(NHR$_{92}$) | C(Br) | C(H) | H |
| N9 a or b | C(=O) | C(H) | N | H |
| N10 a or b | C(=O) | C(CH$_3$) | N | H |
| N11 a or b | C(=O) | C(F) | N | H |
| N12 a or b | C(=O) | C(Br) | N | H |
| N13 a or b | C(=O) | C(H) | C(H) | H |
| N14 a or b | C(=O) | C(CH$_3$) | C(H) | H |
| N15 a or b | C(=O) | C(F) | C(H) | H |
| N16 a or b | C(=O) | C(Br) | C(H) | H |
| N17 a or b | C(=O) | CH$_2$ | Absent | H |
| N18 a or b | C(=O) | CH(CH$_3$) | Absent | H |
| N19 a or b | C(=O) | C(CH$_3$)$_2$ | Absent | H |
| N20 a or b | CH$_2$ | C(=O) | Absent | H |
| N21 a or b | CH(CH$_3$) | C(=O) | Absent | H |
| N22 a or b | C(CH$_3$)$_2$ | C(=O) | Absent | H |
| N23 a or b | C(H) | N | Absent | H |
| N24 a or b | N | C(H) | Absent | H |
| N25 a or b | CH$_2$ | CH$_2$ | Absent | H |
| N26 a or b | C(NHR$_{92}$) | C(H) | N | CH$_3$ |
| N27 a or b | C(NHR$_{92}$) | C(CH$_3$) | N | CH$_3$ |
| N28 a or b | C(NHR$_{92}$) | C(F) | N | CH$_3$ |
| N29 a or b | C(NHR$_{92}$) | C(Br) | N | CH$_3$ |
| N30 a or b | C(NHR$_{92}$) | C(H) | C(H) | CH$_3$ |
| N31 a or b | C(NHR$_{92}$) | C(CH$_3$) | C(H) | CH$_3$ |
| N32 a or b | C(NHR$_{92}$) | C(F) | C(H) | CH$_3$ |
| N33 a or b | C(NHR$_{92}$) | C(Br) | C(H) | CH$_3$ |
| N34 a or b | C(=O) | C(H) | N | CH$_3$ |
| N35 a or b | C(=O) | C(CH$_3$) | N | CH$_3$ |
| N36 a or b | C(=O) | C(F) | N | CH$_3$ |
| N37 a or b | C(=O) | C(Br) | N | CH$_3$ |
| N38 a or b | C(=O) | C(H) | C(H) | CH$_3$ |
| N39 a or b | C(=O) | C(CH$_3$) | C(H) | CH$_3$ |
| N40 a or b | C(=O) | C(F) | C(H) | CH$_3$ |
| N41 a or b | C(=O) | C(Br) | C(H) | CH$_3$ |
| N42 a or b | C(=O) | CH$_2$ | Absent | CH$_3$ |
| N43 a or b | C(=O) | CH(CH$_3$) | Absent | CH$_3$ |
| N44 a or b | C(=O) | C(CH$_3$)$_2$ | Absent | CH$_3$ |
| N45 a or b | CH$_2$ | C(=O) | Absent | CH$_3$ |
| N46 a or b | CH(CH$_3$) | C(=O) | Absent | CH$_3$ |
| N47 a or b | C(CH$_3$)$_2$ | C(=O) | Absent | CH$_3$ |
| N48 a or b | C(H) | N | Absent | CH$_3$ |
| N49 a or b | N | C(H) | Absent | CH$_3$ |
| N50 a or b | CH$_2$ | CH$_2$ | Absent | CH$_3$ |

* (i) Indicates that R$_{92}$ is —H, (ii) indicates that R$_{92}$ is —C(=O)CH$_3$, and (iii) indicates that R$_{92}$ is —CH$_2$—C(=O)OH.

TABLE 15

(a)

TABLE 15-continued

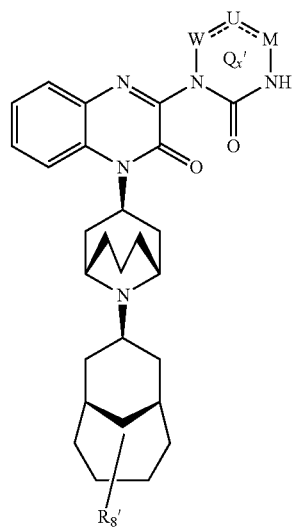

(b)

and pharmaceutically acceptable derivatives thereof, where:

| Compound | M * | U | W | R8' |
|---|---|---|---|---|
| O O1 a or b | C(NHR92) | C(H) | N | H |
| O2 a or b | C(NHR92) | C(CH3) | N | H |
| O3 a or b | C(NHR92) | C(F) | N | H |
| O4 a or b | C(NHR92) | C(Br) | N | H |
| O5 a or b | C(NHR92) | C(H) | C(H) | H |
| O6 a or b | C(NHR92) | C(CH3) | C(H) | H |
| O7 a or b | C(NHR92) | C(F) | C(H) | H |
| O8 a or b | C(NHR92) | C(Br) | C(H) | H |
| O9 a or b | C(=O) | C(H) | N | H |
| O10 a or b | C(=O) | C(CH3) | N | H |
| O11 a or b | C(=O) | C(F) | N | H |
| O12 a or b | C(=O) | C(Br) | N | H |
| O13 a or b | C(=O) | C(H) | C(H) | H |
| O14 a or b | C(=O) | C(CH3) | C(H) | H |
| O15 a or b | C(=O) | C(F) | C(H) | H |
| O16 a or b | C(=O) | C(Br) | C(H) | H |
| O17 a or b | C(=O) | CH2 | Absent | H |
| O18 a or b | C(=O) | CH(CH3) | Absent | H |
| O19 a or b | C(=O) | C(CH3)2 | Absent | H |
| O20 a or b | CH2 | C(=O) | Absent | H |
| O21 a or b | CH(CH3) | C(=O) | Absent | H |
| O22 a or b | C(CH3)2 | C(=O) | Absent | H |
| O23 a or b | C(H) | N | Absent | H |
| O24 a or b | N | C(H) | Absent | H |
| O25 a or b | CH2 | CH2 | Absent | H |
| O26 a or b | C(NHR92) | C(H) | N | CH3 |
| O27 a or b | C(NHR92) | C(CH3) | N | CH3 |
| O28 a or b | C(NHR92) | C(F) | N | CH3 |
| O29 a or b | C(NHR92) | C(Br) | N | CH3 |
| O30 a or b | C(NHR92) | C(H) | C(H) | CH3 |
| O31 a or b | C(NHR92) | C(CH3) | C(H) | CH3 |
| O32 a or b | C(NHR92) | C(F) | C(H) | CH3 |
| O33 a or b | C(NHR92) | C(Br) | C(H) | CH3 |
| O34 a or b | C(=O) | C(H) | N | CH3 |
| O35 a or b | C(=O) | C(CH3) | N | CH3 |
| O36 a or b | C(=O) | C(F) | N | CH3 |
| O37 a or b | C(=O) | C(Br) | N | CH3 |
| O38 a or b | C(=O) | C(H) | C(H) | CH3 |
| O39 a or b | C(=O) | C(CH3) | C(H) | CH3 |
| O40 a or b | C(=O) | C(F) | C(H) | CH3 |
| O41 a or b | C(=O) | C(Br) | C(H) | CH3 |
| O42 a or b | C(=O) | CH2 | Absent | CH3 |
| O43 a or b | C(=O) | CH(CH3) | Absent | CH3 |
| O44 a or b | C(=O) | C(CH3)2 | Absent | CH3 |
| O45 a or b | CH2 | C(=O) | Absent | CH3 |
| O46 a or b | CH(CH3) | C(=O) | Absent | CH3 |
| O47 a or b | C(CH3)2 | C(=O) | Absent | CH3 |
| O48 a or b | C(H) | N | Absent | CH3 |
| O49 a or b | N | C(H) | Absent | CH3 |
| O50 a or b | CH2 | CH2 | Absent | CH3 |

* (i) Indicates that R92 is —H,
(ii) indicates that R92 is —C(=O)CH3, and
(iii) indicates that R92 is —CH2—C(=O)OH.

TABLE 16

(a)

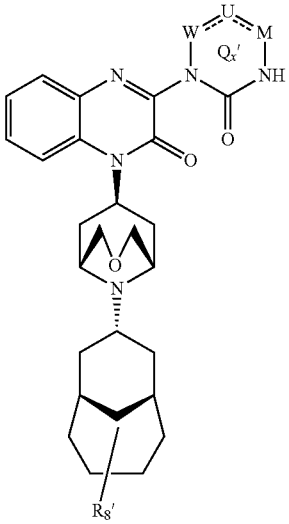

(b)

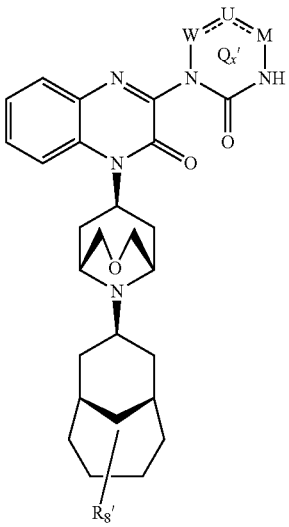

and pharmaceutically acceptable derivatives thereof, where:

| Compound | M * | U | W | R8' |
|---|---|---|---|---|
| P P1 a or b | C(NHR92) | C(H) | N | H |
| P2 a or b | C(NHR92) | C(CH3) | N | H |
| P3 a or b | C(NHR92) | C(F) | N | H |
| P4 a or b | C(NHR92) | C(Br) | N | H |
| P5 a or b | C(NHR92) | C(H) | C(H) | H |
| P6 a or b | C(NHR92) | C(CH3) | C(H) | H |
| P7 a or b | C(NHR92) | C(F) | C(H) | H |
| P8 a or b | C(NHR92) | C(Br) | C(H) | H |
| P9 a or b | C(=O) | C(H) | N | H |
| P10 a or b | C(=O) | C(CH3) | N | H |
| P11 a or b | C(=O) | C(F) | N | H |
| P12 a or b | C(=O) | C(Br) | N | H |

TABLE 16-continued

| | | | | |
|---|---|---|---|---|
| P13 a or b | C(=O) | C(H) | C(H) | H |
| P14 a or b | C(=O) | C(CH$_3$) | C(H) | H |
| P15 a or b | C(=O) | C(F) | C(H) | H |
| P16 a or b | C(=O) | C(Br) | C(H) | H |
| P17 a or b | C(=O) | CH$_2$ | Absent | H |
| P18 a or b | C(=O) | CH(CH$_3$) | Absent | H |
| P19 a or b | C(=O) | C(CH$_3$)$_2$ | Absent | H |
| P20 a or b | CH$_2$ | C(=O) | Absent | H |
| P21 a or b | CH(CH$_3$) | C(=O) | Absent | H |
| P22 a or b | C(CH$_3$)$_2$ | C(=O) | Absent | H |
| P23 a or b | C(H) | N | Absent | H |
| P24 a or b | N | C(H) | Absent | H |
| P25 a or b | CH$_2$ | CH$_2$ | Absent | H |
| P26 a or b | C(NHR$_{92}$) | C(H) | N | CH$_3$ |
| P27 a or b | C(NHR$_{92}$) | C(CH$_3$) | N | CH$_3$ |
| P28 a or b | C(NHR$_{92}$) | C(F) | N | CH$_3$ |
| P29 a or b | C(NHR$_{92}$) | C(Br) | N | CH$_3$ |
| P30 a or b | C(NHR$_{92}$) | C(H) | C(H) | CH$_3$ |
| P31 a or b | C(NHR$_{92}$) | C(CH$_3$) | C(H) | CH$_3$ |
| P32 a or b | C(NHR$_{92}$) | C(F) | C(H) | CH$_3$ |
| P33 a or b | C(NHR$_{92}$) | C(Br) | C(H) | CH$_3$ |
| P34 a or b | C(=O) | C(H) | N | CH$_3$ |
| P35 a or b | C(=O) | C(CH$_3$) | N | CH$_3$ |
| P36 a or b | C(=O) | C(F) | N | CH$_3$ |
| P37 a or b | C(=O) | C(Br) | N | CH$_3$ |
| P38 a or b | C(=O) | C(H) | C(H) | CH$_3$ |
| P39 a or b | C(=O) | C(CH$_3$) | C(H) | CH$_3$ |
| P40 a or b | C(=O) | C(F) | C(H) | CH$_3$ |
| P41 a or b | C(=O) | C(Br) | C(H) | CH$_3$ |
| P42 a or b | C(=O) | CH$_2$ | Absent | CH$_3$ |
| P43 a or b | C(=O) | CH(CH$_3$) | Absent | CH$_3$ |
| P44 a or b | C(=O) | C(CH$_3$)$_2$ | Absent | CH$_3$ |
| P45 a or b | CH$_2$ | C(=O) | Absent | CH$_3$ |
| P46 a or b | CH(CH$_3$) | C(=O) | Absent | CH$_3$ |
| P47 a or b | C(CH$_3$)$_2$ | C(=O) | Absent | CH$_3$ |
| P48 a or b | C(H) | N | Absent | CH$_3$ |
| P49 a or b | N | C(H) | Absent | CH$_3$ |
| P50 a or b | CH$_2$ | CH$_2$ | Absent | CH$_3$ |

* (i) Indicates that R$_{92}$ is —H,
(ii) indicates that R$_{92}$ is —C(=O)CH$_3$, and
(iii) indicates that R$_{92}$ is —CH$_2$—C(=O)OH.

In other embodiments, the Cyclic Urea- or Lactam-Substituted Quinoxaline-Type Piperidine Compound of Formula (I) has one of the formulae of Table 17.

TABLE 17

| Formula | Compound |
|---|---|
| IA' | (structure) |
| IB' | (structure) |
| IC' | (structure) |
| ID' | (structure) |
| ID$_1$'† | (structure) |

TABLE 17-continued

| Formula | Compound |
|---|---|
| ID₂'‡ | (structure) |
| IE' | (structure) |
| IE₁'† | (structure) |
| IE₂'‡ | (structure) |

TABLE 17-continued

| Formula | Compound |
|---|---|
| IF' | (structure) |
| IF₁'† | (structure) |
| IF₂'‡ | (structure) |
| IG' | (structure) |

TABLE 17-continued

| Formula | Compound |
|---|---|
| IG₁'† | (structure) |
| IG₂'‡ | (structure) |
| IH' | (structure) |
| IH₁'† | (structure) |
| IH₂'‡ | (structure) |
| IJ' | (structure) |
| IJ₁'† | (structure) |
| IJ₂'‡ | (structure) |

TABLE 17-continued

| Formula | Compound |
|---|---|
| IK' | (structure) |
| IK$_1$'† | (structure) |
| IK$_2$'‡ | (structure) |
| IL' | (structure) |
| IL$_1$'† | (structure) |
| IL$_2$'‡ | (structure) |
| IM' | (structure) |
| IM$_1$'† | (structure) |

TABLE 17-continued

| Formula | Compound |
|---|---|
| IM₂'‡ | 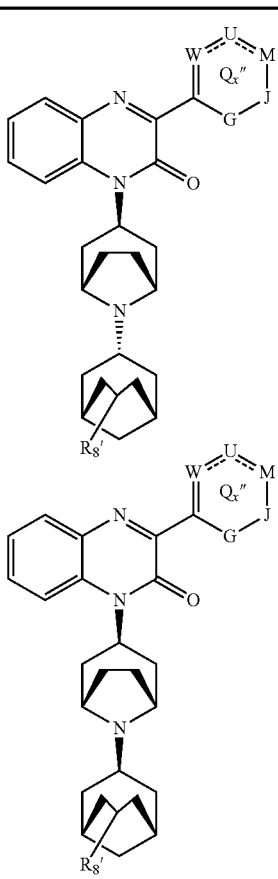 |

†indicates the 6-membered, nitrogen-containing ring that is fused to the benzo or pyridino is in the endo-configuration with respect to the alkyl or —CH₂—O—CH₂— bridge.
‡indicates the 6-membered, nitrogen-containing ring that is fused to the benzo or pyridino is in the exo-configuration with respect to the alkyl or —CH₂—O—CH₂— bridge.

where $R_1$, $R_2$, $R_{90}$, Z, and a are as defined above for the Cyclic Urea- or Lactam-Substituted Quinoxaline-Type Piperidine Compounds of Formula (I).

Illustrative Compounds of Formula (I) are listed below in Tables 18-32.

TABLE 18

(a) [structure shown]

(b) [structure shown]

and pharmaceutically acceptable derivatives thereof, where:

| Compound | G* | J* | M* | U* | W | $R_8'$ |
|---|---|---|---|---|---|---|
| Q Q1 a or b | N($R_{92}$) | C(=O) | C(H) | C(H) | C(H) | H |
| Q2 a or b | N($R_{92}$) | C(=O) | N | C(H) | C(H) | H |
| Q3 a or b | N($R_{92}$) | C(=O) | C(H) | N | C(H) | H |
| Q4 a or b | N($R_{92}$) | C(=O) | CH₂ | CH₂ | CH₂ | H |
| Q5 a or b | N($R_{92}$) | C(=O) | N($R_{92}$) | C(=O) | C(H) | H |
| Q6 a or b | N($R_{92}$) | C(=O) | C(H) | C(H) | N | H |
| Q7 a or b | N($R_{92}$) | C(=O) | C(H) | C(H) | C(H) | CH₃ |
| Q8 a or b | N($R_{92}$) | C(=O) | N | C(H) | C(H) | CH₃ |
| Q9 a or b | N($R_{92}$) | C(=O) | C(H) | N | C(H) | CH₃ |
| Q10 a or b | N($R_{92}$) | C(=O) | CH₂ | CH₂ | CH₂ | CH₃ |
| Q11 a or b | N($R_{92}$) | C(=O) | N($R_{92}$) | C(=O) | C(H) | CH₃ |
| Q12 a or b | N($R_{92}$) | C(=O) | C(H) | C(H) | N | CH₃ |
| Q13 a or b | C(=O) | N($R_{92}$) | C(H) | C(H) | C(H) | H |
| Q14 a or b | C(=O) | N($R_{92}$) | C(H) | C(F) | C(H) | H |
| Q15 a or b | C(=O) | N($R_{92}$) | C(H) | C(Cl) | C(H) | H |
| Q16 a or b | C(=O) | N($R_{92}$) | C(H) | C(COOH) | C(H) | H |
| Q17 a or b | C(=O) | N($R_{92}$) | C(H) | C(H) | N | H |
| Q18 a or b | C(=O) | N($R_{92}$) | C(H) | N | C(H) | H |
| Q19 a or b | C(=O) | N($R_{92}$) | C(=O) | N($R_{92}$) | C(H) | H |
| Q20 a or b | C(=O) | N($R_{92}$) | C(=O) | N($R_{92}$) | N | H |
| Q21 a or b | C(=O) | N($R_{92}$) | C(=O) | C(H) | Absent | H |
| Q22 a or b | C(=O) | N($R_{92}$) | N(H) | C(H) | Absent | H |
| Q23 a or b | C(=O) | N($R_{92}$) | C(H) | C(H) | C(H) | CH₃ |
| Q24 a or b | C(=O) | N($R_{92}$) | C(H) | C(F) | C(H) | CH₃ |
| Q25 a or b | C(=O) | N($R_{92}$) | C(H) | C(Cl) | C(H) | CH₃ |
| Q26 a or b | C(=O) | N($R_{92}$) | C(H) | C(COOH) | C(H) | CH₃ |
| Q27 a or b | C(=O) | N($R_{92}$) | C(H) | C(H) | N | CH₃ |
| Q28 a or b | C(=O) | N($R_{92}$) | C(H) | N | C(H) | CH₃ |
| Q29 a or b | C(=O) | N($R_{92}$) | C(=O) | N($R_{92}$) | C(H) | CH₃ |
| Q30 a or b | C(=O) | N($R_{92}$) | C(=O) | N($R_{92}$) | N | CH₃ |
| Q31 a or b | C(=O) | N($R_{92}$) | C(=O) | C(H) | Absent | CH₃ |
| Q32 a or b | C(=O) | N($R_{92}$) | N(H) | C(H) | Absent | CH₃ |

* (i) Indicates that $R_{92}$ is —H,
(ii) indicates that $R_{92}$ is —C(=O)CH₃, and
(iii) indicates that $R_{92}$ is —CH₂—C(=O)OH.

TABLE 19

(a) [structure shown]

TABLE 19-continued

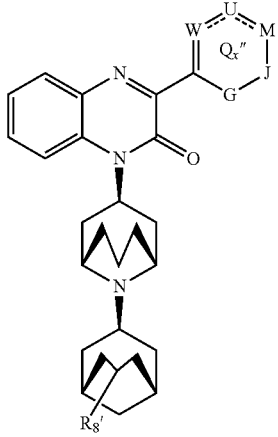

(b)

and pharmaceutically acceptable derivatives thereof, where:

| Compound | G * | J * | M * | U * | W | $R_8'$ |
|---|---|---|---|---|---|---|
| R R1 a or b | $N(R_{92})$ | C(=O) | C(H) | C(H) | C(H) | H |
| R2 a or b | $N(R_{92})$ | C(=O) | N | C(H) | C(H) | H |
| R3 a or b | $N(R_{92})$ | C(=O) | C(H) | N | C(H) | H |
| R4 a or b | $N(R_{92})$ | C(=O) | $CH_2$ | $CH_2$ | $CH_2$ | H |
| R5 a or b | $N(R_{92})$ | C(=O) | $N(R_{92})$ | C(=O) | C(H) | H |
| R6 a or b | $N(R_{92})$ | C(=O) | $N(R_{92})$ | N | Absent | H |
| R7 a or b | $N(R_{92})$ | C(=O) | C(H) | C(H) | N | H |
| R8 a or b | $N(R_{92})$ | C(=O) | C(H) | C(H) | C(H) | $CH_3$ |
| R9 a or b | $N(R_{92})$ | C(=O) | N | C(H) | C(H) | $CH_3$ |
| R10 a or b | $N(R_{92})$ | C(=O) | C(H) | N | C(H) | $CH_3$ |
| R11 a or b | $N(R_{92})$ | C(=O) | $CH_2$ | $CH_2$ | $CH_2$ | $CH_3$ |
| R12 a or b | $N(R_{92})$ | C(=O) | $N(R_{92})$ | C(=O) | C(H) | $CH_3$ |
| R13 a or b | $N(R_{92})$ | C(=O) | $N(R_{92})$ | N | Absent | $CH_3$ |
| R14 a or b | $N(R_{92})$ | C(=O) | C(H) | C(H) | N | $CH_3$ |
| R15 a or b | C(=O) | $N(R_{92})$ | C(H) | C(H) | C(H) | H |
| R16 a or b | C(=O) | $N(R_{92})$ | C(H) | C(F) | C(H) | H |
| R17 a or b | C(=O) | $N(R_{92})$ | C(H) | C(Cl) | C(H) | H |
| R18 a or b | C(=O) | $N(R_{92})$ | C(H) | C(COOH) | C(H) | H |
| R19 a or b | C(=O) | $N(R_{92})$ | C(H) | C(H) | N | H |
| R20 a or b | C(=O) | $N(R_{92})$ | C(H) | N | C(H) | H |
| R21 a or b | C(=O) | $N(R_{92})$ | C(=O) | $N(R_{92})$ | C(H) | H |
| R22 a or b | C(=O) | $N(R_{92})$ | C(=O) | $N(R_{92})$ | N | H |
| R23 a or b | C(=O) | $N(R_{92})$ | C(=O) | C(H) | Absent | H |
| R24 a or b | C(=O) | $N(R_{92})$ | N(H) | C(H) | Absent | H |
| R25 a or b | C(=O) | $N(R_{92})$ | C(H) | C(H) | C(H) | $CH_3$ |
| R26 a or b | C(=O) | $N(R_{92})$ | C(H) | C(F) | C(H) | $CH_3$ |
| R27 a or b | C(=O) | $N(R_{92})$ | C(H) | C(Cl) | C(H) | $CH_3$ |
| R28 a or b | C(=O) | $N(R_{92})$ | C(H) | C(COOH) | C(H) | $CH_3$ |
| R29 a or b | C(=O) | $N(R_{92})$ | C(H) | C(H) | N | $CH_3$ |
| R30 a or b | C(=O) | $N(R_{92})$ | C(H) | N | C(H) | $CH_3$ |
| R31 a or b | C(=O) | $N(R_{92})$ | C(=O) | $N(R_{92})$ | C(H) | $CH_3$ |
| R32 a or b | C(=O) | $N(R_{92})$ | C(=O) | $N(R_{92})$ | N | $CH_3$ |
| R33 a or b | C(=O) | $N(R_{92})$ | C(=O) | C(H) | Absent | $CH_3$ |
| R34 a or b | C(=O) | $N(R_{92})$ | N(H) | C(H) | Absent | $CH_3$ |

* (i) Indicates that $R_{92}$ is —H,
(ii) indicates that $R_{92}$ is —C(=O)$CH_3$, and
(iii) indicates that $R_{92}$ is —$CH_2$—C(=O)OH.

TABLE 20

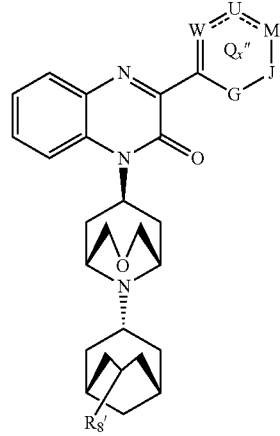

(a)

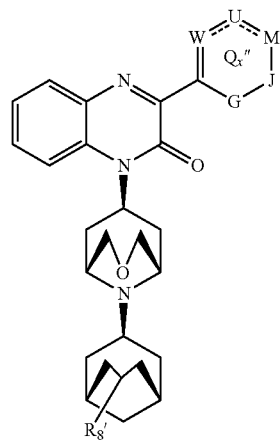

(b)

and pharmaceutically acceptable derivatives thereof, where:

| Compound | G * | J * | M * | U * | W | $R_8'$ |
|---|---|---|---|---|---|---|
| S S1 a or b | $N(R_{92})$ | C(=O) | C(H) | C(H) | C(H) | H |
| S2 a or b | $N(R_{92})$ | C(=O) | N | C(H) | C(H) | H |
| S3 a or b | $N(R_{92})$ | C(=O) | C(H) | N | C(H) | H |
| S4 a or b | $N(R_{92})$ | C(=O) | $CH_2$ | $CH_2$ | $CH_2$ | H |
| S5 a or b | $N(R_{92})$ | C(=O) | $N(R_{92})$ | C(=O) | C(H) | H |
| S6 a or b | $N(R_{92})$ | C(=O) | C(H) | C(H) | N | H |
| S7 a or b | $N(R_{92})$ | C(=O) | C(H) | C(H) | C(H) | $CH_3$ |
| S8 a or b | $N(R_{92})$ | C(=O) | N | C(H) | C(H) | $CH_3$ |
| S9 a or b | $N(R_{92})$ | C(=O) | C(H) | N | C(H) | $CH_3$ |
| S10 a or b | $N(R_{92})$ | C(=O) | $CH_2$ | $CH_2$ | $CH_2$ | $CH_3$ |
| S11 a or b | $N(R_{92})$ | C(=O) | $N(R_{92})$ | C(=O) | C(H) | $CH_3$ |
| S12 a or b | $N(R_{92})$ | C(=O) | C(H) | C(H) | N | $CH_3$ |
| S13 a or b | C(=O) | $N(R_{92})$ | C(H) | C(H) | C(H) | H |
| S14 a or b | C(=O) | $N(R_{92})$ | C(H) | C(F) | C(H) | H |
| S15 a or b | C(=O) | $N(R_{92})$ | C(H) | C(Cl) | C(H) | H |
| S16 a or b | C(=O) | $N(R_{92})$ | C(H) | C(COOH) | C(H) | H |
| S17 a or b | C(=O) | $N(R_{92})$ | C(H) | C(H) | N | H |
| S18 a or b | C(=O) | $N(R_{92})$ | C(H) | N | C(H) | H |
| S19 a or b | C(=O) | $N(R_{92})$ | C(=O) | $N(R_{92})$ | C(H) | H |
| S20 a or b | C(=O) | $N(R_{92})$ | C(=O) | $N(R_{92})$ | N | H |
| S21 a or b | C(=O) | $N(R_{92})$ | C(=O) | C(H) | Absent | H |
| S22 a or b | C(=O) | $N(R_{92})$ | N(H) | C(H) | Absent | H |
| S23 a or b | C(=O) | $N(R_{92})$ | C(H) | C(H) | C(H) | $CH_3$ |
| S24 a or b | C(=O) | $N(R_{92})$ | C(H) | C(F) | C(H) | $CH_3$ |
| S25 a or b | C(=O) | $N(R_{92})$ | C(H) | C(Cl) | C(H) | $CH_3$ |
| S26 a or b | C(=O) | $N(R_{92})$ | C(H) | C(COOH) | C(H) | $CH_3$ |
| S27 a or b | C(=O) | $N(R_{92})$ | C(H) | C(H) | N | $CH_3$ |
| S28 a or b | C(=O) | $N(R_{92})$ | C(H) | N | C(H) | $CH_3$ |
| S29 a or b | C(=O) | $N(R_{92})$ | C(=O) | $N(R_{92})$ | C(H) | $CH_3$ |
| S30 a or b | C(=O) | $N(R_{92})$ | C(=O) | $N(R_{92})$ | N | $CH_3$ |

TABLE 20-continued

| | | | | | | |
|---|---|---|---|---|---|---|
| S31 a or b | C(=O) | N(R$_{92}$) | C(=O) | C(H) | Absent | CH$_3$ |
| S32 a or b | C(=O) | N(R$_{92}$) | N(H) | C(H) | Absent | CH$_3$ |

* (i) Indicates that R$_{92}$ is —H,
(ii) indicates that R$_{92}$ is —C(=O)CH$_3$, and
(iii) indicates that R$_{92}$ is —CH$_2$—C(=O)OH.

TABLE 21

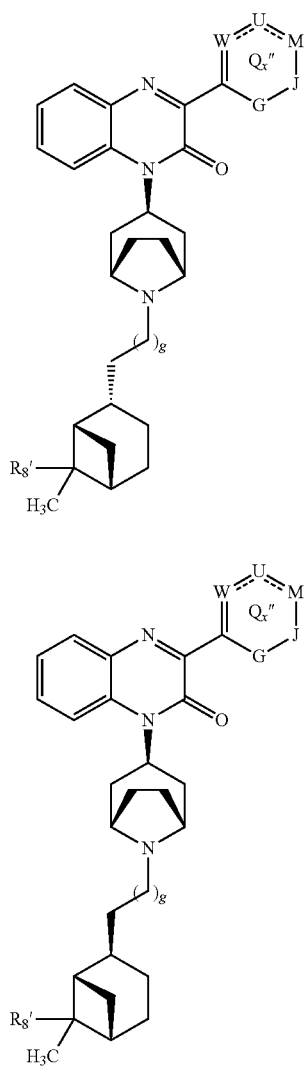

and pharmaceutically acceptable derivatives thereof, where:

| Compound | G * | J * | M * | U * | W | R$_8$' | g |
|---|---|---|---|---|---|---|---|
| T T1 a or b | N(R$_{92}$) | C(=O) | C(H) | C(H) | C(H) | H | 0 |
| T2 a or b | N(R$_{92}$) | C(=O) | N | C(H) | C(H) | H | 0 |
| T3 a or b | N(R$_{92}$) | C(=O) | C(H) | N | C(H) | H | 0 |
| T4 a or b | N(R$_{92}$) | C(=O) | CH$_2$ | CH$_2$ | CH$_2$ | H | 0 |
| T5 a or b | N(R$_{92}$) | C(=O) | N(R$_{92}$) | C(=O) | C(H) | H | 0 |
| T6 a or b | N(R$_{92}$) | C(=O) | C(H) | C(H) | N | H | 0 |
| T7 a or b | N(R$_{92}$) | C(=O) | C(H) | C(H) | C(H) | CH$_3$ | 0 |
| T8 a or b | N(R$_{92}$) | C(=O) | N | C(H) | C(H) | CH$_3$ | 0 |
| T9 a or b | N(R$_{92}$) | C(=O) | C(H) | N | C(H) | CH$_3$ | 0 |
| T10 a or b | N(R$_{92}$) | C(=O) | CH$_2$ | CH$_2$ | CH$_2$ | CH$_3$ | 0 |
| T11 a or b | N(R$_{92}$) | C(=O) | N(R$_{92}$) | C(=O) | C(H) | CH$_3$ | 0 |
| T12 a or b | N(R$_{92}$) | C(=O) | C(H) | C(H) | N | CH$_3$ | 0 |
| T13 a or b | C(=O) | N(R$_{92}$) | C(H) | C(H) | C(H) | H | 0 |
| T14 a or b | C(=O) | N(R$_{92}$) | C(H) | C(F) | C(H) | H | 0 |
| T15 a or b | C(=O) | N(R$_{92}$) | C(H) | C(Cl) | C(H) | H | 0 |
| T16 a or b | C(=O) | N(R$_{92}$) | C(H) | C(COOH) | C(H) | H | 0 |
| T17 a or b | C(=O) | N(R$_{92}$) | C(H) | C(H) | N | H | 0 |
| T18 a or b | C(=O) | N(R$_{92}$) | C(H) | N | C(H) | H | 0 |
| T19 a or b | C(=O) | N(R$_{92}$) | C(=O) | N(R$_{92}$) | C(H) | H | 0 |
| T20 a or b | C(=O) | N(R$_{92}$) | C(=O) | N(R$_{92}$) | N | H | 0 |
| T21 a or b | C(=O) | N(R$_{92}$) | C(=O) | C(H) | Absent | H | 0 |
| T22 a or b | C(=O) | N(R$_{92}$) | N(H) | C(H) | Absent | H | 0 |
| T23 a or b | C(=O) | N(R$_{92}$) | C(H) | C(H) | C(H) | CH$_3$ | 0 |
| T24 a or b | C(=O) | N(R$_{92}$) | C(H) | C(F) | C(H) | CH$_3$ | 0 |
| T25 a or b | C(=O) | N(R$_{92}$) | C(H) | C(Cl) | C(H) | CH$_3$ | 0 |
| T26 a or b | C(=O) | N(R$_{92}$) | C(H) | C(COOH) | C(H) | CH$_3$ | 0 |
| T27 a or b | C(=O) | N(R$_{92}$) | C(H) | C(H) | N | CH$_3$ | 0 |
| T28 a or b | C(=O) | N(R$_{92}$) | C(H) | N | C(H) | CH$_3$ | 0 |
| T29 a or b | C(=O) | N(R$_{92}$) | C(=O) | N(R$_{92}$) | C(H) | CH$_3$ | 0 |
| T30 a or b | C(=O) | N(R$_{92}$) | C(=O) | N(R$_{92}$) | N | CH$_3$ | 0 |
| T31 a or b | C(=O) | N(R$_{92}$) | C(=O) | C(H) | Absent | CH$_3$ | 0 |
| T32 a or b | C(=O) | N(R$_{92}$) | N(H) | C(H) | Absent | CH$_3$ | 0 |
| T33 a or b | N(R$_{92}$) | C(=O) | C(H) | C(H) | C(H) | H | 1 |
| T34 a or b | N(R$_{92}$) | C(=O) | N | C(H) | C(H) | H | 1 |
| T35 a or b | N(R$_{92}$) | C(=O) | C(H) | N | C(H) | H | 1 |
| T36 a or b | N(R$_{92}$) | C(=O) | CH$_2$ | CH$_2$ | CH$_2$ | H | 1 |
| T37 a or b | N(R$_{92}$) | C(=O) | N(R$_{92}$) | C(=O) | C(H) | H | 1 |
| T38 a or b | N(R$_{92}$) | C(=O) | C(H) | C(H) | N | H | 1 |
| T39 a or b | N(R$_{92}$) | C(=O) | C(H) | C(H) | C(H) | CH$_3$ | 1 |
| T40 a or b | N(R$_{92}$) | C(=O) | N | C(H) | C(H) | CH$_3$ | 1 |
| T41 a or b | N(R$_{92}$) | C(=O) | C(H) | N | C(H) | CH$_3$ | 1 |
| T42 a or b | N(R$_{92}$) | C(=O) | CH$_2$ | CH$_2$ | CH$_2$ | CH$_3$ | 1 |
| T43 a or b | N(R$_{92}$) | C(=O) | N(R$_{92}$) | C(=O) | C(H) | CH$_3$ | 1 |
| T44 a or b | N(R$_{92}$) | C(=O) | C(H) | C(H) | N | CH$_3$ | 1 |
| T45 a or b | C(=O) | N(R$_{92}$) | C(H) | C(H) | C(H) | H | 1 |
| T46 a or b | C(=O) | N(R$_{92}$) | C(H) | C(F) | C(H) | H | 1 |
| T47 a or b | C(=O) | N(R$_{92}$) | C(H) | C(Cl) | C(H) | H | 1 |
| T48 a or b | C(=O) | N(R$_{92}$) | C(H) | C(COOH) | C(H) | H | 1 |
| T49 a or b | C(=O) | N(R$_{92}$) | C(H) | C(H) | N | H | 1 |
| T50 a or b | C(=O) | N(R$_{92}$) | C(H) | N | C(H) | H | 1 |
| T51 a or b | C(=O) | N(R$_{92}$) | C(=O) | N(R$_{92}$) | C(H) | H | 1 |
| T52 a or b | C(=O) | N(R$_{92}$) | C(=O) | N(R$_{92}$) | N | H | 1 |
| T53 a or b | C(=O) | N(R$_{92}$) | C(=O) | C(H) | Absent | H | 1 |
| T54 a or b | C(=O) | N(R$_{92}$) | N(H) | C(H) | Absent | H | 1 |
| T55 a or b | C(=O) | N(R$_{92}$) | C(H) | C(H) | C(H) | CH$_3$ | 1 |
| T56 a or b | C(=O) | N(R$_{92}$) | C(H) | C(F) | C(H) | CH$_3$ | 1 |
| T57 a or b | C(=O) | N(R$_{92}$) | C(H) | C(Cl) | C(H) | CH$_3$ | 1 |
| T58 a or b | C(=O) | N(R$_{92}$) | C(H) | C(COOH) | C(H) | CH$_3$ | 1 |
| T59 a or b | C(=O) | N(R$_{92}$) | C(H) | C(H) | N | CH$_3$ | 1 |
| T60 a or b | C(=O) | N(R$_{92}$) | C(H) | N | C(H) | CH$_3$ | 1 |
| T61 a or b | C(=O) | N(R$_{92}$) | C(=O) | N(R$_{92}$) | C(H) | CH$_3$ | 1 |
| T62 a or b | C(=O) | N(R$_{92}$) | C(=O) | N(R$_{92}$) | N | CH$_3$ | 1 |
| T63 a or b | C(=O) | N(R$_{92}$) | C(=O) | C(H) | Absent | CH$_3$ | 1 |
| T64 a or b | C(=O) | N(R$_{92}$) | N(H) | C(H) | Absent | CH$_3$ | 1 |
| T65 a or b | N(R$_{92}$) | C(=O) | C(H) | C(H) | C(H) | H | 2 |
| T66 a or b | N(R$_{92}$) | C(=O) | N | C(H) | C(H) | H | 2 |
| T67 a or b | N(R$_{92}$) | C(=O) | C(H) | N | C(H) | H | 2 |
| T68 a or b | N(R$_{92}$) | C(=O) | CH$_2$ | CH$_2$ | CH$_2$ | H | 2 |
| T69 a or b | N(R$_{92}$) | C(=O) | N(R$_{92}$) | C(=O) | C(H) | H | 2 |
| T70 a or b | N(R$_{92}$) | C(=O) | C(H) | C(H) | N | H | 2 |
| T71 a or b | N(R$_{92}$) | C(=O) | C(H) | C(H) | C(H) | CH$_3$ | 2 |
| T72 a or b | N(R$_{92}$) | C(=O) | N | C(H) | C(H) | CH$_3$ | 2 |
| T73 a or b | N(R$_{92}$) | C(=O) | C(H) | N | C(H) | CH$_3$ | 2 |
| T74 a or b | N(R$_{92}$) | C(=O) | CH$_2$ | CH$_2$ | CH$_2$ | CH$_3$ | 2 |
| T75 a or b | N(R$_{92}$) | C(=O) | N(R$_{92}$) | C(=O) | C(H) | CH$_3$ | 2 |
| T76 a or b | N(R$_{92}$) | C(=O) | C(H) | C(H) | N | CH$_3$ | 2 |
| T77 a or b | C(=O) | N(R$_{92}$) | C(H) | C(H) | C(H) | H | 2 |
| T78 a or b | C(=O) | N(R$_{92}$) | C(H) | C(F) | C(H) | H | 2 |
| T79 a or b | C(=O) | N(R$_{92}$) | C(H) | C(Cl) | C(H) | H | 2 |
| T80 a or b | C(=O) | N(R$_{92}$) | C(H) | C(COOH) | C(H) | H | 2 |
| T81 a or b | C(=O) | N(R$_{92}$) | C(H) | C(H) | N | H | 2 |
| T82 a or b | C(=O) | N(R$_{92}$) | C(H) | N | C(H) | H | 2 |
| T83 a or b | C(=O) | N(R$_{92}$) | C(=O) | N(R$_{92}$) | C(H) | H | 2 |
| T84 a or b | C(=O) | N(R$_{92}$) | C(=O) | N(R$_{92}$) | N | H | 2 |
| T85 a or b | C(=O) | N(R$_{92}$) | C(=O) | C(H) | Absent | H | 2 |
| T86 a or b | C(=O) | N(R$_{92}$) | N(H) | C(H) | Absent | H | 2 |
| T87 a or b | C(=O) | N(R$_{92}$) | C(H) | C(H) | C(H) | CH$_3$ | 2 |
| T88 a or b | C(=O) | N(R$_{92}$) | C(H) | C(F) | C(H) | CH$_3$ | 2 |
| T89 a or b | C(=O) | N(R$_{92}$) | C(H) | C(Cl) | C(H) | CH$_3$ | 2 |
| T90 a or b | C(=O) | N(R$_{92}$) | C(H) | C(COOH) | C(H) | CH$_3$ | 2 |
| T91 a or b | C(=O) | N(R$_{92}$) | C(H) | C(H) | N | CH$_3$ | 2 |
| T92 a or b | C(=O) | N(R$_{92}$) | C(H) | N | C(H) | CH$_3$ | 2 |
| T93 a or b | C(=O) | N(R$_{92}$) | C(=O) | N(R$_{92}$) | C(H) | CH$_3$ | 2 |
| T94 a or b | C(=O) | N(R$_{92}$) | C(=O) | N(R$_{92}$) | N | CH$_3$ | 2 |

TABLE 21-continued

| T95 a or b | C(=O) | N(R$_{92}$) | C(=O) | C(H) | Absent | CH$_3$ | 2 |
| T96 a or b | C(=O) | N(R$_{92}$) | N(H) | C(H) | Absent | CH$_3$ | 2 |

* (i) Indicates that R$_{92}$ is —H,
(ii) indicates that R$_{92}$ is —C(=O)CH$_3$, and
(iii) indicates that R$_{92}$ is —CH$_2$—C(=O)OH.

TABLE 22

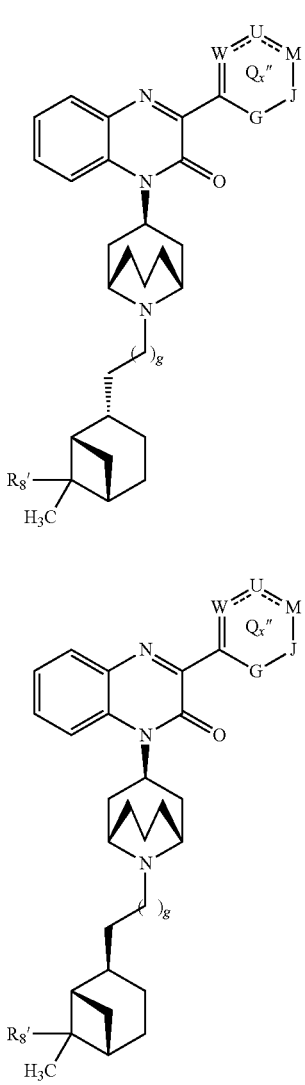

and pharmaceutically acceptable derivatives thereof, where:

| Compound | G* | J* | M* | U* | W | R$_8$' | g |
| --- | --- | --- | --- | --- | --- | --- | --- |
| U U1 a or b | N(R$_{92}$) | C(=O) | C(H) | C(H) | C(H) | H | 0 |
| U2 a or b | N(R$_{92}$) | C(=O) | N | C(H) | C(H) | H | 0 |
| U3 a or b | N(R$_{92}$) | C(=O) | C(H) | N | C(H) | H | 0 |
| U4 a or b | N(R$_{92}$) | C(=O) | CH$_2$ | CH$_2$ | CH$_2$ | H | 0 |
| U5 a or b | N(R$_{92}$) | C(=O) | N(R$_{92}$) | C(=O) | C(H) | H | 0 |
| U6 a or b | N(R$_{92}$) | C(=O) | C(H) | C(H) | N | H | 0 |
| U7 a or b | N(R$_{92}$) | C(=O) | C(H) | C(H) | C(H) | CH$_3$ | 0 |
| U8 a or b | N(R$_{92}$) | C(=O) | N | C(H) | C(H) | CH$_3$ | 0 |
| U9 a or b | N(R$_{92}$) | C(=O) | C(H) | N | C(H) | CH$_3$ | 0 |
| U10 a or b | N(R$_{92}$) | C(=O) | CH$_2$ | CH$_2$ | CH$_2$ | CH$_3$ | 0 |
| U11 a or b | N(R$_{92}$) | C(=O) | N(R$_{92}$) | C(=O) | C(H) | CH$_3$ | 0 |
| U12 a or b | N(R$_{92}$) | C(=O) | C(H) | C(H) | N | CH$_3$ | 0 |
| U13 a or b | C(=O) | N(R$_{92}$) | C(H) | C(H) | C(H) | H | 0 |
| U14 a or b | C(=O) | N(R$_{92}$) | C(H) | C(F) | C(H) | H | 0 |
| U15 a or b | C(=O) | N(R$_{92}$) | C(H) | C(Cl) | C(H) | H | 0 |
| U16 a or b | C(=O) | N(R$_{92}$) | C(H) | C(COOH) | C(H) | H | 0 |
| U17 a or b | C(=O) | N(R$_{92}$) | C(H) | C(H) | N | H | 0 |
| U18 a or b | C(=O) | N(R$_{92}$) | C(H) | N | C(H) | H | 0 |
| U19 a or b | C(=O) | N(R$_{92}$) | C(=O) | N(R$_{92}$) | C(H) | H | 0 |
| U20 a or b | C(=O) | N(R$_{92}$) | C(=O) | N(R$_{92}$) | N | H | 0 |
| U21 a or b | C(=O) | N(R$_{92}$) | C(=O) | C(H) | Absent | H | 0 |
| U22 a or b | C(=O) | N(R$_{92}$) | N(H) | C(H) | Absent | H | 0 |
| U23 a or b | C(=O) | N(R$_{92}$) | C(H) | C(H) | C(H) | CH$_3$ | 0 |
| U24 a or b | C(=O) | N(R$_{92}$) | C(H) | C(F) | C(H) | CH$_3$ | 0 |
| U25 a or b | C(=O) | N(R$_{92}$) | C(H) | C(Cl) | C(H) | CH$_3$ | 0 |
| U26 a or b | C(=O) | N(R$_{92}$) | C(H) | C(COOH) | C(H) | CH$_3$ | 0 |
| U27 a or b | C(=O) | N(R$_{92}$) | C(H) | C(H) | N | CH$_3$ | 0 |
| U28 a or b | C(=O) | N(R$_{92}$) | C(H) | N | C(H) | CH$_3$ | 0 |
| U29 a or b | C(=O) | N(R$_{92}$) | C(=O) | N(R$_{92}$) | C(H) | CH$_3$ | 0 |
| U30 a or b | C(=O) | N(R$_{92}$) | C(=O) | N(R$_{92}$) | N | CH$_3$ | 0 |
| U31 a or b | C(=O) | N(R$_{92}$) | C(=O) | C(H) | Absent | CH$_3$ | 0 |
| U32 a or b | C(=O) | N(R$_{92}$) | N(H) | C(H) | Absent | CH$_3$ | 0 |
| U33 a or b | N(R$_{92}$) | C(=O) | C(H) | C(H) | C(H) | H | 1 |
| U34 a or b | N(R$_{92}$) | C(=O) | N | C(H) | C(H) | H | 1 |
| U35 a or b | N(R$_{92}$) | C(=O) | C(H) | N | C(H) | H | 1 |
| U36 a or b | N(R$_{92}$) | C(=O) | CH$_2$ | CH$_2$ | CH$_2$ | H | 1 |
| U37 a or b | N(R$_{92}$) | C(=O) | N(R$_{92}$) | C(=O) | C(H) | H | 1 |
| U38 a or b | N(R$_{92}$) | C(=O) | C(H) | C(H) | N | H | 1 |
| U39 a or b | N(R$_{92}$) | C(=O) | C(H) | C(H) | C(H) | CH$_3$ | 1 |
| U40 a or b | N(R$_{92}$) | C(=O) | N | C(H) | C(H) | CH$_3$ | 1 |
| U41 a or b | N(R$_{92}$) | C(=O) | C(H) | N | C(H) | CH$_3$ | 1 |
| U42 a or b | N(R$_{92}$) | C(=O) | CH$_2$ | CH$_2$ | CH$_2$ | CH$_3$ | 1 |
| U43 a or b | N(R$_{92}$) | C(=O) | N(R$_{92}$) | C(=O) | C(H) | CH$_3$ | 1 |
| U44 a or b | N(R$_{92}$) | C(=O) | C(H) | C(H) | N | CH$_3$ | 1 |
| U45 a or b | C(=O) | N(R$_{92}$) | C(H) | C(H) | C(H) | H | 1 |
| U46 a or b | C(=O) | N(R$_{92}$) | C(H) | C(F) | C(H) | H | 1 |
| U47 a or b | C(=O) | N(R$_{92}$) | C(H) | C(Cl) | C(H) | H | 1 |
| U48 a or b | C(=O) | N(R$_{92}$) | C(H) | C(COOH) | C(H) | H | 1 |
| U49 a or b | C(=O) | N(R$_{92}$) | C(H) | C(H) | N | H | 1 |
| U50 a or b | C(=O) | N(R$_{92}$) | C(H) | N | C(H) | H | 1 |
| U51 a or b | C(=O) | N(R$_{92}$) | C(=O) | N(R$_{92}$) | C(H) | H | 1 |
| U52 a or b | C(=O) | N(R$_{92}$) | C(=O) | N(R$_{92}$) | N | H | 1 |
| U53 a or b | C(=O) | N(R$_{92}$) | C(=O) | C(H) | Absent | H | 1 |
| U54 a or b | C(=O) | N(R$_{92}$) | N(H) | C(H) | Absent | H | 1 |
| U55 a or b | C(=O) | N(R$_{92}$) | C(H) | C(H) | C(H) | CH$_3$ | 1 |
| U56 a or b | C(=O) | N(R$_{92}$) | C(H) | C(F) | C(H) | CH$_3$ | 1 |
| U57 a or b | C(=O) | N(R$_{92}$) | C(H) | C(Cl) | C(H) | CH$_3$ | 1 |
| U58 a or b | C(=O) | N(R$_{92}$) | C(H) | C(COOH) | C(H) | CH$_3$ | 1 |
| U59 a or b | C(=O) | N(R$_{92}$) | C(H) | C(H) | N | CH$_3$ | 1 |
| U60 a or b | C(=O) | N(R$_{92}$) | C(H) | N | C(H) | CH$_3$ | 1 |
| U61 a or b | C(=O) | N(R$_{92}$) | C(=O) | N(R$_{92}$) | C(H) | CH$_3$ | 1 |
| U62 a or b | C(=O) | N(R$_{92}$) | C(=O) | N(R$_{92}$) | N | CH$_3$ | 1 |
| U63 a or b | C(=O) | N(R$_{92}$) | C(=O) | C(H) | Absent | CH$_3$ | 1 |
| U64 a or b | C(=O) | N(R$_{92}$) | N(H) | C(H) | Absent | CH$_3$ | 1 |
| U65 a or b | N(R$_{92}$) | C(=O) | C(H) | C(H) | C(H) | H | 2 |
| U66 a or b | N(R$_{92}$) | C(=O) | N | C(H) | C(H) | H | 2 |
| U67 a or b | N(R$_{92}$) | C(=O) | C(H) | N | C(H) | H | 2 |
| U68 a or b | N(R$_{92}$) | C(=O) | CH$_2$ | CH$_2$ | CH$_2$ | H | 2 |
| U69 a or b | N(R$_{92}$) | C(=O) | N(R$_{92}$) | C(=O) | C(H) | H | 2 |
| U70 a or b | N(R$_{92}$) | C(=O) | C(H) | C(H) | N | H | 2 |
| U71 a or b | N(R$_{92}$) | C(=O) | C(H) | C(H) | C(H) | CH$_3$ | 2 |
| U72 a or b | N(R$_{92}$) | C(=O) | N | C(H) | C(H) | CH$_3$ | 2 |
| U73 a or b | N(R$_{92}$) | C(=O) | C(H) | N | C(H) | CH$_3$ | 2 |
| U74 a or b | N(R$_{92}$) | C(=O) | CH$_2$ | CH$_2$ | CH$_2$ | CH$_3$ | 2 |
| U75 a or b | N(R$_{92}$) | C(=O) | N(R$_{92}$) | C(=O) | C(H) | CH$_3$ | 2 |
| U76 a or b | N(R$_{92}$) | C(=O) | C(H) | C(H) | N | CH$_3$ | 2 |
| U77 a or b | C(=O) | N(R$_{92}$) | C(H) | C(H) | C(H) | H | 2 |
| U78 a or b | C(=O) | N(R$_{92}$) | C(H) | C(F) | C(H) | H | 2 |
| U79 a or b | C(=O) | N(R$_{92}$) | C(H) | C(Cl) | C(H) | H | 2 |
| U80 a or b | C(=O) | N(R$_{92}$) | C(H) | C(COOH) | C(H) | H | 2 |
| U81 a or b | C(=O) | N(R$_{92}$) | C(H) | C(H) | N | H | 2 |
| U82 a or b | C(=O) | N(R$_{92}$) | C(H) | N | C(H) | H | 2 |
| U83 a or b | C(=O) | N(R$_{92}$) | C(=O) | N(R$_{92}$) | C(H) | H | 2 |
| U84 a or h | C(=O) | N(R$_{92}$) | C(=O) | N(R$_{92}$) | N | H | 2 |
| U85 a or b | C(=O) | N(R$_{92}$) | C(=O) | C(H) | Absent | H | 2 |
| U86 a or b | C(=O) | N(R$_{92}$) | N(H) | C(H) | Absent | H | 2 |
| U87 a or b | C(=O) | N(R$_{92}$) | C(H) | C(H) | C(H) | CH$_3$ | 2 |
| U88 a or b | C(=O) | N(R$_{92}$) | C(H) | C(F) | C(H) | CH$_3$ | 2 |
| U89 a or b | C(=O) | N(R$_{92}$) | C(H) | C(Cl) | C(H) | CH$_3$ | 2 |
| U90 a or b | C(=O) | N(R$_{92}$) | C(H) | C(COOH) | C(H) | CH$_3$ | 2 |
| U91 a or b | C(=O) | N(R$_{92}$) | C(H) | C(H) | N | CH$_3$ | 2 |
| U92 a or b | C(=O) | N(R$_{92}$) | C(H) | N | C(H) | CH$_3$ | 2 |
| U93 a or b | C(=O) | N(R$_{92}$) | C(=O) | N(R$_{92}$) | C(H) | CH$_3$ | 2 |
| U94 a or b | C(=O) | N(R$_{92}$) | C(=O) | N(R$_{92}$) | N | CH$_3$ | 2 |

TABLE 22-continued

| | | | | | | | |
|---|---|---|---|---|---|---|---|
| U95 a or b | C(=O) | N(R$_{92}$) | C(=O) | C(H) | Absent | CH$_3$ | 2 |
| U96 a or b | C(=O) | N(R$_{92}$) | N(H) | C(H) | Absent | CH$_3$ | 2 |

* (i) Indicates that R$_{92}$ is —H,
(ii) indicates that R$_{92}$ is —C(=O)CH$_3$, and
(iii) indicates that R$_{92}$ is —CH$_2$—C(=O)OH.

TABLE 23

(a)

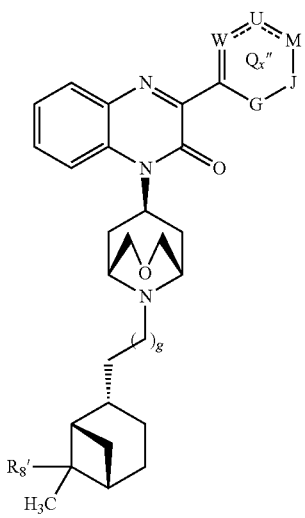

(b)

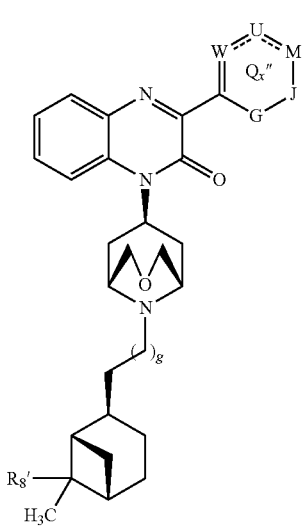

and pharmaceutically acceptable derivatives thereof, where:

| Compound | G* | J* | M* | U* | W | R$_8$' | g |
|---|---|---|---|---|---|---|---|
| V V1 a or b | N(R$_{92}$) | C(=O) | C(H) | C(H) | C(H) | H | 0 |
| V2 a or b | N(R$_{92}$) | C(=O) | N | C(H) | C(H) | H | 0 |
| V3 a or b | N(R$_{92}$) | C(=O) | C(H) | N | C(H) | H | 0 |
| V4 a or b | N(R$_{92}$) | C(=O) | CH$_2$ | CH$_2$ | CH$_2$ | H | 0 |
| V5 a or b | N(R$_{92}$) | C(=O) | N(R$_{92}$) | C(=O) | C(H) | H | 0 |
| V6 a or b | N(R$_{92}$) | C(=O) | C(H) | C(H) | N | H | 0 |
| V7 a or b | N(R$_{92}$) | C(=O) | C(H) | C(H) | C(H) | CH$_3$ | 0 |
| V8 a or b | N(R$_{92}$) | C(=O) | N | C(H) | C(H) | CH$_3$ | 0 |
| V9 a or b | N(R$_{92}$) | C(=O) | C(H) | N | C(H) | CH$_3$ | 0 |
| V10 a or b | N(R$_{92}$) | C(=O) | CH$_2$ | CH$_2$ | CH$_2$ | CH$_3$ | 0 |
| V11 a or b | N(R$_{92}$) | C(=O) | N(R$_{92}$) | C(=O) | C(H) | CH$_3$ | 0 |
| V12 a or b | N(R$_{92}$) | C(=O) | C(H) | C(H) | N | CH$_3$ | 0 |
| V13 a or b | C(=O) | N(R$_{92}$) | C(H) | C(H) | C(H) | H | 0 |
| V14 a or b | C(=O) | N(R$_{92}$) | C(H) | C(F) | C(H) | H | 0 |
| V15 a or b | C(=O) | N(R$_{92}$) | C(H) | C(Cl) | C(H) | H | 0 |
| V16 a or b | C(=O) | N(R$_{92}$) | C(H) | C(COOH) | C(H) | H | 0 |
| V17 a or b | C(=O) | N(R$_{92}$) | C(H) | C(H) | N | H | 0 |
| V18 a or b | C(=O) | N(R$_{92}$) | C(H) | N | C(H) | H | 0 |
| V19 a or b | C(=O) | N(R$_{92}$) | C(=O) | N(R$_{92}$) | C(H) | H | 0 |
| V20 a or b | C(=O) | N(R$_{92}$) | C(=O) | N(R$_{92}$) | N | H | 0 |
| V21 a or b | C(=O) | N(R$_{92}$) | C(=O) | C(H) | Absent | H | 0 |
| V22 a or b | C(=O) | N(R$_{92}$) | N(H) | C(H) | Absent | H | 0 |
| V23 a or b | C(=O) | N(R$_{92}$) | C(H) | C(H) | C(H) | CH$_3$ | 0 |
| V24 a or b | C(=O) | N(R$_{92}$) | C(H) | C(F) | C(H) | CH$_3$ | 0 |
| V25 a or b | C(=O) | N(R$_{92}$) | C(H) | C(Cl) | C(H) | CH$_3$ | 0 |
| V26 a or b | C(=O) | N(R$_{92}$) | C(H) | C(COOH) | C(H) | CH$_3$ | 0 |
| V27 a or b | C(=O) | N(R$_{92}$) | C(H) | C(H) | N | CH$_3$ | 0 |
| V28 a or b | C(=O) | N(R$_{92}$) | C(H) | N | C(H) | CH$_3$ | 0 |
| V29 a or b | C(=O) | N(R$_{92}$) | C(=O) | N(R$_{92}$) | C(H) | CH$_3$ | 0 |
| V30 a or b | C(=O) | N(R$_{92}$) | C(=O) | N(R$_{92}$) | N | CH$_3$ | 0 |
| V31 a or b | C(=O) | N(R$_{92}$) | C(=O) | C(H) | Absent | CH$_3$ | 0 |
| V32 a or b | C(=O) | N(R$_{92}$) | N(H) | C(H) | Absent | CH$_3$ | 0 |
| V33 a or b | N(R$_{92}$) | C(=O) | C(H) | C(H) | C(H) | H | 1 |
| V34 a or b | N(R$_{92}$) | C(=O) | N | C(H) | C(H) | H | 1 |
| V35 a or b | N(R$_{92}$) | C(=O) | C(H) | N | C(H) | H | 1 |
| V36 a or b | N(R$_{92}$) | C(=O) | CH$_2$ | CH$_2$ | CH$_2$ | H | 1 |
| V37 a or b | N(R$_{92}$) | C(=O) | N(R$_{92}$) | C(=O) | C(H) | H | 1 |
| V38 a or b | N(R$_{92}$) | C(=O) | C(H) | C(H) | N | H | 1 |
| V39 a or b | N(R$_{92}$) | C(=O) | C(H) | C(H) | C(H) | CH$_3$ | 1 |
| V40 a or b | N(R$_{92}$) | C(=O) | N | C(H) | C(H) | CH$_3$ | 1 |
| V41 a or b | N(R$_{92}$) | C(=O) | C(H) | N | C(H) | CH$_3$ | 1 |
| V42 a or b | N(R$_{92}$) | C(=O) | CH$_2$ | CH$_2$ | CH$_2$ | CH$_3$ | 1 |
| V43 a or b | N(R$_{92}$) | C(=O) | N(R$_{92}$) | C(=O) | C(H) | CH$_3$ | 1 |
| V44 a or b | N(R$_{92}$) | C(=O) | C(H) | C(H) | N | CH$_3$ | 1 |
| V45 a or b | C(=O) | N(R$_{92}$) | C(H) | C(H) | C(H) | H | 1 |
| V46 a or b | C(=O) | N(R$_{92}$) | C(H) | C(F) | C(H) | H | 1 |
| V47 a or b | C(=O) | N(R$_{92}$) | C(H) | C(Cl) | C(H) | H | 1 |
| V48 a or b | C(=O) | N(R$_{92}$) | C(H) | C(COOH) | C(H) | H | 1 |
| V49 a or b | C(=O) | N(R$_{92}$) | C(H) | C(H) | N | H | 1 |
| V50 a or b | C(=O) | N(R$_{92}$) | C(H) | N | C(H) | H | 1 |
| V51 a or b | C(=O) | N(R$_{92}$) | C(=O) | N(R$_{92}$) | C(H) | H | 1 |
| V52 a or b | C(=O) | N(R$_{92}$) | C(=O) | N(R$_{92}$) | N | H | 1 |
| V53 a or b | C(=O) | N(R$_{92}$) | C(=O) | C(H) | Absent | H | 1 |
| V54 a or b | C(=O) | N(R$_{92}$) | N(H) | C(H) | Absent | H | 1 |
| V55 a or b | C(=O) | N(R$_{92}$) | C(H) | C(H) | C(H) | CH$_3$ | 1 |
| V56 a or b | C(=O) | N(R$_{92}$) | C(H) | C(F) | C(H) | CH$_3$ | 1 |
| V57 a or b | C(=O) | N(R$_{92}$) | C(H) | C(Cl) | C(H) | CH$_3$ | 1 |
| V58 a or b | C(=O) | N(R$_{92}$) | C(H) | C(COOH) | C(H) | CH$_3$ | 1 |
| V59 a or b | C(=O) | N(R$_{92}$) | C(H) | C(H) | N | CH$_3$ | 1 |
| V60 a or b | C(=O) | N(R$_{92}$) | C(H) | N | C(H) | CH$_3$ | 1 |
| V61 a or b | C(=O) | N(R$_{92}$) | C(=O) | N(R$_{92}$) | C(H) | CH$_3$ | 1 |
| V62 a or b | C(=O) | N(R$_{92}$) | C(=O) | N(R$_{92}$) | N | CH$_3$ | 1 |
| V63 a or b | C(=O) | N(R$_{92}$) | C(=O) | C(H) | Absent | CH$_3$ | 1 |
| V64 a or b | C(=O) | N(R$_{92}$) | N(H) | C(H) | Absent | CH$_3$ | 1 |
| V65 a or b | N(R$_{92}$) | C(=O) | C(H) | C(H) | C(H) | H | 2 |
| V66 a or b | N(R$_{92}$) | C(=O) | N | C(H) | C(H) | H | 2 |
| V67 a or b | N(R$_{92}$) | C(=O) | C(H) | N | C(H) | H | 2 |
| V68 a or b | N(R$_{92}$) | C(=O) | CH$_2$ | CH$_2$ | CH$_2$ | H | 2 |
| V69 a or b | N(R$_{92}$) | C(=O) | N(R$_{92}$) | C(=O) | C(H) | H | 2 |
| V70 a or b | N(R$_{92}$) | C(=O) | C(H) | C(H) | N | H | 2 |
| V71 a or b | N(R$_{92}$) | C(=O) | C(H) | C(H) | C(H) | CH$_3$ | 2 |
| V72 a or b | N(R$_{92}$) | C(=O) | N | C(H) | C(H) | CH$_3$ | 2 |
| V73 a or b | N(R$_{92}$) | C(=O) | C(H) | N | C(H) | CH$_3$ | 2 |
| V74 a or b | N(R$_{92}$) | C(=O) | CH$_2$ | CH$_2$ | CH$_2$ | CH$_3$ | 2 |
| V75 a or b | N(R$_{92}$) | C(=O) | N(R$_{92}$) | C(=O) | C(H) | CH$_3$ | 2 |
| V76 a or b | N(R$_{92}$) | C(=O) | C(H) | C(H) | N | CH$_3$ | 2 |
| V77 a or b | C(=O) | N(R$_{92}$) | C(H) | C(H) | C(H) | H | 2 |
| V78 a or b | C(=O) | N(R$_{92}$) | C(H) | C(F) | C(H) | H | 2 |
| V79 a or b | C(=O) | N(R$_{92}$) | C(H) | C(Cl) | C(H) | H | 2 |
| V80 a or b | C(=O) | N(R$_{92}$) | C(H) | C(COOH) | C(H) | H | 2 |
| V81 a or b | C(=O) | N(R$_{92}$) | C(H) | C(H) | N | H | 2 |
| V82 a or b | C(=O) | N(R$_{92}$) | C(H) | N | C(H) | H | 2 |
| V83 a or b | C(=O) | N(R$_{92}$) | C(=O) | N(R$_{92}$) | C(H) | H | 2 |
| V84 a or b | C(=O) | N(R$_{92}$) | C(=O) | N(R$_{92}$) | N | H | 2 |
| V85 a or b | C(=O) | N(R$_{92}$) | C(=O) | C(H) | Absent | H | 2 |
| V86 a or b | C(=O) | N(R$_{92}$) | N(H) | C(H) | Absent | H | 2 |
| V87 a or b | C(=O) | N(R$_{92}$) | C(H) | C(H) | C(H) | CH$_3$ | 2 |
| V88 a or b | C(=O) | N(R$_{92}$) | C(H) | C(F) | C(H) | CH$_3$ | 2 |
| V89 a or b | C(=O) | N(R$_{92}$) | C(H) | C(Cl) | C(H) | CH$_3$ | 2 |
| V90 a or b | C(=O) | N(R$_{92}$) | C(H) | C(COOH) | C(H) | CH$_3$ | 2 |
| V91 a or b | C(=O) | N(R$_{92}$) | C(H) | C(H) | N | CH$_3$ | 2 |
| V92 a or b | C(=O) | N(R$_{92}$) | C(H) | N | C(H) | CH$_3$ | 2 |

TABLE 23-continued

| | | | | | | | |
|---|---|---|---|---|---|---|---|
| V93 a or b | C(=O) | N(R$_{92}$) | C(=O) | N(R$_{92}$) | C(H) | CH$_3$ | 2 |
| V94 a or b | C(=O) | N(R$_{92}$) | C(=O) | N(R$_{92}$) | N | CH$_3$ | 2 |
| V95 a or b | C(=O) | N(R$_{92}$) | C(=O) | C(H) | Absent | CH$_3$ | 2 |
| V96 a or b | C(=O) | N(R$_{92}$) | N(H) | C(H) | Absent | CH$_3$ | 2 |

* (i) Indicates that R$_{92}$ is —H,
(ii) indicates that R$_{92}$ is —C(=O)CH$_3$, and
(iii) indicates that R$_{92}$ is —CH$_2$—C(=O)OH.

TABLE 24

(a)

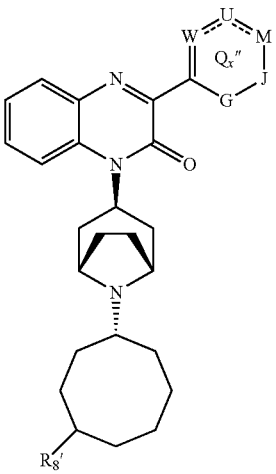

(b)

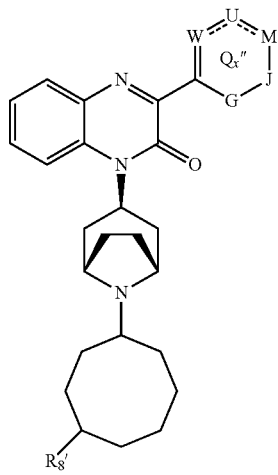

(c)

and pharmaceutically acceptable derivatives thereof, where:

| Compound | G * | J * | M * | U * | W | R$_8$' |
|---|---|---|---|---|---|---|
| W W1 c | N(R$_{92}$) | C(=O) | C(H) | C(H) | C(H) | H |
| W2 c | N(R$_{92}$) | C(=O) | N | C(H) | C(H) | H |
| W3 c | N(R$_{92}$) | C(=O) | C(H) | N | C(H) | H |
| W4 c | N(R$_{92}$) | C(=O) | CH$_2$ | CH$_2$ | CH$_2$ | H |
| W5 c | N(R$_{92}$) | C(=O) | N(R$_{92}$) | C(=O) | C(H) | H |
| W6 c | N(R$_{92}$) | C(=O) | C(H) | C(H) | N | H |
| W7 a or b | N(R$_{92}$) | C(=O) | C(H) | C(H) | C(H) | CH$_3$ |
| W8 a or b | N(R$_{92}$) | C(=O) | N | C(H) | C(H) | CH$_3$ |
| W9 a or b | N(R$_{92}$) | C(=O) | C(H) | N | C(H) | CH$_3$ |
| W10 a or b | N(R$_{92}$) | C(=O) | CH$_2$ | CH$_2$ | CH$_2$ | CH$_3$ |
| W11 a or b | N(R$_{92}$) | C(=O) | N(R$_{92}$) | C(=O) | C(H) | CH$_3$ |
| W12 a or b | N(R$_{92}$) | C(=O) | C(H) | C(H) | N | CH$_3$ |
| W13 c | C(=O) | N(R$_{92}$) | C(H) | C(H) | C(H) | H |
| W14 c | C(=O) | N(R$_{92}$) | C(H) | C(F) | C(H) | H |
| W15 c | C(=O) | N(R$_{92}$) | C(H) | C(Cl) | C(H) | H |
| W16 c | C(=O) | N(R$_{92}$) | C(H) | C(COOH) | C(H) | H |
| W17 c | C(=O) | N(R$_{92}$) | C(H) | C(H) | N | H |
| W18 c | C(=O) | N(R$_{92}$) | C(H) | N | C(H) | H |
| W19 c | C(=O) | N(R$_{92}$) | C(=O) | N(R$_{92}$) | C(H) | H |
| W20 c | C(=O) | N(R$_{92}$) | C(=O) | N(R$_{92}$) | N | H |
| W21 c | C(=O) | N(R$_{92}$) | C(=O) | C(H) | Absent | H |
| W22 c | C(=O) | N(R$_{92}$) | N(H) | C(H) | Absent | H |
| W23 a or b | C(=O) | N(R$_{92}$) | C(H) | C(H) | C(H) | CH$_3$ |
| W24 a or b | C(=O) | N(R$_{92}$) | C(H) | C(F) | C(H) | CH$_3$ |
| W25 a or b | C(=O) | N(R$_{92}$) | C(H) | C(Cl) | C(H) | CH$_3$ |
| W26 a or b | C(=O) | N(R$_{92}$) | C(H) | C(COOH) | C(H) | CH$_3$ |
| W27 a or b | C(=O) | N(R$_{92}$) | C(H) | C(H) | N | CH$_3$ |
| W28 a or b | C(=O) | N(R$_{92}$) | C(H) | N | C(H) | CH$_3$ |
| W29 a or b | C(=O) | N(R$_{92}$) | C(=O) | N(R$_{92}$) | C(H) | CH$_3$ |
| W30 a or b | C(=O) | N(R$_{92}$) | C(=O) | N(R$_{92}$) | N | CH$_3$ |
| W31 a or b | C(=O) | N(R$_{92}$) | C(=O) | C(H) | Absent | CH$_3$ |
| W32 a or b | C(=O) | N(R$_{92}$) | N(H) | C(H) | Absent | CH$_3$ |
| W33 c | N(R$_{92}$) | C(=O) | C(H) | C(H) | C(H) | H |
| W34 c | N(R$_{92}$) | C(=O) | N | C(H) | C(H) | H |
| W35 c | N(R$_{92}$) | C(=O) | C(H) | N | C(H) | H |
| W36 c | N(R$_{92}$) | C(=O) | CH$_2$ | CH$_2$ | CH$_2$ | H |
| W37 c | N(R$_{92}$) | C(=O) | N(R$_{92}$) | C(=O) | C(H) | H |
| W38 c | N(R$_{92}$) | C(=O) | C(H) | C(H) | N | H |
| W39 a or b | N(R$_{92}$) | C(=O) | C(H) | C(H) | C(H) | CH$_3$ |
| W40 a or b | N(R$_{92}$) | C(=O) | N | C(H) | C(H) | CH$_3$ |
| W41 a or b | N(R$_{92}$) | C(=O) | C(H) | N | C(H) | CH$_3$ |
| W42 a or b | N(R$_{92}$) | C(=O) | CH$_2$ | CH$_2$ | CH$_2$ | CH$_3$ |
| W43 a or b | N(R$_{92}$) | C(=O) | N(R$_{92}$) | C(=O) | C(H) | CH$_3$ |
| W44 a or b | N(R$_{92}$) | C(=O) | C(H) | C(H) | N | CH$_3$ |
| W45 c | C(=O) | N(R$_{92}$) | C(H) | C(H) | C(H) | H |
| W46 c | C(=O) | N(R$_{92}$) | C(H) | C(F) | C(H) | H |
| W47 c | C(=O) | N(R$_{92}$) | C(H) | C(Cl) | C(H) | H |
| W48 c | C(=O) | N(R$_{92}$) | C(H) | C(COOH) | C(H) | H |
| W49 c | C(=O) | N(R$_{92}$) | C(H) | C(H) | N | H |
| W50 c | C(=O) | N(R$_{92}$) | C(H) | N | C(H) | H |
| W51 c | C(=O) | N(R$_{92}$) | C(=O) | N(R$_{92}$) | C(H) | H |
| W52 c | C(=O) | N(R$_{92}$) | C(=O) | N(R$_{92}$) | N | H |

TABLE 24-continued

| | | | | | | |
|---|---|---|---|---|---|---|
| W53 c | C(=O) | N(R_92) | C(=O) | C(H) | Absent | H |
| W54 c | C(=O) | N(R_92) | N(H) | C(H) | Absent | H |
| W55 a or b | C(=O) | N(R_92) | C(H) | C(H) | C(H) | CH_3 |
| W56 a or b | C(=O) | N(R_92) | C(H) | C(F) | C(H) | CH_3 |
| W57 a or b | C(=O) | N(R_92) | C(H) | C(Cl) | C(H) | CH_3 |
| W58 a or b | C(=O) | N(R_92) | C(H) | C(COOH) | C(H) | CH_3 |
| W59 a or b | C(=O) | N(R_92) | C(H) | C(H) | N | CH_3 |
| W60 a or b | C(=O) | N(R_92) | C(H) | N | C(H) | CH_3 |
| W61 a or b | C(=O) | N(R_92) | C(=O) | N(R_92) | C(H) | CH_3 |
| W62 a or b | C(=O) | N(R_92) | C(=O) | N(R_92) | N | CH_3 |
| W63 a or b | C(=O) | N(R_92) | C(=O) | C(H) | Absent | CH_3 |
| W64 a or b | C(=O) | N(R_92) | N(H) | C(H) | Absent | CH_3 |

* (i) Indicates the $R_{92}$ is —H, (ii) indicates that $R_{92}$ is —C(=O)CH_3, and (iii) indicates that $R_{92}$ is —CH_2—C(=O)OH.

TABLE 25

(a)

(b)

(c)

and pharmaceutically acceptable derivatives thereof, where:

| Compound | G * | J * | M * | U * | W | R_8' |
|---|---|---|---|---|---|---|
| Y Y1 c | N(R_92) | C(=O) | C(H) | C(H) | C(H) | H |
| Y2 c | N(R_92) | C(=O) | N | C(H) | C(H) | H |
| Y3 c | N(R_92) | C(=O) | C(H) | N | C(H) | H |
| Y4 c | N(R_92) | C(=O) | CH_2 | CH_2 | CH_2 | H |
| Y5 c | N(R_92) | C(=O) | N(R_92) | C(=O) | C(H) | H |
| Y6 c | N(R_92) | C(=O) | C(H) | C(H) | N | H |
| Y7 a or b | N(R_92) | C(=O) | C(H) | C(H) | C(H) | CH_3 |
| Y8 a or b | N(R_92) | C(=O) | N | C(H) | C(H) | CH_3 |
| Y9 a or b | N(R_92) | C(=O) | C(H) | N | C(H) | CH_3 |
| Y10 a or b | N(R_92) | C(=O) | CH_2 | CH_2 | CH_2 | CH_3 |
| Y11 a or b | N(R_92) | C(=O) | N(R_92) | C(=O) | C(H) | CH_3 |
| Y12 a or b | N(R_92) | C(=O) | C(H) | C(H) | N | CH_3 |
| Y13 c | C(=O) | N(R_92) | C(H) | C(H) | C(H) | H |
| Y14 c | C(=O) | N(R_92) | C(H) | C(F) | C(H) | H |
| Y15 c | C(=O) | N(R_92) | C(H) | C(Cl) | C(H) | H |
| Y16 c | C(=O) | N(R_92) | C(H) | C(COOH) | C(H) | H |
| Y17 c | C(=O) | N(R_92) | C(H) | C(H) | N | H |
| Y18 c | C(=O) | N(R_92) | C(H) | N | C(H) | H |
| Y19 c | C(=O) | N(R_92) | C(=O) | N(R_92) | C(H) | H |
| Y20 c | C(=O) | N(R_92) | C(=O) | N(R_92) | N | H |
| Y21 c | C(=O) | N(R_92) | C(=O) | C(H) | Absent | H |
| Y22 c | C(=O) | N(R_92) | N(H) | C(H) | Absent | H |
| Y23 a or b | C(=O) | N(R_92) | C(H) | C(H) | C(H) | CH_3 |
| Y24 a or b | C(=O) | N(R_92) | C(H) | C(F) | C(H) | CH_3 |
| Y25 a or b | C(=O) | N(R_92) | C(H) | C(Cl) | C(H) | CH_3 |
| Y26 a or b | C(=O) | N(R_92) | C(H) | C(COOH) | C(H) | CH_3 |
| Y27 a or b | C(=O) | N(R_92) | C(H) | C(H) | N | CH_3 |
| Y28 a or b | C(=O) | N(R_92) | C(H) | N | C(H) | CH_3 |
| Y29 a or b | C(=O) | N(R_92) | C(=O) | N(R_92) | C(H) | CH_3 |
| Y30 a or b | C(=O) | N(R_92) | C(=O) | N(R_92) | N | CH_3 |
| Y31 a or b | C(=O) | N(R_92) | C(=O) | C(H) | Absent | CH_3 |
| Y32 a or b | C(=O) | N(R_92) | N(H) | C(H) | Absent | CH_3 |
| Y33 c | N(R_92) | C(=O) | C(H) | C(H) | C(H) | H |
| Y34 c | N(R_92) | C(=O) | N | C(H) | C(H) | H |
| Y35 c | N(R_92) | C(=O) | C(H) | N | C(H) | H |
| Y36 c | N(R_92) | C(=O) | CH_2 | CH_2 | CH_2 | H |
| Y37 c | N(R_92) | C(=O) | N(R_92) | C(=O) | C(H) | H |
| Y38 c | N(R_92) | C(=O) | C(H) | C(H) | N | H |
| Y39 a or b | N(R_92) | C(=O) | C(H) | C(H) | C(H) | CH_3 |
| Y40 a or b | N(R_92) | C(=O) | N | C(H) | C(H) | CH_3 |
| Y41 a or b | N(R_92) | C(=O) | C(H) | N | C(H) | CH_3 |
| Y42 a or b | N(R_92) | C(=O) | CH_2 | CH_2 | CH_2 | CH_3 |
| Y43 a or b | N(R_92) | C(=O) | N(R_92) | C(=O) | C(H) | CH_3 |
| Y44 a or b | N(R_92) | C(=O) | C(H) | C(H) | N | CH_3 |
| Y45 c | C(=O) | N(R_92) | C(H) | C(H) | C(H) | H |
| Y46 c | C(=O) | N(R_92) | C(H) | C(F) | C(H) | H |
| Y47 c | C(=O) | N(R_92) | C(H) | C(Cl) | C(H) | H |
| Y48 c | C(=O) | N(R_92) | C(H) | C(COOH) | C(H) | H |
| Y49 c | C(=O) | N(R_92) | C(H) | C(H) | N | H |
| Y50 c | C(=O) | N(R_92) | C(H) | N | C(H) | H |
| Y51 c | C(=O) | N(R_92) | C(=O) | N(R_92) | C(H) | H |
| Y52 c | C(=O) | N(R_92) | C(=O) | N(R_92) | N | H |

TABLE 25-continued

| | | | | | | |
|---|---|---|---|---|---|---|
| Y53 c | C(=O) | N(R$_{92}$) | C(=O) | C(H) | Absent | H |
| Y54 c | C(=O) | N(R$_{92}$) | N(H) | C(H) | Absent | H |
| Y55 a or b | C(=O) | N(R$_{92}$) | C(H) | C(H) | C(H) | CH$_3$ |
| Y56 a or b | C(=O) | N(R$_{92}$) | C(H) | C(F) | C(H) | CH$_3$ |
| Y57 a or b | C(=O) | N(R$_{92}$) | C(H) | C(Cl) | C(H) | CH$_3$ |
| Y58 a or b | C(=O) | N(R$_{92}$) | C(H) | C(COOH) | C(H) | CH$_3$ |
| Y59 a or b | C(=O) | N(R$_{92}$) | C(H) | C(H) | N | CH$_3$ |
| Y60 a or b | C(=O) | N(R$_{92}$) | C(H) | N | C(H) | CH$_3$ |
| Y61 a or b | C(=O) | N(R$_{92}$) | C(=O) | N(R$_{92}$) | C(H) | CH$_3$ |
| Y62 a or b | C(=O) | N(R$_{92}$) | C(=O) | N(R$_{92}$) | N | CH$_3$ |
| Y63 a or b | C(=O) | N(R$_{92}$) | C(=O) | C(H) | Absent | CH$_3$ |
| Y64 a or b | C(=O) | N(R$_{92}$) | N(H) | C(H) | Absent | CH$_3$ |

* (i) Indicates the R$_{92}$ is —H, (ii) indicates that R$_{92}$ is —C(=O)CH$_3$, and (iii) indicates that R$_{92}$ is —CH$_2$—C(=O)OH.

TABLE 26

(a)

(b)

(c)

and pharmaceutically acceptable derivatives thereof, where:

| Compound | G * | J * | M * | U * | W | R$_8$' |
|---|---|---|---|---|---|---|
| Z Z1 c | N(R$_{92}$) | C(=O) | C(H) | C(H) | C(H) | H |
| Z2 c | N(R$_{92}$) | C(=O) | N | C(H) | C(H) | H |
| Z3 c | N(R$_{92}$) | C(=O) | C(H) | N | C(H) | H |
| Z4 c | N(R$_{92}$) | C(=O) | CH$_2$ | CH$_2$ | CH$_2$ | H |
| Z5 c | N(R$_{92}$) | C(=O) | N(R$_{92}$) | C(=O) | C(H) | H |
| Z6 c | N(R$_{92}$) | C(=O) | C(H) | C(H) | N | H |
| Z7 a or b | N(R$_{92}$) | C(=O) | C(H) | C(H) | C(H) | CH$_3$ |
| Z8 a or b | N(R$_{92}$) | C(=O) | N | C(H) | C(H) | CH$_3$ |
| Z9 a or b | N(R$_{92}$) | C(=O) | C(H) | N | C(H) | CH$_3$ |
| Z10 a or b | N(R$_{92}$) | C(=O) | CH$_2$ | CH$_2$ | CH$_2$ | CH$_3$ |
| Z11 a or b | N(R$_{92}$) | C(=O) | N(R$_{92}$) | C(=O) | C(H) | CH$_3$ |
| Z12 a or b | N(R$_{92}$) | C(=O) | C(H) | C(H) | N | CH$_3$ |
| Z13 c | C(=O) | N(R$_{92}$) | C(H) | C(H) | C(H) | H |
| Z14 c | C(=O) | N(R$_{92}$) | C(H) | C(F) | C(H) | H |
| Z15 c | C(=O) | N(R$_{92}$) | C(H) | C(Cl) | C(H) | H |
| Z16 c | C(=O) | N(R$_{92}$) | C(H) | C(COOH) | C(H) | H |
| Z17 c | C(=O) | N(R$_{92}$) | C(H) | C(H) | N | H |
| Z18 c | C(=O) | N(R$_{92}$) | C(H) | N | C(H) | H |
| Z19 c | C(=O) | N(R$_{92}$) | C(=O) | N(R$_{92}$) | C(H) | H |
| Z20 c | C(=O) | N(R$_{92}$) | C(=O) | N(R$_{92}$) | N | H |
| Z21 c | C(=O) | N(R$_{92}$) | C(=O) | C(H) | Absent | H |
| Z22 c | C(=O) | N(R$_{92}$) | N(H) | C(H) | Absent | H |
| Z23 a or b | C(=O) | N(R$_{92}$) | C(H) | C(H) | C(H) | CH$_3$ |
| Z24 a or b | C(=O) | N(R$_{92}$) | C(H) | C(F) | C(H) | CH$_3$ |
| Z25 a or b | C(=O) | N(R$_{92}$) | C(H) | C(Cl) | C(H) | CH$_3$ |
| Z26 a or b | C(=O) | N(R$_{92}$) | C(H) | C(COOH) | C(H) | CH$_3$ |
| Z27 a or b | C(=O) | N(R$_{92}$) | C(H) | C(H) | N | CH$_3$ |
| Z28 a or b | C(=O) | N(R$_{92}$) | C(H) | N | C(H) | CH$_3$ |
| Z29 a or b | C(=O) | N(R$_{92}$) | C(=O) | N(R$_{92}$) | C(H) | CH$_3$ |
| Z30 a or b | C(=O) | N(R$_{92}$) | C(=O) | N(R$_{92}$) | N | CH$_3$ |
| Z31 a or b | C(=O) | N(R$_{92}$) | C(=O) | C(H) | Absent | CH$_3$ |
| Z32 a or b | C(=O) | N(R$_{92}$) | N(H) | C(H) | Absent | CH$_3$ |
| Z33 c | N(R$_{92}$) | C(=O) | C(H) | C(H) | C(H) | H |
| Z34 c | N(R$_{92}$) | C(=O) | N | C(H) | C(H) | H |
| Z35 c | N(R$_{92}$) | C(=O) | C(H) | N | C(H) | H |
| Z36 c | N(R$_{92}$) | C(=O) | CH$_2$ | CH$_2$ | CH$_2$ | H |
| Z37 c | N(R$_{92}$) | C(=O) | N(R$_{92}$) | C(=O) | C(H) | H |
| Z38 c | N(R$_{92}$) | C(=O) | C(H) | C(H) | N | H |
| Z39 a or b | N(R$_{92}$) | C(=O) | C(H) | C(H) | C(H) | CH$_3$ |
| Z40 a or b | N(R$_{92}$) | C(=O) | N | C(H) | C(H) | CH$_3$ |
| Z41 a or b | N(R$_{92}$) | C(=O) | C(H) | N | C(H) | CH$_3$ |
| Z42 a or b | N(R$_{92}$) | C(=O) | CH$_2$ | CH$_2$ | CH$_2$ | CH$_3$ |
| Z43 a or b | N(R$_{92}$) | C(=O) | N(R$_{92}$) | C(=O) | C(H) | CH$_3$ |
| Z44 a or b | N(R$_{92}$) | C(=O) | C(H) | C(H) | N | CH$_3$ |
| Z45 c | C(=O) | N(R$_{92}$) | C(H) | C(H) | C(H) | H |
| Z46 c | C(=O) | N(R$_{92}$) | C(H) | C(F) | C(H) | H |
| Z47 c | C(=O) | N(R$_{92}$) | C(H) | C(Cl) | C(H) | H |
| Z48 c | C(=O) | N(R$_{92}$) | C(H) | C(COOH) | C(H) | H |
| Z49 c | C(=O) | N(R$_{92}$) | C(H) | C(H) | N | H |
| Z50 c | C(=O) | N(R$_{92}$) | C(H) | N | C(H) | H |
| Z51 c | C(=O) | N(R$_{92}$) | C(=O) | N(R$_{92}$) | C(H) | H |
| Z52 c | C(=O) | N(R$_{92}$) | C(=O) | N(R$_{92}$) | N | H |

TABLE 26-continued

| | | | | | | |
|---|---|---|---|---|---|---|
| Z53 c | C(=O) | N(R$_{92}$) | C(=O) | C(H) | Absent | H |
| Z54 c | C(=O) | N(R$_{92}$) | N(H) | C(H) | Absent | H |
| Z55 a or b | C(=O) | N(R$_{92}$) | C(H) | C(H) | C(H) | CH$_3$ |
| Z56 a or b | C(=O) | N(R$_{92}$) | C(H) | C(F) | C(H) | CH$_3$ |
| Z57 a or b | C(=O) | N(R$_{92}$) | C(H) | C(Cl) | C(H) | CH$_3$ |
| Z58 a or b | C(=O) | N(R$_{92}$) | C(H) | C(COOH) | C(H) | CH$_3$ |
| Z59 a or b | C(=O) | N(R$_{92}$) | C(H) | C(H) | N | CH$_3$ |
| Z60 a or b | C(=O) | N(R$_{92}$) | C(H) | N | C(H) | CH$_3$ |
| Z61 a or b | C(=O) | N(R$_{92}$) | C(=O) | N(R$_{92}$) | C(H) | CH$_3$ |
| Z62 a or b | C(=O) | N(R$_{92}$) | C(=O) | N(R$_{92}$) | N | CH$_3$ |
| Z63 a or b | C(=O) | N(R$_{92}$) | C(=O) | C(H) | Absent | CH$_3$ |
| Z64 a or b | C(=O) | N(R$_{92}$) | N(H) | C(H) | Absent | CH$_3$ |

* (i) Indicates the R$_{92}$ is —H, (ii) indicates that R$_{92}$ is —C(=O)CH$_3$, and (iii) indicates that R$_{92}$ is —CH$_2$—C(=O)OH.

TABLE 27

(a)

(b)

(c)

and pharmaceutically acceptable derivatives thereof, where:

| Compound | G * | J * | M * | U * | W | R$_8'$ |
|---|---|---|---|---|---|---|
| AA AA1 c | N(R$_{92}$) | C(=O) | C(H) | C(H) | C(H) | H |
| AA2 c | N(R$_{92}$) | C(=O) | N | C(H) | C(H) | H |
| AA3 c | N(R$_{92}$) | C(=O) | C(H) | N | C(H) | H |
| AA4 c | N(R$_{92}$) | C(=O) | CH$_2$ | CH$_2$ | CH$_2$ | H |
| AA5 c | N(R$_{92}$) | C(=O) | N(R$_{92}$) | C(=O) | C(H) | H |
| AA6 c | N(R$_{92}$) | C(=O) | C(H) | C(H) | N | H |
| AA7 a or b | N(R$_{92}$) | C(=O) | C(H) | C(H) | C(H) | CH$_3$ |
| AA8 a or b | N(R$_{92}$) | C(=O) | N | C(H) | C(H) | CH$_3$ |
| AA9 a or b | N(R$_{92}$) | C(=O) | C(H) | N | C(H) | CH$_3$ |
| AA10 a or b | N(R$_{92}$) | C(=O) | CH$_2$ | CH$_2$ | CH$_2$ | CH$_3$ |
| AA11 a or b | N(R$_{92}$) | C(=O) | N(R$_{92}$) | C(=O) | C(H) | CH$_3$ |
| AA12 a or b | N(R$_{92}$) | C(=O) | C(H) | C(H) | N | CH$_3$ |
| AA13 c | C(=O) | N(R$_{92}$) | C(H) | C(H) | C(H) | H |
| AA14 c | C(=O) | N(R$_{92}$) | C(H) | C(F) | C(H) | H |
| AA15 c | C(=O) | N(R$_{92}$) | C(H) | C(Cl) | C(H) | H |
| AA16 c | C(=O) | N(R$_{92}$) | C(H) | C(COOH) | C(H) | H |
| AA17 c | C(=O) | N(R$_{92}$) | C(H) | C(H) | N | H |
| AA18 c | C(=O) | N(R$_{92}$) | C(H) | N | C(H) | H |
| AA19 c | C(=O) | N(R$_{92}$) | C(=O) | N(R$_{92}$) | C(H) | H |
| AA20 c | C(=O) | N(R$_{92}$) | C(=O) | N(R$_{92}$) | N | H |
| AA21 c | C(=O) | N(R$_{92}$) | C(=O) | C(H) | Absent | H |
| AA22 c | C(=O) | N(R$_{92}$) | N(H) | C(H) | Absent | H |
| AA23 a or b | C(=O) | N(R$_{92}$) | C(H) | C(H) | C(H) | CH$_3$ |
| AA24 a or b | C(=O) | N(R$_{92}$) | C(H) | C(F) | C(H) | CH$_3$ |
| AA25 a or b | C(=O) | N(R$_{92}$) | C(H) | C(Cl) | C(H) | CH$_3$ |
| AA26 a or b | C(=O) | N(R$_{92}$) | C(H) | C(COOH) | C(H) | CH$_3$ |
| AA27 a or b | C(=O) | N(R$_{92}$) | C(H) | C(H) | N | CH$_3$ |
| AA28 a or b | C(=O) | N(R$_{92}$) | C(H) | N | C(H) | CH$_3$ |
| AA29 a or b | C(=O) | N(R$_{92}$) | C(=O) | N(R$_{92}$) | C(H) | CH$_3$ |
| AA30 a or b | C(=O) | N(R$_{92}$) | C(=O) | N(R$_{92}$) | N | CH$_3$ |
| AA31 a or b | C(=O) | N(R$_{92}$) | C(=O) | C(H) | Absent | CH$_3$ |
| AA32 a or b | C(=O) | N(R$_{92}$) | N(H) | C(H) | Absent | CH$_3$ |
| AA33 c | N(R$_{92}$) | C(=O) | C(H) | C(H) | C(H) | H |
| AA34 c | N(R$_{92}$) | C(=O) | N | C(H) | C(H) | H |
| AA35 c | N(R$_{92}$) | C(=O) | C(H) | N | C(H) | H |
| AA36 c | N(R$_{92}$) | C(=O) | CH$_2$ | CH$_2$ | CH$_2$ | H |
| AA37 c | N(R$_{92}$) | C(=O) | N(R$_{92}$) | C(=O) | C(H) | H |
| AA38 c | N(R$_{92}$) | C(=O) | C(H) | C(H) | N | H |
| AA39 a or b | N(R$_{92}$) | C(=O) | C(H) | C(H) | C(H) | CH$_3$ |
| AA40 a or b | N(R$_{92}$) | C(=O) | N | C(H) | C(H) | CH$_3$ |
| AA41 a or b | N(R$_{92}$) | C(=O) | C(H) | N | C(H) | CH$_3$ |
| AA42 a or b | N(R$_{92}$) | C(=O) | CH$_2$ | CH$_2$ | CH$_2$ | CH$_3$ |
| AA43 a or b | N(R$_{92}$) | C(=O) | N(R$_{92}$) | C(=O) | C(H) | CH$_3$ |
| AA44 a or b | N(R$_{92}$) | C(=O) | C(H) | C(H) | N | CH$_3$ |
| AA45 c | C(=O) | N(R$_{92}$) | C(H) | C(H) | C(H) | H |
| AA46 c | C(=O) | N(R$_{92}$) | C(H) | C(F) | C(H) | H |
| AA47 c | C(=O) | N(R$_{92}$) | C(H) | C(Cl) | C(H) | H |
| AA48 c | C(=O) | N(R$_{92}$) | C(H) | C(COOH) | C(H) | H |
| AA49 c | C(=O) | N(R$_{92}$) | C(H) | C(H) | N | H |
| AA50 c | C(=O) | N(R$_{92}$) | C(H) | N | C(H) | H |
| AA51 c | C(=O) | N(R$_{92}$) | C(=O) | N(R$_{92}$) | C(H) | H |

TABLE 27-continued

| | | | | | | |
|---|---|---|---|---|---|---|
| AA52 c | C(=O) | N($R_{92}$) | C(=O) | N($R_{92}$) | N | H |
| AA53 c | C(=O) | N($R_{92}$) | C(=O) | C(H) | Absent | H |
| AA54 c | C(=O) | N($R_{92}$) | N(H) | C(H) | Absent | H |
| AA55 a or b | C(=O) | N($R_{92}$) | C(H) | C(H) | C(H) | $CH_3$ |
| AA56 a or b | C(=O) | N($R_{92}$) | C(H) | C(F) | C(H) | $CH_3$ |
| AA57 a or b | C(=O) | N($R_{92}$) | C(H) | C(Cl) | C(H) | $CH_3$ |
| AA58 a or b | C(=O) | N($R_{92}$) | C(H) | C(COOH) | C(H) | $CH_3$ |
| AA59 a or b | C(=O) | N($R_{92}$) | C(H) | C(H) | N | $CH_3$ |
| AA60 a or b | C(=O) | N($R_{92}$) | C(H) | N | C(H) | $CH_3$ |
| AA61 a or b | C(=O) | N($R_{92}$) | C(=O) | N($R_{92}$) | C(H) | $CH_3$ |
| AA62 a or b | C(=O) | N($R_{92}$) | C(=O) | N($R_{92}$) | N | $CH_3$ |
| AA63 a or b | C(=O) | N($R_{92}$) | C(=O) | C(H) | Absent | $CH_3$ |
| AA64 a or b | C(=O) | N($R_{92}$) | N(H) | C(H) | Absent | $CH_3$ |

* (i) Indicates the $R_{92}$ is —H, (ii) indicates that $R_{92}$ is —C(=O)$CH_3$, and (iii) indicates that $R_{92}$ is —$CH_2$—C(=O)OH.

TABLE 28

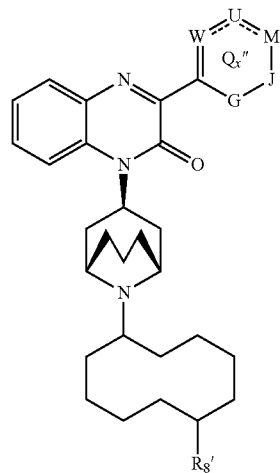

and pharmaceutically acceptable derivatives thereof, where:

| Compound | G * | J * | M * | U * | W | $R_8'$ |
|---|---|---|---|---|---|---|
| BB BB1 c | N($R_{92}$) | C(=O) | C(H) | C(H) | C(H) | H |
| BB2 c | N($R_{92}$) | C(=O) | N | C(H) | C(H) | H |
| BB3 c | N($R_{92}$) | C(=O) | C(H) | N | C(H) | H |
| BB4 c | N($R_{92}$) | C(=O) | $CH_2$ | $CH_2$ | $CH_2$ | H |
| BB5 c | N($R_{92}$) | C(=O) | N($R_{92}$) | C(=O) | C(H) | H |
| BB6 c | N($R_{92}$) | C(=O) | C(H) | C(H) | N | H |
| BB7 a or b | N($R_{92}$) | C(=O) | C(H) | C(H) | C(H) | $CH_3$ |
| BB8 a or b | N($R_{92}$) | C(=O) | N | C(H) | C(H) | $CH_3$ |
| BB9 a or b | N($R_{92}$) | C(=O) | C(H) | N | C(H) | $CH_3$ |
| BB10 a or b | N($R_{92}$) | C(=O) | $CH_2$ | $CH_2$ | $CH_2$ | $CH_3$ |
| BB11 a or b | N($R_{92}$) | C(=O) | N($R_{92}$) | C(=O) | C(H) | $CH_3$ |
| BB12 a or b | N($R_{92}$) | C(=O) | C(H) | C(H) | N | $CH_3$ |
| BB13 c | C(=O) | N($R_{92}$) | C(H) | C(H) | C(H) | H |
| BB14 c | C(=O) | N($R_{92}$) | C(H) | C(F) | C(H) | H |
| BB15 c | C(=O) | N($R_{92}$) | C(H) | C(Cl) | C(H) | H |
| BB16 c | C(=O) | N($R_{92}$) | C(H) | C(COOH) | C(H) | H |
| BB17 c | C(=O) | N($R_{92}$) | C(H) | C(H) | N | H |
| BB18 c | C(=O) | N($R_{92}$) | C(H) | N | C(H) | H |
| BB19 c | C(=O) | N($R_{92}$) | C(=O) | N($R_{92}$) | C(H) | H |
| BB20 c | C(=O) | N($R_{92}$) | C(=O) | N($R_{92}$) | N | H |
| BB21 c | C(=O) | N($R_{92}$) | C(=O) | C(H) | Absent | H |
| BB22 c | C(=O) | N($R_{92}$) | N(H) | C(H) | Absent | H |
| BB23 a or b | C(=O) | N($R_{92}$) | C(H) | C(H) | C(H) | $CH_3$ |
| BB24 a or b | C(=O) | N($R_{92}$) | C(H) | C(F) | C(H) | $CH_3$ |
| BB25 a or b | C(=O) | N($R_{92}$) | C(H) | C(Cl) | C(H) | $CH_3$ |
| BB26 a or b | C(=O) | N($R_{92}$) | C(H) | C(COOH) | C(H) | $CH_3$ |
| BB27 a or b | C(=O) | N($R_{92}$) | C(H) | C(H) | N | $CH_3$ |
| BB28 a or b | C(=O) | N($R_{92}$) | C(H) | N | C(H) | $CH_3$ |
| BB29 a or b | C(=O) | N($R_{92}$) | C(=O) | N($R_{92}$) | C(H) | $CH_3$ |
| BB30 a or b | C(=O) | N($R_{92}$) | C(=O) | N($R_{92}$) | N | $CH_3$ |
| BB31 a or b | C(=O) | N($R_{92}$) | C(=O) | C(H) | Absent | $CH_3$ |
| BB32 a or b | C(=O) | N($R_{92}$) | N(H) | C(H) | Absent | $CH_3$ |
| BB33 c | N($R_{92}$) | C(=O) | C(H) | C(H) | C(H) | H |
| BB34 c | N($R_{92}$) | C(=O) | N | C(H) | C(H) | H |
| BB35 c | N($R_{92}$) | C(=O) | C(H) | N | C(H) | H |
| BB36 c | N($R_{92}$) | C(=O) | $CH_2$ | $CH_2$ | $CH_2$ | H |
| BB37 c | N($R_{92}$) | C(=O) | N($R_{92}$) | C(=O) | C(H) | H |
| BB38 c | N($R_{92}$) | C(=O) | C(H) | C(H) | N | H |
| BB39 a or b | N($R_{92}$) | C(=O) | C(H) | C(H) | C(H) | $CH_3$ |
| BB40 a or b | N($R_{92}$) | C(=O) | N | C(H) | C(H) | $CH_3$ |
| BB41 a or b | N($R_{92}$) | C(=O) | C(H) | N | C(H) | $CH_3$ |
| BB42 a or b | N($R_{92}$) | C(=O) | $CH_2$ | $CH_2$ | $CH_2$ | $CH_3$ |
| BB43 a or b | N($R_{92}$) | C(=O) | N($R_{92}$) | C(=O) | C(H) | $CH_3$ |
| BB44 a or b | N($R_{92}$) | C(=O) | C(H) | C(H) | N | $CH_3$ |
| BB45 c | C(=O) | N($R_{92}$) | C(H) | C(H) | C(H) | H |
| BB46 c | C(=O) | N($R_{92}$) | C(H) | C(F) | C(H) | H |
| BB47 c | C(=O) | N($R_{92}$) | C(H) | C(Cl) | C(H) | H |
| BB48 c | C(=O) | N($R_{92}$) | C(H) | C(COOH) | C(H) | H |
| BB49 c | C(=O) | N($R_{92}$) | C(H) | C(H) | N | H |
| BB50 c | C(=O) | N($R_{92}$) | C(H) | N | C(H) | H |
| BB51 c | C(=O) | N($R_{92}$) | C(=O) | N($R_{92}$) | C(H) | H |

TABLE 28-continued

| | | | | | | |
|---|---|---|---|---|---|---|
| BB52 c | C(=O) | N($R_{92}$) | C(=O) | N($R_{92}$) | N | H |
| BB53 c | C(=O) | N($R_{92}$) | C(=O) | C(H) | Absent | H |
| BB54 c | C(=O) | N($R_{92}$) | N(H) | C(H) | Absent | H |
| BB55 a or b | C(=O) | N($R_{92}$) | C(H) | C(H) | C(H) | $CH_3$ |
| BB56 a or b | C(=O) | N($R_{92}$) | C(H) | C(F) | C(H) | $CH_3$ |
| BB57 a or b | C(=O) | N($R_{92}$) | C(H) | C(Cl) | C(H) | $CH_3$ |
| BB58 a or b | C(=O) | N($R_{92}$) | C(H) | C(COOH) | C(H) | $CH_3$ |
| BB59 a or b | C(=O) | N($R_{92}$) | C(H) | C(H) | N | $CH_3$ |
| BB60 a or b | C(=O) | N($R_{92}$) | C(H) | N | C(H) | $CH_3$ |
| BB61 a or b | C(=O) | N($R_{92}$) | C(=O) | N($R_{92}$) | C(H) | $CH_3$ |
| BB62 a or b | C(=O) | N($R_{92}$) | C(=O) | N($R_{92}$) | N | $CH_3$ |
| BB63 a or b | C(=O) | N($R_{92}$) | C(=O) | C(H) | Absent | $CH_3$ |
| BB64 a or b | C(=O) | N($R_{92}$) | N(H) | C(H) | Absent | $CH_3$ |

\* (i) Indicates the $R_{92}$ is —H, (ii) indicates that $R_{92}$ is —C(=O)$CH_3$, and (iii) indicates that $R_{92}$ is —$CH_2$—C(=O)OH.

TABLE 29

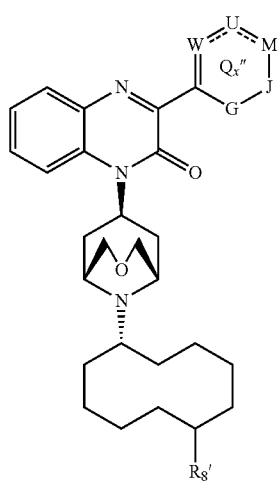

(a)

(b)

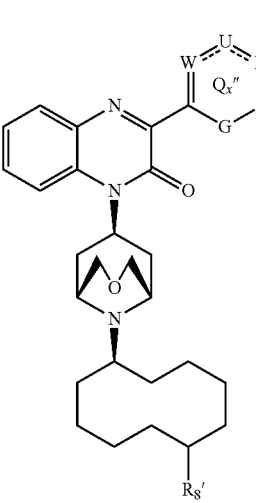

(c)

and pharmaceutically acceptable derivatives thereof, where:

| Compound | G * | J * | M * | U * | W | $R_8'$ |
|---|---|---|---|---|---|---|
| CC CC1 c | N($R_{92}$) | C(=O) | C(H) | C(H) | C(H) | H |
| CC2 c | N($R_{92}$) | C(=O) | N | C(H) | C(H) | H |
| CC3 c | N($R_{92}$) | C(=O) | C(H) | N | C(H) | H |
| CC4 c | N($R_{92}$) | C(=O) | $CH_2$ | $CH_2$ | $CH_2$ | H |
| CC5 c | N($R_{92}$) | C(=O) | N($R_{92}$) | C(=O) | C(H) | H |
| CC6 c | N($R_{92}$) | C(=O) | C(H) | C(H) | N | H |
| CC7 a or b | N($R_{92}$) | C(=O) | C(H) | C(H) | C(H) | $CH_3$ |
| CC8 a or b | N($R_{92}$) | C(=O) | N | C(H) | C(H) | $CH_3$ |
| CC9 a or b | N($R_{92}$) | C(=O) | C(H) | N | C(H) | $CH_3$ |
| CC10 a or b | N($R_{92}$) | C(=O) | $CH_2$ | $CH_2$ | $CH_2$ | $CH_3$ |
| CC11 a or b | N($R_{92}$) | C(=O) | N($R_{92}$) | C(=O) | C(H) | $CH_3$ |
| CC12 a or b | N($R_{92}$) | C(=O) | C(H) | C(H) | N | $CH_3$ |
| CC13 c | C(=O) | N($R_{92}$) | C(H) | C(H) | C(H) | H |
| CC14 c | C(=O) | N($R_{92}$) | C(H) | C(F) | C(H) | H |
| CC15 c | C(=O) | N($R_{92}$) | C(H) | C(Cl) | C(H) | H |
| CC16 c | C(=O) | N($R_{92}$) | C(H) | C(COOH) | C(H) | H |
| CC17 c | C(=O) | N($R_{92}$) | C(H) | C(H) | N | H |
| CC18 c | C(=O) | N($R_{92}$) | C(H) | N | C(H) | H |
| CC19 c | C(=O) | N($R_{92}$) | C(=O) | N($R_{92}$) | C(H) | H |
| CC20 c | C(=O) | N($R_{92}$) | C(=O) | N($R_{92}$) | N | H |
| CC21 c | C(=O) | N($R_{92}$) | C(=O) | C(H) | Absent | H |
| CC22 c | C(=O) | N($R_{92}$) | N(H) | C(H) | Absent | H |
| CC23 a or b | C(=O) | N($R_{92}$) | C(H) | C(H) | C(H) | $CH_3$ |
| CC24 a or b | C(=O) | N($R_{92}$) | C(H) | C(F) | C(H) | $CH_3$ |
| CC25 a or b | C(=O) | N($R_{92}$) | C(H) | C(Cl) | C(H) | $CH_3$ |
| CC26 a or b | C(=O) | N($R_{92}$) | C(H) | C(COOH) | C(H) | $CH_3$ |
| CC27 a or b | C(=O) | N($R_{92}$) | C(H) | C(H) | N | $CH_3$ |
| CC28 a or b | C(=O) | N($R_{92}$) | C(H) | N | C(H) | $CH_3$ |
| CC29 a or b | C(=O) | N($R_{92}$) | C(=O) | N($R_{92}$) | C(H) | $CH_3$ |
| CC30 a or b | C(=O) | N($R_{92}$) | C(=O) | N($R_{92}$) | N | $CH_3$ |
| CC31 a or b | C(=O) | N($R_{92}$) | C(=O) | C(H) | Absent | $CH_3$ |
| CC32 a or b | C(=O) | N($R_{92}$) | N(H) | C(H) | Absent | $CH_3$ |
| CC33 c | N($R_{92}$) | C(=O) | C(H) | C(H) | C(H) | H |
| CC34 c | N($R_{92}$) | C(=O) | N | C(H) | C(H) | H |
| CC35 c | N($R_{92}$) | C(=O) | C(H) | N | C(H) | H |
| CC36 c | N($R_{92}$) | C(=O) | $CH_2$ | $CH_2$ | $CH_2$ | H |
| CC37 c | N($R_{92}$) | C(=O) | N($R_{92}$) | C(=O) | C(H) | H |
| CC38 c | N($R_{92}$) | C(=O) | C(H) | C(H) | N | H |
| CC39 a or b | N($R_{92}$) | C(=O) | C(H) | C(H) | C(H) | $CH_3$ |
| CC40 a or b | N($R_{92}$) | C(=O) | N | C(H) | C(H) | $CH_3$ |
| CC41 a or b | N($R_{92}$) | C(=O) | C(H) | N | C(H) | $CH_3$ |
| CC42 a or b | N($R_{92}$) | C(=O) | $CH_2$ | $CH_2$ | $CH_2$ | $CH_3$ |
| CC43 a or b | N($R_{92}$) | C(=O) | N($R_{92}$) | C(=O) | C(H) | $CH_3$ |
| CC44 a or b | N($R_{92}$) | C(=O) | C(H) | C(H) | N | $CH_3$ |
| CC45 c | C(=O) | N($R_{92}$) | C(H) | C(H) | C(H) | HH |
| CC46 c | C(=O) | N($R_{92}$) | C(H) | C(F) | C(H) | H |
| CC47 c | C(=O) | N($R_{92}$) | C(H) | C(Cl) | C(H) | H |
| CC48 c | C(=O) | N($R_{92}$) | C(H) | C(COOH) | C(H) | H |
| CC49 c | C(=O) | N($R_{92}$) | C(H) | C(H) | N | H |
| CC50 c | C(=O) | N($R_{92}$) | C(H) | N | C(H) | H |
| CC51 c | C(=O) | N($R_{92}$) | C(=O) | N($R_{92}$) | C(H) | H |

TABLE 29-continued

| | | | | | |
|---|---|---|---|---|---|
| CC52 c | C(=O) | N(R$_{92}$) | C(=O) | N(R$_{92}$) | N | H |
| CC53 c | C(=O) | N(R$_{92}$) | C(=O) | C(H) | Absent | H |
| CC54 c | C(=O) | N(R$_{92}$) | N(H) | C(H) | Absent | H |
| CC55 a or b | C(=O) | N(R$_{92}$) | C(H) | C(H) | C(H) | CH$_3$ |
| CC56 a or b | C(=O) | N(R$_{92}$) | C(H) | C(F) | C(H) | CH$_3$ |
| CC57 a or b | C(=O) | N(R$_{92}$) | C(H) | C(Cl) | C(H) | CH$_3$ |
| CC58 a or b | C(=O) | N(R$_{92}$) | C(H) | C(COOH) | C(H) | CH$_3$ |
| CC59 a or b | C(=O) | N(R$_{92}$) | C(H) | C(H) | N | CH$_3$ |
| CC60 a or b | C(=O) | N(R$_{92}$) | C(H) | N | C(H) | CH$_3$ |
| CC61 a or b | C(=O) | N(R$_{92}$) | C(=O) | N(R$_{92}$) | C(H) | CH$_3$ |
| CC62 a or b | C(=O) | N(R$_{92}$) | C(=O) | N(R$_{92}$) | N | CH$_3$ |
| CC63 a or b | C(=O) | N(R$_{92}$) | C(=O) | C(H) | Absent | CH$_3$ |
| CC64 a or b | C(=O) | N(R$_{92}$) | N(H) | C(H) | Absent | CH$_3$ |

* (i) Indicates the R$_{92}$ is —H, (ii) indicates that R$_{92}$ is —C(=O)CH$_3$, and (iii) indicates that R$_{92}$ is —CH$_2$—C(=O)OH.

TABLE 30

(a)

(b)

and pharmaceutically acceptable derivatives thereof, where:

| Compound | G* | J* | M* | U* | W | R$_8$' |
|---|---|---|---|---|---|---|
| DD DD1 a or b | N(R$_{92}$) | C(=O) | C(H) | C(H) | C(H) | H |
| DD2 a or b | N(R$_{92}$) | C(=O) | N | C(H) | C(H) | H |

TABLE 30-continued

| | | | | | | |
|---|---|---|---|---|---|---|
| DD3 a or b | N(R$_{92}$) | C(=O) | C(H) | N | C(H) | H |
| DD4 a or b | N(R$_{92}$) | C(=O) | CH$_2$ | CH$_2$ | CH$_2$ | H |
| DD5 a or b | N(R$_{92}$) | C(=O) | N(R$_{92}$) | C(=O) | C(H) | H |
| DD6 a or b | N(R$_{92}$) | C(=O) | C(H) | C(H) | N | H |
| DD7 a or b | N(R$_{92}$) | C(=O) | C(H) | C(H) | C(H) | CH$_3$ |
| DD8 a or b | N(R$_{92}$) | C(=O) | N | C(H) | C(H) | CH$_3$ |
| DD9 a or b | N(R$_{92}$) | C(=O) | C(H) | N | C(H) | CH$_3$ |
| DD10 a or b | N(R$_{92}$) | C(=O) | CH$_2$ | CH$_2$ | CH$_2$ | CH$_3$ |
| DD11 a or b | N(R$_{92}$) | C(=O) | N(R$_{92}$) | C(=O) | C(H) | CH$_3$ |
| DD12 a or b | N(R$_{92}$) | C(=O) | C(H) | C(H) | N | CH$_3$ |
| DD13 a or b | C(=O) | N(R$_{92}$) | C(H) | C(H) | C(H) | H |
| DD14 a or b | C(=O) | N(R$_{92}$) | C(H) | C(F) | C(H) | H |
| DD15 a or b | C(=O) | N(R$_{92}$) | C(H) | C(Cl) | C(H) | H |
| DD16 a or b | C(=O) | N(R$_{92}$) | C(H) | C(COOH) | C(H) | H |
| DD17 a or b | C(=O) | N(R$_{92}$) | C(H) | C(H) | N | H |
| DD18 a or b | C(=O) | N(R$_{92}$) | C(H) | N | C(H) | H |
| DD19 a or b | C(=O) | N(R$_{92}$) | C(=O) | N(R$_{92}$) | C(H) | H |
| DD20 a or b | C(=O) | N(R$_{92}$) | C(=O) | N(R$_{92}$) | N | H |
| DD21 a or b | C(=O) | N(R$_{92}$) | C(=O) | C(H) | Absent | H |
| DD22 a or b | C(=O) | N(R$_{92}$) | N(H) | C(H) | Absent | H |
| DD23 a or b | C(=O) | N(R$_{92}$) | C(H) | C(H) | C(H) | CH$_3$ |
| DD24 a or b | C(=O) | N(R$_{92}$) | C(H) | C(F) | C(H) | CH$_3$ |
| DD25 a or b | C(=O) | N(R$_{92}$) | C(H) | C(Cl) | C(H) | CH$_3$ |
| DD26 a or b | C(=O) | N(R$_{92}$) | C(H) | C(COOH) | C(H) | CH$_3$ |
| DD27 a or b | C(=O) | N(R$_{92}$) | C(H) | C(H) | N | CH$_3$ |
| DD28 a or b | C(=O) | N(R$_{92}$) | C(H) | N | C(H) | CH$_3$ |
| DD29 a or b | C(=O) | N(R$_{92}$) | C(=O) | N(R$_{92}$) | C(H) | CH$_3$ |
| DD30 a or b | C(=O) | N(R$_{92}$) | C(=O) | N(R$_{92}$) | N | CH$_3$ |
| DD31 a or b | C(=O) | N(R$_{92}$) | C(=O) | C(H) | Absent | CH$_3$ |
| DD32 a or b | C(=O) | N(R$_{92}$) | N(H) | C(H) | Absent | CH$_3$ |

* (i) Indicates the R$_{92}$ is —H, (ii) indicates that R$_{92}$ is —C(=O)CH$_3$, and (iii) indicates that R$_{92}$ is —CH$_2$—C(=O)OH.

TABLE 31

(a)

TABLE 31-continued (b)

and pharmaceutically acceptable derivatives thereof, where:

| Compound | G * | J * | M * | U * | W | $R_8'$ |
|---|---|---|---|---|---|---|
| EE EE1 a or b | $N(R_{92})$ | C(=O) | C(H) | C(H) | C(H) | H |
| EE2 a or b | $N(R_{92})$ | C(=O) | N | C(H) | C(H) | H |
| EE3 a or b | $N(R_{92})$ | C(=O) | C(H) | N | C(H) | H |
| EE4 a or b | $N(R_{92})$ | C(=O) | $CH_2$ | $CH_2$ | $CH_2$ | H |
| EE5 a or b | $N(R_{92})$ | C(=O) | $N(R_{92})$ | C(=O) | C(H) | H |
| EE6 a or b | $N(R_{92})$ | C(=O) | $N(R_{92})$ | N | Absent | H |
| EE7 a or b | $N(R_{92})$ | C(=O) | C(H) | C(H) | N | H |
| EE8 a or b | $N(R_{92})$ | C(=O) | C(H) | C(H) | C(H) | $CH_3$ |
| EE9 a or b | $N(R_{92})$ | C(=O) | N | C(H) | C(H) | $CH_3$ |
| EE10 a or b | $N(R_{92})$ | C(=O) | C(H) | N | C(H) | $CH_3$ |
| EE11 a or b | $N(R_{92})$ | C(=O) | $CH_2$ | $CH_2$ | $CH_2$ | $CH_3$ |
| EE12 a or b | $N(R_{92})$ | C(=O) | $N(R_{92})$ | C(=O) | C(H) | $CH_3$ |
| EE13 a or b | $N(R_{92})$ | C(=O) | $N(R_{92})$ | N | Absent | $CH_3$ |
| EE14 a or b | $N(R_{92})$ | C(=O) | C(H) | C(H) | N | $CH_3$ |
| EE15 a or b | C(=O) | $N(R_{92})$ | C(H) | C(H) | C(H) | H |
| EE16 a or b | C(=O) | $N(R_{92})$ | C(H) | C(F) | C(H) | H |
| EE17 a or b | C(=O) | $N(R_{92})$ | C(H) | C(Cl) | C(H) | H |
| EE18 a or b | C(=O) | $N(R_{92})$ | C(H) | C(COOH) | C(H) | H |
| EE19 a or b | C(=O) | $N(R_{92})$ | C(H) | C(H) | N | H |
| EE20 a or b | C(=O) | $N(R_{92})$ | C(H) | N | C(H) | H |
| EE21 a or b | C(=O) | $N(R_{92})$ | C(=O) | $N(R_{92})$ | C(H) | H |
| EE22 a or b | C(=O) | $N(R_{92})$ | C(=O) | $N(R_{92})$ | N | H |
| EE23 a or b | C(=O) | $N(R_{92})$ | C(=O) | C(H) | Absent | H |
| EE24 a or b | C(=O) | $N(R_{92})$ | N(H) | C(H) | Absent | H |
| EE25 a or b | C(=O) | $N(R_{92})$ | C(H) | C(H) | C(H) | $CH_3$ |
| EE26 a or b | C(=O) | $N(R_{92})$ | C(H) | C(F) | C(H) | $CH_3$ |
| EE27 a or b | C(=O) | $N(R_{92})$ | C(H) | C(Cl) | C(H) | $CH_3$ |
| EE28 a or b | C(=O) | $N(R_{92})$ | C(H) | C(COOH) | C(H) | $CH_3$ |
| EE29 a or b | C(=O) | $N(R_{92})$ | C(H) | C(H) | N | $CH_3$ |
| EE30 a or b | C(=O) | $N(R_{92})$ | C(H) | N | C(H) | $CH_3$ |
| EE31 a or b | C(=O) | $N(R_{92})$ | C(=O) | $N(R_{92})$ | C(H) | $CH_3$ |
| EE32 a or b | C(=O) | $N(R_{92})$ | C(=O) | $N(R_{92})$ | N | $CH_3$ |
| EE33 a or b | C(=O) | $N(R_{92})$ | C(=O) | C(H) | Absent | $CH_3$ |
| EE34 a or b | C(=O) | $N(R_{92})$ | N(H) | C(H) | Absent | $CH_3$ |

* (i) Indicates the $R_{92}$ is —H, (ii) indicates that $R_{92}$ is —C(=O)$CH_3$, and (iii) indicates that $R_{92}$ is —$CH_2$—C(=O)OH.

TABLE 32

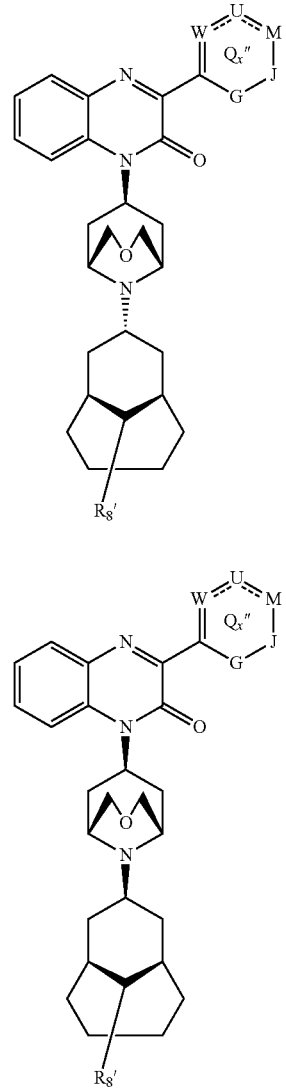

(a)

(b)

and pharmaceutically acceptable derivatives thereof, where:

| Compound | G * | J * | M * | U * | W | $R_8'$ |
|---|---|---|---|---|---|---|
| FF FF1 a or b | $N(R_{92})$ | C(=O) | C(H) | C(H) | C(H) | H |
| FF2 a or b | $N(R_{92})$ | C(=O) | N | C(H) | C(H) | H |
| FF3 a or b | $N(R_{92})$ | C(=O) | C(H) | N | C(H) | H |
| FF4 a or b | $N(R_{92})$ | C(=O) | $CH_2$ | $CH_2$ | $CH_2$ | H |
| FF5 a or b | $N(R_{92})$ | C(=O) | $N(R_{92})$ | C(=O) | C(H) | H |
| FF6 a or b | $N(R_{92})$ | C(=O) | C(H) | C(H) | N | H |
| FF7 a or b | $N(R_{92})$ | C(=O) | C(H) | C(H) | C(H) | $CH_3$ |
| FF8 a or b | $N(R_{92})$ | C(=O) | N | C(H) | C(H) | $CH_3$ |
| FF9 a or b | $N(R_{92})$ | C(=O) | C(H) | N | C(H) | $CH_3$ |
| FF10 a or b | $N(R_{92})$ | C(=O) | $CH_2$ | $CH_2$ | $CH_2$ | $CH_3$ |
| FF11 a or b | $N(R_{92})$ | C(=O) | $N(R_{92})$ | C(=O) | C(H) | $CH_3$ |
| FF12 a or b | $N(R_{92})$ | C(=O) | C(H) | C(H) | N | $CH_3$ |
| FF13 a or b | C(=O) | $N(R_{92})$ | C(H) | C(H) | C(H) | H |
| FF14 a or b | C(=O) | $N(R_{92})$ | C(H) | C(F) | C(H) | H |
| FF15 a or b | C(=O) | $N(R_{92})$ | C(H) | C(Cl) | C(H) | H |
| FF16 a or b | C(=O) | $N(R_{92})$ | C(H) | C(COOH) | C(H) | H |
| FF17 a or b | C(=O) | $N(R_{92})$ | C(H) | C(H) | N | H |
| FF18 a or b | C(=O) | $N(R_{92})$ | C(H) | N | C(H) | H |
| FF19 a or b | C(=O) | $N(R_{92})$ | C(=O) | $N(R_{92})$ | C(H) | H |
| FF20 a or b | C(=O) | $N(R_{92})$ | C(=O) | $N(R_{92})$ | N | H |
| FF21 a or b | C(=O) | $N(R_{92})$ | C(=O) | C(H) | Absent | H |
| FF22 a or b | C(=O) | $N(R_{92})$ | N(H) | C(H) | Absent | H |

TABLE 32-continued

| | | | | | | |
|---|---|---|---|---|---|---|
| FF23 a or b | C(=O) | N($R_{92}$) | C(H) | C(H) | C(H) | $CH_3$ |
| FF24 a or b | C(=O) | N($R_{92}$) | C(H) | C(F) | C(H) | $CH_3$ |
| FF25 a or b | C(=O) | N($R_{92}$) | C(H) | C(Cl) | C(H) | $CH_3$ |
| FF26 a or b | C(=O) | N($R_{92}$) | C(H) | C(COOH) | C(H) | $CH_3$ |
| FF27 a or b | C(=O) | N($R_{92}$) | C(H) | C(H) | N | $CH_3$ |
| FF28 a or b | C(=O) | N($R_{92}$) | C(H) | N | C(H) | $CH_3$ |
| FF29 a or b | C(=O) | N($R_{92}$) | C(=O) | N($R_{92}$) | C(H) | $CH_3$ |
| FF30 a or b | C(=O) | N($R_{92}$) | C(=O) | N($R_{92}$) | N | $CH_3$ |
| FF31 a or b | C(=O) | N($R_{92}$) | C(=O) | C(H) | Absent | $CH_3$ |
| FF32 a or b | C(=O) | N($R_{92}$) | N(H) | C(H) | Absent | $CH_3$ |

* (i) Indicates the $R_{92}$ is —H, (ii) indicates that $R_{92}$ is —C(=O)$CH_3$, and (iii) indicates that $R_{92}$ is —$CH_2$—C(=O)OH.

4.2 Definitions

As used in connection with the Cyclic Urea- or Lactam-Substituted Quinoxaline-Type Piperidine Compounds herein, the terms used herein have the following meaning:

"—($C_1$-$C_{10}$)alkyl" means a straight chain or branched non-cyclic hydrocarbon having 1, 2, 3, 4, 5, 6, 7, 8, 9, or 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —($C_1$-$C_8$)alkyl groups, such as methyl, ethyl or propyl, replace one or both hydrogens in a —$CH_2$— group of a straight chain alkyl. A branched non-cyclic hydrocarbon means that one or more straight chain —($C_1$-$C_{10}$)alkyl groups, such as methyl, ethyl or propyl, replace one or both hydrogens in a —$CH_2$— group of a straight chain non-cyclic hydrocarbon. Representative branched —($C_1$-$C_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

In connection with the Z group, "—($C_1$-$C_{10}$)alkyl-" means a straight chain or branched non-cyclic hydrocarbon moiety having 1, 2, 3, 4, 5, 6, 7, 8, 9, or 10 carbon atoms where two hydrogen atoms on the same or a different carbon atom of the moiety are each figuratively removed and replaced by a bond to one of the two adjoining groups. Representative —($C_1$-$C_{10}$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, n-deca-1,1-diyl, n-deca-1,2-diyl, n-deca-1,3-diyl, n-deca-1,4-diyl, n-deca-1,5-diyl, n-deca-1,6-diyl, n-deca-1,7-diyl, n-deca-1,8-diyl, n-deca-1,9-diyl, n-deca-1,10-diyl, and the like.

"—($C_1$-$C_6$)alkyl" means a straight chain or branched non-cyclic hydrocarbon having 1, 2, 3, 4, 5, or 6 carbon atoms. Representative straight chain —($C_1$-$C_6$)alkyls include -methyl, -ethyl, -n-propyl, -n-butyl, -n-pentyl, and -n-hexyl. Representative branched —($C_1$-$C_6$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

In connection with the Z group, "—($C_1$-$C_6$)alkyl-" means a straight chain or branched non-cyclic hydrocarbon moiety having 1, 2, 3, 4, 5, or 6 carbon atoms where two hydrogen atoms on the same or a different carbon atom of the moiety are each figuratively removed and replaced by a bond to one of the two adjoining groups. Representative —($C_1$-$C_6$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, and the like.

"—($C_1$-$C_4$)alkyl" means a straight chain or branched non-cyclic hydrocarbon having 1, 2, 3, or 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

In connection with the Z group, "—($C_1$-$C_4$)alkyl-" means a straight chain or branched non-cyclic hydrocarbon moiety having 1, 2, 3, or 4 carbon atoms where two hydrogen atoms on the same or a different carbon atom of the moiety are each figuratively removed and replaced by a bond to one of the two adjoining groups. Representative —($C_1$-$C_4$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, and the like.

"—($C_1$-$C_3$)alkyl" means a straight chain or branched non-cyclic hydrocarbon having 1, 2, or 3 carbon atoms. Representative straight chain —($C_1$-$C_3$)alkyls include -methyl, -ethyl, -n-propyl. Representative branched —($C_1$-$C_3$)alkyls include -iso-propyl.

In connection with the Z group, "—($C_1$-$C_3$)alkyl-" means a straight chain or branched non-cyclic hydrocarbon moiety having 1, 2, or 3 carbon atoms where two hydrogen atoms on the same or a different carbon atom of the moiety are each figuratively removed and replaced by a bond to one of the two adjoining groups. Representative —($C_1$-$C_3$)alkyl- moieties include meth-1,1-diyl, eth-1,1-diyl, eth-1,2-diyl, n-prop-1,1-diyl, n-prop-1,2-diyl, n-prop-1,3-diyl, and the like.

"—($C_1$-$C_2$)alkyl" means a straight chain non-cyclic hydrocarbon having 1 or 2 carbon atoms. Representative —($C_1$-$C_2$) alkyls include -methyl and -ethyl.

In connection with the Z group, "—($C_1$-$C_2$)alkyl-" means a straight chain non-cyclic hydrocarbon moiety having 1 or 2 carbon atoms where two hydrogen atoms on the same or a different carbon atom of the moiety are each figuratively removed and replaced by a bond to one of the two adjoining groups. Representative —($C_1$-$C_2$)alkyl- moieties include meth-1,1-diyl, eth-1,1-diyl, and eth-1,2-diyl.

"—($C_2$-$C_{10}$)alkenyl" means a straight chain or branched non-cyclic hydrocarbon having 2, 3, 4, 5, 6, 7, 8, 9, or 10 carbon atoms and including at least one carbon-carbon double bond. A branched alkenyl means that one or more straight chain —($C_1$-$C_8$)alkyl groups, such as methyl, ethyl or propyl, replace one or both hydrogens in a —$CH_2$— or =CH— group of a straight chain alkenyl. Representative straight chain and branched ($C_2$-$C_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

In connection with the Z group, "—($C_2$-$C_{10}$)alkenyl-" means a straight chain or branched non-cyclic hydrocarbon moiety having 2, 3, 4, 5, 6, 7, 8, 9, or 10 carbon atoms and including at least one carbon-carbon double bond where two hydrogen atoms on the same or a different carbon atom of the moiety are each figuratively removed and replaced by a bond to one of the two adjoining groups. Representative —($C_2$-$C_{10}$)alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—($C_2$-$C_6$)alkenyl" means a straight chain or branched non-cyclic hydrocarbon having 2, 3, 4, 5, or 6 carbon atoms and including at least one carbon-carbon double bond. Representative straight chain and branched ($C_2$-$C_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, and the like.

In connection with the Z group, "—($C_2$-$C_6$)alkenyl-" means a straight chain or branched non-cyclic hydrocarbon moiety having 2, 3, 4, 5, or 6 carbon atoms and including at least one carbon-carbon double bond where two hydrogen atoms on the same or a different carbon atom of the moiety are each figuratively removed and replaced by a bond to one of the two adjoining groups. Representative —($C_2$-$C_6$)alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—($C_2$-$C_3$)alkenyl" means a straight chain non-cyclic hydrocarbon having 2 or 3 carbon atoms and including at least one carbon-carbon double bond. Representative ($C_2$-$C_3$)alkenyls include -vinyl, -allyl, and 1-prop-1-enyl.

In connection with the Z group, "—($C_2$-$C_3$)alkenyl-" means a straight chain or branched non-cyclic hydrocarbon moiety having 2 or 3 carbon atoms and including at least one carbon-carbon double bond where two hydrogen atoms on the same or a different carbon atom of the moiety are each figuratively removed and replaced by a bond to one of the two adjoining groups. Representative —($C_2$-$C_3$)alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, and prop-2-en-1,3-diyl.

"—($C_2$-$C_{10}$)alkynyl" means a straight chain or branched non-cyclic hydrocarbon having 2, 3, 4, 5, 6, 7, 8, 9, or 10 carbon atoms and including at least one carbon-carbon triple bond. A branched alkynyl means that one or more straight chain —($C_1$-$C_8$)alkyl groups, such as methyl, ethyl or propyl, replace one or both hydrogens in a —$CH_2$— group of a straight chain alkynyl. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—($C_2$-$C_6$)alkynyl" means a straight chain or branched non-cyclic hydrocarbon having 2, 3, 4, 5, or 6 carbon atoms and including at least one carbon-carbon triple bond. Representative straight chain and branched ($C_2$-$C_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—($C_1$-$C_6$)alkoxy" means a straight chain or branched non-cyclic hydrocarbon having one or more ether groups and 1, 2, 3, 4, 5, or 6 carbon atoms. Representative straight chain and branched ($C_1$-$C_6$)alkoxys include -methoxy, -ethoxy, -methoxymethyl, -2-methoxyethyl, -5-methoxypentyl, -3-ethoxybutyl, (methoxymethoxy)methyl-, 1-(methoxy)-1-methoxyethyl-, trimethoxymethyl-, 2-((methoxy)methoxy)-2-methylpropyl-, 3-(1,1,1-trimethoxypropane), (methoxy) trimethoxymethyl-, (2,2,2-trimethoxyethoxy)-, and the like.

"—($C_1$-$C_4$)alkoxy" means a straight chain or branched non-cyclic hydrocarbon having one or more ether groups and 1, 2, 3, or 4 carbon atoms. Representative straight chain and branched ($C_1$-$C_4$)alkoxys include -methoxy, -ethoxy, -methoxymethyl, -2-methoxyethyl, (methoxymethoxy)methyl-, 1-(methoxy)-1-methoxyethyl-, trimethoxymethyl-, and the like.

"—($C_3$-$C_{14}$)cycloalkyl" means a saturated monocyclic hydrocarbon having 3, 4, 5, 6, 7, 8, 9, 10, 11, 12, 13, or 14 carbon atoms. Representative ($C_3$-$C_{14}$)cycloalkyls are -cyclopropyl, -cyclobutyl, -cyclopentyl, -cyclohexyl, -cycloheptyl, -cyclooctyl, -cyclononyl, -cyclodecyl, cycloundecyl, -cyclododecyl, and -cyclotetradecyl.

"—($C_3$-$C_{12}$)cycloalkyl" means a saturated monocyclic hydrocarbon having 3, 4, 5, 6, 7, 8, 9, 10, 11, or 12 carbon atoms. Representative ($C_3$-$C_{12}$)cycloalkyls are -cyclopropyl, -cyclobutyl, -cyclopentyl, -cyclohexyl, -cycloheptyl, -cyclooctyl, -cyclononyl, -cyclodecyl, -cycloundecyl, and -cyclododecyl.

"—($C_6$-$C_{12}$)cycloalkyl" means a saturated monocyclic hydrocarbon having 6, 7, 8, 9, 10, 11, or 12 carbon atoms. Representative ($C_6$-$C_{12}$)cycloalkyls are -cyclohexyl, -cycloheptyl, -cyclooctyl, -cyclononyl, -cyclodecyl, -cycloundecyl, and -cyclododecyl.

"—($C_4$-$C_8$)cycloalkyl" or "4- to 8-member cycloalkyl ring" means a saturated monocyclic hydrocarbon having 4, 5, 6, 7, or 8 carbon atoms. Representative —($C_4$-$C_8$)cycloalkyls are -cyclobutyl, -cyclopentyl, -cyclohexyl, -cycloheptyl, and -cyclooctyl.

"—($C_3$-$C_8$)cycloalkyl" means a saturated monocyclic hydrocarbon having 3, 4, 5, 6, 7, or 8 carbon atoms. Representative ($C_3$-$C_8$)cycloalkyls include -cyclopropyl, -cyclobutyl, -cyclopentyl, -cyclohexyl, -cycloheptyl, and -cyclooctyl.

"—($C_3$-$C_7$)cycloalkyl" means a saturated monocyclic hydrocarbon having 3, 4, 5, 6, or 7 carbon atoms. Representative ($C_3$-$C_7$)cycloalkyls include cyclopropyl, -cyclobutyl, -cyclopentyl, -cyclohexyl, and -cycloheptyl.

"—($C_6$-$C_{14}$)bicycloalkyl" means a bicyclic hydrocarbon ring system having 6, 7, 8, 9, 10, 11, 12, 13, or 14 carbon atoms and at least one saturated cyclic alkyl ring. In one embodiment, the —($C_6$-$C_{14}$)bicycloalkyl has one saturated cyclic alkyl ring. In another embodiment, the —($C_6$-$C_{14}$)bicycloalkyl has two saturated cyclic alkyl rings. Representative —($C_6$-$C_{14}$)bicycloalkyls include -indanyl, -norbornyl, -1,2,3,4-tetrahydronaphthalenyl, -5,6,7,8-tetrahydronaphthalenyl, -perhydronaphthalenyl, -bicyclo[2.2.1]hexyl, bicyclo[2.2.1.]heptyl, -bicyclo[2.2.2]octyl, -bicyclo[3.3.1]heptyl, -bicyclo[3.2.1]octyl, -bicyclo[3.3.1]nonyl, -bicyclo[3.3.2]decyl, -bicyclo[3.3.3]undecyl, -bicyclo[4.2.2]decyl, -bicyclo[4.3.2]undecyl, -bicyclo[4.3.1]decyl, and the like.

"—($C_8$-$C_{20}$)tricycloalkyl" means a tri-cyclic hydrocarbon ring system having 8, 9, 10, 11, 12, 13, 14, 15, 16, 17, 18, 19, or 20 carbon atoms and at least one saturated cyclic alkyl ring; thus, one of the rings can comprise, e.g., benzo. In one embodiment, the —($C_8$-$C_{20}$)tricycloalkyl has one saturated cyclic alkyl ring. In another embodiment, the —($C_8$-$C_{20}$)tricycloalkyl has two saturated cyclic alkyl rings. In another embodiment, the —($C_8$-$C_{20}$)tricycloalkyl has three saturated cyclic alkyl rings. Representative —($C_8$-$C_{20}$)tricycloalkyls include -pyrenyl, -adamantyl, -noradamantyl, -1,2,3,4-tetrahydroanthracenyl, -1,2,3,4,4a,9,9a,10-octahydroanthracenyl, -perhydroanthracenyl -aceanthrenyl, -1,2,3,4-tetrahydropenanthrenyl, -5,6,7,8-tetrahydrophenanthrenyl, -1,2,3,4,4a,9,10,10a-octahydrophenanthrenyl, -perhydrophenanthrenyl, -tetradecahydro-1H-cyclohepta[a]naphthalenyl, -tetradecahydro-1H-cycloocta[e]indenyl, -tetradecahydro-1H-cyclohepta[e]azulenyl, -hexadecahydrocycloocta[b]naphthalenyl, -hexadecahydrocyclohepta[a]heptalenyl, -tricyclo-pentadecanyl, -tricyclo-octadecanyl, -tricyclo-nonadecanyl, -tricyclo-icosanyl, -2,3-benzobicyclo[2.2.2]octanyl, -6,7-benzobicyclo[3.2.1]octanyl, -9,10-benzobicyclo[3.3.2]decanyl, -2,3,4,4a,9,9a-hexahydro-1H-fluorenyl, -1,2,3,4,4a,8b-hexahydrobiphenylenyl, and the like.

"—$(C_5-C_{14})$cycloalkenyl" means a cyclic non-aromatic hydrocarbon having at least one carbon-carbon double bond in the cyclic system and 5, 6, 7, 8, 9, 10, 11, 12, 13, or 14 carbon atoms. Representative $(C_5-C_{14})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, -cyclododecadienyl, and the like.

"—$(C_5-C_8)$cycloalkenyl" means a cyclic non-aromatic hydrocarbon having at least one carbon-carbon double bond in the cyclic system and 5, 6, 7, or 8 carbon atoms. Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—$(C_7-C_{14})$bicycloalkenyl" means a bicyclic hydrocarbon ring system having at least one carbon-carbon double bond in each ring and 7, 8, 9, 10, 11, 12, 13, or 14 carbon atoms. Representative —$(C_7-C_{14})$bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, -norbornenyl, and the like.

"—$(C_8-C_{20})$tricycloalkenyl" means a tricyclic hydrocarbon ring system having at least one carbon-carbon double bond in each ring and 8, 9, 10, 11, 12, 13, 14, 15, 16, 17, 18, 19, or 20 carbon atoms. Representative —$(C_8-C_{20})$tricycloalkenyls include -anthracenyl, -phenanthrenyl, -phenalenyl, -acenaphthalenyl, -as-indacenyl, -s-indacenyl, -2,3,6,7,8,9,10,11-octahydro-1H-cycloocta[e]indenyl, 2,3,4,7,8,9,10,11-octahydro-1H-cyclohepta[a]naphthalenyl, -8,9,10,11-tetrahydro-7H-cyclohepta[a]naphthalenyl, -2,3,4,5,6,7,8,9,10,11,12,13-dodecahydro-1H-cyclohepta[a]heptalenyl, -1,2,3,4,5,6,7,8,9,10,11,12,13,14-tetradecahydro-dicyclohepta[a,c]cyclooctenyl, -2,3,4,5,6,7,8,9,10,11,12,13-dodecahydro-1H-dibenzo[a,d]cyclononenyl, and the like.

"-(3- to 7-membered)heterocycle", "-(3- to 7-membered)heterocyclyl", or "-(3- to 7-membered)heterocyclo" means a 3- to 7-membered monocyclic heterocyclic ring, i.e., a monocyclic ring comprising at least one heteroatom, which is either saturated, unsaturated non-aromatic or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle", "-(5- or 6-membered)heterocyclyl", or "-(5- or 6-membered)heterocyclo" means a 5- or 6-membered monocyclic heterocyclic ring, i.e., a monocyclic ring comprising at least one heteroatom, which is either saturated, unsaturated non-aromatic or aromatic. A 5-membered heterocycle can contain 1, 2, 3, or 4 heteroatoms and a 6-membered heterocycle can contain 1, 2, 3, or 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(7- to 10-membered)bicycloheterocycle", "-(7- to 10-membered)bicycloheterocyclyl", or "-(7-to 10-membered)bicycloheterocyclo" means a 7- to 10-membered bicyclic, heterocyclic ring, each ring of which is independently either saturated, unsaturated non-aromatic or aromatic, i.e., where at least one ring comprises at least one heteroatom. A -(7- to 10-membered)bicycloheterocycle contains 1, 2, 3, or 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -2,3-dihydrobenzofuranyl, -1,3-dihydroisobenzofuranyl, -benzo[d][1,3]dioxolyl, -2,3-dihydrobenzo[b]thiophenyl, -1,3-dihydrobenzo[c]thiophenyl, -benzo[d][1,3]dithiolyl, -chromonyl, -chromanyl, -2,3-dihydrobenzo[b][1,4]dioxinyl, -thiochromonyl, -thiochromanyl, -2,3-dihydrobenzo[b][1,4]dithiinyl, -coumarinyl, -indolyl, -indolizinyl, -benzo[b]furanyl, -benzo[b]thiophenyl, -indazolyl, -purinyl, -4H-quinolizinyl, -quinolyl, -phthalazinyl, -naphthyridinyl, -indolinyl, -isoindolinyl, -1,2,3,4-tetrahydroquinolinyl, -1,2,3,4-tetrahydroisoquinolinyl, and the like.

"—$(C_3-C_{12})$cycloalkoxy" means a saturated monocyclic hydrocarbon having 3, 4, 5, 6, 7, 8, 9, 10, 11, or 12 carbon atoms where at least one of the carbon atoms is replaced by an oxygen atom. Representative $(C_3-C_{12})$cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—$(C_3-C_7)$cycloalkoxy" means a saturated monocyclic hydrocarbon having 3, 4, 5, 6, or 7 carbon atoms where at least one of the carbon atoms is replaced by an oxygen atom. Representative $(C_3-C_7)$cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—$(C_{14})$aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, i.e., a monocyclic aromatic ring comprising at least one heteroatom independently selected from nitrogen, oxygen, and sulfur or a bicyclic aromatic ring where at least one ring comprises at least one heteroatom independently selected from nitrogen, oxygen, and sulfur. In one embodiment, a monocyclic -(5- to 10-membered)heteroaryl comprises at least two heteroatoms independently selected from nitrogen, oxygen, and sulfur. In another embodiment, a bicyclic -(5- to 10-membered)heteroaryl comprises at least two heteroatoms, present in the same or in different rings, each heteroatom being independently selected from nitrogen, oxygen, and sulfur. In another embodiment, one of the -(5- to 10-membered)heteroaryl's rings contain at least one carbon atom. In another embodiment, both of the bicyclic -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, tliadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members, i.e., a monocyclic aromatic ring comprising at least one heteroatom independently selected from nitrogen, oxygen, and sulfur. In one embodiment, the -(5- or 6-membered)heteroaryl ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—CH$_2$(halo)" means a methyl group where one of the hydrogens of the methyl group has been replaced with a halogen. Representative —CH$_2$(halo) groups include —CH$_2$F, —CH$_2$Cl, —CH$_2$Br, and —CH$_2$I.

"—CH(halo)$_2$" means a methyl group where two of the hydrogens of the methyl group have each been independently replaced with a halogen. Representative —CH(halo)$_2$ groups include —CHF$_2$, —CHCl$_2$, —CHBr$_2$, —CHBrCl, —CHCII, and —CHI$_2$.

"—C(halo)$_3$" means a methyl group where each of the hydrogens of the methyl group has been independently replaced with a halogen. Representative —C(halo)$_3$ groups include —CF$_3$, —CCl$_3$, —CBr$_3$, —CI$_3$, —CF$_2$Br, —CF$_2$Cl, —CCl$_2$F, and —CFClBr.

"-Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

"(C$_2$-C$_6$)bridge" as used herein means a hydrocarbon chain containing 2 to 6 carbon atoms joining two atoms of the piperidine ring of Formula (I) to form a fused bicyclic ring system. For example, compounds of the disclosure can comprise a (C$_2$-C$_6$)bridge joining positions 2 and 6 of the piperidine ring (A-B can together form a (C$_2$-C$_6$)bridge). Exemplary compounds of the disclosure include those with an unsubstituted (C$_2$)bridge, —CH$_2$—CH$_2$—, joining positions 2 and 6 of the piperidine ring (A-B can together form a (C$_2$)bridge); an unsubstituted (C$_3$)bridge, —CH$_2$—CH$_2$—CH$_2$—, joining positions 2 and 6 of the piperidine ring (A-B can together form a (C$_3$)bridge); an unsubstituted (C$_4$)bridge, —CH$_2$—CH$_2$—CH$_2$—CH$_2$—, joining positions 2 and 6 of the piperidine ring (A-B can together form a (C$_4$)bridge); an unsubstituted (C$_5$)bridge, —CH$_2$—CH$_2$—CH$_2$—CH$_2$—CH$_2$—, joining positions 2 and 6 of the piperidine ring (A-B can together form a (C$_5$)bridge); or an unsubstituted (C$_6$) bridge, —CH$_2$—CH$_2$—CH$_2$—CH$_2$—CH$_2$—CH$_2$—, joining positions 2 and 6 of the piperidine ring (A-B can together form a (C$_6$)bridge). Examples of compounds where A-B can together form a (C$_2$-C$_6$)bridge include compounds comprising the following ring systems: 8-aza-bicyclo[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane. Examples of a (C$_2$-C$_6$)bridge which contains —HC=CH— within the (C$_2$-C$_6$)bridge include —HC=CH—, —CH$_2$—HC=CH—, —HC=CH—CH$_2$—, —CH$_2$—HC=CH—CH$_2$—, and the like. Examples of a (C$_2$-C$_6$)bridge which contains —O— within the (C$_2$-C$_6$)bridge include —CH$_2$—O—CH$_2$— (containing 2 carbon atoms), —CH$_2$—O—CH$_2$—CH$_2$— and —CH$_2$—CH$_2$—O—CH$_2$— (each containing 3 carbon atoms), —CH$_2$—CH$_2$—O—CH$_2$—CH$_2$—, —CH$_2$—O—CH$_2$—CH$_2$—CH$_2$— and —CH$_2$—CH$_2$—CH$_2$—O—CH$_2$— (each containing 4 carbon atoms), and the like.

"Lactam group" as used herein in the phrase the "ring atoms of the Q$_x$ ring are constituents of at least one lactam group" means a cyclic structure Q$_x$ comprising at least one amide or a thioamide (e.g., comprising one amide, one thioamide, two amides, two thioamides, or one amide and one thioamide) as part of the Q$_x$ cyclic structure, e.g., a 1-azacycloalkan-2-one or a 1-azacycloalkan-2-thione. In particular, when the ring atoms of the Q$_x$ ring are constituents of one lactam group, that lactam group can be represented by any one of the following Q$_x$ cyclic structures:

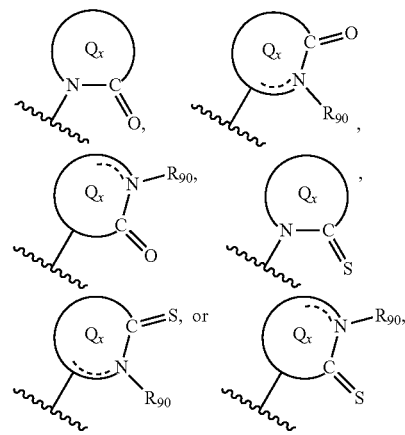

where R$_{90}$ is as defined above for the Cyclic Urea- or Lactam-Substituted Quinoxaline-Type Piperidine Compounds of Formula (I).

"Cyclic urea" as used herein in the phrase the "ring atoms of the Q$_x$ ring are constituents of at least one cyclic urea group" means a cyclic structure Q$_x$ comprising at least one urea or a thiourea as part of the Q$_x$ cyclic structure, e.g., a 1,3-diazacycloalkan-2-one or a 1,3-diazacycloalkan-2-thione. In particular, when the ring atoms of the Q$_x$ ring are constituents of one cyclic urea group, that cyclic urea group can be represented by any one of the following Q$_x$ cyclic structures:

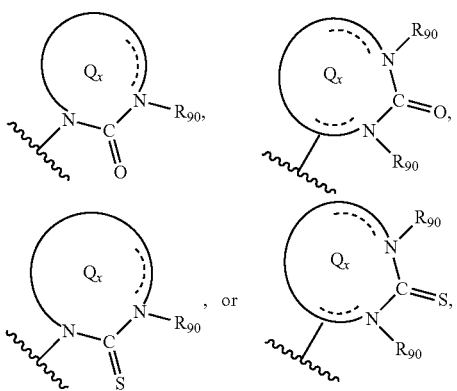

where $R_{90}$ is as defined above for the Cyclic Urea- or Lactam-Substituted Quinoxaline-Type Piperidine Compounds of Formula (I).

As used herein in the phrase the "ring atoms of the $Q_x$ ring are constituents of at least one lactam group or cyclic urea group", a lactam group and a cyclic urea group are mutually exclusive because a lactam group has only one nitrogen atom bonded to the carbon atom of the carbonyl or thiocarbonyl whereas a cyclic urea group has two nitrogen atoms bonded to the carbon atom of the carbonyl or thiocarbonyl.

As used herein in the phrase "the $Q_x$ ring does not contain 3 consecutive ring nitrogen atoms" means that the $Q_x$ ring does not comprise any of the following cyclic structures:

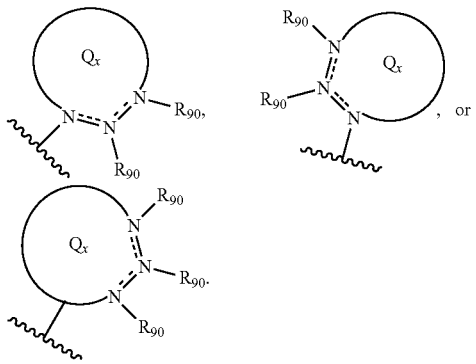

In compounds of the disclosure comprising a bridge joining positions 2 and 6 of the piperidine ring (e.g., A-B can together form a $(C_2\text{-}C_6)$bridge), for, e.g., a compound of Formula (I), the exemplary endo bridge:

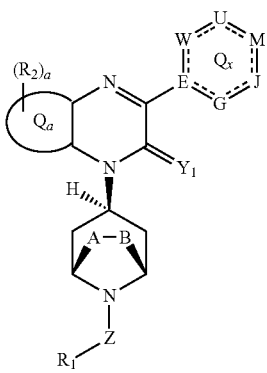

is equivalent to

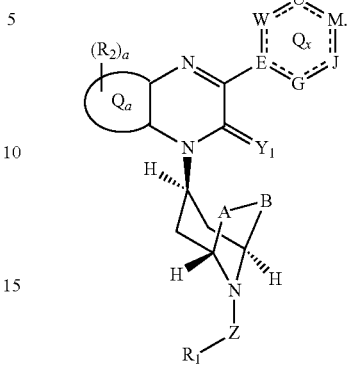

In compounds of the disclosure comprising a bridge joining positions 2 and 6 of the piperidine ring (e.g., A-B can together form a $(C_2\text{-}C_6)$bridge), for, e.g., a compound of Formula (I), the exemplary exo bridge:

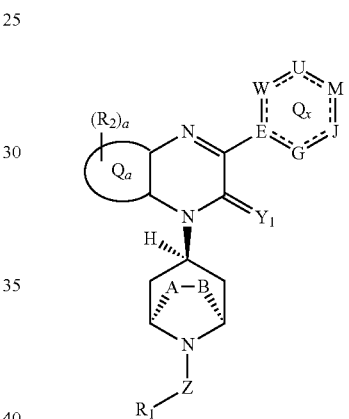

is equivalent to

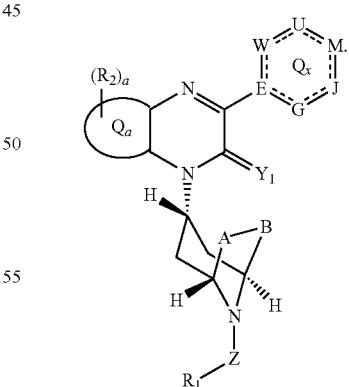

In compounds of the disclosure where the —Z—$R_1$ group comprises a bicyclic group, that bicyclic group can have two orientations. For example, for a —Z—$R_1$ group that is a —$(C_6\text{-}C_{14})$bicycloalkyl, e.g., bicyclo[3.3.1]nonanyl, attached directly to the piperidine ring nitrogen, the following orientations are possible:

Endo:

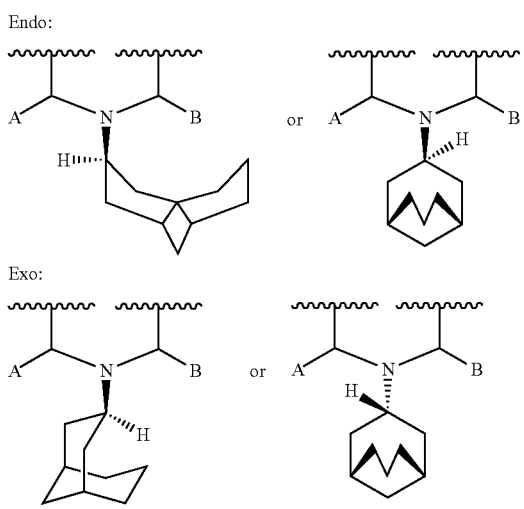

Exo:

As used herein in connection with "—[(C$_1$-C$_{10}$)alkyl optionally substituted by R$_{13}$]$_h$—", when h is 1 means that the Z—R$_1$ bonded to the piperidine ring bearing A and B substituents is understood to appear as follows:

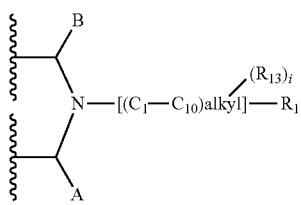

where, when i is 0, the —(C$_1$-C$_{10}$)alkyl- is unsubstituted by a R$_{13}$ group and, when i is 1, the —(C$_1$-C$_{10}$)alkyl- is substituted by a R$_1$ group at the carbon atom furthest removed from the piperidine ring bearing A and B substituents and substituted by a R$_{13}$ group at any carbon atom of the —(C$_1$-C$_{10}$)alkyl- including at the carbon atom furthest removed from the piperidine ring bearing A and B substituents. In one embodiment, R$_{13}$ is selected from:

(a) -halo, —OH, —CH$_2$OH, —CH$_2$CH$_2$OH, —N(R$_6$)$_2$, and —C(=O)OV$_1$; and (b) —(C$_1$-C$_{10}$)alkyl, —(C$_2$-C$_{10}$)alkenyl, —O(C$_1$-C$_6$)alkyl, —(C$_5$-C$_{14}$)cycloalkenyl, and -(5- or 6-membered)heterocycle, each of which is unsubstituted or substituted with 1, 2, 3, or 4 independently selected R$_8$ groups; and (c)

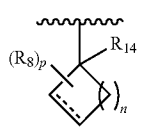

(iv) wherein R$_{14}$ is —H and n is an integer selected from 2, 3, 4, 5, 6, and 7;

(d) -phenyl and -(5- or 6-membered)heteroaryl, each of which is unsubstituted or substituted with 1 or 2 independently selected R$_7$ groups.

In another embodiment, R$_{13}$ is selected from:

(a) -halo, —OH, —CH$_2$OH, —CH$_2$CH$_2$OH, —N(R$_6$)$_2$, and —C(=O)OV$_1$; and (b) —(C$_1$-C$_6$)alkyl, —(C$_2$-C$_6$)alkenyl, —O(C$_1$-C$_4$)alkyl, and -(5- or 6-membered)heterocycle, each of which is unsubstituted or substituted with 1 or 2 independently selected R$_8$ groups; and (c)

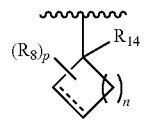

(i) wherein R$_{14}$ is —H and n is an integer selected from 2, 3, 4, 5, 6, and 7;

(d) -phenyl and -(5- or 6-membered)heteroaryl, each of which is unsubstituted or substituted with 1 or 2 independently selected R$_7$ groups.

"—[(C$_2$-C$_{10}$)alkenyl optionally substituted by R$_{13}$]—" as used herein in connection with Z—R$_1$ means that the Z—R$_1$ bonded to the piperidine ring bearing A and B substituents is understood to appear as follows:

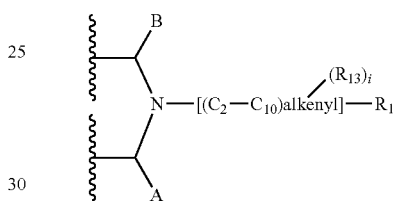

where, when i is 0, the —(C$_2$-C$_{10}$)alkenyl- is unsubstituted by a R$_{13}$ group and, when i is 1, the —(C$_2$-C$_{10}$)alkenyl- is substituted by a R$_1$ group at the carbon atom furthest removed from the piperidine ring bearing A and B substituents and substituted by a R$_{13}$ group at any carbon atom of the —(C$_2$-C$_{10}$)alkenyl-including at the carbon atom furthest removed from the piperidine ring bearing A and B substituents.

As used herein in connection with formula (i) of R$_1$, when the dashed line is present as a bond to provide one bond of a double bond, then formula (i) is understood to appear as follows (i)

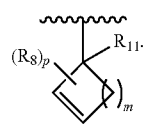

As used herein in connection with formula (i) of R$_1$, when the dashed line is absent, then formula (i) is understood to appear as follows (i)

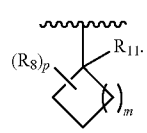

As used herein in connection with formula (iv) of R$_{13}$, when the dashed line is present as a bond to provide one bond of a double bond, then formula (iv) is understood to appear as follows

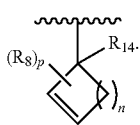
(iv)

As used herein in connection with formula (iv) of $R_{13}$, when the dashed line is absent, then formula (iv) is understood to appear as follows

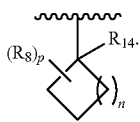
(iv)

As used herein in connection with the $Q_x$ ring, when W is absent the $Q_x$ ring is a 5-membered ring having the formula:

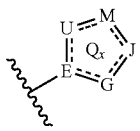

where E, G, J, M, U, and each dashed line are defined above for the Cyclic Urea- or Lactam-Substituted Quinoxaline-Type Piperidine Compounds of Formula (I).

The terms "benzo," "benzo group" and the like, when used in connection with the $Q_a$ ring, means

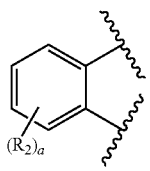

where $R_2$, and a are defined above for the Cyclic Urea- or Lactam-Substituted Quinoxaline-Type Piperidine Compounds of Formula (I).

The terms "pyridino," "pyridino group" and the like, when used in connection with the $Q_a$ ring, means

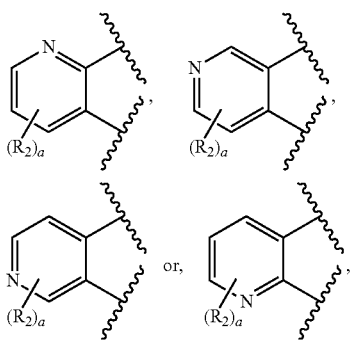

where $R_2$, and a are defined above for the Cyclic Urea- or Lactam-Substituted Quinoxaline-Type Piperidine Compounds of Formula (I). In one embodiment, the optionally-substituted pyridino $Q_a$ ring is

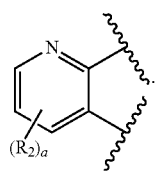

In another embodiment, the optionally-substituted pyridino $Q_a$ ring is

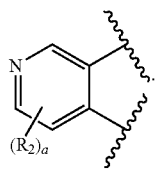

In another embodiment, the optionally-substituted pyridino $Q_a$ ring is

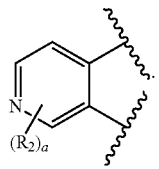

In another embodiment, the optionally-substituted pyridino $Q_a$ ring is

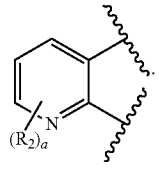

The terms "pyrimidino", "pyrimidino group" and the like, when used in connection with the optionally-substituted $Q_a$ ring, means

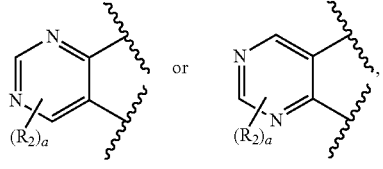

where $R_2$ and a are defined above for the Cyclic Urea- or Lactam-Substituted Quinoxaline-Type Piperidine Compounds of Formula (I). In one embodiment, the optionally-substituted pyrimidino $Q_a$ ring is

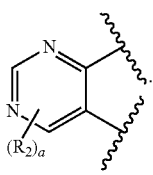

In another embodiment, the optionally-substituted pyrimidino $Q_a$ ring is

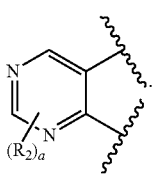

The terms "pyrazino", "pyrazino group" and the like, when used in connection with the optionally-substituted $Q_a$ ring, means

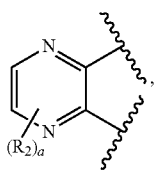

where $R_2$ and a are defined above for the Cyclic Urea- or Lactam-Substituted Quinoxaline-Type Piperidine Compounds of Formula (I).

The terms "pyridazino", "pyridazino group" and the like, when used in connection with the optionally-substituted $Q_a$ ring, means

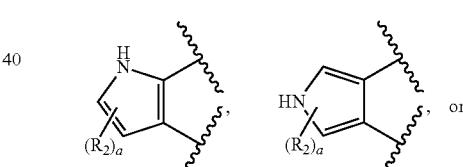

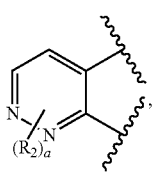

where $R_2$ and a are defined above for the Cyclic Urea- or Lactam-Substituted Quinoxaline-Type Piperidine Compounds of Formula (I). In one embodiment, the optionally-substituted pyridazino $Q_a$ ring is

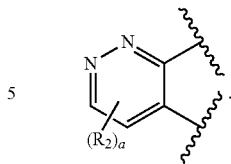

In another embodiment, the optionally-substituted pyridazino $Q_a$ ring is

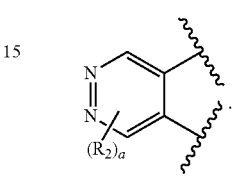

In another embodiment, the optionally-substituted pyridazino $Q_a$ ring is

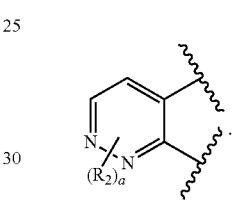

The terms "pyrrolino", "pyrrolino group" and the like, when used in connection with the optionally-substituted $Q_a$ ring, means

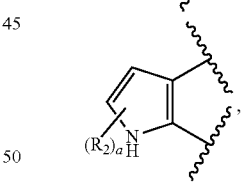

where $R_2$ and a are defined above for the Cyclic Urea- or Lactam-Substituted Quinoxaline-Type Piperidine Compounds of Formula (I). In one embodiment, the optionally-substituted pyrrolino $Q_a$ ring is

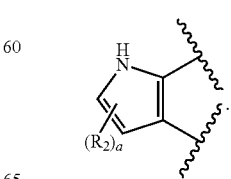

In another embodiment, the optionally-substituted pyrrolino $Q_a$ ring is

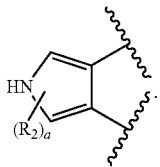

In another embodiment, the optionally-substituted pyrrolino $Q_a$ ring is

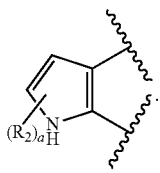

The terms "imidazolino", "imidazolino group" and the like, when used in connection with the optionally-substituted $Q_a$ ring, means

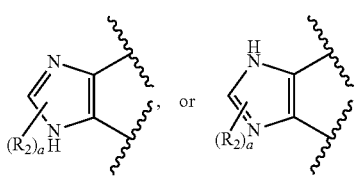

where $R_2$ and a are defined above for the Cyclic Urea- or Lactam-Substituted Quinoxaline-Type Piperidine Compounds of Formula (I). In one embodiment, the optionally-substituted imidazolino $Q_a$ ring is

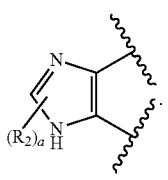

In another embodiment, the optionally-substituted imidazolino $Q_a$ ring is

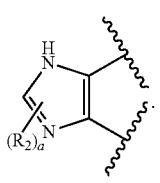

The terms "pyrazolino", "pyrazolino group" and the like, when used in connection with the optionally-substituted $Q_a$ ring, means

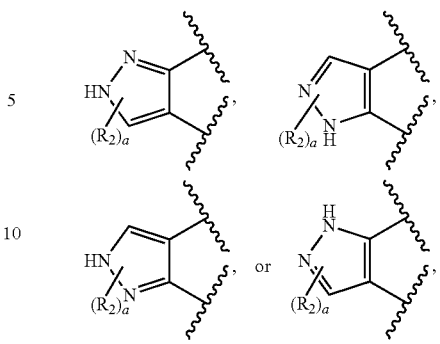

where $R_2$ and a are defined above for the Cyclic Urea- or Lactam-Substituted Quinoxaline-Type Piperidine Compounds of Formula (I). In one embodiment, the optionally-substituted pyrazolino $Q_a$ ring is

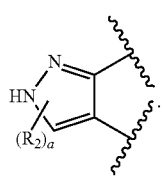

In another embodiment, the optionally-substituted pyrazolino $Q_a$ ring is

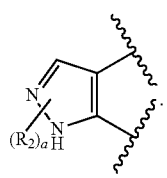

In another embodiment, the optionally-substituted pyrazolino $Q_a$ ring is

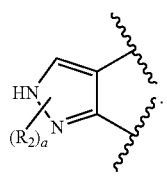

In another embodiment, the optionally-substituted pyrazolino $Q_a$ ring is

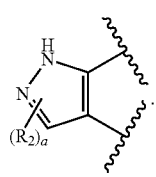

The terms "triazolino", "triazolino group" and the like, when used in connection with the optionally-substituted $Q_a$ ring, means

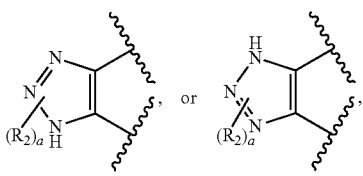

where R₂ and a are defined above for the Cyclic Urea- or Lactam-Substituted Quinoxaline-Type Piperidine Compounds of Formula (I). In one embodiment, the optionally-substituted triazolino $Q_a$ ring is

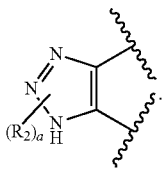

In another embodiment, the optionally-substituted triazolino $Q_a$ ring is

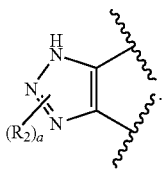

The terms "furano", "furano group" and the like, when used in connection with the optionally-substituted $Q_a$ ring, means

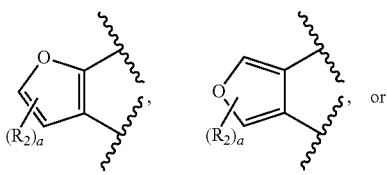

where R₂ and a are defined above for the Cyclic Urea- or Lactam-Substituted Quinoxaline-Type Piperidine Compounds of Formula (I). In one embodiment, the optionally-substituted furano $Q_a$ ring is

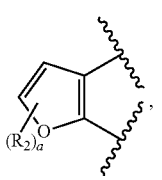

In another embodiment, the optionally-substituted furano $Q_a$ ring is

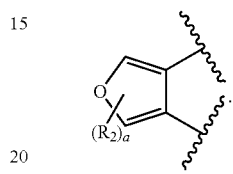

In another embodiment, the optionally-substituted furano $Q_a$ ring is

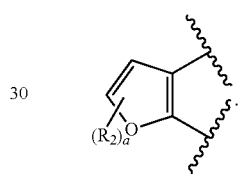

The terms "oxazolino", "oxazolino group" and the like, when used in connection with the optionally-substituted $Q_a$ ring, means

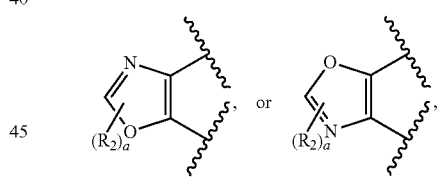

where R₂ and a are defined above for the Cyclic Urea- or Lactam-Substituted Quinoxaline-Type Piperidine Compounds of Formula (I). In one embodiment, the optionally-substituted oxazolino $Q_a$ ring is

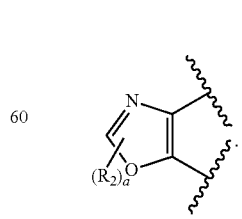

In another embodiment, the optionally-substituted oxazolino $Q_a$ ring is

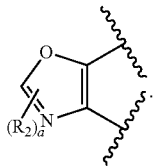

The terms "isoxazolino", "isoxazolino group" and the like, when used in connection with the optionally-substituted $Q_a$ ring, means

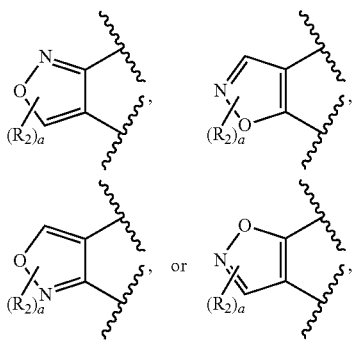

where $R_2$ and a are defined above for the Cyclic Urea- or Lactam-Substituted Quinoxaline-Type Piperidine Compounds of Formula (I). In one embodiment, the optionally-substituted isoxazolino $Q_a$ ring is

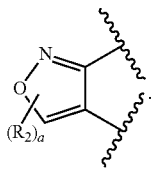

In another embodiment, the optionally-substituted isoxazolino $Q_a$ ring is

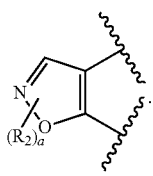

In another embodiment, the optionally-substituted isoxazolino $Q_a$ ring is

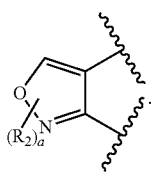

In another embodiment, the optionally-substituted isoxazolino $Q_a$ ring is

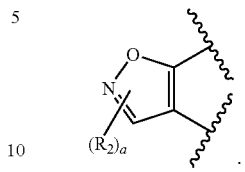

The terms "oxadiazolino", "oxadiazolino group" and the like, when used in connection with the optionally-substituted $Q_a$ ring, means

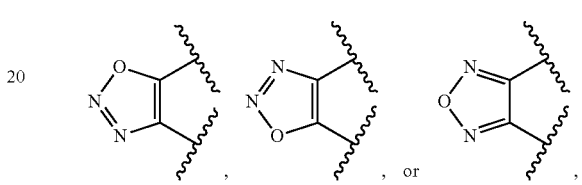

where $R_2$ and a are defined above for the Cyclic Urea- or Lactam-Substituted Quinoxaline-Type Piperidine Compounds of Formula (I). In one embodiment, the optionally-substituted oxadiazolino $Q_a$ ring is

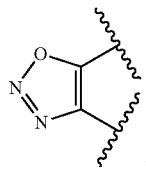

In another embodiment, the optionally-substituted oxadiazolino $Q_a$ ring is

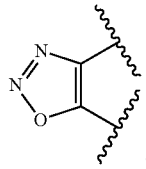

In another embodiment, the optionally-substituted oxadiazolino $Q_a$ ring is

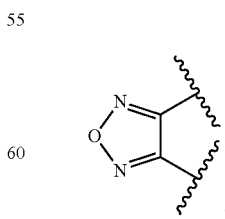

The terms "thiopheno", "thiopheno group" and the like, when used in connection with the optionally-substituted $Q_a$ ring, means

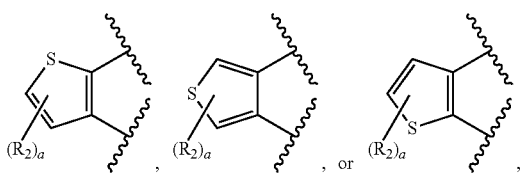

where R₂ and a are defined above for the Cyclic Urea- or Lactam-Substituted Quinoxaline-Type Piperidine Compounds of Formula (I). In one embodiment, the optionally-substituted thiopheno $Q_a$ ring is

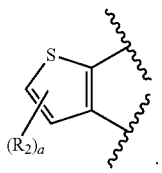

In another embodiment, the optionally-substituted thiopheno $Q_a$ ring is

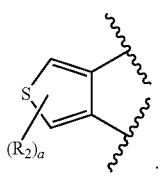

In another embodiment, the optionally-substituted thiopheno $Q_a$ ring is

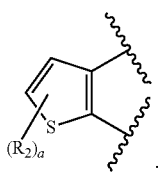

The terms "thiazolino", "thiazolino group" and the like, when used in connection with the optionally-substituted $Q_a$ ring, means

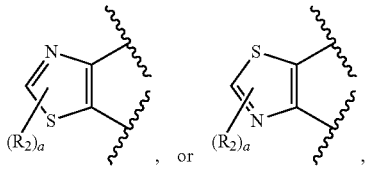

where R₂ and a are defined above for the Cyclic Urea- or Lactam-Substituted Quinoxaline-Type Piperidine Compounds of Formula (I). In one embodiment, the optionally-substituted thiazolino $Q_a$ ring is

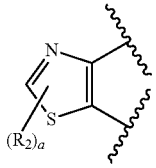

In another embodiment, the optionally-substituted thiazolino $Q_a$ ring is

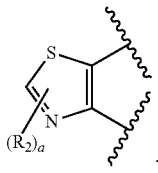

The terms "isothiazolino", "isothiazolino group" and the like, when used in connection with the optionally-substituted $Q_a$ ring, means

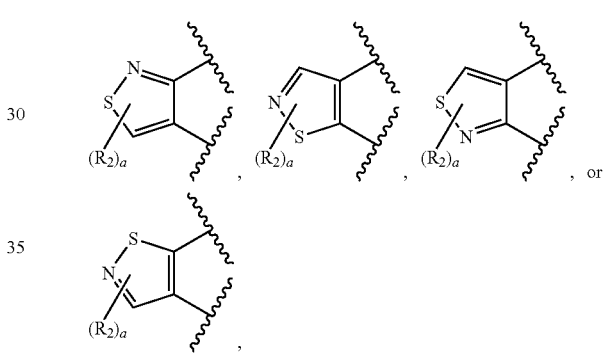

where R₂ and a are defined above for the Cyclic Urea- or Lactam-Substituted Quinoxaline-Type Piperidine Compounds of Formula (I). In one embodiment, the optionally-substituted isothiazolino $Q_a$ ring is

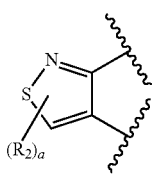

In another embodiment, the optionally-substituted isothiazolino $Q_a$ ring is

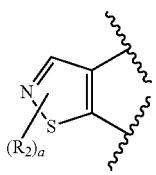

In another embodiment, the optionally-substituted isothiazolino $Q_a$ ring is

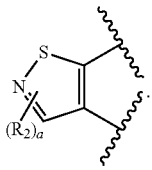

In another embodiment, the optionally-substituted isothiazolino $Q_a$ ring is

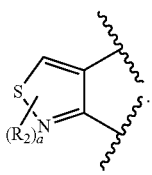

The terms "thiadiazolino", "thiadiazolino group" and the like, when used in connection with the optionally-substituted $Q_a$ ring, means

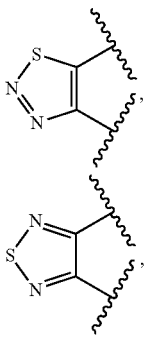

where $R_2$ and a are defined above for the Cyclic Urea- or Lactam-Substituted Quinoxaline-Type Piperidine Compounds of Formula (I). In one embodiment, the optionally-substituted thiadiazolino $Q_a$ ring is

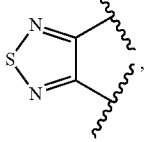

In another embodiment, the optionally-substituted thiadiazolino $Q_a$ ring is

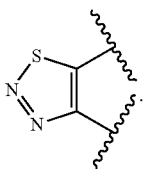

In another embodiment, the optionally-substituted thiadiazolino $Q_a$ ring is

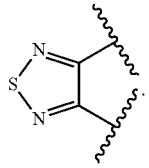 [SMILES: *c1nsnc1*]

The term "3,3-diphenylpropyl-" and the like, when used in connection with the —Z—$R_1$ group, means

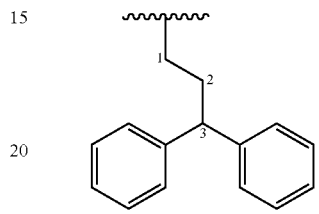

where the 3 carbon of the propyl is indicated by the number 3 in the structure above.

In one embodiment, the term "optionally substituted bicyclo[3.3.1]nonyl" and the like when used in connection with the optionally-substituted $R_1$ group is understood to refer to one of the structures below:

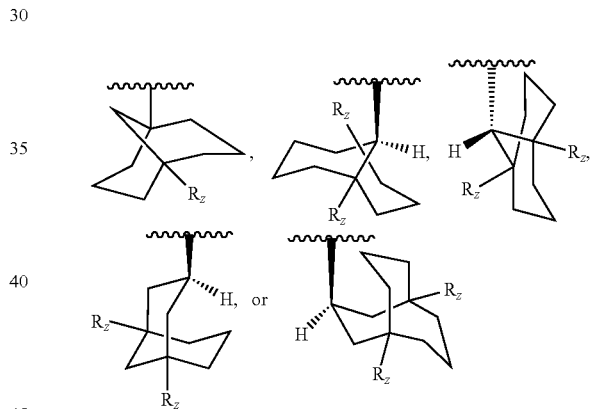

where the substituents are as defined above for the Cyclic Urea- or Lactam-Substituted Quinoxaline-Type Piperidine Compounds of Formula (I); and where in one or more embodiments, the optionally substituted $R_1$ group comprises one or more of the above-recited optionally substituted bicycle[3.3.1]nonyl structures.

In one embodiment, the term "optionally substituted —($C_6$-$C_{14}$)bicycloalkyl" means

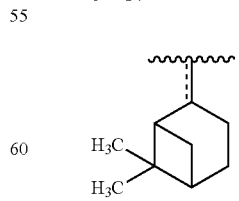

where the dashed line denotes the presence or absence of a bond. When the dashed line is present as a bond to provide one bond of a double bond, then the group above is understood to appear as follows

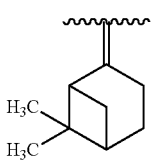

and when the dashed line is absent, then the optionally substituted —($C_6$-$C_{14}$)bicycloalkyl group above is understood to appear as follows

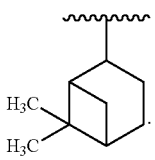

The term "tetrazolyl group" means

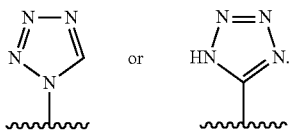 [SMILES: *n1cnnn1 ; *c1nnn[nH]1]

In one embodiment, the tetrazolyl group is

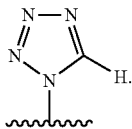

In another embodiment, the tetrazolyl group is

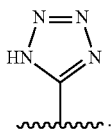

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with two second groups. In another embodiment, a first group is substituted with two second groups and each second group is identical. In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

The term "pharmaceutically acceptable derivative", as used herein, includes any pharmaceutically acceptable salt, polymorph, pseudopolymorph, solvate, prodrug, radiolabeled form, stereoisomer, enantiomer, diastereomer, other stereoisomeric form, racemic mixture, geometric isomer, and/or tautomer, e.g., of a Cyclic Urea- or Lactam-Substituted Quinoxaline-Type Piperidine Compound of the disclosure.

In one embodiment, the pharmaceutically acceptable derivative is a pharmaceutically acceptable salt, polymorph, pseudopolymorph, solvate, prodrug, radiolabeled form, stereoisomer, enantiomer, diastereomer, other stereoisomeric form, racemic mixture, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, polymorph, pseudopolymorph, solvate, radiolabeled form, stereoisomer, enantiomer, diastereomer, other stereoisomeric form, racemic mixture, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, polymorph, pseudopolymorph, solvate, stereoisomer, enantiomer, diastereomer, other stereoisomeric form, racemic mixture, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, polymorph, radiolabeled form, stereoisomer, enantiomer, diastereomer, other stereoisomeric form, racemic mixture, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, radiolabeled form, stereoisomer, enantiomer, diastereomer, other stereoisomeric form, racemic mixture, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, polymorph, pseudopolymorph, solvate, radiolabeled form, stereoisomer, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, polymorph, pseudopolymorph, solvate, stereoisomer, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, polymorph, radiolabeled form, stereoisomer, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, radiolabeled form, stereoisomer, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, polymorph, stereoisomer, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, stereoisomer, geometric isomer, and/or tautomer, e.g., of a Cyclic Urea- or Lactam-Substituted Quinoxaline-Type Piperidine Compound of the disclosure. In another embodiment, the pharmaceutically acceptable derivative is a pharmaceutically acceptable salt, stereoisomer, and/or tautomer, e.g., of a Cyclic Urea- or Lactam-Substituted Quinoxaline-Type Piperidine Compound of the disclosure.

In another embodiment, the pharmaceutically acceptable derivative is a pharmaceutically acceptable salt, e.g., of a Cyclic Urea- or Lactam-Substituted Quinoxaline-Type Piperidine Compound of the disclosure. In another embodiment, the pharmaceutically acceptable derivative is a polymorph, e.g., of a Cyclic Urea- or Lactam-Substituted Quinoxaline-Type Piperidine Compound of the disclosure. In another embodiment, the pharmaceutically acceptable derivative is a pseudopolymorph, e.g., of a Cyclic Urea- or Lactam-Substituted Quinoxaline-Type Piperidine Compound of the disclosure. In another embodiment, the pharmaceutically acceptable derivative is a solvate, e.g., of a Cyclic Urea- or Lactam-Substituted Quinoxaline-Type Piperidine Compound of the disclosure. In another embodiment, the pharmaceutically acceptable derivative is a prodrug, e.g., of a Cyclic Urea- or Lactam-Substituted Quinoxaline-Type Piperidine Compound of the disclosure. In another embodiment, the pharmaceutically acceptable derivative is a radiolabeled form, e.g., of a Cyclic Urea- or Lactam-Substituted Quinoxaline-Type Piperidine Compound of the disclosure. In another embodiment, the pharmaceutically acceptable derivative is a stereoisomer, e.g., of a Cyclic Urea- or Lactam-Substituted Quinoxaline-Type Piperidine Compound of the disclosure. In another embodiment, the pharmaceutically acceptable derivative is an enantiomer, e.g., of a Cyclic Urea- or Lactam-Substituted Quinoxaline-Type Piperidine Compound of the disclosure. In another embodiment, the pharmaceutically acceptable derivative is a diastereomer, e.g., of a Cyclic Urea- or Lactam-Substituted Quinoxaline-Type Piperidine Compound of the disclosure. In another embodiment, the pharmaceutically acceptable derivative is a stereoisomeric form other than a stereoisomer, an enantiomer and a diastereomer, e.g., of a Cyclic Urea- or Lactam-Substituted Quinoxaline-Type Piperidine Compound of the disclosure. In another embodiment, the pharmaceutically acceptable derivative is a racemic mixture, e.g., of a Cyclic Urea- or Lactam-Substituted Quinoxaline-Type Piperidine Compound of the disclosure. In another embodiment, the pharmaceutically acceptable derivative is a geometric isomer, e.g., of a Cyclic Urea- or Lactam-Substituted Quinoxaline-Type Piperidine Compound of the disclosure. In another embodiment, the pharmaceutically acceptable derivative is a tautomer, e.g., of a Cyclic Urea- or Lactam-Substituted Quinoxaline-Type Piperidine Compound of the disclosure.

The term "pharmaceutically acceptable salt", as used herein, is any pharmaceutically acceptable salt that can be prepared from a Cyclic Urea- or Lactam-Substituted Quinoxaline-Type Piperidine Compound including a salt formed from an acid and a basic functional group, such as a nitrogen group, of a Cyclic Urea- or Lactam-Substituted Quinoxaline-Type Piperidine Compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. For example, for a Cyclic Urea- or Lactam-Substituted Quinoxaline-Type Piperidine Compound where J is $N(R_{90})$, a chloride salt can be formed by reacting the compound with HCl to provide the hydrochloride of the Cyclic Urea- or Lactam-Substituted Quinoxaline-Type Piperidine Compound, e.g., J is $N(H)(R_{90})$. The term "pharmaceutically acceptable salt" also includes a salt prepared from a Cyclic Urea- or Lactam-Substituted Quinoxaline-Type Piperidine Compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-Nydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of a Cyclic Urea- or Lactam-Substituted Quinoxaline-Type Piperidine Compound and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of a Cyclic Urea- or Lactam-Substituted Quinoxaline-Type Piperidine Compound and 0.5 equivalents of fumaric acid. One skilled in the art will recognize that, e.g., acid addition salts, of a Cyclic Urea- or Lactam-Substituted Quinoxaline-Type Piperidine Compound can be prepared by reaction of the compounds with the appropriate acid by a variety of known methods.

The compounds of the disclosure provided herein also encompass all polymorphs and pseudopolymorphs of the Cyclic Urea- or Lactam-Substituted Quinoxaline-Type Piperidine Compounds. "Polymorphs" are known in the art (see, e.g., Giron, "Investigations of Polymorphism and Pseudopolymorphism in Pharmaceuticals by Combined Thermoanalytical Techniques," *J. Thermal Anal. Cal.* 64:37-60 (2001)) and are considered to be different crystalline phases in which a Cyclic Urea- or Lactam-Substituted Quinoxaline-Type Piperidine Compound is capable of existing. The crystalline phases can have different arrangements ("packing polymorphism") and/or conformations ("conformational polymorphism") of the molecules in the crystal lattice. The term "anhydrate" as used herein, is any crystalline form of a Cyclic Urea- or Lactam-Substituted Quinoxaline-Type Piperidine Compound in which water molecules are a non-integral part of the crystal. An anhydrate of a Cyclic Urea- or Lactam-Substituted Quinoxaline-Type Piperidine Compound can be prepared, for example, by crystallization from a solvent substantially free of water. In one embodiment, the Cyclic Urea- or Lactam-Substituted Quinoxaline-Type Piperidine Compound is present as an anhydrate, i.e., as a free base where the crystal lattice is substantially free of water molecules and any water molecules present are present as "surface water" (e.g., loosely bound to the crystal's surface) as would be discernable and distinguishable to those in the art by, e.g., thermogravimetric analysis (TGA) and/or differential scanning calorimetry (DSC), from water molecules that are an integral part of the crystal (e.g., a hydrate). An anhydrate of a Cyclic Urea- or Lactam-Substituted Quinoxaline-Type Piperidine Compound has less than about 0.2 mole water in one embodiment, less than about 0.15 mole water in another embodiment, less than about 0.12 mole water in another embodiment, less than about 0.1 mole water in another embodiment, less than about 0.085 mole water in another embodiment, less than about 0.075 mole water in another embodiment, less than about 0.06 mole water in another embodiment, less than about 0.057 mole water in another embodiment, less than about 0.05 mole water in another embodiment, less than about 0.03 mole water in another embodiment, less than about 0.025 mole water in another embodiment, less than about 0.02 mole water in another embodiment, less than about 0.01 mole water in another embodiment, less than about 0.005 mole water in another embodiment, and less than about 0.001 mole water in another embodiment, each said embodiment taking into account the presence of surface water and each said embodiment being per 1 mole of a Cyclic Urea- or Lactam-Substituted Quinoxaline-Type Piperidine Compound.

The compounds of the disclosure provided herein also encompass all solvates of the Cyclic Urea- or Lactam-Substituted Quinoxaline-Type Piperidine Compounds. "Solvates" are known in the art and are considered to be a combination, physical association and/or solvation of a Cyclic Urea- or Lactam-Substituted Quinoxaline-Type Piperidine Compound with a solvent molecule. This physical association can involve varying degrees of ionic and covalent bonding, including hydrogen bonding. When the solvate is of the stoichiometric type, there is a fixed ratio of the solvent molecule to Cyclic Urea- or Lactam-Substituted Quinoxaline-Type Piperidine Compound, e.g., a disolvate, monosolvate or hemisolvate when the solvent molecule:Cyclic Urea- or Lactam-Substituted Quinoxaline-Type Piperidine Compound molecule molar ratio is 2:1, 1:1 or 1:2, respectively. In other embodiments, the solvate is of the nonstoichiometric type. For example, the Cyclic Urea- or Lactam-Substituted Quinoxaline-Type Piperidine Compound crystal can contain solvent molecules in the structural voids, e.g., channels, of the crystal lattice. In certain instances, the solvate can be isolated, for example when one or more solvent molecules are incorporated into the crystal lattice of a crystalline solid. Thus, "solvate", as used herein, encompasses both solution-phase and isolatable solvates. As the crystalline form of a solvate can also be referred to as a "pseudopolymorph", the compounds of the disclosure provided herein also encompass all pseudopolymorphs of the Cyclic Urea- or Lactam-Substituted Quinoxaline-Type Piperidine Compounds. A Cyclic Urea- or Lactam-Substituted Quinoxaline-Type Piperidine Compound of the disclosure can be present as a solvated form with a pharmaceutically acceptable solvent, such as water, methanol, ethanol, and the like, and it is intended that the disclosure include both solvated and unsolvated Cyclic Urea- or Lactam-Substituted Quinoxaline-Type Piperidine Compound forms. As "hydrate" relates to a particular subgroup of solvates, i.e., where the solvent molecule is water, hydrates are included within the solvates of the disclosure. In one embodiment, the Cyclic Urea- or Lactam-Substituted Quinoxaline-Type Piperidine Compound is present as a monohydrate, i.e., as a free base where the water:Cyclic Urea- or Lactam-Substituted Quinoxaline-Type Piperidine Compound molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.*, 93(3):601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. ScL Tech.*, 5(1): Article 12 (2004), and Bingham et al., "Over one hundred solvates of sulfathiazole," *Chem. Comm.*, pp. 603-604 (2001). In one embodiment, a non-limiting, process involves dissolving the Cyclic Urea- or Lactam-Substituted Quinoxaline-Type Piperidine Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The compounds disclosed herein also comprise all prodrugs of the Cyclic Urea- or Lactam-Substituted Quinoxaline-Type Piperidine Compounds. "Prodrugs" are known in the art and, while not necessarily possessing any pharmaceutical activity as such, are considered to be any covalently bonded carrier(s) that releases the active parent drug in vivo. In general, such prodrugs will be a functional derivative of a Cyclic Urea- or Lactam-Substituted Quinoxaline-Type Piperidine Compound of Formula (I) which is readily convertible in vivo, e.g., by being metabolized, into the required Cyclic Urea- or Lactam-Substituted Quinoxaline-Type Piperidine Compound of Formula (I). Conventional procedures for the selection and preparation of suitable prodrug derivatives are described in, for example, Bundgaard, ed., *Design of Prodrugs*, Elsevier, Amsterdam (1985); Colowick et al., "Drug and Enzyme Targeting, Part A," Widder et al., eds., *Methods in Enzymology*, Vol. 112, Academic Press (1985); Bundgaard, "Design and Application of Prodrugs," *A Textbook of Drug Design and Development*, Krogsgaard-Larsen and Bundgaard, eds., Harwood Academic Publishers, Chapter 5, pp. 113-191 (1991); Bundgaard et al., "(C) Means to Enhance Penetration (1) Prodrugs as a means to improve the delivery of peptide drugs," *Adv. Drug Delivery Revs.* 8:1-38 (1992); Bundgaard et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988); and Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2- methoxyiminoacetamido]3-methyl-3-cephem-4-carboxylic Acid," *Chem. Pharm. Bull.* 32:692-698 (1984).

In addition, one or more hydrogen, carbon or other atoms of a Cyclic Urea- or Lactam-Substituted Quinoxaline-Type Piperidine Compound can be replaced by a radioactive isotope of the hydrogen, carbon or other atoms. Such a "radiolabeled", "radiolabeled form", and the like of a Cyclic Urea- or Lactam-Substituted Quinoxaline-Type Piperidine Compound, each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Cyclic Urea- or Lactam-Substituted Quinoxaline-Type Piperidine Compound of the disclosure include isotopes of hydrogen, carbon, nitrogen, oxygen, phosphorous, sulfur, fluorine, chlorine, bromine, and iodine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$O, $^{37}$Cl, $^{76}$Br, $^{77}$Br, $^{81}$Br, $^{123}$I, $^{124}$I, $^{125}$I, and $^{131}$I, respectively. In one embodiment, a radiolabeled Cyclic Urea- or Lactam-Substituted Quinoxaline-Type Piperidine Compound contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Cyclic Urea- or Lactam-Substituted Quinoxaline-Type Piperidine Compound contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Cyclic Urea- or Lactam-Substituted Quinoxaline-Type Piperidine Compound contains 1 radioactive isotope which is selected from hydrogen, carbon, nitrogen, oxygen, phosphorous, sulfur, fluorine, chlorine, bromine, and iodine. In another embodiment, a radiolabeled Cyclic Urea- or Lactam-Substituted Quinoxaline-Type Piperidine Compound contains 1, 2, 3, 4, or more radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{76}$Br, $^{77}$Br, $^{81}$Br, $^{123}$I, $^{124}$I, $^{125}$I, and $^{131}$I. In another embodiment, a radiolabeled Cyclic Urea- or Lactam-Substituted Quinoxaline-Type Piperidine Compound contains 1 or 2 radioactive isotopes, each of which is independently selected from $^2$H, 3H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Cyclic Urea- or Lactam-Substituted Quinoxaline-Type Piperidine Compound contains 1 radioactive isotope which is selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Cyclic Urea- or Lactam-Substituted Quinoxaline-Type Piperidine Compound contains 1, 2, 3, 4, or more radioactive isotopes, each of which is independently selected from $^2$H, $^3$H, $^{13}$C, $^{14}$C, $^{15}$N, $^{18}$O, $^{32}$P, and $^{125}$I. In another embodiment, a radiolabeled Cyclic Urea- or Lactam-Substituted Quinoxaline-Type Piperidine Compound contains 1 or 2 radioactive isotopes, each of which is independently selected from 3H, $^{14}$C, $^{15}$N, $^{18}$O, $^{32}$P, and $^{125}$I. In another embodiment, a radiolabeled Cyclic Urea- or Lactam-Substituted Quinoxaline-Type Piperidine Compound contains 1 radioactive isotope which is selected from $^3$H, $^{14}$C, $^{15}$N, $^{18}$O, $^{32}$P, and $^{125}$I.

Radiolabeled compounds of the disclosure can be prepared by methods known in the art. For example, tritiated Cyclic Urea- or Lactam-Substituted Quinoxaline-Type Piperidine Compounds can be prepared by introducing tritium into the particular Cyclic Urea- or Lactam-Substituted Quinoxaline-Type Piperidine Compound, for example, by catalytic dehalogenation with tritium. This method can include reacting a suitably halogen-substituted precursor of a Cyclic Urea- or Lactam-Substituted Quinoxaline-Type Piperidine Compound with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," *Isotopes in the Physical and Biomedical Sciences, Vol. 1, Labeled Compounds (Part A)*, E. Buncel et al, eds., Chapter 6, pp. 155-192 (1987). $^{14}$C-labeled compounds can be prepared by employing starting materials having a $^{14}$C carbon. Compounds containing piperazine isotopcially enriched with $^{13}$C and/or $^{15}$N can be prepared as described in, e.g., FIG. 5A and the associated description, of U.S. Pat. No. 7,355,045 B2. Radiolabeled compounds containing $^{18}$F at the 6-position of an aniline ring can be prepared as described in column 27 of U.S. Pat. No. 6,562,319 B2.

An Cyclic Urea- or Lactam-Substituted Quinoxaline-Type Piperidine Compound can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. The art recognizes that a geometric isomer is encompassed by a stereoisomer (See, e.g., the definitions of "stereoisomers" and "cis-trans isomers" appearing in the IUPAC Compendium of Chemical Terminology, $2^{nd}$ Ed. (the "Gold Book"), McNaught et al., eds., Blackwell Scientific Publications, Oxford (1997)). When a Cyclic Urea- or Lactam-Substituted Quinoxaline-Type Piperidine Compound contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., lactam-lactim, urea-isourea, ketone-enol, amide-imidic acid, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Cyclic Urea- or Lactam-Substituted Quinoxaline-Type Piperidine Compound can be obtained by known techniques such as chiral chromatography or formation of diastereomeric salts from an optically active acid or base.

Optical purity can be stated in terms of enantiomeric excess (% ee) and/or diastereomeric excess (% de), each which is determined by the appropriate formula below:

$$\% \ ee = \left[ \frac{\text{major enantiomer(mol)} - \text{minor enantiomer(mol)}}{\text{major enantiomer(mol)} + \text{minor enantiomer(mol)}} \right] \times 100\%$$

$$\% \ de = \left[ \frac{\text{major diastereomer(mol)} - \text{minor diastereomer(mol)}}{\text{major diastereomer(mol)} + \text{minor diastereomer(mol)}} \right] \times 100\%.$$

The term "MeOH" means methanol, i.e., methyl alcohol. The term "EtOH" means ethanol, i.e., ethyl alcohol. The term "Et$_2$O" means diethyl ether, i.e., ethoxyethane. The term "THF" means tetrahydrofuran. The term "DMF" means N,N-dimethylformamide. The term "DCM" means methylene chloride, i.e., dichloromethane or CH$_2$Cl$_2$. The term "DCE" means 1,2-dichloroethane. The term "EtOAc" means ethyl acetate. The term "MeCN" means acetonitrile. The term "DMSO" means dimethylsulfoxide, i.e., methylsulfinylmethane. The term "NMP" means N-methylpyrrolidinone, i.e., 1-methylpyrrolidin-2-one. The term "DMA" means N,N-dimethylacetamide. The term "MTBE" means tert-butyl methyl ether, i.e., 2-methoxy-2-methylpropane. The term "AcOH" means acetic acid. The term "TFA" means 2,2,2-trifluoroacetic acid. The term "TEA" means triethylamine. The term "DIEA" means diisopropylethylamine, i.e., N-ethyl-N-isopropylpropan-2-amine. The term "Bn" means benzyl, i.e.:

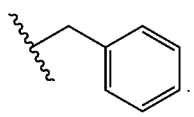

The term "BOC" means tert-butyloxycarbonyl, i.e.:

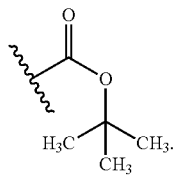

The term "IBD" means inflammatory-bowel disease. The term "IBS" means irritable-bowel syndrome. The term "ALS" means amyotrophic lateral sclerosis.

The term "effective amount", when used in connection with a Cyclic Urea- or Lactam-Substituted Quinoxaline-Type Piperidine Compound, means an amount effective for: (a) treating or preventing a Condition or symptom thereof; (b) detectably inhibiting ORL-1 receptor function in a cell; or (c) detectably activating ORL-1 receptor function in a cell.

The term "effective amount", when used in connection with a second therapeutic agent means an amount for providing the therapeutic effect of the second therapeutic agent.

The terms "modulate", "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross et al., "Pharmacodynamics: Mechanisms of Drug Action and the Relationship Between Drug Concentration and Effect," in *Goodman & Gilman's The Pharmacological Basis of Therapeutics* pp. 31-43 (Goodman et al., eds., 10$^{th}$ Ed., McGraw-Hill, New York 2001)).

The terms "treatment of", "treating", and the like include the amelioration or cessation of a Condition or a symptom thereof. In one embodiment, treating includes inhibiting, for example, decreasing the overall frequency of episodes of a Condition or a symptom thereof.

The terms "prevention of", "preventing", and the like include the avoidance of the onset of a Condition or a symptom thereof.

A "disorder" includes, but is not limited to, the Conditions defined above.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.3 Methods for Making Cyclic Urea- or Lactam-Substituted Quinoxaline-Type Piperidine Compounds Cyclic Urea- or Lactam-Substituted Quinoxaline-Type Piperidine Compounds can be made using conventional organic synthesis, in view of the present disclosure, and including the following illustrative methods shown in the schemes below where R$_1$, R$_2$, R$_{90}$, Q$_a$, Y$_1$, Z, A, B, Q$_x$, E, G, J, M, U, W, and a are defined above, L is a halogen leaving group such as Br or I, L' is F or Cl, R is —(C$_1$-C$_4$)alkyl or —CF$_3$, and R' is —(C$_1$-C$_4$)alkyl. For simplicity, in the following schemes the exemplary Q$_a$ group is benzo which is sometimes unsubstituted with R$_2$; however, the schemes are also applicable to substituted benzo and any of the (5- or 6-membered) heteroaryl Q$_a$ groups, whether unsubstituted or optionally substituted.

Section 4.3.1 describes methods for making Cyclic Urea-Substituted Quinoxaline-Type Piperidine Compounds of Formula (I) where Y$_1$ is oxygen, i.e., referred to as Cyclic Urea-Substituted Quinoxaline-Type Piperidine Compounds of Formula (Ia) in the schemes below. Section 4.3.2 describes methods for making Lactam-Substituted Quinoxaline-Type Piperidine Compounds of Formula (I) where Y$_1$ is oxygen, i.e., referred to as Lactam-Substituted Quinoxaline-Type Piperidine Compounds of Formula (Ib), Formula (Ic) and Formula (Id) in the schemes below. Section 4.3.3 describe methods for making N-Substituted Lactam-Substituted Quinoxaline-Type Piperidine Compounds of Formula (I) where Y$_1$ is oxygen, i.e., referred to as N-Substituted Lactam-Substituted Quinoxaline-Type Piperidine Compounds of Formula (Ie). Section 4.3.4 describes methods for making saturated N-Substituted Lactam-Substituted Quinoxaline-Type Piperidine Compounds of Formula (I) where $Y_1$ is oxygen, i.e., referred to as saturated N-Substituted Lactam-Substituted Quinoxaline-Type Piperidine Compounds of Formula (If). Section 4.3.5 describes methods for making Cyclic Urea-Substituted Quinoxaline-Type Piperidine Compounds of Formula (I) where $Y_1$ is sulfur, i.e., referred to as Cyclic Urea- or Lactam-Substituted Quinoxaline-Type Piperidine Compounds of Formula (Ig) in the schemes below. Sections 4.3.6 through 4.3.8 describe methods for making various stereochemical forms of Cyclic Urea- or Lactam-Substituted Quinoxaline-Type Piperidine Compounds of Formula (I).

4.3.1 Methods for Making Cyclic Urea-Substituted Quinoxaline-Type Piperidine Compounds of Formula (Ia)

Preparation of Cyclic Urea-Substituted Quinoxaline-Type Piperidine Compounds of Formula (Ia) can be carried out through the reaction of a quinoxaline-2,3(1H,4H)-dione (e.g., Compound A5) with a chlorinating agent followed by reaction with a urea-containing ring. Six alternative methods for preparing Compound A5 are shown in Schemes A-F below. Methods for chlorinating Compound A5 to provide Compound G1 are shown in Schemes G and H below. Methods for making Cyclic Urea-Substituted Quinoxaline-Type Piperidine Compounds of Formula (Ia) from Compound G1 are shown in Schemes I-L below.

4.3.1.1 Methods for Making Compound A5

Six alternative methods for making Compound A5 are shown below.

4.3.1.1.1 Synthesis of Compound A5

Method 1 (Scheme A)

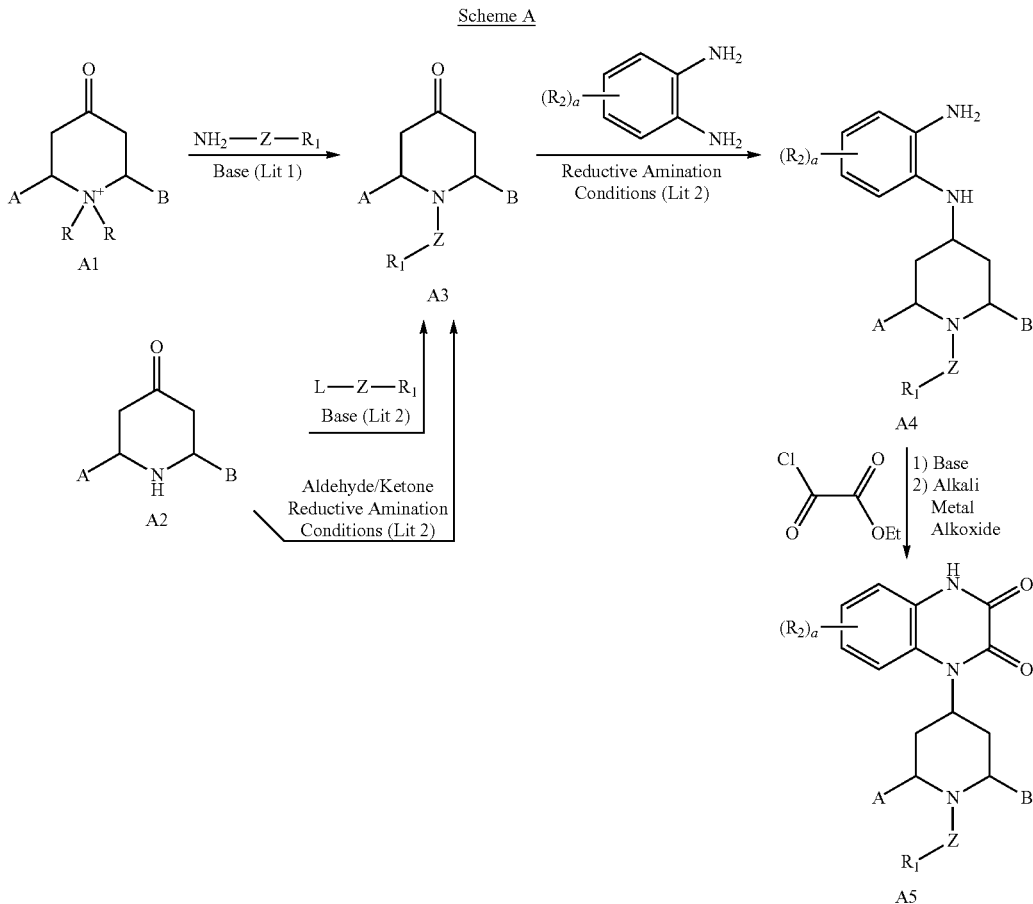

Scheme A

In Scheme A and the other schemes, "Lit 1" refers to the procedures described in the publications Tortolani et al., "A Convenient Synthesis to N-Aryl-Substituted 4-Piperidones," *Org. Lett.* 1:1261-1262 (1999) and/or International PCT Publication No. WO 2005/075459 A1 of Euro-Celtique S. A., "Lit 2" refers to the procedures described in U.S. Pat. No. 6,635,653 by Goehring et al., and "Lit 3" refers to the procedures described in the publication Dudash et al., "Synthesis and evaluation of 3-anilino-quinoxalinones as glycogen phosphorylase inhibitors," *Bioorg. Med. Chem. Lett.*, 15(21):4790-4793 (2005).

Compounds A1 and A2 are commercially available or can be prepared by methods known to the art.

A piperidinium salt of structure A1 can be reacted with a primary amine in a suitable solvent, such as EtOH, under reflux conditions in the presence of a base, such as potassium carbonate, as described in reference "Lit 1" to provide the 1-(substituted)piperidine-4-one Compound A3. As described in reference "Lit 2," Compound A3 can also be prepared by alkylation of a piperidine-4-one of structure A2 with an alkyl bromide or alkyl iodide in a suitable solvent, such as dimethyl formamide, MeCN or DMSO, in the presence of an inorganic base, such as potassium carbonate, or an organic base, such as DIEA. As described in reference "Lit 2," Compound A3 can also be prepared by reductive amination of Compound A2 with an aldehyde or ketone using either sodium triacetoxyborohydride or sodium cyanoborohydride in a suitable solvent, such as DCM or MeOH, respectively. Compound A3 can then be reductively aminated with a substituted or unsubstituted 1,2-phenylenediamine using sodium triacetoxyborohydride or sodium cyanoborohydride in a suitable solvent, such as DCM or MeOH, respectively, to provide Compound A4, as described in reference "Lit 2." Compound A4 can be dissolved in a suitable solvent, such as toluene, and reacted with ethyl 2-chloro-2-oxoacetate in the presence of a base, such as TEA, followed by treatment with an alkali metal alkoxide, such as sodium ethoxide, in a suitable solvent, such as MeOH or EtOH, to provide Compound A5.

4.3.1.1.2 Synthesis of Compound A5

Method 2 (Scheme B)

In Scheme B and the other schemes, "Lit 1b" refers to the procedures described in International PCT Publication No. WO 2005/075459 A1 of Euro-Celtique S. A.

As described in reference "Lit 1b," Compound A3 can be reacted with 50% aqueous hydroxylamine in a suitable solvent, such as hexanes, to provide an intermediate hydroxylamine which can be converted to an oxime by dehydration in a suitable solvent, such as toluene, under reflux conditions using a Dean-Stark apparatus. The oxime intermediate can be reduced to the primary amine Compound B1 by catalytic hydrogenation using a catalyst, such as rhodium on alumina, in a suitable solvent, such as EtOH, under a hydrogen atmosphere at a pressure of 1 atm or greater in a suitable apparatus, such as a Parr Hydrogenator, according to reference "Lit 1b." Compound B1 can be reacted with ethyl 2-chloro-2-oxoacetate in the presence of a base, such as TEA, to provide Compound B2. Compound B2 can be reacted with a substituted or unsubstituted 2-halo-1-nitrobenzene (where the halo is fluoride or chloride) in the presence of a base, such as potassium carbonate, in a suitable solvent, such as MeCN, under reflux conditions to provide Compound B3. Compound B3 can be treated with a hydrogenation catalyst, such as Raney nickel, in a suitable solvent, such as EtOH, under a hydrogen atmosphere, and the product immediately treated with an alkali metal alkoxide, such as sodium ethoxide, in a suitable solvent, such as MeOH or EtOH, to provide Compound A5.

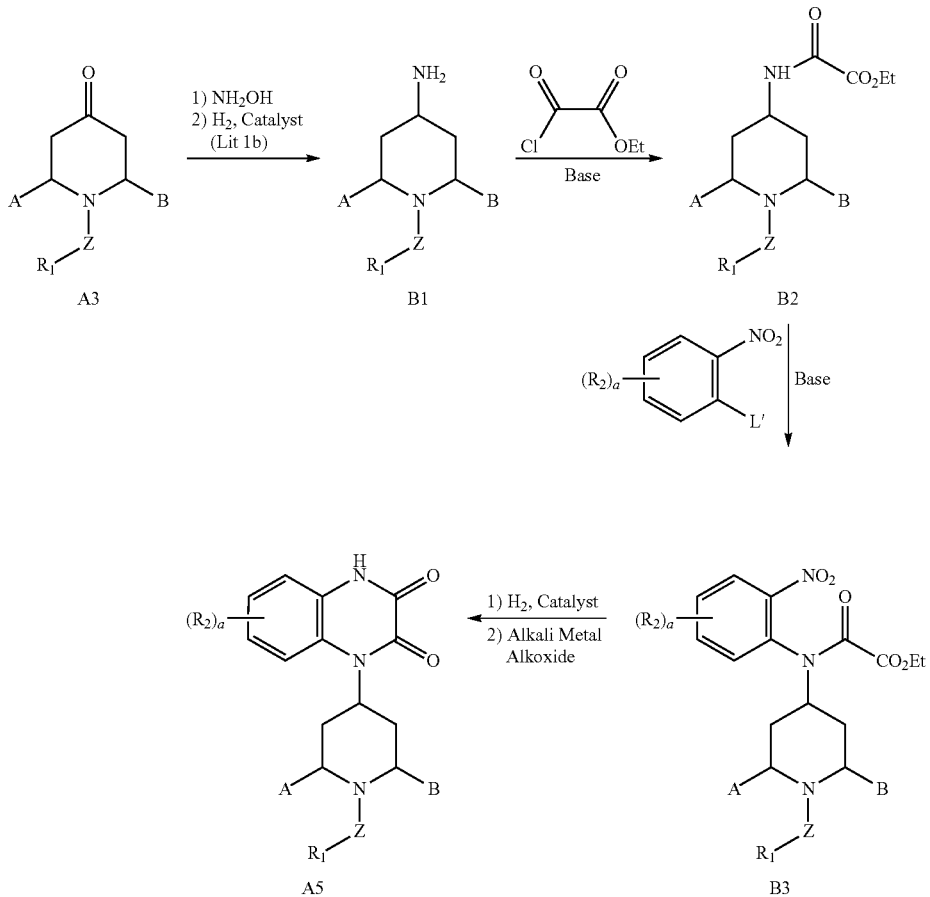

4.3.1.1.3 Synthesis of Compound A5

Method 3 (Scheme C)

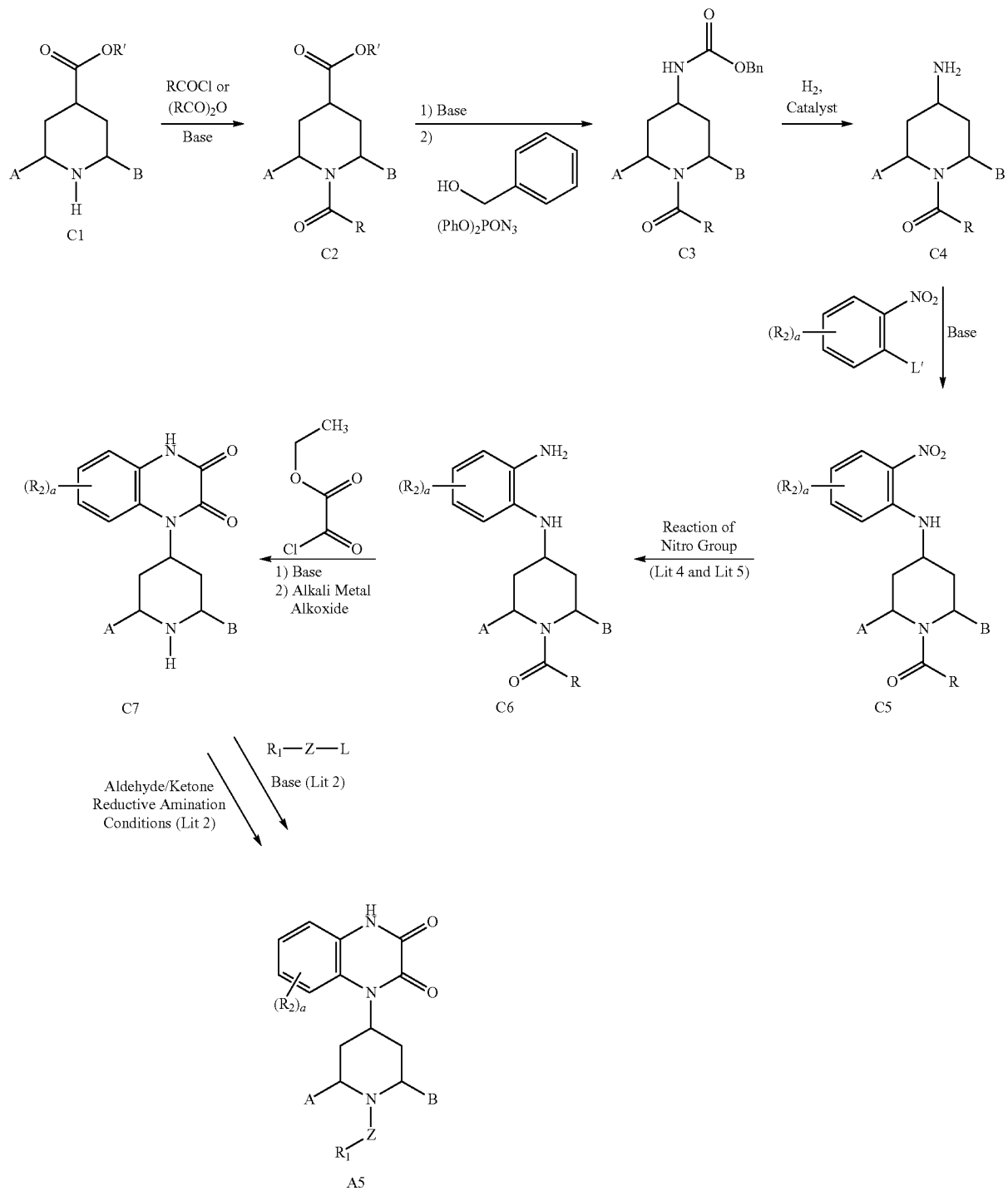

Scheme C

In Scheme C and the other schemes, "Lit 4" refers to the reference Rylander, "Hydrogenation of Nitro Compounds," in *Hydrogenation Methods* pp. 104-116 (Academic Press, London, 1985), which provides a review of the methods available for the reduction of nitro groups, and "Lit 5" refers to the Zinin reduction procedures described in the reference Porter, "The Zinin Reduction of Nitroarenes," *Org. Reactions,* 20:455-481 (1973).

Compound C1 is commercially available or can be prepared by methods known to the art. Compound C1 can be reacted with an acid chloride RC(=O)Cl, such as 2,2,2-trifluoroacetyl chloride, or anhydride (RC(=O))$_2$O, such as 2,2,2-trifluoroacetic anhydride, and a base, such as TEA, in a suitable solvent, such as DCM or THF, to provide Compound C2. Compound C2 can be converted to Compound C3 in a two step procedure by hydrolysis of the ester to the carboxylic acid using an appropriate base, such as aqueous NaOH, followed by treatment with diphenyl phosphorazidate ("(PhO)$_2$P(=O)N$_3$") and phenylmethanol ("BnOH") under Curtius rearrangement conditions. The benzyloxycarbonyl group of Compound C3 can then be removed under hydrogenolysis conditions using a noble metal catalyst, e.g., palladium on carbon, under a hydrogen atmosphere, to provide Compound C4. Compound C4 can be reacted with a substituted or unsubstituted 2-halo-1-nitrobenzene (where the halo is fluoride or chloride) (similar to steps described in Scheme B) to provide Compound C5. In the next step, Compound C5 can be converted to Compound C6 using a catalyst, such as Raney nickel, in a suitable solvent, such as EtOH, under a hydrogen atmosphere as described in reference "Lit 4." Compound C5 can also be converted to Compound C6 by chemical means, such as with Zn, Sn(II) chloride or Fe, or using sulfides or polysulfides by the Zinin Reduction as described in reference "Lit 5." Compound C6 can then be treated with ethyl 2-chloro-2-oxoacetate and a base, such as TEA, in a suitable solvent, such as toluene, followed by treatment with an alkali metal alkoxide, such as sodium ethoxide, in a suitable solvent, such as EtOH, to provide Compound C7. Compound A5 can be prepared by alkylation of Compound C7 with an alkyl bromide or alkyl iodide or by reductive amination of Compound C7 with an aldehyde or ketone, each as described in Scheme A.

4.3.1.1.4 Synthesis of Compound A5

Method 4 (Scheme D)

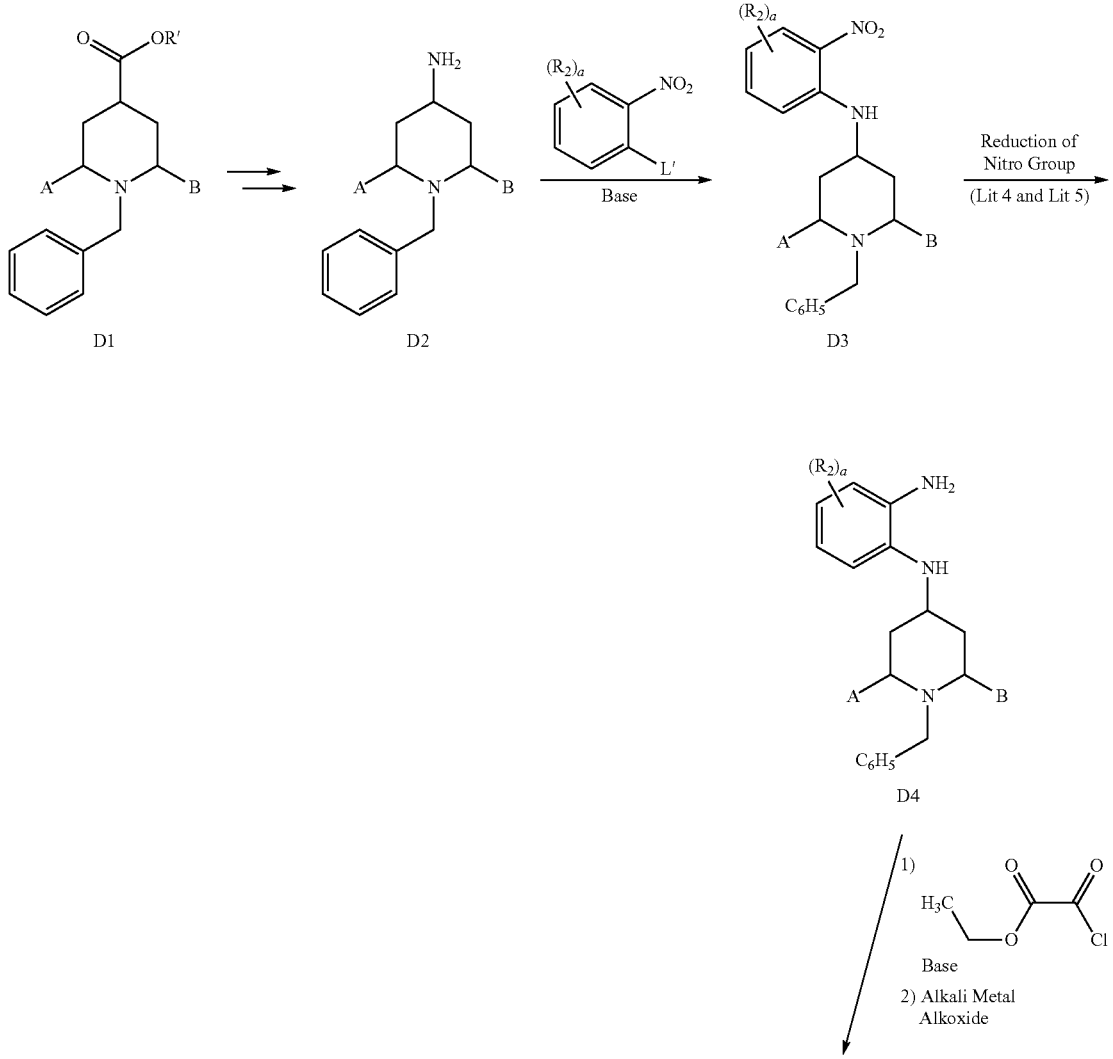

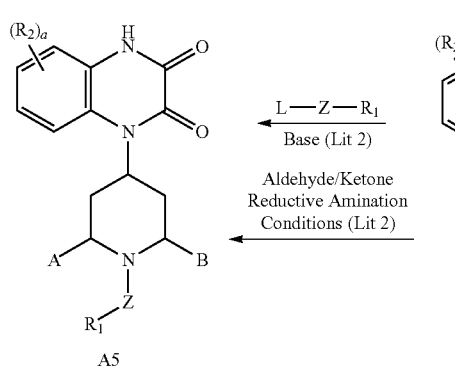
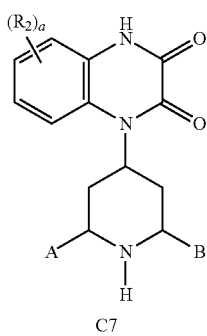
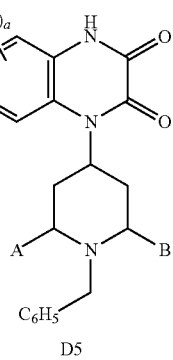

Compound D1 is commercially available or can be prepared from Compound C1 by methods known to the art. Compound D2 can be prepared from Compound D1 in a similar manner to the preparation of Compound C4 from Compound C1 in Scheme C. Compound D2 can be reacted with a substituted or unsubstituted 2-halo-1-nitrobenzene (where the halo is fluoride or chloride) (similar to steps described in Scheme B) to provide Compound D3. In the next step (similar to steps described in Scheme B), Compound D3 can be converted to Compound D4 by treatment with a hydrogenation catalyst, such as Raney nickel, in a suitable solvent, such as EtOH, under a hydrogen atmosphere, or by chemical means using a reducing agent, such as Zn, Sn(II) chloride or Fe, or using sulfide or polysulfides by the Zinin Reduction as described in Scheme C. Thereafter (similar to steps described in Scheme A), Compound D4 can be treated with ethyl 2-chloro-2-oxoacetate in the presence of a base, such as TEA, followed by treatment with an alkali metal alkoxide, such as sodium ethoxide, in a suitable solvent, such as EtOH, to provide Compound D5. Compound D5 can be hydrogenolyzed using a noble metal catalyst, e.g., palladium on carbon, in a suitable solvent, such as MeOH or EtOH, under a hydrogen atmosphere to provide Compound C7. Compound A5 can be prepared by alkylation of Compound C7 with an alkyl bromide or alkyl iodide or by reductive amination of Compound C7 with an aldehyde or ketone (similar to steps described in Scheme C).

4.3.1.1.5 Synthesis of Compound A5

Method 5 (Scheme E)

Scheme E

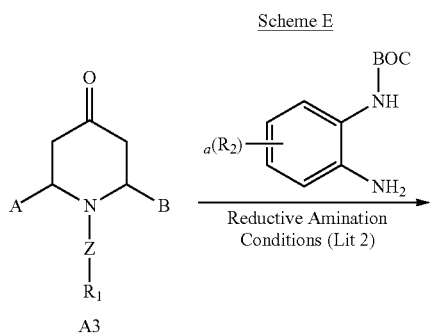

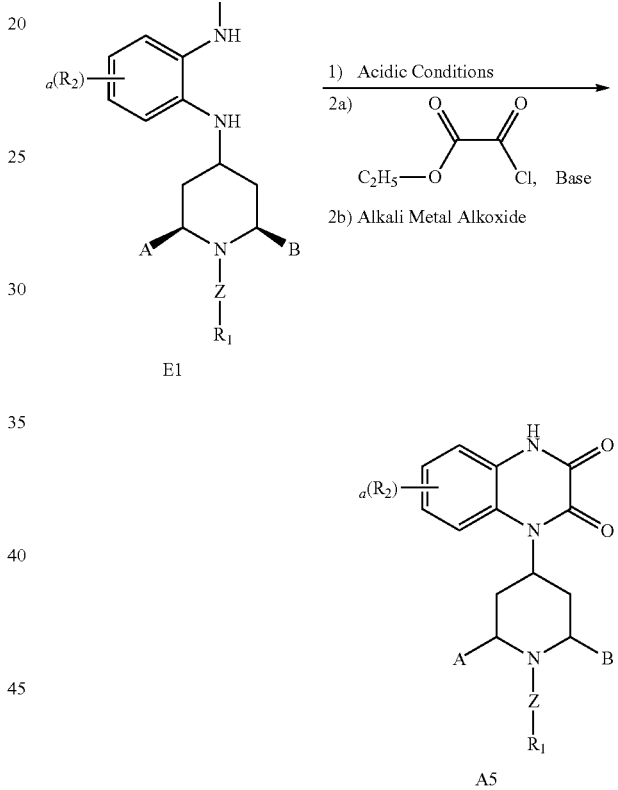

As shown in Scheme E, Compound A3 can be converted to Compound E1 under reductive amination conditions using a BOC protected, substituted or unsubstituted 1,2-phenylenediamine and a reducing agent, such as sodium triacetoxyborohydride or sodium cyanoborohydride, in a suitable solvent, such as DCM or MeOH, respectively as described in reference "Lit 2." The BOC protecting group can be removed using acidic conditions, such as using HCl or TFA, to provide an intermediate which can be converted to Compound A5 in a two step procedure using ethyl 2-chloro-2-oxoacetate and a base, such as TEA, followed by reaction with an alkali metal alkoxide, such as sodium ethoxide, in a suitable solvent, such as EtOH. Where substituent groups A and B together form a bridge, e.g., a two carbon bridge, the "exo" and "endo" isomers which result can be conveniently separated using flash column chromatography.

4.3.1.1.6 Synthesis of Compound A5

Method 6 (Scheme F)

Scheme F

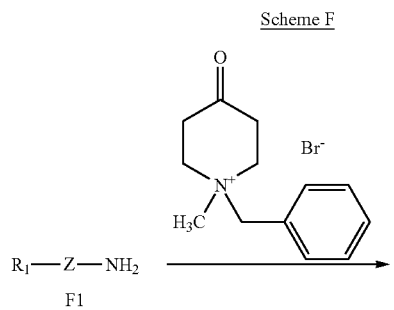

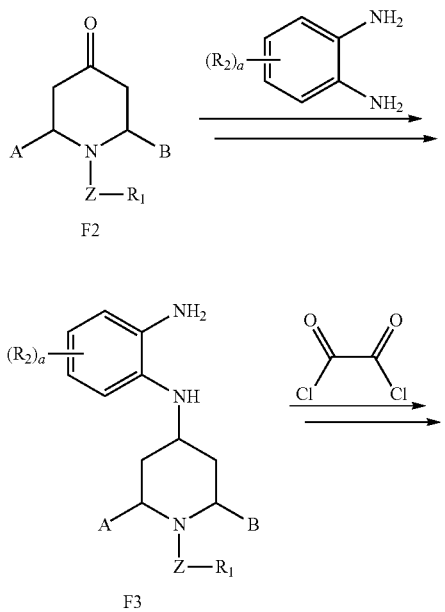

In Scheme F, Compound A5 can be prepared as described in U.S. Patent Application Publication US 2010/0022519 A1 for example, at paragraph [1364] and thereafter. Briefly, the primary amine F1, where —Z—R₁ can be cyclooctyl, adamantyl or noradamantyl, for example, can be treated with a piperidone salt in a polar solvent, such as EtOH or MeOH containing water, and an inorganic base, such as potassium carbonate, under reflux for from about 4 hours to about 6 hours to provide Compound F2. Compound F2 can then be treated with a substituted or unsubstituted 1,2-phenylenediamine and AcOH in a solvent, such as THF or 1,2-dimethoxyethane, to provide an imine, which can be reduced with sodium triacetoxyborohydride to provide Compound F3. Compound F3 can be treated with oxalyl dichloride in a non-aqueous solvent, such as DCM, and a base, such as TEA, to provide an amide which can be cyclized to a Compound A5 using potassium carbonate in a polar solvent, such as EtOH.

4.3.1.2 Methods for Making Compound G1 from Compound A5

Two alternative methods for making Compound G1 from Compound A5 are shown below.

4.3.1.2.1 Synthesis of Compound G1

Method 1 (Scheme G)

Scheme G

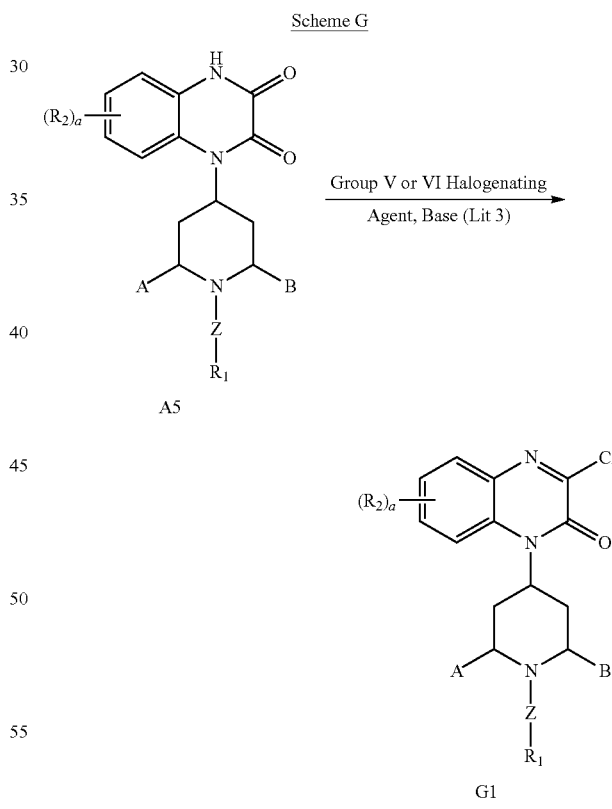

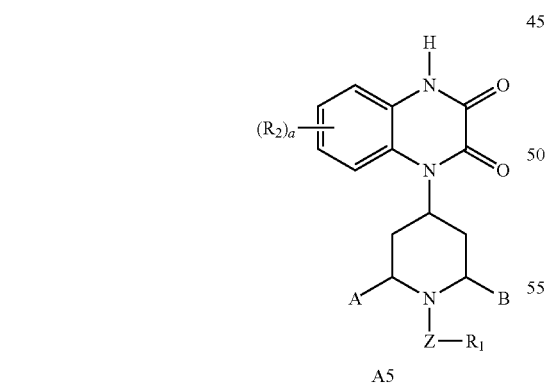

In Scheme G, Compound G1 can be obtained by chlorinating Compound A5, e.g., by adding a chlorinating agent, such as thionyl chloride, phosphorus oxychloride or phosphorus pentachloride, to a mixture of Compound A5, DMF, and a base, such as TEA, in a solvent with a high boiling point, such as toluene or xylene, under reflux conditions such as is described in reference "Lit 3."

4.3.1.2.2 Synthesis of Compound G1

Method 2 (Scheme H)

Scheme H

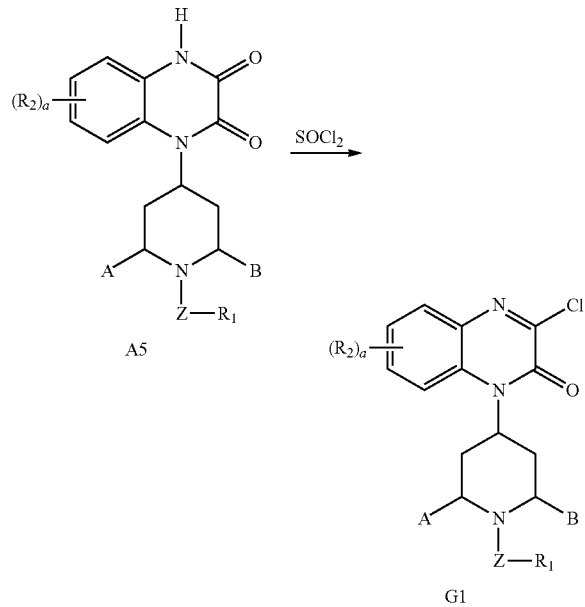

In Scheme H, Compound A2 can be converted to the 2-chloroquinoxaline Compound G1 using thionyl chloride in a solvent, such as DCM, using the procedures described in, e.g., Pizey, "Thionyl Chloride," Ch. 4 in *Synthetic Reagents*, John Wiley & Sons, New York, Vol. 1, pp. 321-357 (1974).

4.3.1.3 Methods or Making Cyclic Urea-Substituted Quinoxaline-Type Piperidine Compounds of Formula (Ia) from Quinoxaline-2,3(1H,4H)-diones Four alternative methods for making Cyclic Urea-Substituted Quinoxaline-Type Piperidine Compounds of Formula (Ia) from quinoxaline-2,3(1H,4H)-diones are shown below.

4.3.1.3.1 Synthesis of Cyclic Urea-Substituted Quinoxaline-Type Piperidine Compounds of Formula (Ia)

Method 1 (Scheme I)

Scheme I

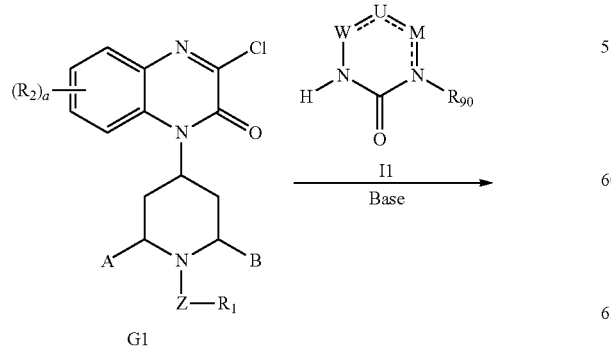

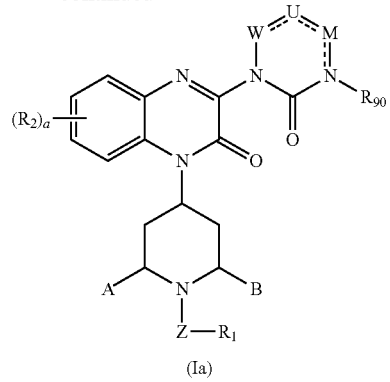

In Scheme I, Compound G1 is reacted with urea-containing ring Compound I1 in the presence of a base such as 1,8-diazabicyclo[5.4.0]undec-7-ene (DBU) or sodium hydride (NaH) to provide Cyclic Urea-Substituted Quinoxaline-Type Piperidine Compounds of Formula (Ia). In one embodiment, the reaction is carried out in an organic solvent, such as NMP, at an elevated temperature (e.g., from about 100° C. to about 120° C.).

4.3.1.3.2 Synthesis of Cyclic Urea-Substituted Quinoxaline-Type Piperidine Compounds of Formula (Ia)

Method 2 (Scheme J)

Scheme J

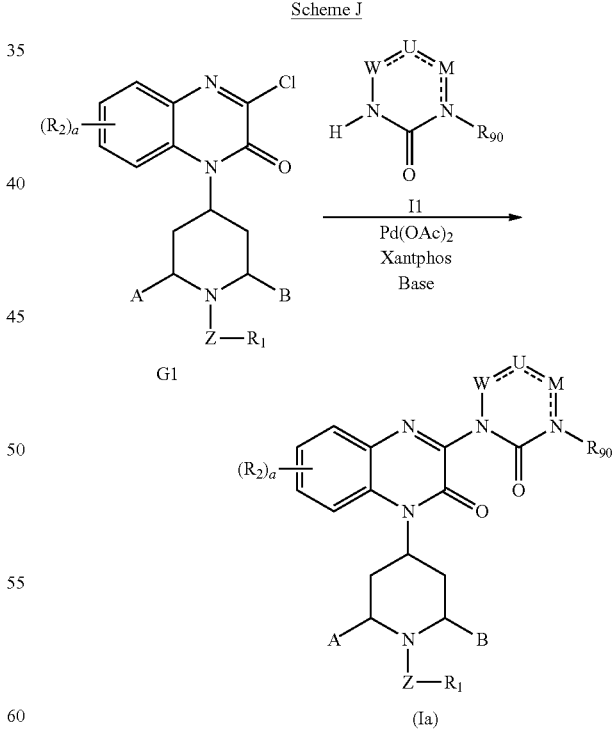

In Scheme J, palladium catalyzed cross-coupling of Compound G1 with Compound I1 using 4,5-bis(diphenylphosphino)-9,9,-dimethylxanthene (Xantphos) as a ligand, in the presence of a base (e.g., $Cs_2CO_3$) provides Cyclic Urea-Substituted Quinoxaline-Type Piperidine Compounds of Formula (Ia). In one embodiment, the reaction is carried out in an organic solvent, such as 1,4-dioxane, at an elevated temperature (e.g., from about 110° C. to about 120° C.).

4.3.1.3.3 Synthesis of Cyclic Urea-Substituted Quinoxaline-Type Piperidine Compounds of Formula (Ia)

Method 3 (Scheme K)

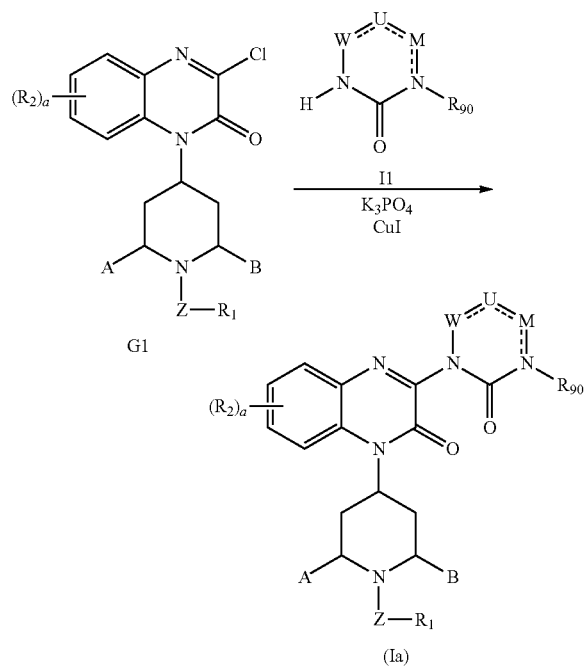

In Scheme K, Compound G1 is reacted with urea-containing ring Compound I1 in the presence of potassium phosphate ($K_3PO_4$) and copper(I) iodide (CuI) to provide Cyclic Urea-Substituted Quinoxaline-Type Piperidine Compounds of Formula (Ia). In one embodiment, the reaction is carried out in an organic solvent, such as DMSO, at an elevated temperature (e.g., from about 90° C. to about 100° C.).

4.3.1.3.4 Synthesis of Cyclic Urea-Substituted Quinoxaline-Type Piperidine Compounds of Formula (Ia)

Method 4 (Scheme L)

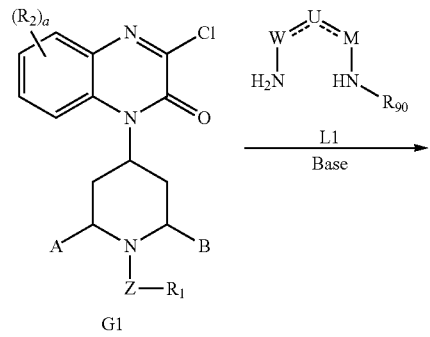

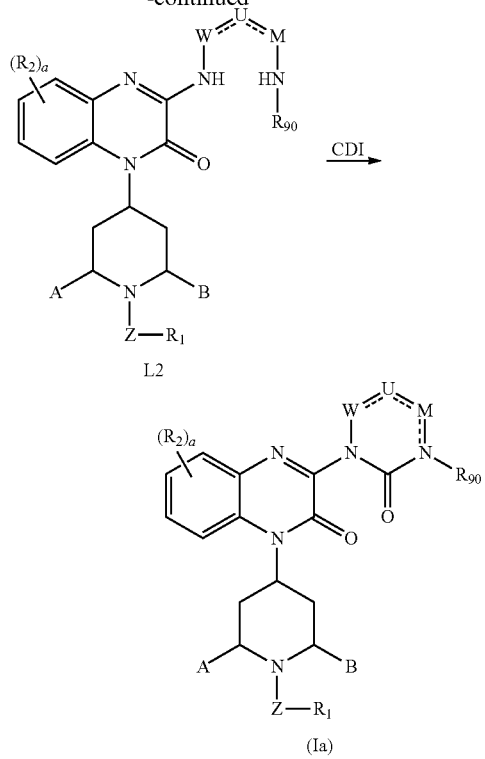

In Scheme L, Compound G1 is reacted with Compound L1 in the presence of a base to provide a compound L2. In one embodiment, the reaction is carried out in an organic solvent such as THF at a temperature of about 25° C. In the next step, Compound L2 is reacted with di(1H-imidazol-1-yl)methanone ("CDI") to provide Cyclic Urea-Substituted Quinoxaline-Type Piperidine Compounds of Formula (Ia). In one embodiment, this step is carried out in an organic solvent, such as 1,4-dioxane, at an elevated temperature (e.g., from about 100° C. to about 120° C.).

4.3.2.1 Methods for Making Lactam-Substituted Quinoxaline-Type Piperidine Compounds of Formula (Ib), Formula (Ic), Formula (Id), and Formula (Ie)

Preparation of Lactam-Substituted Quinoxaline-Type Piperidine Compounds of Formulae (Ib) through (Ie) can be carried out through a multiple step process. First, the reaction of Compound A5 with a chlorinating agent provides Compound G1. Compound G1 is then reacted with a 2-methoxypyridine boronic acid or 2-methoxypyridine-substituted trialkyl stannyl compound M1, M2, M3, or M4 in the presence of a metal catalyst to provide Compounds M5 through M8, respectively. These compounds are subsequently converted to Lactam-Substituted Quinoxaline-Type Piperidine Compounds of Formula (Ib) through (Ie), respectively. Methods for preparing Compound A5 are shown in Schemes A-F above. Methods for chlorinating Compound A5 to provide Compound G1 are shown in Schemes G and H above. Methods for making Lactam-Substituted Quinoxaline-Type Piperidine Compounds of Formulae (Ib) through (Ie) from Compound G1 are shown in Scheme M below.

methoxy-substituted aryl boronic acid or methoxy-substituted trialkyl stannyl compound in the presence of a metal catalyst to provide Compound M2, Compound N2, or Compound P2, which is subsequently converted to a Lactam-Substituted Quinoxaline-Type Piperidine Compound of Formula (Ib), Formula (Ic), or Formula (Id), respectively. Methods for preparing Compound A5 are shown in Schemes A-F above. Methods for chlorinating Compound A5 to provide Compound G1 are shown in Schemes G and H above. Methods for making Lactam-Substituted Quinoxaline-Type Piperidine Compounds of Formula (Ib), Formula (Ic), and Formula (Id) from Compound G1 are shown in Schemes M, N, and P below.

4.3.2.1 Methods or Making Cyclic Urea-Substituted Quinoxaline-Type Piperidine Compounds of Formula (Ia) from Quinoxaline-2,3(1H,4H)-diones (Scheme M)

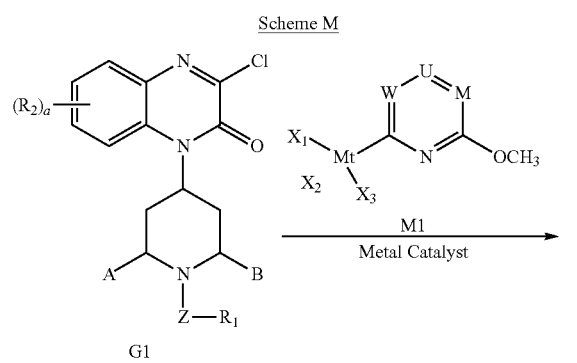

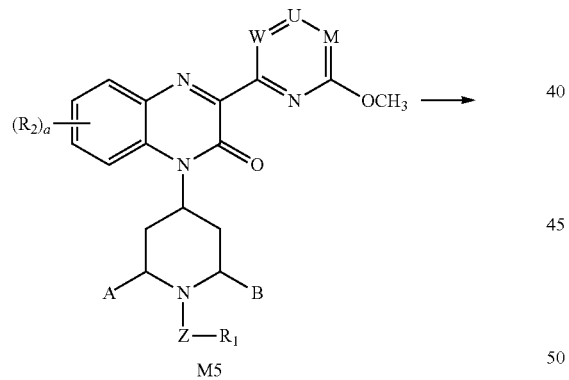

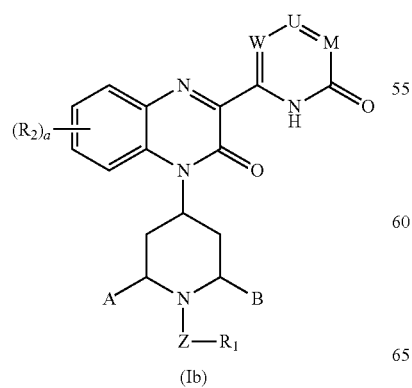

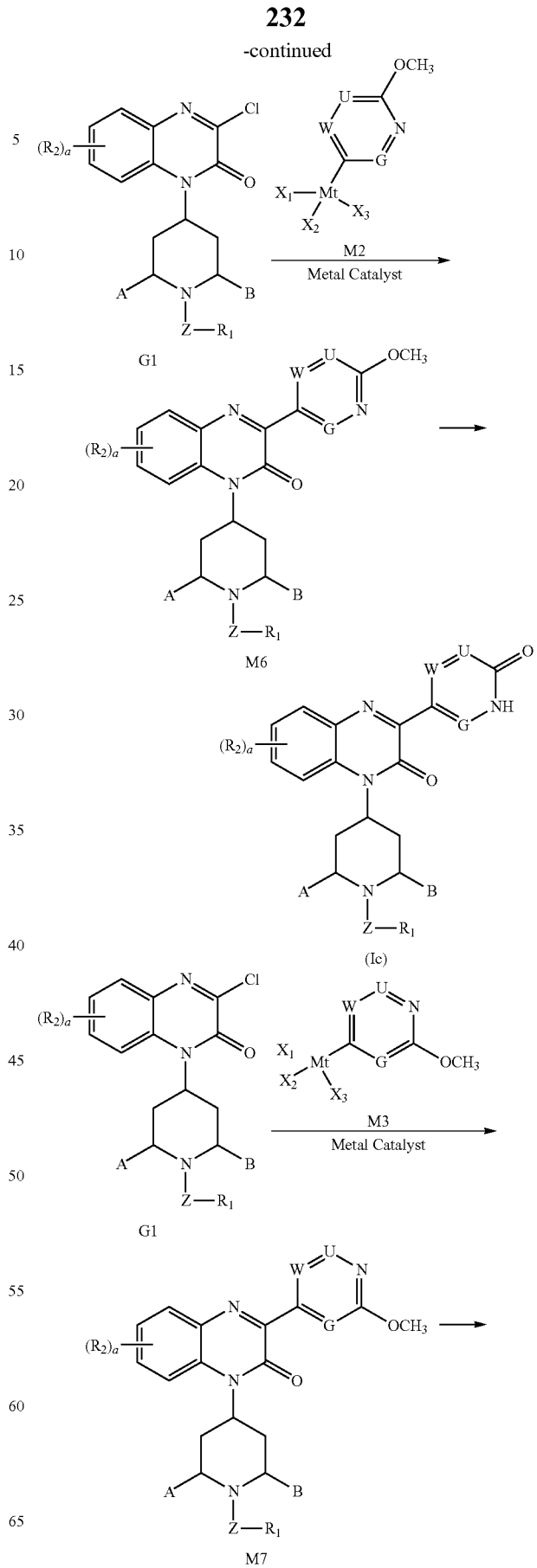

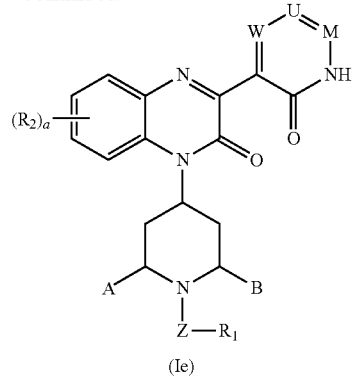

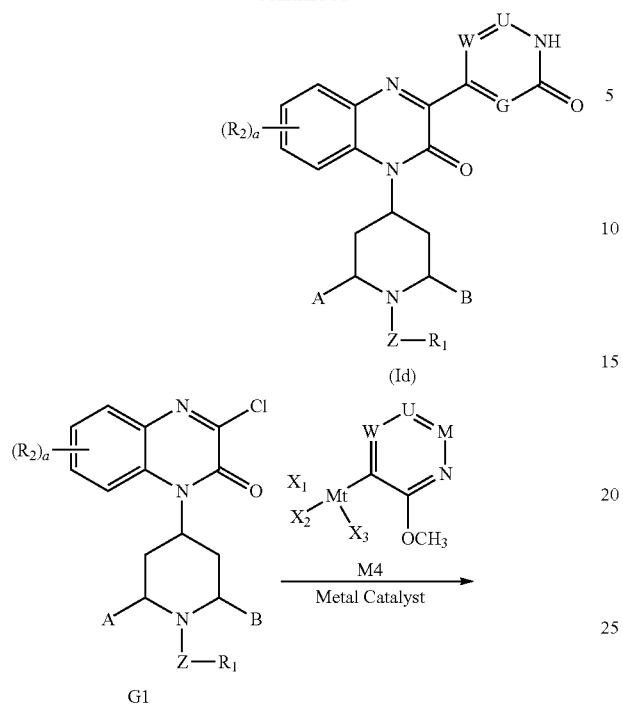

In Scheme M, Compound G1 is first reacted with Compound M1, M2, M3, or M4 in the presence of a metal catalyst to provide Compound M5 through M8, respectively. In certain embodiments, the Mt group can be boron, the $X_1$ and $X_2$ groups can each be hydroxyl, and the $X_3$ group is absent. In other embodiments, the Mt group can be boron, the $X_1$ and $X_2$ groups, taken together, can form a (4,4,5,5-tetramethyl-1,3,-dioxaborolan-2-yl) moiety, and the $X_3$ group is absent. In yet other embodiments, the Mt group can be tin, and the $X_1$, $X_2$, and $X_3$ groups can each be, independently, $(C_1$-$C_4)$alkyl groups (e.g., n-butyl groups). The reaction of Compound G1 and Compounds M1, M2, M3, or M4 can occur in the presence of a metal catalyst, such as a palladium catalyst. In particular embodiments, cesium carbonate can be added to improve the yield of Compound M5, M6, M7, and/or M8. Additionally, a base such as TEA can be added to the reaction mixture. Compound M5, M6, M7, or M8 can then be converted to a Lactam-Substituted Quinoxaline-Type Piperidine Compound of Formula (Ib), (Ic), (Id), or (Ie), respectively. In certain embodiments, the reaction can be conducted in the presence of an acid such as 2N HCl or iodotrimethylsilane. In alternative embodiments, the reaction can be conducted in the presence of a base such as potassium hydroxide.

4.3.2.2 Synthesis of Lactam-Substituted Quinoxaline-Type Piperidine Compounds of Formulae (Ic'), (Ic''), and (Ic''') (Scheme N)

Scheme N

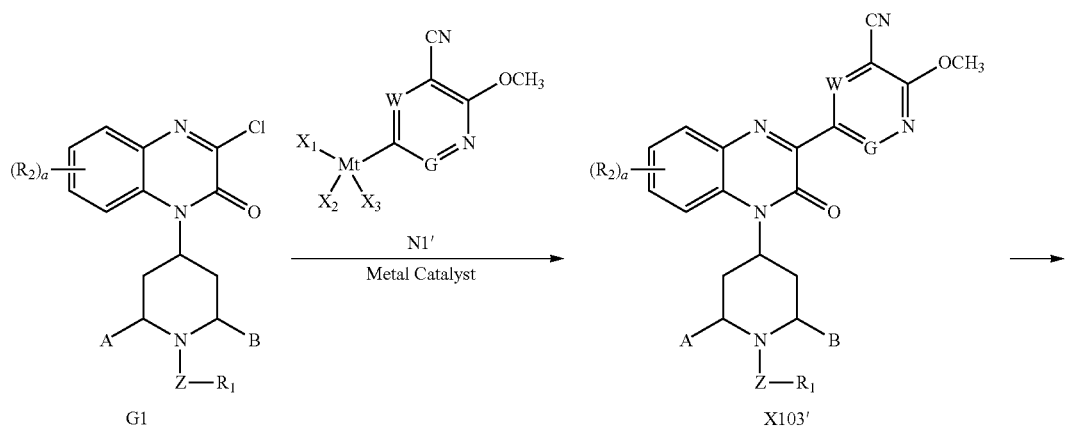

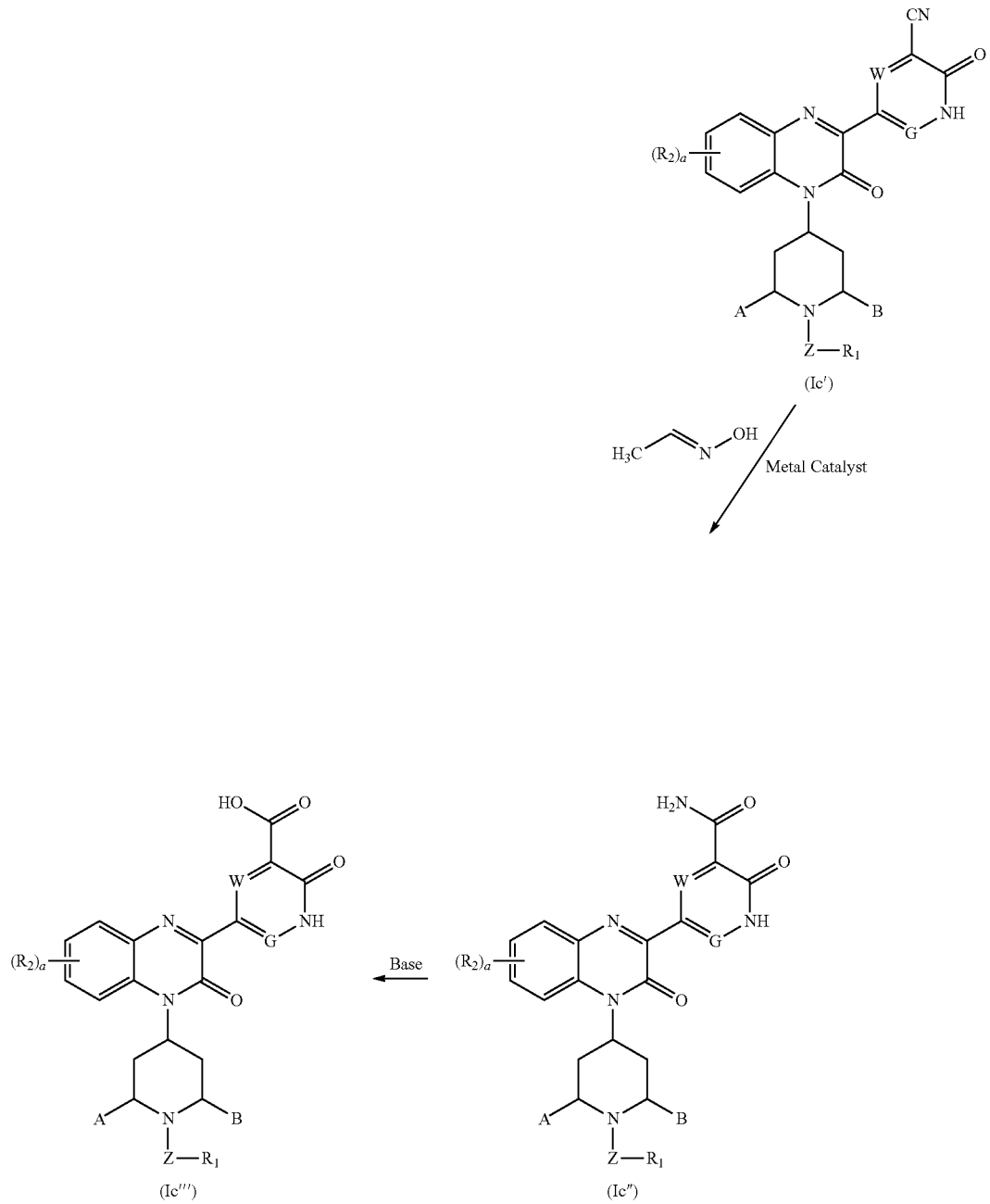

In Scheme N, Lactam-Substituted Quinoxaline-Type Piperidine Compound (Ic') is prepared from Compound G1 by a similar procedure as described for Compound M6 in Scheme M above. Lactam-Substituted Quinoxaline-Type Piperidine Compound (Ic') can be reacted with (E)-acetaldehyde oxime in the presence of a metal catalyst to provide Lactam-Substituted Quinoxaline-Type Piperidine Compound (Ic"). In one embodiment, the metal catalyst is a rhodium catalyst (e.g., $Rh(PPh_3)_3Cl$). Lactam-Substituted Quinoxaline-Type Piperidine Compound (Ic") can be hydrolyzed under basic conditions to provide a Lactam-Substituted Quinoxaline-Type Piperidine Compound of Formula (Ic="').

4.3.3 Methods for Making N-Substituted Lactam-Substituted Quinoxaline-Type Piperidine Compounds of Formula (If) (Scheme O)

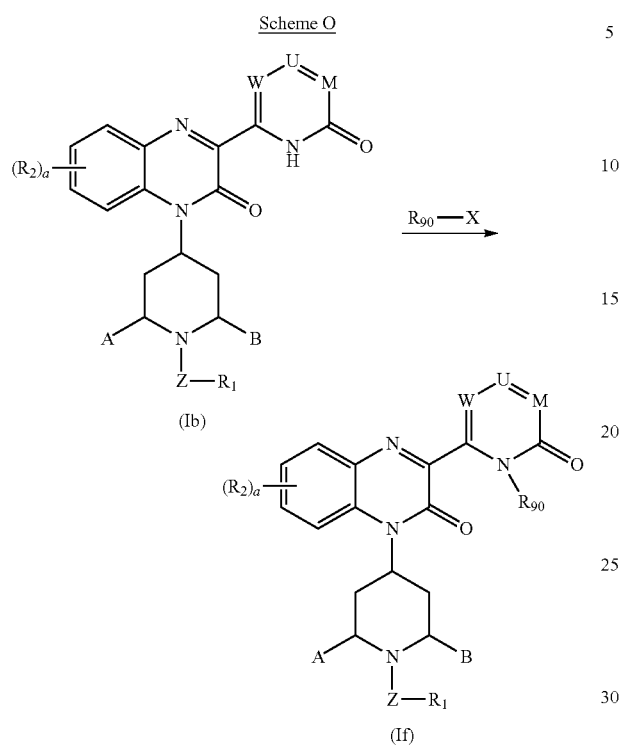

In Scheme O, a Lactam-Substituted Quinoxaline-Type Piperidine Compound of Formula (Ib) is reacted with alkylating agent $R_{90}$—X to provide a N-Substituted Lactam-Substituted Quinoxaline-Type Piperidine Compound of Formula (If). In certain embodiments, the alkylating agent $R_{90}$—X can be an α-halo ester. In other embodiments, the alkylating agent can be a β-halo ester. In embodiments where the alkylating agent is an α-halo ester or a β-halo ester, the resultant ester functionality can be hydrolyzed to a carboxylic acid under acid or base catalyzed conditions. It will be understood by one of skill in the art that, inter alia, a Lactam-Substituted Quinoxaline-Type Piperidine Compound of Formula (Ic), (Id), or (Ie) can be alkylated in similar fashion as shown in Scheme O.

4.3.4 Methods for Making Saturated N-Substituted Lactam-Substituted Quinoxaline-Type Piperidine Compounds of Formula (Ig) (Scheme P)

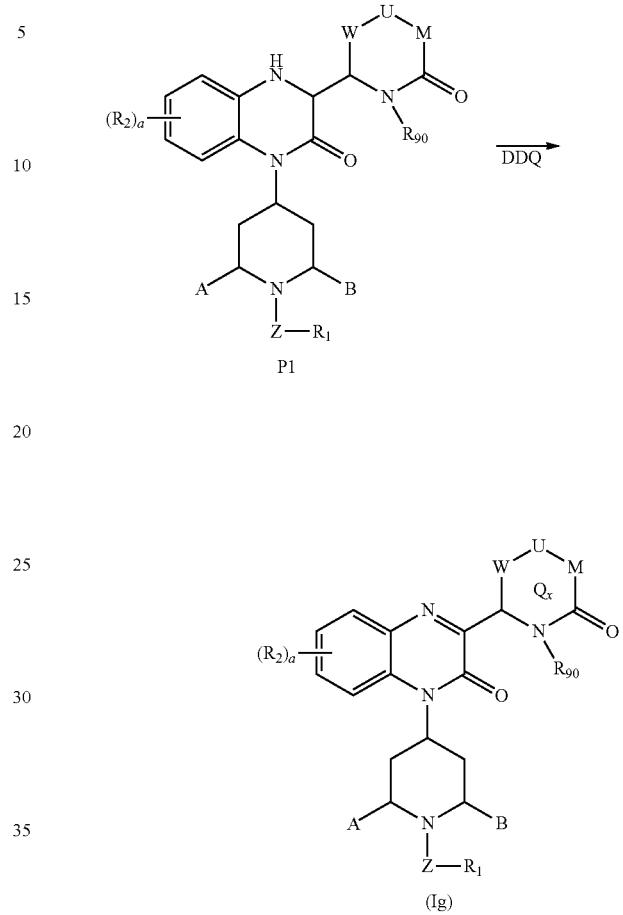

In Scheme P, a N-Substituted Lactam-Substituted Quinoxaline-Type Piperidine Compound of Formula (If) is hydrogenated in the presence of a platinum catalyst to provide Compound P1. Compound P1 is next reacted with 4,5-dichloro-3,6-dioxocyclohexa-1,4-diene-1,2-dicarbonitrile (DDQ) to provide N-Substituted Lactam-Substituted Quinoxaline-Type Piperidine Compounds of Formula (Ig). In certain embodiments, the reaction between P1 and DDQ is carried out in DCM at about 25° C.

4.3.5 Methods for Making Cyclic Urea- or Lactam-Substituted Quinoxaline-Type Piperidine Compounds of Formula (Ih)

Preparation of Cyclic Urea- or Lactam-Substituted Quinoxaline-Type Piperidine Compounds of Formula (Ih), where $Y_1$ is sulfur, can be carried out through the reaction of a quinoxaline-2,3(1H,4H)-dithione (e.g., Compound Q1) with a halogenating agent followed by reaction with a compound comprising a urea-containing ring. Preparation of Compound Q1 from Compound A5 (Scheme Q) and subsequent conversion of Compound Q1 to a Cyclic Urea- or Lactam-Substituted Quinoxaline-Type Piperidine Compound of Formula (III) (Scheme R) are described below.

4.3.5.1 Synthesis of Compound Q1 from Compound A5 (Scheme Q)

Scheme Q

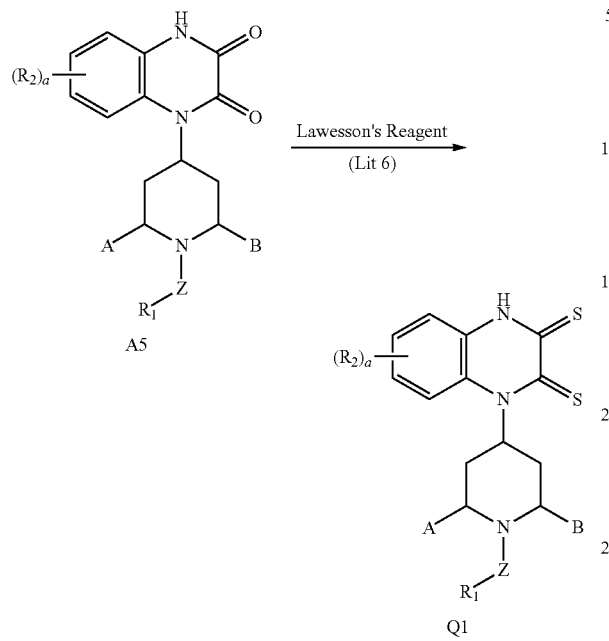

In Scheme Q and the other schemes, "Lit 6" refers to the reference Perregaard et al., "Studies on Organophosphorus Compounds XVIII*. Oxidation of Tertiary Alicyclic Amines with Elemental Sulfur in Hexamethylphosphoric Triamide (HMPA). Oxidative Rearrangements of Hexahydroazepines and Octahydroazocines to bis(3-Pyrrolyl)Polysulfides.," Bull. Soc. Chim. Belg. 86:679-691 (1977).

Compound Q1, comprising a quinoxaline-2,3(1H,4H)-dithione, can be made by, e.g., reacting Compound A5 (i.e., comprising a quinoxaline-2,3(1H,4H)-dione) with Lawesson's reagent (i.e., 2,4-bis(4-methoxyphenyl)-1,3-dithia-2,4-diphosphetane-2,4-disulfide) according to the procedure described in reference "Lit 6." In one embodiment, Compound Q1 can be made by reacting Compound A5 with Lawesson's reagent in a nonpolar solvent, such as THF or toluene, at a temperature of about 100° C. for about 2-3 hours as shown above.

4.3.5.2 Synthesis of Cyclic Urea-Substituted Quinoxaline-Type Piperidine Compounds of Formula (Ih) from Compound Q1 (Scheme R)

Scheme R

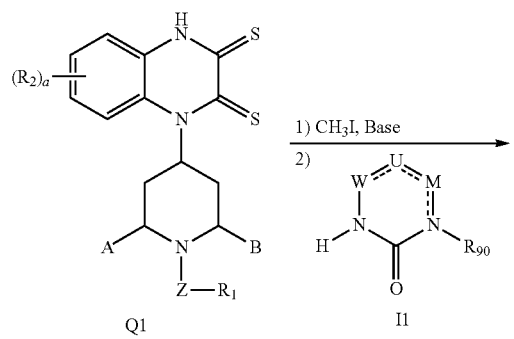

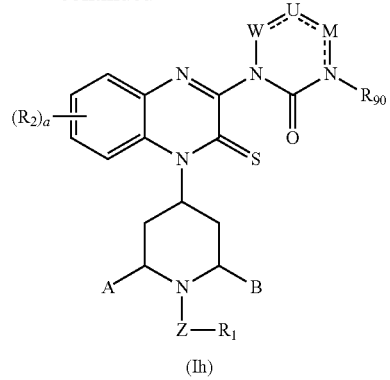

In Scheme R, Compound Q1 is dissolved in a suitable solvent, such as toluene, and reacted with methyl iodide in the presence of a base, such as DIEA, to generate an intermediate compound which is reacted with urea-containing ring Compound I1 to provide Cyclic Urea-Substituted Quinoxaline-Type Piperidine Compounds of Formula (Ih).

4.3.6 Methods for Making Specific Stereoisomeric Forms of Cyclic Urea- or Lactam-Substituted Quinoxaline-Type Piperidine Compounds of Formula (I)

Specific stereoisomeric forms of Cyclic Urea- or Lactam-Substituted Quinoxaline-Type Piperidine Compounds of Formula (I) can be prepared using methods described above. As described below, the desired stereochemical form can be introduced into the optionally-bridged piperidine portion of the molecule prior to the addition of the quinoxaline portion of the molecule.

4.3.6.1 Synthesis of Stereoisomeric Forms of Cyclic Urea- or Lactam-Substituted Quinoxaline-Type Piperidine Precursors (Scheme S)

Scheme S

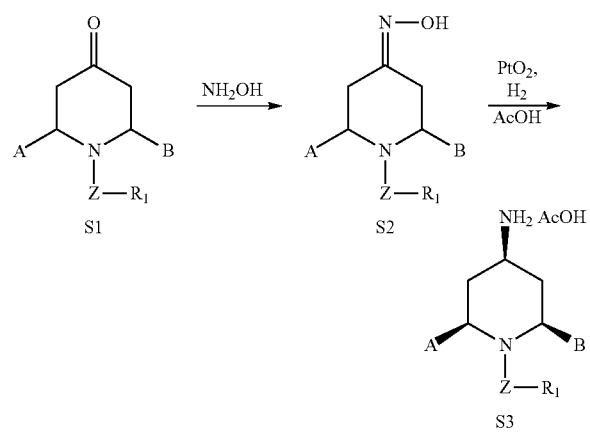

In Scheme S, Compound S3 can be prepared according to the methods described in U.S. Patent Application Publication US 2010/0216726 A1, for example, at paragraph [1745] and thereafter. Briefly, Compound S1 can be converted to oxime Compound S2 using aqueous hydroxylamine in an acidic solvent, such as AcOH. Compound S2 can be reduced to an endo amine Compound S3 by hydrogenation using a noble metal catalyst, such as platinum oxide, in a solvent, such as AcOH.

4.3.6.2 Alternative Synthesis of Stereoisomeric Forms of Cyclic Urea- or Lactam-Substituted Quinoxaline-Type Piperidine Precursors (Scheme T)

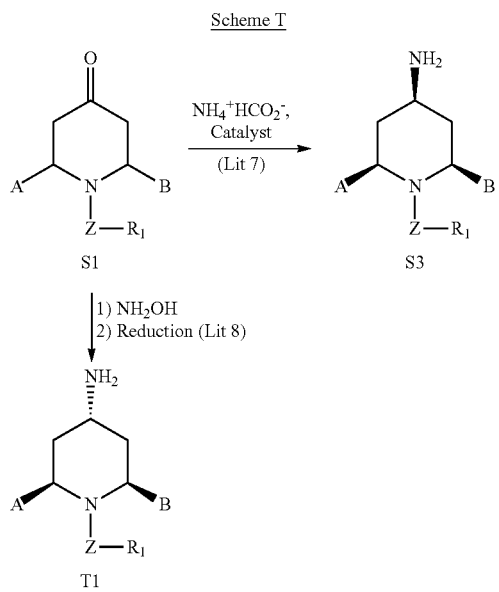

In Scheme T and the other schemes, "Lit 7" refers to Berdini et al., "A Modified Palladium Catalyzed Reductive Amination Procedure," *Tetrahedron*, 58:5669-5674 (2002) and "Lit 8" refers to Lewin et al., "Molecular Features Associated with Polyamine Modulation of NMDA Receptors," *J. Med. Chem.* 41:988-995 (1998).

Compound S1, where substituent groups A and B together form a bridge, e.g., a two carbon bridge, is commercially available or can be prepared by methods known to the art.

When substituent groups A and B together form a bridge, e.g., a two carbon bridge, Compound S1 can be converted to Compound S3, the "endo" isomer, under reductive amination conditions using, e.g., ammonium formate and a noble metal catalyst, e.g., palladium on carbon, in a solvent, such as EtOH or MeOH, as described in reference "Lit 7." Similarly, where substituent groups A and B together form a bridge, e.g., a two carbon bridge, Compound S1 can be reacted with aqueous hydroxylamine in a solvent, such as hexanes, to form an intermediate hydroxylamine, which can be converted to its oxime by dehydration in a solvent with a high boiling point, such as toluene, under Dean-stark conditions. The oxime intermediate can be converted to Compound T1, the "exo" isomer, by reduction using, e.g., sodium in propanol as described in reference "Lit 8."

4.3.6.3 Synthesis of Stereoisomeric Forms of Cyclic Urea- or Lactam-Substituted Quinoxaline-Type Piperidine Compounds of Formula (I) from Compound S3 (Scheme U)

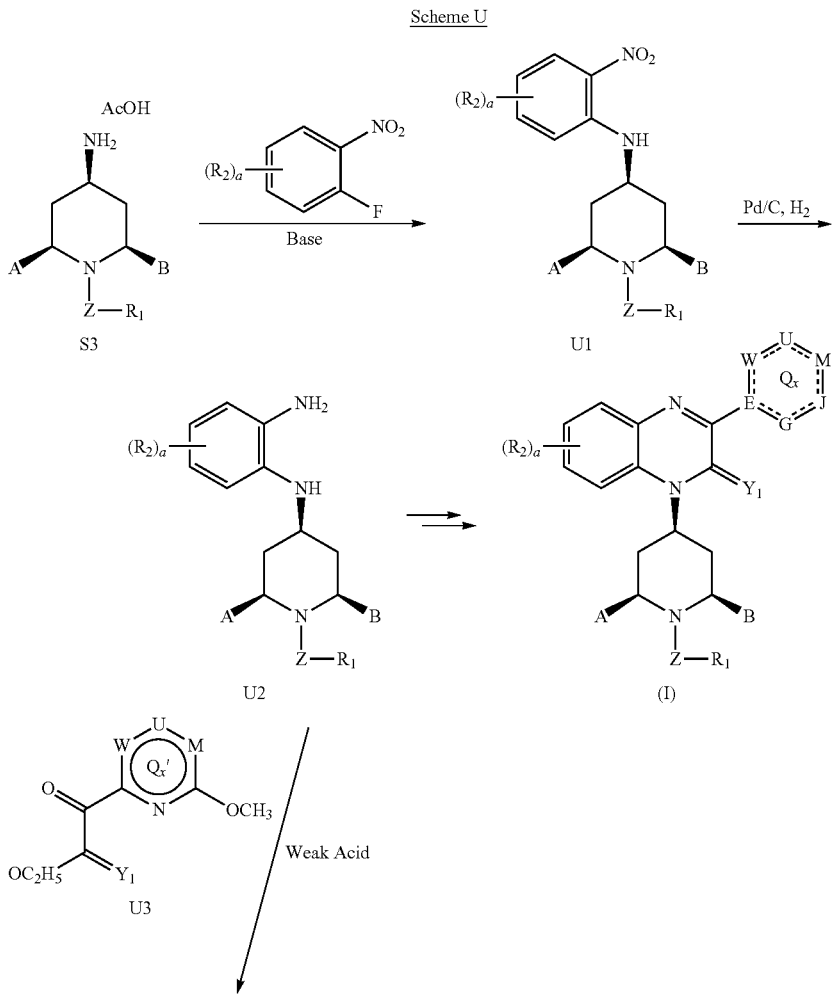

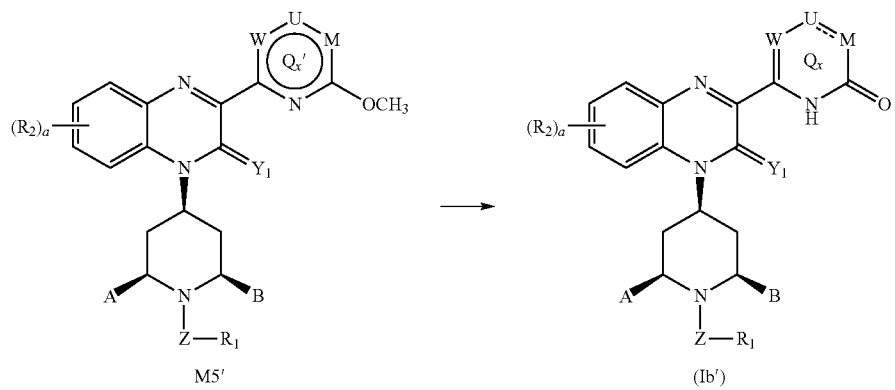

In Scheme U, Compound U2 can be prepared according to the methods described in U.S. Patent Application Publication US 2010/0216726 A1, for example, at paragraph [1745] and thereafter. Briefly, amine Compound S3 or its salt, such as the acetate, can be reacted with a substituted or unsubstituted 2-fluoronitrobenzene in a polar solvent, such as MeCN or DMF, and a base, such as TEA or potassium carbonate, to provide Compound U1. Compound U1 can be reduced to Compound U2 by hydrogenation using a noble metal catalyst, such as palladium on charcoal or Raney nickel, in a solvent, such as EtOAc or DCM. Thereafter, a Cyclic Urea- or Lactam-Substituted Quinoxaline-Type Piperidine Compound of Formula (I) can be prepared using methods described in Sections 4.3.1 through 4.3.5.

Alternatively, Compound U2 can be reacted with Compound U3 to provide Compound M5'. The reaction can be carried out in the presence of a dilute acid, such as AcOH. In one embodiment, the reaction is carried out in EtOH at a temperature of from about 80° C. to about 100° C. Alkoxide Compound M5' can then be converted into the Cyclic Urea- or Lactam-Substituted Quinoxaline-Type Piperidine Compound of Formula (Ib'), e.g., as described in the final step of Scheme M or using LiOH in THF:H$_2$O as disclosed in the final step in Scheme 1 of Bulusu et al., "Selective photochemical cleavage of an α-ketoamide in a highly functionalised macrolide ascomycin," *Tetrahedron Lett.* 45(12):2527-2530 (2004).

In these embodiments, the final product of the reaction, i.e., the Cyclic Urea- or Lactam-Substituted Quinoxaline-Type Piperidine Compound of Formula (I), has a percent diastereomeric excess (% de) of at least about 90%. In another embodiment, the final product of the reaction has a % de of at least about 95%. In another embodiment, the final product of the reaction has a % de of at least about 97%. In another embodiment, the final product of the reaction has a % de of at least about 98%. In another embodiment, the final product of the reaction has a % de of at least about 99%. In another embodiment, the final product of the reaction has a % de of greater than 99% (e.g., 99.1% to 99.9%).

4.3.7 Methods for Making 3-Chloroquinoxalin-2 (1H)-one Intermediates and Cyclic Urea- or Lactam-Substituted Quinoxaline-Type Piperidine Compounds Comprising a 3-(Bicyclo[3.3.1]nonanyl) R$_1$ Group (Scheme V)

Scheme V

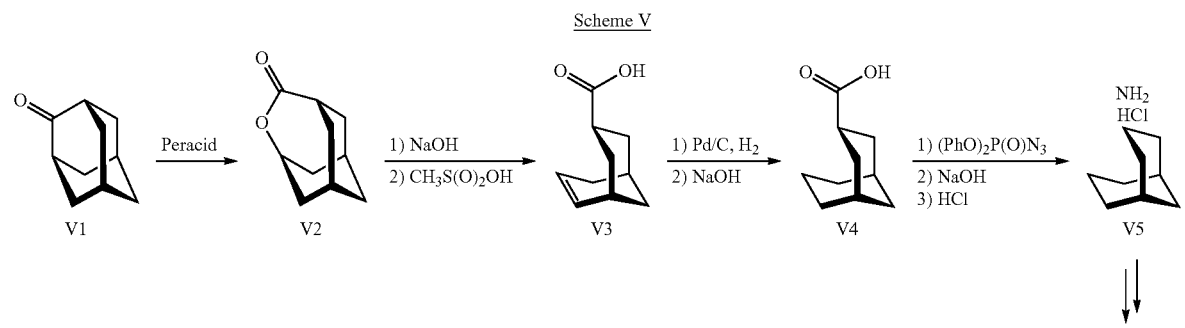

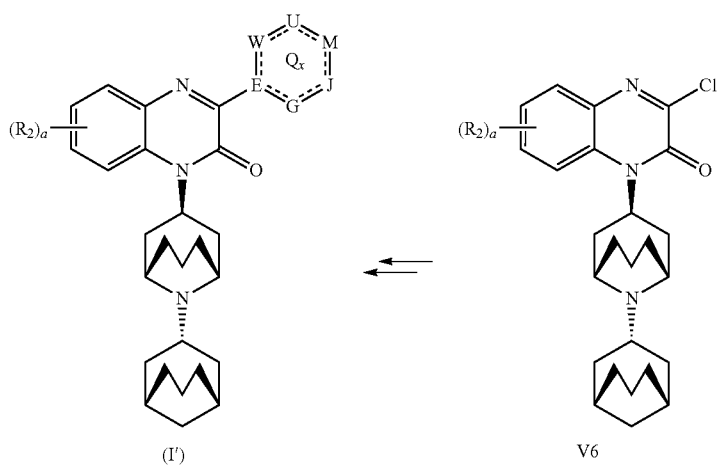

In Scheme V, 2-adamantanone V1 can be dissolved in TFA and treated with a peracid, such sodium percarbonate, at from about 20° C. to about 30° C. to provide a lactone Compound V2. Compound V2 can be hydrolyzed to a hydroxyl acid using sodium hydroxide in a solvent, such as MeOH, under reflux. The stereochemistry of the acid epimerizes from endo to exo. The hydroxyl acid can be dehydrated to Compound V3 using an acid, such as methanesulfonic acid, in a solvent, such as toluene, by azeotropic drying. Compound V3 can be hydrogenated using a catalyst, such as palladium on charcoal, in a mixed solvent system, such as MeOH and EtOAc, to provide a mixture of acid Compound V4 and its methyl ester (Compound V4', not shown). The mixture can be hydrolyzed to the acid Compound V4 using sodium hydroxide in aqueous MeOH. Compound V4 can be converted to Compound V5 using di-phenyl phosphoryl azide and TEA in a solvent, such as toluene, in a Curtius type reaction to provide an isocyanate that can be hydrolyzed to the amine of Compound V5 using sodium hydroxide in aqueous THF or another aprotic water miscible solvent. The isolated amine of Compound V5 can be converted to its hydrochloride salt by treatment with hydrochloric acid. Compound V5 can be converted to a 2-chloroquinoxaline Compound V6 according to the methods described in Sections 4.3.1.1 and 4.3.1.2. Compound V6 can be converted to Cyclic Urea- or Lactam-Substituted Quinoxaline-Type Piperidine Compounds of Formula (I') according to the methods described in Sections 4.3.1.3 through 4.3.5.

4.3.8 Methods for Making 3-Chloroquinoxalin-2(1H)-one Intermediates and Cyclic Urea- or Lactam-Substituted Quinoxaline-Type Piperidine Compounds Comprising a 3-(7-Methylbicyclo[3.3.1]nonanyl) $R_1$ Group (Scheme W)

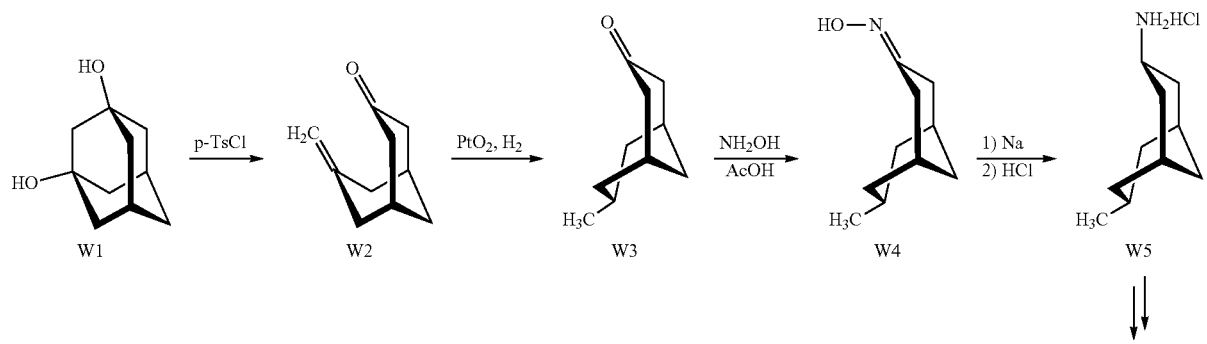

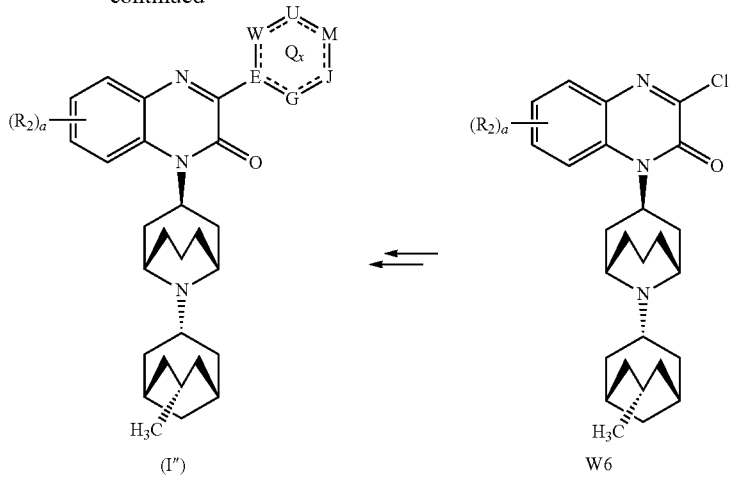

In Scheme W, 1,3-dihydroxyadamantane W1 can be treated with p-toluenesulfonyl chloride in pyridine at a temperature of about 70° C. for from about 2 h to about 6 h to provide Compound W2. Compound W2 can be hydrogenated to Compound W3 using platinum oxide in a non-polar solvent, such cyclohexane. Compound W3 can be converted to the oxime Compound W4 using hydroxylamine in AcOH at a temperature from about 25° C. to about 40° C. Compound W4 can be reacted with sodium metal and iso-propanol in a solvent, such as toluene, at a temperature of about 100° C. to provide the amine of Compound W5. The isolated amine of Compound W5 can be converted to its hydrochloride salt by treatment with hydrochloric acid in a solvent, such as Et$_2$O. Compound W5 can be converted to Compound W6 according to the methods described in Sections 4.3.1.1 and 4.3.1.2. Compound W6 can be converted to Cyclic Urea- or Lactam-Substituted Quinoxaline-Type Piperidine Compounds of Formula (I″) according to the method described in Sections 4.3.1.3 through 4.3.5.

4.4 Therapeutic Uses of the Cyclic Urea- or Lactam-Substituted Quinoxaline-Type Piperidine Compounds In accordance with the disclosure, the Cyclic Urea- or Lactam-Substituted Quinoxaline-Type Piperidine Compounds are administered to an animal in need of treatment or prevention of a Condition.

In one embodiment, an effective amount of a Cyclic Urea- or Lactam-Substituted Quinoxaline-Type Piperidine Compound can be used to treat or prevent any condition treatable or preventable by inhibiting the activity of the ORL-1 receptor. Examples of Conditions that are treatable or preventable by inhibiting the activity of the ORL-1 receptor include, but are not limited to: pain (CNS effect), memory disorders, obesity, constipation, depression, dementia, and Parkinsonism.

In another embodiment, an effective amount of a Cyclic Urea- or Lactam-Substituted Quinoxaline-Type Piperidine Compound can be used to treat or prevent any condition treatable or preventable by activating the ORL-1 receptor. Examples of Conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, and drug abuse.

The Cyclic Urea- or Lactam-Substituted Quinoxaline-Type Piperidine Compounds can be used to treat or prevent acute or chronic pain. Examples of pain that can be treated or prevented using a Cyclic Urea- or Lactam-Substituted Quinoxaline-Type Piperidine Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Cyclic Urea- or Lactam-Substituted Quinoxaline-Type Piperidine Compounds can also be used to treat or prevent pain associated with inflammation or with an inflammatory disease in an animal. Such pain can arise where there is an inflammation of the body tissue which can be a local inflammatory response or a systemic inflammation. For example, a Cyclic Urea- or Lactam-Substituted Quinoxaline-Type Piperidine Compound can be used to treat or prevent pain associated with inflammatory diseases including, but not limited to, organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell. Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. An Cyclic Urea- or Lactam-Substituted Quinoxaline-Type Piperidine Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Cyclic Urea- or Lactam-Substituted Quinoxaline-Type Piperidine Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Cyclic Urea- or Lactam-Substituted Quinoxaline-Type Piperidine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

According to the disclosure, some of the Cyclic Urea- or Lactam-Substituted Quinoxaline-Type Piperidine Compounds are agonists at the ORL-1 receptor, some of the Cyclic Urea- or Lactam-Substituted Quinoxaline-Type Piperidine Compounds are partial agonists at the ORL-1 receptor, and some of the Cyclic Urea- or Lactam-Substituted Quinoxaline-Type Piperidine Compounds are antagonists at the ORL-1 receptor. In another embodiment, a Cyclic Urea- or Lactam-Substituted Quinoxaline-Type Piperidine Compound is an agonist at the ORL-1 receptor and an agonist at a and/or δ opioid receptor, particularly at a μ opioid receptor. In another embodiment, a Cyclic Urea- or Lactam-Substituted Quinoxaline-Type Piperidine Compound is a partial agonist at the ORL-1 receptor and an agonist at a μ, κ and/or δ opioid receptor, particularly at a μ opioid receptor. In another embodiment, a Cyclic Urea- or Lactam-Substituted Quinoxaline-Type Piperidine Compound is an antagonist at the ORL-1 receptor and an agonist at μ, κ and/or δ opioid receptor, particularly at a μ opioid receptor. In another embodiment, a Cyclic Urea- or Lactam-Substituted Quinoxaline-Type Piperidine Compound is an agonist at the ORL-1 receptor and an antagonist at a μ, κ and/or δ opioid receptor, particularly at a μ opioid receptor. In another embodiment, a Cyclic Urea- or Lactam-Substituted Quinoxaline-Type Piperidine Compound is a partial agonist at the ORL-1 receptor and an antagonist at μ, κ and/or δ opioid receptor, particularly at a μ opioid receptor. In another embodiment, a Cyclic Urea- or Lactam-Substituted Quinoxaline-Type Piperidine Compound is an antagonist at the ORL-1 receptor and an antagonist at a μ, κ and/or δ opioid receptor, particularly at a μ opioid receptor.

The disclosure also provides methods for inhibiting ORL-1 receptor function in a cell, comprising contacting a cell capable of expressing the ORL-1 receptor with an amount of a Cyclic Urea- or Lactam-Substituted Quinoxaline-Type Piperidine Compound effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of a Cyclic Urea- or Lactam-Substituted Quinoxaline-Type Piperidine Compound. In one embodiment, the method is useful for treating or preventing pain in an animal in need of such treatment or prevention. In another embodiment, the method is useful for treating or preventing a memory disorder, obesity, constipation, depression, dementia, or Parkinsonism in an animal in need of such treatment or prevention.

The disclosure also relates to methods for activating ORL-1 receptor function in a cell, comprising contacting a cell capable of expressing the ORL-1 receptor with an amount of a Cyclic Urea- or Lactam-Substituted Quinoxaline-Type Piperidine Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of a Cyclic Urea- or Lactam-Substituted Quinoxaline-Type Piperidine Compound. In one embodiment, the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S] GTPγS Binding Assays," *TIPS* 24(2):87-90 (2003); and Lazareno, "Measurement of Agonist-stimulated [$^{35}$S]GTPγS Binding to Cell Membranes," *Methods in Molecular Biology* 106:231-245 (1999).

4.5 Therapeutic/Prophylactic Administration and Compositions of the Disclosure Due to their activity, the Cyclic Urea- or Lactam-Substituted Quinoxaline-Type Piperidine Compounds are advantageously useful in human and veterinary medicine. As described above, the Cyclic Urea- or Lactam-Substituted Quinoxaline-Type Piperidine Compounds are useful for treating or preventing a Condition in an animal in need thereof. The Cyclic Urea- or Lactam-Substituted Quinoxaline-Type Piperidine Compounds of the disclosure can be administered to any animal requiring modulation of the opioid and/or ORL-1 receptors.

When administered to an animal, a Cyclic Urea- or Lactam-Substituted Quinoxaline-Type Piperidine Compound can be administered as a component of a composition that comprises a pharmaceutically acceptable carrier or excipient. The compositions, which comprise a Cyclic Urea- or Lactam-Substituted Quinoxaline-Type Piperidine Compound, can be administered orally. An Cyclic Urea- or Lactam-Substituted Quinoxaline-Type Piperidine Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Cyclic Urea- or Lactam-Substituted Quinoxaline-Type Piperidine Compound.

Methods of administration include, but are not limited to, intradermal, intramuscular, intraperitoneal, parenteral, intravenous, subcutaneous, intranasal, epidural, oral, sublingual, intracerebral, intravaginal, transdermal, rectal, by inhalation, or topical, particularly to the ears, nose, eyes, or skin. The method of administration is left to the discretion of the practitioner. In most instances, administration will result in the release of a Cyclic Urea- or Lactam-Substituted Quinoxaline-Type Piperidine Compound into the bloodstream.

In specific embodiments, it can be desirable to administer a Cyclic Urea- or Lactam-Substituted Quinoxaline-Type Piperidine Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Cyclic Urea- or Lactam-Substituted Quinoxaline-Type Piperidine Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Cyclic Urea- or Lactam-Substituted Quinoxaline-Type Piperidine Compound can be formulated as a suppository, with traditional binders and excipients such as triglycerides.

When a Cyclic Urea- or Lactam-Substituted Quinoxaline-Type Piperidine Compound of the disclosure is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. An Cyclic Urea- or Lactam-Substituted Quinoxaline-Type Piperidine Compound of the disclosure can also be in the form of a powder for reconstitution as an injectable formulation.

In another embodiment, a Cyclic Urea- or Lactam-Substituted Quinoxaline-Type Piperidine Compound can be delivered in a vesicle, in particular a liposome (see Langer, "New Methods of Drug Delivery," *Science* 249:1527-1533 (1990); and Treat et al., "Liposome Encapsulated Doxorubicin Preliminary Results of Phase I and Phase II Trials," pp. 317-327 and 353-365 in *Liposomes in the Therapy of Infectious Disease and Cancer* (1989)).

In yet another embodiment, a Cyclic Urea- or Lactam-Substituted Quinoxaline-Type Piperidine Compound can be delivered in a controlled-release system or sustained-release system (see, e.g., Goodson, "Dental Applications," in *Medical Applications of Controlled Release, Vol. 2, Applications and Evaluation*, Langer and Wise, eds., CRC Press, Chapter 6, pp. 115-138 (1984), hereafter "Goodson"). Other controlled- or sustained-release systems discussed in the review by Langer, *Science* 249:1527-1533 (1990) can be used. In one embodiment, a pump can be used (Langer, *Science* 249:1527-1533 (1990); Sefton, "Implantable Pumps," in *CRC Crit. Rev. Biomed Eng.* 14(3):201-240 (1987); Buchwald et al., "Long-term, Continuous Intravenous Heparin Administration by an Implantable Infusion Pump in Ambulatory Patients with Recurrent Venous Thrombosis," *Surgery* 88:507-516 (1980); and Saudek et al., "A Preliminary Trial of the Programmable Implantable Medication System for Insulin Delivery," *New Engl. J. Med.* 321:574-579 (1989)). In another embodiment, polymeric materials can be used (see Goodson; Smolen et al., "Drug Product Design and Performance," *Controlled Drug Bioavailability Vol.* 1, John Wiley & Sons, New York (1984); Langer et al., "Chemical and Physical Structure of Polymers as Carriers for Controlled Release of Bioactive Agents: A Review," *J. Macromol. Sci. Rev. Macromol. Chem.* C23(1): 61-126 (1983); Levy et al., "Inhibition of Calcification of Bioprosthetic Heart Valves by Local Controlled-Release Diphosphonate," *Science* 228:190-192 (1985); During et al., "Controlled Release of Dopamine from a Polymeric Brain Implant: In Vivo Characterization," *Ann. Neurol.* 25:351-356

(1989); and Howard et al., "Intracerebral drug delivery in rats with lesion-induced memory deficits," *J. Neurosurg.* 71:105-112 (1989)). In yet another embodiment, a controlled- or sustained-release system can be placed in proximity of a target of a Cyclic Urea- or Lactam-Substituted Quinoxaline-Type Piperidine Compound, e.g., the spinal column, brain, or gastrointestinal tract, thus requiring only a fraction of the systemic dose.

The compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Cyclic Urea- or Lactam-Substituted Quinoxaline-Type Piperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, EtOH, and the like. The compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, (Amer. Pharmaceutical Ass'n, Washington, D.C., 1986), incorporated herein by reference.

The compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described by Radebough et al., "Preformulation," pp. 1447-1676 in *Remington's Pharmaceutical Sciences Vol.* 2 (Gennaro, ed., 19$^{th}$ Ed., Mack Publishing, Easton, Pa., 1995), incorporated herein by reference.

In one embodiment, the Cyclic Urea- or Lactam-Substituted Quinoxaline-Type Piperidine Compounds are formulated in accordance with routine procedures as a composition adapted for oral administration to human beings. An Cyclic Urea- or Lactam-Substituted Quinoxaline-Type Piperidine Compound to be orally delivered can be in the form of tablets, capsules, gelcaps, caplets, lozenges, aqueous or oily solutions, suspensions, granules, powders, emulsions, syrups, or elixirs, for example. When a Cyclic Urea- or Lactam-Substituted Quinoxaline-Type Piperidine Compound is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman et al., eds., 2$^{nd}$ Ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., 16$^{th}$ Ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., 2$^{nd}$ Ed., Marcel Dekker, Inc., 1996 & 1998).

When a Cyclic Urea- or Lactam-Substituted Quinoxaline-Type Piperidine Compound is to be injected parenterally, it can be, e.g., in the form of an isotonic sterile solution. Alternatively, when a Cyclic Urea- or Lactam-Substituted Quinoxaline-Type Piperidine Compound is to be inhaled, it can be formulated into a dry aerosol or can be formulated into an aqueous or partially aqueous solution.

An orally administered Cyclic Urea- or Lactam-Substituted Quinoxaline-Type Piperidine Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Cyclic Urea- or Lactam-Substituted Quinoxaline-Type Piperidine Compounds can be formulated for intravenous administration. In certain embodiments, compositions for intravenous administration comprise sterile isotonic aqueous buffer. Where necessary, the compositions can also include a solubilizing agent. An Cyclic Urea- or Lactam-Substituted Quinoxaline-Type Piperidine Compound for intravenous administration can optionally include a local anesthetic such as benzocaine or prilocalne to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Cyclic Urea- or Lactam-Substituted Quinoxaline-Type Piperidine Compound is to be administered by infusion, it can be dispensed, for example, with an infusion bottle containing sterile pharmaceutical grade water or saline. Where a Cyclic Urea- or Lactam-Substituted Quinoxaline-Type Piperidine Compound is administered by injection, an ampule of sterile water for injection or saline can be provided so that the ingredients can be mixed prior to administration.

An Cyclic Urea- or Lactam-Substituted Quinoxaline-Type Piperidine Compound can be administered by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Cyclic Urea- or Lactam-Substituted Quinoxaline-Type Piperidine Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Cyclic Urea- or Lactam-Substituted Quinoxaline-Type Piperidine Compound, and can thus reduce the occurrence of adverse side effects.

Controlled- or sustained-release compositions can initially release an amount of a Cyclic Urea- or Lactam-Substituted Quinoxaline-Type Piperidine Compound that promptly produces the desired therapeutic or prophylactic effect, and gradually and continually release other amounts of the Cyclic Urea- or Lactam-Substituted Quinoxaline-Type Piperidine Compound to maintain this level of therapeutic or prophylactic effect over an extended period of time. To maintain a constant level of the Cyclic Urea- or Lactam-Substituted Quinoxaline-Type Piperidine Compound in the body, the Cyclic Urea- or Lactam-Substituted Quinoxaline-Type Piperidine Compound can be released from the dosage form at a rate that will replace the amount of Cyclic Urea- or Lactam-Substituted Quinoxaline-Type Piperidine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Cyclic Urea- or Lactam-Substituted Quinoxaline-Type Piperidine Compound that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are, in certain embodiments, from about 0.01 mg/kg of body weight to about 2500 mg/kg of body weight of the animal per day or from about 0.01 mg/kg of body weight to about 1000 mg/kg of body weight of the animal per day. In another embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Cyclic Urea- or Lactam-Substituted Quinoxaline-Type Piperidine Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one Cyclic Urea- or Lactam-Substituted Quinoxaline-Type Piperidine Compound is administered, the effective dosage amounts correspond to the total amount administered.

Where a cell capable of expressing the ORL-1 receptor, the μ-opioid receptor, the κ-opioid receptor and/or the δ-opioid receptor is contacted with a Cyclic Urea- or Lactam-Substituted Quinoxaline-Type Piperidine Compound in vitro, the amount effective for inhibiting or activating that receptor function in a cell will, in certain embodiments, range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Cyclic Urea- or Lactam-Substituted Quinoxaline-Type Piperidine Compound will be from about 0.01 μL, to about 1 mL. In another embodiment, the volume of solution or suspension will be about 200 μL.

An Cyclic Urea- or Lactam-Substituted Quinoxaline-Type Piperidine Compound has a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

In certain embodiments, a Cyclic Urea- or Lactam-Substituted Quinoxaline-Type Piperidine Compound has a Ki (nM) of about 300 or less for binding to ORL-1 receptors. In one embodiment, a Cyclic Urea- or Lactam-Substituted Quinoxaline-Type Piperidine Compound of the disclosure has a $K_i$ (nM) of about 100 or less. In another embodiment, a Cyclic Urea- or Lactam-Substituted Quinoxaline-Type Piperidine Compound of the disclosure has a $K_i$ (nM) of about 35 or less. In another embodiment, a Cyclic Urea- or Lactam-Substituted Quinoxaline-Type Piperidine Compound of the disclosure has a $K_i$ (nM) of about 20 or less. In another embodiment, a Cyclic Urea- or Lactam-Substituted Quinoxaline-Type Piperidine Compound of the disclosure has a $K_i$ (nM) of about 15 or less. In another embodiment, a Cyclic Urea- or Lactam-Substituted Quinoxaline-Type Piperidine Compound of the disclosure has a $K_i$ (nM) of about 10 or less. In another embodiment, a Cyclic Urea- or Lactam-Substituted Quinoxaline-Type Piperidine Compound of the disclosure has a K (nM) of about 4 or less. In another embodiment, a Cyclic Urea- or Lactam-Substituted Quinoxaline-Type Piperidine Compound of the disclosure has a $K_i$ (nM) of about 1 or less. In another embodiment, a Cyclic Urea- or Lactam-Substituted Quinoxaline-Type Piperidine Compound of the disclosure has a $K_i$ (nM) of about 0.4 or less. In another embodiment, a Cyclic Urea- or Lactam-Substituted Quinoxaline-Type Piperidine Compound of the disclosure has a $K_i$ (nM) of about 0.1 or less.

ORL-1 GTP $EC_{50}$ is the concentration of a compound providing 50% of the maximal response for the compound at an ORL-1 receptor. In one embodiment, a Cyclic Urea- or Lactam-Substituted Quinoxaline-Type Piperidine Compound has an ORL-1 GTP $EC_{50}$ (nM) of about 5000 or less to stimulate ORL-1 receptor function. In another embodiment, a Cyclic Urea- or Lactam-Substituted Quinoxaline-Type Piperidine Compound of the disclosure has an ORL-1 GTP $EC_{50}$ (nM) of about 1000 or less. In another embodiment, a Cyclic Urea- or Lactam-Substituted Quinoxaline-Type Piperidine Compound of the disclosure has an ORL-1 GTP $EC_{50}$ (nM) of about 100 or less. In another embodiment, a Cyclic Urea- or Lactam-Substituted Quinoxaline-Type Piperidine Compound of the disclosure has an ORL-1 GTP $EC_{50}$ (nM) of about 80 or less. In another embodiment, a Cyclic Urea- or Lactam-Substituted Quinoxaline-Type Piperidine Compound of the disclosure has an ORL-1 GTP $EC_{50}$ (nM) of about 50 or less. In another embodiment, a Cyclic Urea- or Lactam-Substituted Quinoxaline-Type Piperidine Compound of the disclosure has an ORL-1 GTP $EC_{50}$ (nM) of about 35 or less. In another embodiment, a Cyclic Urea- or Lactam-Substituted Quinoxaline-Type Piperidine Compound of the disclosure has an ORL-1 GTP $EC_{50}$ (nM) of about 15 or less. In another embodiment, a Cyclic Urea- or Lactam-Substituted Quinoxaline-Type Piperidine Compound has an ORL-1 GTP $EC_{50}$ (nM) of about 10 or less. In another embodiment, a Cyclic Urea- or Lactam-Substituted Quinoxaline-Type Piperidine Compound has an ORL-1 GTP $EC_{50}$ (nM) of about 4 or less. In another embodiment, a Cyclic Urea- or Lactam-Substituted Quinoxaline-Type Piperidine Compound has an ORL-1 GTP $EC_{50}$ (nM) of about 1 or less. In another embodiment, a Cyclic Urea- or Lactam-Substituted Quinoxaline-Type Piperidine Compound has an ORL-1 GTP $EC_{50}$ (nM) of about 0.4 or less. In another embodiment, a Cyclic Urea- or Lactam-Substituted Quinoxaline-Type Piperidine Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In certain embodiments, a Cyclic Urea- or Lactam-Substituted Quinoxaline-Type Piperidine Compound of the disclosure acting as an agonist has an ORL-1 GTP Emax (%) of about 50% or greater. In one embodiment, agonist Cyclic Urea- or Lactam-Substituted Quinoxaline-Type Piperidine Compounds has an ORL-1 GTP Emax (%) of about 75% or greater. In another embodiment, agonist Cyclic Urea- or Lactam-Substituted Quinoxaline-Type Piperidine Compounds has an ORL-1 GTP Emax (%) of about 85% or greater. In another embodiment, agonist Cyclic Urea- or Lactam-Substituted Quinoxaline-Type Piperidine Compounds has an ORL-1 GTP Emax (%) of about 95% or greater. In another embodiment, agonist Cyclic Urea- or Lactam-Substituted Quinoxaline-Type Piperidine Compounds has an ORL-1 GTP Emax (%) of about 100% or greater. In certain embodiments, a Cyclic Urea- or Lactam-Substituted Quinoxaline-Type Piperidine Compound of the disclosure acting as a partial agonist has an ORL-1 GTP Emax (%) of less than about 10%. In one embodiment, partial agonist Cyclic Urea- or Lactam-Substituted Quinoxaline-Type Piperidine Compounds has an ORL-1 GTP Emax (%) of less than about 20%. In another embodiment, partial agonist Cyclic Urea- or Lactam-Substituted Quinoxaline-Type Piperidine Compounds has an ORL-1 GTP Emax (%) of less than about 30%. In another embodiment, partial agonist Cyclic Urea- or Lactam-Substituted Quinoxaline-Type Piperidine Compounds has an ORL-1 GTP Emax (%) of less than about 40%. In another embodiment, partial agonist Cyclic Urea- or Lactam-Substituted Quinoxaline-Type Piperidine Compounds has an ORL-1 GTP Emax (%) of less than about 50%.

In certain embodiments, a Cyclic Urea- or Lactam-Substituted Quinoxaline-Type Piperidine Compound has a binding affinity ($K_i$) for the human μ-opioid receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

In certain embodiments, a Cyclic Urea- or Lactam-Substituted Quinoxaline-Type Piperidine Compound has a $K_i$ (nM) for the human μ-opioid receptor of about 3000 or less for binding to a human μ-opioid receptor, or about 1000 or less, or about 650 or less, or about 525 or less, or about 250 or less, or about 100 or less, or about 10 or less, or about 1 or less. In one embodiment, a Cyclic Urea- or Lactam-Substituted Quinoxaline-Type Piperidine Compound has substantially no activity.

μ GTP $EC_{50}$ is the concentration of a compound providing 50% of the maximal response for the compound at a human μ-opioid receptor. In certain embodiments, a Cyclic Urea- or Lactam-Substituted Quinoxaline-Type Piperidine Compound has a μ GTP $EC_{50}$ (nM) of about 20,000 or less to stimulate human μ-opioid receptor function, or about 10,000 or less. In other embodiments, a Cyclic Urea- or Lactam-Substituted Quinoxaline-Type Piperidine Compound has a μ GTP $EC_{50}$ (nM) of about 5000 or less to stimulate human μ-opioid receptor function, or about 4100 or less, or about 3100 or less, or about 2000 or less, or about 1000 or less, or about 100 or less, or about 10 or less, or about 1 or less, or about 0.4 or less.

μ GTP Emax (%) is the maximal effect elicited by a compound relative to the effect elicited by DAMGO, a standard μ agonist. In certain embodiments, a Cyclic Urea- or Lactam-Substituted Quinoxaline-Type Piperidine Compound has a μ GTP Emax (%) of about 10% or greater, or about 20% or greater, or about 50% or greater, or about 65% or greater, or about 75% or greater, or about 88% or greater. In other embodiments, a Cyclic Urea- or Lactam-Substituted Quinoxaline-Type Piperidine Compound has a µ GTP Emax (%) of about 10% or less, or about 5% or less, or about 2% or less.

In one embodiment, a Cyclic Urea- or Lactam-Substituted Quinoxaline-Type Piperidine Compound has a $K_i$ (nM) of about 20,000 or less for binding to a human κ-opioid receptor. In another embodiment, a Cyclic Urea- or Lactam-Substituted Quinoxaline-Type Piperidine Compound has substantially no activity. In certain embodiments, a Cyclic Urea- or Lactam-Substituted Quinoxaline-Type Piperidine Compound that bind to the human x-opioid receptor has a $K_i$ (nM) of about 10,000 or less, or about 5000 or less, or about 1000 or less, or about 500 or less, or about 300 or less, or about 100 or less, or about 50 or less, or about 20 or less, or about 15 or less.

κ GTP $EC_{50}$ is the concentration of a compound providing 50% of the maximal response for the compound at a human κ-opioid receptor. In certain embodiments, a Cyclic Urea- or Lactam-Substituted Quinoxaline-Type Piperidine Compound has a κ GTP $EC_{50}$ (nM) of about 20,000 or less to stimulate human κ-opioid receptor function, or about 10,000 or less, or about 5000 or less, or about 2000 or less, or about 1500 or less, or about 800 or less, or about 500 or less, or about 300 or less, or about 100 or less, or about 50 or less, or about 25 or less.

κ GTP Emax (%) is the maximal effect elicited by a compound relative to the effect elicited by U69,593. In certain embodiments, a Cyclic Urea- or Lactam-Substituted Quinoxaline-Type Piperidine Compound has a κ GTP Emax (%) of about 10% or greater, or about 15% or greater, or about 30% or greater, or about 40% or greater, or about 45% or greater, or about 75% or greater, or about 90% or greater. In other embodiments, a Cyclic Urea- or Lactam-Substituted Quinoxaline-Type Piperidine Compound has a κ GTP Emax (%) of about 10% or less, or about 5% or less, or about 2% or less.

In one embodiment, a Cyclic Urea- or Lactam-Substituted Quinoxaline-Type Piperidine Compound has a $K_i$ (nM) of about 20,000 or less for binding to a human δ-opioid receptor. In another embodiment, a Cyclic Urea- or Lactam-Substituted Quinoxaline-Type Piperidine Compound has substantially no activity. In other embodiments, a Cyclic Urea- or Lactam-Substituted Quinoxaline-Type Piperidine Compound that binds to the human δ-opioid receptor has a $K_i$ (nM) of about 10,000 or less, or about 9000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less.

δ GTP $EC_{50}$ is the concentration of a compound providing 50% of the maximal response for the compound at a human δ-opioid receptor. In certain embodiments, a Cyclic Urea- or Lactam-Substituted Quinoxaline-Type Piperidine Compound has a δ GTP $EC_{50}$ (nM) of about 20,000 or less to stimulate human δ-opioid receptor function, or about 10,000 or less, or about 1000 or less, or about 100 or less, or about 90 or less, or about 50 or less, or about 25 or less or less.

δ GTP Emax (%) is the maximal effect elicited by a compound relative to the effect elicited by met-enkephalin. In certain embodiments, a Cyclic Urea- or Lactam-Substituted Quinoxaline-Type Piperidine Compound has a δ GTP Emax (%) of about 10% or greater, or about 30% or greater, or about 50% or greater, or about 75% or greater, or about 90% or greater, or about 100% or greater. In other embodiments, a Cyclic Urea- or Lactam-Substituted Quinoxaline-Type Piperidine Compound has a δ GTP Emax (%) of about 10% or less, or about 5% or less, or about 2% or less.

The Cyclic Urea- or Lactam-Substituted Quinoxaline-Type Piperidine Compounds can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal being administered a Cyclic Urea- or Lactam-Substituted Quinoxaline-Type Piperidine Compound (i.e., a first therapeutic agent) a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range. An Cyclic Urea- or Lactam-Substituted Quinoxaline-Type Piperidine Compound and the second therapeutic agent combined can act either additively or synergistically to treat the same Condition, or they may act independently of each other such that the Cyclic Urea- or Lactam-Substituted Quinoxaline-Type Piperidine Compound treats or prevents a first Condition and the second therapeutic agent treats or prevents a second disorder, which can be the same as the first Condition or another disorder. In one embodiment of the disclosure, where a second therapeutic agent is administered to an animal for treatment of a Condition (e.g., pain), the minimal effective amount of the Cyclic Urea- or Lactam-Substituted Quinoxaline-Type Piperidine Compound will be less than its minimal effective amount would be where the second therapeutic agent is not administered. In this embodiment, the Cyclic Urea- or Lactam-Substituted Quinoxaline-Type Piperidine Compound and the second therapeutic agent can act synergistically to treat or prevent a Condition. In one embodiment, a Cyclic Urea- or Lactam-Substituted Quinoxaline-Type Piperidine Compound is administered concurrently with a second therapeutic agent as a single composition comprising an effective amount of a Cyclic Urea- or Lactam-Substituted Quinoxaline-Type Piperidine Compound and an effective amount of the second therapeutic agent. Alternatively, a composition comprising an effective amount of a Cyclic Urea- or Lactam-Substituted Quinoxaline-Type Piperidine Compound and a second composition comprising an effective amount of the second therapeutic agent are concurrently administered. In another embodiment, an effective amount of a Cyclic Urea- or Lactam-Substituted Quinoxaline-Type Piperidine Compound is administered prior or subsequent to administration of an effective amount of the second therapeutic agent. In this embodiment, the Cyclic Urea- or Lactam-Substituted Quinoxaline-Type Piperidine Compound is administered while the second therapeutic agent exerts its therapeutic effect, or the second therapeutic agent is administered while the Cyclic Urea- or Lactam-Substituted Quinoxaline-Type Piperidine Compound exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., eds., 9th Ed., McGraw-Hill, New York 1996), and Hanson, "Analgesic, Antipyretic and Anti-Inflammatory Drugs," pp. 1196-1221 in *Remington: The Science and Practice of Pharmacy Vol. II* (Gennaro, ed., 19th Ed., Mack Publishing, Easton, Pa., 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocominine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, tanazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the disclosure is prepared by a method comprising admixing a Cyclic Urea- or Lactam-Substituted Quinoxaline-Type Piperidine Compound or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the Cyclic Urea- or Lactam-Substituted Quinoxaline-Type Piperidine Compound is present in the composition in an effective amount.

The disclosure further provides kits that can simplify the handling and administration of a Cyclic Urea- or Lactam-Substituted Quinoxaline-Type Piperidine Compound to an animal.

A typical kit of the disclosure comprises a unit dosage form of a Cyclic Urea- or Lactam-Substituted Quinoxaline-Type Piperidine Compound. In one embodiment, the unit dosage form comprises a first container, which can be sterile, containing an effective amount of a Cyclic Urea- or Lactam-Substituted Quinoxaline-Type Piperidine Compound and a pharmaceutically acceptable carrier or excipient. The kit can further comprise a label or printed instructions instructing the use of the Cyclic Urea- or Lactam-Substituted Quinoxaline-Type Piperidine Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Cyclic Urea- or Lactam-Substituted Quinoxaline-Type Piperidine Compound, an effective amount of a second therapeutic agent and a pharmaceutically acceptable carrier or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

Certain Examples below relate to the synthesis of illustrative Cyclic Urea- or Lactam-Substituted Quinoxaline-Type Piperidine Compounds.

5.1 Example 1

Synthesis of Cyclic Urea- or Lactam-Substituted Quinoxaline-Type Piperidine Compound B9a by Method 1

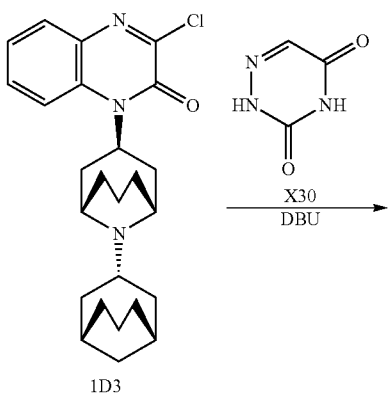

1D3

265
-continued

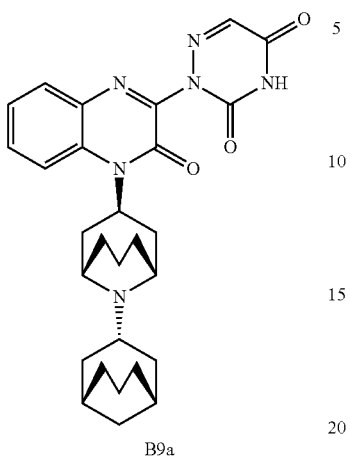

B9a

Compound 1D3,1-((1R,1'R,3R,3'R,5S,5'S)-[3,9'-bi(9'-azabicyclo[3.3.1]nonan)]-3'-yl)-3-chloroquinoxalin-2(1H)-one, was prepared as described in Example 7 herein.

Under a nitrogen atmosphere, to a solution of Compound 1D3 (0.822 mmol, 350 mg) in NMP (7 mL) at a temperature of about 25° C. was added 1,2,4-triazine-3,5(2H,4H)-dione (Compound X30, 2.465 mmol, 279 mg, Sigma-Aldrich, St. Louis, Mo.) and 1,8-diazabicyclo[5,4,0]undec-7-ene ("DBU," i.e., 2,3,4,6,7,8,9,10-octahydropyrimido[1,2-a]azepine, 4.10 mmol, 0.619 mL, Sigma-Aldrich). The resulting reaction mixture was heated to 120° C. and stirred at that temperature for 2 hours. Thereafter, the mixture was cooled to a temperature of about 25° C., diluted with 5% aqueous citric acid:brine (1:1), and extracted with EtOAc:CHCl$_3$ (5:2). The organic portion was dried (over Na$_2$SO$_4$), and evaporated to dryness to provide an oil which was chromatographed on a silica-gel column (Yamazen Corp. W001, Osaka, Japan) eluted with a gradient of from 10:90 MeOH (28% NH$_4$OH):CHCl$_3$ to 50:50 MeOH (28% NH$_4$OH):CHCl$_3$. The fractions containing the product were combined, evaporated to dryness under reduced pressure, and triturated with MeOH. The resulting solid was filtered and dried under reduced pressure at 80° C. to provide 115.3 mg of Cyclic Urea- or Lactam-Substituted Quinoxaline-Type Piperidine Compound B9a, 2-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-1,2,4-triazine-3,5(2H,4H)-dione, as a yellow solid (yield 28%).

The identity of Cyclic Urea- or Lactam-Substituted Quinoxaline-Type Piperidine Compound B9a was confirmed using H-NMR and LC/MS.

Cyclic Urea- or Lactam-Substituted Quinoxaline-Type Piperidine Compound B9a: $^1$H-NMR: $\delta_H$ (ppm, 400 MHz, CDCl$_3$ with one drop each of DCl and d4-MeOH): 1.31-2.12 (m, 14H), 2.13-2.35 (m, 2H), 2.41-3.12 (m, 18H), 4.05-4.33 (m, 3H), 6.32-6.50 (m, 1H), 7.46 (dd, J=7.81, 7.81 Hz, 1H), 7.79 (d, J=7.89 Hz, 1H), 7.88 (dd, J=11.1, 7.88 Hz, 1H), 8.78 (d, J=8.73 Hz, 1H); LC/MS: m/z 503.2 [M+H]$^+$ (Calc: 502).

266

5.2 Example 2

Synthesis of Cyclic Urea- or Lactam-Substituted Quinoxaline-Type Piperidine Compound B9a by Method 2

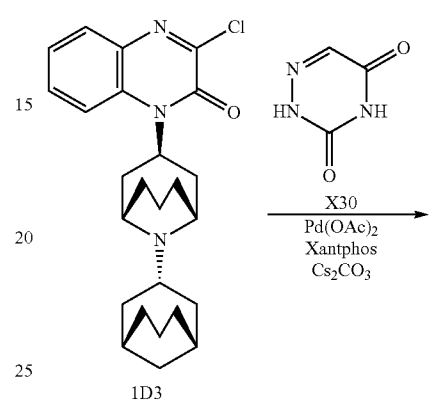

1D3

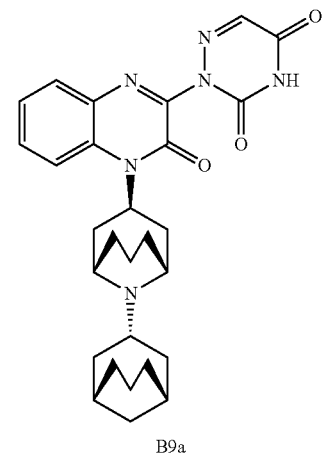

B9a

Compound 1D3 was prepared as described in Example 7 herein.

To a suspension of Compound 1D3 (0.5 mmol, 213 mg) and Compound X30 (1.5 mmol, 170 mg) in 1,4-dioxane (7.5 mL) at a temperature of about 25° C. was added palladium (II) acetate (Pd(OAc)$_2$, 0.25 mmol, 56 mg, Sigma-Aldrich), 4,5-bis(diphenylphosphino)-9,9-dimethylxanthene (Xantphos, 0.5 mmol, 289 mg, Sigma-Aldrich), and Cs$_2$CO$_3$ (1.0 mmol, 326 mg, Sigma-Aldrich). The resulting reaction mixture was heated to 110° C. and stirred at that temperature for 1.5 hours. Thereafter, the mixture was cooled to a temperature of about 25° C., quenched with water, and extracted twice with CHCl$_3$ (100 mL for each extraction). The organic portions were combined, dried (over Na$_2$SO$_4$), and evaporated to dryness under reduced pressure to provide a product which was chromatographed on a flash column eluted with a gradient of from 0:100 MeOH (10% NH$_4$OH):DCM to 20:80 MeOH (10% NH$_4$OH):DCM. The fractions containing the product were combined and, under reduced pressure, evaporated and dried

5.3 Example 3

Synthesis of Cyclic Urea- or Lactam-Substituted Quinoxaline-Type Piperidine Compound B9a by Method 3

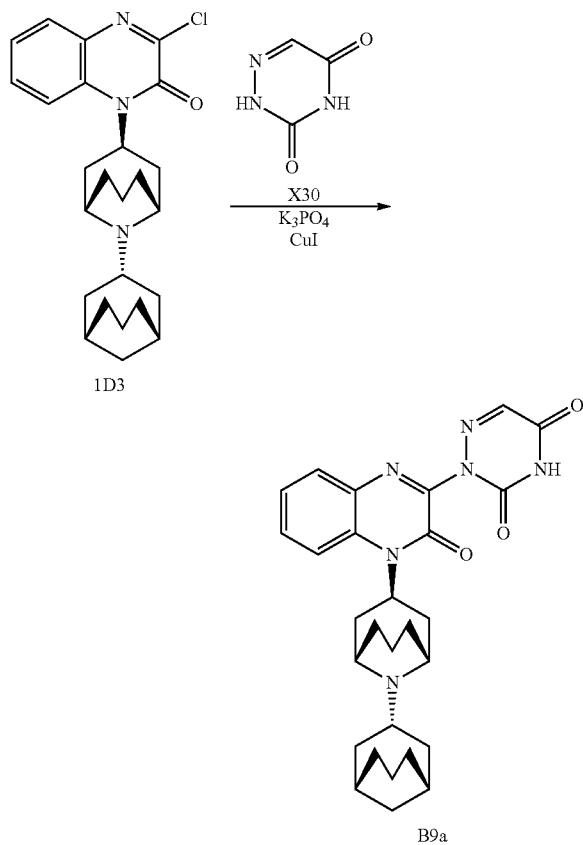

To a suspension of Compound 1D3 (0.47 mmol, 200 mg) and Compound X30 (1.24 mmol, 140 mg) in anhydrous DMSO (3 mL) at a temperature of about 25° C. was added potassium phosphate ($K_3PO_4$, 0.53 mmol, 184 mg, Sigma-Aldrich) and copper(I) iodide (CuI, 0.24 mmol, 50 mg, Sigma-Aldrich). The resulting reaction mixture was heated to 100° C. and stirred at that temperature for 18 hours. Thereafter, the mixture was cooled to a temperature of about 25° C., poured into a dilute aqueous ammonia solution (200 mL), and extracted twice with $CHCl_3$ (200 mL for each extraction). The organic portions were combined, dried (over $MgSO_4$), and evaporated to dryness under reduced pressure to provide a product which was chromatographed on a flash column eluted with a gradient of from 0:100 MeOH (10% $NH_4OH$):DCM to 20:80 MeOH (10% $NH_4OH$):DCM. The fractions containing the product were combined and, under reduced pressure, evaporated and dried to provide Cyclic Urea- or Lactam-Substituted Quinoxaline-Type Piperidine Compound B9a as a white solid (yield 76%).

5.4 Example 4

Synthesis of Cyclic Urea- or Lactam-Substituted Quinoxaline-Type Piperidine Compounds B5a(i) and B22a by Method 4

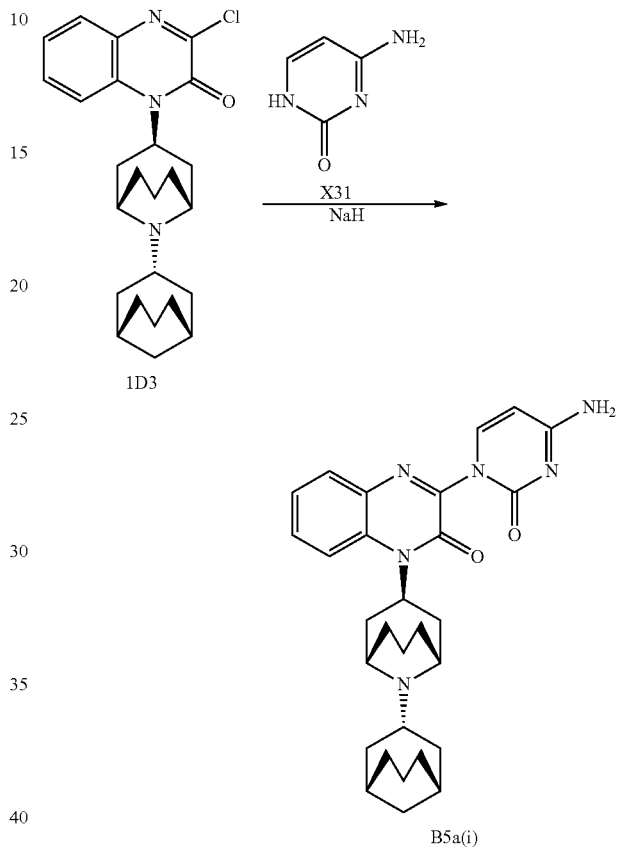

Method 4.1:

Under a nitrogen atmosphere, to a suspension of 4-aminopyrimidin-2(1H)-one (Compound X31, 1.467 mmol, 163 mg, Sigma-Aldrich) in NMP (5 mL) at a temperature of about 25° C. was added NaH (1.174 mmol, 46.9 mg, Sigma-Aldrich). The resulting mixture was heated to 80° C. and stirred at that temperature for 15 minutes. To the mixture was added Compound 1D3 (0.293 mmol, 125 mg). The resulting reaction mixture was stirred at 80° C. for 30 minutes. Thereafter, the mixture was cooled to a temperature of about 25° C., diluted with 10% aqueous citric acid:brine (1:1), extracted with MeOH:$CHCl_3$ (1:4), and washed with brine. The organic portion was dried (over $Na_2SO_4$) and evaporated to dryness to provide an oil which was chromatographed on a silica-gel column (REDISEP RF GOLD 12 g, Teledyne ISCO, Lincoln, Nebr.) eluted with a gradient of from 0:100 MeOH (28% $NH_4OH$):$CHCl_3$ to 50:50 MeOH (28% $NH_4OH$):$CHCl_3$. The fractions containing the product were combined, evaporated to dryness under reduced pressure, and triturated with MeOH:$Et_2O$ (1:1). The resulting solid was filtered and dried under reduced pressure at 80° C. to provide 73.7 mg of Cyclic Urea- or Lactam-Substituted Quinoxaline-Type Piperidine Compound B5a(i), 1-((1R,1'R,3r,3'R,5S,5'S)-[3,9'-bi(9'-azabicyclo[3.3.1]nonan)]-3'-yl)-3-(4-amino-2-oxopyrimidin-1(2H)-yl)quinoxalin-2(1H)-one, as an off-white solid (yield 50.2%).

The identity of Cyclic Urea- or Lactam-Substituted Quinoxaline-Type Piperidine Compound B5a(i) was confirmed using $^1$H-NMR and LC/MS.

Cyclic Urea- or Lactam-Substituted Quinoxaline-Type Piperidine Compound B5a(i): $^1$H-NMR: $\delta_H$ (ppm, 400 MHz, d6-DMSO with one drop of DCl): 1.44-1.73 (m, 11H), 1.93-2.15 (m, 6H), 2.27-2.49 (m, 5H), 2.69-2.80 (m, 2H), 4.04-4.22 (m, 3H), 6.18-6.32 (m, 1H), 6.41 (d, J=7.78 Hz, 1H), 7.53 (d, J=7.53 Hz, 1H), 7.78 (ddd, J=7.91, 7.91, 1.51 Hz, 1H), 7.90 (dd, J=8.03, 1.51 Hz, 1H), 8.11 (d, J=7.78 Hz, 1H), 8.78 (d, J=9.04 Hz, 1H); LC/MS: m/z=501.40 [M+H]$^+$ (Calc: 500).

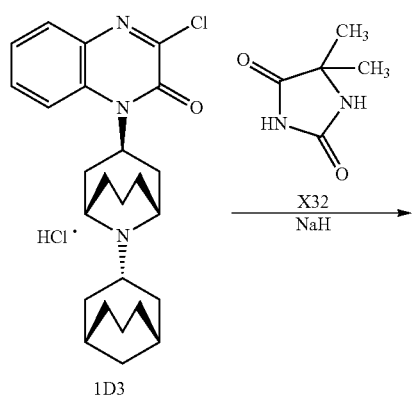

1D3 in EtOAc (2 mL), 2N HCl in EtOAc (2 mL) was added, and the mixture was evaporated to dryness. The resulting solid was triturated with EtOAc, filtered, and dried under reduced pressure at 80° C. to provide 62.0 mg of Cyclic Urea- or Lactam-Substituted Quinoxaline-Type Piperidine Compound B22a, 3-(4-(((1R,1'R,3r,3'R,5S,5'S)-[3,9'-bi(9'-azabicyclo[3.3.1]nonan)]-3'-yl)-3-oxo-3,4-dihydroquinoxalin-2-yl)-5,5-dimethylimidazolidine-2,4-dione, as a-white solid (yield 52%).

The identity of Cyclic Urea- or Lactam-Substituted Quinoxaline-Type Piperidine Compound B22a was confirmed using $^1$H-NMR and LC/MS.

Cyclic Urea- or Lactam-Substituted Quinoxaline-Type Piperidine Compound B22a: $^1$H-NMR: $\delta_H$ (ppm, 400 MHz, d6-DMSO): 1.39-1.74 (m, 18H), 1.97-2.19 (m, 8H), 2.23-2.58 (m, 2H), 2.67-2.81 (m, 2H), 4.01-4.24 (m, 3H), 5.77-5.95 (m, 1H), 7.52 (dd, J=7.63, 7.63 Hz, 1H), 7.81 (dd, J=8.69, 7.32 Hz, 1H), 7.92 (dd, J=7.77, 1.53 Hz, 1H), 8.41 (d, J=9.15 Hz, 1H), 8.76 (s, 1H), 9.13-9.21 (br, 1H); LC/MS: m/z=518.5 [M+H]$^+$ (Calc: 517).

5.5 Example 5

Synthesis of Cyclic Urea- or Lactam-Substituted Quinoxaline-Type Piperidine Compound B25a by Method 5

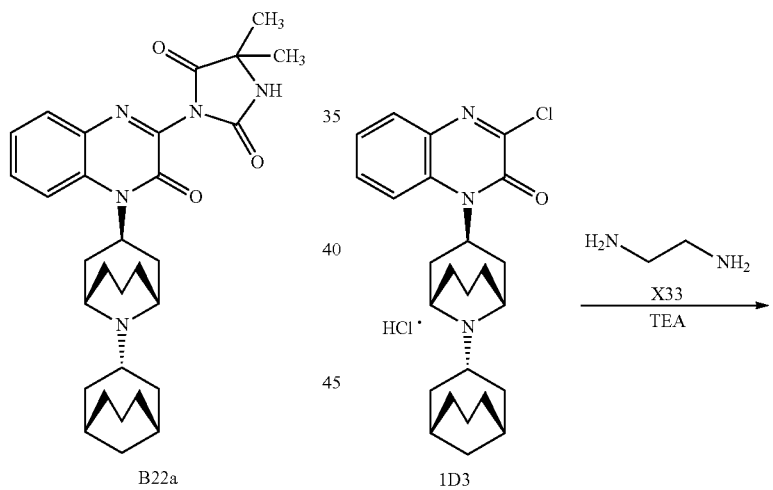

B22a

Method 4.2:

Under a nitrogen atmosphere, to a solution of 5,5-dimethylimidazolidine-2,4-dione (Compound X32, 2.162 mmol, 277 mg, Sigma-Aldrich) in DMA (2 mL) at a temperature of 0° C. was added NaH (2.162 mmol, 86 mg). The resulting mixture was stirred at that temperature for 30 minutes. To the mixture was added a suspension of the hydrochloride of Compound 1D3 (0.216 mmol, 100 mg) in DMA (2 mL). The resulting reaction mixture was heated to 80° C. and stirred at that temperature for 4 hours. Thereafter, the mixture was cooled to a temperature of about 25° C., diluted with water: brine (1:1), and extracted with EtOAc. The organic portion was dried (over Na$_2$SO$_4$) and evaporated to dryness to provide a solid which was chromatographed on an amino silica-gel column (Yamazen Corp. WO93) eluted with a gradient of from 75:25 EtOAc:n-hexane to 100:0 EtOAc:n-hexane to provide a colorless amorphous solid. The solid was dissolved

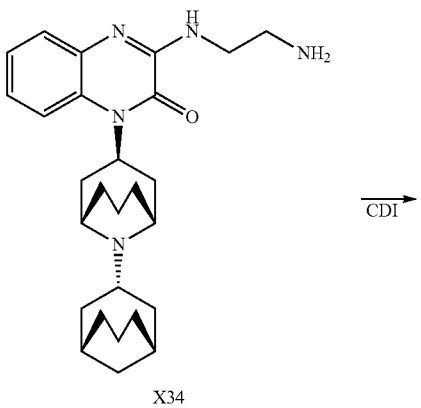

X34

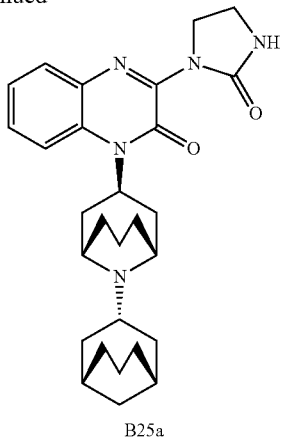

B25a

Under a nitrogen atmosphere, to a solution of the hydrochloride of Compound 1D3 (0.541 mmol, 250 mg) in CH$_2$Cl$_2$ (4 mL) at a temperature of about 25° C. was added TEA (5.41 mmol, 0.750 mL, Sigma-Aldrich), ethane-1,2-diamine (Compound X33, 16.2 mmol, 1.096 mL, Sigma-Aldrich) and THF (4 mL). The resulting reaction mixture was stirred at that temperature for 9 hours. Thereafter, the mixture was evaporated under reduced pressure to provide an oil which was chromatographed on a silica-gel column (Yamazen Corp. W001) eluted with a gradient of from 10:90 MeOH (28% NH$_4$OH):CHCl$_3$ to 40:60 MeOH (28% NH$_4$OH):CHCl$_3$ to provide 209.9 mg of Compound X34, 1-((1R,1'R,3r,3'R,5S,5'S)-[3,9'-bi(9'-azabicyclo[3.3.1]nonan)]-3'-yl)-3-((2-aminoethyl)amino)quinoxalin-2(1H)-one, as a white amorphous solid (yield 86%).

The identity of Compound X34 was confirmed using $^1$H-NMR.

Compound X34: $^1$H-NMR: $\delta_H$ (ppm, 400 MHz, CDCl$_3$ with one drop each of DCl and d4-MeOH): 1.06-1.18 (m, 1H), 1.35-1.93 (m, 13H), 1.93-2.09 (m, 6H), 2.33-2.51 (m, 1H), 2.60-2.77 (m, 2H), 3.00 (t, J=5.95 Hz, 2H), 3.44-3.61 (m, 3H), 3.60 (dt, J=5.95, 5.95 Hz, 2H), 5.03-5.27 (m, 1H), 6.60-6.69 (m, 1H), 7.18-7.28 (m, 2H), 7.46-7.57 (m, 2H).

Under a nitrogen atmosphere, to a solution of Compound X34 (0.334 mmol, 150 mg) in dioxane (10 mL) at a temperature of about 25° C. was added CDI (0.467 mmol, 76 mg, Sigma-Aldrich). The resulting reaction mixture was stirred at that temperature for 45 minutes, heated to 130° C., and stirred at that temperature for 6 hours. Thereafter, the mixture was cooled to a temperature of about 25° C., diluted with water (10 mL), and filtrated to provide a white solid which was chromatographed on an amino silica-gel column (Yamazen Corp. W091-01) eluted with a gradient of from 0:100 MeOH:CHCl$_3$ to 5:95 MeOH:CHCl$_3$ to provide a white amorphous solid. That solid was chromatographed using a preparative thin layer chromatography apparatus (Merck, alumina-TLC, 1.5 mm×20 cm×20 cm×4 sections, 7.5%:92.5% THF:EtOAc) to provide a white solid which was triturated with 1:1 EtOAc:n-hexane, filtered, and dried under reduced pressure at 90° C. to provide 53.8 mg of Cyclic Urea- or Lactam-Substituted Quinoxaline-Type Piperidine Compound B25a, 1-((1R,1'R,3r,3'R,5S,5'S)-[3,9'-bi(9'-azabicyclo[3.3.1]nonan)]-3'-yl)-3-(2-oxoimidazolidin-1-yl)quinoxalin-2(1H)-one, as a white solid (yield 34%).

The identity of Cyclic Urea- or Lactam-Substituted Quinoxaline-Type Piperidine Compound B25a was confirmed using $^1$H-NMR and LC/MS.

Cyclic Urea- or Lactam-Substituted Quinoxaline-Type Piperidine Compound B25a: $^1$H-NMR: $\delta_H$ (ppm, 400 MHz, d6-DMSO with one drop of TFA): 1.47-1.96 (m, 14H), 2.01-2.23 (m, 6H), 2.28-2.43 (m, 2H), 2.78-2.91 (m, 2H), 3.47 (t, J=7.81 Hz, 2H), 4.01 (t, J=7.03 Hz, 2H), 4.10-4.22 (m, 3H), 5.29-5.45 (m, 1H), 7.25-7.36 (br, 1H), 7.41 (dd, J=7.64, 7.64 Hz, 1H), 7.61 (ddd, J=7.89, 7.89, 1.68 Hz, 1H), 7.70 (dd, J=7.80 Hz, 1H), 7.84 (d, J=8.73 Hz, 1H), 8.19-8.30 (br, 1H); LC/MS: m/z=476.35 [M+H]$^+$ (Calc: 475).

5.6 Example 6

Synthesis of Compound 1C3

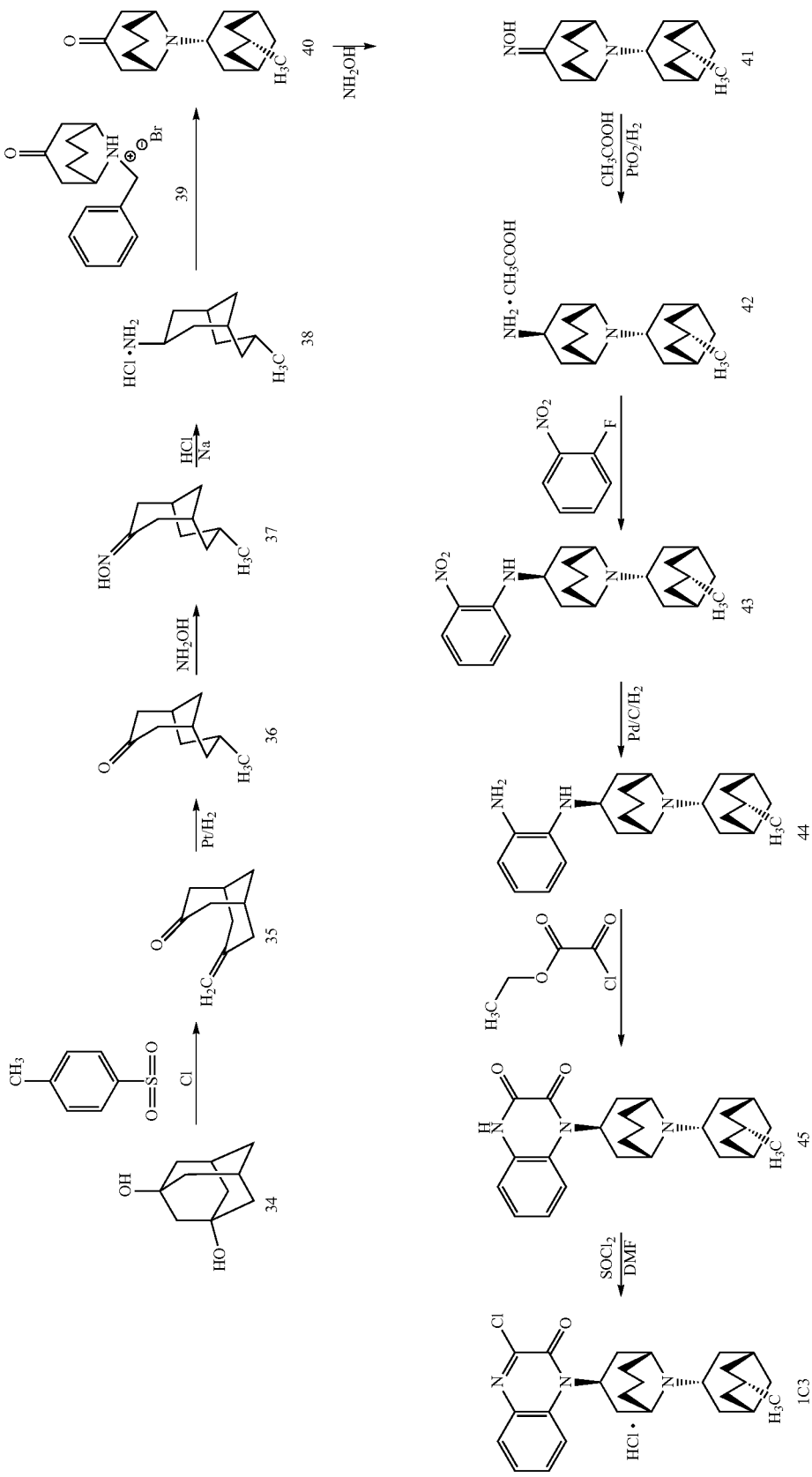

-continued
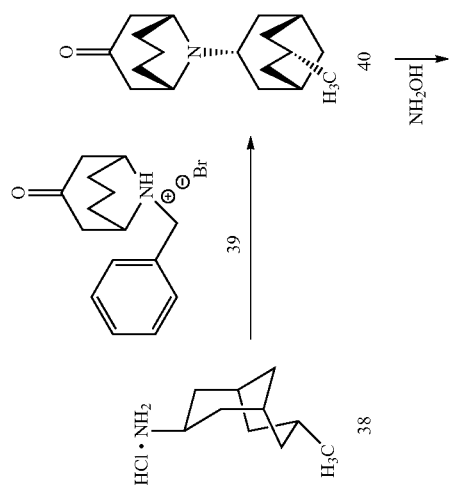

2-Adamantanediol (34, 500 g, 2.97 mol, Sigma-Aldrich), p-tosyl chloride (624 g, 3.27 mol, Sigma-Aldrich), and pyridine (1.5 L) were combined and stirred under an argon atmosphere. The reaction mixture was heated to a temperature in the range of 68-71° C. and remained at that temperature for 2.5 h. The reaction mixture was cooled to a temperature of about 25° C. and poured into saturated brine (6 L). The resulting mixture was extracted three times with MTBE (4 L for each extraction). The organic portions were combined, dried (over $MgSO_4$), filtered, and concentrated onto lkg silica gel (pre-treated with hexanes:TEA). The adsorbed material was chromatographed on 1.5 kg silica eluted sequentially with 1:10 EtOAc:hexanes (5 L) then 2:10 EtOAc:hexanes (5 L). All product fractions were combined and evaporated under reduced pressure to provide a residue. The residue was suspended in deionized water (2 L), stirred for 10 min, and filtered under reduced pressure to remove any excess reactants. The remaining solids were taken up in MTBE (2 L), dried (over $MgSO_4$), filtered, and evaporated under reduced pressure to provide 301 g of Compound 35, (1R,5S)-7-methylenebicyclo[3.3.1]nonan-3-one, as a white crystalline solid (yield 67%).

The identity of Compound 35 was confirmed using $^1$H-NMR and TLC.

Compound 35: $^1$H-NMR: $\delta_H$ (ppm, 400 MHz, $CDCl_3$): 4.79 (2H, s), 2.51 (8H, m), 2.29 (2H, m), 1.94 (2H, m), 1.60 (1H, m); TLC ($SiO_2$) 1:10 EtOAc:hexanes: $R_f$=0.25 (visualized with $KMnO_4$ spray reagent).

Compound 35 (250 g, 1.66 mol) was divided into five equal batches. Under a hydrogen atmosphere, the first batch was hydrogenated over platinum black (5 g, Sigma-Aldrich) at 50 psi in dry 99:1 cyclohexane:EtOAc (200 mL) for 2 h. The reaction mixture was decanted and the remaining catalyst washed with cyclohexane until no product remained as determined by TLC. The reaction flask was then recharged with the next batch of Compound 35, cyclohexane (200 mL), and hydrogen and the reaction mixture was hydrogenated at 50 psi for 2 h. This procedure was repeated until all batches were reacted. All filtrates were combined, filtered through CELITE, and concentrated at a temperature of about 25° C. to provide Compound 36, 7-methylbicyclo[3.3.1]nonan-3-one, as a colorless oil.

The identity of Compound 36 was confirmed using $^1$H-NMR and TLC.

Compound 36: $^1$H-NMR: $\delta_H$ (ppm, 400 MHz, $CDCl_3$): 2.42 (4H, m), 2.26 (2H, m), 1.98-2.00 (3H, m), 1.65 (1H, m), 1.54 (1H, m), 0.80 (1H, m); TLC ($SiO_2$) 2:10 EtOAc:hexanes: $R_f$=0.30 (visualized with $KMnO_4$ spray reagent).

Compound 36, taken directly from the previous step, was taken up in AcOH (1 L). To this was added 50% aqueous $NH_2OH$ (100 mL, Sigma-Aldrich). With stirring, the reaction mixture was heated to a gentle reflux and refluxed for 1 h. The mixture was cooled to a temperature of about 25° C. and slowly poured into 2.5M $Na_2CO_3$ aqueous solution (5 L) with stirring. Thereafter, the mixture was stirred vigorously for 1 h. Deionized water (1 L) was added and the mixture was stirred for another 0.5 h. The precipitate that formed was collected by filtering under reduced pressure and washed with deionized water (2 L). The residue was taken up in DCM (1 L), dried (over $MgSO_4$), filtered, and evaporated under reduced pressure to provide 231.5 g of Compound 37, 7-methylbicyclo[3.3.1]nonan-3-one oxime, as a white fluffy solid (85% yield from Compound 35).

The identity of Compound 37 was confirmed using $^1$H-NMR.

Compound 37: $^1$H-NMR: $\delta_H$ (ppm, 400 MHz, $CDCl_3$): 3.21 (1H, d), 2.05-2.41 (4H, m), 1.73-2.11 (4H, m), 1.51-1.73 (2H, m), 1.33 (1H, d), 0.82 (4H, m), 0.63 (1H, t).

To a three neck 5 L round bottom flask equipped with an overhead stirrer, 1 L pressure equalizing dropping funnel, and temperature probe was added toluene (about 3 L) and Na metal (67.17 g, 2.8 mol, Sigma-Aldrich). Under an argon atmosphere, the mixture was heated to a gentle reflux until the Na metal became molten. A solution of a portion of Compound 37 (66.66 g, 0.40 mol) in dry isopropyl alcohol (230 mL) was then added dropwise via the dropping funnel over 1.5 h. With stirring, the resulting reaction mixture was heated to reflux and refluxed for 16 h. After cooling to a temperature of about 25° C., the following materials were added in sequential order: EtOH (164 mL) dropwise over 15 min, 1:1 EtOH:$H_2O$ (164 mL) dropwise over 15 min, and water (500 mL) dropwise over 30 min. The resulting mixture was stirred for 2 h. The mixture was poured into a 6 L separatory funnel and the organic layer was separated. The aqueous portion was extracted three times with $Et_2O$ (1 L for each extraction).

The process just described was repeated twice more with 66.66 g of Compound 37 being used each time. All organic portions were combined, dried (over $MgSO_4$), and filtered into a 6 L Erlenmeyer flask. To the mixture was added 2M HCl in $Et_2O$ (1.5 L, 2.5 eq). The mixture was allowed to stir and cool in an ice:MeOH bath for 1 h. The solids that formed were filtered under reduced pressure and dried under reduced pressure at 50° C. for 18 h to provide 100.01 g of Compound 38, (3s,7s)-7-methylbicyclo[3.3.1]nonan-3-amine hydrochloride, as a white crystalline solid. The filtrate was evaporated under reduced pressure to provide a residue which was triturated with $Et_2O$ (2 L). The solids that remained were filtered and washed with $Et_2O$ (2 L) to provide 87.1 g of a second crop of Compound 38 after drying (overall yield 39%).

The identity of Compound 38 was confirmed using $^1$H-NMR.

Compound 38: $^1$H-NMR: $\delta_H$ (ppm, 400 MHz, $CDCl_3$): 8.28 (3H, bs), 3.55 (1H, m), 2.25 (2H, m), 1.81-2.09 (4H, m), 1.85 m), 1.61 (3H, m) 1.08 (1H, d), 0.70-0.88 (5H, m).

Compound 38 (87.1 g, 0.463 mol), 9-benzyl-3-oxo-9-azoniabicyclo[3.3.1]nonane bromide (39, 165.20 g, 0.509 mol, Sigma-Aldrich), potassium carbonate (67.83 g, 0.491 mol), EtOH (1.07 L), and water (346 mL) were combined. The resulting reaction mixture was stirred for about 16 h at a temperature of about 25° C. The reaction mixture was then heated to reflux and refluxed for 3 h. Thereafter, the mixture was cooled to a temperature of about 25° C. then further cooled to 5° C. in an ice/MeOH bath and allowed to stir for 30 min at that temperature. The solids that formed were filtered under reduced pressure, washed with deionized water, and dried under reduced pressure to provide 102.1 g of Compound 40, (1R,3r,5S,7s)-7-methyl-9'-aza[3,9'-bi(bicyclo[3.3.1]nonan)]-3'-one, as an off-white crystalline solid (yield 80%).

The identity of Compound 40 was confirmed using $^1$H-NMR.

Compound 40: $^1$H-NMR: $\delta_H$ (ppm, 400 MHz, CDCl$_3$): 3.68 (2H, m), 3.05 (1H, m), 2.61 (2H, m), 2.25 (4H, m), 1.98 (1H, m), 1.85 (4H, m), 1.49-1.78 (7H, m), 1.25 (2H, m), 1.07 (1H, d), 0.86 (3H, d), 0.78 (2H, t).

Compound 40 (67 g, 0.243 mol), THF (500 mL), and AcOH (41.78 mL, 0.730 mol) were combined. To this mixture was added 50% aqueous NH$_2$OH (45 mL, 0.730 mol). With stirring, the resulting reaction mixture was heated to reflux and refluxed for 1 h. The mixture was cooled to a temperature of about 25° C. and deionized water was added (500 mL). Potassium carbonate (100 g, 0.730 mol) in deionized water (500 mL) was then added in one portion. The resulting mixture was stirred and cooled in an ice bath for 1 h. The solids that formed were filtered under reduced pressure and dried under reduced pressure at 60° C. to provide Compound 41, (1R,3r,5S,7s)-7-methyl-9'-aza[3,9'-bi(bicyclo [3.3.1]nonan)]-3'-one oxime (yield >99%).

The identity of Compound 41 was confirmed using $^1$H-NMR.

Compound 41: $^1$H-NMR: $\delta_H$ (ppm, 400 MHz, CD$_3$OD): 3.76 (1H, m), 3.45 (2H, m), 3.18 (1H, m), 3.02 (1H, m), 2.62 (1H, m), 2.27 (4H, m), 1.78-2.08 (7H, m), 1.67 (1H, m), 1.58 (2H, m), 1.46 (1H, m), 1.22 (2H, t), 1.09 (1H, d), 0.85 (5H, m).

Compound 41 (70.01 g, 0.241 mol) was taken up in AcOH (400 mL). This mixture was divided into two batches. Under a hydrogen atmosphere, to each batch was added platinum (IV) oxide (5.98 g, 0.2 eq, Sigma-Aldrich) and each batch was then hydrogenated at 50 psi for 16 h to 18 h. The batches were combined and filtered through CELITE. The filter cake was washed with AcOH (500 mL). The filtrate was concentrated under reduced pressure at 70° C. to provide an oil. To the oil was added MTBE (6 L). The mixture was stirred and cooled to 0° C. for 1 h. The white precipitate that formed was filtered under reduced pressure, washed with Et$_2$O (2 L), and dried under reduced pressure to provide 76.2 g of Compound 42, (1R,1R,3 r,3'R,5S,5'S,7S)-7-methyl-9'-aza[3,9'-bi(bicyclo [3.3.1]nonan)]-3'-amine acetate, as a white solid (yield 94%).

The identity of Compound 42 was confirmed using $^1$H-NMR and LC/MS.

Compound 42: $^1$H-NMR: $\delta_H$ (ppm, 400 MHz, CD$_3$OD): 3.73 (2H, m), 3.55 (1H, m), 2.46 (2H, m), 2.24 (2H, m), 1.75-2.12 (11H, m), 1.45-1.75 (4H, m), 1.28 (4H, m), 1.06 (1H, d), 0.89 (3H, d), 0.80 (2H, t); LC/MS (t$_r$=1.689 min): m/z=277.3 [M+H]$^+$ (Calc: 276.5).

Compound 42 (80.0 g, 0.23 mol), 1-fluoro-2-nitrobenzene (35.69 g, 0.253 mol, Sigma-Aldrich), and potassium carbonate (95.36 g, 0.69 mol) were combined in dry DMF (400 mL). The reaction mixture was heated to 110° C. under an argon atmosphere for 1 h then cooled to a temperature of about 25° C. Deionized water (2 L) was added and the mixture was stirred and cooled in an ice/MeOH bath for 1 h. The resulting solids were filtered under reduced pressure, washed with deionized water (4 L), and dried under reduced pressure to provide 66.81 g of Compound 43, (1R,1'R,3r,3'R,5S,5'S,7S)-7-methyl-N-(2-nitrophenyl)-9'-aza[3,9'-bi(bicyclo[3.3.1] nonan)]-3'-amine, as a orange solid (yield 73%).

The identity of Compound 43 was confirmed using $^1$H-NMR and LC/MS.

Compound 43: $^1$H-NMR: $\delta_H$ (ppm, 400 MHz, CDCl$_3$): 8.17 (1H, d), 8.01 (1H, m), 7.43 (1H, t), 6.93 (1H, d), 6.61 (1H, t), 3.95 (1H, m), 3.45 (2H, m), 3.06 (1H, m), 2.48 (2H, m), 2.20 (2H, m), 1.87-2.08 (4H, m), 1.45-1.89 (6H, m), 1.35 (2H, t), 0.95-1.22 (5H, m), 0.87 (5H, m); LC/MS (t$_r$=2.732 min): m/z=398.4 [M+H]$^+$ (Calc: 397.6).

Compound 43 (30.0 g, 75.57 mmol) was taken up in DCM (100 mL). Under a hydrogen atmosphere, to this was added Pd/C (3 g) and, with stirring, the reaction mixture was hydrogenated at 50 psi for 2 h at a temperature of about 25° C. to provide Compound 44, N$^1$-((1R,1'R,3r,3'R,5S,5'S,7 S)-7-methyl-[3,9'-bi(9'-azabicyclo[3.3.1]nonan)]-3'-yl)benzene-1,2-diamine.

The identity of Compound 44 was confirmed using LC/MS.

Compound 44: LC/MS (t$_r$=2.045 min): m/z=368.9 [M+H]$^+$ (Calc: 367.6).

The reaction mixture containing Compound 44, taken directly from the previous step, was filtered through CELITE. Ethyl 2-chloro-2-oxoacetate (12.65 mL, 113.36 mmol, Sigma-Aldrich) was added and the reaction mixture was stirred at a temperature of about 25° C. for 30 min. Thereafter, the mixture was evaporated under reduced pressure in a rotary evaporator to provide a residue. The residue was taken up in EtOH (800 mL) and potassium carbonate (31.33 g, 226.71 mmol) was added. The resulting mixture was heated to reflux, refluxed for 1 h, then cooled to a temperature of about 25° C. The solids that formed were filtered and washed with EtOH. The filtered solids were then triturated with deionized water and filtered under reduced pressure to provide 27.49 g of Compound 45, 1-((1R,1'R,3r,3'R,5S,5'S,7S)-7-methyl-[3,9'-bi(9'-azabicyclo[3.3.1]nonan)]-3'-yl)quinoxaline-2,3(1H, 4H)-dione, as an off-white crystalline solid.

The identity of Compound 45 was confirmed using $^1$H-NMR and LC/MS.

Compound 45: $^1$H-NMR: $\delta_H$ (ppm, 400 MHz, d6-DMSO): 7.26 (1H, m), 7.05 (3H, m), 4.80 (1H, bs), 3.44 (2H, m), 3.08 (1H, m), 2.25-2.46 (3H, m), 2.05 (2H, m), 1.93 (4H, m), 1.82 (2H, m), 1.69 (4H, m), 1.54 (1H, m), 1.18 (4H, m), 1.01 (1H, m), 0.88 (5H, m); LC/MS (t$_r$=2.048 min): m/z=422.3 [M+H]$^+$ (Calc: 421.6).

Compound 45, taken directly from the previous step, was suspended in DCE (250 mL) and DMF (2.5 mL). Thionyl chloride (20 equivalents, Sigma-Aldrich) was added dropwise. The resulting reaction mixture was heated to reflux and refluxed for 2 h. The mixture was evaporated under reduced pressure to provide a residue which was triturated with MTBE. The residue was stirred for 1 h in MTBE then filtered under reduced pressure to provide 24.13 g of Compound 1C3, 3-chloro-1-((1R,1'R,3R,3'R,5S,5'S,7S)-7-methyl-9'-aza[3, 9'-bi(bicyclo[3.3.1]nonan)]-3'-yl)quinoxalin-2(1H)-one, as the hydrochloride (82% yield from Compound 43).

The identity of Compound 1C3 was confirmed using $^1$H-NMR and LC/MS.

Compound 1C3: $^1$H-NMR: $\delta_H$ (ppm, 400 MHz, CDCl$_3$): 11.05 (1H, bs), 8.79 (1H, d), 7.79 (2H, m), 7.43 (1H, t), 6.55 (1H, m), 4.10 (2H, m), 3.81 (1H, m), 3.00 (2H, t), 2.92 (1H, m), 2.47 (6H, m), 2.09 (4H, m), 1.50-1.93 (7H, m), 1.39 (1H, d), 0.92 (3H, d), 0.65 (2H, m); LC/MS (t$_r$=2.588 min): m/z=442.3 [M+H]$^+$ (Calc: 440.0).

5.7 Example 7

Synthesis of Compound 1D3

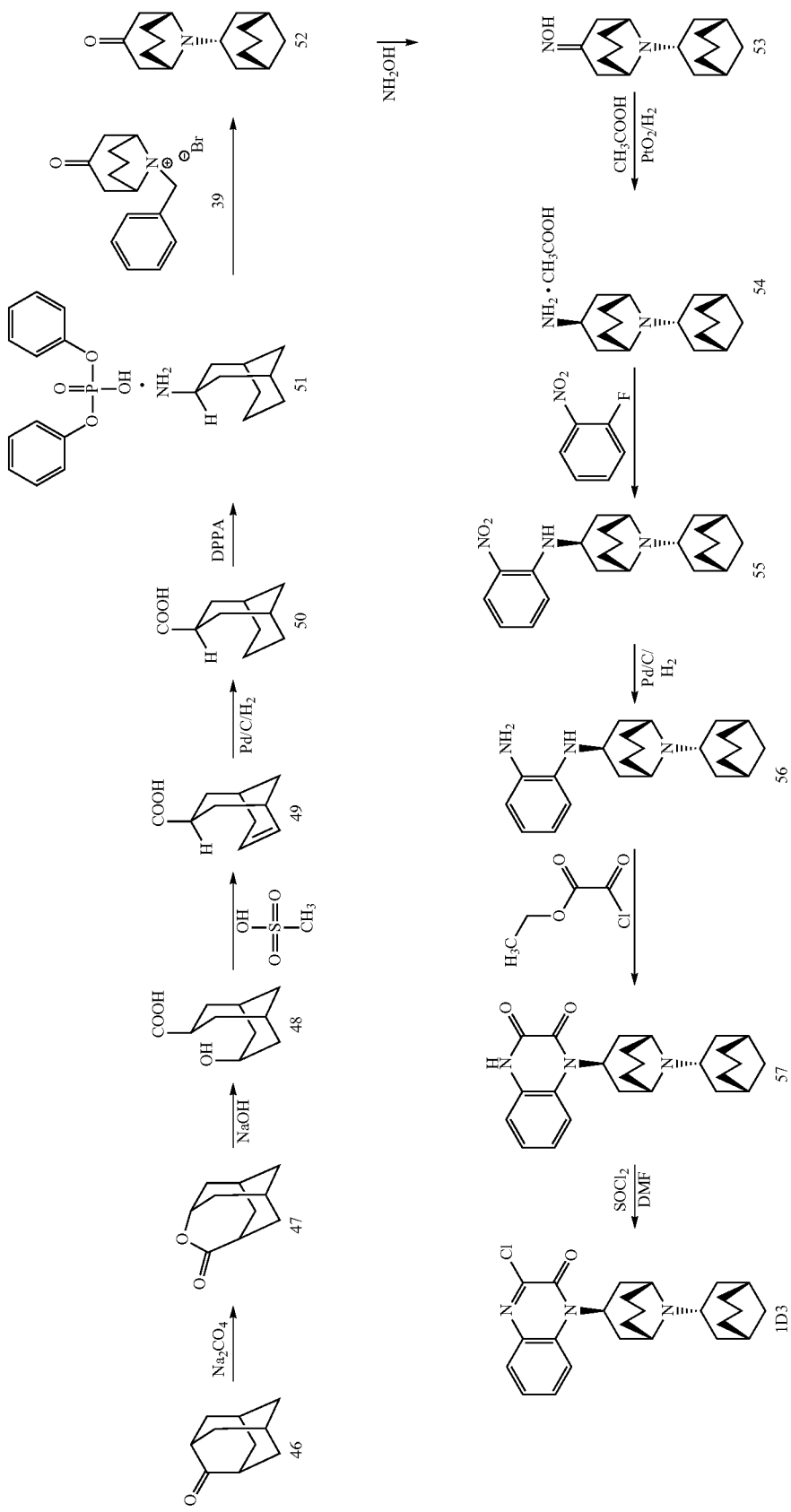

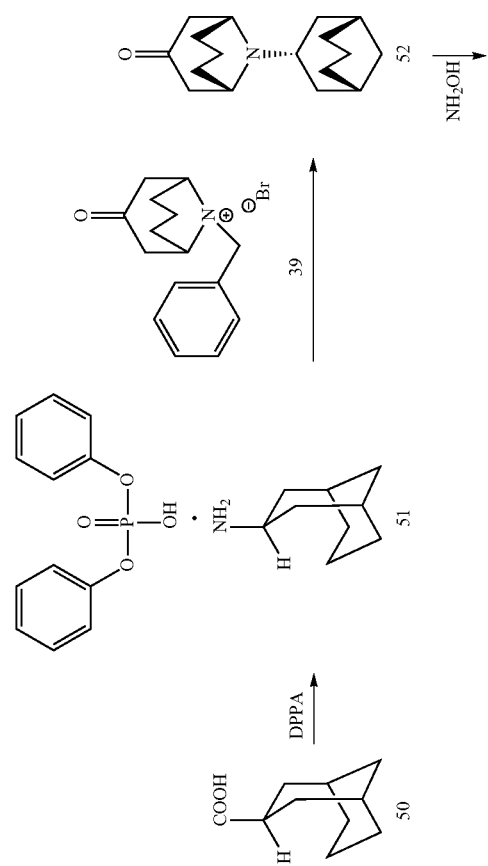

2-Adamantanone (46, 1000 g, 6.66 mol, Sigma-Aldrich) was dissolved in TFA (3 L, Sigma-Aldrich). To this mechanically stirred mixture surrounded by a cooling bath with a temperature maintained at 20° C. was added sodium percarbonate (1254.8 g, 7.99 mol, Sigma-Aldrich) portion-wise over 1 h; the temperature of the reaction mixture increased to 60° C. during the addition. After 2 h additional stirring, deionized water (4 L) was added followed by four extractions with DCM (2 L for each extraction). The organic portions were combined, dried (over $MgSO_4$), filtered, and evaporated under reduced pressure to provide 1180 g of Compound 47, (1R,3r,6s,8S)-4-oxatricyclo[4.3.1.13,8]undecan-5-one, as a white crystalline solid (yield 97%).

The identity of Compound 47 was confirmed using $^1$H-NMR and TLC.

Compound 47: $^1$H-NMR: $\delta_H$ (ppm, 400 MHz, $CDCl_3$): 4.48 (1H, s), 3.06 (1H, m), 2.09 (2H, m), 2.00 (3H, m), 1.95 (2H, m), 1.81 (2H, m), 1.70 (2H, m); TLC ($SiO_2$) 1:1 EtOAc: hexanes: $R_f$=0.8 (visualized with molybdenum blue spray reagent).

Compound 47 (1572.7 g, 9.46 mol) was taken up in MeOH (2 L). To this was added NaOH (2270 g, 56.7 mol) in deionized water (6 L); the temperature of the mixture increased from about 25° C. to 54° C. during the addition. With stirring, the resulting reaction mixture was heated to a gentle reflux and refluxed for 36 h. After cooling to a temperature of about 25° C., the MeOH was removed by vacuum distillation at 60° C. The resulting solution was stirred and acidified with concentrated HCl to a pH of about 2.5. The white precipitate that formed was allowed to stir for 18 h at a temperature of about 25° C. then filtered under reduced pressure to provide partially dried Compound 48, (1R,3r,5S,7r)-7-hydroxybicyclo[3.3.1]nonane-3-carboxylic acid.

The identity of Compound 48 was confirmed using $^1$H-NMR and TLC.

Compound 48: $^1$H-NMR: $\delta_H$ (ppm, 400 MHz, d6-DMSO): 11.88 (1H, s), 4.44 (1H, s), 3.73 (1H, m), 1.95 (4H, m), 1.63 (2H, m), 1.41 (3H, m), 1.22 (2H, m), 1.16 (1H, m); TLC ($SiO_2$) 2:1:0.1 EtOAc:hexanes:AcOH: $R_f$=0.3 (visualized with molybdenum blue spray reagent).

Compound 48, taken directly from the previous step, was suspended in toluene (8 L). To this was added methane sulfonic acid (367 mL, 4.73 mol, Sigma-Aldrich). With stirring, the resulting reaction mixture was heated to reflux and water removed azeotropically for 5 h. After cooling to a temperature of about 25° C., deionized water (4 L) was added with stirring. The organic layer was separated, dried (over $MgSO_4$), filtered, and concentrated to provide Compound 49, (1R,3S,5S)-bicyclo[3.3.1]non-6-ene-3-carboxylic acid.

The identity of Compound 49 was confirmed using $^1$H-NMR and TLC.

Compound 49: $^1$H-NMR: $\delta_H$ (ppm, 400 MHz, $CDCl_3$): 10.45 (1H, bs), 5.85 (1H, m), 5.70 (1H, m), 2.79 (1H, m), 2.37 (2H, m), 2.11 (1H, m), 1.81 (3H, m), 1.61 (4H, m); TLC ($SiO_2$) 1:1:0.1 EtOAc:hexanes:AcOH: $R_f$=0.8 (visualized with molybdenum blue spray reagent).

Compound 49, taken directly from the previous step, was taken up in MeOH (1 L). This was divided into six batches and to each, under a hydrogen atmosphere, was added 10% Pd/C (0.01 mol). The reaction mixtures were each hydrogenated at 50 psi until hydrogen uptake ceased (10 h to 15 h). The mixtures were combined, filtered through CELITE, and NaOH (1kg) in deionized water (400 mL) was added. The mixture was stirred for 4 h at a temperature of about 25° C. The mixture was concentrated under reduced pressure and deionized water (4 L) was added. Concentrated HCl was added until a pH within the range of 3-4 was achieved. The white solid that formed was allowed to stir for 1 h at a temperature of about 25° C. and then was filtered under reduced pressure to provide 1.232 kg of Compound 50, (1R,3r,5S)-bicyclo[3.3.1]nonane-3-carboxylic acid, as an off-white crystalline solid (78% yield from Compound 47).

The identity of Compound 50 was confirmed using $^1$H-NMR and TLC.

Compound 50: $^1$H-NMR: $\delta_H$ (ppm, 400 MHz, $CDCl_3$): 9.25 (1H, bs), 3.13 (1H, m), 1.97 (4H, m), 1.80 (2H, m), 1.70 (5H, m), 1.57 (3H, m); TLC ($SiO_2$) 1:1:0.1 EtOAc:hexanes: AcOH: $R_f$=0.8 (visualized with molybdenum blue spray reagent).

Compound 50 (1108.5 g, 6.59 mol) was taken up in toluene (5 L) in a 20 L reaction vessel. To this was added TEA (1013.3 mL, 7.26 mol). The resulting mixture was stirred and heated to 75° C. under a nitrogen atmosphere. The diphenyl phosphoryl azide (DPPA, 1564 mL, 7.26 mol, Sigma-Aldrich) was diluted with toluene to 2 L total volume and added slowly via addition funnel over 1.5 h; during this addition the temperature increased by about 10° C. to 15° C. The resulting reaction mixture was allowed to stir for 3 h at 75° C. The mixture was then concentrated to a brownish-yellow oil by vacuum distillation at 90° C. The oil was cooled to 5° C. and THF (2.5 L) was added. The mixture was allowed to stir and cool to 0° C. NaOH (792 g, 19.80 mol) in deionized water (3 L) was added over 1 h keeping the temperature below 5° C. The mixture was stirred for 18 h at 5° C. The resulting mixture was then extracted twice with $Et_2O$ (4 L for each extraction). To the remaining aqueous mixture at 5° C. was slowly added concentrated HCl until a pH of about 6-7 was reached; no significant change in temperature occurred during this neutralization. The resulting white precipitate was allowed to stir for 2 h at 0° C. The precipitate was then filtered under reduced pressure and dried under reduced pressure at 50° C. to provide 1.875 kg of Compound 51, (1R,3r,5S)-bicyclo[3.3.1]nonan-3-amine diphenyl phosphate salt, as a white solid (yield 73.1%).

The identity of Compound 51 was confirmed using $^1$H-NMR.

Compound 51: $^1$H-NMR: $\delta_H$ (ppm, 400 MHz, d6-DMSO): 7.78 (2H, s), 7.22 (4H, t), 7.11 (4H, m), 6.93 (2H, t), 3.61 (1H, m), 3.31 (1H, s), 1.93 (4H, m), 1.33-1.60 (10H, m).

Compound 51 (1037.5 g, 2.67 mol) and Compound 39 (1000 g, 3.08 mol) were suspended in EtOH (6.2 L) and deionized water (2 L). To this stirred mixture was added potassium carbonate (390.72 g, 2.83 mol) in deionized water (800 mL). The resulting reaction mixture was stirred for 18 h at a temperature of about 25° C. The reaction mixture was then heated to reflux, about 81° C., and refluxed for 3 h. Thereafter, the mixture was allowed to cool slowly over 4 h to a temperature of about 25° C. with vigorous stirring during which time a white precipitate formed. The mixture was then cooled to 5° C. and allowed to stir for 2 h at that temperature. The white precipitate was filtered under reduced pressure, washed with deionized water (8 L), and dried under reduced pressure at 60° C. to provide 580.1 g of Compound 52, (1R,1'R,3r,5S,5'S)-9'-aza[3,9'-bi(bicyclo[3.3.1]nonan)]-3'-one, as a white crystalline solid (yield 83.1%).

The identity of Compound 52 was confirmed using $^1$H-NMR and TLC.

Compound 52: $^1$H-NMR: $\delta_H$ (ppm, 400 MHz, $CDCl_3$): 3.69 (2H, s), 3.38 (1H, m), 2.62 (2H, m), 2.21 (2H, d), 2.12 (4H, m), 1.85 (2H, m), 1.41-1.78 (14H, m); TLC ($SiO_2$) 7:3 hexanes:EtOAc: $R_f$=0.4 (visualized with potassium iodoplatinate spray).

Compound 52 (580.1 g, 2.22 mol) and THF (4 L) were introduced into a reactor; the reactor temperature control was set to 18° C. 50% Aqueous NH$_2$OH (415 mL, 6.66 mol) was added followed by the slow addition of AcOH (381.25 mL, 6.66 mol). The temperature of the reaction mixture increased to 28° C. during the addition. The reaction mixture was stirred for 16 h at a temperature of about 25° C. then heated to a gentle reflux and refluxed for 1 h. The mixture was cooled to a temperature of about 25° C. and deionized water (4 L) and DCM (4 L) were added. With vigorous stirring, solid NaHCO$_3$ (560 g, 6.66 mol) was then slowly added over 30 min and the mixture was allowed to stir until effervescence ceased. The white precipitate that formed was filtered under reduced pressure, washed with deionized water (1 L), and dried under reduced pressure at 60° C. for 72 h to provide 432.5 g of Compound 53, (1R,1'R,3r,5S,5'S)-9'-aza[3,9'-bi(bicyclo[3.3.1]nonan)]-3'-one oxime, as a white solid (yield 70.6%). The filtrate was allowed to form layers and the organic layer was separated. The aqueous layer was washed three times with DCM (2 L for each wash). The organic portions were combined, dried (over MgSO$_4$), filtered, and evaporated under reduced pressure to provide a pale yellow solid. The solid was triturated with 10:1 Et$_2$O:EtOAc (1 L), stirred for 1 h, and filtered under reduced pressure to provide a residue which was dried under reduced pressure at 60° C. for 72 h to provide an additional 138.4 g of Compound 53 as a white solid (yield 22.6%, overall yield 93.2%).

Compound 53 (570.9 g, 2.07 mol) was taken up in AcOH (3 L). This mixture, with a total dissolved volume of 3.3 L, was divided into ten 330 mL batches. Under a hydrogen atmosphere, to each batch was added platinum (IV) oxide (9.40 g, 0.041 mol) and each batch was then hydrogenated at 50 psi for 16 h to 18 h. The batches were combined and filtered through CELITE. The filter cake was washed with AcOH (500 mL). The filtrate was concentrated under reduced pressure at 70° C. to provide an oil. To the oil was added Et$_2$O (6 L). The mixture was stirred and cooled to 0° C. for 1 h. The white precipitate that formed was filtered under reduced pressure and washed with Et$_2$O (2 L) to provide 253.4 g of Compound 54, (1R,1'R,3r,3'R,5S,5'S)-9'-aza[3,9'-bi(bicyclo[3.3.1]nonan)]-3'-amine acetate (yield 35.3%). The filtrate was evaporated under reduced pressure to provide a residue which was subjected to the same treatment with Et$_2$O. A second crop of 213.7 g of Compound 54 was isolated (yield 32.1%). The filtrate was again evaporated under reduced pressure to provide 201.1 g of Compound 54 (yield 25.4%, overall yield 92.8%).

The identity of Compound 54 was confirmed using $^1$H-NMR.

Compound 54: $^1$H-NMR: δ$_H$ (ppm, 400 MHz, CD$_3$OD): 3.63 (3H, m), 3.42 (1H, m), 2.36 (2H, m), 2.01 (5H, m), 1.89 (5H, m), 1.39-1.78 (13H, m), 1.12 (2H, m).

In part 1, Compound 54 (439.0 g, 1.36 mol) and MeCN (4 L) were introduced into a reactor; the reactor temperature control was set to 25° C. To this mixture were added TEA (412.9 g, 4.08 mol, 3 eq) and 1-fluoro-2-nitrobenzene (194.2 g, 1.38 mol, 1 eq). The reaction mixture was heated to reflux, refluxed for 6 days, then cooled to 0° C. The yellow precipitate that formed was collected by filtration under reduced pressure. The filter cake was washed four times with DCM (2 L for each wash) and the filtrates were set aside. The remaining 91 g of solids, comprising recovered Compound 54, were dried and set aside.

In part 2, the reaction described in part 1 above was repeated using the recovered Compound 54 starting material except DMF (2 L) and K$_2$CO$_3$ (3 eq) were used. After stirring for 2 h at 110° C., the reaction mixture was cooled to a temperature of about 25° C. and poured into deionized water (4 L). This mixture was extracted six times with Et$_2$O (2 L for each extraction). The organic portions were combined and evaporated under reduced pressure to provide a residue.

The residue from part 2 and the filtrates from part 1 were combined and the resulting combination was evaporated under reduced pressure to provide an oil which was triturated with deionized water (4 L). The solids that formed were filtered under reduced pressure and washed with further deionized water. The solids were then dried under reduced pressure at 60° C. for 48 h to provide 402 g of Compound 55, (1R,1'R,3r,3'R,5S,5'S)—N-(2-nitrophenyl)-9'-aza[3,9'-bi(bicyclo[3.3.1]nonan)]-3'-amine, as a bright yellow solid (yield 77%).

Compound 55 (402 g, 1.05 mol) was taken up in MeOH (2.5 L). This mixture was divided into ten batches. Under a hydrogen atmosphere, to each batch was added 10% Pd/C (0.04 mol) and, with stirring, each batch was hydrogenated at 50 psi for 3 h at a temperature of about 25° C. The batches were filtered through CELITE and the filter cake washed with MeOH. The filtrate was evaporated under reduced pressure to provide a residue which was triturated with Et$_2$O then filtered under reduced pressure to provide Compound 56, N$^1$-((1R,1'R,3r,3'R,5S,5'S)-[3,9'-bi(9'-azabicyclo[3.3.1]nonan)]-3'-yl)benzene-1,2-diamine, as a light brown solid (yield >99%).

Compound 57, 1-((1R,1'R,3r,3'R,5S,5'S)-[3,9'-bi(9'-azabicyclo[3.3.1]nonan)]-3'-yl)quinoxaline-2,3(1H,4H)-dione, was prepared from Compound 56 and ethyl 2-chloro-2-oxoacetate in a similar manner to the previously-described preparation of Compound 45 from Compound 44 (yield 95%).

The identity of Compound 57 was confirmed using $^1$H-NMR.

Compound 57: $^1$H-NMR: δ$_H$ (ppm, 400 MHz, CDCl$_3$): 7.74, (1H, d, J=8.7 Hz), 7.55 (2H, m), 7.30 (1H, dt, J=8.7, 1.5 Hz), 5.13 (1H, bs), 3.50-3.40 (3H, m), 2.65 (2H, bt), 2.40 (1H, m), 2.00-1.87 (6H, m), 1.86-1.30 (15H, m), 1.03 (2H, m).

Compound 57 (6.5 g, 15.95 mmol) was suspended in DCM (150 mL). Thionyl chloride (20 mL) was added followed by the addition of DMF (1 mL). The resulting reaction mixture was heated to reflux and refluxed for 1 h. The mixture was evaporated under reduced pressure to provide a residue which was triturated with MTBE (100 mL) to provide a light brown solid. The solid was partitioned between ice-water:aqueous sodium carbonate solution (400 mL) and DCM (400 mL). The organic layer was separated, dried (over MgSO$_4$), and evaporated under reduced pressure to provide a yellow solid which was triturated with Et$_2$O (150 mL) to provide 4.8 g of Compound 1D3 as a white solid (yield 71%).

The identity of Compound 1D3 was confirmed using $^1$H-NMR and LC/MS.

Compound 1D3: $^1$H-NMR: δ$_H$ (ppm, 400 MHz, CDCl$_3$): 8.82 (1H, d, J=7.4 Hz), 7.62 (2H, m), 7.37 (1H, m), 5.19 (1H, br), 3.55 (3H, m), 2.73 (2H, m), 2.47 (1H, m), 2.10-1.94 (5H, m), 1.90-1.50 (11H, m), 1.43 (3H, m), 1.10 (2H, d, J=13.0 Hz); LC/MS (t$_r$=2.925 min): m/z=426.1 [M+H]$^+$ (Calc: 425.2).

5.8 Example 8

Synthesis of Cyclic Urea- or Lactam-Substituted Quinoxaline-Type Piperidine Compounds where E is N Using procedures similar to those described above for Method 1 in Example 1, the following Cyclic Urea- or Lactam-Substituted Quinoxaline-Type Piperidine Compounds were prepared from Compound 1D3 and the appropriate co-reactants. The co-reactant compounds are commercially available from, e.g., Sigma-Aldrich, or can be prepared by methods known to the art.

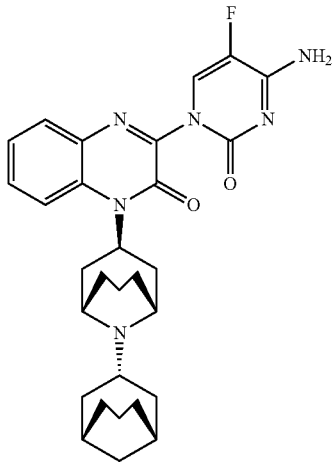

B7a(i)

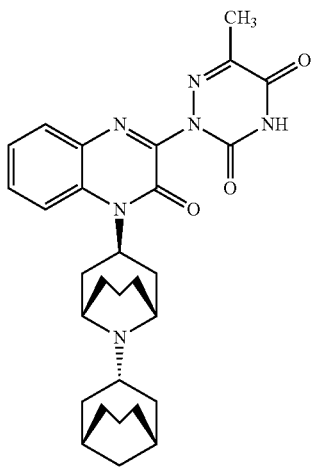

B10a

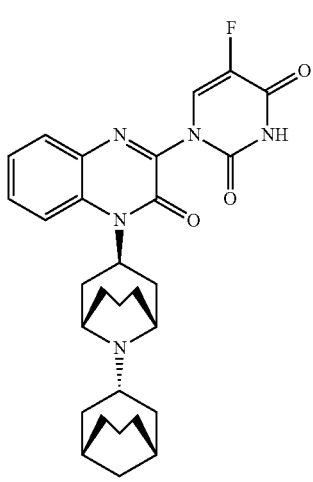

B15a

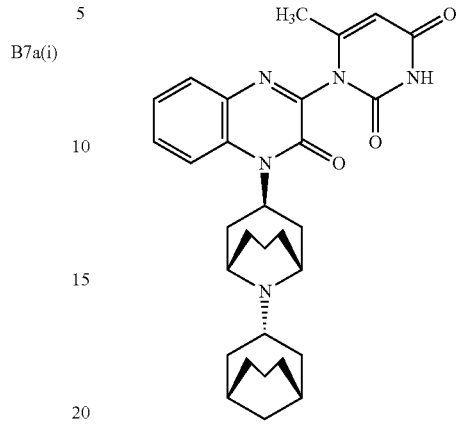

U065

B7a(i): 1-((1R,1'R,3r,3'R,5S,5'S)-[3,9'-bi(9'-azabicyclo[3.3.1]nonan)]-3'-yl)-3-(4-amino-5-fluoro-2-oxopyrimidin-1(2H)-yl)quinoxalin-2(1H)-one.

B7a(i): $^1$H-NMR: $\delta_H$ (ppm, 400 MHz, CDCl$_3$ with one drop each of DCl and d4-MeOH): 1.30-1.46 (m, 1H), 1.50-2.07 (m, 14H), 2.19-2.27 (m, 2H), 2.42-2.75 (m, 5H), 2.86-2.97 (m, 2H) 4.05-4.13 (m, 2H), 4.17-4.27 (m, 1H), 6.28-6.40 (m, 1H), 7.45 (dd, J=7.09, 7.09 Hz, 1H), 7.79-7.88 (m, 2H), 8.01 (d, J=4.64 Hz, 1H), 8.05 (br, 2H), 8.72 (d, J=8.64 Hz, 1H); LC/MS: m/z=519.35 [M+H]$^+$518).

B10a: 2-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-6-methyl-1,2,4-triazine-3,5(2H,4H)-dione.

B10a: $^1$H-NMR: $\delta_H$ (ppm, 400 MHz, DMSO): 7.93 (m, 1H), 7.86 (t, J=, 8.6 Hz, 1H), 7.80 (m, 1H), 7.54 (t, J=7.9 Hz, 1H), 5.29 (br, 1H), 3.60 (br, 3H), 3.40 (br, 2H), 2.36 (m, 1H), 2.10 (m, 3H), 2.17 (m, 6H), 1.86 (m, 3H), 1.69 (m, 4H), 1.53 (m, 4H), 1.12 (d, J=, 13.2 Hz, 3H); MS: m/z=517.2 [M+H]$^+$.

B15a: 1-(4-((1R,1R,3r,3'R,5S,5'S)-[3,9'-bi(9'-azabicyclo[3.3.1]nonan)]-3'-yl)-3-oxo-3,4-dihydroquinoxalin-2-yl)-5-fluoropyrimidine-2,4(1H,3H)-dione.

B15a: $^1$H-NMR: $\delta_H$ (ppm, 400 MHz, CDCl$_3$ with one drop each of DCl and d4-MeOH): 1.24-1.39 (m, 1H), 1.46-2.01 (m, 14H), 2.12-2.22 (m, 2H), 2.36-2.75 (m, 5H), 2.85-2.97 (m, 2H), 3.99-4.08 (m, 2H), 4.11-4.21 (m, 1H), 6.24-6.35 (m, 1H), 7.38 (dd, J=7.65, 7.65 Hz, 1H), 7.55 (d, J=5.15 Hz, 1H), 7.74-7.80 (m, 2H), 8.66 (d, J=8.91 Hz, 1H), 10.2 (br, 1H); LC/MS: m/z=520.30 [M+H]$^+$ (Calc: 519).

U065: 1-(4-((1R,1R,3r,3'R,5S,5'S)-[3,9'-bi(9'-azabicyclo[3.3.1]nonan)]-3'-yl)-3-oxo-3,4-dihydroquinoxalin-2-yl)-6-methylpyrimidine-2,4(1H,3H)-dione.

U065: $^1$H-NMR: $\delta_H$ (ppm, 300 MHz, CDCl$_3$+CD$_3$OD+DCl): 1.33-1.47 (m, 1H), 1.52-1.82 (m, 9H), 1.84-2.07 (m, 6H), 2.17-2.29 (m, 5H), 2.42-2.84 (m, 5H), 2.98 (dd, J=22.1, 12.8 Hz, 2H), 4.10 (d, J=10.8 Hz, 2H), 4.16-4.31 (m, 1H), 5.64 (s, 1H), 6.25-6.38 (m, 1H), 7.41 (t, J=7.5 Hz, 1H), 7.80 (t, J=8.3 Hz, 1H), 7.86 (d, J=8.0 Hz, 1H), 8.69 (d, J=8.8 Hz, 1H); LC/MS: m/z=516.2 [M+H]$^+$ (Calc: 515).

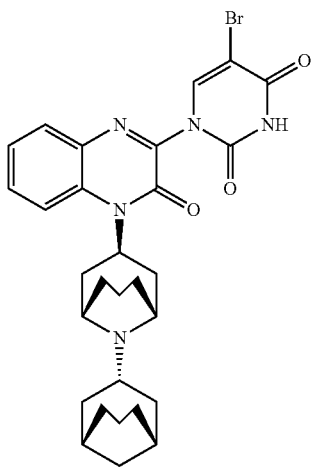

B16a

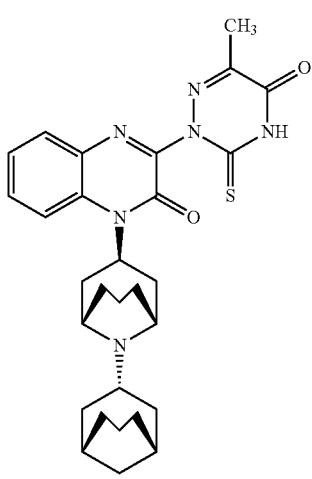

U001

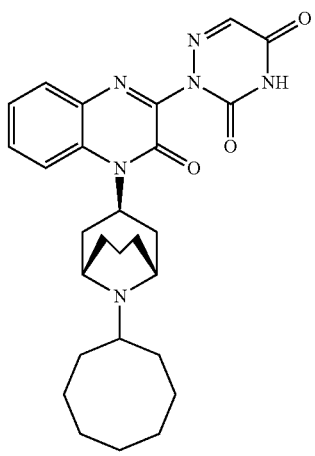

H9c

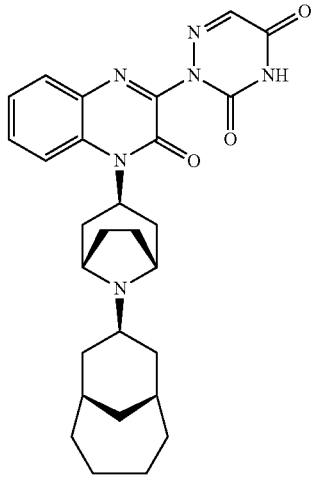

N9b

U066

A1, and/or International PCT Publication No. WO 2012/085648 A1 (see, e.g., Examples 1, 2, and 10), which are hereby incorporated by reference in their entireties. The co-reactant compounds are commercially available from, e.g., Sigma-Aldrich, or can be prepared by methods known to the art.

B16a: 1-(4-((1R,1'R,3r,3R,5S,5'S)-[3,9'-bi(9'-azabicyclo[3.3.1]nonan)]-3'-yl)-3-oxo-3,4-dihydroquinoxalin-2-yl)-5-bromopyrimidine-2,4(1H,3H)-dione.

B16a: $^1$H-NMR: $\delta_H$ (ppm, 400 MHz, CDCl$_3$): 1.33-1.47 (m, 1H), 1.52-1.87 (m, 7H), 1.87-2.08 (m, 6H), 2.24 (br, 2H), 2.50 (td, J=11.98, 7.95 Hz, 2H), 2.62 (td, J=12.05, 4.77 Hz, 2H), 2.68-2.84 (m, 1H), 2.86-3.04 (m, 3H), 3.58 (s, 5H), 4.12 (d, J=10.54 Hz, 2H), 4.24 (br, 1H), 6.33-6.43 (m, 1H), 7.46 (t, J=7.53 Hz, 1H), 7.82-7.89 (m, 3H), 8.08 (s, 1H), 8.76 (dd, J=9.16, 2.89 Hz, 1H); LC/MS: m/z=580.3 and 582.2 [M+H]$^+$ (Calc: 580).

U001: 1-((1R,1'R,3r,3'R,5S,5'S)-[3,9'-bi(9'-azabicyclo[3.3.1]nonan)]-3'-yl)-3-(6-methyl-5-oxo-3-thioxo-4,5-dihydro-1,2,4-triazin-2(3H)-yl)quinoxalin-2(1H)-one.

U001: $^1$H-NMR: $\delta_H$ (ppm, 400 MHz, CD$_3$OD): 7.87 (d, J=13.2 Hz, 2H), 7.77 (t, J=8.6 Hz, 1H), 7.50 (t, J=13.2 Hz, 1H), 5.49 (br, 1H), 4.35 (m, 3H), 3.12 (m, 3H), 2.64 (m, 3H), 2.24 (m, 7H), 2.11 (m, 2H), 1.84 (m, 12H); MS: m/z=533.3 [M+H]$^+$ (Calc: 532).

Using procedures similar to those described above for Method 1 in Example 1, the following Cyclic Urea- or Lactam-Substituted Quinoxaline-Type Piperidine Compounds were prepared from the appropriate 3-chloroquinoxalin-2(1H)-one and the appropriate co-reactants. The 3-chloroquinoxalin-2(1H)-ones are commercially available or can be prepared by methods known to the art, e.g., as described in U.S. Patent Application Publication Nos. US 2010/0216726 A1 (see, e.g., Examples 3, 14, 17, and 29), US 2011/0178090

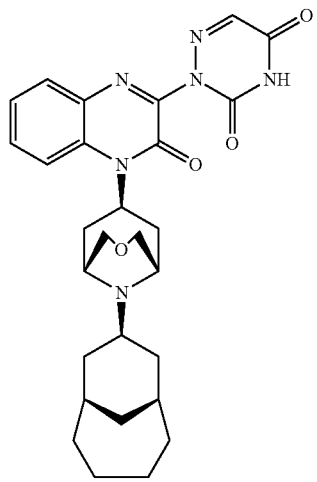

P9b

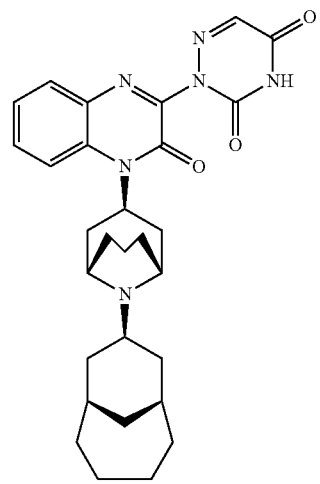

O9b

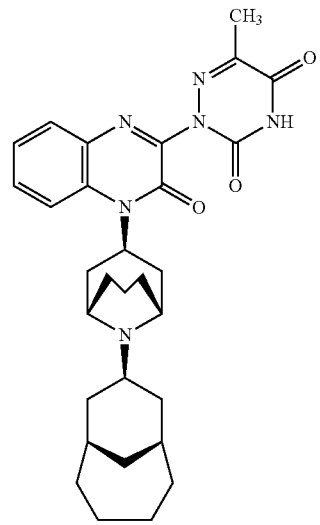

O10b

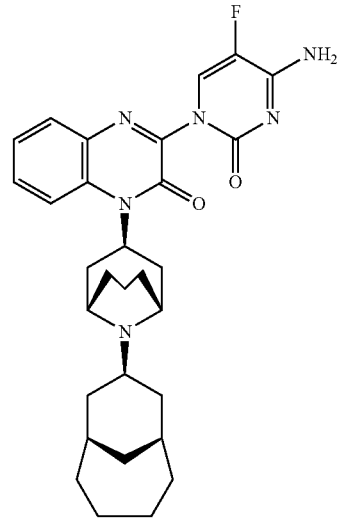

U067

H9c: 2-(4-((1R,3r,5S)-9-cyclooctyl-9-azabicyclo[3.3.1]nonan-3-yl)-3-oxo-3,4-dihydroquinoxalin-2-yl)-1,2,4-triazine-3,5(2H,4H)-dione.

H9c: $^1$H-NMR: $\delta_H$ (ppm, 400 MHz, d6-DMSO): 7.92 (m, 1H), 7.85 (m, 1H), 7.71 (m, 2H), 7.51 (m, 1H), 5.20 (br, 1H), 3.45 (m, 2H), 3.25 (m, 1H), 2.08 (m, 2H), 1.75-1.48 (m, 14H), 1.44 (m, 2H), 1.28 (m, 2H), 1.12 (m, 2H), 0.86 (m, 2H); MS: m/z=491.2 [M+H]$^+$ (Calc: 490).

N9b: 2-(4-((1R,3R,5S)-8-((1R,6S,8s)-bicyclo[4.3.1]decan-8-yl)-8-azabicyclo[3.2.1]octan-3-yl)-3-oxo-3,4-dihydroquinoxalin-2-yl)-1,2,4-triazine-3,5(2H,4H)-dione.

N9b: $^1$H-NMR: $\delta_H$ (ppm, 400 MHz, CDCl$_3$ with one drop of DCl): 1.22-1.46 (m, 5.0H), 1.61-1.93 (m, 5.0H), 2.10-2.26 (m, 2.0H), 2.33-2.55 (m, 9.0H), 2.90-3.10 (m, 2.0H), 4.25 (s, 2.0H), 6.35-6.44 (m, 1.0H), 7.44 (t, J=7.53 Hz, 1.0H), 7.60 (s, 1.0H), 7.82 (dd, J=10.29, 5.52 Hz, 1.0H), 7.89 (dd, J=8.03, 1.25 Hz, 1.0H), 8.31 (dd, J=8.53, 3.76 Hz, 1.0H), 9.35 (d, J=3.01 Hz, 0.3H), 11.09 (d, J=4.27 Hz, 0.7H); LC/MS (t$_r$=1.46 min): m/z=503.2 [M+H]$^+$ (Calc: 502).

U066: 3-(4-amino-2-oxopyrimidin-1(2H)-yl)-1-((1R,3R,5S)-8-((1R,6S,8s)-bicyclo[4.3.1]decan-8-yl)-8-azabicyclo[3.2.1]octan-3-yl)quinoxalin-2(1H)-one.

U066: $^1$H-NMR: $\delta_H$ (ppm, 400 MHz, d6-DMSO+DCl): 1.34-1.80 (m, 10H), 1.92-2.38 (m, 12H), 2.56-2.70 (m, 2H), 2.87-2.98 (m, 1H), 4.35-4.40 (m, 2H), 6.12-6.25 (m, 1H), 6.47 (d, J=7.8 Hz, 1H), 7.53 (dd, J=7.7, 7.7 Hz, 1H), 7.82 (ddd, J=8.0, 8.0, 1.4 Hz, 1H), 7.91 (dd, J=7.9, 1.5 Hz, 1H), 8.13 (d, J=7.7 Hz, 1H), 8.24 (d, J=8.9 Hz, 1H); LC/MS: m/z=501.35 [M+H]$^+$ (Calc: 500).

P9b: 2-(4-((1R,5S,7 S)-9-((1R,6S,8s)-bicyclo[4.3.1]decan-8-yl)-3-oxa-9-azabicyclo[3.3.1]nonan-7-yl)-3-oxo-3,4-dihydroquinoxalin-2-yl)-1,2,4-triazine-3,5(2H,4H)-dione.

P9b: $^1$H-NMR: $\delta_H$ (ppm, 400 MHz, CDCl$_3$): 8.75 (br, 1H), 7.91 (d, J=8.6 Hz, 1H), 7.68 (t, J=7.3 Hz, 1H), 7.52 (s, 1H), 7.41 (t, J=7.9 Hz, 1H), 5.82 (br, 1H), 4.13 (m, 5H), 3.88 (br, 1H), 3.41 (m, 2H), 2.63 (br, 1H), 2.44 (br, 2H), 2.08 (m, 2H), 1.88-1.31 (m, 13H); MS: m/z=519.3 [M+H]$^+$ (Calc: 518).

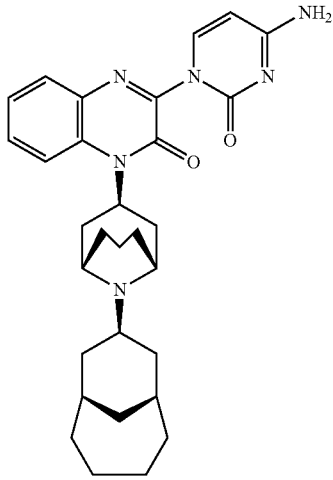

U068

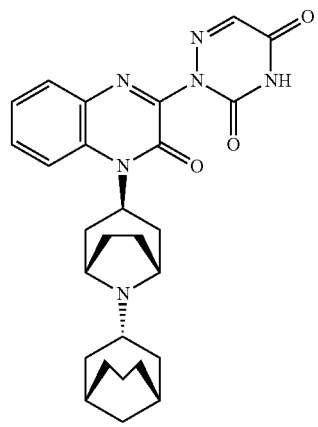

A9a

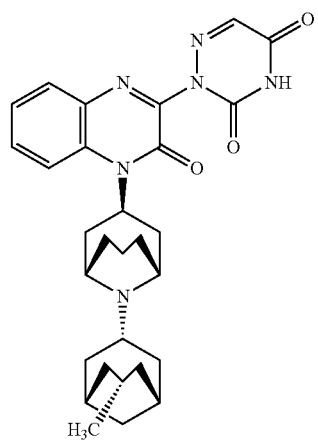

B34a

O9b: 2-(4-((1R,3R,5S)-9-((1R,6S,8s)-bicyclo[4.3.1]decan-8-yl)-9-azabicyclo[3.3.1]nonan-3-yl)-3-oxo-3,4-dihydroquinoxalin-2-yl)-1,2,4-triazine-3,5(2H,4H)-dione.

O9b: $^1$H-NMR: $\delta_H$ (ppm, 400 MHz, d6-DMSO with one drop of DCl): 1.36-2.88 (m, 26H), 3.67-3.86 (m, 1H), 4.17-4.28 (m, 2H), 6.17-6.35 (m, 1H), 7.55 (dd, J=7.47, 7.47 Hz, 1H), 7.81 (dd, J=8.23, 7.55 Hz, 1H), 7.93 (d, J=8.06 Hz, 1H), 8.76 (d, J=8.73 Hz, 1H); LC/MS: m/z=517.30 [M+H]$^+$ (Calc: 516).

O10b: 2-(4-((1R,3R,5 S)-9-((1R,6S,8s)-bicyclo[4.3.1]decan-8-yl)-9-azabicyclo[3.3.1]nonan-3-yl)-3-oxo-3,4-dihydroquinoxalin-2-yl)-6-methyl-1,2,4-triazine-3,5(2H,4H)-dione.

O10b: $^1$H-NMR: $\delta_H$ (ppm, 400 MHz, CDCl$_3$+CD$_3$OD+DCl): 1.36-1.48 (m, 5H), 1.69-2.04 (m, 16H), 2.31 (s, 4H), 2.38-2.56 (m, 7H), 2.72-2.82 (m, 1H), 3.02 (t, J=12.1 Hz, 2H), 3.38 (s, 2H), 3.86 (s, 1H), 4.20 (d, J=10.4 Hz, 2H), 6.28 (t, J=10.0 Hz, 1H), 7.46 (t, J=7.6 Hz, 1H), 7.83-7.90 (m, 2H), 8.69 (d, J=8.7 Hz, 1H); LC/MS: m/z=531.3 [M+H]$^+$ (Calc: 530.7).

U067: 3-(4-amino-5-fluoro-2-oxopyrimidin-1(2H)-yl)-1-((1R,3R,5S)-94(1R,6S,8s)-bicyclo[4.3.1]decan-8-yl)-9-azabicyclo[3.3.1]nonan-3-yl)quinoxalin-2(1H)-one.

U067: $^1$H-NMR: $\delta_H$ (ppm, 400 MHz, CDCl$_3$+CD$_3$OD+DCl): 1.31-1.52 (m, 5H), 1.64-2.07 (m, 12H), 2.37-2.57 (m, 6H), 2.65-2.82 (m, 1H), 2.87-3.00 (m, 2H), 3.77-3.94 (m, 1H), 4.12-4.23 (m, 2H), 6.32-6.46 (m, 1H), 7.46 (dd, J=7.5, 7.5 Hz, 1H), 7.83 (d, J=7.9 Hz, 1H), 7.87 (dd, J=8.2 Hz, 1H), 7.97 (d, J=4.8 Hz, 1H), 8.07 (s, 2H), 8.75 (d, J=8.9 Hz, 1H); LC/MS: m/z=533.35 [M+H]$^+$ (Calc: 532).

U068: 3-(4-amino-2-oxopyrimidin-1(2H)-yl)-1-((1R,3R,5S)-9-((1R,6S,8s)-bicyclo[4.3.1]decan-8-yl)-9-azabicyclo[3.3.1]nonan-3-yl)quinoxalin-2(1H)-one.

U068: $^1$H-NMR: $\delta_H$ (ppm, 400 MHz, d6-DMSO+DCl): 1.32-2.01 (m, 18H), 2.15-2.60 (m, 6H), 2.70-2.83 (m, 2H), 3.68-3.80 (m, 1H), 4.16-4.28 (m, 2H), 6.18-6.31 (m, 1H), 6.47 (d, J=7.5 Hz, 1H), 7.53 (dd, J=7.5 Hz, 1H), 7.79 (ddd, J=7.9, 7.9, 1.4 Hz, 1H), 7.90 (dd, J=8.0, 1.4 Hz, 1H), 8.14 (d, J=7.9 Hz, 1H), 8.74 (d, J=9.0 Hz, 1H); LC/MS: m/z=515.40 [M+H]$^+$ (Calc: 514).

A9a: 2-(4-((1R,3R,5S)-8-((1R,3r,5S)-bicyclo[3.3.1]nonan-3-yl)-8-azabicyclo[3.2.1]octan-3-yl)-3-oxo-3,4-dihydroquinoxalin-2-yl)-1,2,4-triazine-3,5(2H,4H)-dione.

A9a: $^1$H-NMR: $\delta_H$ (ppm, 300 MHz, CDCl$_3$+CD$_3$OD+DCl): 1.20-1.39 (m, 1H), 1.54-1.79 (m, 6H), 1.85 (d, J=12.5 Hz, 1H), 1.99-2.10 (m, 2H), 2.18-2.33 (m, 4H), 2.36-2.59 (m, 6H), 2.93 (dd, J=24.5, 9.9 Hz, 2H), 3.42-3.54 (m, 1H), 4.24 (br s, 2H), 6.22-6.31 (m, 1H), 7.45 (t, J=7.4 Hz, 1H), 7.58 (s, 1H), 7.82 (t, J=7.8 Hz, 1H), 7.89 (d, J=8.0 Hz, 1H), 8.24 (d, J=9.0 Hz, 1H); LC/MS: m/z=489.2 [M+H]$^+$ (Calc: 488).

B34a: 2-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-1,2,4-triazine-3,5(2H,4H)-dione.

B34a: $^1$H-NMR: $\delta_H$ (ppm, 400 MHz, CDCl$_3$+CD$_3$OD+DCl): 0.62 (t, J=12.8 Hz, 2H), 0.89 (d, J=5.4 Hz, 3H), 1.36 (d, J=10.9 Hz, 1H), 1.66-2.09 (m, 10H), 2.46 (s, 5H), 2.82 (s, 2H), 3.02 (s, 2H), 3.84 (s, 1H), 4.12 (s, 2H), 6.21 (s, 1H), 7.70 (dd, J=148.4, 23.3 Hz, 5H), 8.71 (s, 1H); LC/MS: m/z=517.25 [M+H]$^+$ (Calc: 516.63).

5.9 Example 9

Synthesis of Cyclic Urea- or Lactam-Substituted Quinoxaline-Type Piperidine Compounds B17a and B23a Using procedures similar to those described above for Method 2 in Example 2, the following Cyclic Urea- or Lactam-Substituted Quinoxaline-Type Piperidine Compounds were prepared from Compound 1D3 and the appropriate co-reactants. The co-reactant compounds are commercially available from, e.g., Sigma-Aldrich, or can be prepared by methods known to the art.

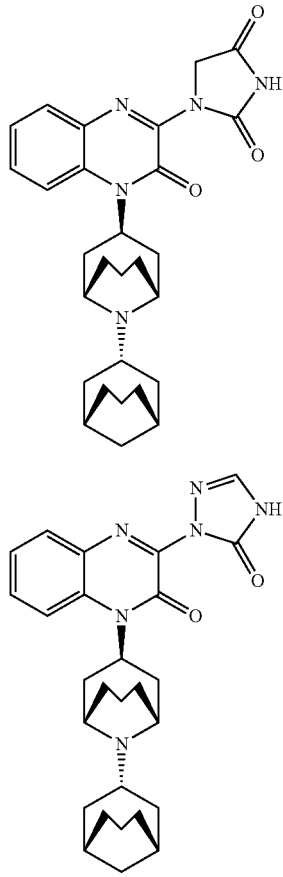

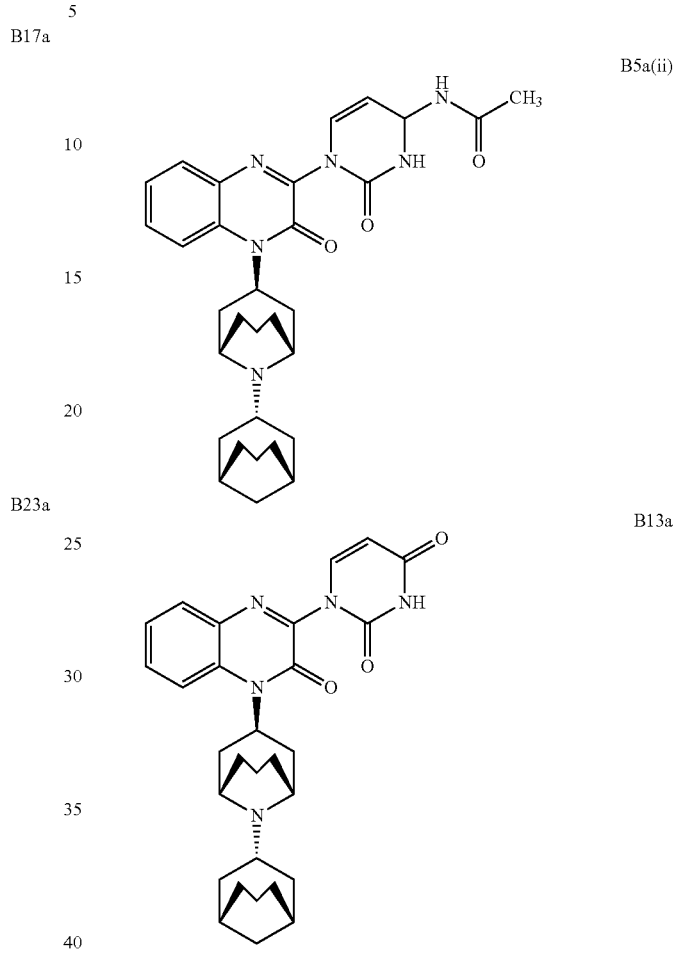

B17a: 1-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)imidazolidine-2,4-dione.

B17a: $^1$H-NMR: $\delta_H$ (ppm, 400 MHz, CD$_3$OD): 7.80 (m, 2H), 7.62 (m, 1H), 7.38 (dd, J=7.5, 7.5 Hz, 1H), 5.33 (br, 1H), 4.67 (s, 2H), 3.65 (m, 3H), 2.76 (m, 2H), 2.51 (m, 1H), 2.08 (m, 6H), 1.95 (m, 2H), 1.72-1.45 (m, 11H), 1.16 (m, 2H); MS: m/z=490.2 [M+H]$^+$ (Calc: 489).

B23a: 1-((1R,3r,3'R,5S,5'S)-[3,9'-bi(9'-azabicyclo[3.3.1]nonan)]-3'-yl)-3-(5-oxo-4,5-dihydro-1H-1,2,4-triazol-1-yl)quinoxalin-2(1H)-one.

B23a: $^1$H-NMR: $\delta_H$ (ppm, 400 MHz, CD$_3$OD): 8.28 (s, 1H), 7.96 (dd, J=1.2, 8.0 Hz, 1H), 7.89 (d, J=8.8 Hz, 1H), 7.74 (m, 1H), 7.47 (dd, J=7.4, 7.4 Hz, 1H), 5.39 (br, 1H), 3.68 (m, 3H), 2.80 (m, 2H), 2.56 (m, 1H), 2.09 (m, 6H), 1.98 (m, 2H), 1.81-1.50 (m, 11H), 1.16 (m, 2H); MS: m/z=475.2 [M+H]$^+$ (Calc: 474).

5.10 Example 10

Synthesis of Cyclic Urea- or Lactam-Substituted Quinoxaline-Type Piperidine Compounds B5a(ii), B13a, and 013b Using procedures similar to those described above for Method 4.1 in Example 4, the following Cyclic Urea- or Lactam-Substituted Quinoxaline-Type Piperidine Compounds were prepared from Compound 1D3 and the appropriate co-reactants. The co-reactant compounds are commercially available from, e.g., Sigma-Aldrich, or can be prepared by methods known to the art.

B5a(ii): N-(1-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxo-1,2,3,4-tetrahydropyrimidin-4-ypacetamide.

B5a(ii): $^1$H-NMR: $\delta_H$ (ppm, 400 MHz, CDCl$_3$ with one drop each of DCl and d4-MeOH): 1.26-1.39 (m, 1H), 1.45-2.02 (m, 14H), 2.12-2.23 (m, 2H), 2.39-2.69 (m, 8H), 2.81-2.93 (m, 2H), 6.43-6.55 (m, 1H), 7.41 (dd, J=7.53, 7.53 Hz, 1H), 7.61 (br, 1H), 7.79 (dd, J=7.15, 7.15 Hz, 1H), 7.84 (dd, J=7.02, 7.02 Hz, 1H), 8.10 (br, 1H), 8.82 (br, 1H); LC/MS: m/z=543.35 [M+H]$^+$ (Calc: 542).

B13a: 1-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)pyrimidine-2,4(1H,3H)-dione.

B13a: $^1$H-NMR: $\delta_H$ (ppm, 400 MHz, CDCl$_3$ with one drop each of DCl and d4-MeOH): 1.33-1.48 (m, 1H), 1.52-2.09 (m, 14H), 2.21-2.30 (m, 2H), 2.46-2.58 (m, 2H), 2.66-2.83 (m, 3H), 2.93-3.04 (m, 2H), 4.08-4.15 (m, 2H), 4.18-4.29 (m, 1H), 5.91 (d, J=8.03 Hz, 1H), 6.41-6.55 (m, 1H), 7.45 (dd, J=7.59, 7.59 Hz, 1H), 7.52 (d, J=8.03 Hz, 1H), 7.82-7.89 (m, 2H), 8.84 (d, J=8.16 Hz, 2H), 10.7 (br, 1H); LC/MS: m/z=502.30 [M+H]$^+$ (Calc: 501).

Using procedures similar to those described above for Method 4.1 in Example 4, the following Cyclic Urea- or Lactam-Substituted Quinoxaline-Type Piperidine Compound was prepared from the appropriate 3-chloroquinoxalin-2(1H)-one and the appropriate co-reactant. The 3-chloro-quinoxalin-2(1H)-ones are commercially available or can be prepared by methods known to the art, e.g., as described in U.S. Patent Application Publication Nos. US 2010/0216726 A1 (see, e.g., Examples 3, 14, 17, and 29), US 2011/0178090 A1, and/or International PCT Publication No. WO 2012/085648 A1 (see, e.g., Examples 1, 2, and 10), which are hereby incorporated by reference in their entireties. The co-reactant compound is commercially available from, e.g., Sigma-Aldrich, or can be prepared by methods known to the art.

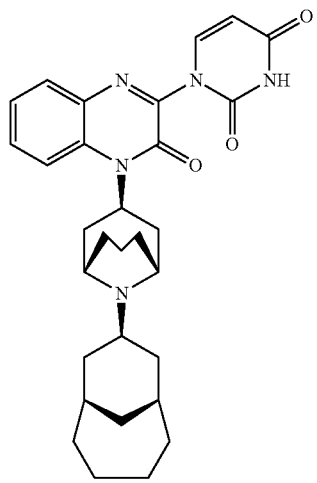

O13b: 1-(4-((1R,3R,5S)-9-((1R,6S,8s)-bicyclo[4.3.1]de-can-8-yl)-9-azabicyclo[3.3.1]nonan-3-yl)-3-oxo-3,4-dihyd-roquinoxalin-2-yl)pyrimidine-2,4(1H,3H)-dione.

O13b: $^1$H-NMR: $\delta_H$ (ppm, 400 MHz, CDCl$_3$ with one drop each of DCl and d4-MeOH): 1.24-1.48 (m, 4H), 1.56-1.87 (m, 11H), 1.87-1.99 (m, 2H), 2.36-2.51 (m, 2H), 2.64-2.77 (m, 1H), 2.87-2.98 (m, 2H), 3.70-3.83 (m, 1H), 4.06-4.15 (m, 2H), 5.83 (d, J=8.03 Hz, 1H), 6.33-6.46 (m, 1H), 7.37 (dd, J=7.59, 7.59 Hz, 1H), 7.43 (d, J=8.03 Hz, 1H), 7.74-7.80 (m, 2H), 8.62-8.76 (m, 2H), 10.5 (br, 1H); LC/MS: m/z=516.35 [M+H]$^+$ (Calc: 515).

5.11 Example 11

Synthesis of Cyclic Urea- or Lactam-Substituted Quinoxaline-Type Piperidine Compounds B20a, B47a, and O22b Using procedures similar to those described above for Method 4.2 in Example 4 Cyclic Urea- or Lactam-Substituted Quinoxaline-Type Piperidine Compound B20a was prepared from Compound 1C3 and the appropriate co-reactant. The co-reactant compound is commercially available from, e.g., Sigma-Aldrich, or can be prepared by methods known to the art.

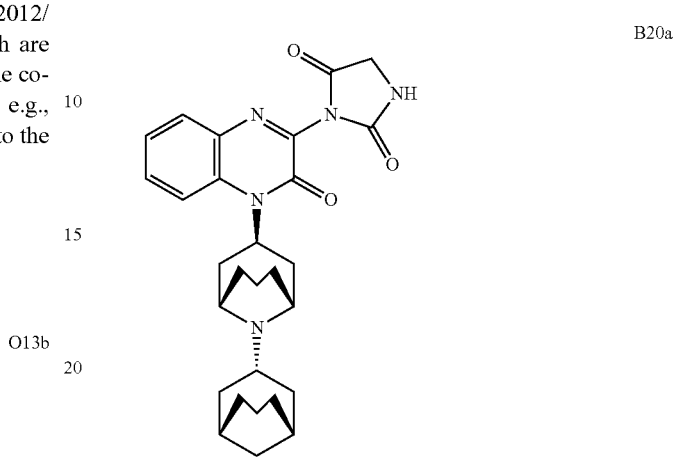

B20a: 3-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)imidazolidine-2,4-dione.

B20a: $^1$H-NMR: $\delta_H$ (ppm, 300 MHz, CDCl$_3$+CD$_3$OD): 1.13 (s, 2H), 1.48-2.05 (m, 20H), 2.41 (s, br, 1H), 2.69 (s, br, 2H), 3.37-3.65 (m, 2H), 4.64-4.77 (m, 2H), 5.26 (s, br, 1H), 7.36 (s, 1H), 7.58 (s, 1H), 7.71 (d, J=8.3 Hz, 1H), 7.81 (d, J=6.7 Hz, 1H); LC/MS: m/z=490.2 [M+H]$^+$ (Calc: 489).

Using procedures similar to those described above for Method 4.2 in Example 4, except that either the hydrochloride of Compound 1C3 (prepared as described in Example 6 herein) or Compound 1B3 (prepared as described in Example 31 herein) was used in place of Compound 1D3, the Cyclic Urea- or Lactam-Substituted Quinoxaline-Type Piperidine Compounds below were prepared from Compound X32 as the co-reactant.

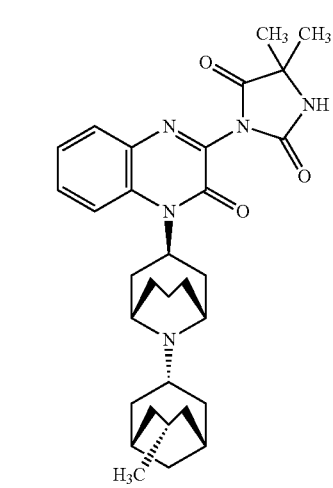

-continued

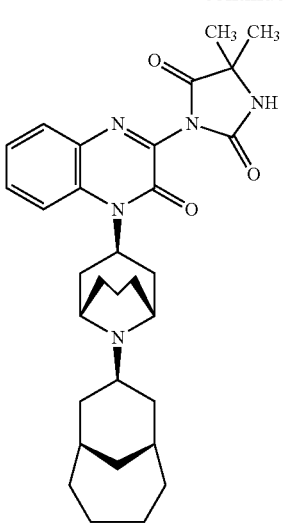

B47a: 5,5-dimethyl-3-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-ypimidazolidine-2,4-dione.

B47a: ¹H-NMR: $\delta_H$ (ppm, 400 MHz, d6-DMSO with one drop of DCl): 0.67-0.80 (m, 2H), 0.85 (d, J=6.12 Hz, 3H), 1.00-1.09 (m, 1H), 1.38-2.44 (m, 19H), 1.42 (s, 3H), 1.45 (s, 3H), 2.65-2.78 (m, 1H), 3.70-3.86 (m, 1H), 4.02-4.14 (m, 2H), 6.12-6.28 (m, 1H), 7.48 (dd, J=7.63, 7.63 Hz, 1H), 7.73 (dd, J=7.93, 7.93 Hz, 1H), 7.89 (d, J=7.93 Hz, 1H), 8.73 (d, J=9.30 Hz); LC/MS (t$_r$=1.69 min): m/z=532.5 [M+11]$^+$ (Calc: 531.0).

O22b: 3-(4-((1R,3R,5S)-9-((1R,6S,8s)-bicyclo[4.3.1]decan-8-yl)-9-azabicyclo[3.3.1]nonan-3-yl)-3-oxo-3,4-dihydroquinoxalin-2-yl)-5,5-dimethylimidazolidine-2,4-dione.

O22b: ¹H-NMR: $\delta_H$ (ppm, 300 MHz, CDCl$_3$+CD$_3$OD+DCl): 1.34-1.47 (m, 4H), 1.55-2.07 (m, 19H), 2.47 (s, br, 6H), 2.79 (d, br, J=13.3 Hz, 1H), 2.99 (t, J=12.8 Hz, 2H), 3.84 (s, br, 1H), 4.17 (d, j=11.3 Hz, 2H), 6.25-6.39 (m, 1H), 7.41 (t, J=7.7 Hz, 1H), 7.82 (d, J=8.3 Hz, 1H), 7.89 (d, J=7.5 Hz, 1H), 8.70 (d, J=8.8 Hz, 1H); LC/MS: m/z=532.4 [M+H]$^+$ (Calc: 531).

5.12 Example 12

Synthesis of Cyclic Urea- or Lactam-Substituted Quinoxaline-Type Piperidine Compounds R1a(i), U003, and R1a(iii) by Method 6.1

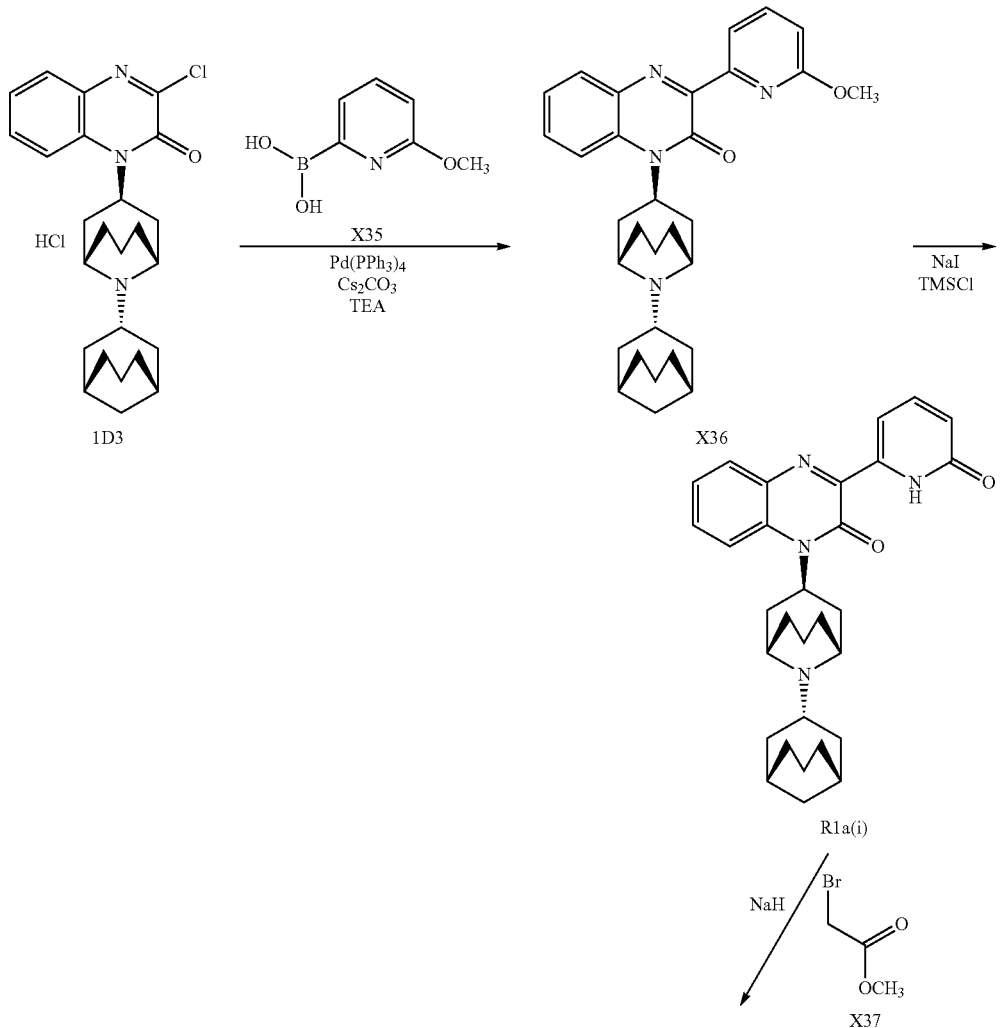

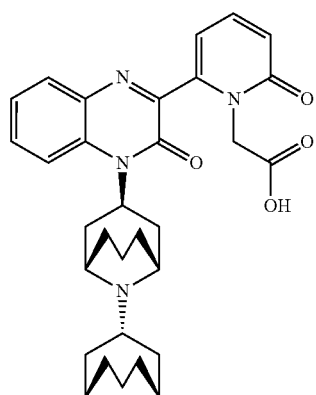
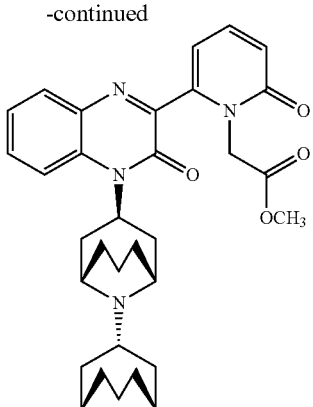

R1a(iii)    U003

To a suspension of the hydrochloride of Compound 1D3 (0.865 mmol, 400 mg), (6-methoxypyridin-2-yl)boronic acid (Compound X35, 1.297 mmol, 198 mg, Sigma-Aldrich), Cs$_2$CO$_3$ (2.59 mmol, 845 mg), and TEA (2.59 mmol, 0.360 mL) in 1,4-dioxane (12 mL) at a temperature of about 25° C. was added tetrakis(triphenylphosphine)palladium(0) (Pd (PPh$_3$)$_4$, 0.052 mmol, 60.0 mg, Sigma-Aldrich). The resulting reaction mixture was heated to 120° C. and stirred at that temperature for 3 hours. Thereafter, the mixture was cooled to a temperature of about 25° C., held for 16 hours, quenched with water, and extracted twice with CHCl$_3$/H$_2$O (120 mL for each extraction). The organic portions were combined, dried (over MgSO$_4$), and concentrated under reduced pressure to provide a yellow oil which was chromatographed on a on a silica-gel column (REDISEP RF GOLD 40 g, Teledyne ISCO) eluted with a gradient of from 0:100 MeOH (10% NH$_3$):CHCl$_3$ to 5:95 MeOH (10% NH$_3$):CHCl$_3$ to provide 361 mg of Compound X36, 1-((1R,1'R,3r,3'R,5S,5'S)-[3,9'-bi(9'-azabicyclo[3.3.1]nonan)]-3'-yl)-3-(6-methoxypyridin-2-yl)quinoxalin-2(1H)-one, as a pale yellow amorphous solid (yield 84%).

The identity of Compound X36 was confirmed using $^1$H-NMR and LC/MS.

Compound X36: $^1$H-NMR: δ$_H$ (ppm, 400 MHz, CDCl$_3$): 8.00 (t, J=4.53 Hz, 1H), 7.73-7.59 (m, 4H), 7.35 (t, J=7.42 Hz, 1H), 7.20 (dd, J=11.67, 7.00 Hz, 1H), 6.84 (dd, J=7.14, 1.92 Hz, 1H), 5.25 (br, 1H), 4.04 (s, 3H), 3.48-3.56 (m, 3H), 2.77 (t, J=11.40 Hz, 2H), 2.45 (br, 1H), 2.31-2.02 (m, 6H), 1.88-1.41 (m, 12H), 1.20-1.10 (m, 1H); LC/MS: m/z=499.06 [M+H]$^+$ (Calc: 498.66).

Under a nitrogen atmosphere, to a solution of NaI (3.26 mmol, 488 mg, Sigma-Aldrich) in MeCN (5 mL) at a temperature of about 25° C. was added trimethylchlorosilane ("TMSCl," 3.26 mmol, 0.416 mL, Sigma-Aldrich) to form a pale yellow suspension that was stirred at that temperature for 15 min. To a suspension of Compound X36 (0.724 mmol, 361 mg) in MeCN (6 mL) at 0° C. was added dropwise over 5 min the pale yellow suspension. With stirring, the resulting reaction mixture was heated to a temperature of about 25° C. then stirred at that temperature for an additional 10 min. Thereafter, the reaction mixture was heated to a temperature of 70° C. and stirred at that temperature for 1.5 hours. The mixture was cooled to a temperature of about 25° C., quenched with water, a 20% Na$_2$S$_2$O$_3$ aqueous solution was added, and 2N aqueous HCl was added until a pH of about 6-7 was reached. The pale yellow precipitate that formed was collected by filtration and dried at 80° C. for 16 hr to provide 350 mg of Cyclic Urea- or Lactam-Substituted Quinoxaline-Type Piperidine Compound R1a(i), 1-((1R,1'R,3r,3'R,5S,5'S)-[3,9'-bi(9'-azabicyclo[3.3.1]nonan)]-3'-yl)-3-(6-oxo-1,6-dihydropyridin-2-yl)quinoxalin-2(1H)-one, as a pale yellow solid (yield 99%).

The identity of Cyclic Urea- or Lactam-Substituted Quinoxaline-Type Piperidine Compound R1a(i) was confirmed using $^1$H-NMR and LC/MS.

Cyclic Urea- or Lactam-Substituted Quinoxaline-Type Piperidine Compound R1a(i): $^1$H-NMR: δ$_H$ (ppm, 400 MHz, CDCl$_3$): 8.77 (d, J=8.79 Hz, 1H), 8.40 (d, J=7.42 Hz, 1H), 8.07 (t, J=8.24 Hz, 2H), 7.90 (t, J=7.97 Hz, 1H), 7.54 (t, J=7.55 Hz, 1H), 7.26 (d, J=9.06 Hz, 1H), 6.44-6.29 (m, 1H), 4.33-4.15 (m, 3H), 3.07 (t, J=13.18 Hz, 1.9H), 2.88 (br, 1H), 2.55 (m, 4H), 2.26 (s, 2H), 2.00 (m, 5H), 1.90-1.74 (m, 6H), 1.70-1.60 (m, 1H), 1.45 (t, J=9.34 Hz, 1H); LC/MS: m/z=485.1 [M+H]$^+$ (Calc: 484.6).

Under a nitrogen atmosphere, to a solution of Cyclic Urea- or Lactam-Substituted Quinoxaline-Type Piperidine Compound R1a(i) (0.303 mmol, 147 mg) in DMF (4 mL) at a temperature of about 25° C. was added NaH (0.607 mmol, 24.26 mg); the resulting mixture was stirred at that temperature for 15 min. Then, methyl 2-bromoacetate (Compound X37, 0.455 mmol, 0.042 mL, Sigma-Aldrich) was added and the resulting reaction mixture was heated to 110° C. and stirred at that temperature for 6 hours. Thereafter, the mixture was cooled to a temperature of about 25° C. and extracted twice with EtOAc/H$_2$O (70 mL for each extraction). The organic portions were combined, washed with brine, dried (over MgSO$_4$), and concentrated under reduced pressure to provide an oil which was chromatographed on a on a silica-gel column (REDISEP RF GOLD 12g) eluted with a gradient of from 1:99 MeOH (10% NH$_3$):CHCl$_3$ to 5:95 MeOH (10% NH$_3$):CHCl$_3$ to provide 65 mg of Cyclic Urea- or Lactam-Substituted Quinoxaline-Type Piperidine Compound U003, methyl 2-(6-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)acetate, as a yellow oil (yield 39%).

The identity of Cyclic Urea- or Lactam-Substituted Quinoxaline-Type Piperidine Compound U003 was confirmed using $^1$H-NMR and LC/MS.

Cyclic Urea- or Lactam-Substituted Quinoxaline-Type Piperidine Compound U003: $^1$H-NMR: δ$_H$ (ppm, 400 MHz, CDCl$_3$): 8.04 (s, 1H), 7.92 (dd, J=7.97, 1.37 Hz, 1H), 7.77 (dd, J=8.79, 6.59 Hz, 2H), 7.69 (d, J=6.87 Hz, 1H), 7.39 (t, J=7.55 Hz, 1H), 7.00 (d, J=7.97 Hz, 1H), 6.33 (br, 1H), 5.00 (s, 2H), 4.32-4.13 (m, 4H), 3.88 (s, 2H), 3.77 (s, 4H), 3.11-3.02 (m, 3H), 2.59-2.48 (m, 3H), 2.26 (s, 2H), 2.10-1.92 (m, 6H), 1.89-1.68 (m, 9H); LC/MS: m/z=557.1 [M+H]$^+$ (Calc: 556.7).

To a suspension of Cyclic Urea- or Lactam-Substituted Quinoxaline-Type Piperidine Compound U003 (0.117 mmol, 65 mg) in MeOH (1 mL) at a temperature of about 25° C. was added 2N aqueous NaOH (0.350 mmol, 0.175 mL). The resulting reaction mixture was stirred at that temperature for 4 hours. Thereafter, the mixture was concentrated under reduced pressure, neutralized with 2N aqueous HCl, and additional 2N aqueous HCl was added until a pH of about 4-5 was reached. The precipitate that formed was extracted twice with CHCl₃/H₂O (40 mL for each extraction). The organic portions were combined, dried (over MgSO₄), and concentrated under reduced pressure to provide a yellow oil. The oil was added to EtOAc; a precipitate formed which was collected by filtration and washed with 9:1 EtOAc:Et₂O to provide 32 mg of Cyclic Urea- or Lactam-Substituted Quinoxaline-Type Piperidine Compound R1a(iii), 2-(6-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl) acetic acid, as a pale yellow solid (yield 51%).

The identity of Cyclic Urea- or Lactam-Substituted Quinoxaline-Type Piperidine Compound R1a(iii) was confirmed using ¹H-NMR and LC/MS.

Cyclic Urea- or Lactam-Substituted Quinoxaline-Type Piperidine Compound R1a(iii): ¹H-NMR: $\delta_H$ (ppm, 400 MHz, CDCl₃): 8.78 (d, J=8.79 Hz, 1H), 8.33-8.24 (m, 2H), 8.05 (dd, J=8.10, 1.51 Hz, 1H), 7.90 (dt, J=15.20, 3.85 Hz, 1H), 7.54-7.48 (m, 2H), 6.41-6.33 (m, 1H), 5.23 (s, 2H), 4.19-4.14 (m, 2H), 3.12-3.03 (m, 2H), 2.87-2.80 (m, 1H), 2.64-2.48 (m, 4H), 2.25 (s, 2H), 2.11-1.42 (m, 14H); LC/MS: m/z=543.25 [M+H]⁺ (Calc: 542.67).

5.13 Example 13

Synthesis of Cyclic Urea- or Lactam-Substituted Quinoxaline-Type Piperidine Compounds Where E is C Using procedures similar to those described above for Method 6.1 in Example 12, the following Cyclic Urea- or Lactam-Substituted Quinoxaline-Type Piperidine Compounds were prepared from Compound 1D3 and the appropriate co-reactants. The co-reactant compounds are commercially available from, e.g., Sigma-Aldrich, or can be prepared by methods known to the art.

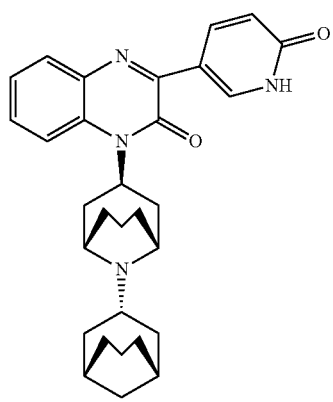
U005

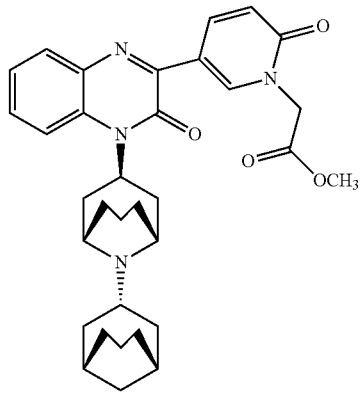
U006

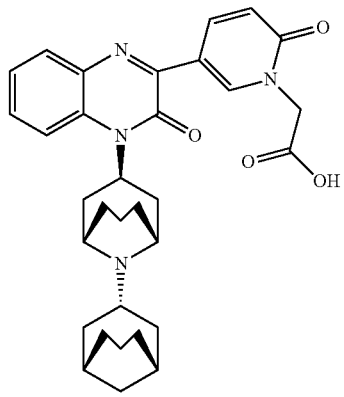
U007

U005: 1-((1R,1'R,3r,3'R,5S,5'S)-[3,9'-bi(9'-azabicyclo[3.3.1]nonan)]-3'-yl)-3-(6-oxo-1,6-dihydropyridin-3-yl)quinoxalin-2(1H)-one.

U005: ¹H-NMR: $\delta_H$ (ppm, 400 MHz, CDCl₃): 9.28 (d, J=2.44 Hz, 1H), 8.97 (dd, J=9.46, 2.29 Hz, 1H), 8.62 (d, J=9.15 Hz, 1H), 7.84 (dd, J=8.01, 1.45 Hz, 1H), 7.71 (t, J=8.01 Hz, 1H), 7.37 (t, J=7.63 Hz, 1H), 7.16 (d, J=9.30 Hz, 1H), 6.27-6.14 (m, 1H), 4.29-4.22 (m, 1H), 4.09 (d, J=10.37 Hz, 2H), 2.99 (t, J=12.96 Hz, 2H), 2.83 (d, J=13.27 Hz, 1H), 2.64-2.55 (m, 2H), 2.44 (dd, J=19.98, 12.20 Hz, 2H), 2.20 (s, 2H), 2.06-1.80 (m, 6H), 1.67 (m, 7H), 1.52 (d, J=12.51 Hz, 1H), 1.35 (m, 1H); LC/MS: m/z=485.01 [M+H]⁺ (Calc: 484.63).

U006: methyl 2-(5-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)acetate.

U006: LC/MS: m/z=557.1 [M+H]⁺ (Calc: 556.7).

U007: 2-(5-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)acetic acid.

U007: ¹H-NMR: $\delta_H$ (ppm, 400 MHz, CDCl₃) 9.13 (d, J=1.92 Hz, 1H), 8.64-8.58 (m, 2H), 7.86 (dd, J=7.97, 1.37 Hz, 1H), 7.72 (dd, J=10.03, 5.91 Hz, 1H), 7.40 (t, J=7.42 Hz, 1H), 6.72 (d, J=9.61 Hz, 1H), 6.28-6.20 (m, 1H), 4.77 (s, 2H), 4.28-4.22 (m, 1H), 4.14 (d, J=9.61 Hz, 2H), 3.06 (t, J=12.64 Hz, 2H), 2.92-2.88 (m, 1H), 2.66-2.43 (m, 4H), 2.25 (s, 2H), 2.11-1.88 (m, 5H), 1.72 (d, J=14.01 Hz, 6H), 1.58 (t, J=6.46 Hz, 1H), 1.43 (m, 1H); LC/MS: m/z=543.25 [M+H]⁺ (Calc: 542.67).

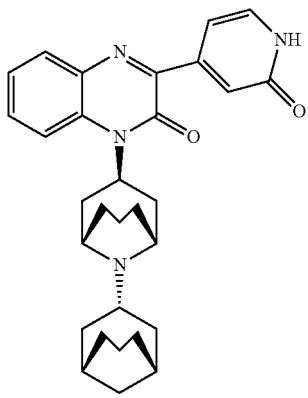

U008

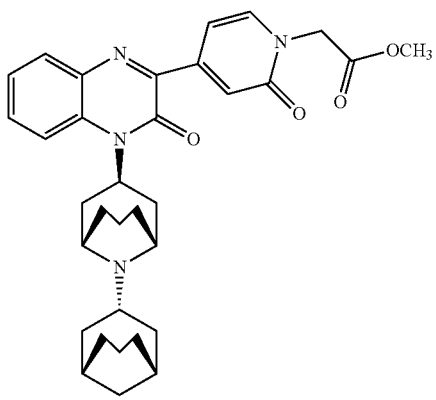

U009

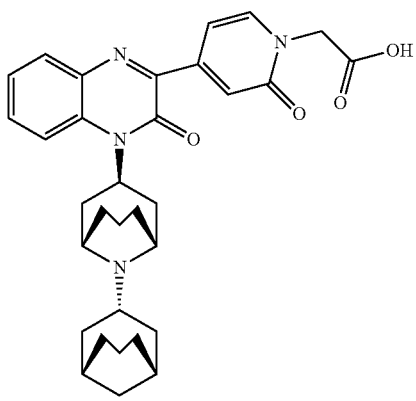

U010

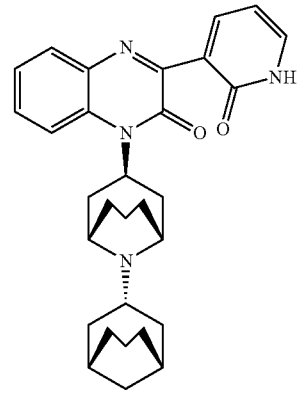

R15a(i)

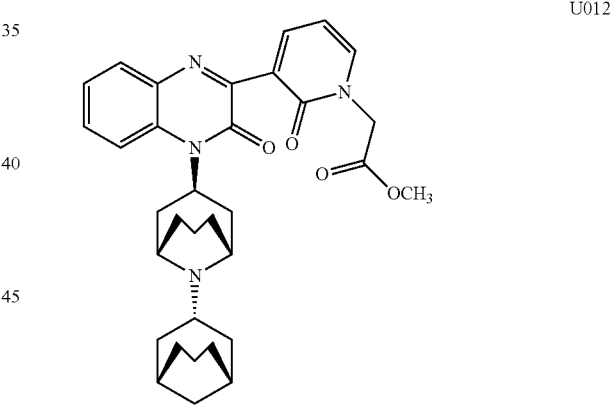

U012

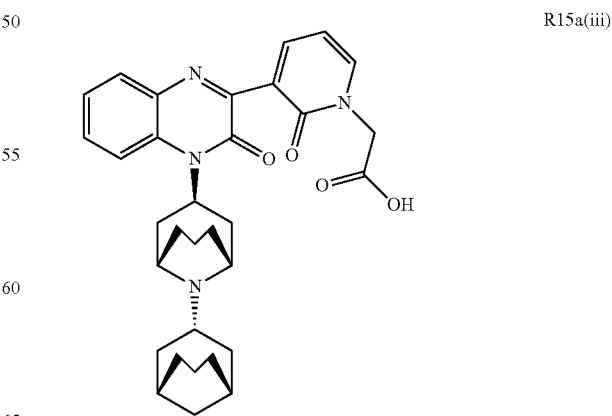

R15a(iii)

U008: 1-((1R,1'R,3r,3'R,5 S,5'S)-[3,9'-bi(9'-azabicyclo[3.3.1]nonan)]-3'-yl)-3-(2-oxo-1,2-dihydropyridin-4-yl)quinoxalin-2(1H)-one.

U008: $^1$H-NMR: $\delta_H$ (ppm, 400 MHz, CDCl$_3$): 8.75 (d, J=8.52 Hz, 1H), 8.37 (s, 1H), 8.16-8.08 (m, 2H), 7.99-7.95 (m, 1H), 7.86 (t, J=7.97 Hz, 1H), 7.47 (t, J=7.69 Hz, 1H), 6.45-6.32 (m, 1H), 4.45-4.32 (m, 1H), 4.15 (s, J=10.44 Hz, 2H), 3.05 (t, J=13.18 Hz, 2H), 2.90-2.86 (m, 1H), 2.70-2.47 (m, 4H), 2.26 (s, 2H), 2.11-1.37 (m, 14H); LC/MS: m/z=485.2 [M+H]$^+$ (Calc: 484.6).

U009: methyl 2-(4-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)acetate.

U009: $^1$H-NMR: $\delta_H$ (ppm, 400 MHz, CDCl$_3$): 7.92 (d, J=7.97 Hz, 1H), 7.74-7.55 (m, 2H), 7.37 (dd, J=9.61, 4.94 Hz, 1H), 7.09-7.05 (m, 1H), 5.27-5.19 (m, 1H), 4.70 (s, 2H), 3.78 (s, 3H), 3.62-3.45 (m, 3H), 2.79-2.70 (m, 2H), 2.57-2.32 (m, 1H), 2.02 (d, J=14.01 Hz, 6H), 1.90-1.65 (m, 13H), 1.12 (d, J=12.91 Hz, 1H); LC/MS: m/z=557.1 [M+H]$^+$ (Calc: 556.7).

U010: 2-(4-(4-((1R,1'R,3r,3R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)acetic acid.

U010: $^1$H-NMR: $\delta_H$ (ppm, 400 MHz, CDCl$_3$): 8.62 (d, J=9.06 Hz, 1H), 7.96 (dd, J=7.97, 1.10 Hz, 1H), 7.89 (d, J=1.65 Hz, 1H), 7.80 (dd, J=12.36, 4.67 Hz, 1H), 7.68 (d, J=7.14 Hz, 1H), 7.48 (s, 0.5H), 7.41 (dd, J=7.28, 1.79 Hz, 1.5H), 6.30-6.12 (m, 1H), 4.84 (s, 2H), 4.34-4.25 (m, 1H), 4.17 (t, J=5.22 Hz, 2H), 3.08 (dd, J=20.05, 6.59 Hz, 2H), 2.87 (dd, J=8.65, 7.83 Hz, 1H), 2.59-2.45 (m, 4H), 2.26 (s, 2H), 2.19 (s, 2H), 2.13-2.00 (m, 3H), 1.89-1.72 (m, 7H), 1.67-1.36 (m, 2H); LC/MS: m/z=543.25 [M+H]$^+$ (Calc: 542.67).

R15a(i): 1-((1R,1'R,3r,3'R,5S,5'S)-[3,9'-bi(9'-azabicyclo[3.3.1]nonan)]-3'-yl)-3-(2-oxo-1,2-dihydropyridin-3-yl)quinoxalin-2(1H)-one.

R15a(i): $^1$H-NMR: $\delta_H$ (ppm, 400 MHz, CDCl$_3$): 9.79 (dd, J=7.83, 1.79 Hz, 1.0H), 8.87 (d, J=8.79 Hz, 1.0H), 8.35 (dd, J=6.18, 1.79 Hz, 1.0H), 7.93 (t, J=7.83 Hz, 2.0H), 7.56 (dd, J=9.61, 5.77 Hz, 1.0H), 7.21 (dd, J=7.97, 6.32 Hz, 1.0H), 6.49-6.27 (m, 1.0H), 4.29 (dd, J=10.99, 5.49 Hz, 0.9H), 4.18 (d, J=10.16 Hz, 1.8H), 3.04 (t, J=11.67 Hz, 2.0H), 2.81 (dt, J=23.53, 8.03 Hz, 1.0H), 2.65-2.50 (m, 4.0H), 2.27 (s, 2.0H), 2.14-1.57 (m, 12.0H), 1.53-1.32 (m, 1.0H); LC/MS: m/z=485.25 [M+H]$^+$ (Calc: 484.63).

U012: methyl 2-(3-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)acetate.

U012: $^1$H-NMR: $\delta_H$ (ppm, 400 MHz, CDCl$_3$): 7.89 (d, J=6.59 Hz, 1H), 7.77 (dd, J=6.87, 2.20 Hz, 1H), 7.70-7.50 (m, 2H), 7.33 (td, J=8.45, 3.85 Hz, 2H), 6.34 (dd, J=8.65, 5.08 Hz, 1H), 5.44-5.03 (br, 1H), 4.74 (s, 2H), 3.73 (s, 3H), 3.62-3.40 (m, 3H), 2.87-2.61 (m, 2H), 2.51-2.28 (m, 1H), 2.15-1.90 (m, 5H), 1.85-1.40 (m, 12H), 1.15-0.99 (m, 1H); LC/MS: m/z=557.1 [M+H]$^+$ (Calc: 556.7).

R15a(iii): 2-(3-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)acetic acid.

R15a(iii): $^1$H-NMR: $\delta_H$ (ppm, 400 MHz, CDCl$_3$): 8.73 (d, J=8.52 Hz, 1H), 8.61 (d, J=7.69 Hz, 1H), 7.91-7.80 (m, 3H), 7.47 (t, J=7.42 Hz, 1H), 6.67 (t, J=7.00 Hz, 1H), 6.37-6.17 (m, 1H), 4.87 (d, J=7.69 Hz, 2H), 4.30 (t, J=10.44 Hz, 1H), 4.14 (d, J=10.44 Hz, 2H), 3.04 (t, J=12.64 Hz, 2H), 2.78 (d, J=14.28 Hz, 1H), 2.60-2.45 (m, 4H), 2.25 (s, 2H), 1.75 (ddt, J=110.15, 59.15, 17.61 Hz, 14H); LC/MS: m/z=543.25 [M+H]$^+$ (Calc: 542.67).

5.14 Example 14

Synthesis of Cyclic Urea- or Lactam-Substituted Quinoxaline-Type Piperidine Compounds Where E is C Using procedures similar to those described above for Method 6.1 in Example 12, the following Cyclic Urea- or Lactam-Substituted Quinoxaline-Type Piperidine Compounds were prepared from the appropriate 3-chloroquinoxalin-2(1H)-one and the appropriate co-reactants. The 3-chloroquinoxalin-2(1H)-ones are commercially available or can be prepared by methods known to the art, e.g., as described in U.S. Patent Application Publication Nos. US 2010/0216726 A1 (see, e.g., Examples 3, 14, 17, and 29), US 2011/0178090 A1, and/or International PCT Publication No. WO 2012/085648 A1 (see, e.g., Examples 1, 2, and 10), which are hereby incorporated by reference in their entireties. The co-reactant compounds are commercially available from, e.g., Sigma-Aldrich, or can be prepared by methods known to the art.

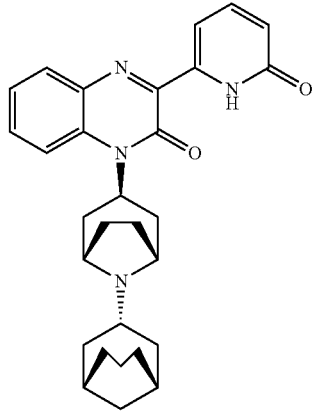

Q1a(i)

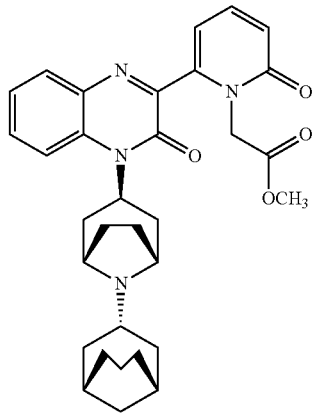

U015

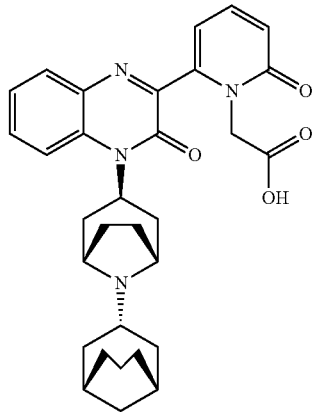

Q1a(iii)

Q1a(i): 1-((1R,3R,5S)-8-((1R,3r,5S)-bicyclo[3.3.1]nonan-3-yl)-8-azabicyclo[3.2.1]octan-3-yl)-3-(6-oxo-1,6-dihydropyridin-2-yl)quinoxalin-2(1H)-one.

Q1a(i): $^1$H-NMR: $\delta_H$ (ppm, 400 MHz, CDCl$_3$): 11.23 (s, 1H), 9.51 (s, 1H), 8.42 (d, J=8.79 Hz, 1H), 7.94 (dd, J=17.99, 7.00 Hz, 2H), 7.78 (t, J=7.97 Hz, 1H), 7.55 (dd, J=9.06, 7.14 Hz, 1H), 7.46 (t, J=7.83 Hz, 1H), 6.76 (d, J=9.06 Hz, 1H), 6.41-6.14 (m, 1H), 4.30 (s, 2H), 3.73 (s, 1H), 3.06 (dd, J=19.50, 14.28 Hz, 2H), 2.82 (d, J=7.69 Hz, 2H), 2.66 (d, J=8.52 Hz, 2H), 2.31 (dd, J=14.28, 7.42 Hz, 6H), 2.00 (t, J=14.56 Hz, 4H), 1.90-1.64 (m, 12H), 1.26 (t, J=7.00 Hz, 1H); LC/MS: m/z=471.26 [M+H]$^+$ (Calc: 470.61).

U015: methyl 2-(6-(4-((1R,3R,5S)-8-((1R,3r,5S)-bicyclo[3.3.1]nonan-3-yl)-8-azabicyclo[3.2.1]octan-3-yl)-3-oxo-3,4-dihydroquinoxalin-2-yl)-2-oxopyridin-1(2H)-yl)acetate.

U015: LC/MS: m/z=543.36 [M+H]$^+$ (Calc: 542.67).

Q1a(iii): 2-(6-(4-((1R,3R,5S)-8-((1R,3r,5S)-bicyclo[3.3.1]nonan-3-yl)-8-azabicyclo[3.2.1]octan-3-yl)-3-oxo-3,4-dihydroquinoxalin-2-yl)-2-oxopyridin-1(2H)-yl)acetic acid.

Q1a(iii): $^1$H-NMR: $\delta_H$ (ppm, 400 MHz, CDCl$_3$): 8.42 (d, J=7.69 Hz, 0.8H), 8.33 (dd, J=14.83, 8.52 Hz, 1.2H), 8.23 (d, J=8.52 Hz, 0.3H), 8.09-8.00 (m, 1.7H), 7.88 (t, J=7.97 Hz, 0.6H), 7.78 (d, J=7.97 Hz, 0.4H), 7.50 (ddd, J=23.90, 11.40, 5.08 Hz, 1.6H), 7.25 (t, J=4.67 Hz, 0.4H), 6.40-6.14 (m, 1.0H), 5.27 (s, 1.3H), 5.16 (s, 0.7H), 4.31 (s, 2.0H), 3.61-3.42 (m, 2.0H), 2.93 (dd, J=23.35, 9.89 Hz, 2.0H), 2.52 (tt, J=21.97, 6.59 Hz, 5.0H), 2.30 (t, J=17.99 Hz, 3.0H), 2.08 (dd, J=11.26, 3.57 Hz, 2.0H), 1.84 (d, J=13.18 Hz, 1.0H), 1.65 (dd, J=35.43, 10.99 Hz, 5.0H), 1.42-1.19 (m, 1.0H); LC/MS: m/z=529.4 [M+H]$^+$ (Calc: 528.6).

Q13a(i)

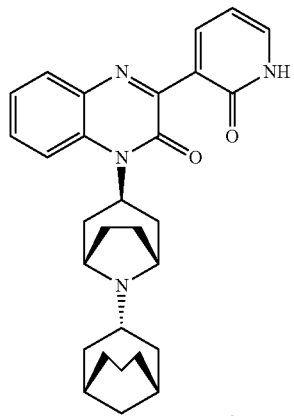

Q23a(i)

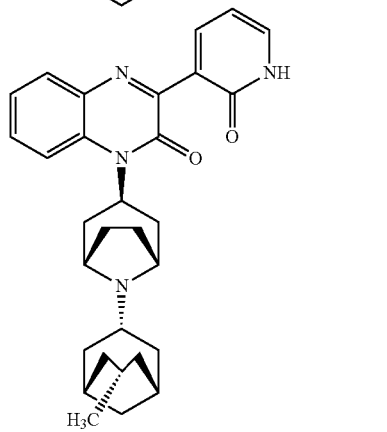

U018

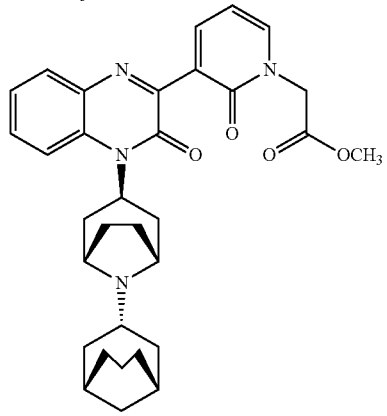

Q13a(iii)

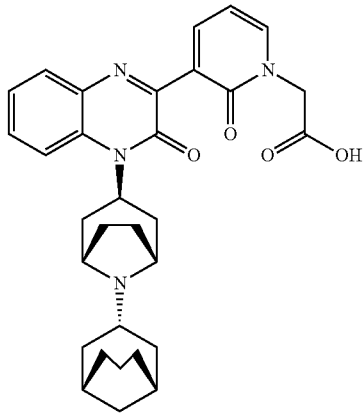

Q13a(i): 1-((1R,3R,5S)-8-((1R,3r,5S)-bicyclo[3.3.1]nonan-3-yl)-8-azabicyclo[3.2.1]octan-3-yl)-3-(2-oxo-1,2-dihydropyridin-3-yl)quinoxalin-2(1H)-one.

Q13a(i): $^1$H-NMR: $\delta_H$ (ppm, 400 MHz, CDCl$_3$): 9.86 (dd, J=7.97, 1.37 Hz, 1H), 8.38-8.34 (m, 2H), 7.98-7.88 (m, 2H), 7.57 (t, J=7.69 Hz, 1H), 7.25 (dd, J=7.83, 6.18 Hz, 1H), 6.42-6.22 (m, 1H), 4.32 (s, 2H), 3.52 (dd, J=11.67, 5.63 Hz, 1H), 2.96 (dt, J=17.12, 7.07 Hz, 2H), 2.47 (dtd, J=41.07, 13.87, 6.82 Hz, 7H), 2.25 (s, 2H), 2.10 (dd, J=11.81, 5.49 Hz, 2H), 1.72 (dt, J=48.89, 18.20 Hz, 6H), 1.33 (d, J=5.49 Hz, 1H); LC/MS: m/z=471.4 [M+H]$^+$ (Calc: 470.6).

Q23a(i): 1-((1R,3R,5S)-8-((1R,3r,5S,7S)-7-methylbicyclo[3.3.1]nonan-3-yl)-8-azabicyclo[3.2.1]octan-3-yl)-3-(2-oxo-1,2-dihydropyridin-3-yl)quinoxalin-2(1H)-one.

Q23a(i): $^1$H-NMR: $\delta_H$ (ppm, 400 MHz, CD$_3$OD): 7.88-8.00 (m, 2H), 7.56-7.77 (m, 3H), 7.34-7.53 (m, 1H), 6.49-6.66 (m, 1H), 6.49-6.66 (br, 1H), 5.26-5.46 (br, 2H), 4.33-4.48 (br, 1H), 4.16-4.32 (br, 1H), 3.01-3.19 (m, 5H), 2.69-2.92 (m, 14H), 2.52-2.67 (m, 4H); LC/MS: m/z=485.2 [M+H]$^+$.

U018: methyl 2-(3-(4-((1R,3R,5S)-8-((1R,3r,5S)-bicyclo[3.3.1]nonan-3-yl)-8-azabicyclo[3.2.1]octan-3-yl)-3-oxo-3,4-dihydroquinoxalin-2-yl)-2-oxopyridin-1(2H)-yl)acetate.

U018: LC/MS: m/z=543.4 [M+H]$^+$ (Calc: 542.7).

Q13a(iii): 2-(3-(4-((1R,3R,5S)-8-((1R,3r,5S)-bicyclo[3.3.1]nonan-3-yl)-8-azabicyclo[3.2.1]octan-3-yl)-3-oxo-3,4-dihydroquinoxalin-2-yl)-2-oxopyridin-1(2H)-yl)acetic acid.

Q13a(iii): $^1$H-NMR: $\delta_H$ (ppm, 400 MHz, CDCl$_3$): 9.30 (d, J=6.0 Hz, 1H), 8.32 (d, j=11.4 Hz, 1H), 8.17 (d, J=6.0 Hz, 1H), 7.94-7.84 (m, 2H), 7.53 (m, 1H), 6.87 (m, 1H), 6.27 (m, 1H), 5.01 (s, 2H), 4.31 (m, 2H), 3.48 (m, 1H), 2.93 (m, 2H), 2.62-2.01 (m, 12H), 1.91-1.60 (m, 6H), 1.29 (m, 1H); LC/MS: m/z=529.4 [M+H]$^+$ (Calc: 528.6).

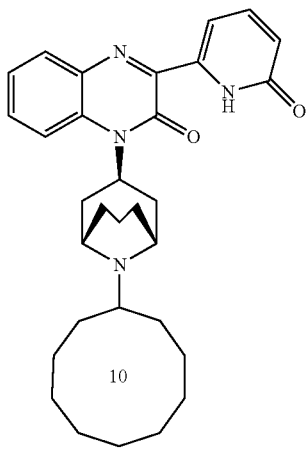

BB1c(i)

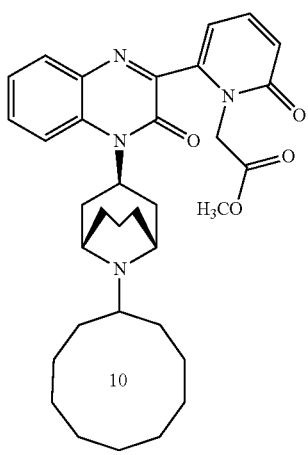

BB1c(iii)

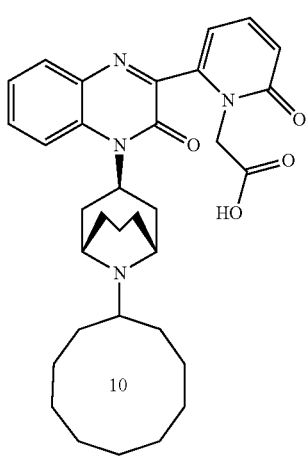

BB1c(i): 1-(((1R,3r,5S)-9-cyclodecyl-9-azabicyclo[3.3.1]nonan-3-yl)-3-(6-oxo-1,6-dihydropyridin-2-yl)quinoxalin-2(1H)-one.

BB1c(i): $^1$H-NMR: $\delta_H$ (ppm, 400 MHz, CDCl$_3$): 11.08 (s, 1H), 8.09 (d, J=6.87 Hz, 1H), 7.92 (d, J=7.97 Hz, 1H), 7.58 (dt, J=25.09, 8.38 Hz, 3H), 7.42 (d, J=8.24 Hz, 1H), 6.74 (d, J=9.06 Hz, 1H), 5.39-4.95 (m, 1H), 3.54 (d, J=12.09 Hz, 2H), 3.07 (s, 1H), 2.72 (t, J=12.50 Hz, 2H), 2.43 (t, J=8.38 Hz, 1H), 2.07-1.97 (m, 2H), 1.96-1.71 (m, 24H), 1.19 (d, J=10.71 Hz, 1H); LC/MS: m/z=501.35 [M+H]$^+$ (Calc: 500.67).

U021: methyl 2-(6-(4-((1R,3r,5S)-9-cyclodecyl-9-azabicyclo[3.3.1]nonan-3-yl)-3-oxo-3,4-dihydroquinoxalin-2-yl)-2-oxopyridin-1(2H)-yl)acetate.

U021: LC/MS: m/z=573.4 [M+H]$^+$ (Calc: 572.7).

BB1c(iii): 2-(6-(4-((1R,3r,5S)-9-cyclodecyl-9-azabicyclo[3.3.1]nonan-3-yl)-3-oxo-3,4-dihydroquinoxalin-2-yl)-2-oxopyridin-1(2H)-yl)acetic acid.

BB1c(iii): $^1$H-NMR: $\delta_H$ (ppm, 400 MHz, CDCl$_3$): 8.77 (d, J=8.79 Hz, 1.0H), 8.29-8.19 (m, 2.0H), 8.05 (dd, J=8.10, 1.51 Hz, 1.0H), 7.88 (t, J=7.14 Hz, 1.0H), 7.49 (dd, J=16.89, 8.10 Hz, 2.0H), 6.47-6.32 (m, 1.0H), 5.22 (s, 2.0H), 4.15 (d, J=10.16 Hz, 2.0H), 3.80 (s, 1.1H), 3.07 (t, J=12.91 Hz, 2.0H), 2.86 (d, J=15.11 Hz, 1.0H), 2.56 (dd, J=20.19, 12.50 Hz, 2.0H), 2.29 (dd, J=13.18, 5.22 Hz, 2.0H), 2.08 (dt, J=25.91, 10.09 Hz, 4.0H), 1.87-1.32 (m, 18.0H); LC/MS: m/z=559.4 [M+H]$^+$ (Calc: 558.7).

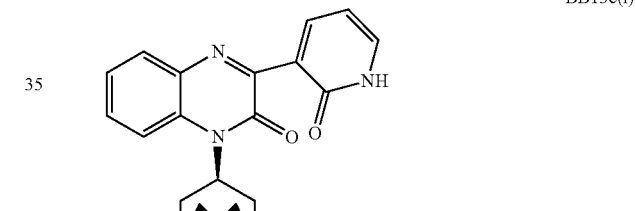

BB13c(i)

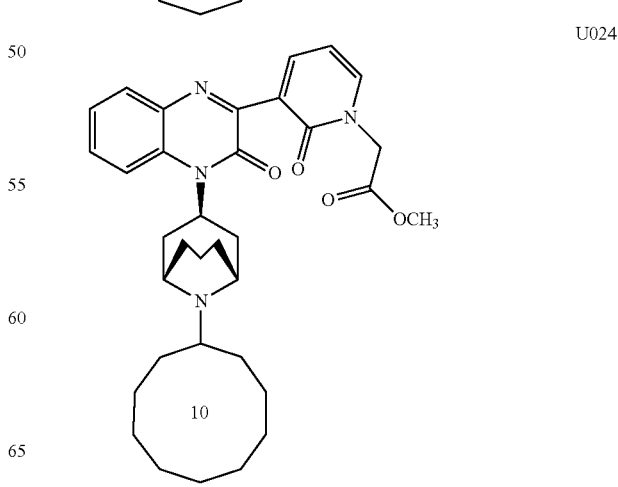

U024

-continued

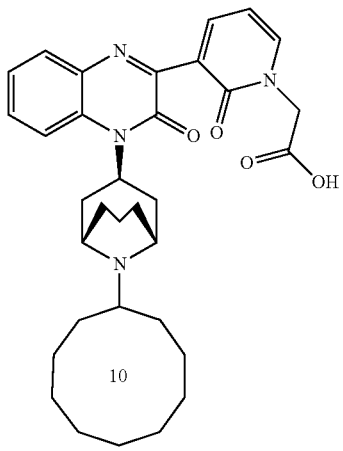

BB13c(iii)

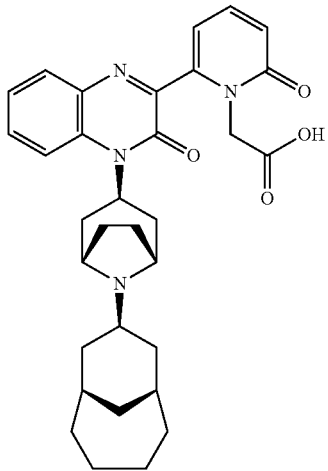

DD1b(iii)

BB13c(i): 1-((1R,3r,5S)-9-cyclodecyl-9-azabicyclo[3.3.1]nonan-3-yl)-3-(2-oxo-1,2-dihydropyridin-3-yl)quinoxalin-2(1H)-one.

BB13c(i): $^1$H-NMR: $\delta_H$ (ppm, 400 MHz, CDCl$_3$): 10.07 (dd, J=7.97, 1.65 Hz, 1H), 8.90 (d, J=9.34 Hz, 1H), 8.46 (dd, J=6.18, 1.79 Hz, 1H), 7.97-7.93 (m, 2H), 7.58 (t, J=7.69 Hz, 1H), 7.31 (dd, J=8.79, 6.87 Hz, 1H), 6.49-6.35 (m, 1H), 4.18 (d, J=11.54 Hz, 2H), 3.83 (s, 1H), 3.03 (t, J=13.18 Hz, 2H), 2.85 (d, J=13.18 Hz, 1H), 2.65-2.55 (m, 2H), 2.30 (dd, J=14.70, 6.46 Hz, 2H), 2.14-2.04 (m, 4H), 1.93-1.54 (m, 16H); LC/MS: m/z=501.35 [M+H]$^+$ (Calc: 500.67).

U024: methyl 2-(3-(4-((1R,3r,5S)-9-cyclodecyl-9-azabicyclo[3.3.1]nonan-3-yl)-3-oxo-3,4-dihydroquinoxalin-2-yl)-2-oxopyridin-1(2H)-yl)acetate.

U024: $^1$H-NMR: $\delta_H$ (ppm, 400 MHz, CDCl$_3$): 7.89 (d, J=7.69 Hz, 1H), 7.77 (d, J=7.42 Hz, 1H), 7.57 (s, 2H), 7.34 (t, J=6.04 Hz, 3H), 6.44-6.26 (m, 1H), 4.74 (s, 2H), 3.73 (s, 3H), 3.52 (s, 2H), 3.05 (s, 1H), 2.70 (s, 2H), 2.46-2.29 (m, 1H), 2.03 (s, 2H), 1.61 (t, J=17.99 Hz, 22H), 1.21 (d, J=26.64 Hz, 5H), 0.87 (d, J=7.42 Hz, 2H); LC/MS: m/z=575.35 [M+H]$^+$ (Calc: 572.74).

BB13c(iii): 2-(3-(4-((1R,3r,5S)-9-cyclodecyl-9-azabicyclo[3.3.1]nonan-3-yl)-3-oxo-3,4-dihydroquinoxalin-2-yl)-2-oxopyridin-1(2H)-yl)acetic acid.

BB13c(iii): $^1$H-NMR: $\delta_H$ (ppm, 400 MHz, CDCl$_3$): 8.94 (dd, J=7.02, 1.22 Hz, 1H), 8.78 (d, J=8.85 Hz, 1H), 8.02 (dd, J=6.86, 2.14 Hz, 1H), 7.87 (dd, J13.27, 7.63 Hz, 2H), 7.49 (t, J=7.63 Hz, 1H), 6.76 (t, J=7.09 Hz, 1H), 6.40-6.26 (m, 1H), 4.94 (s, 2H), 4.14 (d, J=9.00 Hz, 2H), 3.79 (t, J=5.19 Hz, 1H), 3.03 (t, J=12.51 Hz, 2H), 2.81 (dd, J=25.70, 13.34 Hz, 1H), 2.55 (dd, J=19.29, 11.82 Hz, 2H), 2.32-2.28 (m, 2H), 2.20-2.08 (m, 4H), 1.91-1.42 (m, 18H); LC/MS: m/z=559.4 [M+H]$^+$ (Calc: 558.7).

DD1b(iii): 2-(6-(4-((1R,3R,5S)-8-((1R,6S,8s)-bicyclo[4.3.1]decan-8-yl)-8-azabicyclo[3.2.1]octan-3-yl)-3-oxo-3,4-dihydroquinoxalin-2-yl)-2-oxopyridin-1(2H)-yl)acetic acid.

DD1b(iii): $^1$H-NMR: $\delta_H$ (ppm, 300 MHz, CDCl$_3$+CD$_3$OD+DCl): 1.30-1.78 (m, 10H), 1.89-2.38 (m, 12H), 2.55-2.67 (m, 2H), 2.85-2.96 (m, 1H), 4.30-4.40 (m, 1H), 4.90 (s, 2H), 5.98-6.12 (m, 1H), 7.03 (d, J=8.5 Hz, 1H), 7.42 (dd, J=7.5, 7.5 Hz, 1H), 7.65-7.71 (m, 2H), 7.86-7.93 (m, 2H), 8.10 (d, J=8.8 Hz, 1H); LC/MS: m/z=543.25 [M+H]$^+$ (Calc: 542).

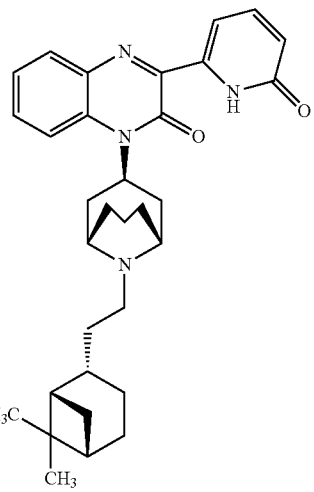

U39a(i)

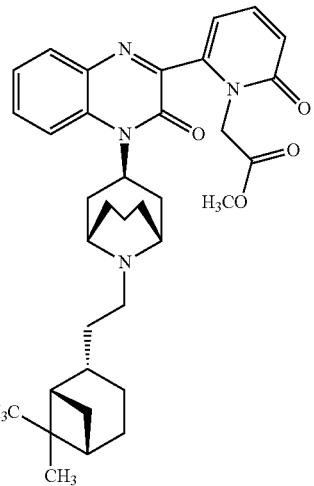

U027

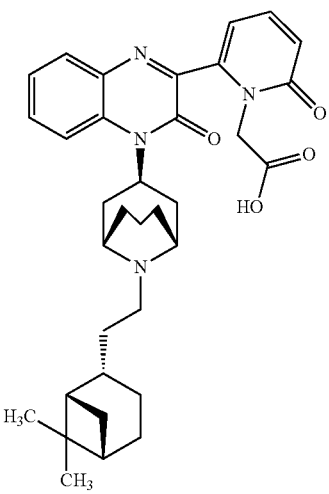

U39a(i): 1-((1R,3S,5S)-9-(2-((1S,2S,5S)-6,6-dimethylbicyclo[3.1.1]heptan-2-yl)ethyl)-9-azabicyclo[3.3.1]nonan-3-yl)-3-(6-oxo-1,6-dihydropyridin-2-yl)quinoxalin-2(1H)-one.

U39a(i): $^1$H-NMR: $\delta_H$ (ppm, 400 MHz, CDCl$_3$): 11.18 (s, 1H), 9.88 (s, 1H), 8.80 (d, J=8.90 Hz, 1H), 7.93 (dd, J=15.53, 6.97 Hz, 1H), 7.80 (t, J=7.81 Hz, 1H), 7.56-7.44 (m, 1H), 6.75 (d, J=9.06 Hz, 1H), 6.25-6.02 (m, 1H), 3.87 (d, J=10.24 Hz, 2H), 3.26 (d, J=5.54 Hz, 2H), 2.96 (ddd, J=52.67, 19.01, 10.11 Hz, 2H), 2.60-2.48 (m, 2H), 2.43-2.32 (m, 1H), 2.23-1.50 (m, 18H), 1.22 (s, 2H), 1.11 (s, 2H), 0.91 (d, J=9.57 Hz, 1H); LC/MS: m/z=513.35 [M+H]$^+$ (Calc: 512.69).

U027: methyl 2-(6-(4-((1R,3S,5S)-9-(2-((1S,2S,5S)-6,6-dimethylbicyclo[3.1.1]heptan-2-yl)ethyl)-9-azabicyclo[3.3.1]nonan-3-yl)-3-oxo-3,4-dihydroquinoxalin-2-yl)-2-oxopyridin-1(2H)-yl)acetate.

U027: LC/MS: m/z=585.35 [M+H]$^+$ (Calc: 584.75).

U39a(iii): 2-(6-(4-((1R,3S,5S)-9-(2-((1S,2S,5S)-6,6-dimethylbicyclo[3.1.1]heptan-2-yl)ethyl)-9-azabicyclo[3.3.1]nonan-3-yl)-3-oxo-3,4-dihydroquinoxalin-2-yl)-2-oxopyridin-1(2H)-yl)acetic acid.

U39a(iii): $^1$H-NMR: $\delta_H$ (ppm, 400 MHz, CDCl$_3$): 8.67 (d, J=8.85 Hz, 1H), 8.30-8.21 (m, 2H), 8.04 (d, J=7.78 Hz, 1H), 7.87 (t, J=8.01 Hz, 1H), 7.54-7.45 (m, 2H), 6.32-6.12 (m, 1H), 5.21 (s, 2H), 3.86 (d, J=10.68 Hz, 2H), 3.24 (t, J=8.01 Hz, 2H), 3.07 (t, J=12.66 Hz, 2H), 2.77 (d, J=16.01 Hz, 1H), 2.53 (dd, J=17.54, 10.52 Hz, 2H), 2.42-2.35 (m, 1H), 2.07-1.60 (m, 14H), 1.22 (s, 3H), 1.10 (s, 3H), 0.92 (d, J=9.76 Hz, 1H); LC/MS: m/z=571.45 [M+H]$^+$ (Calc: 570.72).

5.15 Example 15

Synthesis of Cyclic Urea- or Lactam-Substituted Quinoxaline-Type Piperidine Compounds R8a(i), U030, and R8a(iii) by Method 6.2

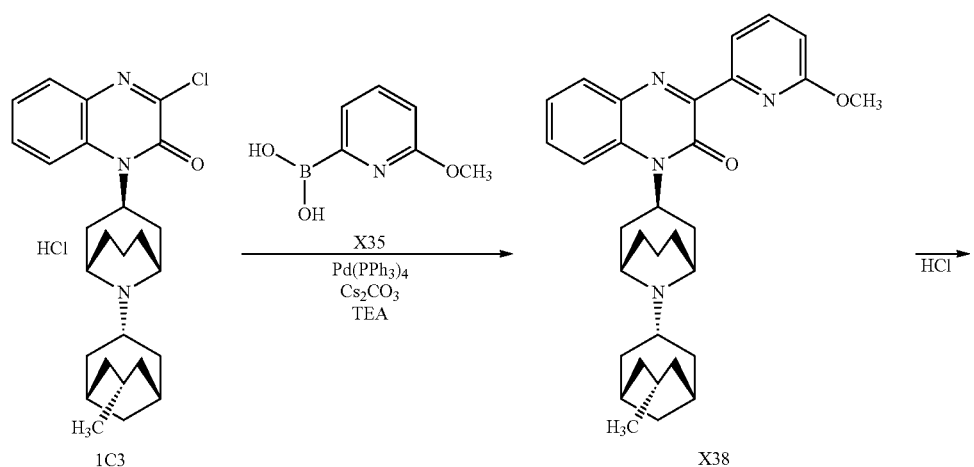

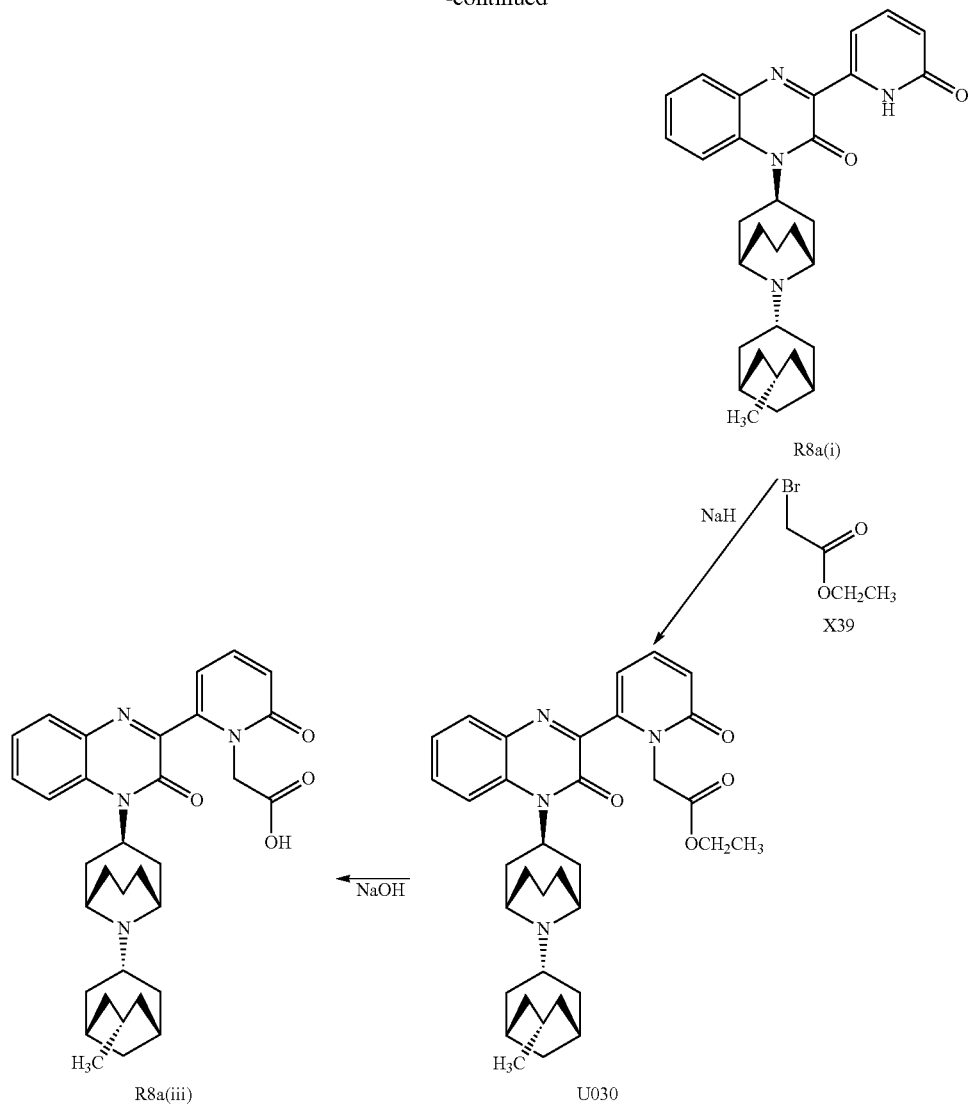

Cyclic Urea- or Lactam-Substituted Quinoxaline-Type Piperidine Compounds R8a(i), U030, and R8a(iii) were prepared using procedures similar to those described above for Method 6.1 in Example 12 except that the hydrochloride of Compound 1C3 was used in the first step in place of Compound 1D3, ethyl 2-bromoacetate (Compound X39, Sigma-Aldrich) was used in the third step in place of methyl 2-bromoacetate (Compound X37), and the conversion of the methoxy-substituted intermediate X38 to the oxo-substituted Cyclic Urea- or Lactam-Substituted Quinoxaline-Type Piperidine Compound R8a(i) in step two was as described below.

Intermediate X38 (0.648 mmol, 332 mg) was added to 2N aqueous HCl (20 mL, 40.0 mmol) to form a suspension. The resulting reaction mixture was heated to 110° C. and stirred at that temperature for 9 hours. Thereafter, the mixture was cooled to a temperature of about 25° C., neutralized with NaHCO$_3$, and extracted with CHCl$_3$. The organic portion was washed with brine, dried (over Na$_2$SO$_4$), and concentrated under reduced pressure to provide Cyclic Urea- or Lactam-Substituted Quinoxaline-Type Piperidine Compound R8a(i), 1-((1R,1'R,3r,3'R,5S,5'S,7S)-7-methyl-[3,9'-bi(9'-azabicyclo[3.3.1]nonan)]-3'-yl)-3-(6-oxo-1,6-dihydropyridin-2-yl)quinoxalin-2(1H)-one.

U030: ethyl 2-(6-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-2-oxopyridin-1(2H)-yl)acetate.

U030: $^1$H-NMR: $\delta_H$ (ppm, 400 MHz, CDCl$_3$ with one drop of DCl and one drop of d4-MeOH): 0.81-1.34 (m, 11H), 1.55-2.10 (m, 7H), 2.12-2.28 (m, 2H), 2.29-2.51 (m, 1H), 2.58-2.79 (m, 2H), 3.06-3.22 (m, 1H), 3.46-3.60 (m, 2H), 3.71 (s, 3H), 5.01-5.36 (m, 1H), 6.60 (d, J=6.71 Hz, 1H), 6.74 (d, J=9.15 Hz, 1H), 7.39 (dd, J=8.03, 4.12 Hz, 1H), 7.45 (ddd, J=9.30, 6.86, 0.92 Hz, 1H), 7.62-7.71 (m, 2H), 7.86 (dd, J=7.61, 0.61 Hz).

R8a(iii): 2-(6-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-2-oxopyridin-1(2H)-yl)acetic acid.

R8a(iii): $^1$H-NMR: $\delta_H$ (ppm, 400 MHz, CDCl$_3$ with one drop of DCl and one drop of d4-MeOH): 0.52-0.67 (m, 2H), 0.83-0.91 (d, J=6.25 Hz, 3H), 1.22-1.37 (m, 2H), 1.60-2.15 (m, 11H), 2.27-2.56 (m, 6H), 2.92-3.04 (m, 2H), 3.71-3.87 (m, 1H), 4.03-4.16 (m, 2H), 4.79 (s, 2H), 6.29-6.45 (m, 1H), 6.76 (d, J=6.86 Hz, 1H), 6.94 (d, J=9.30 Hz, 1H), 7.42 (dd, J=7.70, 7.70 Hz, 1H), 7.61 (dd, J=9.00, 6.86 Hz, 1H), 7.79-7.89 (m, 2H), 8.70 (d, J=8.69 Hz, 1H); LC/MS: m/z=557.4 [M+H]$^+$ (Calc: 556.0).

5.16 Example 16

Synthesis of Cyclic Urea- or Lactam-Substituted Quinoxaline-Type Piperidine Compound R11a(iii)

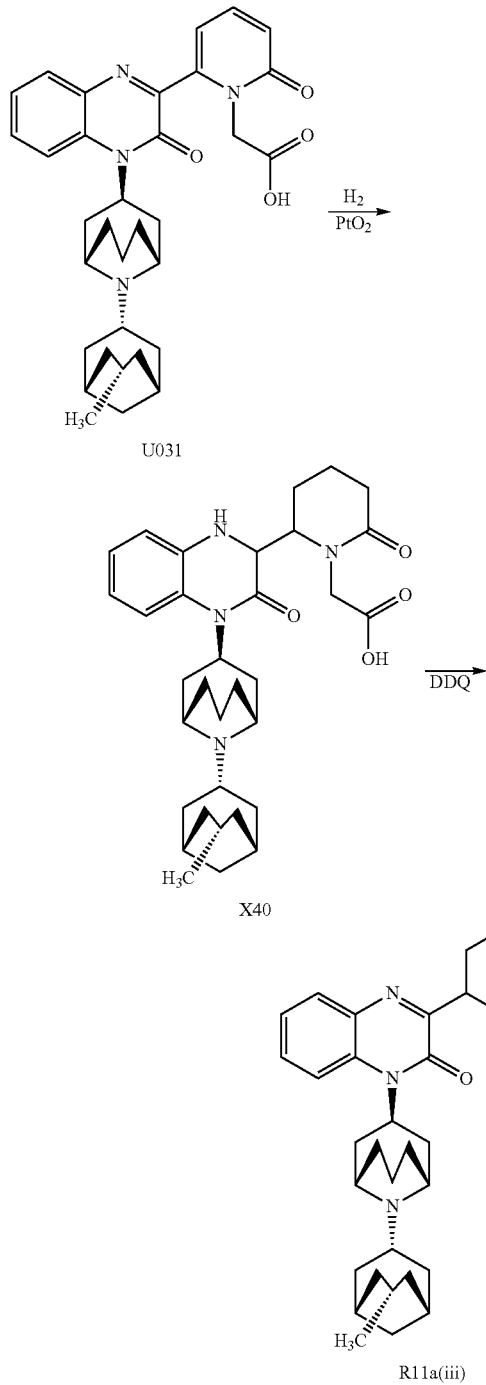

To a suspension of Cyclic Urea- or Lactam-Substituted Quinoxaline-Type Piperidine Compound R8a(iii) (0.173 mmol, 96.4 mg) in EtOH (10 mL) at a temperature of about 25° C. was added PtO$_2$ (0.205 mmol, 46.6 mg, Sigma-Aldrich). Under a hydrogen atmosphere (5 bar), the resulting reaction mixture was stirred at that temperature for 22 hours. Thereafter, the mixture was filtered through CELITE and concentrated to dryness to provide Compound X40, 2-(2-(4-((1R,1'R,3r,3R,5S,5'S,7S)-7-methyl-[3,9'-bi(9'-azabicyclo[3.3.1]nonan)]-3'-yl)-3-oxo-1,2,3,4-tetrahydroquinoxalin-2-yl)-6-oxopiperidin-1-yl)acetic acid, as a brown amorphous solid. Compound X40, taken directly from the previous step, was dissolved in CH$_2$Cl$_2$ (1.5 mL) at a temperature of about 25° C.; then, 4,5-dichloro-3,6-dioxocyclohexa-1,4-diene-1,2-dicarbonitrile (DDQ, 0.208 mmol, 47.2 mg, Sigma-Aldrich) was added. The resulting reaction mixture was stirred at that temperature for 2 hours. Thereafter, the mixture was concentrated to dryness to provide a residue which was chromatographed on a silica-gel column (Yamazen Corp. W003) eluted with a gradient of from 20:80 MeOH (28% NH$_4$OH):CHCl$_3$ to 50:50 MeOH (28% NH$_4$OH):CHCl$_3$ to provide a brown solid which was triturated with MeCN, filtered, and dried under reduced pressure at 100° C. to provide 57.5 mg of Cyclic Urea- or Lactam-Substituted Quinoxaline-Type Piperidine Compound R11a(iii), 2-(2-(4-((1R,1'R,3r,5'R,5S,5'S,7S)-7-methyl-[3,9'-bi(9'-azabicyclo[3.3.1]nonan)]-3'-yl)-3-oxo-3,4-dihydroquinoxalin-2-yl)-6-oxopiperidin-1-yl)acetic acid, as an off-white solid (yield 59.2%).

The identity of Cyclic Urea- or Lactam-Substituted Quinoxaline-Type Piperidine Compound R11a(iii) was confirmed using $^1$H-NMR and LC/MS.

Cyclic Urea- or Lactam-Substituted Quinoxaline-Type Piperidine Compound R11a(iii): $^1$H-NMR: $\delta_H$ (ppm, 400 MHz, CDCl$_3$ with one drop each of DCl and d4-MeOH): 0.51-0.68 (m, 1H), 0.83-0.91 (d, J=6.41 Hz, 3H), 1.27-1.37 (m, 1H), 1.61-3.08 (m, 28H), 3.36-3.50 (m, 1H), 3.72-3.86 (m, 1H), 4.05-4.16 (m, 2H), 4.44-4.56 (m, 1H), 5.26-5.33 (m, 1H), 6.20-6.36 (m, 1H), 7.36 (dd, J=7.55, 7.55 Hz, 1H), 7.72 (dd, J=8.00, 8.00 Hz, 1H), 7.82 (d, J=7.91 Hz, 1H), 8.63 (d, J=8.54 Hz, 1H); LC/MS: m/z=561.5 [M+H]$^+$ (Calc: 560.0).

5.17 Example 17

Synthesis of Cyclic Urea- or Lactam-Substituted Quinoxaline-Type Piperidine Compounds EE1b(i), U034, EE1b(iii), DD13b(i), EE15b(i), and FF13b(i)

Using procedures similar to those described above for Method 6.2 in Example 15, the following Cyclic Urea- or Lactam-Substituted Quinoxaline-Type Piperidine Compounds were prepared from the appropriate 3-chloroquinoxalin-2(1H)-one. The 3-chloroquinoxalin-2(1H)-one is commercially available or can be prepared by methods known to the art, e.g., as described in U.S. Patent Application Publication Nos. US 2010/0216726 A1 (see, e.g., Examples 3, 14, 17, and 29), US 2011/0178090 A1, and/or International PCT Publication No. WO 2012/085648 A1 (see, e.g., Examples 1, 2, and 10), which are hereby incorporated by reference in their entireties.

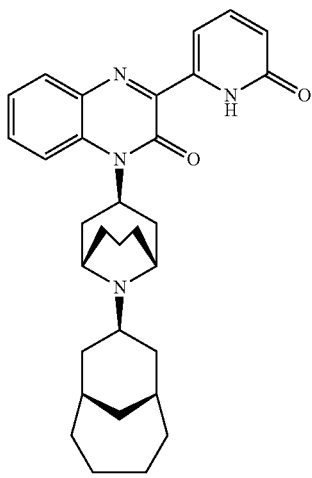

EE1b(i)

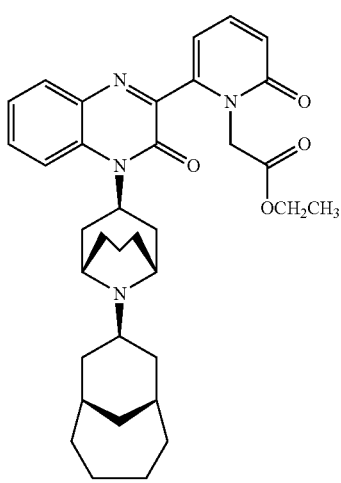

U034

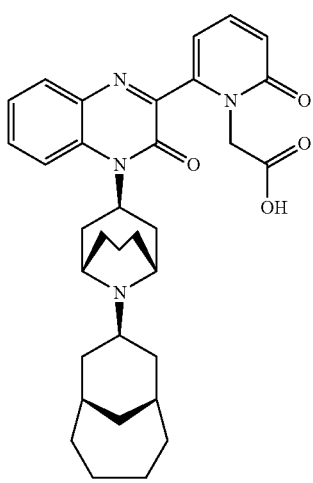

EE1b(iii)

EE1b(i): 1-((1R,3R,5S)-9-((1R,6S,8s)-bicyclo[4.3.1]decan-8-yl)-9-azabicyclo[3.3.1]nonan-3-yl)-3-(6-oxo-1,6-dihydropyridin-2-yl)quinoxalin-2(1H)-one.

EE1b(i): ¹H-NMR: δ$_H$ (ppm, 400 MHz, CDCl$_3$ with one drop of DCl and one drop of d4-MeOH): 1.30-1.52 (m, 4H), 1.65-2.02 (m, 14H), 2.40-2.60 (m, 6H), 3.01-3.10 (m, 2H), 3.80-3.92 (m, 1H), 4.11-4.31 (m, 2H), 5.32 (s, 2H), 6.37-6.63 (m, 1H), 6.76 (d, J=8.98 Hz, 1H), 7.56 (dd, J=7.80 Hz, 1H), 7.66 (ddd, J=8.10, 8.10, 1.49 Hz, 1H), 7.76 (dd, J=8.20, 1.47 Hz, 1H), 7.94 (m, 2H), 8.54 (d, J=7.87 Hz, 1H), 9.57 (d, J=6.90 Hz, 1H); LC/MS: m/z=499.8 [M+H]⁺ (Calc: 498.3).

U034: ethyl 2-(6-(4-((1R,3R,5S)-94(1R,6S,8s)-bicyclo[4.3.1]decan-8-yl)-9-azabicyclo[3.3.1]nonan-3-yl)-3-oxo-3,4-dihydroquinoxalin-2-yl)-2-oxopyridin-1(2H)-yl)acetate.

U034: ¹H-NMR: δ$_H$ (ppm, 400 MHz, CDCl$_3$ with one drop of DCl and one drop of d4-MeOH): 1.33-1.56 (m, 4H), 1.63-2.10 (m, 17H), 2.42-2.61 (m, 6H), 3.00-3.19 (m, 2H), 3.87-3.99 (m, 1H), 4.13-4.34 (m, 4H), 5.30 (s, 2H), 6.31-6.61 (m, 1H), 7.38-7.45 (m, 2H), 7.89 (ddd, J=8.01, 8.01, 1.47 Hz, 1H), 8.02 (dd, J=8.00, 1.47 Hz, 1H), 8.21 (dd, J=7.90, 7.90 Hz, 1H), 8.30 (d, J=7.44 Hz, 1H), 8.81 (d, J=8.70 Hz, 1H); LC/MS: m/z=585.8 [M+H]⁺ (Calc: 584.3).

EE1b(iii): 2-(6-(4-((1R,3R,5S)-9-((1R,6S,8s)-bicyclo[4.3.1]decan-8-yl)-9-azabicyclo[3.3.1]nonan-3-yl)-3-oxo-3,4-dihydroquinoxalin-2-yl)-2-oxopyridin-1(2H)-yl)acetic acid.

EE1b(iii): ¹H-NMR: δ$_H$ (ppm, 400 MHz, CDCl$_3$ with one drop of DCl and one drop of d4-MeOH): 1.34-1.57 (m, 4H), 1.67-2.15 (m, 14H), 2.43-2.66 (m, 6H), 3.04-3.20 (m, 2H), 3.82-3.97 (m, 1H), 4.16-4.31 (m, 2H), 5.28 (s, 2H), 6.35-6.58 (m, 1H), 7.46-7.57 (m, 2H), 7.91 (ddd, J=8.06, 8.06, 1.50 Hz, 1H), 8.08 (dd, J=8.06, 1.50 Hz, 1H), 8.21 (dd, J=7.97, 7.97 Hz, 1H), 8.29 (d, J=7.55 Hz, 1H), 8.84 (d, J=8.73 Hz, 1H); LC/MS: m/z=557.8 [M+H]⁺ (Calc: 556.0).

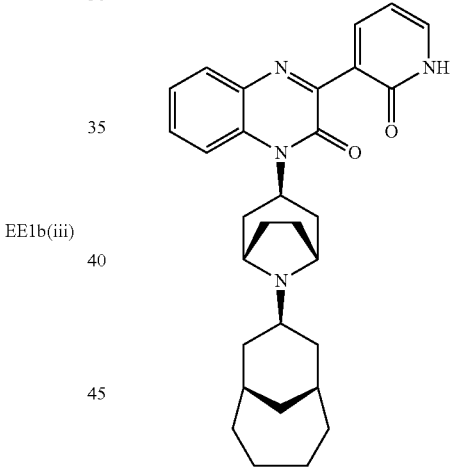

DD13b(i)

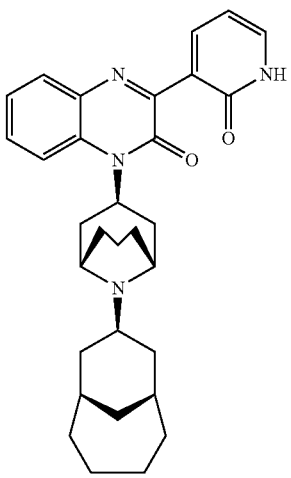

EE15b(i)

326

5.18 Example 18

Synthesis of Cyclic Urea- or Lactam-Substituted Quinoxaline-Type Piperidine Compounds U037, U038, and U040 by Method 7

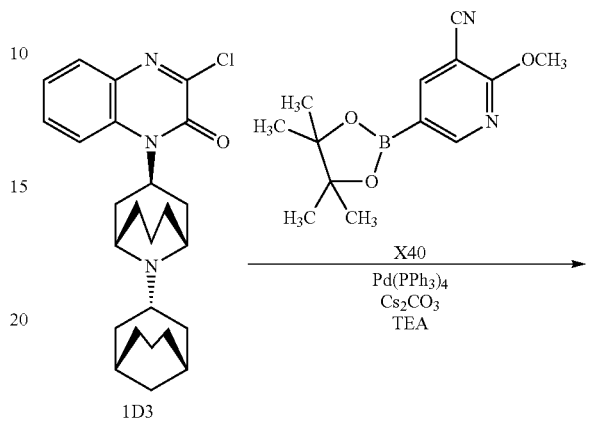

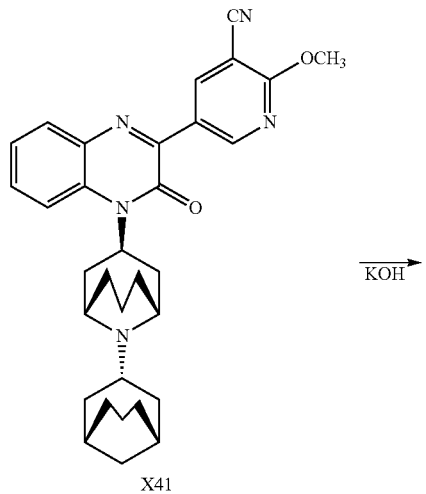

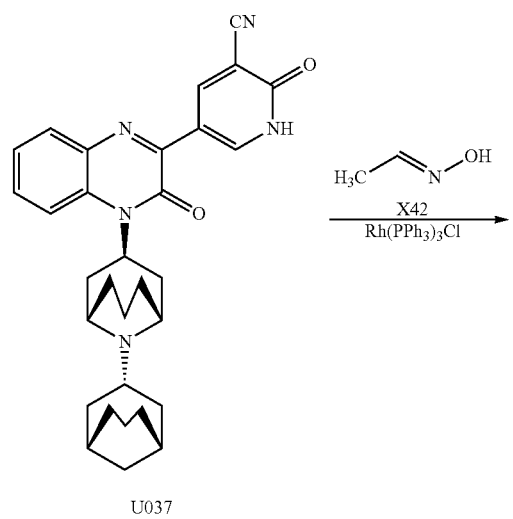

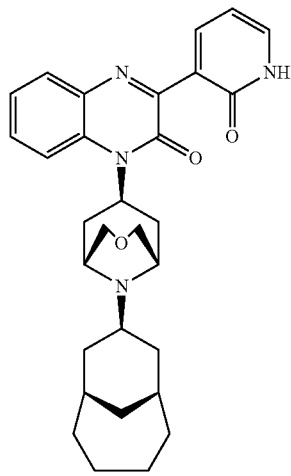

FF13b(i)

DD13b(i): 1-((1R,3R,5S)-8-((1R,6S,8s)-bicyclo[4.3.1]decan-8-yl)-8-azabicyclo[3.2.1]octan-3-yl)-3-(2-oxo-1,2-dihydropyridin-3-yl)quinoxalin-2(1H)-one.

DD13b(i): $^1$H-NMR: $\delta_H$ (ppm, 300 MHz, CDCl$_3$ with one drop of DCl and one drop of d4-MeOH): 1.24-1.48 (m, 4H), 1.62-1.78 (m, 4H), 1.80-1.96 (m, 4H), 2.22-2.62 (m, 10H), 2.90-3.10 (m, 3H), 4.20-4.36 (m, 2H), 6.43 (quint, J=9.30 Hz, 1H), 7.36-7.44 (m, 2H), 7.44 (brs, 1H), 7.55 (t, J=7.50 Hz, 1H), 7.89 (d, J=7.50 Hz, 1H), 7.95 (d, J=7.50 Hz, 1H), 8.40 (d, J=8.70 Hz, 1H), 8.48 (dd, J=1.50 Hz and 6.00 Hz, 1H); LC/MS: m/z=485.3 [M+H]$^+$ (Calc: 484.3).

EE15b(i): 1-((1R,3R,5S)-9-((1R,6S,8s)-bicyclo[4.3.1]decan-8-yl)-9-azabicyclo[3.3.1]nonan-3-yl)-3-(2-oxo-1,2-dihydropyridin-3-yl)quinoxalin-2(1H)-one.

EE15b(i): $^1$H-NMR: $\delta_H$ (ppm, 400 MHz, CDCl$_3$ with one drop of DCl and one drop of d4-MeOH): 1.30-1.62 (m, 4H), 1.65-2.22 (m, 13H), 2.39 (m, 9H), 3.83-3.99 (m, 1H), 4.19-4.31 (m, 2H), 6.50-6.68 (m, 1H), 7.29-7.36 (m, 1H), 7.58 (dd, J=7.72, 7.72 Hz, 1H), 7.93-8.02 (m, 2H), 8.50 (d, J=6.02 Hz, 1H), 8.99 (d, J=8.73 Hz, 1H), 9.93 (d, J=7.89 Hz, 1H); LC/MS: m/z=499.4 [M+H]$^+$ (Calc: 498).

FF13b(i): 1-((1R,5S,7S)-9-((1R,6S,8s)-bicyclo[4.3.1]decan-8-yl)-3-oxa-9-azabicyclo[3.3.1]nonan-7-yl)-3-(2-oxo-1,2-dihydropyridin-3-yl)quinoxalin-2(1H)-one.

FF13b(i): $^1$H-NMR: $\delta_H$ (ppm, 400 MHz, CD$_3$OD): 7.69-7.90 (m, 3H), 7.44-7.63 (m, 2H), 7.24-7.40 (t, J=7.9 Hz, 1H), 6.35-6.52 (t, J=6.6 Hz, 1H), 6.03-6.26 (br, 1H), 3.97-4.28 (br, 6H), 3.60-3.89 (br, 1H), 2.31-2.81 (br, 4H), 1.40-1.72 (br, 2H), 1.73-1.90 (br, 2H), 1.99-2.19 (br, 3H), 0.18-0.10 (br, 10H); LC/MS: m/z=501.3 [M+H]$^+$.

-continued

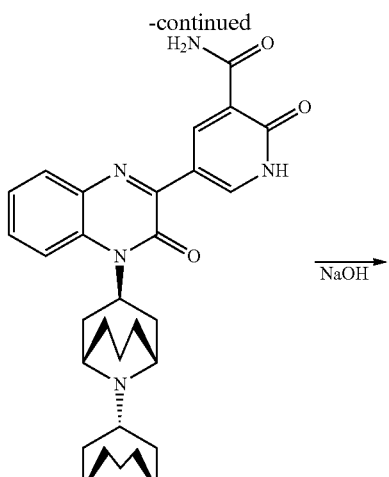

U038

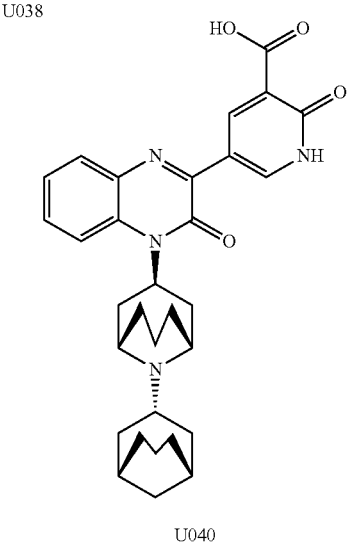

U040

To a mixture of Compound 1D3 (1.174 mmol, 500 mg), 2-methoxy-5-(4,4,5,5-tetramethyl-1,3,2-dioxaborolan-2-yl)nicotinonitrile (Compound X40, 1.291 mmol, 336 mg, Sigma-Aldrich), Cs$_2$CO$_3$ (3.52 mmol, 1.147 mg), and Pd(PPh$_3$)$_4$ (0.117 mmol, 136 mg) at a temperature of about 25° C. was added 1,4-dioxane (25 mL) and TEA (3.52 mmol, 0.491 mL). The resulting reaction mixture was heated to 120° C. and stirred at that temperature for 1.5 hours. Thereafter, the mixture was cooled to a temperature of about 25° C., concentrated under reduced pressure, water (50 mL) was added, then the mixture was extracted twice with CHCl$_3$ (50 mL for each extraction). The organic portions were combined, washed with brine, dried (over MgSO$_4$), and concentrated under reduced pressure to provide a brown amorphous solid which was chromatographed on a on a silica-gel column (REDISEP RF GOLD 12 g) eluted with 0:100 MeOH (10% NH$_3$):CHCl$_3$ to 5:95 MeOH (10% NH$_3$):CHCl$_3$ to provide a brown solid. That solid was chromatographed on a on a silica-gel column (FL60D, Fuji Silysia Chemical USA Ltd., Greenville, N.C.) eluted with 1:99 MeOH (10% NH$_3$):CHCl$_3$ to provide 575.7 mg of Compound X41, 5-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-methoxynicotinonitrile, as a yellow solid (yield 94%).

The identity of Compound X41 was confirmed using $^1$H-NMR and LC/MS.

Compound X41: $^1$H-NMR: δ$_H$ (ppm, 300 MHz, CDCl$_3$): 1.34-1.51 (br, 1H), 1.58 (d, J=11.13 Hz, 1H), 1.63-1.82 (m, 8H), 1.82-2.15 (m, 7H), 2.25 (s, br, 2H), 2.50 (td, J=11.78, 8.08 Hz, 2H), 2.66 (td, J=11.86, 5.24 Hz, 2H), 2.80-3.00 (m, 1H), 3.06 (d, J=14.10 Hz, 2H), 4.13 (d, J=11.70 Hz, 2H), 4.150 (s, 3H), 4.19-4.32 (m, 1H), 6.34 (m, 1H), 7.42 (t, J=7.47 Hz, 1H), 7.49-7.59 (m, 1H), 7.58-7.75 (m, 2H), 7.77-7.86 (m, 1H), 7.95 (dd, J=8.14, 1.59 Hz, 2H), 8.70 (d, J=8.70 Hz, 1H), 9.01 (d, J=2.44 Hz, 1H), 9.38 (d, J=2.44 Hz, 1H); LC/MS: m/z=524.3 [M+H]$^+$ (Calc: 523).

To a suspension of Compound X41 (1.090 mmol, 571 mg) in 2-methoxyethanol (2.85 mL) at a temperature of about 25° C. was added KOH (4.91 mmol, 275 mg). The resulting reaction mixture was heated to 120° C. and stirred at that temperature for 1.5 hours. Thereafter, the mixture was concentrated under reduced pressure, 2N aqueous HCl was added until a pH of about 7 was reached, and water (15 mL) was added. The precipitate that formed was collected by filtration and dried for 2 hours to provide a gray solid which was chromatographed on a on a silica-gel column (REDISEP RF GOLD 12 g) eluted with 10:90 MeOH (10% NH$_3$):CHCl$_3$ to 20:80 MeOH (10% NH$_3$):CHCl$_3$ to provide a yellow solid which was triturated with EtOAc (8 mL), collected by filtration, and dried under reduced pressure to provide 355.9 mg of Cyclic Urea- or Lactam-Substituted Quinoxaline-Type Piperidine Compound U037, 5-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxo-1,2-dihydropyridine-3-carbonitrile, as a yellow solid (yield 64%).

The identity of Cyclic Urea- or Lactam-Substituted Quinoxaline-Type Piperidine Compound U037 was confirmed using $^1$H-NMR and LC/MS.

Cyclic Urea- or Lactam-Substituted Quinoxaline-Type Piperidine Compound U037: $^1$H-NMR: δ$_H$ (ppm, 300 MHz, CDCl$_3$): 1.34-1.51 (br, 1H), 1.58 (d, J=11.13 Hz, 1H), 1.63-1.82 (m, 8H), 1.90-2.12 (m, 7H), 2.25 (s, br, 2H), 2.50 (td, J=11.78, 8.08 Hz, 2H), 2.66 (td, J=11.86, 5.24 Hz, 2H), 2.97-3.19 (m, 2H), 4.14 (d, J=11.29 Hz, 2H), 4.26 (s, 1H), 6.34 (m, 1H), 7.41 (t, J=7.47 Hz, 1H), 7.72-7.78 (m, 1H), 7.86 (dd, J=7.93, 1.37 Hz, 1H), 8.69 (d, J=8.54 Hz, 1H), 9.14 (d, J=2.59 Hz, 1H), 9.26 (d, J=2.44 Hz, 1H); LC/MS: m/z=510.3 [M+H]$^+$ (Calc: 509).

To a mixture of Cyclic Urea- or Lactam-Substituted Quinoxaline-Type Piperidine Compound U037 (0.697 mmol, 355 mg) and Rh(PPh$_3$)$_3$Cl (0.174 mmol, 161 mg, Sigma-Aldrich) in toluene (21.3 mL) at a temperature of about 25° C. was added (E)-acetaldehyde oxime (6.97 mmol, 0.425 mL, Sigma-Aldrich). The resulting reaction mixture was heated to 110° C. and stirred at that temperature for 17 hours. Thereafter, the mixture was concentrated under reduced pressure to provide a yellow solid which was triturated with EtOAc (6 mL) and collected by filtration to provide 336.9 mg of Cyclic Urea- or Lactam-Substituted Quinoxaline-Type Piperidine Compound U038, 5-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxo-1,2-dihydropyridine-3-carboxamide, as a yellow solid (yield 92%).

The identity of Cyclic Urea- or Lactam-Substituted Quinoxaline-Type Piperidine Compound U038 was confirmed using $^1$H-NMR and LC/MS.

Cyclic Urea- or Lactam-Substituted Quinoxaline-Type Piperidine Compound U038: $^1$H-NMR: δ$_H$ (Ppm, 300 MHz, CDCl$_3$): 1.36-1.51 (br, 1H), 1.57 (d, J=12.60 Hz, 1H), 1.63-1.81 (m, 8H), 1.81-2.13 (m, 7H), 2.25 (s, br, 2H), 2.50 (td, J=12.30, 8.08 Hz, 2H), 2.64 (td, J=12.00, 5.10 Hz, 2H), 2.77-2.98 (m, 2H), 3.05 (t, J=13.20 Hz, 2H), 4.13 (d, J=9.90 Hz, 2H), 4.25 (s, br, 1H), 6.32 (m, 1H), 7.38 (t, J=7.50 Hz, 1H), 7.69-7.78 (m, 1H), 7.89 (dd, J=7.80, 1.5, 1H), 8.67 (d, J=9.00 Hz, 1H), 9.16 (d, J=2.70 Hz, 1H), 9.59 (d, J=2.40 Hz, 1H); LC/MS: m/z=528.3 [M+H]⁺ (Calc: 527).

To a suspension of Cyclic Urea- or Lactam-Substituted Quinoxaline-Type Piperidine Compound U038 (0.559 mmol, 295 mg) in EtOH (35 mL) at a temperature of about 25° C. was added 8N aqueous NaOH (48.0 mmol, 6 mL). The resulting reaction mixture was heated to 80° C. and stirred at that temperature for 63 hours. Thereafter, the mixture was cooled to a temperature of about 25° C., 2N aqueous HCl was added until a pH of about 4 was reached, and the mixture was concentrated under reduced pressure to provide a yellow amorphous solid which was triturated, collected by filtration, and washed with water to provide a yellow solid. The solid was chromatographed on a on a silica-gel column (REDISEP RF GOLD 12 g) eluted with 10:90 MeOH (10% NH$_3$):CHCl$_3$ to 30:70 MeOH (10% NH$_3$):CHCl$_3$ to provide a yellow amorphous solid which was triturated with water:MeCN (10 mL:1.5 mL), collected by filtration, and dried for 8 hours under reduced pressure at 80° C. to provide 226.4 mg of Cyclic Urea- or Lactam-Substituted Quinoxaline-Type Piperidine Compound U040, 5-(4-(((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxo-1,2-dihydropyridine-3-carboxylic acid, as a yellow solid (yield 77%).

The identity of Cyclic Urea- or Lactam-Substituted Quinoxaline-Type Piperidine Compound U040 was confirmed using ¹H-NMR and LC/MS.

Cyclic Urea- or Lactam-Substituted Quinoxaline-Type Piperidine Compound U040: ¹H-NMR: δ$_H$ (ppm, 300 MHz, CDCl$_3$): 1.36-1.51 (br, 1H), 1.57 (d, J=12.60 Hz, 1H), 1.63-1.81 (m, 7H), 1.81-2.13 (m, 7H), 2.25 (s, br, 2H), 2.50 (td, J=12.30, 8.08 Hz, 2H), 2.64 (td, J=12.00, 5.10 Hz, 2H), 2.77-2.98 (m, 1H), 3.05 (t, J=13.20 Hz, 2H), 4.14 (d, J=9.90 Hz, 2H), 4.25 (s, br, 1H), 6.32 (m, 1H), 7.39 (t, J=7.50 Hz, 1H), 7.69-7.78 (m, 1H), 7.88 (d, J=7.80, 1H), 8.69 (d, J=8.54 Hz, 1H), 9.15 (d, J=2.70 Hz, 1H), 9.61 (d, J=2.70 Hz, 1H); LC/MS: m/z=529.3 [M+H]⁺ (Calc: 528).

5.19 Example 19

Synthesis of Cyclic Urea- or Lactam-Substituted Quinoxaline-Type Piperidine Compound R16a(i)

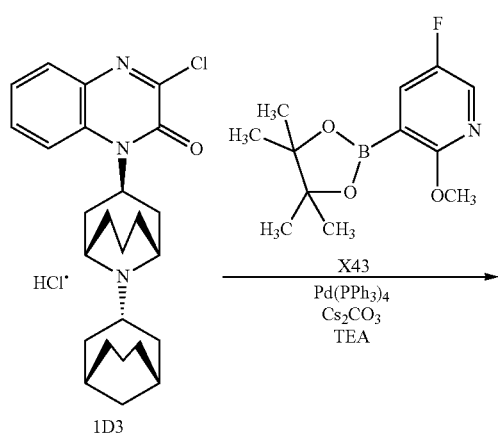

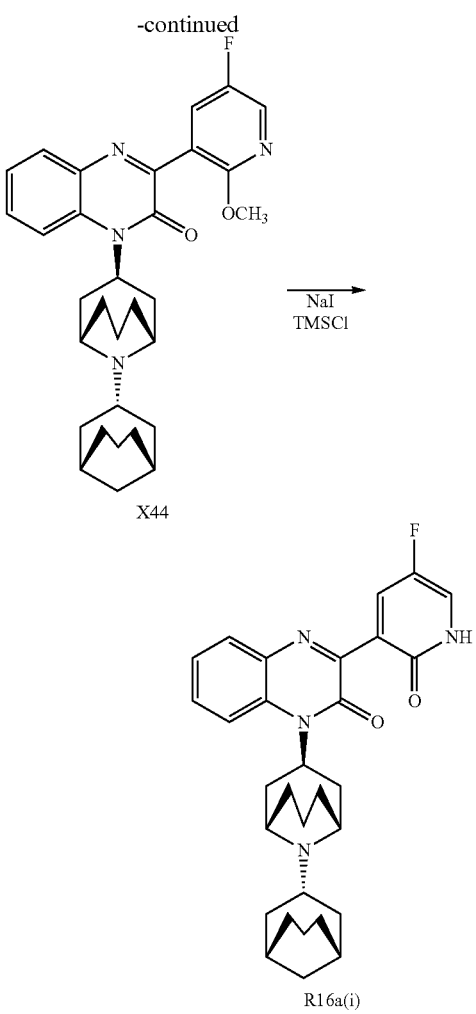

Using procedures similar to those described in the first step of Method 7 in Example 18 for the first step shown above, except that 5-fluoro-2-methoxy-3-(4,4,5,5-tetramethyl-1,3,2-dioxaborolan-2-yl)pyridine (Compound X43, Sigma-Aldrich) was used in place of Compound X40, and using procedures similar to those described in the second step of Method 6.1 in Example 12 for the second step shown above, Cyclic Urea- or Lactam-Substituted Quinoxaline-Type Piperidine Compound R16a(i), 1-((1R,1'R,3r,3'R,5S,5'S)-[3,9'-bi(9'-azabicyclo[3.3.1]nonan)]-3'-yl)-3-(5-fluoro-2-oxo-1,2-dihydropyridin-3-yl)quinoxalin-2(1H)-one, was prepared.

The identity of Cyclic Urea- or Lactam-Substituted Quinoxaline-Type Piperidine Compound R16a(i) was confirmed using ¹H-NMR and LC/MS.

Cyclic Urea- or Lactam-Substituted Quinoxaline-Type Piperidine Compound R16a(i): ¹H-NMR: δ$_H$ (ppm, 400 MHz, CDCl$_3$): 9.09-8.74 (m, 2H), 7.94-7.87 (m, 2H), 7.79 (dd, J=11.67, 4.26 Hz, 1H), 7.45 (t, J=7.55 Hz, 1H), 6.30-6.07 (m, 1H), 4.60-4.35 (m, 1H), 4.18 (d, J=10.16 Hz, 2H), 3.07-2.85 (m, 5H), 2.65-2.52 (m, 2H), 2.26 (d, J=12.36 Hz, 2H), 2.05 (dt, 10.64 Hz, 5H), 1.73 (tt, J=38.32, 12.54 Hz, 8H), 1.33 (dt, J=27.65, 9.55 Hz, 1H); LC/MS: m/z=503.35 [M+H]⁺ (Calc: 502.62).

5.20 Example 20

Synthesis of Cyclic Urea- or Lactam-Substituted Quinoxaline-Type Piperidine Compounds U041, U042, and U043

Using procedures similar to those described above for Method 7 in Example 18, the following Cyclic Urea- or Lactam-Substituted Quinoxaline-Type Piperidine Compounds were prepared from the appropriate 3-chloroquinoxalin-2(1H)-one and 2-methoxy-5-(4,4,5,5-tetramethyl-1,3,2-dioxaborolan-2-yl)nicotinonitrile (Sigma-Aldrich). The 3-chloroquinoxalin-2(1H)-ones are commercially available or can be prepared by methods known to the art, e.g., as described in U.S. Patent Application Publication Nos. US 2010/0216726 A1 (see, e.g., Examples 3, 14, 17, and 29), US 2011/0178090 A1, and/or International PCT Publication No. WO 2012/085648 A1 (see, e.g., Examples 1, 2, and 10), which are hereby incorporated by reference in their entireties.

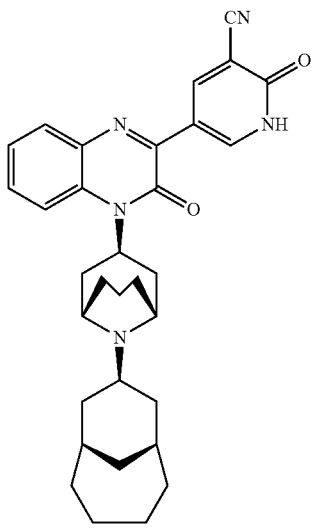

U041

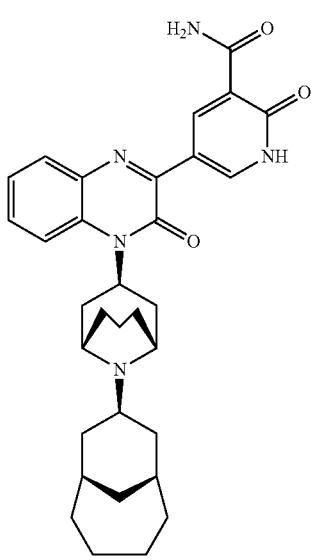

U042

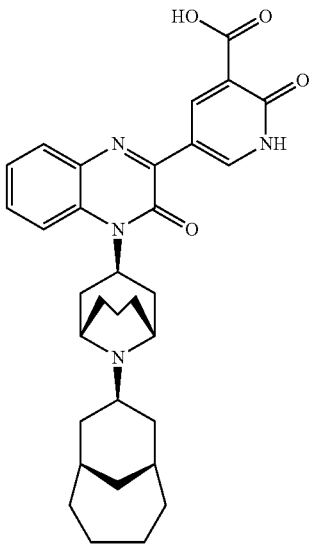

U043

U041: 5-(4-(((1R,3R,5S)-9-((1R,6S,8s)-bicyclo[4.3.1]decan-8-yl)-9-azabicyclo[3.3.1]nonan-3-yl)-3-oxo-3,4-dihydroquinoxalin-2-yl)-2-oxo-1,2-dihydropyridine-3-carbonitrile.

U041: $^1$H-NMR: $\delta_H$ (ppm, 400 MHz, CDCl$_3$): 1.38-1.57 (m, 4H), 1.79-2.14 (m, 14H), 2.49-2.62 (m, 7H), 3.09 (t, J=13.01 Hz, 2H), 3.92 (s, br, 1H), 4.25 (d, J=10.58 Hz, 2H), 6.26-6.48 (m, 1H), 7.45 (t, J=7.47 Hz, 1H), 7.76-7.82 (m, 1H), 7.91 (dd, J=7.72, 1.34 Hz, 1H), 8.72 (d, J=8.56 Hz, 1H), 9.19 (d, J=2.69 Hz, 1H), 9.33 (d, J=2.52 Hz, 1H); LC/MS: m/z=524.3 [M+H]$^+$ (Calc: 524).

U042: 5-(4-(((1R,3R,5S)-9-((1R,6S,8s)-bicyclo[4.3.1]decan-8-yl)-9-azabicyclo[3.3.1]nonan-3-yl)-3-oxo-3,4-dihydroquinoxalin-2-yl)-2-oxo-1,2-dihydropyridine-3-carboxamide.

U042: $^1$H-NMR: $\delta_H$ (ppm, 400 MHz, CDCl$_3$): 1.21-1.32 (m, 2H), 1.32-1.56 (m, 4H), 1.65-2.12 (m, 13H), 2.48 (m, 6H), 3.06 (t, J=13.34 Hz, 2H), 3.87 (s, br, 1H), 4.19 (d, J=16.00 Hz, 2H), 6.20-6.42 (m, 1H), 7.39 (t, J=7.63 Hz, 1H), 7.70-7.76 (m, 1H), 7.90 (dd, J=8.01, 1.45 Hz, 1H), 8.66 (d, J=8.69 Hz, 1H), 9.13 (d, J=2.75 Hz, 1H), 9.60 (d, J=2.44 Hz, 1H); LC/MS: m/z=542.4 [M+H]$^+$ (Calc: 541).

U043: 5-(4-(((1R,3R,5S)-9-((1R,6S,8s)-bicyclo[4.3.1]decan-8-yl)-9-azabicyclo[3.3.1]nonan-3-yl)-3-oxo-3,4-dihydroquinoxalin-2-yl)-2-oxo-1,2-dihydropyridine-3-carboxylic acid.

U043: $^1$H-NMR: $\delta_H$ (ppm, 400 MHz, CDCl$_3$): 1.38-1.57 (m, 4H), 1.71-2.18 (m, 14H), 2.45-2.64 (m, 6H), 3.09-3.17 (m, 2H), 3.92 (s, br, 1H), 4.25 (d, J=10.74 Hz, 2H), 6.38 (m, 1H), 7.45 (t, J=7.64 Hz, 1H), 7.76-7.82 (m, 1H), 7.94 (dd, J=7.89, 1.34 Hz, 1H), 8.72 (d, J=8.56 Hz, 1H), 9.19 (d, J=2.52 Hz, 1H), 9.67 (d, J=2.52 Hz, 1H); LC/MS: m/z=543.4 [M+H]$^+$ (Calc: 542).

5.21 Example 21

Synthesis of Cyclic Urea- or Lactam-Substituted Quinoxaline-Type Piperidine Compound U044 by Method 8

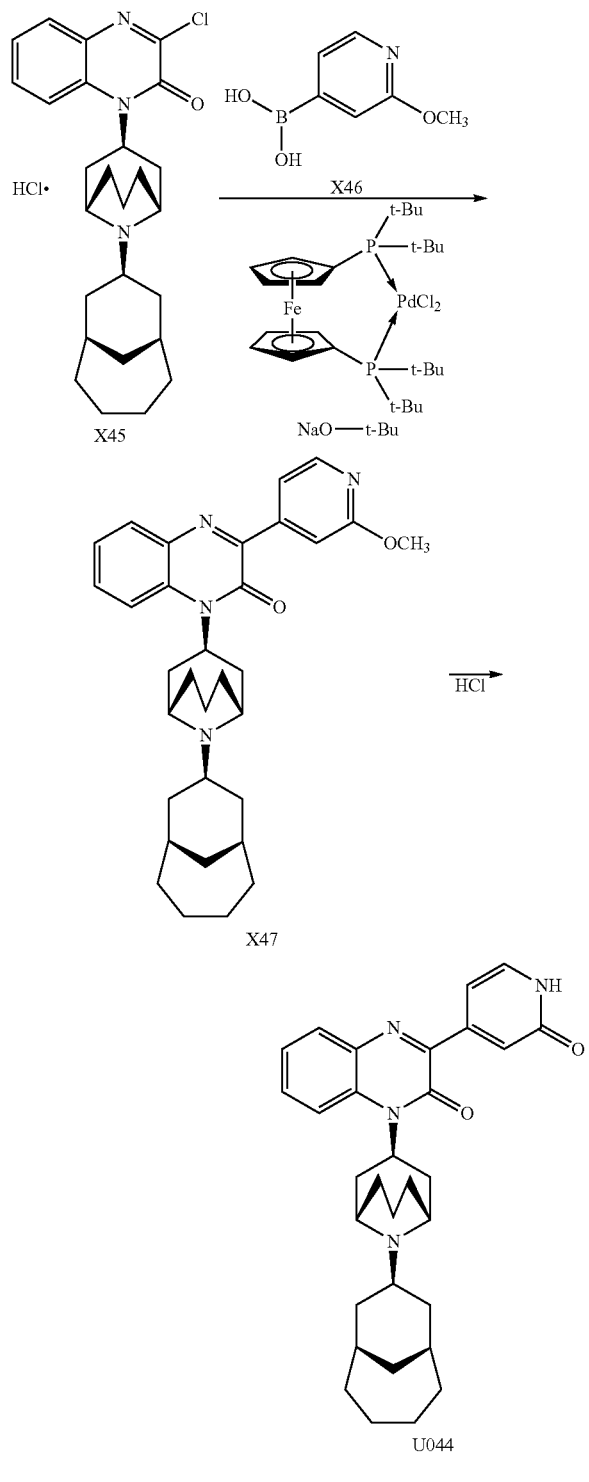

To a suspension of the hydrochloride of Compound X45 (0.315 mmol, 150 mg), sodium 2-methylpropan-2-olate (NaO-t-Bu, 1.259 mmol, 121 mg, Sigma-Aldrich), and (2-methoxypyridin-4-yl)boronic acid (Compound X46, 0.630 mmol, 96 mg, Sigma-Aldrich) in 1,4-dioxane (4.5 mL) at a temperature of about 25° C. was added 1,1'-bis(di-t-butylphosphino)ferrocene palladium(II) dichloride (0.031 mmol, 20.52 mg, Sigma-Aldrich). The resulting reaction mixture was then irradiated for 2 h at 150° C. using a Biotage Initiator focused microwave heating apparatus (Uppsala, Sweden) operating at 2.45 GHz. Thereafter, the mixture was diluted with 5% $NaHCO_3$ in EtOAc (100 mL) and filtrated. The filtrate was extracted with EtOAc, washed with water, washed with brine, dried (over $Na_2SO_4$), and evaporated to dryness. The resulting solid was chromatographed on a on a silica-gel column (Yamazen Corp. W003) eluted with a gradient of from 0:100 MeOH (28% $NH_4OH$):$CHCl_3$ to 30:70 MeOH (28% $NH_4OH$):$CHCl_3$ to provide 91.6 mg of Compound X47, 1-((1R,3R,5S)-9-((1R,6S,8s)-bicyclo[4.3.1]decan-8-yl)-9-azabicyclo[3.3.1]nonan-3-yl)-3-(2-methoxypyridin-4-yl)quinoxalin-2(1H)-one, as an orange solid (yield 56.8%).

The identity of Compound X47 was confirmed using $^1$H-NMR.

Compound X47: $^1$H-NMR: $\delta_H$ (ppm, 400 MHz, $CDCl_3$ with one drop each of DCl and d4-MeOH): 1.33-2.21 (m, 17H), 2.46-2.66 (m, 6H), 2.80-2.99 (m, 1H), 3.02-3.16 (m, 2H), 3.83-3.97 (m, 1H), 4.17-4.30 (m, 2H), 4.49 (s, 3H), 6.45-6.66 (m, 1H), 7.52 (dd, J=7.47, 7.47 Hz, 1H), 7.94 (dd, J=7.80, 7.80 Hz, 1H), 8.02 (dd, J=7.89, 1.34 Hz, 1H), 8.45-8.57 (m, 3H), 8.89 (d, J=8.73 Hz, 1H).

At a temperature of about 25° C., a suspension of Compound X47 (0.179 mmol, 91.6 mg) in concentrated aqueous HCl (10 mL) was prepared. The resulting reaction mixture was heated to 110° C. and stirred at that temperature for 3 hours. Thereafter, the mixture was cooled to a temperature of about 25° C. and evaporated to dryness. The resulting solid was chromatographed on a on a silica-gel column (Yamazen Corp. W003) eluted with a gradient of from 10:90 MeOH (28% $NH_4OH$):$CHCl_3$ to 30:70 MeOH (28% $NH_4OH$):$CHCl_3$ to provide a yellow solid which was triturated with 1:4 $CHCl_3$:$Et_2O$, collected by filtration, and dried for 8 hours under reduced pressure at 80° C. to provide 63.2 mg of Cyclic Urea- or Lactam-Substituted Quinoxaline-Type Piperidine Compound U044, 1-((1R,3R,5S)-9-((1R,6S,8s)-bicyclo[4.3.1]decan-8-yl)-9-azabicyclo[3.3.1]nonan-3-yl)-3-(2-oxo-1,2-dihydropyridin-4-yl)quinoxalin-2(1H)-one, as a yellow solid (yield 70.9%).

The identity of Cyclic Urea- or Lactam-Substituted Quinoxaline-Type Piperidine Compound U044 was confirmed using $^1$H-NMR and LC/MS.

Cyclic Urea- or Lactam-Substituted Quinoxaline-Type Piperidine Compound U044: $^1$H-NMR: $\delta_H$ (ppm, 400 MHz, $CDCl_3$ with one drop each of DCl and d4-MeOH): 1.32-2.12 (m, 17H), 2.41-2.63 (m, 6H), 2.81-3.15 (m, 3H), 3.81-3.96 (m, 1H), 4.16-4.27 (m, 2H), 6.33-6.51 (m, 1H), 7.48 (dd, J=7.55, 7.55 Hz, 1H), 7.89 (ddd, J=7.89, 7.89, 1.60 Hz, 1H), 7.98 (dd, J=7.89, 1.50 Hz, 1H), 8.09-8.18 (m, 2H), 8.42 (s, 1H), 8.78 (d, J=8.88 Hz, 1H); LC/MS: m/z=499.4 [M+H]$^+$ (Calc: 498).

5.22 Example 22

Synthesis of Cyclic Urea- or Lactam-Substituted Quinoxaline-Type Piperidine Compounds R17a(i), R18a(i), U048, and R21a(i)(i)

Using procedures similar to those described above for Method 8 in Example 21, the following Cyclic Urea- or Lactam-Substituted Quinoxaline-Type Piperidine Compounds were prepared from the hydrochloride of Compound 1D3 and the appropriate co-reactants. The co-reactant compounds are commercially available from, e.g., Sigma-Aldrich, or can be prepared by methods known to the art.

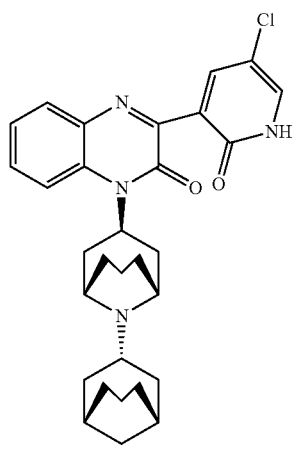

R17a(i)

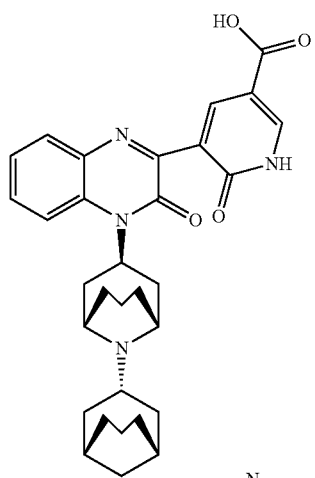

R18a(i)

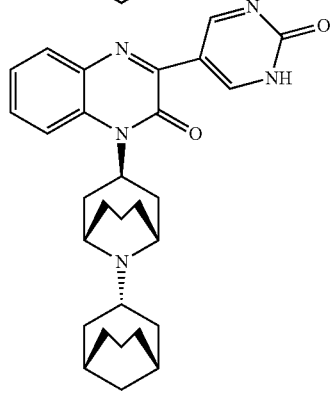

U048

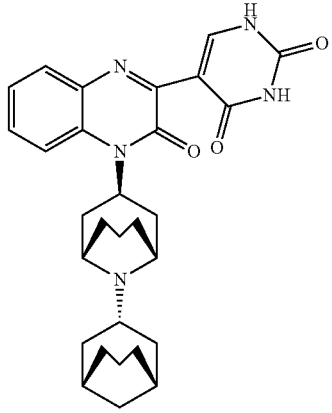

R21a(i)(i)

R17a(i): 1-((1R,1'R,3r,3'R,5S,5'S)-[3,9'-bi(9'-azabicyclo[3.3.1]nonan)]-3'-yl)-3-(5-chloro-2-oxo-1,2-dihydropyridin-3-yl)quinoxalin-2(1H)-one.

R17a(i): $^1$H-NMR: $\delta_H$ (ppm, 400 MHz, CDCl$_3$ with one drop each of DCl and d4-MeOH): 1.26-1.49 (m, 1H), 1.49-2.12 (m, 14H), 2.15-2.28 (m, 2H), 2.42-2.68 (m, 4H), 2.68-2.89 (m, 1H), 2.92-3.07 (m, 2H), 4.05-4.18 (m, 2H), 4.18-4.32 (m, 1H), 6.30-6.49 (m, 1H), 7.49 (dd, J=7.53, 7.53 Hz, 1H), 7.83-7.92 (m, 2H), 8.26 (s, 1H), 8.84 (d, J=8.85 Hz, 1H), 9.48 (s, 1H); LC/MS: m/z=519.3 [M+H]$^+$ (Calc: 518).

R18a(i): 5-(4-((1R,1'R,3r,3'R,5S,5'S)-[3,9'-biazabicyclo[3.3.1]nonan)]-3'-yl)-3-oxo-3,4-dihydroquinoxalin-2-yl)-6-oxo-1,6-dihydropyridine-3-carboxylic acid.

R18a(i): $^1$H-NMR: $\delta_H$ (ppm, 400 MHz, d6-DMSO with one drop of DCl): 1.43-1.78 (m, 11H), 1.95-2.18 (m, 6H), 2.23-2.68 (m, 5H), 2.73-2.90 (m, 2H), 4.01-4.24 (m, 3H), 6.06-6.30 (m, 1H), 7.44 (dd, J=7.52, 7.52 Hz, 1H), 7.65 (ddd, J=8.55, 7.22, 1.42 Hz, 1H), 7.86 (dd, J=7.89, 1.57 Hz, 1H), 8.03 (d, J=2.69 Hz, 1H), 8.18 (d, J=2.52 Hz, 1H), 8.66 (d, J=8.73 Hz, 1H); LC/MS: m/z=529.4 [M+H]$^+$ (Calc: 528).

U048: 1-((1R,1'R,3r,3'R,5S,5'S)-[3,9'-bi(9'-azabicyclo[3.3.1]nonan)]-3'-yl)-3-(2-oxo-1,2-dihydropyrimidin-5-yl)quinoxalin-2(1H)-one.

U048: $^1$H-NMR: $\delta_H$ (ppm, 400 MHz, d6-DMSO with one drop of DCl): 1.46-1.86 (m, 9H), 1.93-2.20 (m, 5H), 2.20-2.74 (m, 7H), 2.80-2.98 (m, 2H), 4.02-4.27 (m, 3H), 6.13-6.34 (m, 1H), 7.49 (dd, J=7.45 Hz, 1H), 7.67 (ddd, J=8.56, 7.21, 1.18 Hz, 1H), 7.93 (dd, J=7.89, 1.50 Hz, 1H), 8.74 (d, J=8.56 Hz, 1H), 9.40 (s, 2H); LC/MS: m/z=486.4 [M+H]$^+$ (Calc: 485).

R21a(i)(i): 5-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)pyrimidine-2,4(1H,3H)-dione.

R21a(i)(i): $^1$H-NMR: $\delta_H$ (ppm, 400 MHz, d6-DMSO with one drop of DCl): 1.44-1.73 (m, 11H), 1.94-2.11 (m, 6H), 2.23-2.50 (m, 4H), 2.75-2.83 (m, 2H), 4.08-4.12 (m, 3H), 6.09-6.14 (m, 1H), 7.41 (dd, J=7.82, 7.82 Hz, 1H), 7.62 (dd, J=7.99, 7.99 Hz, 1H), 7.78-7.85 (m, 2H), 8.64 (d, J=7.55 Hz, 1H); LC/MS: m/z=502.4 [M+H]$^+$ (Calc: 501).

5.23 Example 23

Synthesis of Cyclic Urea- or Lactam-Substituted Quinoxaline-Type Piperidine Compound U050

Using procedures similar to those described above for Method 8 in Example 22 except that the dioxaborolane compound 2-methoxy-5-(4,4,5,5-tetramethyl-1,3,2-dioxaborolan-2-yl)pyrazine (Sigma-Aldrich) was used, Cyclic Urea- or Lactam-Substituted Quinoxaline-Type Piperidine Compound U050 was prepared from the hydrochloride of Compound 1D3.

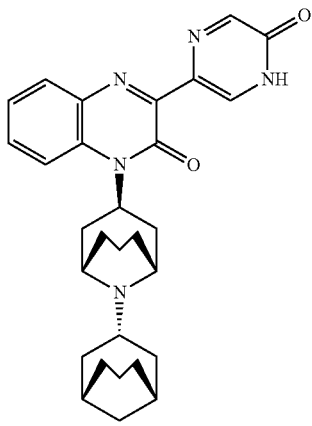

U050: 1-((1R,1'R,3r,3'R,5S,5'S)-[3,9'-bi(9'-azabicyclo[3.3.1]nonan)]-3'-yl)-3-(5-oxo-4,5-dihydropyrazin-2-yl)quinoxalin-2(1H)-one.

U050: $^1$H-NMR: $\delta_H$ (ppm, 400 MHz, d6-DMSO with one drop of DCl): 1.46-1.77 (m, 11H), 1.90-2.16 (m, 6H), 2.19-2.66 (m, 5H), 2.77-2.95 (m, 2H), 3.97-4.24 (m, 3H), 5.96-6.14 (m, 1H), 7.42 (dd, J=7.55, 7.55 Hz, 1H), 7.61 (dd, J=7.93, 7.93 Hz, 1H), 7.88 (dd, J=7.93, 1.33 Hz, 1H), 8.16 (d, J=1.22 Hz, 1H), 8.54 (d, J=8.85 Hz, 1H), 8.65 (d, J=1.22 Hz, 1H), 9.95 (br, 1H); LC/MS: m/z=486.4 [M+H]$^+$ (Calc: 485).

5.24 Example 24

Synthesis of Cyclic Urea- or Lactam-Substituted Quinoxaline-Type Piperidine Compound R28a(i)

Using procedures similar to those described above for Method 8 in Example 21, Cyclic Urea- or Lactam-Substituted Quinoxaline-Type Piperidine Compound R28a(i) was prepared from the hydrochloride of Compound 1C3 and (5-cyano-2-methoxypyridin-3-yl)boronic acid (Sigma-Aldrich).

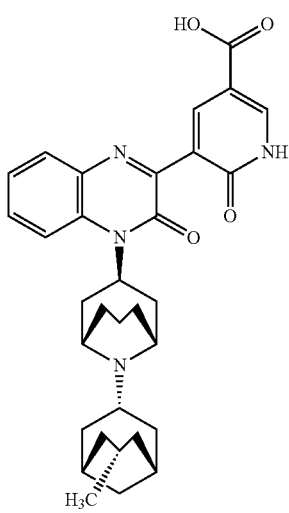

R28a(i): 5-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-6-oxo-1,6-dihydropyridine-3-carboxylic acid.

R28a(i): $^1$H-NMR: $\delta_H$ (ppm, 400 MHz, d6-DMSO with one drop of DCl): 0.70-0.83 (m, 1H), 0.87 (d, J=6.21 Hz, 3H), 1.03-1.15 (m, 1H), 1.42-2.41 (m, 15H), 2.42-2.66 (m, 4H), 2.72-2.90 (m, 2H), 3.70-3.87 (m, 1H), 4.04-4.19 (m, 2H), 6.04-6.26 (m, 1H), 7.43 (dd, J=7.63, 7.63 Hz, 1H), 7.65 (ddd, J=8.34, 7.39, 1.51 Hz, 1H), 7.86 (dd, J=7.89, 1.34 Hz, 1H), 8.03 (d, J=2.52 Hz, 1H), 8.17 (d, J=2.69 Hz, 1H), 8.63 (d, J=8.90 Hz, 1H); LC/MS: m/z=543.5 [M+H]$^+$ (Calc: 542).

5.25 Example 25

Synthesis of Cyclic Urea- or Lactam-Substituted Quinoxaline-Type Piperidine Compound U052

Using procedures similar to those described above for Method 8 in Example 24 except that the dioxaborolane compound 2-methoxy-5-(4,4,5,5-tetramethyl-1,3,2-dioxaborolan-2-yl)pyrazine was used, Cyclic Urea- or Lactam-Substituted Quinoxaline-Type Piperidine Compound U052 was prepared from the hydrochloride of Compound 1C3.

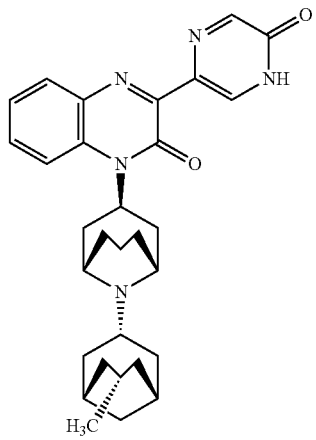

U052: 1-((1R,1'R,3r,3'R,5S,5'S,7S)-7-methyl-[3,9'-bi(9'-azabicyclo[3.3.1]nonan)]-3'-yl)-3-(5-oxo-4,5-dihydropyrazin-2-yl)quinoxalin-2(1H)-one.

U052: $^1$H-NMR: $\delta_H$ (ppm, 400 MHz, d6-DMSO with one drop of DCl): 0.68-0.81 (d, 1H), 0.85 (d, J=6.41 Hz, 1H), 0.99-1.10 (m, 1H), 1.44-2.65 (m, 19H), 2.79-2.91 (m, 2H), 3.69-3.88 (m, 1H), 4.02-4.19 (m, 2H), 6.03-6.26 (m, 1H), 7.40 (dd, J=7.45, 7.45 Hz, 1H), 7.58 (dd, J=7.70, 7.70 Hz, 1H), 7.87 (d, J=7.63 Hz, 1H), 8.15 (s, 1H), 8.63 (d, J=9.46 Hz, 1H), 8.67 (s, 1H); LC/MS: m/z=500.4 [M+H]$^+$ (Calc: 499).

5.26 Example 26

Synthesis of Cyclic Urea- or Lactam-Substituted Quinoxaline-Type Piperidine Compound U55a(i)

Using procedures similar to those described in the first step of Method 8 in Example 21 for the first step and using procedures similar to those described in the second step of Method 6.1 in Example 12 for the second step, Cyclic Urea- or Lactam-Substituted Quinoxaline-Type Piperidine Compound U55a(i) was prepared from the appropriate 3-chloroquinoxalin-2(1H)-one and (2-methoxypyridin-3-yl)boronic acid (Sigma-Aldrich). The 3-chloroquinoxalin-2(1H)-ones are commercially available or can be prepared by methods known to the art, e.g., as described in U.S. Patent Application Publication Nos. US 2010/0216726 A1 (see, e.g., Examples 3, 14, 17, and 29), US 2011/0178090 A1, and/or International PCT Publication No. WO 2012/085648 A1 (see, e.g., Examples 1, 2, and 10), which are hereby incorporated by reference in their entireties.

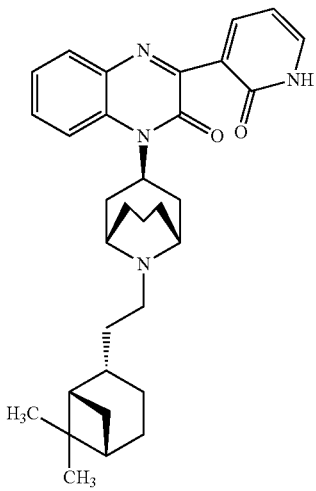

U55a(i)

U55a(i): 1-((1R,3S,5S)-9-(2-((1S,2S,5S)-6,6-dimethylbicyclo[3.1.1]heptan-2-yl)ethyl)-9-azabicyclo[3.3.1]nonan-3-yl)-3-(2-oxo-1,2-dihydropyridin-3-yl)quinoxalin-2(1H)-one.

U55a(i): $^1$H-NMR: $\delta_H$ (ppm, 400 MHz, CDCl$_3$): 9.94 (d, J=6.25 Hz, 1.0H), 8.82 (d, J=8.39 Hz, 1.0H), 8.42 (dd, J=6.18, 1.60 Hz, 1.0H), 7.93 (t, J=7.93 Hz, 2.0H), 7.56 (t, J=7.63 Hz, 1.0H), 7.27 (dd, J=7.78, 6.10 Hz, 1.0H), 6.31-6.18 (m, 1.0H), 3.87 (s, 1.0H), 3.26 (d, J=8.69 Hz, 2.0H), 3.02 (t, J=12.28 Hz, 2.0H), 2.76 (d, J=13.12 Hz, 1.0H), 2.57 (dd, J=18.23, 10.14 Hz, 2.0H), 2.39 (dd, J=14.49, 6.56 Hz, 1.0H), 2.02 (ddt, J=45.91, 24.05, 10.50 Hz, 10.9H), 1.69 (dd, j=36.91, 9.00 Hz, 2.9H), 1.28 (d, J=7.17 Hz, 0.2H), 1.23 (s, 3.0H), 1.10 (s, 3.0H), 0.92 (d, J=9.61 Hz, 1.0H); LC/MS: m/z=513.4 [M+H]$^+$ (Calc: 512.7).

5.27 Example 27

Synthesis of Cyclic Urea- or Lactam-Substituted Quinoxaline-Type Piperidine Compound R3a(i) by Method 9

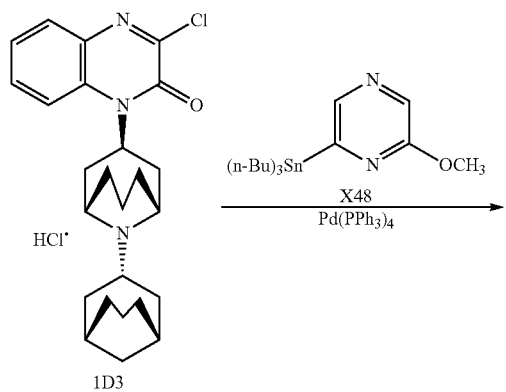

1D3

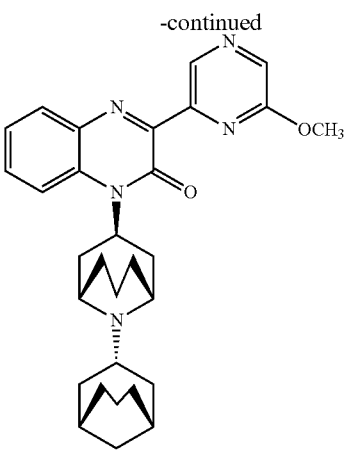

X49

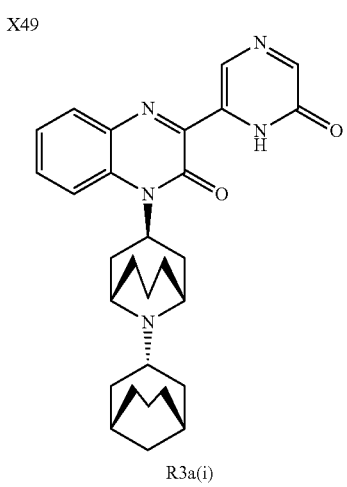

R3a(i)

To a solution of the hydrochloride of Compound 1D3 (0.432 mmol, 200 mg) and 2-methoxy-6-(tri-n-butylstannyl) pyrazine (Compound X48, 0.649 mmol, 259 mg, Sigma-Aldrich) in 1,4-dioxane (10 mL) at a temperature of about 25° C. was added Pd(PPh$_3$)$_4$ (0.043 mmol, 50.0 mg). The resulting reaction mixture was then irradiated for 2 h at 130° C. using a Biotage Initiator focused microwave heating apparatus operating at 2.45 GHz. Thereafter, the mixture was evaporated to dryness to provide an oil which was chromatographed on a silica-gel column (Yamazen Corp. W003) eluted with a gradient of from 0:100 MeOH (28% NH$_4$OH):CHCl$_3$ to 15:85 MeOH (28% NH$_4$OH):CHCl$_3$ to provide a brown amorphous solid. That solid was chromatographed on an amino silica-gel column (Yamazen Corp. W091-01) eluted with a gradient of from 20:80 EtOAc:n-hexane to 50:50 EtOAc:n-hexane to provide 129.1 mg of Compound X49, 1-((1R,1'R,3r,3'R,5S,5'S)-[3,9'-bi(9'-azabicyclo[3.3.1] nonan)]-3'-yl)-3-(6-methoxypyrazin-2-yl)quinoxalin-2(1H)-one, as a yellow amorphous solid (yield 59.7%).

At a temperature of about 25° C., a suspension of Compound X49 (0.126 mmol, 63 mg) in concentrated aqueous HCl (7.5 mL) was prepared. The resulting reaction mixture was heated to 100° C. and stirred at that temperature for 9 hours. Thereafter, the mixture was cooled to a temperature of about 25° C. and concentrated under reduced pressure to dryness. The resulting solid was neutralized with saturated aqueous NaHCO$_3$ and extracted with CHCl$_3$. The organic portion was washed with brine, dried (over Na$_2$SO$_4$), and concentrated under reduced pressure to provide an oil which was chromatographed on a silica-gel column (Yamazen Corp.

WO03) eluted with a gradient of from 0:100 MeOH (28% NH₄OH):CHCl₃ to 20:80 MeOH (28% NH₄OH):CHCl₃ to provide a yellow solid which was triturated with CHCl₃: hexanes, collected by filtration, and dried under reduced pressure at 80° C. to provide 50.4 mg of Cyclic Urea- or Lactam-Substituted Quinoxaline-Type Piperidine Compound R3a(i), 1-((1R,1'R,3r,3'R,5S,5'S)-[3,9'-bi(9'-azabicyclo[3.3.1] nonan)]-3'-yl)-3-(6-oxo-1,6-dihydropyrazin-2-yl)quinoxalin-2(1H)-one, as an off-white solid (yield 82.3%).

The identity of Cyclic Urea- or Lactam-Substituted Quinoxaline-Type Piperidine Compound R3a(i) was confirmed using ¹H-NMR and LC/MS.

Cyclic Urea- or Lactam-Substituted Quinoxaline-Type Piperidine Compound R3a(i): ¹H-NMR: $\delta_H$ (ppm, 400 MHz, d6-DMSO with one drop of DCl): 1.39-1.79 (m, 11H), 1.89-2.17 (m, 6H), 2.20-2.67 (m, 5H), 2.76-2.96 (m, 2H), 4.04-4.28 (m, 3H), 6.04-6.29 (m, 1H), 7.47 (dd, J=7.47, 7.47 Hz, 1H), 7.70 (dd, J=7.85, 7.85 Hz, 1H), 7.97 (dd, J=7.93, 1.37 Hz, 1H), 8.18 (s, 1H), 8.53 (s, 1H), 8.67 (d, J=9.15 Hz, 1H); LC/MS: m/z=486.4 [M+H]⁺ (Calc: 485).

5.28 Example 28

Synthesis of Cyclic Urea- or Lactam-Substituted Quinoxaline-Type Piperidine Compound R2a(i) by Method 10

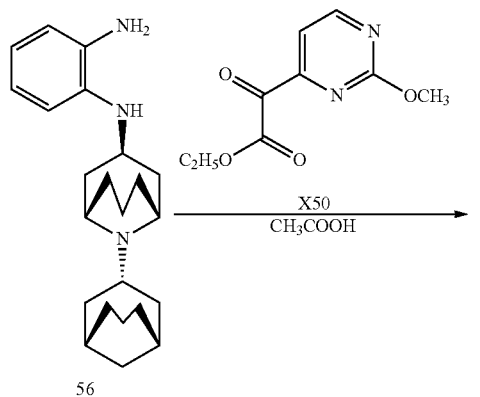

56

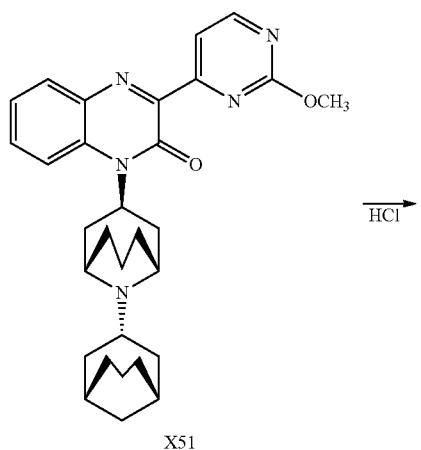

X51

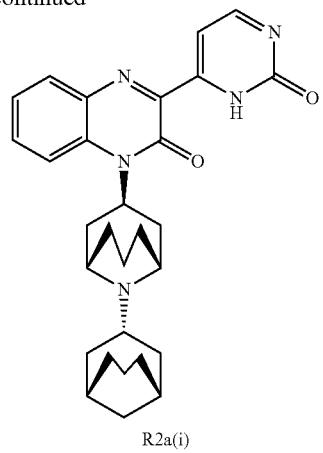

R2a(i)

Compound 56 was prepared as described in Example 7 herein.

To a solution of ethyl 2-(2-methoxypyrimidin-4-yl)-2-oxoacetate (Compound X50, 0.295 mmol, 62 mg, Sigma-Aldrich) in EtOH (2 mL) at a temperature of about 25° C. was added Compound 56 (0.246 mmol, 87 mg) and AcOH (0.615 mmol, 0.035 mL). The resulting reaction mixture was heated to 100° C. and stirred at that temperature for 17 hours. Thereafter, the mixture was cooled to a temperature of about 25° C. and evaporated to dryness to provide an oil which was chromatographed on a silica-gel column (Yamazen Corp. W002) eluted with a gradient of from 0:100 MeOH (28% NH₄OH): CHCl₃ to 10:90 MeOH (28% NH₄OH):CHCl₃ to provide a pale yellow amorphous solid. That solid was chromatographed on an amino silica-gel column (Yamazen Corp. W091-01) eluted with a gradient of from 20:80 EtOAc:n-hexane to 50:50 EtOAc:n-hexane to provide Compound X51, 1-((1R,1'R,3r,3'R,5S,5'S)-[3,9'-bi(9'-azabicyclo[3.3.1] nonan)]-3'-yl)-3-(2-methoxypyrimidin-4-yl)quinoxalin-2 (1H)-one, as a yellow amorphous solid.

At a temperature of about 25° C., a suspension of the quantity of Compound X51 prepared above in 2N aqueous HCl (12.00 mmol, 6 mL) was prepared. The resulting reaction mixture was heated to 80° C. and stirred at that temperature for 7 hours. Thereafter, the mixture was cooled to a temperature of about 25° C. and evaporated to dryness. The resulting solid was neutralized with saturated aqueous NaHCO₃, triturated with 1:1 MeOH:water, collected by filtration, and dried under reduced pressure at 80° C. to provide 103.1 mg of Cyclic Urea- or Lactam-Substituted Quinoxaline-Type Piperidine Compound R2a(i), 1-((1R,1'R,3r,3'R,5S,5'S)-[3,9'-bi (9'-azabicyclo[3.3.1]nonan)]-3'-yl)-3-(2-oxo-2,3-dihydropyrimidin-4-yl)quinoxalin-2(1H)-one, as an off-white solid (overall yield 86.4%).

The identity of Cyclic Urea- or Lactam-Substituted Quinoxaline-Type Piperidine Compound R2a(i) was confirmed using ¹H-NMR and LC/MS.

Cyclic Urea- or Lactam-Substituted Quinoxaline-Type Piperidine Compound R2a(i): ¹H-NMR: $\delta_H$ (ppm, 400 MHz, CDCl₃ with one drop each of DCl and d4-MeOH): 1.32-2.16 (m, 15H), 2.20-2.31 (m, 2H), 2.45-2.58 (m, 2H), 2.67-2.94 (m, 3H), 2.99-3.12 (m, 2H), 4.06-4.19 (m, 2H), 4.19-4.34 (m, 1H), 6.54-6.69 (m, 1H), 6.57 (d, J=6.56 Hz, 1H), 7.53 (dd, J=7.62, 7.62 Hz, 1H), 7.93 (dd, J=7.77, 7.77 Hz, 1H), 8.17 (dd, J=8.08, 1.07 Hz, 1H), 8.27 (d, J=6.56 Hz, 1H), 8.96 (d, J=9.00 Hz, 1H); LC/MS: m/z=486.4 [M+H]⁺ (Calc: 485).

5.29 Example 29

Synthesis of Cyclic Urea- or Lactam-Substituted Quinoxaline-Type Piperidine Compounds U056, U057, U058, and U059

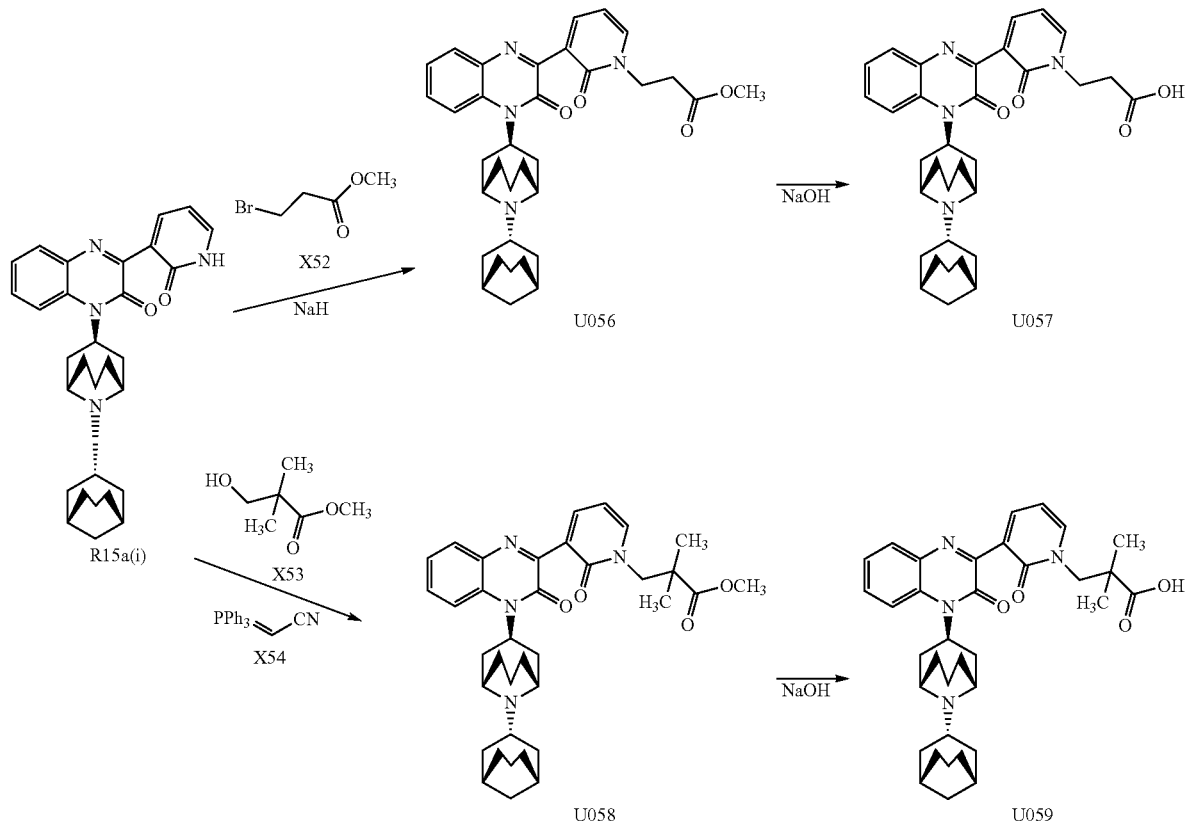

To a solution of Cyclic Urea- or Lactam-Substituted Quinoxaline-Type Piperidine Compound R15a(i) (0.468 mmol, 227 mg) in DMA (2.3 mL) at a temperature of about 25° C. was added NaH (1.874 mmol, 74.9 mg); the resulting mixture was stirred at that temperature for 30 min. Then, methyl 3-bromopropanoate (Compound X52, 1.405 mmol, 0.153 mL, Sigma-Aldrich) was added and the resulting reaction mixture was stirred at a temperature of about 25° C. for 1 hour. Thereafter, the mixture was diluted with water and extracted with EtOAc. The organic portion was washed with water, washed with brine, dried (over $Na_2SO_4$), and evaporated to dryness to provide an amorphous solid which was chromatographed on a silica-gel column (Yamazen Corp. WO03) eluted with a gradient of from 0:100 MeOH (28% $NH_4OH$):$CHCl_3$ to 15:85 MeOH (28% $NH_4OH$):$CHCl_3$ to provide 188.2 mg of Cyclic Urea- or Lactam-Substituted Quinoxaline-Type Piperidine Compound U056, methyl 3-(3-(4-((1R,1'R,3r,3'R,5S,5'S)-[3,9'-bi(9'-azabicyclo[3.3.1]nonan]-3'-yl)-3-oxo-3,4-dihydroquinoxalin-2-yl)-2-oxopyridin-1(2H)-yl)propanoate, as an orange amorphous solid (yield 70.4%).

The identity of Cyclic Urea- or Lactam-Substituted Quinoxaline-Type Piperidine Compound U056 was confirmed using $^1$H-NMR.

Cyclic Urea- or Lactam-Substituted Quinoxaline-Type Piperidine Compound U056: $^1$H-NMR: $\delta_H$ (ppm, 400 MHz, $CDCl_3$ with one drop each of DCl and d4-MeOH): 0.83-1.14 (m, 2H), 1.27-2.06 (m, 14H), 2.14-2.38 (m, 1H), 2.40-2.63 (m, 2H), 2.67-2.88 (m, 2H), 3.27-3.70 (m, 9H), 4.00-4.27 (m, 2H), 4.83-5.30 (m, 1H), 6.24-6.42 (m, 1H), 7.30-7.45 (m, 1H), 7.48-7.72 (m, 3H), 7.72-7.92 (m, 2H), 8.24-8.37 (m, 1H).

To a solution of Cyclic Urea- or Lactam-Substituted Quinoxaline-Type Piperidine Compound U056 (0.322 mmol, 184 mg) in MeOH (7.2 mL) at a temperature of about 25° C. was added 2N aqueous NaOH (0.967 mmol, 0.484 mL). The resulting reaction mixture was stirred at that temperature for 30 min, heated to 85° C., and stirred at that temperature for 30 min. Thereafter, the mixture was cooled to a temperature of about 25° C., acidified with 2N aqueous HCl (720 µL), and evaporated to dryness. The resulting solid was chromatographed on a silica-gel column (Yamazen Corp. WO03) eluted with a gradient of from 10:90 MeOH (28% $NH_4OH$):$CHCl_3$ to 50:50 MeOH (28% $NH_4OH$):$CHCl_3$ to provide a yellow solid that was triturated with MeOH, filtered, and dried under reduced pressure at 80° C. to provide 91.8 mg of Cyclic Urea- or Lactam-Substituted Quinoxaline-Type Piperidine Compound U057, 3-(3-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)propanoic acid, as a yellow solid (yield 51.1%).

The identity of Cyclic Urea- or Lactam-Substituted Quinoxaline-Type Piperidine Compound U057 was confirmed using $^1$H-NMR and LC/MS.

Cyclic Urea- or Lactam-Substituted Quinoxaline-Type Piperidine Compound U057: $^1$H-NMR: $\delta_H$ (ppm, 400 MHz, d6-DMSO with one drop of DCl): 1.34-1.79 (m, 11H), 1.86-2.17 (m, 6H), 2.17-2.59 (m, 5H), 2.60-2.90 (m, 4H), 3.99-

4.22 (m, 5H), 6.01-6.24 (m, 1H), 6.34 (dd, J=6.79, 6.79 Hz, 1H), 7.39 (dd, J=7.48, 7.48 Hz, 1H), 7.57-7.65 (m, 2H), 7.78-7.85 (m, 2H), 8.61 (d, J=8.54 Hz, 1H); LC/MS: m/z=557.4 [M+H]⁺ (Calc: 556).

To a solution of methyl 3-hydroxy-2,2-dimethylpropanoate (Compound X53, 2.042 mmol, 260.3 µL, Sigma-Aldrich) in toluene (3 mL) at a temperature of about 25° C. was added Cyclic Urea- or Lactam-Substituted Quinoxaline-Type Piperidine Compound R15a(i) (0.309 mmol, 150 mg) and 2-(triphenylphosphoranylidene)acetonitrile (Compound X54, 1.414 mmol, 371 µL, Sigma-Aldrich); the resulting mixture was stirred at that temperature for 30 min. Then, to the mixture was added methyl 3-bromopropanate Thereafter, the resulting reaction mixture was heated to 130° C. and stirred at that temperature for 2 hours. Thereafter, the mixture was cooled to a temperature of about 25° C. and evaporated to dryness. The resulting oil was chromatographed on an amino silica-gel column (Yamazen Corp. W091-01) eluted with a gradient of from 20:80 EtOAc:n-hexane to 50:50 EtOAc:n-hexane to provide 89.4 mg of Cyclic Urea- or Lactam-Substituted Quinoxaline-Type Piperidine Compound U058, methyl 3-(3-(4-((1R,1'R,3r,3'R,5S,5'S)- [3,9'-bi(9'-azabicyclo[3.3.1]nonan)]-3'-yl)-3-oxo-3,4-dihydroquinoxalin-2-yl)-2-oxopyridin-1(2H)-yl)-2,2-dimethylpropanoate, as a yellow amorphous solid (yield 66.8%).

To a suspension of Cyclic Urea- or Lactam-Substituted Quinoxaline-Type Piperidine Compound U058 (0.149 mmol, 89 mg) in 1:1 MeOH:THF (1.1 mL) at a temperature of about 25° C. was added 2N aqueous NaOH (0.446 mmol, 0.223 mL). The resulting reaction mixture was stirred at that temperature for 70 min, heated to 65° C., and stirred at that temperature for 4 hours. Thereafter, the mixture was cooled to a temperature of about 25° C., diluted with 5% aqueous citric acid, and extracted with 5:1 CHCl₃:MeOH. The organic portion was dried (over Na₂SO₄) and evaporated to dryness to provide a solid which was triturated with 1:1 2-isopropoxypropane:MeOH, filtered, and dried under reduced pressure at 80° C. to provide 68.7 mg of Cyclic Urea- or Lactam-Substituted Quinoxaline-Type Piperidine Compound U059, 3-(3-(4-((1R,1'R,3r,3R,5S,5'S)-[3,9'-bi(9'-azabicyclo[3.3.1]nonan)]-3'-yl)-3-oxo-3,4-dihydroquinoxalin-2-yl)-2-oxopyridin-1(2H)-yl)-2,2-dimethylpropanoic acid, as an off-white solid (yield 79.0%).

The identity of Cyclic Urea- or Lactam-Substituted Quinoxaline-Type Piperidine Compound U059 was confirmed using ¹H-NMR and LC/MS.

Cyclic Urea- or Lactam-Substituted Quinoxaline-Type Piperidine Compound U059: ¹H-NMR: δ$_H$ (ppm, 400 MHz, d6-DMSO with one drop of DCl): 1.07 (s, 6H), 1.38-1.72 (m, 11H), 1.92-2.15 (m, 6H), 2.19-2.55 (m, 5H), 2.75-2.91 (m, 2H), 3.84-4.39 (m, 3H), 6.07-6.24 (m, 1H), 7.11 (dd, J=7.32, 5.03 Hz, 1H), 7.41 (dd, J=7.52, 7.52 Hz, 1H), 7.63 (dd, J=7.93, 7.93 Hz, 1H), 7.80-7.86 (m, 2H), 8.25 (dd, J=5.03, 1.08 Hz, 1H), 8.62 (d, J=8.85 Hz, 1H); LC/MS: m/z=585.5 [M+H]⁺ (Calc: 584).

5.30 Example 30

Synthesis of Cyclic Urea- or Lactam-Substituted Quinoxaline-Type Piperidine Compounds U060, U061, R25a(i), U063, and U064

Using procedures similar to those described above for Cyclic Urea- or Lactam-Substituted Quinoxaline-Type Piperidine Compounds R1a(iii) (Example 12), U008 and R15a(i) (Example 13), and U038 and U040 (Example 18), respectively, except that Compound 1C3 (prepared as described in Example 6 herein) or its hydrochloride was used in place of Compound 1D3, the following Cyclic Urea- or Lactam-Substituted Quinoxaline-Type Piperidine Compounds were prepared from Compound 1C3 and the appropriate co-reactant.

U060: 1-((1R,1'R,3r,3'R,5S,5'S,7S)-7-methyl-[3,9'-bi(9'-azabicyclo[3.3.1]nonan)]-3'-yl)-3-(6-oxo-1,6-dihydropyridin-3-yl)quinoxalin-2(1H)-one.

U060: $^1$H-NMR: $\delta_H$ (ppm, 400 MHz, CD$_3$OD): 9.41-9.47 (m, 1H), 9.20-9.29 (d, J=11.6 Hz, 1H), 8.43-8.50 (d, J=8.3 Hz, 1H), 7.96-8.02 (d, J=8.1 Hz, 1H), 7.72-7.79 (t, J=8.8 Hz, 1H), 7.46-7.53 (t, J=9.9 Hz, 1H), 7.30-7.38 (d, J=9.2 Hz, 1H), 5.96-6.08 (br, 1H), 4.22-4.32 (d, J=10.5 Hz, 2H), 3.88-4.02 (br, 1H), 3.09-3.21 (t, J=14.0 Hz, 2H), 2.81-2.92 (br, 1H), 2.35-2.55 (m, 5H), 2.00-2.21 (m, 9H), 1.83-1.92 (d, 6H), 1.65-1.74 (d, 2H); LC/MS: m/z=499.3 [M+H]$^+$.

U061: 1-((1R,1'R,3r,3'R,5S,5'S,7S)-7-methyl-[3,9'-bi(9'-azabicyclo[3.3.1]nonan)]-3'-yl)-3-(2-oxo-1,2-dihydropyridin-4-yl)quinoxalin-2(1H)-one.

U061: $^1$H-NMR: $\delta_H$ (ppm, 400 MHz, CD$_3$OD): 8.46-8.61 (m, 2H), 8.18-8.40 (m, 2H), 7.99-8.12 (d, J=8.1 Hz, 1H), 7.71-7.92 (t, J=7.2 Hz, 1H), 7.45-7.60 (t, J=7.9 Hz, 1H), 5.96-6.17 (br, 1H), 4.19-4.32 (d, J=9.4 Hz, 2H), 3.85-4.07 (m, 1H), 3.07-3.21 (t, J=12.5 Hz, 3H), 2.75-2.94 (m, 1H), 2.33-2.57 (m, 5H), 1.99-2.22 (br, 16H), 1.55-1.95 (m, 1H); LC/MS: m/z=499.3 [M+H]$^+$.

R25a(i): S)-7-methyl-[3,9'-bi(9'-azabicyclo[3.3.1]nonan)]-3'-yl)-3-(2-oxo-1,2-dihydropyridin-3-yl)quinoxalin-2(1H)-one.

R25a(i): $^1$H-NMR: $\delta_H$ (ppm, 400 MHz, CD$_3$OD): 7.73-7.85 (m, 2H), 7.57-7.65 (m, 2H), 7.49-7.55 (t, J=8.1 Hz 1H), 7.32-7.40 (t, J=6.6 Hz, 1H), 6.43-6.51 (br, 1H), 5.30-5.45 (d, J=6.4 Hz, 2H), 4.07-4.20 (br, 1H), 3.78-3.91 (t, J=12.5 Hz, 2H), 2.98-3.09 (m, 5H), 2.11-2.66 (m, 15H), 1.46-2.09 (m, 7H); LC/MS: m/z=499.3 [M+H]$^+$.

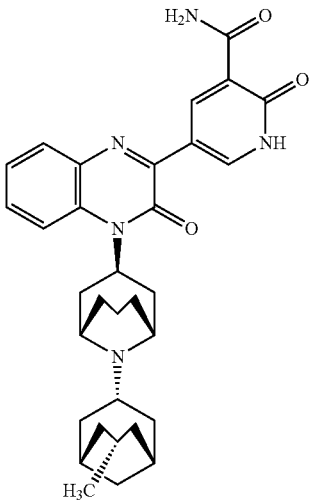

U063

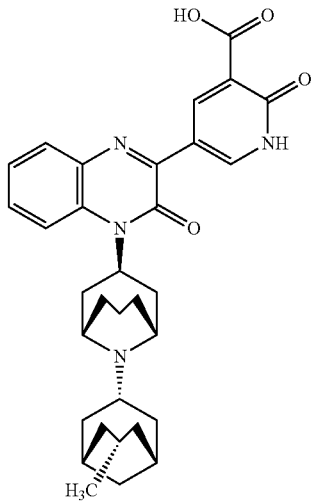

U064

U063: 5-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-2-oxo-1,2-dihydropyridine-3-carboxamide.

U063: $^1$H-NMR: $\delta_H$ (ppm, 400 MHz, CDCl$_3$): 9.33 (s, 1H), 8.86 (s, 1H), 8.27 (s, 1H), 7.69 (s, 1H), 7.47 (s, 1H), 7.18 (s, 1H), 5.89 (br, 1H), 3.93 (m, 2H), 3.64 (m, 1H), 2.87 (m, 2H), 2.68 (m, 1H), 2.23 (m, 4H), 2.06-1.42 (m, 12H), 0.67 (m, 4H), 0.43 (m, 2H); LC/MS: m/z=542.3 [M+H]$^+$.

U064: 5-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-2-oxo-1,2-dihydropyridine-3-carboxylic acid.

U064: $^1$H-NMR: $\delta_H$ (ppm, 400 MHz, CDCl$_3$): 9.42 (d, J=2.3 Hz, 1H), 8.98 (s, 1H), 8.41 (d, J=8.8 Hz, 1H), 7.75 (d, J=8.0 Hz, 1H), 7.57 (s, 1H), 7.26 (s, 1H), 6.02 (br, 1H), 3.71 (m, 1H), 2.91 (m, 2H), 2.72 (m, 1H), 2.33 (m, 2H), 2.23 (m, 2H), 2.10 (m, 2H), 2.00-1.47 (m, 10H), 0.71 (m, 4H), 0.48 (m, 2H); LC/MS: m/z=543.3 [M+H]$^+$.

5.31 Example 31

Synthesis of Compound 1B3

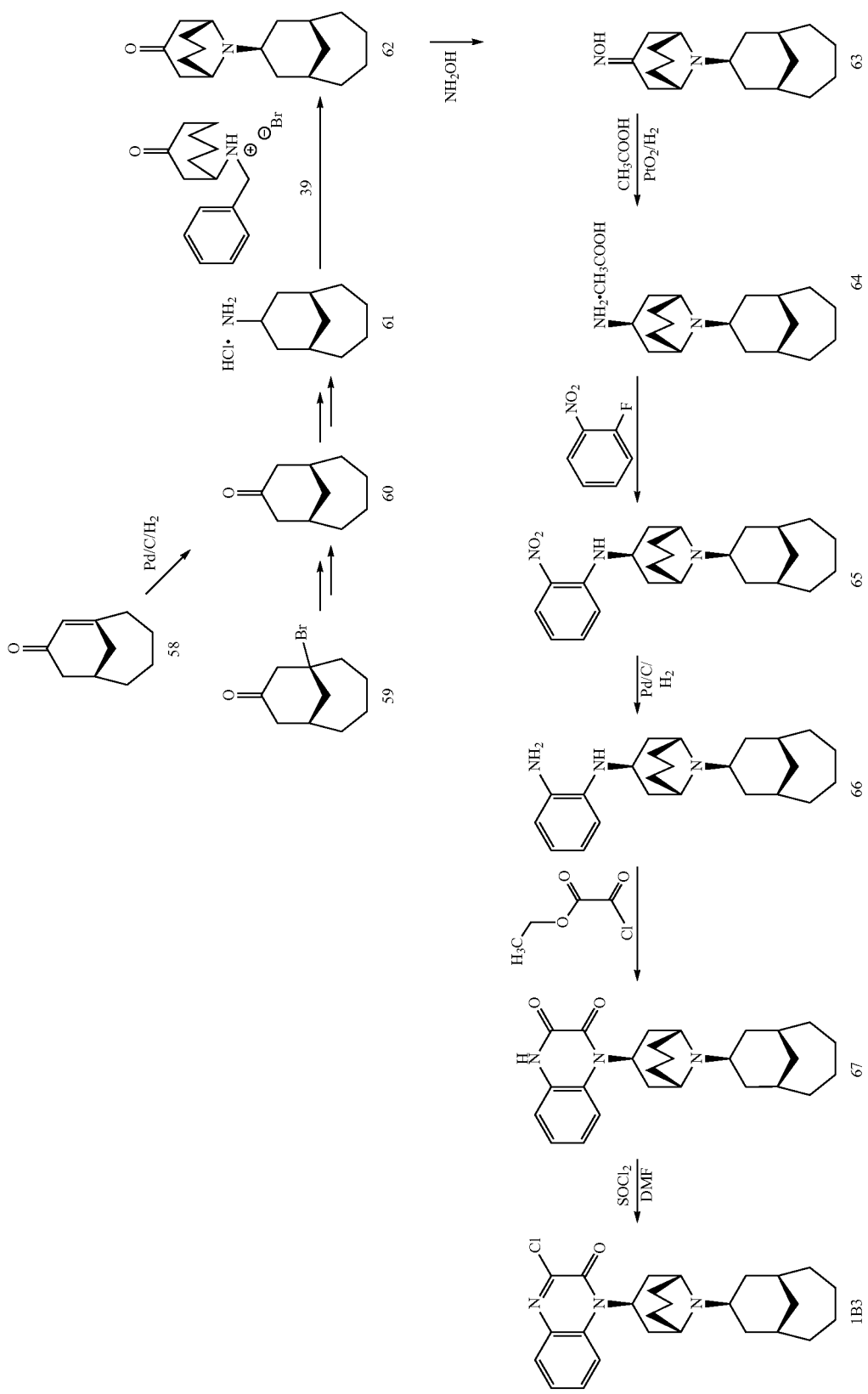

Using procedures similar to those described in Examples 6 and 7, Compound 1B3, 1-((1R,3R,5S)-9-((1R,6S,8s)-bicyclo[4.3.1]decan-8-yl)-9-azabicyclo[3.3.1]nonan-3-yl)-3-chloroquinoxalin-2(1H)-one, was prepared from Compound 60.

The identity of Compound 61, (1R,6S)-bicyclo[4.3.1]decan-8-amine, was confirmed using MS.

Compound 61: MS: m/z=154.4 [M+H]$^+$.

The identity of Compound 62, (1R,5S)-9-01R,6S,8s)-bicyclo[4.3.1]decan-8-yl)-9-azabicyclo[3.3.1]nonan-3-one, was confirmed using $^1$H-NMR and MS.

Compound 62: $^1$H-NMR: $\delta_H$ (ppm, CD$_3$OD): 3.76 (br, 2H), 3.45 (m, 1H), 3.13 (m; 1H), 2.70 (m, 2H), 2.38-2.20 (m, 4H), 1.99-1.76 (m, 9H), 1.75-1.34 (m, 10H); MS: m/z=276.4 [M+H]$^+$.

The identity of Compound 63, (1R,5S)-9-((1R,6S,8s)-bicyclo[4.3.1]decan-8-yl)-9-azabicyclo[3.3.1]nonan-3-one oxime, was confirmed using $^1$H-NMR and MS.

Compound 63: $^1$H-NMR: $\delta_H$ (ppm, CDCl$_3$): 8.29 (br, 1H), 3.52 (br, 2H), 3.03 (m, 2H), 2.63 (m, 1H), 2.27 (m, 4H), 1.95-1.26 (m, 20H); MS: m/z=291.4 [M+H]$^+$.

The identity of Compound 64, (1R,3R,5S)-9-((1R,6S,8s)-bicyclo[4.3.1]decan-8-yl)-9-azabicyclo[3.3.1]nonan-3-amine acetate, was confirmed using $^1$H-NMR and MS.

Compound 64: $^1$H-NMR: $\delta_H$ (ppm, CD$_3$OD): 3.49 (m, 2H), 3.20 (m, 1H), 3.05 (m, 1H), 2.27 (m, 4H), 2.04 (m, 1H), 1.91 (s, 3H), 1.81 (m, 7H), 1.71-1.42 (m, 8H), 1.31-1.15 (m, 6H); MS: m/z=277.4 [M+H]$^+$.

The identity of Compound 65, (1R,3R,5S)-9-((1R,6S,8s)-bicyclo[4.3.1]decan-8-yl)-N-(2-nitrophenyl)-9-azabicyclo[3.3.1]nonan-3-amine, was confirmed using $^1$H-NMR and MS.

Compound 65: $^1$H-NMR: $\delta_H$ (ppm, CDCl$_3$): 8.17 (dd, J=1.7, 8.4 Hz, 1H), 8.04 (d, J=7.3 Hz, 1H), 7.41 (m, 1H), 6.94 (d, J=8.4 Hz, 1H), 6.60 (m, 1H), 3.98 (m, 1H), 3.51 (m, 2H), 3.05 (m, 1H), 2.46 (m, 2H), 2.27 (m, 2H), 2.02 (m, 1H), 1.86-1.52 (m, 12H), 1.49-1.32 (m, 4H), 1.25 (m, 2H), 1.13 (m, 2H); MS: m/z=398.4 [M+H]$^+$.

The identity of Compound 66, N$^1$-((1R,3R,5S)-9-((1R,6S,8s)-bicyclo[4.3.1]decan-8-yl)-9-azabicyclo[3.3.1]nonan-3-yl)benzene-1,2-diamine, was confirmed using $^1$H-NMR and MS.

Compound 66: $^1$H-NMR: $\delta_H$ (ppm, CDCl$_3$): 6.78 (m, 4H), 6.60 (m, 1H), 4.46 (m, 1H), 3.91 (m, 3H), 3.74 (m, 1H), 3.11 (m, 2H), 2.79 (m, 2H), 2.55 (m, 1H), 2.42 (m, 4H), 2.02-1.55 (m, 12H), 1.52-1.27 (m, 5H); MS: m/z=368.4 [M+H]$^+$.

The identity of Compound 67, 1-((1R,3R,5S)-9-((1R,6S,8s)-bicyclo[4.3.1]decan-8-yl)-9-azabicyclo[3.3.1]nonan-3-yl)quinoxaline-2,3(1H,4H)-dione, was confirmed using MS.

Compound 67: MS: m/z=422.4 [M+H]$^+$.

The identity of Compound 1B3 was confirmed using $^1$H-NMR and MS.

Compound 1B3: $^1$H-NMR: $\delta_H$ (ppm, CDCl$_3$): 8.77 (d, J=8.6 Hz, 1H), 7.78 (m, 2H), 7.41 (m, 1H), 6.52 (m, 1H), 4.18 (m, 2H), 3.85 (m, 1H), 3.01 (m, 2H), 2.92 (m, 1H), 2.60-2.44 (m, 6H), 2.10-1.66 (m, 13H), 1.54-1.33 (m, 4H); MS: m/z=440.4 [M+H]$^+$.

Compound 60, (1R,6S)-bicyclo[4.3.1]decan-8-one, was prepared by hydrogenating Compound 58 using palladium on carbon under a hydrogen atmosphere, for example, similarly to the preparation of Compound 50 in Example 5. Alternately, Compound 60 can be prepared by protecting the oxo group of Compound 59 followed by debromination with n-butyl lithium, quenching with water, and deprotection of the oxo group.

The identity of Compound 60 was confirmed using MS.

Compound 60: MS: m/z=153.4 [M+H]$^+$.

Compound 58, (R)-bicyclo[4.3.1]dec-6-en-8-one, was prepared by methods known to the art, e.g., as described in House et al., *J. Org. Chem.* 44(16):2819-2824 (1979) and House et al., *J. Org. Chem.* 45(10):1800-1806 (1980). These House et al. references also describe the preparation of Compound 59, (1S,6S)-1-bromobicyclo[4.3.1]decan-8-one.

The identity of Compound 58 was confirmed using MS.

Compound 58: MS: m/z=151.4 [M+H]$^+$.

5.32 Example 32

Synthesis of Cyclic Urea- or Lactam-Substituted Quinoxaline-Type Piperidine Compound B19a by Method 11

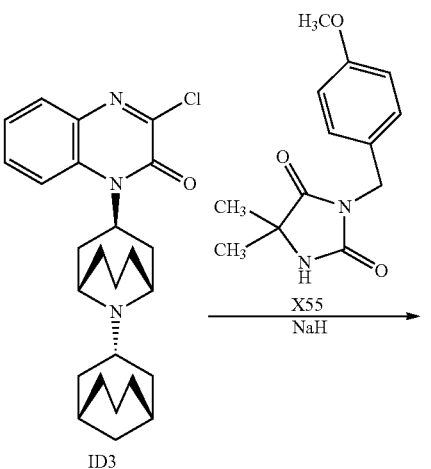

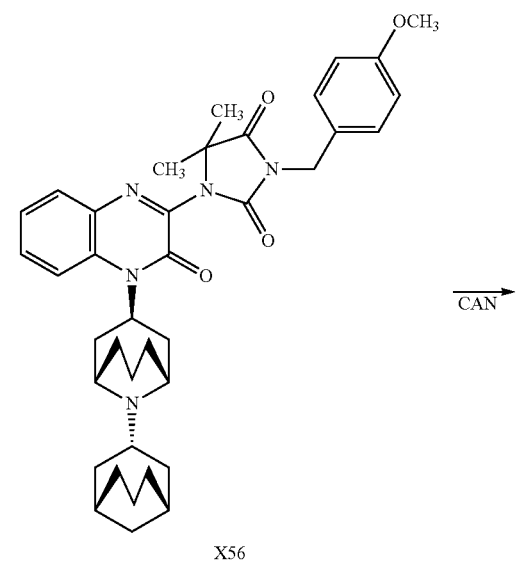

-continued

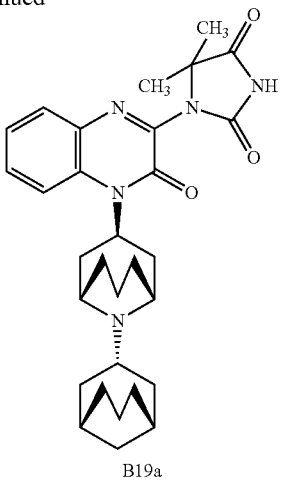

B19a

To a solution of 3-(4-methoxybenzyl)-5,5-dimethylimidazolidine-2,4-dione (Compound X55, 280 mg, 1.127 mmol) in DMA (4 mL) at 0° C. was added NaH (45.1 mg, 1.127 mmol). The resulting mixture was stirred at that temperature for 30 minutes. To the mixture was added Compound 1D3 (400 mg, 0.939 mmol). The resulting reaction mixture was heated to 80° C. and stirred at that temperature for 1 hour. Thereafter, the mixture was cooled to a temperature of about 25° C. and diluted with water; a precipitate formed. The precipitate was collected by filtration and evaporated to dryness under reduced pressure to provide a solid which was chromatographed on a silica gel column (Fuji Silysia Chemical NH60 Size20) eluted with a gradient of from 10:90 EtOAc:hexanes to 20:80 EtOAc:hexanes to provide 192 mg of Compound X56, 1-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-3-(4-methoxybenzyl)-5,5-dimethylimidazolkline-2,4-dione, as a colorless solid (yield 32%).

The identity of Compound X56 was confirmed using $^1$H-NMR and LC/MS.

Compound X56: $^1$H-NMR: $\delta_H$ (ppm, 300 MHz, CDCl$_3$): 1.11 (d, J=12.8 Hz, 2H), 1.39-1.90 (m, 18H), 1.96-2.10 (m, 7H), 2.38 (d, J=10.5 Hz, 1H), 2.67 (t, J=11.2 Hz, 2H), 3.46-3.60 (m, 3H), 3.79 (s, 3H), 4.73 (s, 2H), 5.22 (s, 1H), 6.85 (d, J=7.8 Hz, 2H), 7.32 (t, J=7.2 Hz, 1H), 7.39 (d, J=8.3 Hz, 2H), 7.57 (t, J=7.2 Hz, 1H), 7.63 (d, J=8.5 Hz, 1H), 7.76 (d, J=7.8 Hz, 1H); LC/MS: m/z=638.3 [M+H]$^+$ (Calc: 637).

To a solution of Compound X56 (170 mg, 0.267 mmol) in MeCN (17 mL) at a temperature of about 25° C. was added ceric ammonium nitrate (CAN, 1.096 g, 1.999=101, Sigma-Aldrich) in water (8.5 mL). The resulting reaction mixture was stirred at that temperature for 1 hour. Thereafter, the mixture was diluted with water and the aqueous portion was extracted twice with CHCl$_3$ (100 mL for each extraction). The organic portions were combined, washed with brine, dried (over MgSO$_4$), filtered, and concentrated under reduced pressure to provide a solid which was chromatographed on a on a silica gel column (12 g, Teledyne ISCO) eluted with a gradient of from 0:100 MeOH (10% aqueous NH$_3$):CHCl$_3$ to 5:95 MeOH (10% aqueous NH$_3$):CHCl$_3$ to provide 66.8 mg of Cyclic Urea- or Lactam-Substituted Quinoxaline-Type Piperidine Compound B19a, 1-(4-((1R,1'R,3r,3'R,5S,5'S)-[3,9'-bi(9'-azabicyclo[3.3.1]nonan)]-3'-yl)-3-oxo-3,4-dihydroquinoxalin-2-yl)-5,5-dimethylimidazolidine-2,4-dione, as a white solid (yield 48%).

The identity of Cyclic Urea- or Lactam-Substituted Quinoxaline-Type Piperidine Compound B19a was confirmed using $^1$H-NMR and LC/MS.

Cyclic Urea- or Lactam-Substituted Quinoxaline-Type Piperidine Compound B19a: $^1$H-NMR: $\delta_H$ (ppm, 300 MHz, CDCl$_3$): 1.32-2.08 (m, 22H), 2.24 (br s, 2H), 2.49 (dd, J=20.3, 12.1 Hz, 2H), 2.58-2.68 (m, 2H), 2.70-2.85 (m, 1H), 2.98 (t, J=13.3 Hz, 2H), 4.11 (d, J=10.4 Hz, 2H), 4.23 (br s, 1H), 6.21-6.34 (m, 1H), 7.39 (t, J=6.9 Hz, 1H), 7.70-7.82 (m, 2H), 8.66 (d, J=8.2 Hz, 1H); LC/MS: m/z=518.3 [M+H]$^+$ (Calc: 517).

Compound X55 was prepared as follows.

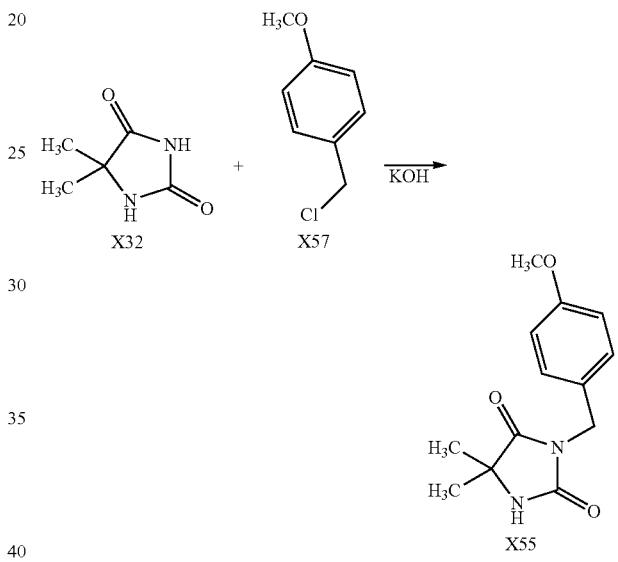

To a suspension of KOH (565 mg, 10.07 mmol) in EtOH (10 mL) at a temperature of about 25° C. was added Compound X32 (1.29 g, 10.07 mmol). The resulting mixture was heated to 90° C. and stirred at that temperature for 10 min then cooled to a temperature of about 25° C. To the mixture was added MeOH (5 mL) and 1-(chloromethyl)-4-methoxybenzene (Compound X57, 1.365 mL, 10.07 mmol, Sigma-Aldrich). The resulting reaction mixture was heated to 60° C. and stirred at that temperature for 18 hours. Thereafter, the mixture evaporated under reduced pressure to provide a residue which was triturated with CHCl$_3$; the insoluble white solid that formed was removed by filtration. The resulting filtrate was concentrated under reduced pressure and chromatographed on a on a silica gel column (24 g, Teledyne ISCO) eluted with a gradient of from 0:100 EtOAc:hexanes to 50:50 EtOAc:hexanes to provide 338.0 mg of Compound X55 as a colorless oil (yield 14%).

The identity of Compound X55 was confirmed using $^1$H-NMR and LC/MS.

Compound X55: $^1$H-NMR: $\delta_H$ (ppm, 300 MHz, CDCl$_3$): 1.41 (s, 6H), 3.79 (s, 3H), 4.59 (s, 2H), 5.64 (br s, 1H), 6.84 (d, J=7.5 Hz, 2H), 7.32 (d, J=7.4 Hz, 2H); LC/MS: m/z=249.2 [M+H]$^+$ (Calc: 248).

5.33 Example 33

Synthesis of Cyclic Urea- or Lactam-Substituted Quinoxaline-Type Piperidine Compound O19a

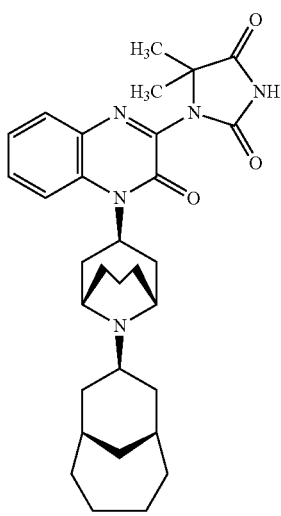

O19a

Using procedures similar to those described above for Method 11 in Example 32, except that Compound 1B3 (prepared as described in Example 31 herein) was used in place of Compound 1D3, Cyclic Urea- or Lactam-Substituted Quinoxaline-Type Piperidine Compound O19a, 1-(4-((1R,3R,5S)-9-((1R,6S,8s)-bicyclo[4.3.1]decan-8-yl)-9-azabicyclo[3.3.1]nonan-3-yl)-3-oxo-3,4-dihydroquinoxalin-2-yl)-5,5-dimethylimidazolidine-2,4-dione, was prepared from Compound X55 as the co-reactant.

O19a: $^1$H-NMR: $\delta_H$ (ppm, 300 MHz, CDCl$_3$+CD$_3$OD+DCl): 1.33-1.52 (m, 4H), 1.62-2.07 (m, 19H), 2.43-2.55 (m, 6H), 2.80 (d, J=13.6 Hz, 1H), 2.99 (t, J=12.8 Hz, 2H), 3.80-3.91 (m, 1H), 4.17 (d, J=10.3 Hz, 2H), 6.19-6.34 (m, 1H), 7.39 (t, J=7.3 Hz, 1H), 7.73-7.82 (m, 2H), 8.64 (d, J=8.8 Hz, 1H); LC/MS: m/z=532.3 [M+H]$^+$ (Calc: 531).

5.34 Example 34

Synthesis of Cyclic Urea- or Lactam-Substituted Quinoxaline-Type Piperidine Compound R6a(i)(i) by Method 12

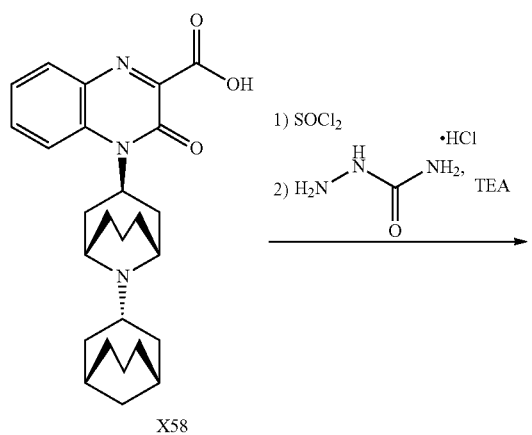

X58

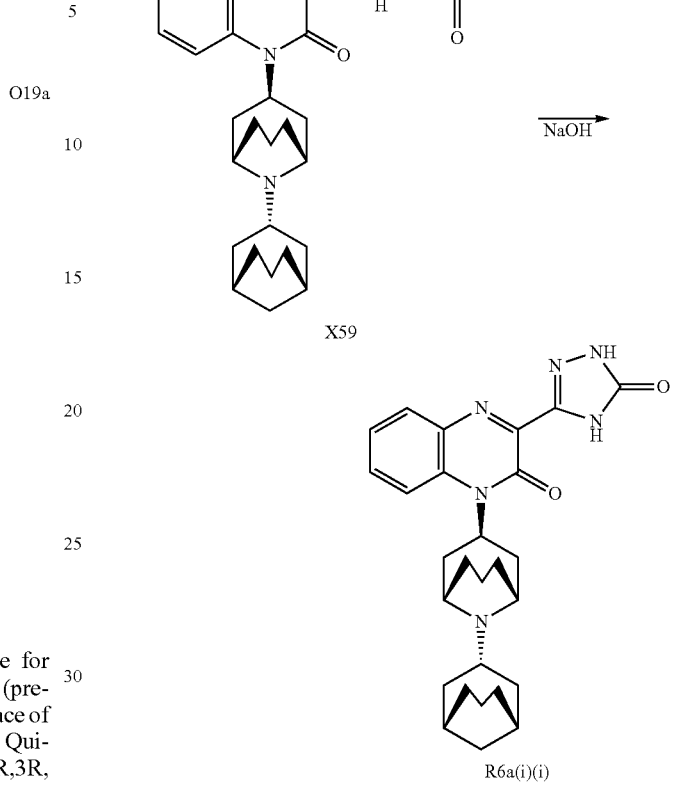

To a mixture of 4-((1R,1'R,3r,3'R,5S,5'S)-[3,9'-bi(9'-azabicyclo[3.3.1]nonan)]-3'-yl)-3-oxo-3,4-dihydroquinoxaline-2-carboxylic acid (Compound X58, 300 mg, 0.689 mmol) and SOCl$_2$ (2.011 mL, 27.6 mmol, Sigma-Aldrich) at 0° C. was added DMF (5.36 µL, 0.069 mmol). The resulting reaction mixture was heated to 100° C. and stirred at that temperature for 20 minutes. Thereafter, the mixture was cooled to a temperature of about 25° C. and concentrated under reduced pressure to provide the acid chloride of Compound X58 as an oil which was dried under reduced pressure at a temperature of about 25° C. for 15 min. To a mixture of the acid chloride of Compound X58 in THF (9 mL) at 0° C. was added the hydrochloride of hydrazinecarboxamide (230 mg, 2.066 mmol, Sigma-Aldrich) and TEA (0.573 mL, 4.13 mmol). The resulting reaction mixture was heated to a temperature of about 25° C. and stirred at that temperature for 7 hours. Thereafter, the mixture was diluted with water and a saturated aqueous NaHCO$_3$ solution then extracted twice with CHCl$_3$/H$_2$O (70 mL for each extraction). The organic portions were combined, dried (over MgSO$_4$), and concentrated under reduced pressure to provide a residue which was chromatographed on a on a silica gel column (12 g, Teledyne ISCO) eluted with a gradient of from 2:98 MeOH (10% aqueous NH$_3$):CHCl$_3$ to 10:90 MeOH (10% aqueous NH$_3$):CHCl$_3$ to provide 80 mg of Compound X59, 2-(4-((1R,1'R,3r,3'R,5S,5'S)-[3,9'-bi(9'-azabicyclo[3.3.1]nonan)]-3'-yl)-3-oxo-3,4-dihydroquinoxaline-2-carbonyl)hydrazinecarboxamide, as a yellow solid (yield 23%).

The identity of Compound X59 was confirmed using $^1$H-NMR and LC/MS.

Compound X59: $^1$H-NMR: $\delta_H$ (ppm, 400 MHz, CDCl$_3$+CD$_3$OD+DCl): 1.21-2.05 (m, 16H), 2.26 (s, 2H), 2.52 (t, J=22.0 Hz, 4H), 2.83 (s, 1H), 3.03 (t, J=12.0 Hz, 2H), 4.15 (s, 2H), 4.27 (s, 1H), 6.33 (s, 1H), 7.50 (t, J=7.3 Hz, 1H), 7.89 (t, J=7.7 Hz, 1H), 8.06 (d, J=7.5 Hz, 1H), 8.74 (d, J=8.5 Hz, 1H); LC/MS: m/z=493.25 [M+H]$^+$ (Calc: 492.6).

To a suspension of Compound X59 (80 mg, 0.162 mmol) in EtOH (2.4 mL) at a temperature of about 25° C. was added 2N NaOH (0.244 mL, 0.487 mmol). The resulting reaction mixture was heated to 100° C. and stirred at that temperature for 3 days. Thereafter, the mixture was cooled to a temperature of about 25° C., concentrated under reduced pressure, 10% citric acid was added, and the mixture was extracted twice with CHCl$_3$/H$_2$O (10 mL for each extraction). The organic portions were combined, dried (over MgSO$_4$), and concentrated under reduced pressure to provide a residue which was chromatographed on a on a silica gel column eluted with a gradient of from 1:99 MeOH (10% aqueous NH$_3$):CHCl$_3$ to 15:85 MeOH (10% aqueous NH$_3$):CHCl$_3$ to provide 31 mg of Cyclic Urea- or Lactam-Substituted Quinoxaline-Type Piperidine Compound R6a(i)(i), 1-((1R,1'R,3r,3'R,5S,5'S)-[3,9'-bi(9'-azabicyclo[3.3.1]nonan)]-3'-yl)-3-(5-oxo-4,5-dihydro-1H-1,2,4-triazol-3-yl)quinoxalin-2(1H)-one, as a pale yellow solid (yield 40%).

The identity of Cyclic Urea- or Lactam-Substituted Quinoxaline-Type Piperidine Compound R6a(i)(i) was confirmed using $^1$H-NMR and LC/MS.

Cyclic Urea- or Lactam-Substituted Quinoxaline-Type Piperidine Compound R6a(i)(i): $^1$H-NMR: δ$_H$ (ppm, 400 MHz, CDCl$_3$+CD$_3$OD+DCl): 1.41 (s, 1H), 1.57-2.08 (m, 15H), 2.25 (s, 2H), 2.48-2.58 (m, 4H), 2.92 (dd, J=30.9, 13.6 Hz, 1H), 3.08 (t, J=12.8 Hz, 2H), 4.37 (s, 1H), 6.27-6.36 (m, 1H), 7.46 (t, J=7.7 Hz, 1H), 7.83 (t, J=7.9 Hz, 1H), 7.97 (d, J=8.0 Hz, 1H), 8.72 (d, J=8.8 Hz, 1H); LC/MS: m/z=475.2 [M+H]$^+$ (Calc: 474.6).

Compound X58 was prepared as described in U.S. Patent Application Publication US 2011/0178090 A1, at paragraph [0395] and thereafter, which is hereby incorporated by reference in its entirety.

5.35 Example 35

Synthesis of Cyclic Urea- or Lactam-Substituted Quinoxaline-Type Piperidine Compound EE6b(i)(i)

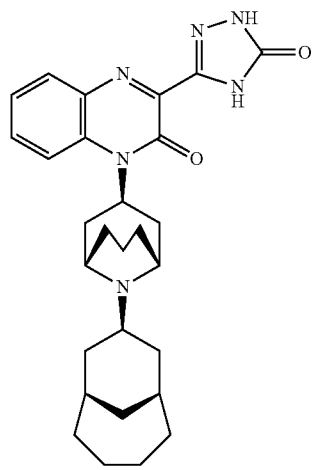

EE6b(i)(i)

Using procedures similar to those described above for Method 12 in Example 34, except that Compound 1B3 (prepared as described in Example 31 herein) was used in place of Compound 1D3, Cyclic Urea- or Lactam-Substituted Quinoxaline-Type Piperidine Compound EE6b(i)(i), 1-((1R,3R,5S)-9-((1R,6S,8s)-bicyclo[4.3.1]decan-8-yl)-9-azabicyclo[3.3.1]nonan-3-yl)-3-(5-oxo-4,5-dihydro-1H-1,2,4-triazol-3-yl)quinoxalin-2(1H)-one, was prepared.

EE6b(i)(i): $^1$H-NMR: δ$_H$ (ppm, 400 MHz, CDCl$_3$+CD$_3$OD+DCl): 1.32-1.58 (m, 4H), 1.68-2.02 (m, 15H), 2.47 (s, 6H), 3.89-3.05 (m, 3H), 3.87 (s, 1H), 6.32 (s, 1H), 7.46 (t, J=7.3 Hz, 1H), 7.82 (d, J=7.0 Hz, 1H), 7.97 (d, J=6.8 Hz, 1H), 8.70 (d, J=8.0 Hz, 1H); LC/MS: m/z=489.25 [M+H]$^+$ (Calc: 488.62).

5.36 Example 36

Synthesis of Cyclic Urea- or Lactam-Substituted Quinoxaline-Type Piperidine Compound R6a(iii)(i) by Method 13

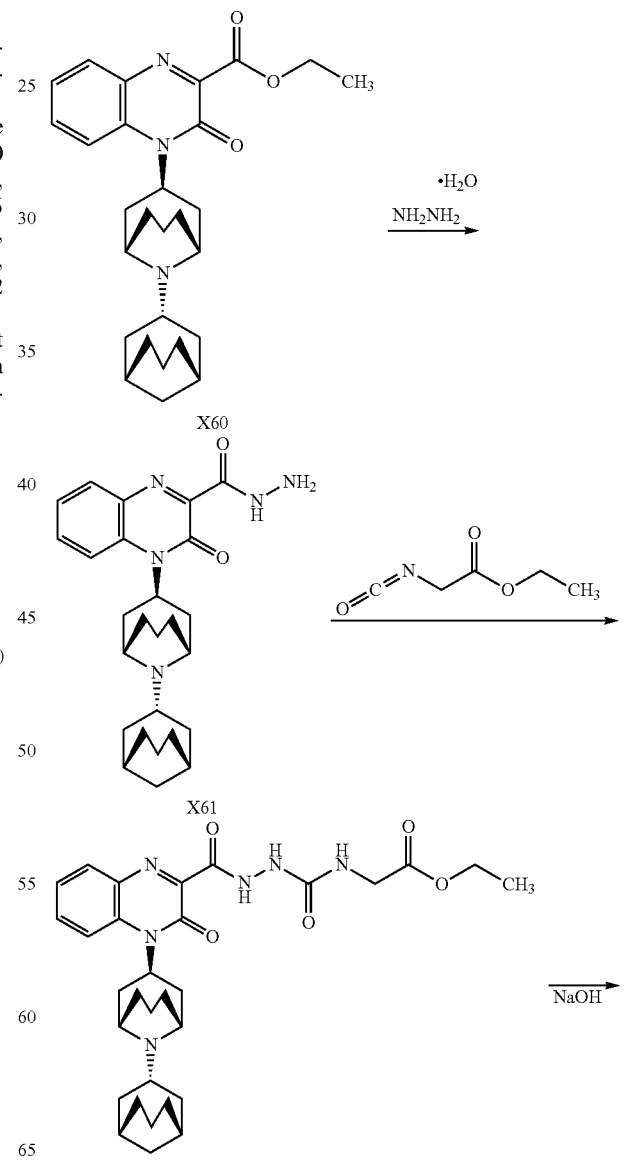

-continued

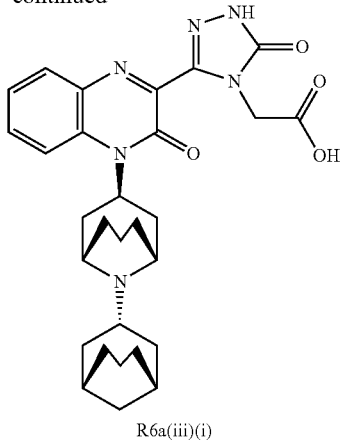

R6a(iii)(i)

To a solution of Compound X60 (769 mg, 1.659 mmol) in EtOH (15 mL) at a temperature of about 25° C. was added hydrazine mono-hydrate (0.403 mL, 8.29 mmol, Sigma-Aldrich). The resulting reaction mixture was heated to 100° C. and stirred at that temperature for 3 hours. Thereafter, the mixture was filtered to provide a solid that was washed with EtOH and dried under reduced pressure at 60° C. to provide 548 mg of Compound X61, 4-((1R,1'R,3r,3'R,5S,5'S)-[3,9'-bi(9'-azabicyclo[3.3.1]nonan)]-3'-yl)-3-oxo-3,4-dihydroquinoxaline-2-carbohydrazide, as a yellow solid (yield 73%).

The identity of Compound X61 was confirmed using $^1$H-NMR and LC/MS.

Compound X61: $^1$H-NMR: $\delta_H$ (ppm, 400 MHz, CDCl$_3$): 1.11 (d, J=12.5 Hz, 2H), 1.42-1.78 (m, 19H), 1.86 (t, J=13.2 Hz, 2H), 2.009-2.08 (m, 6H), 2.38 (s, 1H), 2.70 (s, 2H), 3.48-3.59 (m, 3H), 4.35 (d, J=4.1 Hz, 2H), 5.25 (s, 1H), 7.44 (t, J=7.2 Hz, 1H), 7.70 (d, J=5.5 Hz, 2H), 8.20 (d, J=7.9 Hz, 1H), 10.74 (s, 1H); LC/MS: m/z=450.2 [M+H]$^+$ (Calc: 449.6).

To a solution of Compound X61 (150 mg, 0.334 mmol) in THF (4.5 mL) at a temperature of about 25° C. was added ethyl 2-isocyanatoacetate (0.112 mL, 1.001 mmol, Sigma-Aldrich). The resulting reaction mixture was stirred at that temperature for 2.5 hours. Thereafter, the mixture was filtered to provide a solid that was washed with THF to provide 165 mg of Compound X62, ethyl 2-(2-(4-((1R,1'R,3r,3'R,5S,5'S)-[3,9'-bi(9'-azabicyclo[3.3.1]nonan)]-3'-yl)-3-oxo-3,4-dihydroquinoxaline-2-carbonyl)hydrazinecarboxamido)acetate, as a yellow solid (yield 85%).

The identity of Compound X62 was confirmed using LC/MS.

Compound X62: LC/MS: m/z=579.3 [M+H]$^+$ (Calc: 578.7).

Compound X62 (165 mg, 0.285 mmol), taken directly from the previous step, was suspended in EtOH (4.8 mL) at a temperature of about 25° C. 2N NaOH (0.713 mL, 1.426 mmol) was added and the resulting reaction mixture was heated to 100° C. and stirred at that temperature for about 16 hours. Thereafter, the mixture was concentrated under reduced pressure and neutralized with 10% citric acid; a precipitate formed. The precipitate was collected by filtration, washed with water, and dried for 16 hours under reduced pressure at 80° C. to provide 160 mg of Cyclic Urea- or Lactam-Substituted Quinoxaline-Type Piperidine Compound R6a(iii)(i), 2-(3-(4-((1R,1'R,3 r,3'R,5S,5'S)-[3,9'-bi(9'-azabicyclo[3.3.1]nonan)]-3'-yl)-3-oxo-3,4-dihydroquinoxalin-2-yl)-5-oxo-1H-1,2,4-triazol-4(5H)-yl)acetic acid, as a yellow solid (yield 98%).

The identity of Cyclic Urea- or Lactam-Substituted Quinoxaline-Type Piperidine Compound R6a(iii)(i) was confirmed using $^1$H-NMR and LC/MS.

Cyclic Urea- or Lactam-Substituted Quinoxaline-Type Piperidine Compound R6a(iii)(i): $^1$H-NMR: $\delta_H$ (ppm, 400 MHz, CDCl$_3$+CD$_3$OD): 1.69-1.85 (m, 18H), 2.24 (s, 2H), 2.47-2.55 (m, 4H), 2.87 (s, 1H), 3.10 (dd, J=26.5, 14.4 Hz, 2H), 4.12 (t, J=6.1 Hz, 2H), 4.24 (s, 1H), 4.90 (s, 2H), 6.23 (s, 1H), 7.39 (s, 1H), 7.83 (t, J=19.7 Hz, 2H), 8.67 (s, 1H); LC/MS: m/z=533.3 [M+H]$^+$ (Calc: 532.6).

Compound X60 was prepared as described in U.S. Patent Application Publication US 2011/0178090 A1, at paragraph [0395] and thereafter, which is hereby incorporated by reference in its entirety.

5.37 Example 37

In Vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/mL. Protein concentrations were determined using the BioRad protein assay reagent with bovine serum albumen as a standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 µg membrane protein in a final volume of 500 µL binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma-Aldrich). Harvesting was performed using a 96-well tissue harvester (Packard) followed by three filtration washes with 5004 ice-cold binding buffer. Filter plates were subsequently dried at 50° C. for 2-3 hours. Fifty µL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data: An Cyclic Urea- or Lactam-Substituted Quinoxaline-Type Piperidine Compound has a binding affinity (K$_i$) for the human ORL-1 receptor of about 1000 nM or less in one embodiment, or about 500 nM or less in another embodiment. In certain embodiments, a Cyclic Urea- or Lactam-Substituted Quinoxaline-Type Piperidine Compound has a K$_i$ (nM) of about 300 or less for binding to ORL-1 receptors. In one embodiment, a Cyclic Urea- or Lactam-Substituted Quinoxaline-Type Piperidine Compound has a K$_i$ (nM) of about 100 or less. In another embodiment, a Cyclic Urea- or Lactam-Substituted Quinoxaline-Type Piperidine Compound of the disclosure has a K, (nM) of about 35 or less. In another embodiment, a Cyclic Urea- or Lactam-Substituted Quinoxaline-Type Piperidine Compound of the disclosure has a K$_i$ (nM) of about 20 or less.

In another embodiment, a Cyclic Urea- or Lactam-Substituted Quinoxaline-Type Piperidine Compound of the disclosure has a $K_i$ (nM) of about 15 or less. In another embodiment, a Cyclic Urea- or Lactam-Substituted Quinoxaline-Type Piperidine Compound of the disclosure has a $K_i$ (nM) of about 10 or less. In another embodiment, a Cyclic Urea- or Lactam-Substituted Quinoxaline-Type Piperidine Compound of the disclosure has a $K_i$ (nM) of about 4 or less. In another embodiment, a Cyclic Urea- or Lactam-Substituted Quinoxaline-Type Piperidine Compound of the disclosure has a $K_i$ (nM) of about 1 or less. In another embodiment, a Cyclic Urea- or Lactam-Substituted Quinoxaline-Type Piperidine Compound of the disclosure has a $K_i$ (nM) of about 0.4 or less. In another embodiment, a Cyclic Urea- or Lactam-Substituted Quinoxaline-Type Piperidine Compound of the disclosure has a K, (nM) of about 0.1 or less.

5.38 Example 38

In Vitro ORL-1 Receptor Functional Assay

ORL-1 Receptor [$^{35}$S]GTPγS Binding Assay Procedures: Membranes from recombinant FMK-293 cells expressing the human opioid receptor-like (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 μg/μL ORL-1 membrane protein, 10 μg/mL saponin, 3 μM GDP and 0.20 nM [35S] GTPγS to binding buffer (100 mM NaCl, 10 mM $MgCl_2$, 20 mM HEPES, pH 7.4) on ice. The prepared membrane solution (190 μL/well) was transferred to 96-shallow well polypropylene plates containing 10 μL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 2-3 hours. Fifty μL/well scintillation cocktail (BetaScint; Wallac) was added and plates were counted in Packard Top-Count for 1 min/well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. In one embodiment, a Cyclic Urea- or Lactam-Substituted Quinoxaline-Type Piperidine Compound has an ORL-1 GTP $EC_{50}$ (nM) of about 5000 or less to stimulate ORL-1 receptor function. In another embodiment, a Cyclic Urea- or Lactam-Substituted Quinoxaline-Type Piperidine Compound has an ORL-1 GTP $EC_{50}$ (nM) of about 1000 or less. In another embodiment, a Cyclic Urea- or Lactam-Substituted Quinoxaline-Type Piperidine Compound has an ORL-1 GTP $EC_{50}$ (nM) of about 100 or less. In another embodiment, a Cyclic Urea- or Lactam-Substituted Quinoxaline-Type Piperidine Compound has an ORL-1 GTP $EC_{50}$ (nM) of about 80 or less. In another embodiment, a Cyclic Urea- or Lactam-Substituted Quinoxaline-Type Piperidine Compound has an ORL-1 GTP $EC_{50}$ (nM) of about 50 or less. In another embodiment, a Cyclic Urea- or Lactam-Substituted Quinoxaline-Type Piperidine Compound has an ORL-1 GTP $EC_{50}$ (nM) of about 35 or less. In another embodiment, a Cyclic Urea- or Lactam-Substituted Quinoxaline-Type Piperidine Compound has an ORL-1 GTP $EC_{50}$ (nM) of about 15 or less. In another embodiment, a Cyclic Urea- or Lactam-Substituted Quinoxaline-Type Piperidine Compound has an ORL-1 GTP $EC_{50}$ (nM) of about 10 or less. In another embodiment, a Cyclic Urea- or Lactam-Substituted Quinoxaline-Type Piperidine Compound has an ORL-1 GTP $EC_{50}$ (nM) of about 4 or less. In another embodiment, a Cyclic Urea- or Lactam-Substituted Quinoxaline-Type Piperidine Compound has an ORL-1 GTP $EC_{50}$ (nM) of about 1 or less. In another embodiment, a Cyclic Urea- or Lactam-Substituted Quinoxaline-Type Piperidine Compound has an ORL-1 GTP $EC_{50}$ (nM) of about 0.4 or less. In another embodiment, a Cyclic Urea- or Lactam-Substituted Quinoxaline-Type Piperidine Compound has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In one embodiment, a Cyclic Urea- or Lactam-Substituted Quinoxaline-Type Piperidine Compound has an ORL-1 GTP Emax (%) of about 50% or greater. In another embodiment, a Cyclic Urea- or Lactam-Substituted Quinoxaline-Type Piperidine Compound has an ORL-1 GTP Emax (%) of about 75% or greater. In another embodiment, a Cyclic Urea- or Lactam-Substituted Quinoxaline-Type Piperidine Compound has an ORL-1 GTP Emax (%) of about 85% or greater. In another embodiment, a Cyclic Urea- or Lactam-Substituted Quinoxaline-Type Piperidine Compound has an ORL-1 GTP Emax (%) of about 95% or greater. In another embodiment, a Cyclic Urea- or Lactam-Substituted Quinoxaline-Type Piperidine Compound has an ORL-1 GTP Emax (%) of about 100% or greater. In another embodiment, a Cyclic Urea- or Lactam-Substituted Quinoxaline-Type Piperidine Compound has an ORL-1 GTP Emax (%) of about 110% or greater. In certain embodiments, a Cyclic Urea- or Lactam-Substituted Quinoxaline-Type Piperidine Compound acting as a partial agonist has an ORL-1 GTP Emax (%) of less than about 10%. In one embodiment, partial agonist Cyclic Urea- or Lactam-Substituted Quinoxaline-Type Piperidine Compounds has an ORL-1 GTP Emax (%) of less than about 20%. In another embodiment, partial agonist Cyclic Urea- or Lactam-Substituted Quinoxaline-Type Piperidine Compounds has an ORL-1 GTP Emax (%) of less than about 30%. In another embodiment, partial agonist Cyclic Urea- or Lactam-Substituted Quinoxaline-Type Piperidine Compounds has an ORL-1 GTP Emax (%) of less than about 40%. In another embodiment, partial agonist Cyclic Urea- or Lactam-Substituted Quinoxaline-Type Piperidine Compounds has an ORL-1 GTP Emax (%) of less than about 50%.

5.39 Example 39

In Vitro Mu-Opioid Receptor Binding Assays

μ-Opioid Receptor Binding Assay Procedures: Radioligand binding assays were conducted using freshly thawed membranes expressing human μ-receptors (Perkin Elmer, Shelton, Conn.). Radioligand dose-displacement binding assays for human μ-opioid receptors used 0.2 nM[$^3$H]-diprenorphine (NEN, Boston, Mass.), with 5-20 mg membrane protein/well in a final volume of 500 µL binding buffer (10 mM MgCl$_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 hr at about 25° C. Binding reactions were terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed by performing three filtration washes with 500 µL of ice-cold binding buffer. Filter plates were subsequently dried at 50° C. for 2-3 hours. BetaScint scintillation cocktail (Wallac, Turku, Finland) was added (50 µL/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

µ-Opioid Receptor Binding Data: In certain embodiments, a Cyclic Urea- or Lactam-Substituted Quinoxaline-Type Piperidine Compound has a K$_i$ (nM) of about 3000 or less for binding to µ-opioid receptors, or about 1000 or less, or about 650 or less, or about 525 or less, or about 250 or less, or about 100 or less, or about 10 or less, or about 1 or less, or about 0.1 or less.

5.40 Example 40

In Vitro Mu-Opioid Receptor Functional Assays

µ-Opioid Receptor Functional Assay Procedures: [$^{35}$S]GTPγS functional assays were conducted using freshly thawed membranes expressing human p-receptors. Assay reactions were prepared by sequentially adding the following reagents to binding buffer (100 mM NaCl, 10 mM MgCl$_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (1904/well) was transferred to 96-shallow well polypropylene plates containing 10 µL of 20× concentrated stock solutions of the agonist DAMGO ([D-Ala2, N-methyl-Phe4 Gly-ol5]-enkephalin) prepared in DMSO. Plates were incubated for 30 min at about 25° C. with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 µL of ice-cold wash buffer (10 mM NaH$_2$PO$_4$, 10 mM Na$_2$HPO$_4$, pH 7.4). Filter plates were subsequently dried at 50° C. for 2-3 hr. BetaScint scintillation cocktail (Wallac, Turku, Finland) was added (50 µL/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

µ-Opioid Receptor Functional Data: µ GTP EC$_{50}$ is the concentration of a compound providing 50% of the maximal response for the compound at a µ-opioid receptor. In certain embodiments, a Cyclic Urea- or Lactam-Substituted Quinoxaline-Type Piperidine Compound has a g GTP EC$_{50}$ (nM) of about 5000 or less, or about 4100 or less, or about 3100 or less, or about 2000 or less, or about 1000 or less, or about 100 or less, or about 10 or less, or about 1 or less, or about 0.4 or less, or about 0.1 or less.

µ GTP Emax (%) is the maximal effect elicited by a compound relative to the effect elicited by DAMGO, a standard µ agonist. In certain embodiments, a Cyclic Urea- or Lactam-Substituted Quinoxaline-Type Piperidine Compound has a µ GTP Emax (%) of about 10% or greater, or about 20% or greater, or about 50% or greater, or about 65% or greater, or about 75% or greater, or about 88% or greater, or about 100% or greater. In other embodiments, a Cyclic Urea- or Lactam-Substituted Quinoxaline-Type Piperidine Compound has a µ GTP Emax (%) of about 10% or less, or about 5% or less, or about 2% or less.

5.41 Example 41

In Vitro Kappa-Opioid Receptor Binding Assays

κ-Opioid Receptor Binding Assay Procedures: Membranes from recombinant HEK-293 cells expressing the human kappa opioid receptor (kappa) (cloned in house) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/mL. Protein concentrations were determined using the BioRad protein assay reagent with bovine serum albumen as a standard. Aliquots of kappa receptor membranes were stored at −80° C.

Radioligand dose displacement assays used 0.4-0.8 nM [$^3$H]-U69,593 (NEN; 40 Ci/mmole) with 10-20 µg membrane protein (recombinant kappa opioid receptor expressed in HEK 293 cells; in-house prep) in a final volume of 200 µL binding buffer (5% DMSO, 50 mM Trizma base, pH 7.4). Non-specific binding was determined in the presence of 10 µM unlabeled naloxone or U69,593. All reactions were performed in 96-well polypropylene plates for 1 h at a temperature of about 25° C. Binding reactions were determined by rapid filtration onto 96-well Unifilter GF/C filter plates (Packard) presoaked in 0.5% polyethylenimine (Sigma-Aldrich). Harvesting was performed using a 96-well tissue harvester (Packard) followed by five filtration washes with 200 µL ice-cold binding buffer. Filter plates were subsequently dried at 50° C. for 1-2 hours. Fifty pt/well scintillation cocktail (MicroScint20, Packard) was added and plates were counted in a Packard Top-Count for 1 min/well.

κ-Opioid Receptor Binding Data: In one embodiment, a Cyclic Urea- or Lactam-Substituted Quinoxaline-Type Piperidine Compound has substantially no activity at a κ-opioid receptor. In certain embodiments, a Cyclic Urea- or Lactam-Substituted Quinoxaline-Type Piperidine Compound has a Ki (nM) of about 20,000 or less, or about 10,000 or less, or about 5000 or less, or about 500 or less, or about 300 or less, or about 100 or less, or about 50 or less, or about 20 or less, or about 15 or less, or about 10 or less.

5.42 Example 42

In Vitro Kappa-Opioid Receptor Functional Assays

κ-Opioid Receptor Functional Assay Procedures: Functional [$^{35}$S]GTPγS binding assays were conducted as follows. Kappa opioid receptor membrane solution was prepared by sequentially adding final concentrations of 0.026 µg/µL kappa membrane protein (in-house), 10 µg/mL saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 µL/well) was transferred to 96-shallow well polypropylene plates containing 10 µL, of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 µL, ice-cold binding buffer (10 mM $NaH_2PO_4$, 10 mM $Na_2HPO_4$, pH 7.4). Filter plates were subsequently dried at 50° C. for 2-3 hours. Fifty pt/well scintillation cocktail (MicroScint20, Packard) was added and plates were counted in a Packard Top-Count for 1 min/well.

κ-Opioid Receptor Functional Data: κ GTP $EC_{50}$ is the concentration of a compound providing 50% of the maximal response for the compound at a κ-opioid receptor. In certain embodiments, a Cyclic Urea- or Lactam-Substituted Quinoxaline-Type Piperidine Compound has a κ GTP $EC_{50}$ (nM) of about 20,000 or less, or about 10,000 or less, or about 5000 or less, or about 2000 or less, or about 1500 or less, or about 800 or less, or about 500 or less, or about 300 or less, or about 100 or less, or about 50 or less, or about 10 or less.

κ GTP Emax (%) is the maximal effect elicited by a compound relative to the effect elicited by U69,593. In certain embodiments, a Cyclic Urea- or Lactam-Substituted Quinoxaline-Type Piperidine Compound has a κ GTP Emax (%) of about 10% or greater, or about 15% or greater, or about 30% or greater, or about 40% or greater, or about 45% or greater, or about 75% or greater, or about 90% or greater, or about 100% or greater. In other embodiments, a Cyclic Urea- or Lactam-Substituted Quinoxaline-Type Piperidine Compound has a κ GTP Emax (%) of about 10% or less, or about 5% or less, or about 2% or less.

5.43 Example 43

In Vitro Delta-opioid Receptor Binding Assays

δ-Opioid Receptor Binding Assay Procedures: Radioligand dose-displacement assays used 0.2 nM [$^3$H]-Naltrindole (NEN; 33.0 Ci/mmole) with 10-20 µg membrane protein (recombinant delta opioid receptor expressed in CHO-K1 cells; Perkin Elmer) in a final volume of 500 µL binding buffer (5 mM $MgCl_2$, 5% DMSO, 50 mM Trizma base, pH 7.4). Non-specific binding was determined in the presence of 25 µM unlabeled naloxone. All reactions were performed in 96-deep well polypropylene plates for 1 h at a temperature of about 25° C. Binding reactions were determined by rapid filtration onto 96-well Unifilter GF/C filter plates (Packard) presoaked in 0.5% polyethylenimine (Sigma-Aldrich). Harvesting was performed using a 96-well tissue harvester (Packard) followed by five filtration washes with 500 µL, ice-cold binding buffer. Filter plates were subsequently dried at 50° C. for 1-2 hours. Fifty µL/well scintillation cocktail (MicroScint20, Packard) was added and plates were counted in a Packard Top-Count for 1 min/well.

δ-Opioid Receptor Binding Data: In one embodiment, a Cyclic Urea- or Lactam-Substituted Quinoxaline-Type Piperidine Compound has substantially no activity at a δ-opioid receptor. In certain embodiments, a Cyclic Urea- or Lactam-Substituted Quinoxaline-Type Piperidine Compound has a Ki (nM) of about 20,000 or less, or about 10,000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less, or about 10 or less.

5.44 Example 44

In Vitro Delta-Opioid Receptor Functional Assays

δ-Opioid Receptor Functional Assay Procedures: Functional [$^{35}$S]GTPγS binding assays were conducted as follows using membranes expressing human δ-opioid receptors. Delta opioid receptor membrane solution was prepared by sequentially adding final concentrations of 0.026 µg/µL delta membrane protein (Perkin Elmer), 10 µg/mL saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µL/well) was transferred to 96-shallow well polypropylene plates containing 10 µL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 µL ice-cold binding buffer (10 mM $NaH_2PO_4$, 10 mM $Na_2HPO_4$, pH 7.4). Filter plates were subsequently dried at 50° C. for 1-2 hours. Fifty µL/well scintillation cocktail (MicroScint20, Packard) was added and plates were counted in a Packard Top-count for 1 min/well.

δ-Opioid Receptor Functional Data: δ GTP $EC_{50}$ is the concentration of a compound providing 50% of the maximal response for the compound at a δ receptor. In certain embodiments, a Cyclic Urea- or Lactam-Substituted Quinoxaline-Type Piperidine Compound has a δ GTP $EC_{50}$ (nM) of about 20,000 or less, or about 10,000 or less, or about 100 or less, or about 1000 or less, or about 90 or less, or about 50 or less, or about 25 or less, or about 10 or less.

δ GTP Emax (%) is the maximal effect elicited by a compound relative to the effect elicited by met-enkephalin. In certain embodiments, a Cyclic Urea- or Lactam-Substituted Quinoxaline-Type Piperidine Compound has a δ GTP Emax (%) of about 10% or greater, or about 30% or greater, or about 50% or greater, or about 75% or greater, or about 90% or greater, or about 100% or greater, or about 110% or greater. In other embodiments, a Cyclic Urea- or Lactam-Substituted Quinoxaline-Type Piperidine Compound has a δ GTP Emax (%) of about 10% or less, or about 5% or less, or about 2% or less.

5.45 Example 45

Cytochrome P450 2D6

Cytochrome P450 2D6 (CYP2D6) is an enzyme of the cytochrome P450 super family known to be involved in metabolizing and eliminating many drugs, e.g., orally-administered opiates, particularly at lower concentrations.

Using commercially available pooled human hepatic microsome and employing, as an indicator, the O-demethylation of dextromethorphan ((4bR,8aS,9R)-3-methoxy-11-methyl-6,7,8,8a,9,10-hexahydro-5H-9,4-b-(epiminoethano) phenanthrene) as a typical substrate metabolism reaction for human CYP2D6, Cyclic Urea- or Lactam-Substituted Quinoxaline-Type Piperidine Compounds were tested for the extent to which they inhibited reference metabolite production. The reaction conditions were as follows: 5 µmol/L dextromethorphan substrate, 15 minute reaction time, 37° C. reaction temperature, 0.2 mg protein/mL pooled human hepatic microsome enzyme, and Cyclic Urea- or Lactam-Substituted Quinoxaline-Type Piperidine Compound concentrations of 1, 5, 10, and 20 µmol/L (four concentrations for each compound).

The substrate, human hepatic microsome, or a Cyclic Urea- or Lactam-Substituted Quinoxaline-Type Piperidine Compound in 50 mmol/L HEPES buffer as a reaction solution was added to a 96-well plate at the concentrations as described above, cofactor NADPH was added to initiate metabolism reactions as a marker and, after incubation at 37°

C. for 15 minutes, a 1:1 MeOH:MeCN (vol.:vol.) solution was added to stop the reaction. Following centrifugation at 3000 rpm for 15 minutes, the amount of dextrorphan ((4bR,8aS,9R)-11-methyl-6,7,8,8a,9,10-hexahydro-5H-9,4b-(epiminoethano)phenanthren-3-ol, the CYP2D6 metabolite) present was determined quantitatively by LC/MS/MS.

As a control, addition of only DMSO (a solvent for Cyclic Urea- or Lactam-Substituted Quinoxaline-Type Piperidine Compounds) to a reaction system was adopted (i.e., 100% metabolite production). At each concentration of a Cyclic Urea- or Lactam-Substituted Quinoxaline-Type Piperidine Compound added, the activity (%) was calculated from the amount of dextrorphan present. The $IC_{50}$ was determined by reverse presumption by a logistic model using a concentration and an inhibition rate.

A "low" value of CYP2D6 $IC_{50}$, e.g., about 1 µM or less, is an indicator that undesirable drug-drug interactions are possible. In contrast, a "high" value of CYP2D6 $IC_{50}$, e.g., about 17-20 µM or greater, is an indicator of the absence of undesirable drug-drug interactions.

In certain embodiments, a Cyclic Urea- or Lactam-Substituted Quinoxaline-Type Piperidine Compound has a CYP2D6 $IC_{50}$ of about 15 µM or greater, or of about 16 µM or greater, or of about 17 µM or greater, or of about 17.5 µM or greater, or of about 18 µM or greater, or of about 18.5 µM or greater, or of about 19 µM or greater, or of about 20 µM or greater,

5.46 Example 46

Efficacy of Receptor Binding and Activity Response

The following Tables provide, for several Cyclic Urea- or Lactam-Substituted Quinoxaline-Type Piperidine Compounds and certain other compounds of interest, results on the efficacy of binding and activity response to the ORL-1 receptor, the mu-opioid receptor, the kappa-opioid receptor, and/or the delta-opioid receptor and CYP2D6 response.

In Table 33, binding efficacy to the ORL-1 receptor was determined by the procedure in Example 37. Binding efficacy to the mu-opioid receptor was determined by the procedure in Example 39. Binding efficacy to the kappa-opioid receptor was determined by the procedure in Example 41. Binding efficacy to the delta-opioid receptor was determined by the procedure in Example 43. Also in Table 33, CYP2D6 response, in the form of $IC_{50}$, was determined by the procedure in Example 45.

In Table 34, activity response to the ORL-1 receptor was determined by the procedure in Example 38. Activity response to the mu-opioid receptor was determined by the procedure in Example 40. Activity response to the kappa-opioid receptor was determined by the procedure in Example 42. Activity response to the delta-opioid receptor can be determined by the procedure in Example 44.

TABLE 33

Efficacy of Receptor Binding and CYP2D6 Response of Cyclic Urea- or Lactam- Substituted Quinoxaline-Type Piperidine Compounds and Certain Other Compounds of Interest

| | | Ki [Average ± Std Deviation] (nM) | | | | CYP2D6 |
|---|---|---|---|---|---|---|
| | | | Opioid Receptor | | | |
| Ref No. | Compound | ORL-1 | Mu | Kappa | Delta | $IC_{50}$ (µM) |
| A9a | | 43.5 ± 4.6 | — | — | — | >20 |
| B5a(i) | | 4.4 ± 0.7 | — | — | — | >20 |
| B5a(ii) | | 3.1 ± 0.5 | 38.2 ± 10.4 | 7.8 ± 1.2 | 8750 ± 1150 | >20 |
| B7a(i) | | 3.0 ± 0.7 | — | — | — | >20 |
| B9a | | 5.4 ± 0.6 | 297 ± 7 | 115 ± 6 | 5820 ± 710 | >20 |
| B10a | | 13.8 ± 2.0 | — | — | — | >20 |
| B13a | | 2.44 ± 0.28 | — | — | — | >20 |
| B15a | | 5.07 ± 0.35 | — | — | — | — |
| B16a | | 6.37 ± 0.69 | — | — | — | >20 |
| B17a | | 2.5 ± 0.5 | — | — | — | >20 |
| B19a | | 4.14 ± 0.70 | — | — | — | >20 |
| B20a | | 0.74 ± 0.10 | — | — | — | >20 |
| B22a | | 7.5 ± 0.2 | 222 ± 48 | 5.0 ± 0.5 | >20,000 | >20 |
| B23a | | 3.6 ± 0.5 | — | — | — | 17.8 |
| B25a | | 1.67 ± 0.24 | — | — | — | — |
| B34a | | 2.26 ± 0.43 | — | — | — | >20 |
| B47a | | 2.0 ± 0.4 | 5.1 ± 0.6 | 0.60 ± 0.09 | 3611 ± 508 | >20 |
| H9c | | 145 ± 25 | — | — | — | >20 |
| N9b | | 4.2 ± 0.7 | 152 ± 34 | 143 ± 16 | 5522 ± 1331 | >20 |
| O9b | | 0.97 ± 0.07 | — | — | — | >20 |
| O10b | | 4.06 ± 0.68 | — | — | — | >20 |
| O13b | | 0.34 ± 0.07 | — | — | — | >20 |
| O19a | | 0.82 ± 0.18 | — | — | — | >20 |
| O22b | | 2.4 ± 0.5 | — | — | — | >20 |
| P9b | | 13.01 ± 1.08 | 10,300 ± 3440 | 13,100 | >20,000 | >20 |
| Q1a(iii) | | 12.8 ± 2.2 | 293 ± 27 | 138 ± 31 | 7040 ± 690 | >20 |
| Q13a(i) | | 17.03 ± 0.18 | 609 ± 92 | 19.3 ± 1.2 | >20,000 | >20 |
| Q13a(iii) | | 34.8 ± 7.8 | — | — | — | >20 |
| Q23a(i) | | 7.2 ± 0.7 | 45.9 ± 5.2 | 13.9 ± 0.2 | 6970 ± 520 | 8.0 |
| R1a(i) | | 6.19 ± 0.56 | 216 ± 70 | 10.9 ± 0.8 | >20,000 | >20 |
| R1a(iii) | | 5.58 ± 0.29 | — | — | — | — |
| R2a(i) | | 1.69 ± 0.13 | 522 ± 120 | 77.9 ± 4.2 | 4351 ± 766 | — |
| R3a(i) | | 3.05 ± 0.23 | 151 ± 30 | 93.4 ± 11.3 | >20,000 | >20 |
| R6(i)(i) | | 0.97 ± 0.27 | — | 51.6 ± 5.0 | — | >20 |
| R6(iii)(i) | | 6.93 ± 0.74 | — | — | — | — |
| R8a(iii) | | 11.0 ± 0.4 | 59.5 ± 12.0 | 63.3 ± 20.2 | 3650 ± 350 | >20 |

TABLE 33-continued

Efficacy of Receptor Binding and CYP2D6 Response of Cyclic Urea- or Lactam- Substituted Quinoxaline-Type Piperidine Compounds and Certain Other Compounds of Interest

| | | Ki [Average ± Std Deviation] (nM) | | | | CYP2D6 |
| | | | Opioid Receptor | | | |
| Ref No. | Compound | ORL-1 | Mu | Kappa | Delta | $IC_{50}$ (μM) |
| --- | --- | --- | --- | --- | --- | --- |
| R11a(iii) | | 2.96 ± 0.27 | 115 ± 13 | 245 ± 54 | 5407 ± 372 | >20 |
| R15a(i) | | 8.01 ± 0.71 | 286 ± 58 | 117 ± 6 | >20,000 | >20 |
| R15a(iii) | | 29.5 ± 1.4 | — | — | — | >20 |
| R16a(i) | | 4.1 ± 1.2 | — | — | — | >20 |
| R17a(i) | | 4.1 ± 0.6 | 100 ± 7 | 11.8 ± 1.0 | 13,360 ± 1690 | — |
| R18a(i) | | 7.7 ± 0.6 | — | — | — | >20 |
| R21a(i)(i) | | 1.47 ± 0.02 | 227 ± 32 | 27.7 ± 3.6 | >20,000 | — |
| R25a(i) | | 1.36 ± 0.03 | 33.0 ± 6.6 | — | — | >20 |
| R28a(i) | | 11.8 ± 1.5 | — | — | — | >20 |
| U39a(iii) | | 4.7 ± 0.5 | — | — | — | 18.9 |
| U55a(i) | | 2.27 ± 0.36 | — | — | — | >20 |
| BB1c(iii) | | 7.1 ± 0.9 | — | — | — | >20 |
| BB13c(i) | | 3.1 ± 0.6 | 231 ± 63 | 7.6 ± 1.4 | 12,780 ± 4500 | >20 |
| BB13c(iii) | | 8.1 ± 0.8 | — | — | — | >20 |
| DD1b(iii) | | 3.54 ± 0.65 | 243 ± 71 | 143 ± 15 | 3100 ± 725 | >20 |
| DD13b(i) | | 1.37 ± 0.16 | — | — | — | >20 |
| EE1b(iii) | | 0.80 ± 0.12 | 87 ± 30 | 23.7 ± 1.0 | 877 ± 92 | >20 |
| EE6b(i)(i) | | 0.15 ± 0.03 | 28.8 ± 3.4 | 22.6 ± 1.9 | 9810 ± 1900 | >20 |
| EE15b(i) | | 0.55 ± 0.04 | — | — | — | >20 |
| FF13b(i) | | 31.2 ± 1.5 | 2460 ± 870 | 549 ± 183 | >20,000 | >20 |
| U001 | | 16.0 ± 1.6 | — | — | — | >20 |
| U005 | | 2.2 ± 0.4 | 146 ± 16 | 46.7 ± 2.8 | >20,000 | >20 |
| U007 | | 9.16 ± 0.22 | — | — | — | >20 |
| U008 | | 5.33 ± 0.95 | 66 ± 13 | 82.4 ± 5.2 | 16,540 ± 3430 | >20 |
| U010 | | 12.2 ± 1.8 | — | — | — | >20 |
| U040 | | 1.52 ± 0.13 | — | — | — | — |
| U043 | | 0.23 ± 0.01 | — | — | — | >20 |
| U044 | | 0.40 ± 0.05 | — | — | — | — |
| U048 | | 1.08 ± 0.05 | — | — | — | >20 |
| U050 | | 1.72 ± 0.08 | 513 ± 72 | 117 ± 28 | 9300 ± 1800 | >20 |
| U052 | | 1.07 ± 0.25 | 14.5 ± 2.3 | 58.3 ± 3.9 | 669 ± 29 | >20 |
| U057 | | 25.0 ± 1.5 | — | — | — | >20 |
| U059 | | 39.9 ± 6.4 | 261 ± 16 | 147.5 ± 7.6 | 523 ± 88 | >20 |
| U060 | | 0.50 ± 0.04 | 6.7 ± 0.4 | 3.47 ± 0.48 | 4650 ± 760 | >20 |
| U061 | | 1.26 ± 0.09 | 9.32 ± 1.56 | 1.4 ± 0.1 | 2510 ± 830 | >20 |
| U063 | | 1.03 ± 0.30 | 16.1 ± 2.0 | 2.9 ± 1.0 | 10,500 ± 1020 | 7.2 |
| U064 | | 1.12 ± 0.28 | 7.35 ± 1.07 | 95.8 ± 16.9 | 15,900 ± 3400 | >20 |
| U065 | | 8.2 ± 1.1 | — | — | — | >20 |
| U066 | | 0.63 ± 0.11 | 51 ± 18 | 9.7 ± 1.8 | >20,000 | >20 |
| U067 | | 0.29 ± 0.01 | 14.4 ± 4.6 | 1.12 ± 0.06 | 17,650 ± 1030 | >20 |
| U068 | | 0.31 ± 0.04 | — | — | — | >20 |
| CC18 | 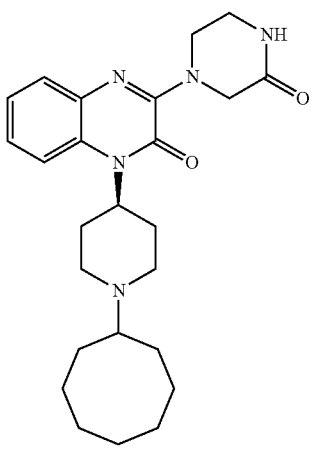 | 182 ± 29 | 2078 ± 57 | 303 ± 9 | 55,229 | <1 |

TABLE 33-continued

Efficacy of Receptor Binding and CYP2D6 Response of Cyclic Urea- or Lactam- Substituted Quinoxaline-Type Piperidine Compounds and Certain Other Compounds of Interest

| | | Ki [Average ± Std Deviation] (nM) | | | | CYP2D6 |
|---|---|---|---|---|---|---|
| | | | Opioid Receptor | | | |
| Ref No. | Compound | ORL-1 | Mu | Kappa | Delta | IC$_{50}$ (μM) |
| CC212 | | 14.6 ± 0.4 | 1140 ± 60 | 25.9 ± 1.8 | >20,000 | — |
| CC201 | | 44.8 ± 1.8 | 1600 ± 260 | 1360 ± 170 | 2740 ± 850 | — |
| CC10 | | 72.1 ± 9.1 | 1480 ± 20 | 73.5 ± 18.2 | 27,675 | <1 |

TABLE 33-continued

Efficacy of Receptor Binding and CYP2D6 Response of Cyclic Urea- or Lactam- Substituted Quinoxaline-Type Piperidine Compounds and Certain Other Compounds of Interest

| | | Ki [Average ± Std Deviation] (nM) | | | | CYP2D6 |
|---|---|---|---|---|---|---|
| | | | Opioid Receptor | | | |
| Ref No. | Compound | ORL-1 | Mu | Kappa | Delta | IC$_{50}$ (µM) |
| CC337 | | 26.5 ± 1.6 | 706 ± 121 | 220.0 ± 121 | 8840 | 13.0 |
| CC22 | | 35.2 ± 2.3 | 3037 ± 579 | 30.4 ± 2.2 | 19,407 | 1.0 |
| CC119 | | 73.2 ± 7.1 | 3330 ± 350 | 381 ± 50 | >10$^5$ | >20 |

TABLE 33-continued
Efficacy of Receptor Binding and CYP2D6 Response of Cyclic Urea- or Lactam- Substituted Quinoxaline-Type Piperidine Compounds and Certain Other Compounds of Interest
| | | Ki [Average ± Std Deviation] (nM) | | | | CYP2D6 |
| | | | Opioid Receptor | | | |
| Ref No. | Compound | ORL-1 | Mu | Kappa | Delta | IC$_{50}$ (µM) |
|---|---|---|---|---|---|---|
| CC39 | 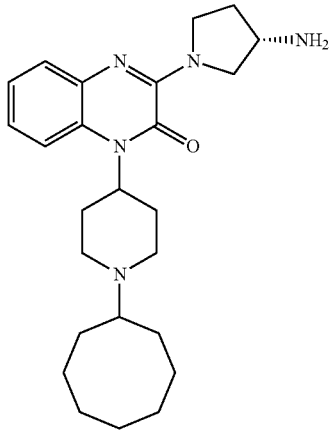 [SMILES: N[C@H]1CCN(c2nc3ccccc3n(C3CCN(C4CCCCCCC4)CC3)c2=O)C1] | 8.6 ± 1.9 | 624 ± 22 | 57.3 ± 7.4 | 52,574 | <1 |
| CC51 | 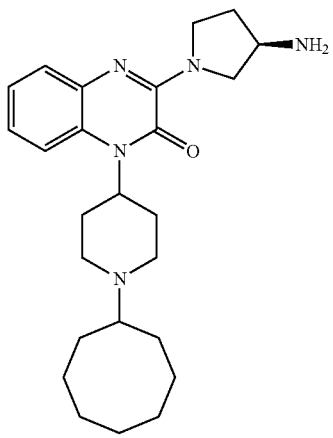 [SMILES: N[C@@H]1CCN(c2nc3ccccc3n(C3CCN(C4CCCCCCC4)CC3)c2=O)C1] | 4.0 ± 0.6 | 512 ± 79 | 22 ± 2.1 | 28,106 | <1 |
| CC101 | 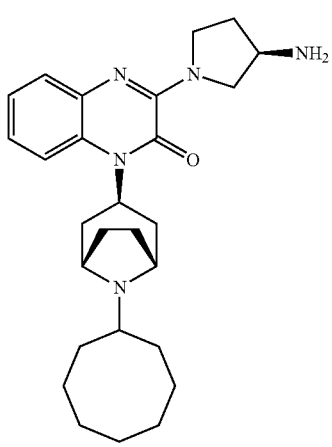 [SMILES: N[C@@H]1CCN(c2nc3ccccc3n([C@H]3C[C@H]4CC[C@@H](C3)N4C3CCCCCCC3)c2=O)C1] | 1.6 ± 0.2 | 590 ± 47 | 14.9 ± 2.0 | 13,970 ± 1.80 | <1 |

TABLE 34

Activity Response of Cyclic Urea- or Lactam-Substituted Quinoxaline-Type Piperidine Compounds GTPγS ($EC_{50}$: nM, Emax: %) [mean ± SEM]

| Ref. No. | ORL-1 $EC_{50}$ | ORL-1 $E_{max}$ | Opioid Receptor $EC_{50}$ Mu | Opioid Receptor $EC_{50}$ Kappa | Opioid Receptor $EC_{50}$ Delta |
|---|---|---|---|---|---|
| A9a | 378 ± 55 | 15.3 ± 1.7 | — | — | — |
| B5a(i) | >20,000 | −0.3 ± 0.7 | — | — | — |
| B5a(ii) | 10.6 ± 0.9 | 36 ± 3 | >20,000 | >20,000 | — |
| B7a(i) | 22.5 ± 5.7 | 18 ± 1 | — | — | — |
| B9a | 5.43 ± 1.69 | 19 ± 2 | >20,000 | >20,000 | — |
| B10a | >20,000 | — | — | — | — |
| B13a | >20,000 | 0.3 ± 0.7 | — | — | — |
| B15a | 42.9 ± 5.1 | 9.7 ± 0.9 | — | — | — |
| B16a | 11.9 ± 2.2 | 14.3 ± 1.7 | — | — | — |
| B17a | >20,000 | — | — | — | — |
| B19a | >20,000 | — | — | — | — |
| B20a | >20,000 | — | — | — | — |
| B22a | 17.9 ± 2.4 | 27.7 ± 1.5 | >20,000 | >20,000 | — |
| B23a | >20,000 | — | — | — | — |
| B25a | 0.55 ± 0.04 | 15.3 ± 1.2 | — | — | — |
| B34a | 3.9 ± 1.4 | 21.3 ± 2.7 | — | — | — |
| B47a | 4.7 ± 0.9 | 36 ± 3 | >20,000 | >20,000 | — |
| H9c | 376 ± 16 | 41 ± 2 | — | — | — |
| N9b | 10.5 ± 3.6 | 27.7 ± 1.2 | >20,000 | >20,000 | — |
| O9b | >20,000 | −1 | — | — | — |
| O10b | 17.1 ± 3.9 | 14.3 ± 2.0 | — | — | — |
| O13b | >20,000 | −1 | — | — | — |
| O19a | >20,000 | — | — | — | — |
| O22b | 8.0 ± 0.9 | 23.3 ± 1.2 | — | — | — |
| P9b | 104 ± 43 | 34.3 ± 4.4 | — | — | — |
| Q1a(iii) | 87 ± 11 | 35.0 ± 1.2 | >20,000 | >20,000 | — |
| Q13a(i) | 35.7 ± 8.3 | 36.5 ± 1.7 | >20,000 | >20,000 | — |
| Q13a(iii) | 255 ± 42 | 41.7 ± 1.8 | — | — | — |
| Q23a(i) | 72.1 ± 6.5 | 57 ± 5 | >20,000 | >20,000 | — |
| R1a(i) | 10.9 ± 2.0 | 30 | >20,000 | >20,000 | — |
| R1a(iii) | 18.7 ± 4.5 | 24.0 ± 4.5 | — | — | — |
| R2a(i) | 2.0 ± 0.5 | 34.7 ± 3.8 | >20,000 | >20,000 | — |
| R3a(i) | 7.5 ± 1.2 | 36.8 ± 2.5 | >20,000 | >20,000 | — |
| R6a(i)(i) | 5.6 ± 0.4 | 23.7 ± 1.2 | — | >20,000 | — |
| R6a(iii)(i) | 47.6 ± 4.2 | 20.3 ± 1.9 | — | — | — |
| R8a(iii) | 29.1 ± 1.3 | 35.3 ± 0.9 | >20,000 | >20,000 | — |
| R11a(iii) | 8.5 ± 1.2 | 37.3 ± 1.7 | >20,000 | >20,000 | — |
| R15a(i) | 15.1 ± 2.4 | 25.3 ± 0.3 | >20,000 | >20,000 | — |
| R15a(iii) | 106 ± 37 | 22 ± 1 | — | — | — |
| R16a(i) | 1612 ± 441 | 29.3 ± 3.5 | — | — | — |
| R17a(i) | 8.5 ± 2.3 | 39.7 ± 2.7 | >20,000 | >20,000 | — |
| R18a(i) | 5.2 ± 1.6 | 23.7 ± 0.7 | — | — | — |
| R21a(i)(i) | 1.52 ± 0.29 | 25.3 ± 1.9 | >20,000 | >20,000 | — |
| R25a(i) | 2.08 ± 0.12 | 87.7 ± 1.9 | — | — | — |
| R28a(i) | 39.7 ± 5.9 | 18.5 ± 3.5 | — | — | — |
| U39a(iii) | 26.7 ± 3.8 | 91 ± 8 | — | — | — |
| U55a(i) | 12.3 ± 0.5 | 82.8 ± 2.7 | — | — | — |
| BB13c(i) | 22.3 ± 6.4 | 110.3 ± 6.6 | >20,000 | >20,000 | — |
| BB13c(iii) | 101 ± 20 | 127.3 ± 1.3 | — | — | — |
| DD1b(iii) | 94.7 ± 12.1 | 31.7 ± 2.7 | 87 ± 14 | >20,000 | — |
| DD13b(i) | 8.0 ± 0.6 | 23.7 ± 0.9 | — | — | — |
| EE1b(iii) | 6.2 ± 0.2 | 31.3 ± 2.3 | >20,000 | >20,000 | 863 ± 83 |
| EE6b(i)(i) | 1.03 ± 0.07 | 33 ± 1 | 12.5 ± 0.6 | >20,000 | — |
| EE15b(i) | 2.96 ± 0.26 | 21.7 ± 2.3 | — | — | — |
| FF13b(i) | 86.1 ± 11.7 | 54.3 ± 1.9 | — | >20,000 | — |
| U001 | >20,000 | — | — | — | — |
| U005 | 3.38 ± 0.64 | 31.3 ± 3.9 | >20,000 | >20,000 | — |
| U007 | 32 ± 10 | 19 ± 2 | — | — | — |
| U008 | 9.9 ± 0.7 | 28.7 ± 0.3 | >20,000 | >20,000 | — |
| U010 | 18.0 ± 5.3 | 16.6 ± 1.4 | — | — | — |
| U040 | 1.08 ± 0.13 | 18.0 ± 1.1 | — | — | — |
| U043 | 0.94 ± 0.14 | 22.3 ± 1.2 | — | — | — |
| U044 | 3.0 ± 0.7 | 23.7 ± 1.2 | — | — | — |
| U048 | >20,000 | — | — | — | — |
| U050 | 1.34 ± 0.39 | 28.0 ± 0.6 | >20,000 | >20,000 | — |
| U052 | 2.54 ± 0.52 | 28.3 ± 3.7 | >20,000 | >20,000 | >20,000 |
| U057 | >20,000 | — | — | — | — |
| U059 | 45.9 ± 6.8 | 25.3 ± 2.7 | >20,000 | >20,000 | 486 ± 41 |
| U060 | 0.48 ± 0.07 | 65.3 ± 3.6 | >20,000 | >20,000 | — |
| U061 | 1.05 ± 0.14 | 62.3 ± 1.8 | 2600 ± 600 | 4640 ± 1030 | — |

TABLE 34-continued

Activity Response of Cyclic Urea- or Lactam-Substituted Quinoxaline-Type Piperidine Compounds GTPγS (EC$_{50}$: nM, Emax: %) [mean ± SEM]

| | ORL-1 | | Opioid Receptor EC$_{50}$ | | |
|---|---|---|---|---|---|
| Ref. No. | EC$_{50}$ | E$_{max}$ | Mu | Kappa | Delta |
| U063 | 3.12 ± 0.74 | 50.7 ± 6.2 | 3630 ± 791 | 6980 ± 2510 | — |
| U064 | 1.97 ± 0.40 | 38.7 ± 4.3 | >20,000 | >20,000 | — |
| U066 | 5.47 ± 0.83 | 39.7 ± 2.2 | 95.2 ± 28.9 | >20,000 | — |
| U067 | 2.45 ± 0.33 | 28.5 ± 0.9 | >20,000 | >20,000 | — |
| U068 | >20,000 | −1 | — | — | — |
| CC18 | 1284 ± 84 | 69.0 ± 2.7 | — | 5125 ± 716 | — |
| CC212 | 195 ± 13 | 78.7 ± 3 | — | 382 ± 97 | — |
| CC201 | 1299 ± 240 | 84 ± 1.2 | — | — | — |
| CC10 | 553 ± 59 | 34 ± 1.5 | — | 2227 ± 565 | — |
| CC337 | 438 ± 15 | 78 | 7120 ± 380 | >20,000 | — |
| CC22 | 440 ± 39 | 64 ± 3.6 | — | 690 ± 86 | — |
| CC119 | 3663 ± 171 | 62.0 ± 1.5 | — | 5997 ± 517 | — |
| CC39 | 88 ± 30 | 78 ± 10 | — | 285 ± 54 | — |
| CC51 | 49.1 ± 8.2 | 107 ± 3.1 | 6125 ± 419 | 276 ± 42 | — |
| CC101 | 17.0 ± 4.2 | 105.7 ± 5.0 | 4900 ± 2050 | 32,770 | — |

5.47 Example 47

In Vivo Assays for Prevention or Treatment of Pain

Test Animals: Each experiment uses rats weighing between 200-260 g at the start of the experiment. The rats are group-housed and have free access to food and water at all times, except prior to oral administration of a Cyclic Urea- or Lactam-Substituted Quinoxaline-Type Piperidine Compound when food is removed for 16 hours before dosing. A control group acts as a comparison to rats treated with a Cyclic Urea- or Lactam-Substituted Quinoxaline-Type Piperidine Compound. The control group is administered the carrier for the Cyclic Urea- or Lactam-Substituted Quinoxaline-Type Piperidine Compound. The volume of carrier administered to the control group is the same as the volume of carrier and Cyclic Urea- or Lactam-Substituted Quinoxaline-Type Piperidine Compound administered to the test group.

Acute Pain: To assess the actions of a Cyclic Urea- or Lactam-Substituted Quinoxaline-Type Piperidine Compound for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Cyclic Urea- or Lactam-Substituted Quinoxaline-Type Piperidine Compound. Data are expressed as tail flick latency(s) and the percentage of the maximal possible effect (% MPE), i.e., 20 seconds, is calculated as follows:

$$\% \, MPE = \frac{[(\text{post administration latency}) - (\text{pre-administration latency})]}{(20 \, \text{s pre-administration latency})} \times 100$$

The rat tail flick test is described in D'Amour et al., "A Method for Determining Loss of Pain Sensation," *J. Pharmacol. Exp. Ther.* 72:74-79 (1941).

Inflammatory Pain: To assess the actions of a Cyclic Urea- or Lactam-Substituted Quinoxaline-Type Piperidine Compound for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990)). The left hind paw of each animal is administered a 50 μL intraplantar injection of 50% FCA. 24 hour post injection, the animal is assessed for response to noxious mechanical stimuli by determining the PWT, as described below. Rats are then administered a single injection of 1, 3, 10 or 30 mg/kg of either a Cyclic Urea- or Lactam-Substituted Quinoxaline-Type Piperidine Compound; 30 mg/kg of a control selected from Celebrex, indomethacin, and naproxen; or carrier. Responses to noxious mechanical stimuli are then determined 1, 3, 5 and 24 hours post administration. Percentage reversal of hyperalgesia for each animal is defined as:

$$\% \, \text{Reversal} = \frac{[(\text{post administration } PWT) - (\text{pre-administration } PWT)]}{[(\text{baseline } PWT) - (\text{pre-administration } PWT)]} \times 100$$

Neuropathic Pain: To assess the actions of a Cyclic Urea- or Lactam-Substituted Quinoxaline-Type Piperidine Compound for the treatment or prevention of neuropathic pain, either the Seltzer model or the Chung model can be used.

In the Seltzer model, the partial sciatic nerve ligation model of neuropathic pain was used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve was performed under isoflurane/$O_2$ inhalation anaesthesia. Following induction of anesthesia, the left thigh of the male, 6-7 week old Jcl:SD rat was shaved. The sciatic nerve was exposed at high thigh level through a small incision and was carefully cleared of surrounding connective tissues at a site near the trocanther just distal to the point at which the posterior biceps semitendinosus nerve branches off of the common sciatic nerve. A 7-0 silk suture was inserted into the nerve with a ⅜ curved, reversed-cutting mini-needle and tightly ligated so that the dorsal ⅓ to ½ of the nerve thickness was held within the ligature. The wound was closed with a single muscle suture (4-0 nylon (Vicryl)) and vetbond tissue glue. The wound area was then dusted with antibiotic powder. Sham treatment involved an identical surgical procedure except that the sciatic nerve was not manipulated or ligated.

Following surgery, animals were weighed and placed on a warm pad until they recovered from anesthesia. Animals were then returned to their home cages until behavioral testing began. The animal was assessed for response to noxious mechanical stimuli by determining PWT for the rear paw of the animal, as described below, prior to surgery (baseline), then immediately prior to and 1, 3, and 5 hours after oral drug-in-vehicle administration (for day 1). Thus, the 24 hour time point was the start of the next day when drug-in-vehicle was again orally administered (24 hours after the prior administration). On days 4 and 7, PWT response was determined 1, 3, and 5 hours thereafter. Percentage reversal of neuropathic hyperalgesia at each of the specified times after administration was defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Additionally, 10 mg/kg of pregabalin (Kemprotec, Ltd., Middlesbrough, UK), an anticonvulsant accepted for relief of particular neuropathic pain, in vehicle and the vehicle alone (0.5% weight/volume methylcellulose (400cP, Wako Pure Chemical Industries, Ltd.)/aqueous solution) were orally administered as controls. Eight rats that underwent partial ligation of the left sciatic nerve were used for each treatment group except for pregabalin, where six rats were treated. Dunnett's test was conducted for the % reversal; values with $p<0.05$ were considered to be statistically significant. The results for administration of Cyclic Urea- or Lactam-Substituted Quinoxaline-Type Piperidine Compound B9a are provided in Table 35.

TABLE 35

Neuropathic Pain Relief after Administration of a Cyclic Urea- or Lactam-Substituted Quinoxaline-Type Piperidine Compound

| Time after Administration (hours) | % Reversal [mean] | | | | |
|---|---|---|---|---|---|
| | Cyclic Urea- or Lactam-Substituted Quinoxaline-Type Piperidine Compound B9a | | | Pregabalin | Vehicle |
| | 1 mg/kg | 3 mg/kg | 10 mg/kg | 10 mg/kg | 2 mL/kg |
| Pre-administration | 0 | 0 | 0 | 0 | 0 |
| 1 (day 1) | 27.0* | 33.1** | 49.2** | 17.0 | 0.4 |
| 3 (day 1) | 37.0** | 46.2** | 61.5** | 28.0** | 0.5 |
| 5 (day 1) | 27.0* | 34.6** | 46.9** | 15.0 | 2.3 |

TABLE 35-continued

Neuropathic Pain Relief after Administration of a Cyclic Urea- or Lactam-Substituted Quinoxaline-Type Piperidine Compound

| Time after Administration (hours) | % Reversal [mean] | | | | |
|---|---|---|---|---|---|
| | Cyclic Urea- or Lactam-Substituted Quinoxaline-Type Piperidine Compound B9a | | | Pregabalin | Vehicle |
| | 1 mg/kg | 3 mg/kg | 10 mg/kg | 10 mg/kg | 2 mL/kg |
| 1 (day 4) | | 40.8** | 53.8** | | 1.9 |
| 3 (day 4) | | 46.2** | 64.2** | | −1.9 |
| 5 (day 4) | | 36.9** | 47.7** | | 1.5 |
| 1 (day 7) | | 47.7** | 50.0** | | −1.9 |
| 3 (day 7) | | 55.2** | 63.5** | | 2.3 |
| 5 (day 7) | | 42.2** | 42.2** | | 0 |

*indicates p < 0.05 (Dunnett's test),
**indicates p < 0.01 (Dunnett's test).

Additionally, as a control the rats underwent sham surgery in which an identical surgical procedure was followed with regard to the right thigh but the sciatic nerve was neither manipulated nor ligated.

As demonstrated by the results in Table 35, administration of 1, 3, or 10 mg/kg of Cyclic Urea- or Lactam-Substituted Quinoxaline-Type Piperidine Compound B9a provided more effective reversal than the pregabalin control at all the measured time-points on the first day of administration. As also demonstrated by the results in Table 35, once daily administration of Cyclic Urea- or Lactam-Substituted Quinoxaline-Type Piperidine Compound B9a (3 or 10 mg/kg) for seven days showed statistically significant effects against mechanical hyperalgesia in rats subjected to partial sciatic nerve ligation in the Seltzer model of neuropathic pain. Thus, Compounds of Formula (I) are effective in relieving neuropathic pain in vivo.

In particular, a single administration of Cyclic Urea- or Lactam-Substituted Quinoxaline-Type Piperidine Compound B9a demonstrated analgesic effects in the Selzer model. Following dosing at 10 mg/kg, Cyclic Urea- or Lactam-Substituted Quinoxaline-Type Piperidine Compound B9a evidenced significant analgesic effects at 1, 3, and 5 hours post-administration. The maximum analgesic efficacy observed with Cyclic Urea- or Lactam-Substituted Quinoxaline-Type Piperidine Compound B9a was 61.5% reversal achieved 3 hours after administration. Similarly, following dosing at 1 and 3 mg/kg, Cyclic Urea- or Lactam-Substituted Quinoxaline-Type Piperidine Compound B9a evidenced significant analgesic effects at 1, 3, and 5 hours after administration. The maximum analgesic efficacy at 1 and 3 mg/kg of Cyclic Urea- or Lactam-Substituted Quinoxaline-Type Piperidine Compound B9a was 37.0% and 46.2% reversal, respectively, also at 3 hours after administration. These results demonstrate that a dose-dependent significant analgesic effect was achieved.

The results of repeated administration for 7 days of Cyclic Urea- or Lactam-Substituted Quinoxaline-Type Piperidine Compound B9a also demonstrate a dose-dependent significant analgesic effect. On day 4 of dosing, Cyclic Urea- or Lactam-Substituted Quinoxaline-Type Piperidine Compound B9a demonstrated a dose-dependent significant analgesic effect at 1, 3, and 5 hours after administration. The maximum analgesic efficacy following dosing at 3 and 10 mg/kg of Cyclic Urea- or Lactam-Substituted Quinoxaline-Type Piperidine Compound B9a was 46.2% and 64.2% reversal, respectively, each at the 3 hour time point. On day 7 of dosing, 3 and 10 mg/kg of Cyclic Urea- or Lactam-Substituted Quinoxaline-Type Piperidine Compound B9a demonstrated dose-dependent significant analgesic effects with maxima of 55.2% reversal at 3 mg/kg and 63.5% reversal at 10 mg/kg, each at the 3 hour time point.

Moreover, these results demonstrate that there is, desirably, a lack of tolerance development with repeated administration. For example, dosing at 3 mg/kg of Cyclic Urea- or Lactam-Substituted Quinoxaline-Type Piperidine Compound B9a evidenced roughly comparable maximum analgesic efficacy 3 hours after each administration, 46.2%, 46.2%, and 55.2% reversal, respectively, after day 1, 4, and 7 administration.

Oral single dosing of pregabalin, the positive control, also produced an analgesic effect in the Selzer model. Following dosing at 10 mg/kg, pregabalin showed a significant analgesic effect at 3 hours post-administration. However, the maximum analgesic efficacy observed with pregabalin, 28.0% reversal 3 hours after day 1 administration of the 10 mg/kg dose, was less than half (about 0.46) of the 61.5% reversal achieved 3 hours after day 1 administration of the 10 mg/kg dose of Cyclic Urea- or Lactam-Substituted Quinoxaline-Type Piperidine Compound B9a. Moreover, the maximum analgesic efficacy observed with the 10 mg/kg dose of pregabalin (28.0% reversal) was less than two thirds (about 0.61) of the 46.2% reversal achieved 3 hours after day 1 administration of the 3 mg/kg dose, just three tenths of the pregabalin dose, of the of Cyclic Urea- or Lactam-Substituted Quinoxaline-Type Piperidine Compound B9a and only about three quarters (about 0.76) of the 37.0% reversal achieved 3 hours after day 1 administration of the 1 mg/kg dose, just one tenth of the pregabalin dose, of the of Cyclic Urea- or Lactam-Substituted Quinoxaline-Type Piperidine Compound B9a.

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Cyclic Urea- or Lactam-Substituted Quinoxaline-Type Piperidine Compound for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay was used to assess mechanical hyperalgesia. For this assay, hind paw withdrawal thresholds (PWT) to a noxious mechanical stimulus were determined using an analgesymeter (Model 37215, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," *Pharmacol. Biochem. Behavior* 31:451-455 (1988). The maximum weight that could be applied to the hind paw was set at 250 g and the end point was taken as complete withdrawal of the paw. PWT was determined once for each rat at each time point and either only the affected (ipsilateral) paw was tested, or both the ipsilateral and contralateral (non-injured) paw were tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed:

1. A compound of Formula (I):

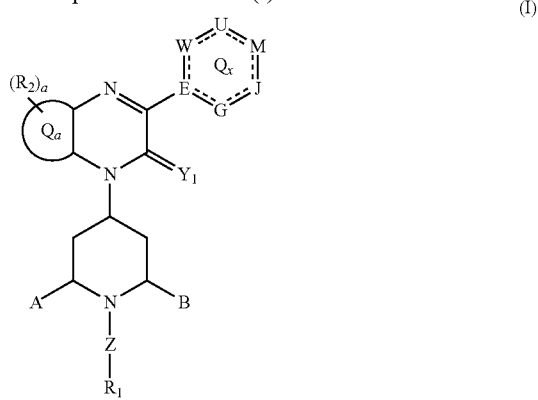

(I)

or a pharmaceutically acceptable salt thereof wherein:
$Y_1$ is O or S;
$Q_a$ is benzo;

each $R_2$ is independently selected from:
- (a) -halo, —CN, —NO$_2$, —OT$_3$, —C(=O)T$_3$, —C(=O)OT$_3$, —C(=O)N(T$_1$)(T$_2$), —S(=O)$_2$OT$_3$, —S(=O)T$_3$, —S(=O)$_2$T$_3$, —O—S(=O)$_2$T$_3$, —S(=O)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(=O)T$_3$, —N(T$_3$)S(=O)$_2$T$_3$, —N(T$_3$)C(=O)OT$_3$, and —N(T$_3$)S(=O)$_2$N(T$_1$)(T$_2$); and
- (b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, -(5- or 6-membered)heterocyclyl, and -(7- to 10-membered)bicycloheterocyclyl, each of which is unsubstituted or substituted with 1, 2, or 3 independently selected $R_8$ groups; and
- (c) -phenyl, -naphthalenyl, —(C$_{14}$)aryl, or -(5- or 6-membered)heteroaryl, each of which is unsubstituted or substituted with 1, 2, or 3 independently selected $R_7$ groups;

a is an integer selected from 0, 1, and 2;

E is N or C($R_{90}$);

G, M, and U are independently selected from N($R_{90}$), C(=O), C(=S), and C($R_{90}$)($R_{91}$);

J is N($R_{90}$), C(=O), or C(=S);

W is N($R_{90}$), C($R_{90}$)($R_{91}$), or absent;

each dashed line of the $Q_x$ ring independently is either present and denotes the presence of one bond of a double bond or is absent, provided that when one dashed line attached to an atom is present to form a double bond, then the other dashed line attached to said atom is absent and the $R_{90}$ group attached to said atom is absent, wherein the maximum number of double bonds is 3 for a 6-membered $Q_x$ ring and the maximum number of double bonds is 2 for a 5-membered $Q_x$ ring;

each $R_{90}$, when present, and each $R_{91}$ is independently selected from —H, —CN, -halo, —(C$_1$-C$_3$)alkyl, —N($R_{92}$)($R_{93}$), —(CH$_2$)$_c$—(C($R_{94}$)($R_{95}$))$_d$—C(=O)$R_{92}$, —(CH$_2$)$_c$—(C($R_{94}$)($R_{95}$))$_d$—C(=O)OR$_{92}$, —(CH$_2$)$_c$—(C($R_{94}$)($R_{95}$))$_d$—N($R_{92}$)—C(=O)$R_{92}$, and —(CH$_2$)$_c$—(C($R_{94}$)($R_{95}$))$_d$—C(=O)N($R_{92}$)($R_{93}$);

each $R_{92}$, $R_{93}$, $R_{94}$, and $R_{95}$ is independently selected from —H and —(C$_1$-C$_3$)alkyl;

each c is independently an integer selected from 0, 1, 2, and 3;

each d is independently an integer selected from 0, 1, and 2;

provided that the ring atoms of the $Q_x$ ring are constituents of at least one lactam group or cyclic urea group, G is C(=O) or C(=S) when E is N, at least two of the ring atoms of the $Q_x$ ring are carbon, 1, 2, or 3 of the ring atoms of the $Q_x$ ring are nitrogen, and the $Q_x$ ring is not:

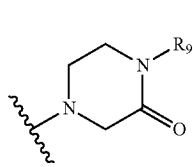 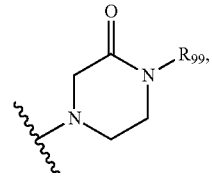

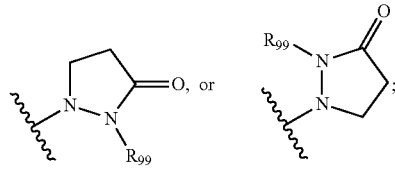

$R_{99}$ is —H, —(C$_1$-C$_3$)alkyl, —(CH$_2$)$_j$—C(=O)OH, or —(CH$_2$)$_j$—C(=O)O—(C$_1$-C$_3$)alkyl;

j is an integer selected from 0, 1, 2, and 3;

A and B are independently selected from:
- (a) —H, —CN, —C(=O)OT$_3$, and —C(=O)N(T$_1$)(T$_2$); and
- (b) —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl, and —(C$_1$-C$_6$)alkoxy, each of which is unsubstituted or substituted with 1 or 2 substituents independently selected from —OH, —S(=O)$_2$NH$_2$, —N($R_6$)$_2$, =NR$_6$, —C(=O)OT$_3$, —C(=O)N($R_6$)$_2$, —N($R_6$)C(=O)$R_9$, and -(5- or 6-membered)heterocyclyl, or 1, 2, or 3 independently selected -halo; or
- (c) A-B can together form a (C$_2$-C$_6$)bridge, which is unsubstituted or substituted with 1, 2, 3, 4, 5, 6, 7 or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the A-B bridge can be in the endo- or exo- configuration with respect to the 6-membered, nitrogen-containing ring that is fused to the $Q_a$ ring; or
- (d) A-B can together form a —CH$_2$—N($R_a$)—CH$_2$— bridge, a

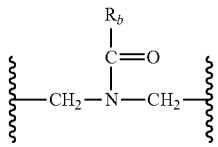

bridge, or a

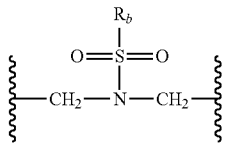

bridge;

wherein the A-B bridge can be in the endo- or exo- configuration with respect to the 6-membered, nitrogen-containing ring that is fused to the $Q_a$ ring;

$R_a$ is —H, —(C$_1$-C$_6$)alkyl, —(C$_3$-C$_7$)cycloalkyl, —CH$_2$—C(=O)—R$_c$, —(CH$_2$)—C(=O)—OR$_c$, —(CH$_2$)—C(=O)—N(R$_c$)$_2$, —(CH$_2$)$_2$—O—R$_c$, —(CH$_2$)$_2$—S(=O)$_2$—N(R$_c$)$_2$, R$_c$, or —(CH$_2$)$_2$—N(R$_c$)S(=O)$_2$—R$_c$;

$R_b$ is selected from:
- (a) —H, —(C$_1$-C$_6$)alkyl, —(C$_3$-C$_7$)cycloalkyl, -(3- to 7-membered)heterocyclyl, —N(R$_c$)$_2$, —N(R$_c$)—(C$_3$-C$_7$)cycloalkyl, and —N(R$_c$)-(3- to 7-membered)heterocyclyl; and (b) -phenyl, -naphthalenyl, and -(5- or 6-membered) heteroaryl, each of which is unsubstituted or substituted with 1, 2, or 3 independently selected $R_7$ groups; and (c) —N($R_c$)-phenyl, —N($R_c$)-naphthalenyl, —N($R_c$)—($C_{14}$)aryl, and —N($R_c$)-(5- to 10-membered)heteroaryl, each of which is unsubstituted or substituted with 1, 2, or 3 independently selected $R_7$ groups;

each $R_c$ is independently —H or —($C_1$-$C_4$)alkyl;

Z is —[($C_1$-$C_{10}$)alkyl optionally substituted by $R_{13}$]$_h$—, wherein h is 0 or 1; or —[($C_2$-$C_{10}$)alkenyl optionally substituted by $R_{13}$]—; or —($C_1$-$C_{10}$)alkyl-N($R_6$)C(=Y)—, wherein Y is O or S;

$R_1$ is selected from:
(a) —H, -halo, —CN, —OH, —CH$_2$OH, —CH$_2$CH$_2$OH, —NO$_2$, —N($R_6$)$_2$, —S(=O)NH$_2$, —S(=O)$_2$NH$_2$, —C(=O)OV$_1$, and —C(=O)CN; and
(b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_3$-$C_{14}$)cycloalkyl, —($C_6$-$C_{14}$)bicycloalkyl, —($C_8$-$C_{20}$)tricycloalkyl, —($C_5$-$C_{14}$)cycloalkenyl, —($C_7$-$C_{14}$)bicycloalkenyl, —($C_8$-$C_{20}$)tricycloalkenyl, and -(3- to 7-membered)heterocyclyl, each of which is unsubstituted or substituted with 1, 2, 3, or 4 independently selected $R_8$ groups; and (c)

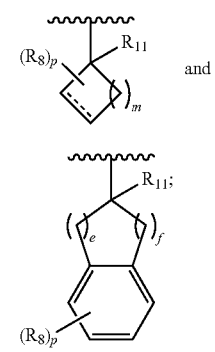

and (d) -phenyl, -naphthalenyl, —($C_{14}$)aryl, and -(5- to 10-membered)heteroaryl, each of which is unsubstituted or substituted with 1, 2, or 3 independently selected $R_7$ groups; or —Z—$R_1$ is 3,3-diphenylpropyl- optionally substituted at the 3 carbon of the propyl with —CN, —C(=O)N($R_6$)$_2$, —C(=O)OV$_1$, or -tetrazolyl; or —Z—$R_1$ is —($C_1$-$C_4$)alkyl substituted with tetrazolyl;

each $R_5$ is independently —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N($R_9$), —N($R_9$)($C_1$-$C_6$)alkyl-C(=O)OR$_9$, —N($R_9$)$_2$, —N($R_9$)OH, —N($R_9$)S(=O)R$_{12}$, —N($R_9$)S(=O)$_2$R$_{12}$, —N($R_9$)C(=O)R$_{12}$, —N($R_9$)C(=O)OR$_{12}$, —C(=O)R$_9$, —C(=O)OR$_9$, —OC(=O)R$_9$, —OC(=O)OR$_9$, —S(=O)R$_9$, or —S(=O)$_2$R$_9$;

each $R_6$ is independently —H, —($C_1$-$C_6$)alkyl, or —($C_3$-$C_7$)cycloalkyl, or two $R_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N(T$_3$);

each $R_7$ is independently —($C_1$-$C_4$)alkyl, —($C_2$-$C_6$)alkenyl, —($C_2$-$C_6$)alkynyl, —OR$_9$, —SR$_9$, —C(halo)$_3$, —CH(halo)$_2$, —CH$_2$(halo), —CN, -halo, —N$_3$, —NO$_2$, —CH=N($R_9$), —N($R_9$)$_2$, —N($R_9$)OH, —N($R_9$)S(=O)R$_{12}$, —N($R_9$)S(=O)$_2$R$_{12}$, —N($R_9$)C(=O)R$_{12}$, —N($R_9$)C(=O)N(T$_1$)(T$_2$), —N($R_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(=O)R$_9$, or —S(=O)$_2$R$_9$;

each $R_8$ is independently —($C_1$-$C_4$)alkyl, —($C_2$-$C_6$)alkenyl, —($C_2$-$C_6$)alkynyl, -(5- or 6-membered)heteroaryl, —($C_1$-$C_6$)alkyl-C(=O)OR$_9$, —N($R_9$)($C_1$-$C_6$)alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N($R_9$), —N($R_9$)$_2$, —N($R_9$)OH, —N($R_9$)S(=O)R$_{12}$, —N($R_9$)S(=O)$_2$R$_{12}$, —N($R_9$)C(=O)R$_{12}$, —N($R_9$)C(=O)N(T$_1$)(T$_2$), —N($R_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(=O)R$_9$, or —S(=O)$_2$R$_9$;

each $R_9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 7-membered)heterocyclyl, —C(halo)$_3$, —CH(halo)$_2$, or —CH$_2$(halo);

if h is 0, then $R_{11}$ can be —H, —CN, —C(=O)OR$_9$, or —C(=O)N($R_6$)$_2$ or $R_{11}$ can be —($C_1$-$C_4$)alkyl which is unsubstituted or substituted with —OH, —($C_1$-$C_4$)alkoxy, —N($R_6$)$_2$, —C(=O)OR$_9$, or —C(=O)N($R_6$)$_2$;

if h is 1, then $R_{11}$ can be —H, —CN, —OH, -halo, —C(=O)OR$_9$, or —C(=O)N($R_6$)$_2$ or $R_{11}$ can be —($C_1$-$C_4$)alkyl which is unsubstituted or substituted with —OH, —($C_1$-$C_4$)alkoxy, —N($R_6$)$_2$, —C(=O)OR$_9$, or —C(=O)N($R_6$)$_2$;

otherwise, wherein Z is —[($C_2$-$C_{10}$)alkenyl optionally substituted by $R_{13}$]- or —($C_1$-$C_{10}$)alkyl-N($R_6$)C(=Y)—, then $R_{11}$ can be —H, —CN, —C(=O)OR$_9$, or —C(=O)N($R_6$)$_2$ or $R_{11}$ can be —($C_1$-$C_4$)alkyl which is unsubstituted or substituted with —OH, —($C_1$-$C_4$)alkoxy, —N($R_6$)$_2$, —C(=O)OR$_9$, or —C(=O)N($R_6$)$_2$;

each $R_{12}$ is independently —H or —($C_1$-$C_4$)alkyl;

$R_{13}$ is selected from:
(a) -halo, —CN, —OH, —CH$_2$OH, —CH$_2$CH$_2$OH, —NO$_2$, —N($R_6$)$_2$, —S(=O)NH$_2$, —S(=O)$_2$NH$_2$, —C(=O)OV$_1$, and —C(=O)CN; and
(b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_5$-$C_{14}$)cycloalkenyl, and -(3- to 7-membered) heterocyclyl, each of which is unsubstituted or substituted with 1, 2, 3, or 4 independently selected $R_8$ groups; and (c)

and (d) -phenyl and -(5- to 10-membered)heteroaryl, each of which is unsubstituted or substituted with 1, 2, or 3 independently selected $R_7$ groups;

$R_{14}$ is —H, —CN, —OH, -halo, —C(=O)OR$_9$, or —C(=O)N(R$_6$)$_2$ or $R_{14}$ can be —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

m is an integer selected from 0, 1, 2, 3, 4, 5, 6, 7, 8, 9, 10, and 11;

n is an integer selected from 0, 1, 2, 3, 4, 5, 6, 7, 8, and 9;

e and f are each an integer independently selected from 0, 1, 2, 3, 4, and 5 provided that 2≤(e+f)≤5;

each p is an integer independently selected from 0, 1, 2, 3, and 4;

each $T_1$ and $T_2$ is independently —H or —(C$_1$-C$_{10}$)alkyl which is unsubstituted or substituted with 1, 2, or 3 independently selected $R_5$ groups and, optionally, in which any —(C$_1$-C$_{10}$)alkyl carbon atom except the carbon atom bonded directly to the atom to which $T_1$ or $T_2$ is attached is independently replaced by O, S, or N(R$_6$), or $T_1$ and $T_2$ can together form a 5- to 8-membered ring wherein the number of atoms in the ring includes the nitrogen atom to which $T_1$ and $T_2$ are bonded, said 5- to 8-membered ring is unsubstituted or substituted with 1, 2, or 3 independently selected $R_5$ groups and, optionally, any carbon atom in said 5- to 8-membered ring is independently replaced by O, S, or N(R$_6$);

each $T_3$ is independently —H or —(C$_1$-C$_{10}$)alkyl which is unsubstituted or substituted with 1, 2, or 3 independently selected $R_5$ groups and, optionally, in which any —(C$_1$-C$_{10}$)alkyl carbon atom except the carbon atom bonded directly to the atom to which $T_3$ is attached is independently replaced by O, S, or N(R$_{12}$);

each $V_1$ is independently —H, —(C$_1$-C$_6$)alkyl, —(C$_3$-C$_7$)cycloalkyl, -phenyl, or benzyl; and each halo is independently —F, —Cl, —Br, or —I.

2. The compound of claim 1 or a pharmaceutically acceptable salt thereof, wherein $Y_1$ is O.

3. The compound of claim 2 or a pharmaceutically acceptable salt thereof, wherein $R_1$ is selected from:

(a) -halo, —CN, —OH, —CH$_2$OH, —CH$_2$CH$_2$OH, —NO$_2$, —N(R$_6$)$_2$, —S(=O)NH$_2$, —S(=O)$_2$NH$_2$, —C(=O)OV$_1$, and —C(=O)CN; and (b) —(C$_1$-C$_{10}$)alkyl, —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$)tricycloalkenyl, and -(3- to 7-membered)heterocyclyl, each of which is unsubstituted or substituted with 1, 2, 3, or 4 independently selected $R_8$ groups; and (c) -phenyl, -naphthalenyl, —(C$_{14}$)aryl, and -(5- to 10-membered)heteroaryl, each of which is unsubstituted or substituted with 1, 2, or 3 independently selected $R_7$ groups.

4. The compound of claim 3 or a pharmaceutically acceptable salt thereof, wherein A and B are independently —H or —(C$_1$-C$_6$)alkyl.

5. The compound of claim 3 or a pharmaceutically acceptable salt thereof, wherein a is 1 and $R_2$ is -halo.

6. The compound of claim 3 or a pharmaceutically acceptable salt thereof, wherein a is 0.

7. The compound of claim 6 or a pharmaceutically acceptable salt thereof, wherein:

A-B together form a (C$_2$-C$_6$)bridge, which is unsubstituted or substituted with 1, 2, 3, 4, 5, 6, 7 or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the A-B bridge can be in the endo- or exo-configuration with respect to the 6-membered, nitrogen-containing ring that is fused to the Q$_a$ ring;

Z is —[(C$_1$-C$_{10}$)alkyl]$_h$—, wherein h is 0 or 1; and $R_1$ is selected from:

(a) —CN, —OH, —CH$_2$OH, —CH$_2$CH$_2$OH, —NO$_2$, —N(R$_6$)$_2$, —S(=O)NH$_2$, —S(=O)$_2$NH$_2$, —C(=O)OV$_1$, and —C(=O)CN; and (b) —(C$_1$-C$_{10}$)alkyl, —O(C$_1$-C$_6$)alkyl, —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{14}$)cycloalkenyl, —(C$_7$-C$_{14}$)bicycloalkenyl, —(C$_8$-C$_{20}$) tricycloalkenyl, and -(3- to 7-membered) heterocyclyl, each of which is unsubstituted or substituted with 1, 2, 3, or 4 independently selected $R_8$ groups; and (c)

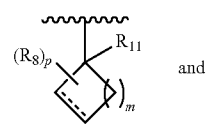

(i)

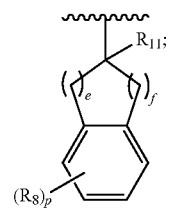

(ii)

and (d) -phenyl and -(5- to 10-membered)heteroaryl, each of which is unsubstituted or substituted with 1, 2, or 3 independently selected $R_7$ groups.

8. The compound of claim 7 or a pharmaceutically acceptable salt thereof, wherein --E---G---J-- of the Q$_x$ ring is —N—C(=O)—N(R$_{90}$)— or —N—C(=O)—N=.

9. The compound of claim 8 or a pharmaceutically acceptable salt thereof, wherein the Q$_x$ ring is:

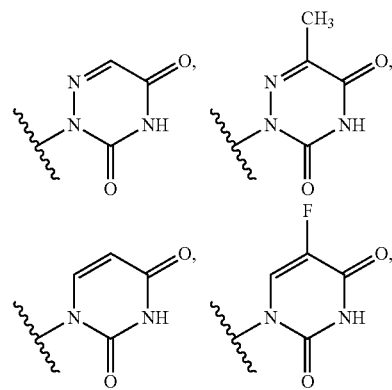

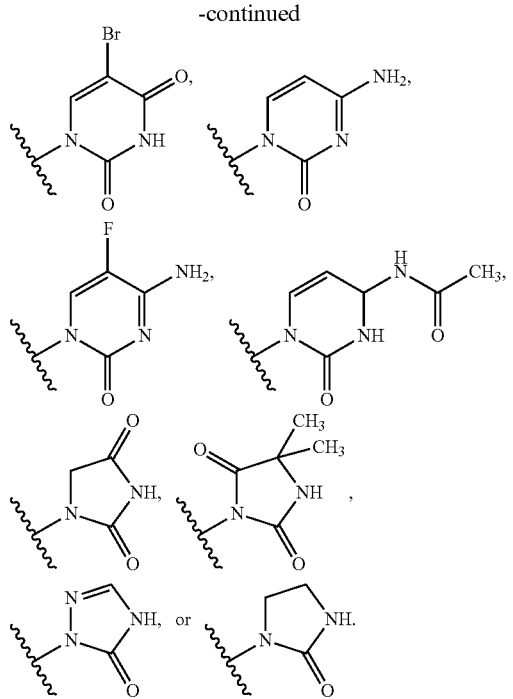
10. The compound of claim 9 or a pharmaceutically acceptable salt thereof, wherein the $Q_x$ ring is:
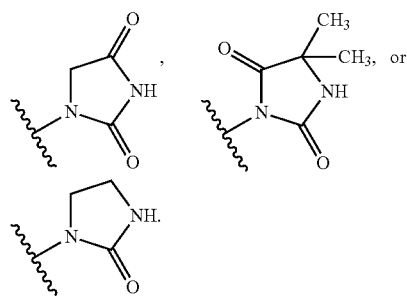
11. The compound of claim 9, which is:
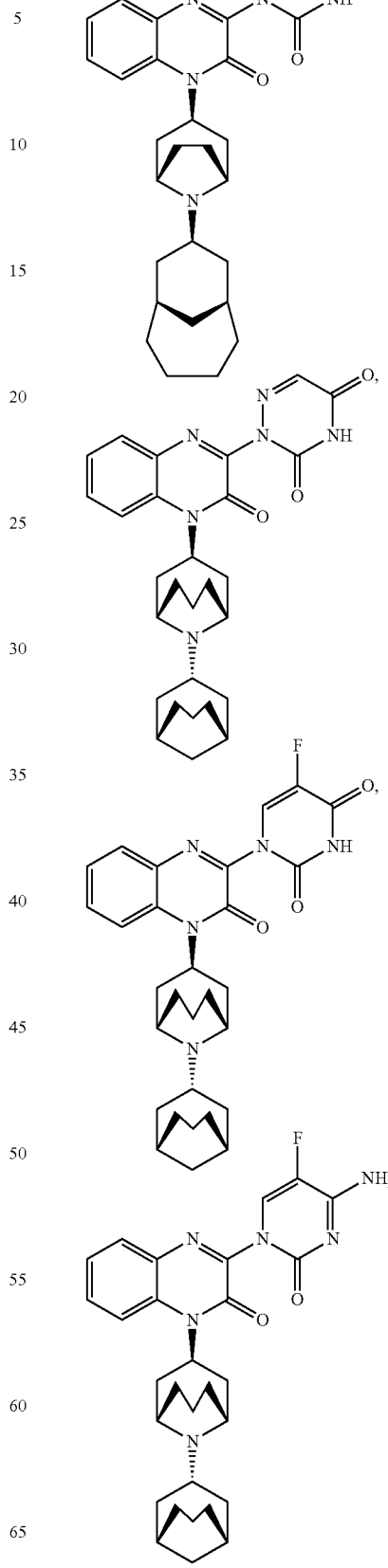

-continued
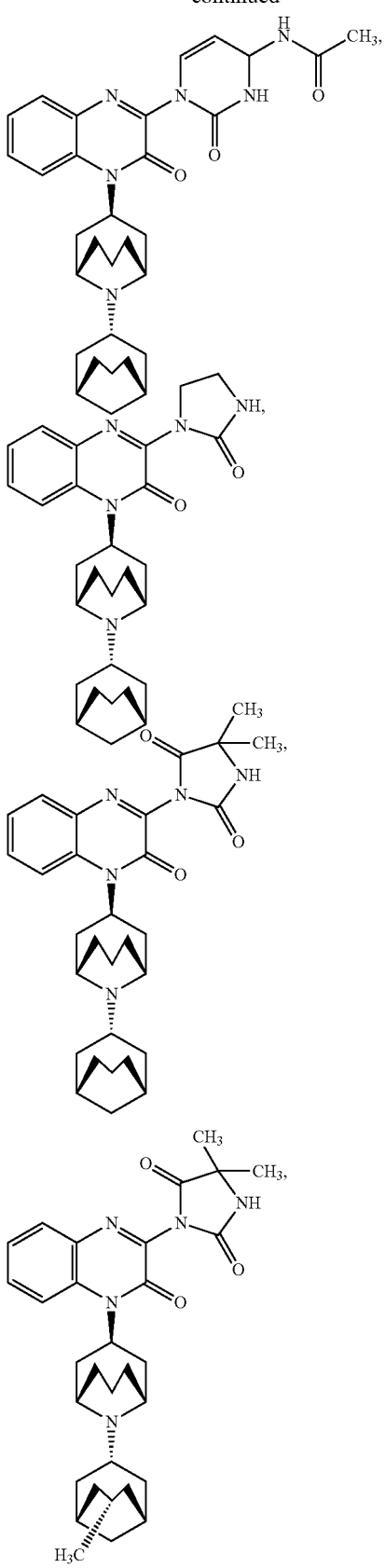
or a pharmaceutically acceptable salt thereof.
12. The compound of claim 9 or a pharmaceutically acceptable salt thereof, wherein the $Q_x$ ring is:
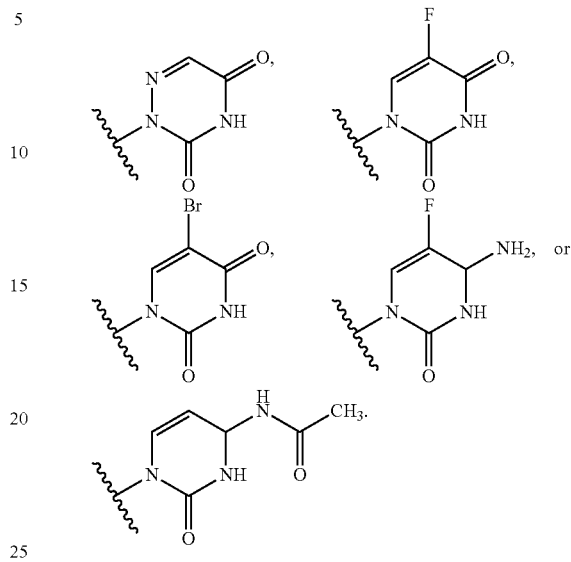
13. The compound of claim 12, which is:
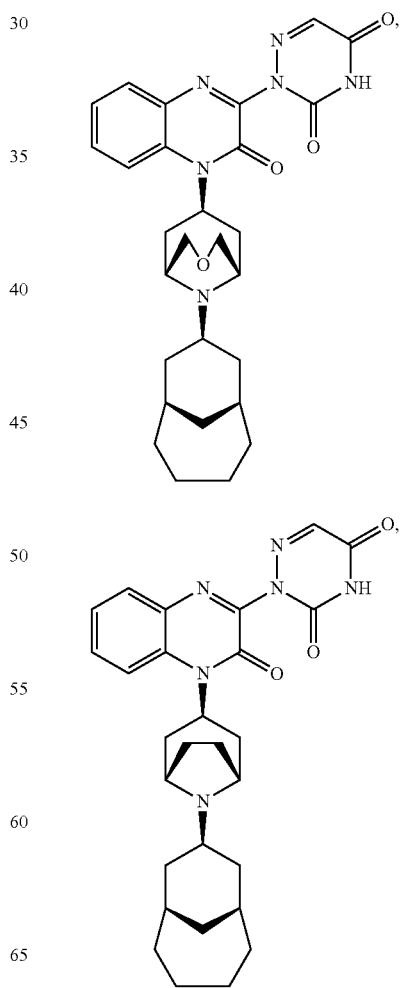

-continued
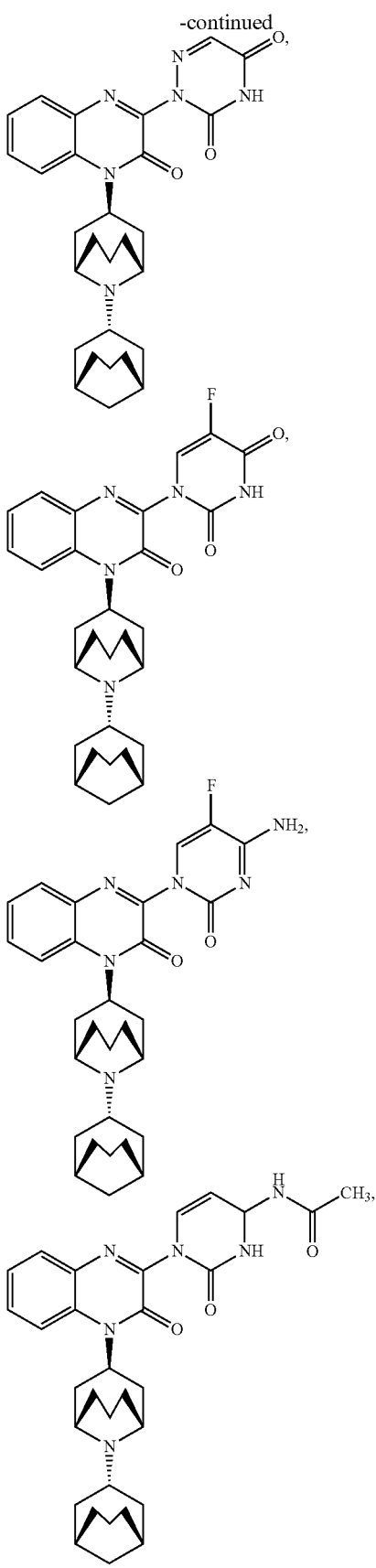
or a pharmaceutically acceptable salt thereof.
14. The compound of claim 7 or a pharmaceutically acceptable salt thereof, wherein E of the $Q_x$ ring is $C(R_{90})$.
15. The compound of claim 14 or a pharmaceutically acceptable salt thereof, wherein the $Q_x$ ring is:
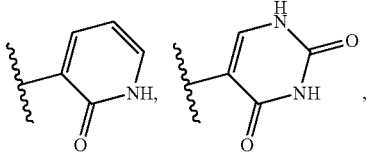
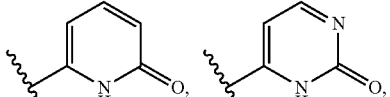
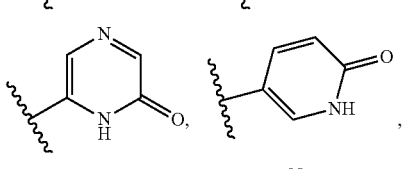
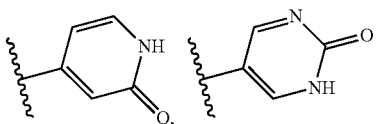
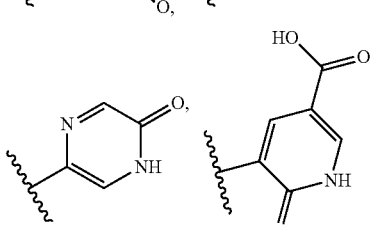
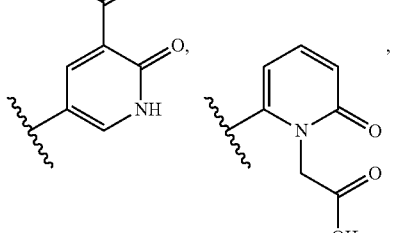
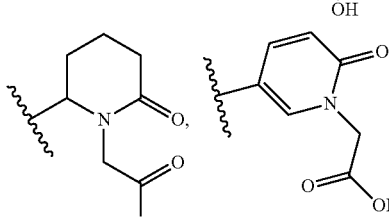
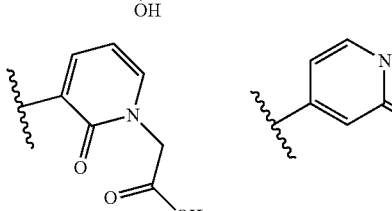
or
16. The compound of claim 15 or a pharmaceutically acceptable salt thereof, wherein the $Q_x$ ring is:

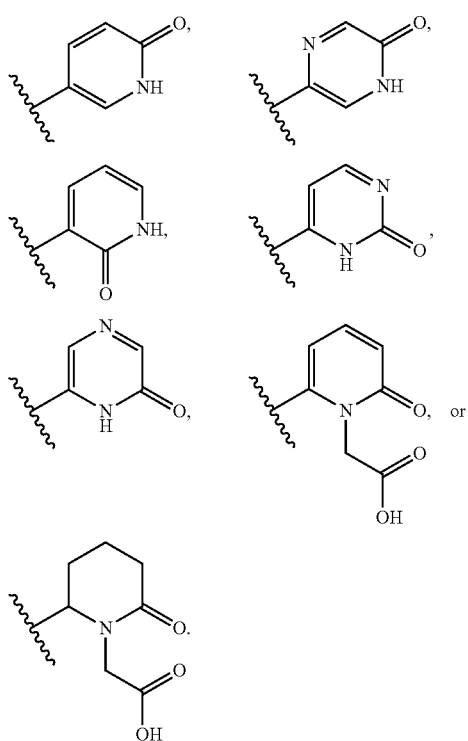
17. The compound of claim 16, which is:
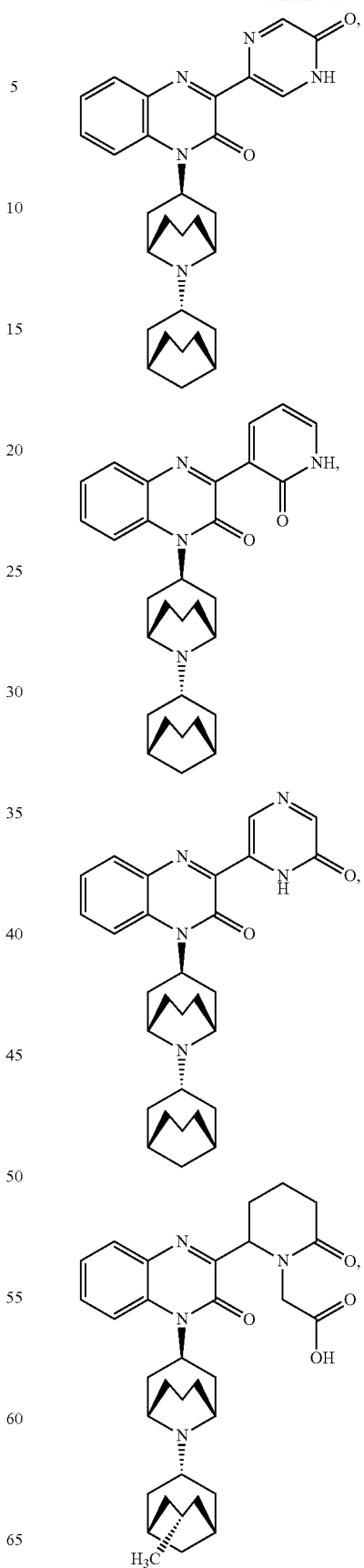

399

-continued

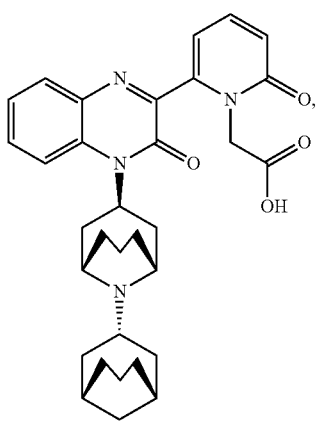

or a pharmaceutically acceptable salt thereof.

18. The compound of claim 7 or a pharmaceutically acceptable salt thereof, wherein in the C(R$_{90}$) of the E of the Q$_x$ ring, R$_{90}$ is absent.

19. The compound of claim 18 or a pharmaceutically acceptable salt thereof, wherein the Q$_x$ ring is:

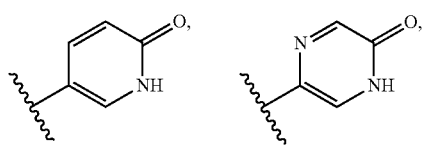

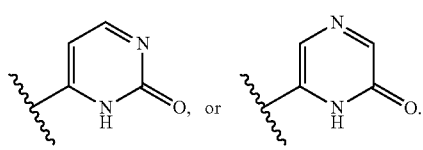

20. The compound of claim 19, which is:

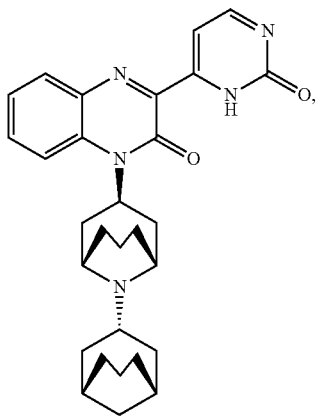

400

-continued

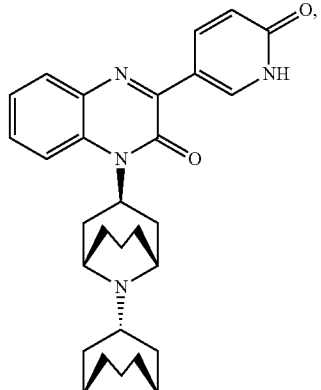

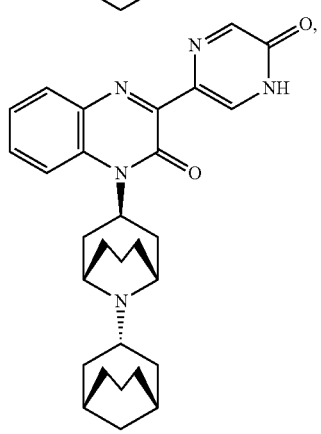

or a pharmaceutically acceptable salt thereof.

21. The compound of claim 7 or a pharmaceutically acceptable salt thereof, wherein h is 1.

22. The compound of claim 21 or a pharmaceutically acceptable salt thereof, wherein Z is —(C$_1$-C$_3$)alkyl- optionally substituted by R$_{13}$.

23. The compound of claim 21 or a pharmaceutically acceptable salt thereof, wherein R$_{13}$ is absent.

24. The compound of claim 23 or a pharmaceutically acceptable salt thereof, wherein Z is —CH$_2$—CH$_2$—.

25. The compound of claim 24 or a pharmaceutically acceptable salt thereof, wherein —Z—R$_1$ is:

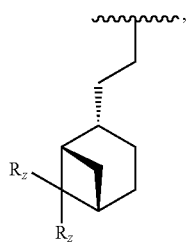

wherein each R$_z$ is independently —H, —CH$_3$, or —CH$_2$CH$_3$.

26. The compound of claim 7 or a pharmaceutically acceptable salt thereof, wherein h is 0.

27. The compound of claim 26 or a pharmaceutically acceptable salt thereof, wherein A and B together form a bridge such that the bridged-piperidine is:

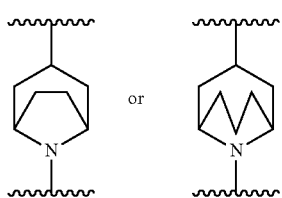

28. The compound of claim 27 or a pharmaceutically acceptable salt thereof, wherein:
(a) $R_1$ is —$(C_3$-$C_{14})$cycloalkyl, —$(C_5$-$C_{14})$cycloalkenyl, —$(C_6$-$C_{14})$bicycloalkyl, —$(C_7$-$C_{14})$bicycloalkenyl, or —$(C_8$-$C_{20})$tricycloalkyl, each of which is unsubstituted or substituted with 1, 2, 3, or 4 independently selected $R_8$ groups; and
(b) each $R_8$ is independently —$(C_1$-$C_4)$alkyl, —$(C_1$-$C_6)$alkyl-$C(=O)OR_9$, —$N(R_9)(C_1$-$C_6)$alkyl-$C(=O)OR_9$, —$OR_9$, —$C(halo)_3$, —$CH(halo)_2$, —$CH_2(halo)$, -halo, —$N(R_9)_2$, —$C(=O)N(T_1)(T_2)$, or —$C(=O)OR_9$.

29. The compound of claim 28 or a pharmaceutically acceptable salt thereof, wherein the $R_1$ group is in the exo-configuration with respect to the A-B bridge of the bridged piperidine.

30. The compound of claim 7 or a pharmaceutically acceptable salt thereof, wherein A and B together form a bridge such that the bridged-piperidine is:

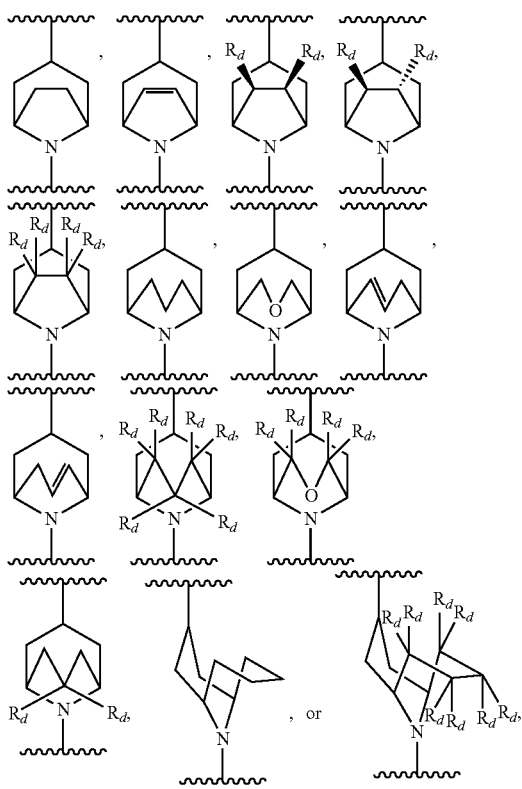

wherein each $R_d$ is independently —H, —$(C_1$-$C_4)$alkyl, -halo, or —$C(halo)_3$.

31. The compound of claim 30 or a pharmaceutically acceptable salt thereof, wherein the A-B bridge of the bridged-piperidine is in the endo- configuration with respect to the 6-membered, nitrogen-containing ring that is fused to the $Q_a$ ring.

32. The compound of claim 7 or a pharmaceutically acceptable salt thereof, wherein A and B together form a bridge such that the bridged-piperidine is:

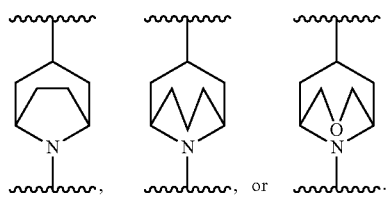 [SMILES: *C1CC2CCC(C1)N2* ; *C1CC2CCCC(C1)N2* ; *C1CC2COCC(C1)N2*]

33. The compound of claim 32 or a pharmaceutically acceptable salt thereof, wherein —Z—$R_1$ is:

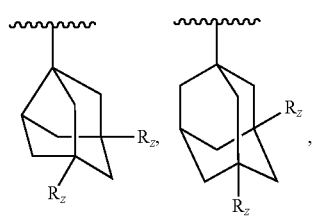

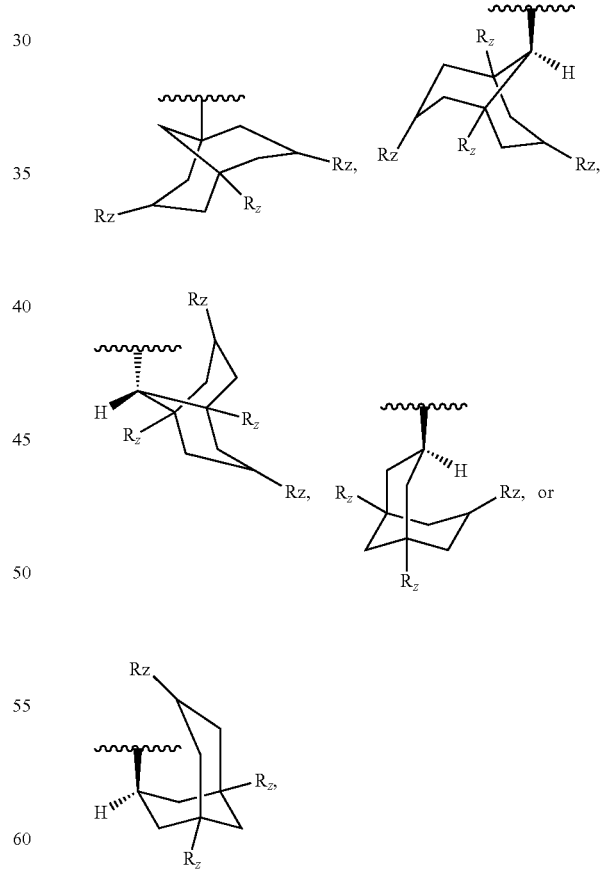

wherein each $R_z$ is independently —H, —$CH_3$, or —$CH_2CH_3$.

34. The compound of claim 32 or a pharmaceutically acceptable salt thereof, wherein —Z—$R_1$ is:

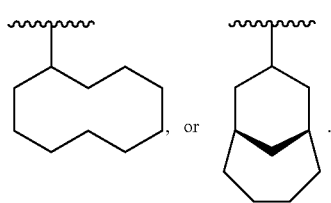 [SMILES: *C1CCCCCCCCC1 ; *C1C[C@H]2CCCC[C@@H](C1)C2], or

35. The compound of claim 32 or a pharmaceutically acceptable salt thereof, wherein —Z—R$_1$ is:

, wherein R$_z$ is —H, —CH$_3$, or —CH$_2$CH$_3$.

36. The compound of claim 1, wherein the pharmaceutically acceptable salt is a hydrochloride salt, a sodium salt, a potassium salt, or a para-toluenesulfonic acid salt.

37. A composition comprising an effective amount of the compound or a pharmaceutically acceptable salt of the compound of claim 1 and a pharmaceutically acceptable carrier or excipient.

38. A method for modulating opioid receptor like-1 receptor function in a cell, comprising contacting a cell capable of expressing the opioid receptor like-1 receptor with an effective amount of the compound of claim 1 or a pharmaceutically acceptable salt thereof.

39. The method of claim 38, wherein the compound or the pharmaceutically acceptable salt of the compound acts as an agonist at the opioid receptor like-1 receptor.

40. The method of claim 38, wherein the compound or the pharmaceutically acceptable salt of the compound acts as a partial agonist at the opioid receptor like-1 receptor.

41. A method for preparing a composition, comprising the step of admixing a compound or a pharmaceutically acceptable salt of the compound of claim 1 and a pharmaceutically acceptable carrier or excipient.

42. A compound or a pharmaceutically acceptable salt thereof, wherein the compound is:

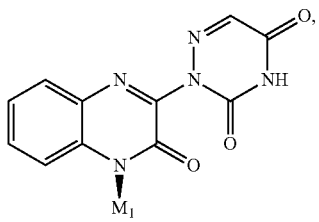

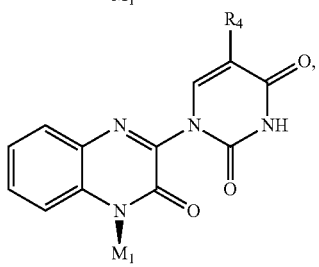

-continued

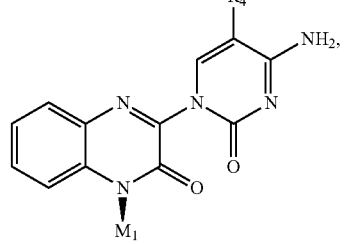

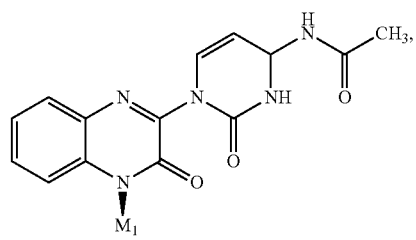

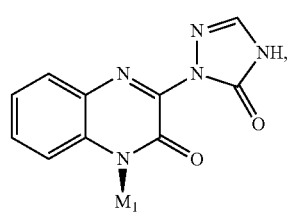

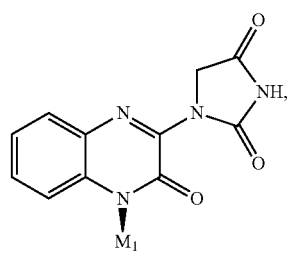

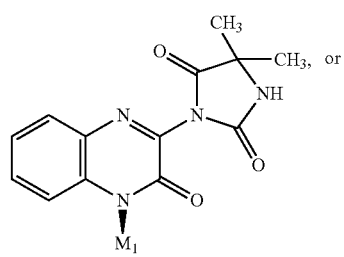, or

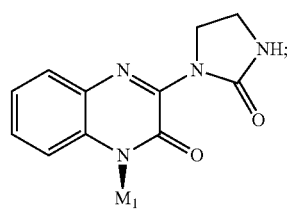;

wherein R$_4$ is H or halo;

$M_1$ is:

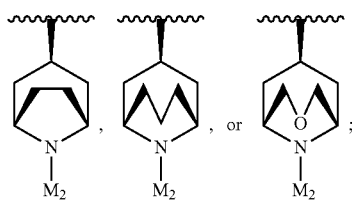

and $M_2$ is:

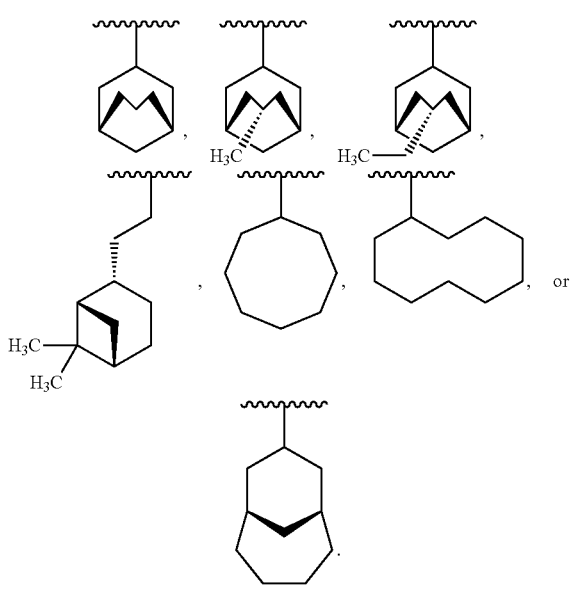

43. The compound of claim 42 or a pharmaceutically acceptable salt thereof, wherein the compound is:

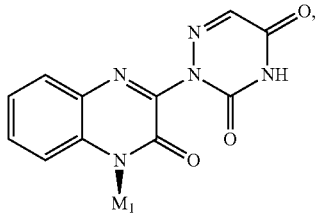

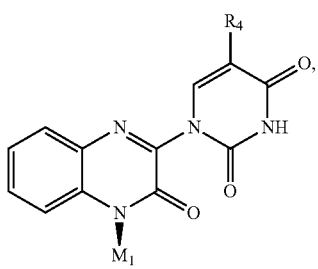

-continued

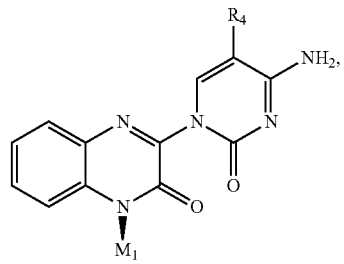

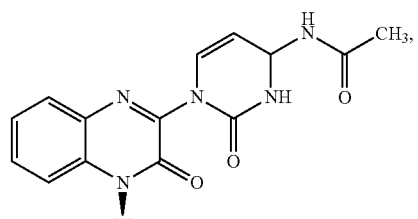

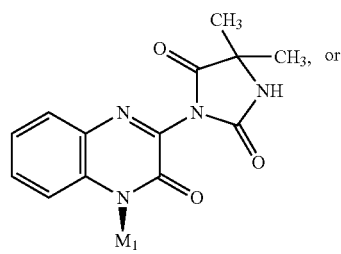

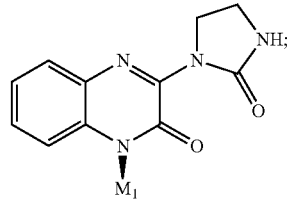

and wherein $M_2$ is:

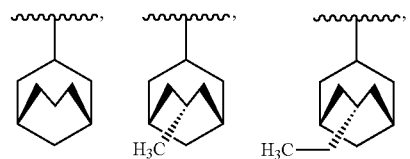

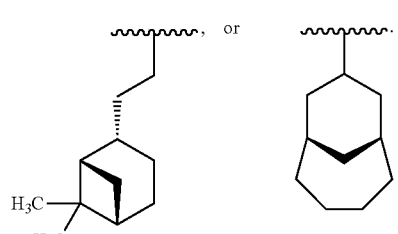

44. A method for modulating opioid receptor like-1 receptor function in a cell, comprising contacting a cell capable of expressing the opioid receptor like-1 receptor with an effective amount of the compound of claim 42 or a pharmaceutically acceptable salt thereof.

45. A compound which is:
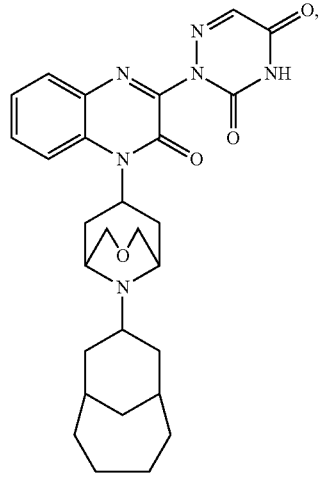
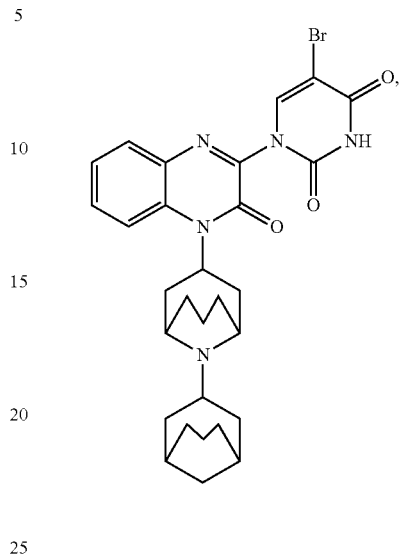
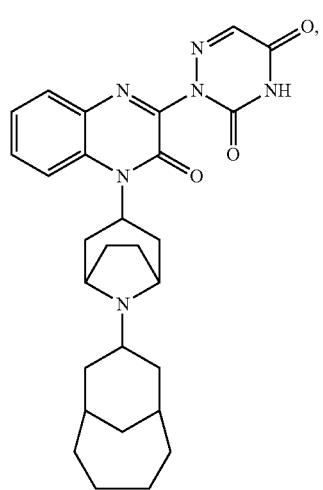
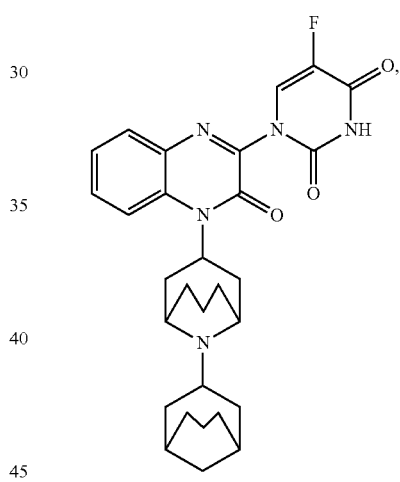
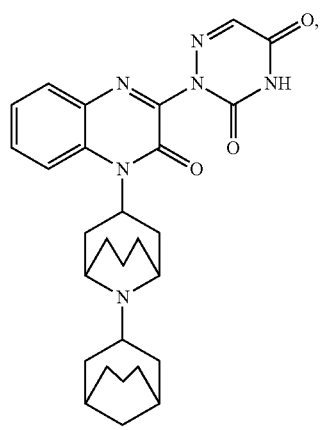
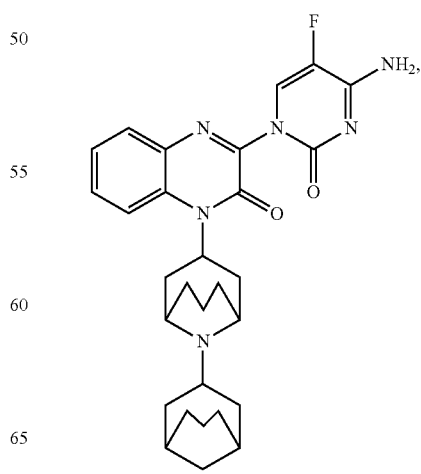

-continued
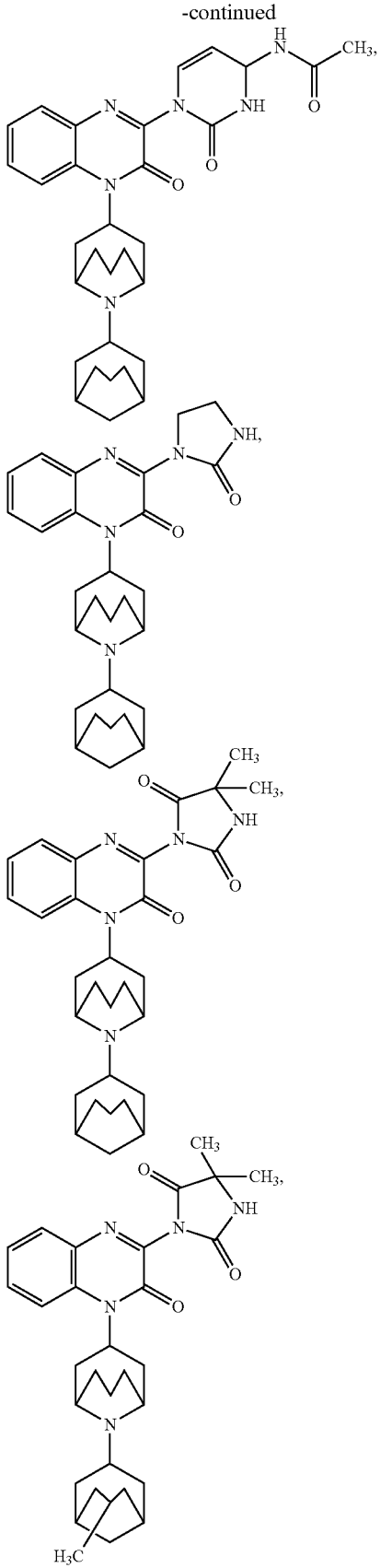
or a pharmaceutically acceptable salt thereof.
46. The compound of claim 45, which is:
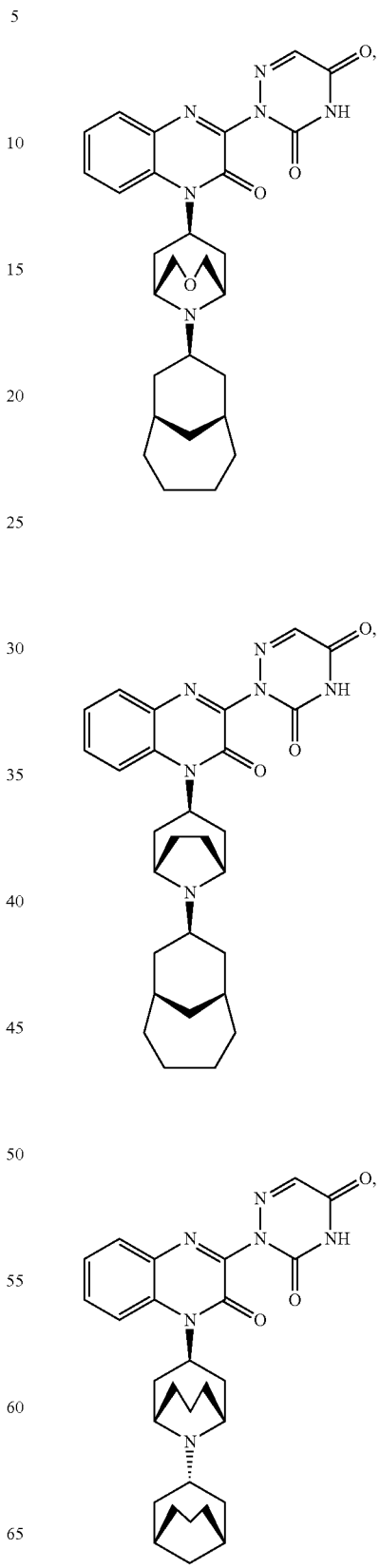

411
-continued
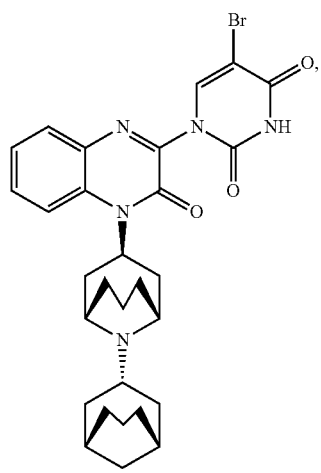
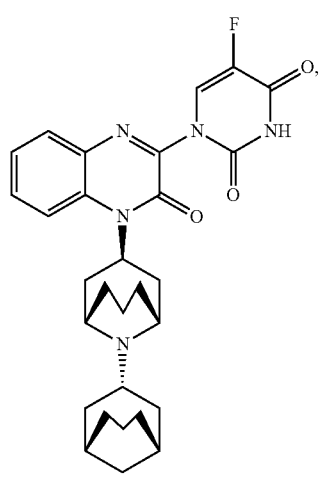
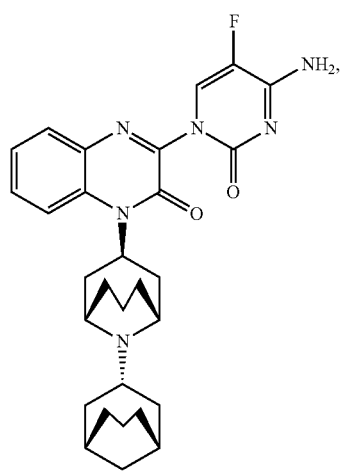
412
-continued
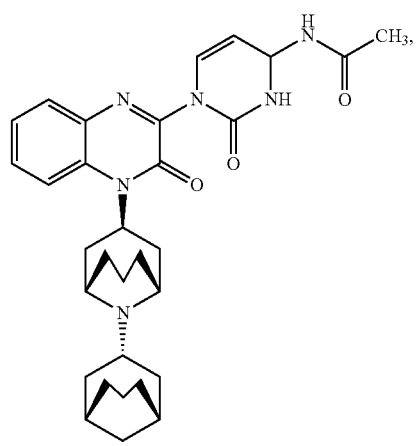
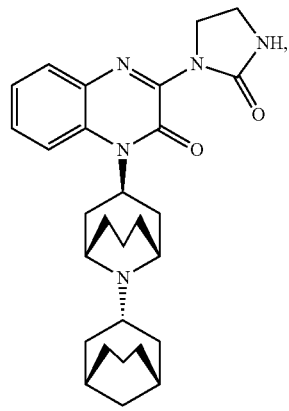
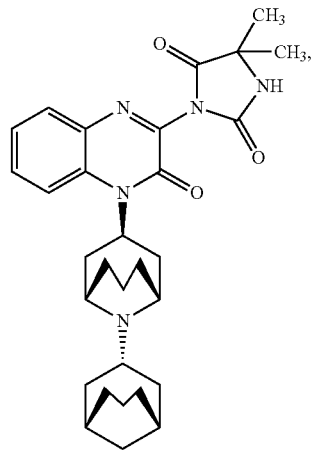

-continued

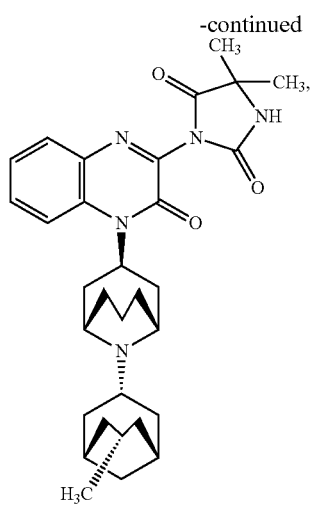

or a pharmaceutically acceptable salt thereof.

47. The compound of claim 46 having the formula:

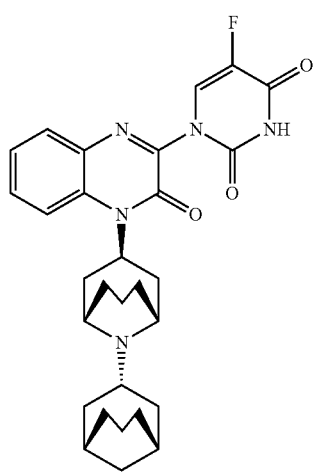 [SMILES: O=c1[nH]c(=O)n(-c2nc3ccccc3n([C@H]3C[C@H]4CCC[C@@H](C3)N4[C@H]3C[C@@H]4CCC[C@@H](C4)C3)c2=O)cc1F]

or a pharmaceutically acceptable salt thereof.

48. The compound of claim 46 having the formula:

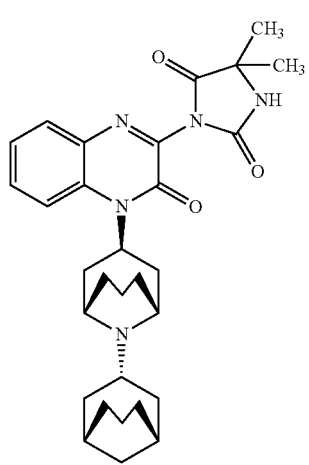 [SMILES: CC1(C)NC(=O)N(c2nc3ccccc3n([C@H]3C[C@H]4CCC[C@@H](C3)N4[C@H]3C[C@@H]4CCC[C@@H](C4)C3)c2=O)C1=O]

or a pharmaceutically acceptable salt thereof.

49. The compound of claim 46 having the formula:

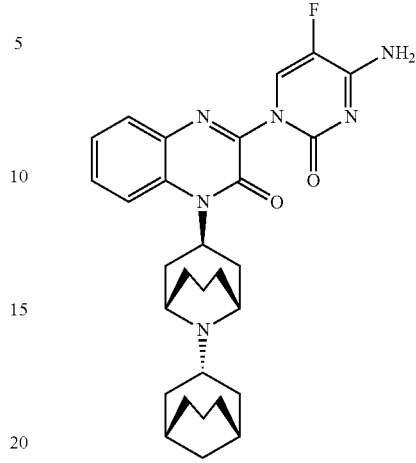

or a pharmaceutically acceptable salt thereof.

50. The compound of claim 46 having the formula:

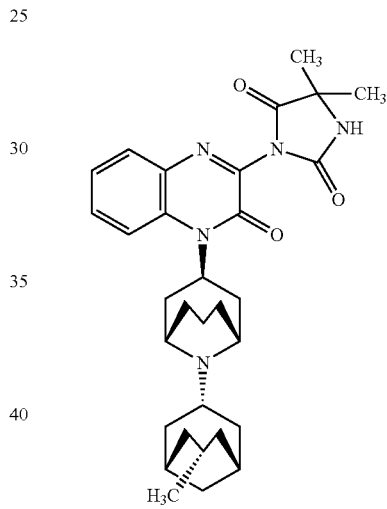

or a pharmaceutically acceptable salt thereof.

51. The compound of claim 46 having the formula:

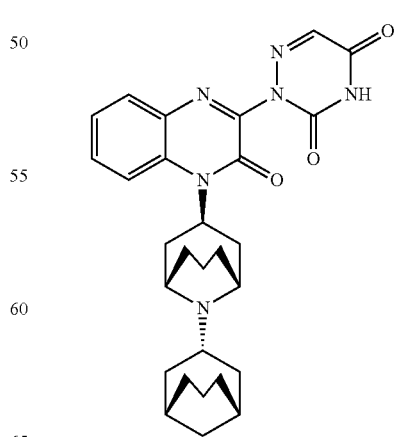

or a pharmaceutically acceptable salt thereof.

52. The compound of claim 46 having the formula:

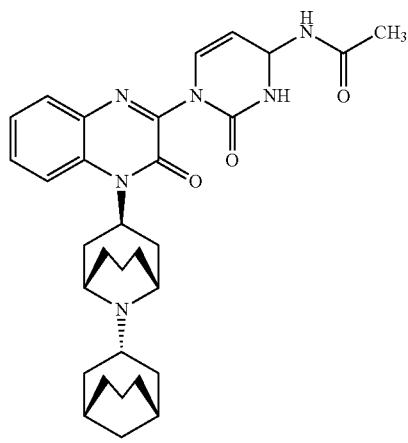 [SMILES: CC(=O)NC1C=CN(c2nc3ccccc3n([C@H]3C[C@H]4CCC[C@@H](C3)N4[C@H]3C[C@@H]4CCC[C@@H](C4)C3)c2=O)C(=O)N1]

or a pharmaceutically acceptable salt thereof.

53. The compound of claim 46 having the formula:

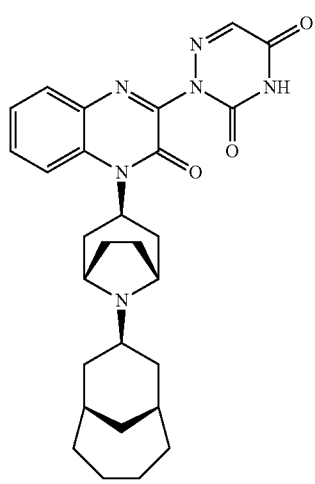 [SMILES: O=c1cnn(-c2nc3ccccc3n([C@H]3C[C@H]4CC[C@@H](C3)N4[C@@H]3C[C@@H]4CCCC[C@@H](C4)C3)c2=O)c(=O)[nH]1]

or a pharmaceutically acceptable salt thereof.

54. The compound of claim 46 having the formula:

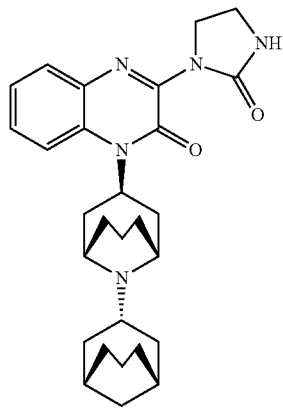 [SMILES: O=C1NCCN1c1nc2ccccc2n([C@H]2C[C@H]3CCC[C@@H](C2)N3[C@H]2C[C@@H]3CCC[C@@H](C3)C2)c1=O]

or a pharmaceutically acceptable salt thereof.

55. A method for modulating opioid receptor like-1 receptor function in a cell, comprising contacting a cell capable of expressing the opioid receptor like-1 receptor with an effective amount of the compound of claim 45 or a pharmaceutically acceptable salt thereof.

56. A compound which is:

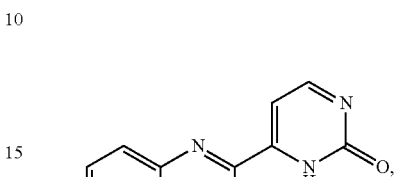
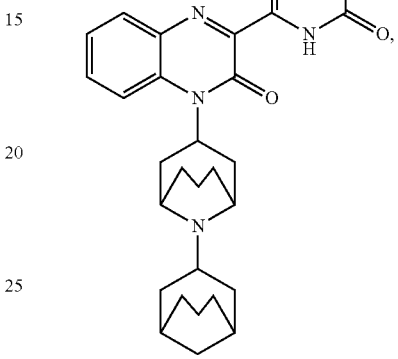

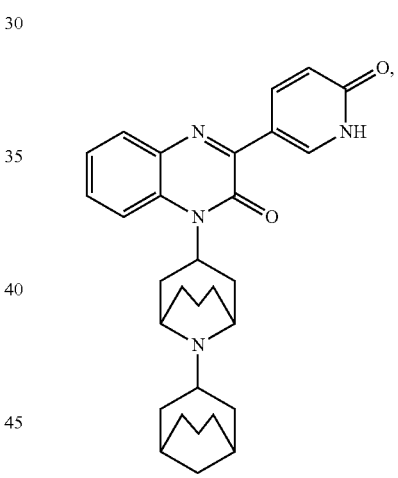
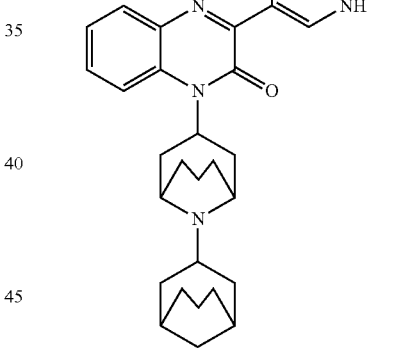
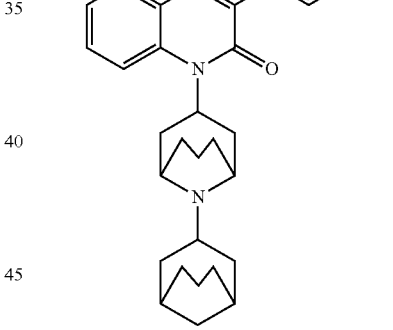

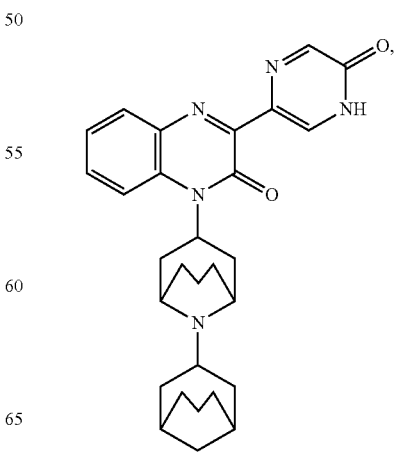
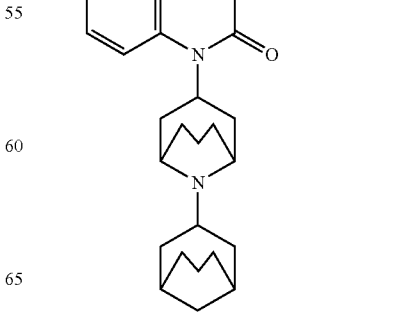
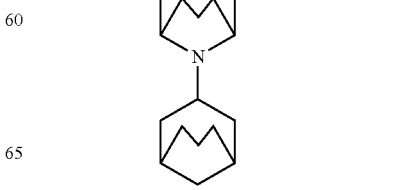

-continued
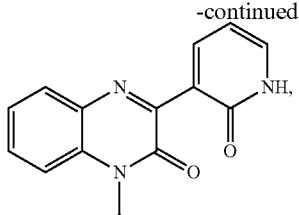
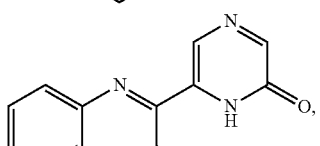
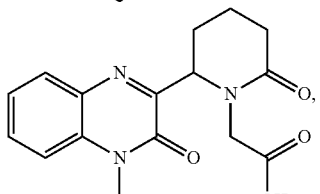
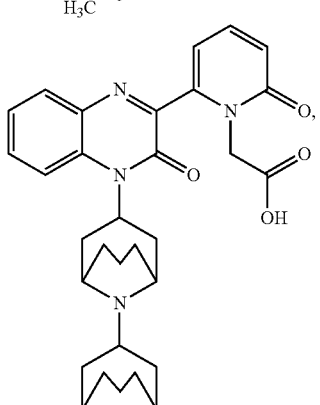
or a pharmaceutically acceptable salt thereof.
57. The compound of claim 56, which is:
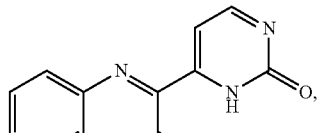
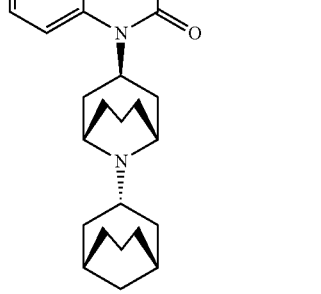
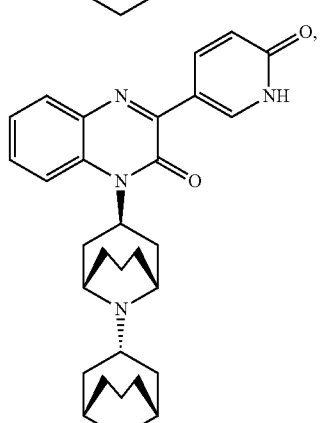
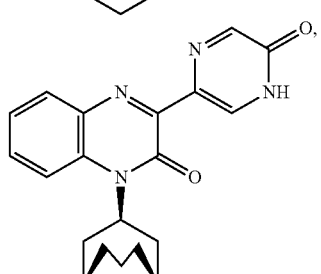
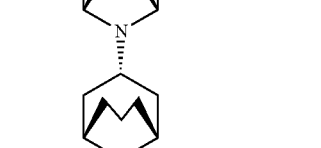
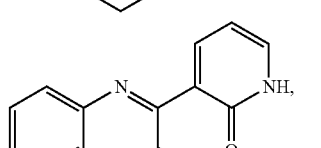
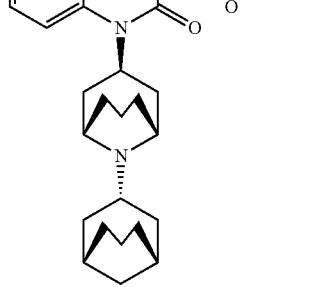

419
-continued
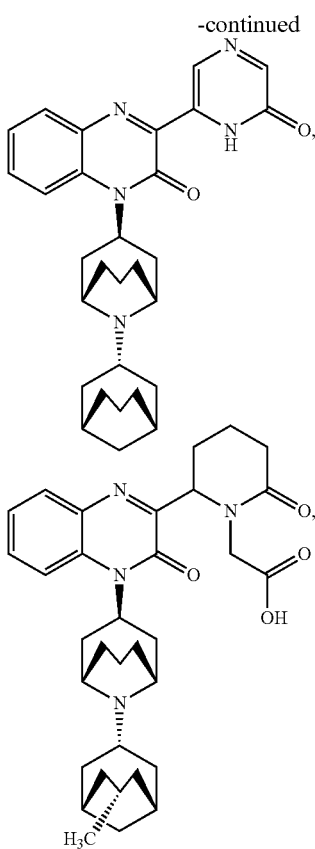
420
-continued
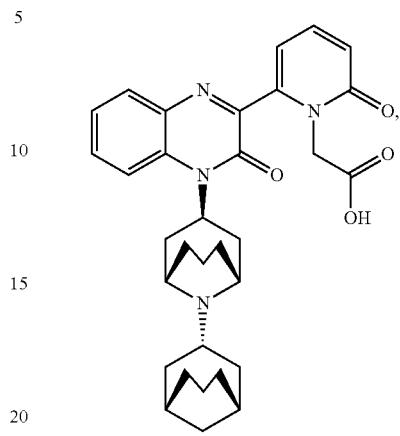
or a pharmaceutically acceptable salt thereof.
58. A method for modulating opioid receptor like-1 receptor function in a cell, comprising contacting a cell capable of expressing the opioid receptor like-1 receptor with an effective amount of the compound of claim 56 or a pharmaceutically acceptable salt thereof.
* * * * *